(12) United States Patent
Braun et al.

(10) Patent No.: US 10,435,414 B2
(45) Date of Patent: Oct. 8, 2019

(54) TRICYCLIC PI3K INHIBITOR COMPOUNDS AND METHODS OF USE

(71) Applicant: Genentech, Inc., South San Francisco, CA (US)

(72) Inventors: Marie-Gabrielle Braun, San Francisco, CA (US); Keira Garland, South San Francisco, CA (US); Emily Hanan, South San Francisco, CA (US); Hans Purkey, South San Francisco, CA (US); Steven T. Staben, San Francisco, CA (US); Robert Andrew Heald, Harlow Essex (GB); Jamie Knight, Harlow Essex (GB); Calum Macleod, Harlow Essex (GB); Aijun Lu, Beijing (CN); Guosheng Wu, Beijing (CN); Siew Kuen Yeap, Harlow Essex (GB)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/044,862

(22) Filed: Jul. 25, 2018

(65) Prior Publication Data
US 2018/0327420 A1 Nov. 15, 2018

Related U.S. Application Data

(62) Division of application No. 15/258,175, filed on Sep. 7, 2016, now Pat. No. 10,065,970.

(30) Foreign Application Priority Data

Sep. 8, 2015 (WO) ............. PCT/CN2015/089121
Mar. 11, 2016 (WO) ............. PCT/CN2016/076126

(51) Int. Cl.
| | |
|---|---|
| *A61K 31/4188* | (2006.01) |
| *A61K 31/424* | (2006.01) |
| *A61K 31/498* | (2006.01) |
| *A61K 31/5365* | (2006.01) |
| *A61K 45/06* | (2006.01) |
| *C07D 498/04* | (2006.01) |
| *C07D 498/06* | (2006.01) |
| *C07D 519/00* | (2006.01) |
| *A61K 31/4196* | (2006.01) |
| *A61K 31/423* | (2006.01) |
| *A61K 31/428* | (2006.01) |
| *A61K 31/4439* | (2006.01) |
| *A61K 31/5383* | (2006.01) |
| *A61K 31/553* | (2006.01) |
| *C07D 491/044* | (2006.01) |

(52) U.S. Cl.
CPC ........ *C07D 498/04* (2013.01); *A61K 31/4188* (2013.01); *A61K 31/4196* (2013.01); *A61K 31/423* (2013.01); *A61K 31/428* (2013.01); *A61K 31/4439* (2013.01); *A61K 31/498* (2013.01); *A61K 31/5365* (2013.01); *A61K 31/5383* (2013.01); *A61K 31/553* (2013.01); *A61K 45/06* (2013.01); *C07D 491/044* (2013.01); *C07D 498/06* (2013.01); *C07D 519/00* (2013.01)

(58) Field of Classification Search
CPC ............. A61K 31/4188; A61K 31/424; A61K 31/498; A61K 31/5365; A61K 45/06
See application file for complete search history.

(56) References Cited

U.S. PATENT DOCUMENTS

| | | | |
|---|---|---|---|
| 8,242,104 | B2 | 8/2012 | Blaquiere et al. |
| 8,263,633 | B2 | 9/2012 | Blaquiere et al. |
| 8,343,955 | B2 | 1/2013 | Blaquiere et al. |

(Continued)

FOREIGN PATENT DOCUMENTS

| | | |
|---|---|---|
| KR | 2015037711 | 4/2015 |
| KR | 2016078317 A | 7/2016 |

(Continued)

OTHER PUBLICATIONS

Saura C et al., "Phase Ib Study of the PI3K Inhibitor Taselisib (GDC-0032) in Combination with Letrozole in Patients with Hormone Receptor-Positive Advanced Breast Cancer" Poster PD5-2, San Antonio Breast Cancer Symposium, ( Dec. 12, 2014).

Staben et al., "Cis-amide isosteric replacement in thienobenzoxepin inhibitors of PI3-kinase" Bioorg Med Chem Lett. 23(3):897-901 (2013).

Heffron et al., "Rational design of phosphoinositide 3-kinase α inhibitors that exhibit selectivity over the phosphoinositide 3-kinase β isoform" J Med Chem. 54:7815-33 ( 2011).

(Continued)

*Primary Examiner* — Sahar Javanmard
(74) *Attorney, Agent, or Firm* — Zong-Qiang Bill Tian

(57) ABSTRACT

Described herein are tricyclic compounds with phosphoinositide-3 kinase (PI3K) modulation activity or function having the Formula I structure:

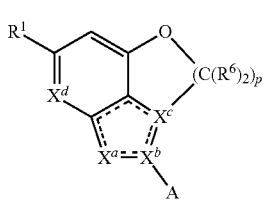

or stereoisomers, tautomers, or pharmaceutically acceptable salts thereof, and with the substituents and structural features described herein. Also described are pharmaceutical compositions and medicaments that include the Formula I compounds, as well as methods of using such PI3K modulators, alone and in combination with other therapeutic agents, for treating diseases or conditions that are mediated or dependent upon PI3K dysregulation.

23 Claims, No Drawings

(56) References Cited

U.S. PATENT DOCUMENTS

| | | | |
|---|---|---|---|
| 8,586,574 | B2 | 11/2013 | Blaquiere et al. |
| 8,785,626 | B2 | 7/2014 | Blaquiere et al. |
| 10,065,970 | B2 | 9/2018 | Braun et al. |
| 2007/0032469 | A1 | 2/2007 | Isaac |
| 2008/0318938 | A1 | 12/2008 | Ryckman |
| 2012/0202785 | A1 | 8/2012 | Heald |
| 2013/0005706 | A1 | 1/2013 | Corkey et al. |
| 2014/0275030 | A1 | 9/2014 | Combs |
| 2017/0002022 | A1 | 1/2017 | Braun et al. |
| 2017/0015678 | A1 | 1/2017 | Braun et al. |

FOREIGN PATENT DOCUMENTS

| | | |
|---|---|---|
| WO | 2011/036280 A1 | 3/2011 |
| WO | 2011/036284 A1 | 3/2011 |
| WO | 2012/126901 A1 | 9/2012 |

OTHER PUBLICATIONS

Staben et al., "Discovery of thiazolobenzoxepin PI3-kinase inhibitors that spare the PI3-kinase β isoform" Bioorg Med Chem Lett 23(9):2606-13 (May 1, 2013).

Staben et al., "Structure-based design of thienobenzoxepin inhibitors of PI3-kinase" Bioorg Med Chem Lett. 21:4054-8 ( 2011).

(CAS Reg. No. 1695559-51-3 (SciFinder)).

Castanedo et al., "Synthesis of Fused Imidazole-Containing Ring Systems via Dual Oxidative Amination of C(sp(3))-H Bonds" J Org Chem. 81(18):8617-24 (Sep. 16, 2016).

Friedman et al., "Selective PI3K and dual PI3K/mTOR inhibitors enhance the efficacy of endocrine therapies breast cancer models" Cancer Research (AACR San Antonio Breast Cancer Symposium, Dec. 4-8, 2012, Abstract), 72(24 SUPPL 3) (2012).

Heffron et al., "The Rational Design of Selective Benzoxazepin Inhibitors of the α-Isoform of Phosphoinositide 3-Kinase Culminating in the Identification of (S)-2-((2-(1-Isopropyl-1H-1,2,4-triazol-5-yl)-5,6-dihydrobenzo[f]imidazo[1,2-d][1,4]oxazepin-9-yl)oxy)propanamide (GDC-0326)" J Med Chem. 59(3):985-1002 (Feb. 11, 2016).

Zhou et al., "Rh(III)-Catalyzed Intramolecular Redox-Neutral or Oxidative Cyclization of Alkynes: Short, Efficient Synthesis of 3,4-Fused Indole Skeletons" Organic Letters 16:3900-3903 ( 2014).

Ndubaku et al., "Discovery of 2-{3-[2-(1-Isopropyl-3-methyl-1H-1,2-4-triazol-5-yl)-5,6-dihydrobenzo[f]imidazo[1,2-d][1,4]oxazepin-9-yl]-1H-pyrazol-1-yl}-2-methylpropanamide (GDC-0032): A β-Sparing Phosphoinositide 3-Kinase Inhibitor with High Unbound Exposure and Robust in Vivo Antitumor Activity" J Med Chem 56:4597-4610 ( 2013).

Nacht et al., "Discovery of a potent and isoform-selective targeted covalent inhibitor of the lipid kinase PI3Kβ" J Med Chem. 56(3):712-21 (Feb. 14, 2013).

Demonchaux Patrice et al., "Design of Pyrrolo-1,4-Benzoxazine Derivatives as inhibitors of 5-Lipoxygenase and PAF Antagonists with Antihistaminic Properties" Bioorganic & Medicinal Chemisty Letters 4(20):2383-2388 ( 1994).

Database Registry (Online), Chemical Abstracts Service, Columbus, Ohio, US; Apr. 30, 2015 (Apr. 30, 2015), XP002762789, Database accession no. 1695559-51-3, RN 1695559-51-3 & KR 2016 0078317 A, Jul. 4, 2016 (Jul. 4, 2016) p. 63.

Lopez et al., "Taselisib, a selective inhibitor of PIK3CA, is highly effective on PIK3CA-mutated and HER2/neu amplified uterine serous carcinoma in vitro and in vivo" Gynecol Oncol. 135(2):312-7 (Nov. 2014).

ISR for PCT/EP2016/071015 completed on Oct. 27, 2016.

Edgar et al., "Isoform-Specific Phosphoinositide 3-Kinase Inhibitors Exert Distinct Effects in Solid Tumors" Cancer Res 70(3):1164-1172 (Feb. 1, 2010).

Edgar et al., "Amphiregulin and PTEN evoke a multimodal mechanism of acquired resistance to PI3K inhibition" Genes Cancer 5( SUPPL 3-4):113-26 (2014).

TRICYCLIC PI3K INHIBITOR COMPOUNDS AND METHODS OF USE

CROSS REFERENCE TO RELATED APPLICATIONS

This application is a division of U.S. application Ser. No. 15/258,175 filed 7 Sep. 2016, now U.S. Pat. No. 10,065,970, which claims the benefit under 35 USC § 119(a) and § 365 of International Application No. PCT/CN2015/089121 filed on 8 Sep. 2015, and International Application No. PCT/CN2016/076126 filed on 11 Mar. 2016, which are incorporated by reference in their entireties.

FIELD OF THE INVENTION

The invention relates generally to tricyclic PI3K inhibitor compounds with activity against hyperproliferative disorders such as cancer. The invention also relates to methods of using the compounds for in vitro, in situ, and in vivo diagnosis or treatment of mammalian cells, or associated pathological conditions.

BACKGROUND OF THE INVENTION

Upregulation of the phosphoinositide-3 kinase (PI3K)/Akt signaling pathway is a common feature in most cancers (Yuan and Cantley (2008) Oncogene 27:5497-510). Genetic deviations in the pathway have been detected in many human cancers (Osaka et al (2004) Apoptosis 9:667-76) and act primarily to stimulate cell proliferation, migration and survival. Activation of the pathway occurs following activating point mutations or amplifications of the PIK3CA gene encoding the p110α (alpha) PI3K isoforms (Hennessy et al (2005) Nat. Rev. Drug Discov. 4:988-1004). Genetic deletion or loss of function mutations within the tumor suppressor PTEN, a phosphatase with opposing function to PI3K, also increases PI3K pathway signaling (Zhang and Yu (2010) Clin. Cancer Res. 16:4325-30. These aberrations lead to increased downstream signaling through kinases such as Akt and mTOR and increased activity of the PI3K pathway has been proposed as a hallmark of resistance to cancer treatment (Opel et al (2007) Cancer Res. 67:735-45; Razis et al (2011) Breast Cancer Res. Treat. 128:447-56).

Phosphatidylinositol 3-Kinase (PI3K) is a major signaling node for key survival and growth signals for lymphomas and is opposed by the activity of the phosphatase PTEN. The phosphoinositide 3-dependent kinase (PI3K) signaling pathway is the most dysregulated pathway in hormone receptor positive breast cancer (HR+BC). The PI3K pathway is also dysregulated in aggressive forms of lymphoma (Abubaker (2007) Leukemia 21:2368-2370). Eight percent of DLBCL (diffuse large B-cell lymphoma) cancers have PI3CA (phosphatidylinositol-3 kinase catalytic subunit alpha) missense mutations and 37% are PTEN negative by immunohistochemistry test.

Phosphatidylinositol is one of a number of phospholipids found in cell membranes, and which participate in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem. 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60). Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and PDK1, phosphoinositide-dependent kinase-1 (Vivanco et al (2002) Nature Rev. Cancer 2:489; Phillips et al (1998) Cancer 83:41).

The PI3 kinase family comprises at least 15 different enzymes sub-classified by structural homology and are divided into 3 classes based on sequence homology and the product formed by enzyme catalysis. The class I PI3 kinases are composed of 2 subunits: a 110 kd catalytic subunit and an 85 kd regulatory subunit. The regulatory subunits contain SH2 domains and bind to tyrosine residues phosphorylated by growth factor receptors with a tyrosine kinase activity or oncogene products, thereby inducing the PI3K activity of the p110 catalytic subunit which phosphorylates its lipid substrate. Class I PI3 kinases are involved in important signal transduction events downstream of cytokines, integrins, growth factors and immunoreceptors, which suggests that control of this pathway may lead to important therapeutic effects such as modulating cell proliferation and carcinogenesis. Class I PI3Ks can phosphorylate phosphatidylinositol (PI), phosphatidylinositol-4-phosphate, and phosphatidylinositol-4,5-biphosphate (PIP2) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate. Class III PI3Ks can only phosphorylate PI. A key PI3-kinase isoform in cancer is the Class I PI3-kinase, p110α as indicated by recurrent oncogenic mutations in p110α (Samuels et al (2004) Science 304:554; U.S. Pat. Nos. 5,824,492; 5,846,824; 6,274,327). Other isoforms may be important in cancer and are also implicated in cardiovascular and immune-inflammatory disease (Workman P (2004) Biochem Soc Trans 32:393-396; Patel et al (2004) Proc. Am. Assoc. of Cancer Res. (Abstract LB-247) 95th Annual Meeting, March 27-31, Orlando, Fla., USA; Ahmadi K and Waterfield M D (2004) "Phosphoinositide 3-Kinase: Function and Mechanisms" Encyclopedia of Biological Chemistry (Lennarz W J, Lane M D eds) Elsevier/Academic Press), Oncogenic mutations of p110α (alpha) have been found at a significant frequency in colon, breast, brain, liver, ovarian, gastric, lung, and head and neck solid tumors. About 35-40% of hormone receptor positive (HR+) breast cancer tumors harbor a PIK3CA mutation. PTEN abnormalities are found in glioblastoma, melanoma, prostate, endometrial, ovarian, breast, lung, head and neck, hepatocellular, and thyroid cancers.

PI3 kinase (PI3K) is a heterodimer consisting of p85 and p110 subunits (Otsu et al (1991) Cell 65:91-104; Hiles et al (1992) Cell 70:419-29). Four distinct Class I PI3Ks have been identified, designated PI3K α (alpha), β (beta), δ (delta), and γ (gamma), each consisting of a distinct 110 kDa catalytic subunit and a regulatory subunit. Three of the catalytic subunits, i.e., p110 alpha, p110 beta and p110 delta, each interact with the same regulatory subunit, p85; whereas p110 gamma interacts with a distinct regulatory subunit, p101. The patterns of expression of each of these PI3Ks in human cells and tissues are distinct. In each of the PI3K alpha, beta, and delta subtypes, the p85 subunit acts to localize PI3 kinase to the plasma membrane by the interaction of its SH2 domain with phosphorylated tyrosine residues (present in an appropriate sequence context) in target proteins (Rameh et al (1995) Cell, 83:821-30; Volinia et al (1992) Oncogene, 7:789-93).

The PI3 kinase/Akt/PTEN pathway is an attractive target for cancer drug development since such agents would be expected to inhibit cellular proliferation, to repress signals from stromal cells that provide for survival and chemoresistance of cancer cells, to reverse the repression of apoptosis and surmount intrinsic resistance of cancer cells to cytotoxic agents. PI3K is activated through receptor tyrosine kinase signaling as well as activating mutations in the p110 catalytic subunit of PI3K, loss of the tumor suppressor PTEN, or through rare activating mutations in AKT.

SUMMARY OF THE INVENTION

The invention relates generally to tricyclic compounds with activity in modulating PI3K, including mutant forms of the PI3Kα (alpha) isoform, and having the Formula I structure:

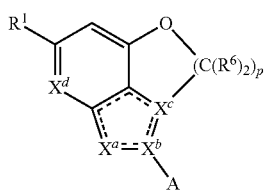

I or stereoisomers, tautomers, and pharmaceutically acceptable salts thereof. The various substituents are defined herein.

Another aspect of the invention is a pharmaceutical composition comprising a Formula I compound and a pharmaceutically acceptable carrier, glidant, diluent, or excipient.

Another aspect of the invention is a process for making the pharmaceutical composition.

Another aspect of the invention is a method of treating cancer in a patient having cancer comprising administering to said patient a therapeutically effective amount of a compound of a Formula I compound wherein the cancer is selected from breast cancer, lung cancer, ovarian cancer, endometrial cancer, prostate cancer, and uterine cancer. A therapeutic agent selected from 5-FU, docetaxel, eribulin, gemcitabine, cobimetinib, ipatasertib, paclitaxel, tamoxifen, fulvestrant, GDC-0810, dexamethasone, palbociclib, bevacizumab, pertuzumab, trastuzumab emtansine, trastuzumab and letrozole may be administered to the patient.

Another aspect of the invention is a kit for the therapeutic treatment of breast cancer, comprising:

a) a first pharmaceutical composition comprising a Formula I compound; and b) instructions for use in the therapeutic treatment of breast cancer.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. The nomenclature used in this Application is based on IUPAC systematic nomenclature, unless indicated otherwise.

DEFINITIONS

When indicating the number of substituents, the term "one or more" refers to the range from one substituent to the highest possible number of substitution, i.e. replacement of one hydrogen up to replacement of all hydrogens by substituents. The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)$ (CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-di methyl-2-butyl (—CH(CH$_3$)C(CH$_3$)$_3$, 1-heptyl, 1-octyl, and the like.

The terms "carbocycle", "carbocyclyl", "carbocyclic ring" and "cycloalkyl" refer to a monovalent non-aromatic, saturated or partially unsaturated ring having 3 to 12 carbon atoms (C$_3$-C$_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Spiro carbocyclyl moieties are also included within the scope of this definition. Examples of spiro carbocyclyl moieties include [2.2]pentanyl, [2.3]hexanyl, and [2.4]heptanyl. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

"Aryl" means a monovalent aromatic hydrocarbon radical of 6-20 carbon atoms (C$_6$-C$_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro heterocyclyl moieties are also included within the scope of this definition. Examples of spiro heterocyclyl moieties include azaspiro[2.5]octanyl and azaspiro[2.4]heptanyl. Examples of a heterocyclic group wherein 2 ring atoms are substituted with oxo (=O) moieties are pyrimidinonyl and 1,1-dioxo-thiomorpholinyl.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The terms "treat" and "treatment" refer to therapeutic treatment, wherein the object is to slow down (lessen) an undesired physiological change or disorder, such as the development or spread of arthritis or cancer. For purposes of this invention, beneficial or desired clinical results include, but are not limited to, alleviation of symptoms, diminishment of extert of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those with the condition or disorder.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extert and preferably stop) cancer cell infiltration into peripheral organs; inhibit (i.e., slow to some extert and preferably stop) tumor metastasis; inhibit, to some extent, tumor growth; and/or relieve to some extert one or more of the symptoms associated with the cancer. To the extert the drug may prevent growth and/or kill existing cancer cells, it may be cytostatic and/or cytotoxic.

For cancer therapy, efficacy can be measured, for example, by assessing the time to disease progression (TTP) and/or determining the response rate (RR).

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

"Hematological malignancies" (British spelling "Haematological" malignancies) are the types of cancer that affect blood, bone marrow, and lymph nodes. As the three are intimately connected through the immune system, a disease affecting one of the three will often affect the others as well: although lymphoma is a disease of the lymph nodes, it often spreads to the bone marrow, affecting the blood. Hematological malignancies are malignant neoplasms ("cancer"), and they are generally treated by specialists in hematology and/or oncology. In some centers "Hematology/oncology" is a single subspecialty of internal medicine while in others they are considered separate divisions (there are also surgical and radiation oncologists). Not all hematological disorders are malignant ("cancerous"); these other blood conditions may also be managed by a hematologist. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin. Leukemias include Acute lymphoblastic leukemia (ALL), Acute myelogenous leukemia (AML), Chronic lymphocytic leukemia (CLL), Chronic myelogenous leukemia (CML), Acute monocytic leukemia (AMOL) and small lymphocytic lymphoma (SLL). Lymphomas include Hodgkin's lymphomas (all four subtypes) and Non-Hodgkin's lymphomas (NHL, all subtypes).

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: ibrutinib (IMBRUVICA™, APCI-32765, Pharmacyclics Inc./Janssen Biotech Inc.; CAS Reg. No. 936563-96-1, U.S. Pat. No. 7,514,444), idelalisib (formerly CAL-101, GS 1101, GS-1101, Gilead Sciences Inc.; CAS Reg. No. 1146702-54-6), erlotinib (TARCEVA®, Genentech/OSI Pharm.), docetaxel (TAXOTERE®, Sanofi-Aventis), 5-FU (fluorouracil, 5-fluorouracil, CAS Reg. No. 51-21-8), gemcitabine (GEMZAR®, Lilly), PD-0325901 (CAS No. 391210-10-9, Pfizer), cisplatin (Platinol®, (SP-4-2)-diamminedichloroplatinum(II), cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®, CAS No. 23214-92-8), Akti-1/2, HPPD, and rapamycin.

Chemotherapeutic agents include inhibitors of B-cell receptor targets such as BTK, Bcl-2 and JAK inhibitors.

More examples of chemotherapeutic agents include: oxaliplatin (ELOXATIN®, Sanofi), bortezomib (VELCADE®, Millennium Pharm.), sutert (SUNITINIB®, SU11248, Pfizer), letrozole (FEMARA®, Novartis), imatinib mesylate (GLEEVEC®, Novartis), XL-518 (MEK inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chlorambucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate) and selective estrogen receptor modulators (SERDs) such as fulvestrant (FASLODEX®, Astra Zeneca); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors, such as cobimetinib (WO 2007/044515); (v) lipid kinase inhibitors, such as taselisib (GDC-0032, Genentech Inc.); (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (PERJETA™, 2C4, Genentech), trastuzumab (HERCEPTIN®, Genentech), trastuzumab emtansine (KADCYLA®, Genentech Inc.), and tositumomab (BEXXAR, Corixia).

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a Formula I compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative, and depicted in Table 1 structures for illustrative purposes, while stereochemistry is definitively established, such as from x-ray crystallographic data.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "pharmaceutically acceptable salts" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, aryl-aliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid "mesylate", ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The term "$EC_{50}$" is the half maximal effective concentration" and denotes the plasma concentration of a particular compound required for obtaining 50% of the maximum of a particular effect in vivo.

The term "Ki" is the inhibition constant and denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "$IC_{50}$" is the half maximal inhibitory concentration and denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed, and can be converted to an absolute inhibition constant (Ki) using the Cheng-Prusoff equation (Biochem. Pharmacol. (1973) 22:3099). Other percent inhibition parameters, such as $IC_{70}$, $IC_{90}$, etc., may be calculated.

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labeled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

Tricyclic PI3K Inhibitor Compounds

The present invention provides tricyclic inhibitor compounds of Formula I, and pharmaceutical formulations thereof, which are potentially useful in the treatment of cancer, having the structure:

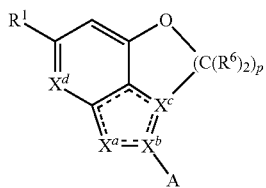

or stereoisomers, tautomers, and pharmaceutically acceptable salts thereof, wherein:
the dotted/solid lines represent a single or double bond;
$X^a$ is $CR^a$, N, $NR^b$, O, or S;
$X^b$ is C or N;
$X^c$ is C or N;
$X^d$ is $CR^2$ or N;
where at least one of $X^a$, $X^b$, and $X^c$ is N, O, or S;
$R^a$ is selected from H, $C_1$-$C_6$ alkyl, —CN and F;
$R^b$ is selected from H and $C_1$-$C_6$ alkyl;
$R^1$ is selected from Br, Cl, I, $C_2$-$C_{20}$ heterocyclyl, $C_1$-$C_{20}$ heteroaryl, —$NR^3R^4$, and —$OR^5$;
$R^2$ is selected from H, F, Cl, $C_1$-$C_6$ alkyl, and —O($C_1$-$C_6$ alkyl);
$R^3$ is selected from H, and $C_1$-$C_6$ alkyl;
$R^4$ is selected from H, $C_1$-$C_6$ alkyl, $C_2$-$C_{20}$ heterocyclyl, and $C_1$-$C_{20}$ heteroaryl;
or $R^3$ and $R^4$ form a 4-membered, 5-membered or 6-membered heterocyclyl ring;
$R^5$ is selected from $C_1$-$C_6$ alkyl, $C_2$-$C_{20}$ heterocyclyl, and $C_1$-$C_{20}$ heteroaryl;
$R^6$ is independently selected from H, $C_1$-$C_4$ alkyl, and F;
or two geminal or vicinal $R^6$ groups can form a 3, 4, or 5 membered-carbocyclic ring;
p is 2, 3, or 4;

A is selected from $C_6$-$C_{20}$ aryl, —($C_6$-$C_{20}$ aryl)-($C_6$-$C_{20}$ aryl), —($C_6$-$C_{20}$ aryl)-($C_1$-$C_{20}$ heteroaryl), —($C_6$-$C_{20}$ aryl)-($C_2$-$C_{20}$ heterocyclyl), —($C_1$-$C_{20}$ heteroaryl)-($C_2$-$C_{20}$ heterocyclyl), —($C_1$-$C_{20}$ heteroaryl)-($C_1$-$C_{20}$ heteroaryl), $C_2$-$C_{20}$ heterocyclyl, and $C_1$-$C_{20}$ heteroaryl; and where alkyl, aryl, heterocyclyl and heteroaryl are optionally substituted with one or more groups independently selected from F, Cl, Br, I, —CN, —$CH_3$, —$CH_2CH_3$, —$CH(CH_3)_2$, $C(CH_3)_3$, —$CH_2CH(CH_3)_2$, —$CH_2OH$, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CH_2NH_2$, —$CH_2NHSO_2CH_3$, —$CH_2NHCH_3$, —$CH_2N(CH_3)_2$, —$CF_3$, —$CH_2CF_3$, —$CH_2CHF_2$, —$CH(CH_3)CN$, —$C(CH_3)_2CN$, —$CH_2CN$, —$CO_2H$, —$COCH_3$, —$CO_2CH_3$, —$CO_2C(CH_3)_3$, —$COCH(OH)CH_3$, —$CONH_2$, —$CONHCH_3$, —$CONHCH_2CH_3$, —$CONHCH(CH_3)_2$, —$CON(CH_3)_2$, —$C(CH_3)_2CONH_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —$S(O)_2N(CH_3)_2$, —$SCH_3$, —$S(O)_2CH_3$, —$S(O)_3H$, cyclopropyl, cyclobutyl, azetidinyl, oxetanyl, cyclopentyl, tetrahydrofuranyl, morpholinyl, piperidyl, piperazinyl, and tetrahydropyranyl.

Exemplary embodiments of the invention include compounds of Formulas Ia-If:

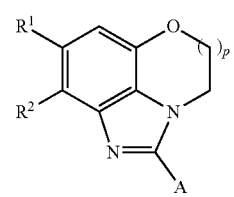

Ia

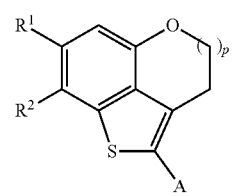

Ib

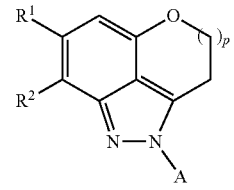

Ic

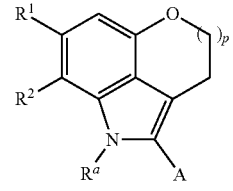

Id

-continued

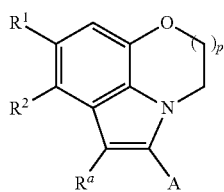
Ie

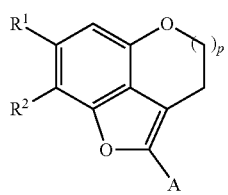
If wherein p is 1, 2, or 3.

Exemplary embodiments of the invention include compounds of Formula Ig:

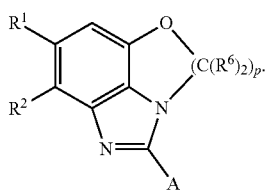
Ig

Exemplary embodiments of the invention include compounds of Formulas Ih-j:

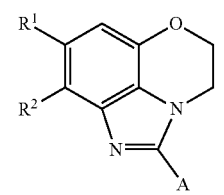
Ih

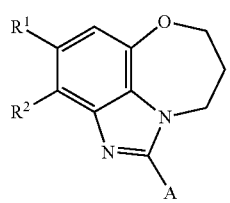
Ii

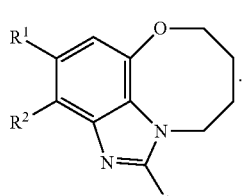
Ij

Exemplary embodiments of the invention include compounds of Formula Ik-m:

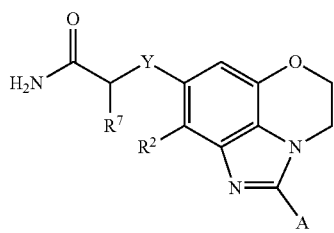

Exemplary embodiments of the invention include compounds of Formula In-p:

wherein Y is O or NR$^3$; and

R$^7$ is selected from H, cyclopropyl, cyclobutyl and C$_1$-C$_6$ alkyl optionally substituted with F, Cl, —OCH$_3$, or —OH; or R$^3$ and R$^7$ form a 4-membered, 5-membered or 6-membered heterocyclyl ring.

Exemplary Formula Ij-1 compounds include wherein Y is NH.

Exemplary Formula Ij-1 compounds include wherein Y is NR³, and R³ and R⁷ form a pyrrolidinyl ring.

Exemplary Formula Ij-1 compounds include wherein Y is O.

Exemplary Formula I compounds include wherein R¹ is Br or substituted pyrazolyl.

Exemplary Formula I compounds include wherein R¹ is selected from:

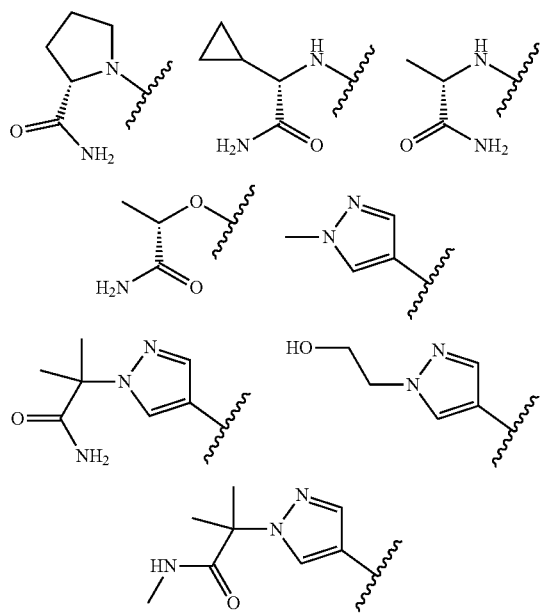

where the wavy line indicates the site of attachment.

Exemplary Formula I compounds include wherein A is substituted benzo[d]oxazolyl or substituted benzothiazolyl.

Exemplary Formula I compounds include wherein A is selected from the structures:

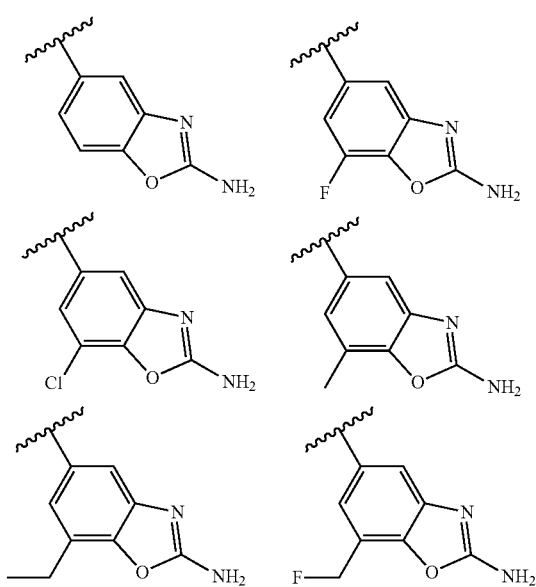

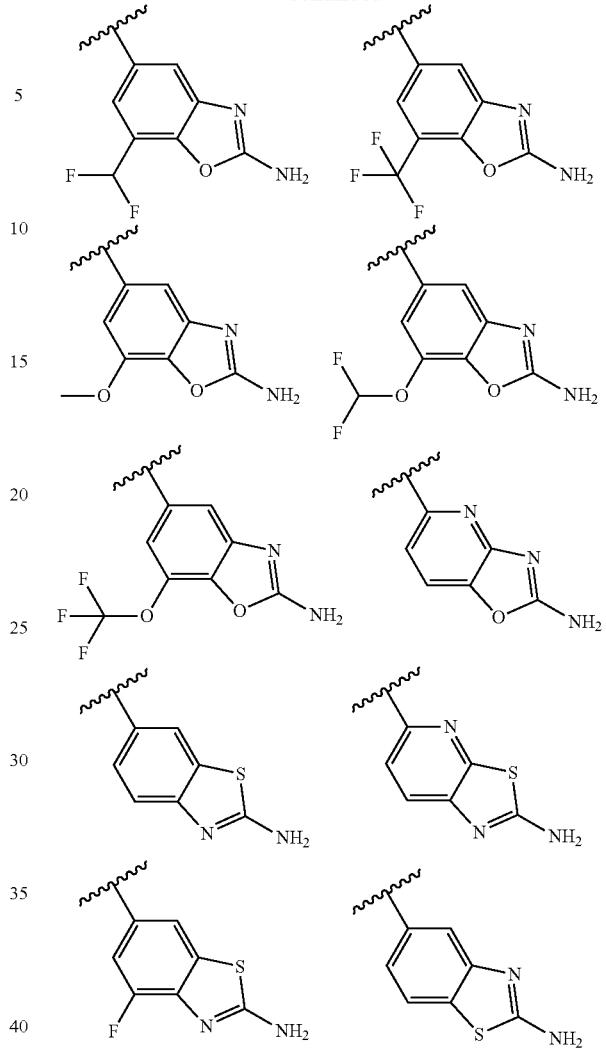

where the wavy line indicates the site of attachment.

Exemplary embodiments of Formula I compounds include the compounds in Table 1.

The Formula I compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. In some instances, the stereochemistry has not been determined or has been provisionally assigned.

In addition, the present invention embraces all diastereomers, including cis-trans (geometric) and conformational isomers. For example, if a Formula I compound incorporates a double bond or a fused ring, the cis- and trans-forms, as well as mixtures thereof, are embraced within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Biological Evaluation

The relative efficacies of Formula I compounds as inhibitors of an enzyme activity (or other biological activity) can be established by determining the concentrations at which each compound inhibits the activity to a predefined extert and then comparing the results. Typically, the preferred determination is the concentration that inhibits 50% of the activity in a biochemical assay, i.e., the 50% inhibitory concentration or "$IC_{50}$". Determination of $IC_{50}$ values can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

The ability of a compound of the invention to act as an inhibitor of PI3Kα was determined using the methods of Example 901. Representative compounds of the invention exhibit strong activity against PI3Kα (alpha) isoform.

Exemplary Formula I compounds in Tables 1 and 2 were made, characterized, and tested for binding to PI3Kα (alpha) according to the methods of this invention, and have the following structures, corresponding names (ChemBioDraw, Version 14.0.0, CambridgeSoft Corp., Cambridge Mass.), and biological activity. Where more than one name is associated with a Formula I compound or intermediate, the chemical structure shall define the compound.

TABLE 1

| | | | | |
|---|---|---|---|---|
| | | Formula I compounds | | |
| Compound No. | Structure | Name | PI3Kα-(alpha) ATP (Ki) micromolar (μM) | Mass Spec. M + H/1 (daltons) |
| 101 | 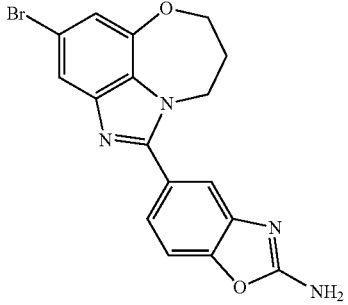 [SMILES: Nc1nc2cc(-c3nc4cc(Br)cc5c4n3CCCO5)ccc2o1] | 5-(4-bromo-8,9-dihydro-7H-6-oxa-2,9a-diazabenzo[cd]azulen-1-yl)benzo[d]oxazol-2-amine | 0.00775 | 385.10 |
| 102 | 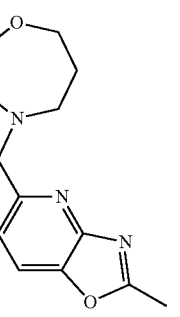 | 4-bromo-1-(2-methyloxazolo[4,5-b]pyridin-5-yl)-8,9-dihydro-7H-6-oxa-2,9a-diazabenzo[cd]azulene | 0.322 | 385.10 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 103 | 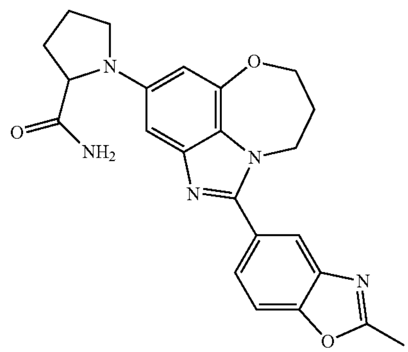 [SMILES: Cc1nc2cc(-c3nc4cc(N5CCCC5C(N)=O)cc5c4n3CCCO5)ccc2o1] | 1-(1-(2-methylbenzo[d]oxazol-5-yl)-8,9-dihydro-7H-6-oxa-2,9a-diazabenzo[cd]azulen-4-yl)pyrrolidine-2-carboxamide | 0.0162 | 418.18 |
| 104 | 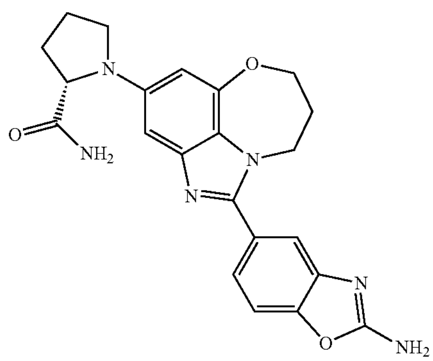 [SMILES: NC(=O)[C@@H]1CCCN1c1cc2c3c(c1)nc(-c1ccc4oc(N)nc4c1)n3CCCO2] | (S)-1-(1-(2-aminobenzo[d]oxazol-5-yl)-8,9-dihydro-7H-6-oxa-2,9a-diazabenzo[cd]azulen-4-yl)pyrrolidine-2-carboxamide | 0.000071 | 419.17 |
| 105 | 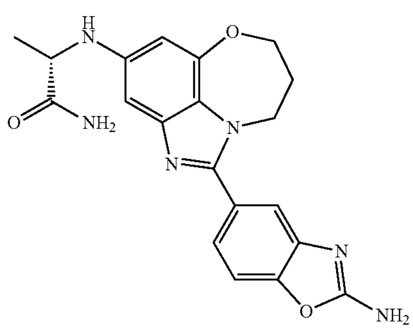 [SMILES: C[C@H](Nc1cc2c3c(c1)nc(-c1ccc4oc(N)nc4c1)n3CCCO2)C(N)=O] | (S)-2-((1-(2-aminobenzo[d]oxazol-5-yl)-8,9-dihydro-7H-6-oxa-2,9a-diazabenzo[cd]azulen-4-yl)amino)propanamide | 0.000032 | 393.16 |
| 106 | 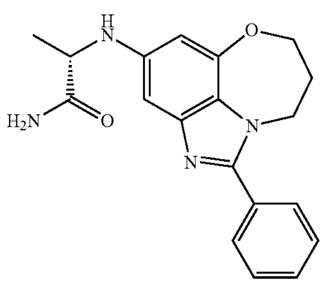 [SMILES: C[C@H](Nc1cc2c3c(c1)nc(-c1ccccc1)n3CCCO2)C(N)=O] | (S)-2-((1-phenyl-8,9-dihydro-7H-6-oxa-2,9a-diazabenzo[cd]azulen-4-yl)amino)propanamide | 0.13 | 337 |

TABLE 1-continued

Formula I compounds

| Compound No. | Structure | Name | PI3Kα-(alpha) ATP (Ki) micromolar (μM) | Mass Spec. M + H/1 (daltons) |
| --- | --- | --- | --- | --- |
| 107 | 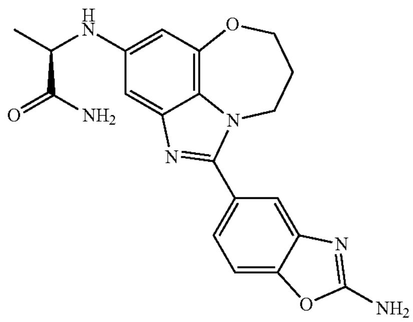 [SMILES: C[C@@H](Nc1cc2c3c(c1)nc(-c1ccc4oc(N)nc4c1)n3CCCO2)C(N)=O] | (R)-2-((1-(2-aminobenzo[d]oxazol-5-yl)-8,9-dihydro-7H-6-oxa-2,9a-diazabenzo[cd]azulen-4-yl)amino)propanamide | 0.00058 | 393 |
| 108 | 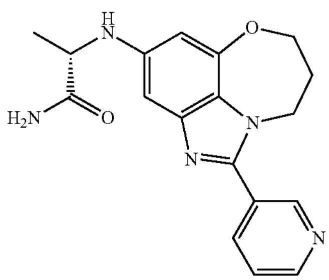 [SMILES: C[C@H](Nc1cc2c3c(c1)nc(-c1cccnc1)n3CCCO2)C(N)=O] | (S)-2-((1-(pyridin-3-yl)-8,9-dihydro-7H-6-oxa-2,9a-diazabenzo[cd]azulen-4-yl)amino)propanamide | 0.0221 | 338 |
| 109 | 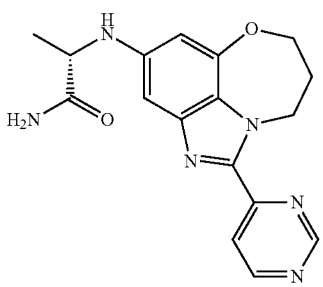 [SMILES: C[C@H](Nc1cc2c3c(c1)nc(-c1ccncn1)n3CCCO2)C(N)=O] | (S)-2-((1-(pyrimidin-4-yl)-8,9-dihydro-7H-6-oxa-2,9a-diazabenzo[cd]azulen-4-yl)amino)propanamide | 0.0243 | 339.1 |
| 110 | 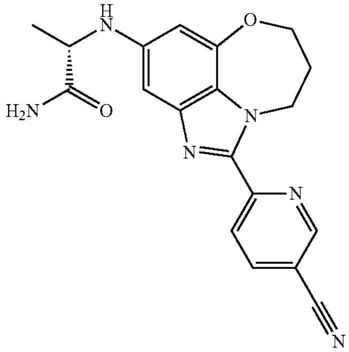 [SMILES: C[C@H](Nc1cc2c3c(c1)nc(-c1ccc(C#N)cn1)n3CCCO2)C(N)=O] | (S)-2-((1-(5-cyanopyridin-2-yl)-8,9-dihydro-7H-6-oxa-2,9a-diazabenzo[cd]azulen-4-yl)amino)propanamide | 0.261 | 363.1 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 111 | 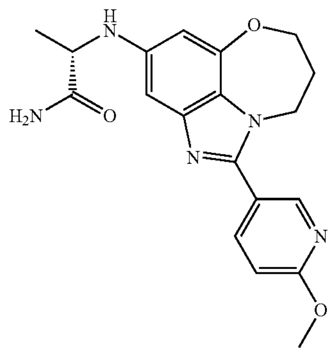 [SMILES: COc1ccc(-c2nc3cc(N[C@@H](C)C(N)=O)cc4c3n2CCCO4)cn1] | (S)-2-((1-(6-methoxy-pyridin-3-yl)-8,9-dihydro-7H-6-oxa-2,9a-diazabenzo[cd]azulen-4-yl)amino)propanamide | 0.0116 | 368 |
| 112 | 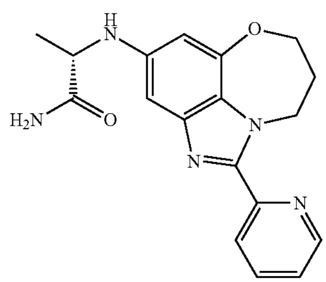 | (S)-2-((1-(pyridin-2-yl)-8,9-dihydro-7H-6-oxa-2,9a-diazabenzo[cd]azulen-4-yl)amino)propanamide | 0.16 | 338 |
| 113 | 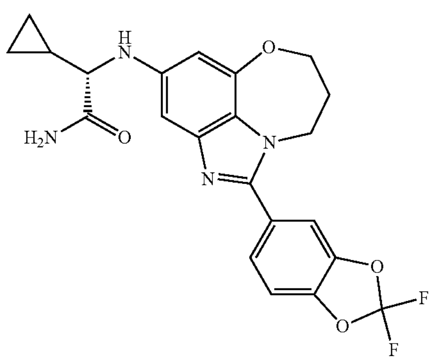 [SMILES: NC(=O)[C@@H](Nc1cc2c3c(c1)nc(-c1ccc4c(c1)OC(F)(F)O4)n3CCCO2)C1CC1] | (S)-2-cyclopropyl-2-((1-(2,2-difluorobenzo[d][1,3]dioxol-5-yl)-8,9-dihydro-7H-6-oxa-2,9a-diazabenzo[cd]azulen-4-yl)amino)acetamide | 0.268 | 443 |
| 114 | 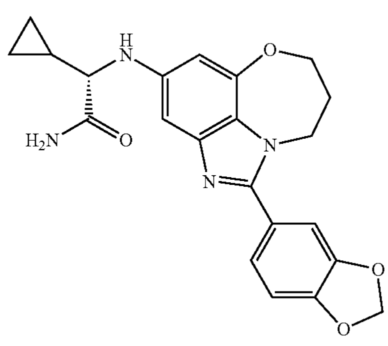 [SMILES: NC(=O)[C@@H](Nc1cc2c3c(c1)nc(-c1ccc4c(c1)OCO4)n3CCCO2)C1CC1] | (S)-2-((1-(benzo[d][1,3]dioxol-5-yl)-8,9-dihydro-7H-6-oxa-2,9a-diazabenzo[cd]azulen-4-yl)amino)-2-cyclopropyl-acetamide | 0.0233 | 407 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 115 | 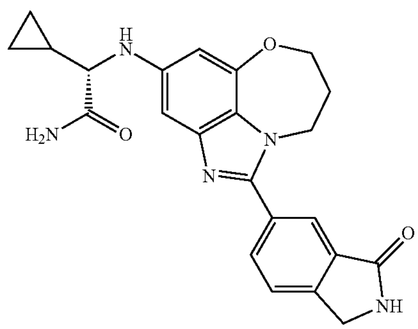 [SMILES: NC(=O)[C@@H](Nc1cc2c3c(c1)nc(-c1ccc4c(c1)C(=O)NC4)n3CCCO2)C1CC1] | (S)-2-cyclopropyl-2-((1-(3-oxo-isoindolin-5-yl)-8,9-dihydro-7H-6-oxa-2,9a-diazabenzo[cd]azulen-4-yl)amino)acetamide | 0.0367 | 418 |
| 116 | 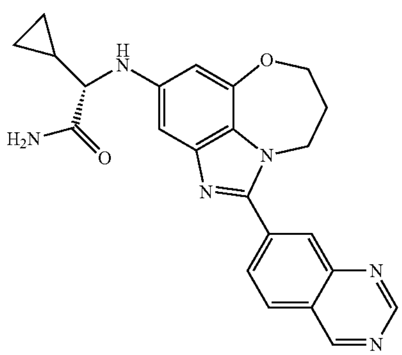 [SMILES: NC(=O)[C@@H](Nc1cc2c3c(c1)nc(-c1ccc4cncnc4c1)n3CCCO2)C1CC1] | (S)-2-cyclopropyl-2-((1-(quinazolin-7-yl)-8,9-dihydro-7H-6-oxa-2,9a-diazabenzo[cd]azulen-4-yl)amino)acetamide | 0.019 | 415 |
| 117 | 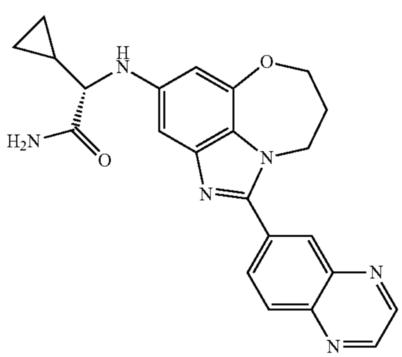 [SMILES: NC(=O)[C@@H](Nc1cc2c3c(c1)nc(-c1ccc4nccnc4c1)n3CCCO2)C1CC1] | (S)-2-cyclopropyl-2-((1-(quinoxalin-6-yl)-8,9-dihydro-7H-6-oxa-2,9a-diazabenzo[cd]azulen-4-yl)amino)acetamide | 0.00118 | 415 |
| 118 | 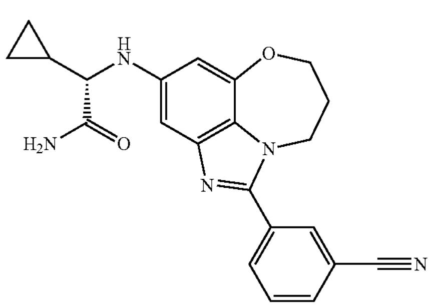 [SMILES: N#Cc1cccc(-c2nc3cc(N[C@H](C(N)=O)C4CC4)cc4c3n2CCCO4)c1] | (S)-2-((1-(3-cyanophenyl)-8,9-dihydro-7H-6-oxa-2,9a-diazabenzo[cd]azulen-4-yl)amino)-2-cyclopropyl-acetamide | 0.561 | 388 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 119 | 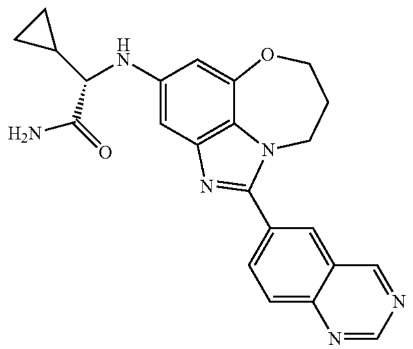 [SMILES: NC(=O)[C@@H](Nc1cc2c3c(c1)nc(-c1ccc4ncncc4c1)n3CCCO2)C1CC1] | (S)-2-cyclopropyl-2-((1-(quinazolin-6-yl)-8,9-dihydro-7H-6-oxa-2,9a-diazabenzo[cd]azulen-4-yl)amino)acetamide | 0.215 | 415 |
| 120 | 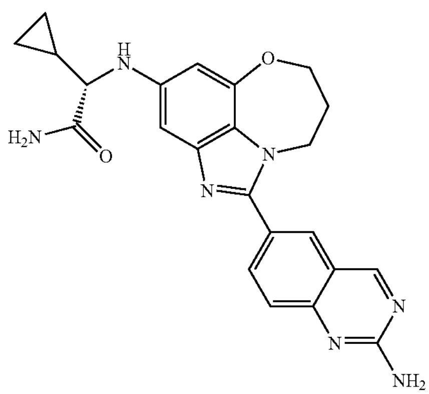 [SMILES: NC(=O)[C@@H](Nc1cc2c3c(c1)nc(-c1ccc4nc(N)ncc4c1)n3CCCO2)C1CC1] | (S)-2-((1-(2-aminoquinazolin-6-yl)-8,9-dihydro-7H-6-oxa-2,9a-diazabenzo[cd]azulen-4-yl)amino)-2-cyclopropyl-acetamide | 0.00534 | 430 |
| 121 | 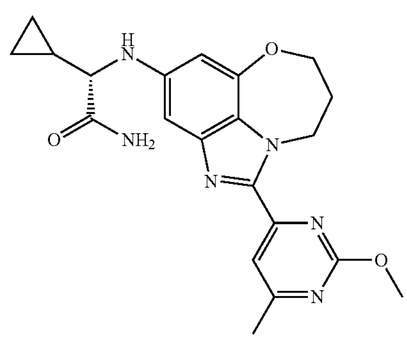 [SMILES: COc1nc(C)cc(-c2nc3cc(N[C@H](C(N)=O)C4CC4)cc4c3n2CCCO4)n1] | (S)-2-cyclopropyl-2-((1-(2-methoxy-6-methyl-pyrimidin-4-yl)-8,9-dihydro-7H-6-oxa-2,9a-diazabenzo[cd]azulen-4-yl)amino)acetamide | 0.0306 | 409 |
| 122 | 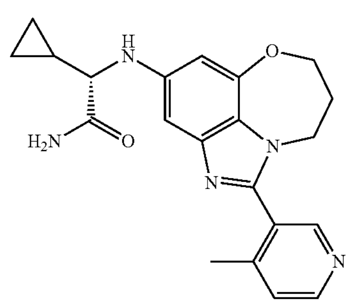 [SMILES: Cc1ccncc1-c1nc2cc(N[C@H](C(N)=O)C3CC3)cc3c2n1CCCO3] | (S)-2-cyclopropyl-2-((1-(4-methyl-pyridin-3-yl)-8,9-dihydro-7H-6-oxa-2,9a-diazabenzo[cd]azulen-4-yl)amino)acetamide | 0.296 | 378 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 123 | 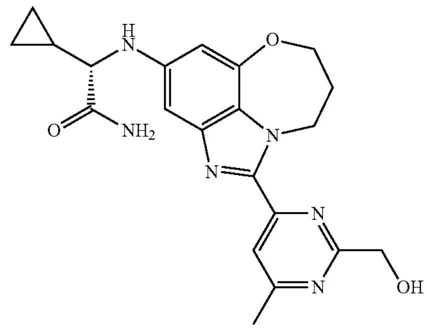 [SMILES: Cc1cc(-c2nc3cc(N[C@H](C(N)=O)C4CC4)cc4c3n2CCCO4)nc(CO)n1] | (S)-2-cyclopropyl-2-((1-(2-(hydroxymethyl)-6-methylpyrimidin-4-yl)-8,9-dihydro-7H-6-oxa-2,9a-diazabenzo[cd]azulen-4-yl)amino)acetamide | 0.045 | 409 |
| 124 | 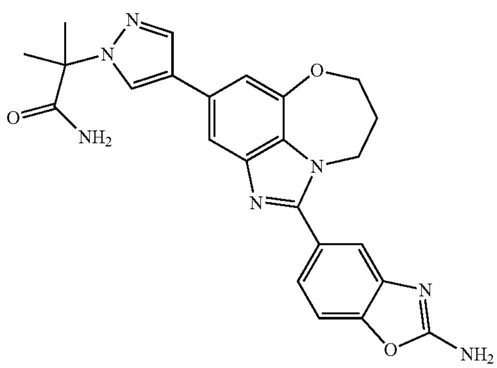 [SMILES: CC(C)(C(N)=O)n1cc(-c2cc3c4c(c2)nc(-c2ccc5oc(N)nc5c2)n4CCCO3)cn1] | 2-(4-(1-(2-aminobenzo[d]oxazol-5-yl)-8,9-dihydro-7H-6-oxa-2,9a-diazabenzo[cd]azulen-4-yl)-1H-pyrazol-1-yl)-2-methylpropanamide | 0.000117 | 458 |
| 125 | 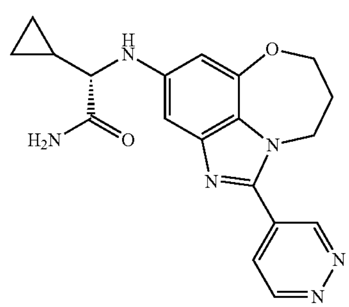 [SMILES: NC(=O)[C@@H](Nc1cc2c3c(c1)nc(-c1ccnnc1)n3CCCO2)C1CC1] | (S)-2-cyclopropyl-2-((1-(pyridazin-4-yl)-8,9-dihydro-7H-6-oxa-2,9a-diazabenzo[cd]azulen-4-yl)amino)acetamide | 0.221 | 365 |
| 126 | 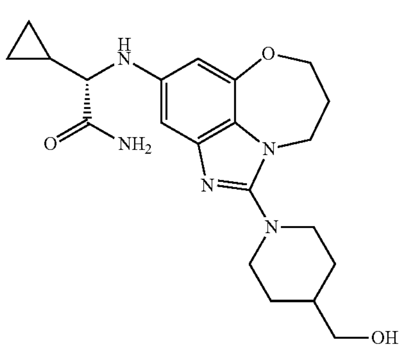 [SMILES: NC(=O)[C@@H](Nc1cc2c3c(c1)nc(N1CCC(CO)CC1)n3CCCO2)C1CC1] | (S)-2-cyclopropyl-2-((1-(4-(hydroxymethyl)piperidin-1-yl)-8,9-dihydro-7H-6-oxa-2,9a-diazabenzo[cd]azulen-4-yl)amino)acetamide | 0.678 | 400.2 |

TABLE 1-continued

Formula I compounds

| Compound No. | Structure | Name | PI3Kα-(alpha) ATP (Ki) micromolar (μM) | Mass Spec. M + H/1 (daltons) |
| --- | --- | --- | --- | --- |
| 127 | 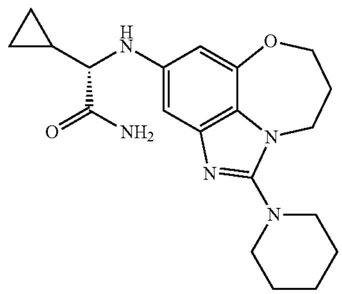 [SMILES: NC(=O)[C@@H](Nc1cc2c3c(c1)nc(N1CCCCC1)n3CCCO2)C1CC1] | (S)-2-cyclopropyl-2-((1-(piperidin-1-yl)-8,9-dihydro-7H-6-oxa-2,9a-diazabenzo[cd]azulen-4-yl)amino)acetamide | 0.719 | 370.1 |
| 128 | 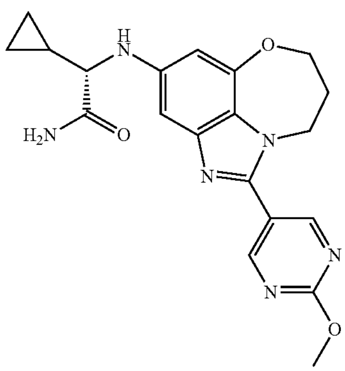 [SMILES: COc1ncc(-c2nc3cc(N[C@H](C(N)=O)C4CC4)cc4c3n2CCCO4)cn1] | (S)-2-cyclopropyl-2-((1-(2-methoxypyrimidin-5-yl)-8,9-dihydro-7H-6-oxa-2,9a-diazabenzo[cd]azulen-4-yl)amino)acetamide | 0.0735 | 395 |
| 129 | 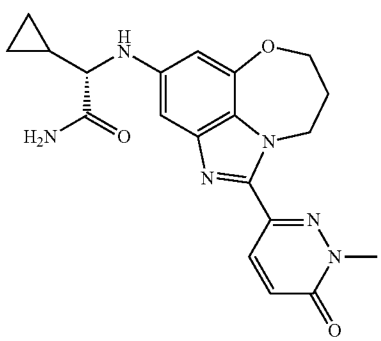 [SMILES: Cn1nc(-c2nc3cc(N[C@H](C(N)=O)C4CC4)cc4c3n2CCCO4)ccc1=O] | (S)-2-cyclopropyl-2-((1-(1-methyl-6-oxo-1,6-dihydropyridazin-3-yl)-8,9-dihydro-7H-6-oxa-2,9a-diazabenzo[cd]azulen-4-yl)amino)acetamide | 0.257 | 395 |
| 130 | 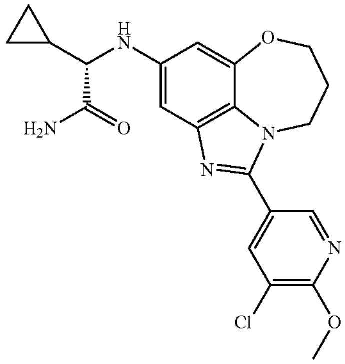 [SMILES: COc1ncc(-c2nc3cc(N[C@H](C(N)=O)C4CC4)cc4c3n2CCCO4)cc1Cl] | (S)-2-((1-(5-chloro-6-methoxypyridin-3-yl)-8,9-dihydro-7H-6-oxa-2,9a-diazabenzo[cd]azulen-4-yl)amino)-2-cyclopropylacetamide | 0.00767 | 428 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 131 | 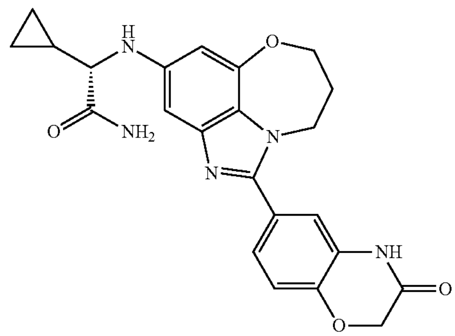 [SMILES: NC(=O)[C@@H](Nc1cc2c3c(c1)nc(-c1ccc4c(c1)NC(=O)CO4)n3CCCO2)C1CC1] | (S)-2-cyclopropyl-2-((1-(3-oxo-3,4-dihydro-2H-benzo[b][1,4]oxazin-6-yl)-8,9-dihydro-7H-6-oxa-2,9a-diazabenzo[cd]azulen-4-yl)amino)acetamide | 0.821 | 434 |
| 132 | 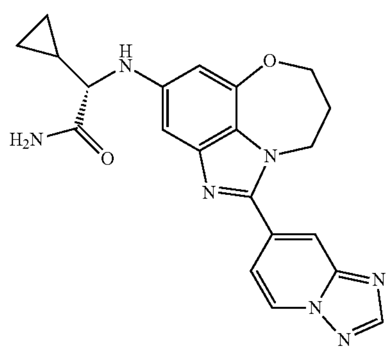 [SMILES: NC(=O)[C@@H](Nc1cc2c3c(c1)nc(-c1ccn4ncnc4c1)n3CCCO2)C1CC1] | (S)-2-((1-([1,2,4]triazolo[1,5-a]pyridin-7-yl)-8,9-dihydro-7H-6-oxa-2,9a-diazabenzo[cd]azulen-4-yl)amino)-2-cyclopropyl-acetamide | 0.0016 | 404 |
| 133 | 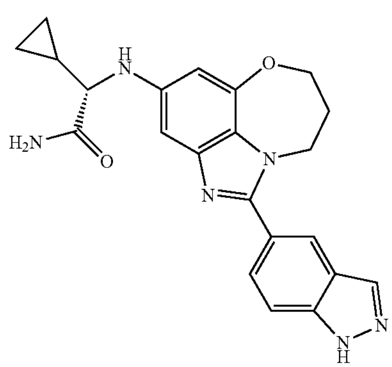 [SMILES: NC(=O)[C@@H](Nc1cc2c3c(c1)nc(-c1ccc4[nH]ncc4c1)n3CCCO2)C1CC1] | (S)-2-((1-(1H-indazol-5-yl)-8,9-dihydro-7H-6-oxa-2,9a-diazabenzo[cd]azulen-4-yl)amino)-2-cyclopropyl-acetamide | 0.0434 | 403 |
| 134 | 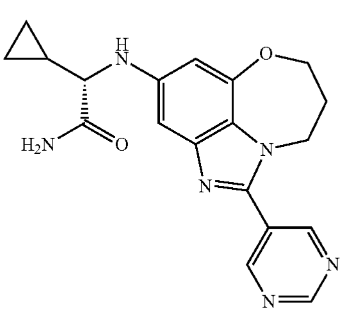 [SMILES: NC(=O)[C@@H](Nc1cc2c3c(c1)nc(-c1cncnc1)n3CCCO2)C1CC1] | (S)-2-cyclopropyl-2-((1-(pyrimidin-5-yl)-8,9-dihydro-7H-6-oxa-2,9a-diazabenzo[cd]azulen-4-yl)amino)acetamide | 0.242 | 365 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 135 | 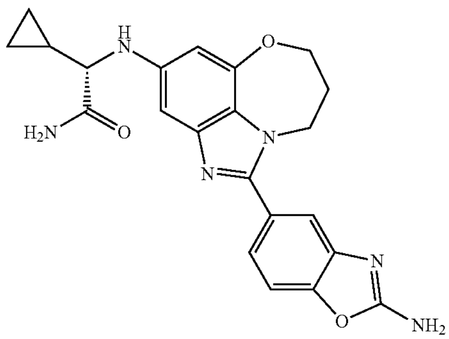 [SMILES: NC(=O)[C@@H](Nc1cc2c3c(c1)nc(-c1ccc4oc(N)nc4c1)n3CCCO2)C1CC1] | (S)-2-((1-(2-aminobenzo[d]oxazol-5-yl)-8,9-dihydro-7H-6-oxa-2,9a-diazabenzo[cd]azulen-4-yl)amino)-2-cyclopropyl-acetamide | 0.000076 | 419 |
| 136 | 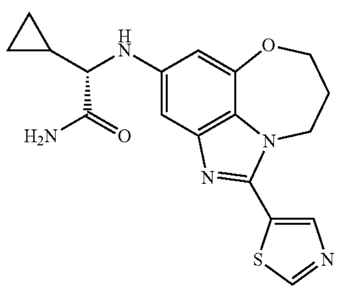 [SMILES: NC(=O)[C@@H](Nc1cc2c3c(c1)nc(-c1cncs1)n3CCCO2)C1CC1] | (S)-2-cyclopropyl-2-((1-(thiazol-5-yl)-8,9-dihydro-7H-6-oxa-2,9a-diazabenzo[cd]azulen-4-yl)amino)acetamide | 0.0764 | 370 |
| 137 | 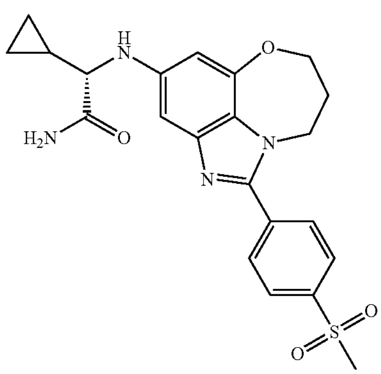 [SMILES: CS(=O)(=O)c1ccc(-c2nc3cc(N[C@H](C(N)=O)C4CC4)cc4c3n2CCCO4)cc1] | (S)-2-cyclopropyl-2-((1-(4-(methylsulfonyl)phenyl)-8,9-dihydro-7H-6-oxa-2,9a-diazabenzo[cd]azulen-4-yl)amino)acetamide | 0.916 | 441.2 |
| 138 | 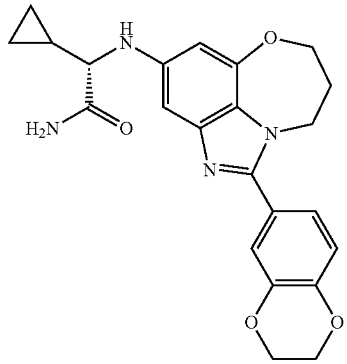 [SMILES: NC(=O)[C@@H](Nc1cc2c3c(c1)nc(-c1ccc4c(c1)OCCO4)n3CCCO2)C1CC1] | (S)-2-cyclopropyl-2-((1-(2,3-dihydrobenzo[b][1,4]dioxin-6-yl)-8,9-dihydro-7H-6-oxa-2,9a-diazabenzo[cd]azulen-4-yl)amino)acetamide | 0.0229 | 421.2 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 139 | 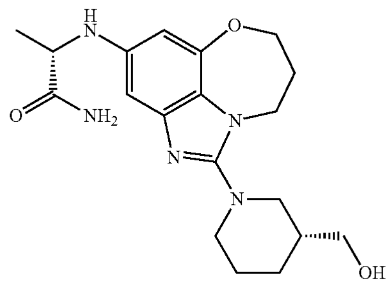 [SMILES: C[C@H](Nc1cc2c3c(c1)nc(N1CCC[C@@H](CO)C1)n3CCCO2)C(N)=O] | (S)-2-((1-((R)-3-(hydroxymethyl)piperidin-1-yl)-8,9-dihydro-7H-6-oxa-2,9a-diazabenzo[cd]azulen-4-yl)amino)propanamide | 0.288 | 374.2 |
| 140 | 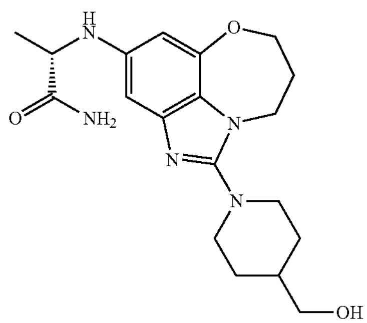 [SMILES: C[C@H](Nc1cc2c3c(c1)nc(N1CCC(CO)CC1)n3CCCO2)C(N)=O] | (S)-2-((1-(4-(hydroxymethyl)piperidin-1-yl)-8,9-dihydro-7H-6-oxa-2,9a-diazabenzo[cd]azulen-4-yl)amino)propanamide | 0.681 | 374.2 |
| 141 | 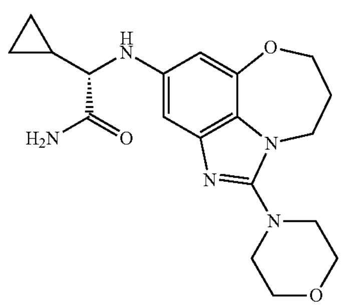 [SMILES: NC(=O)[C@@H](Nc1cc2c3c(c1)nc(N1CCOCC1)n3CCCO2)C1CC1] | (S)-2-cyclopropyl-2-((1-morpholino-8,9-dihydro-7H-6-oxa-2,9a-diazabenzo[cd]azulen-4-yl)amino)acetamide | 0.74 | 372 |
| 142 | 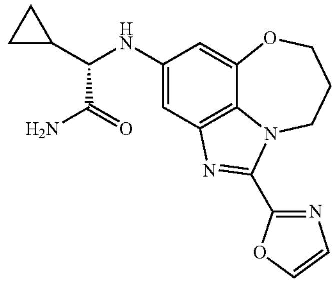 [SMILES: NC(=O)[C@@H](Nc1cc2c3c(c1)nc(-c1ncco1)n3CCCO2)C1CC1] | (S)-2-cyclopropyl-2-((1-(oxazol-2-yl)-8,9-dihydro-7H-6-oxa-2,9a-diazabenzo[cd]azulen-4-yl)amino)acetamide | 0.103 | 354 |

TABLE 1-continued

| Compound No. | Structure | Name | PI3Kα-(alpha) ATP (Ki) micromolar (μM) | Mass Spec. M + H/1 (daltons) |
|---|---|---|---|---|
| 143 | 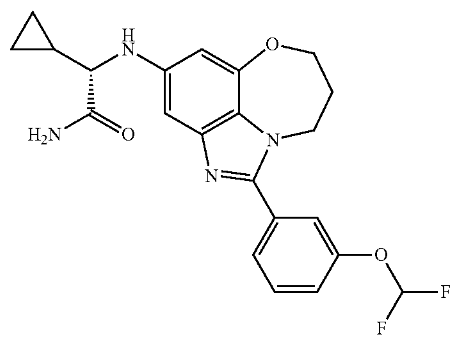 [SMILES: NC(=O)[C@@H](Nc1cc2c3c(c1)nc(-c1cccc(OC(F)F)c1)n3CCCO2)C1CC1] | (S)-2-cyclopropyl-2-((1-(3-(difluoromethoxy)phenyl)-8,9-dihydro-7H-6-oxa-2,9a-diazabenzo[cd]azulen-4-yl)amino)acetamide | 0.187 | 429 |
| 144 | 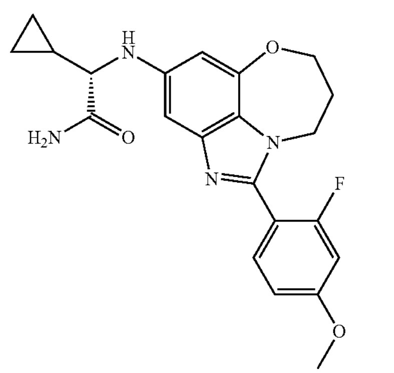 [SMILES: COc1ccc(-c2nc3cc(N[C@H](C(N)=O)C4CC4)cc4c3n2CCCO4)c(F)c1] | (S)-2-cyclopropyl-2-((1-(2-fluoro-4-methoxyphenyl)-8,9-dihydro-7H-6-oxa-2,9a-diazabenzo[cd]azulen-4-yl)amino)acetamide | 0.34 | 411 |
| 145 | 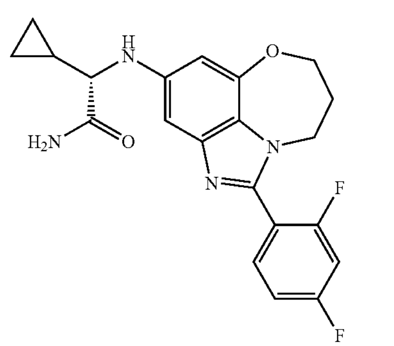 [SMILES: NC(=O)[C@@H](Nc1cc2c3c(c1)nc(-c1ccc(F)cc1F)n3CCCO2)C1CC1] | (S)-2-cyclopropyl-2-((1-(2,4-difluorophenyl)-8,9-dihydro-7H-6-oxa-2,9a-diazabenzo[cd]azulen-4-yl)amino)acetamide | 0.382 | 399 |
| 146 | 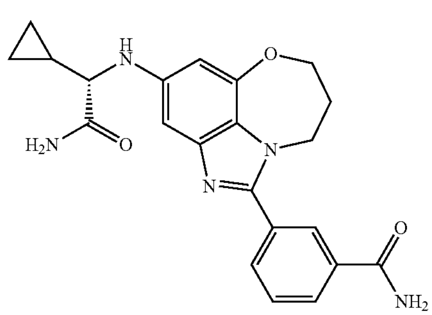 [SMILES: NC(=O)c1cccc(-c2nc3cc(N[C@H](C(N)=O)C4CC4)cc4c3n2CCCO4)c1] | (S)-3-(4-((2-amino-1-cyclopropyl-2-oxoethyl)amino)-8,9-dihydro-7H-6-oxa-2,9a-diazabenzo[cd]azulen-1-yl)benzamide | 0.0529 | 406 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 147 | 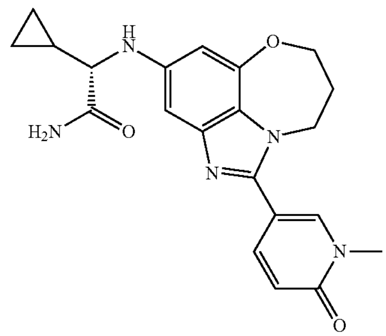 [SMILES: Cn1cc(-c2nc3cc(N[C@H](C(N)=O)C4CC4)cc4c3n2CCCO4)ccc1=O] | (S)-2-cyclopropyl-2-((1-(1-methyl-6-oxo-1,6-dihydropyridin-3-yl)-8,9-dihydro-7H-6-oxa-2,9a-diazabenzo[cd]azulen-4-yl)amino)acetamide | 0.139 | 394 |
| 148 | 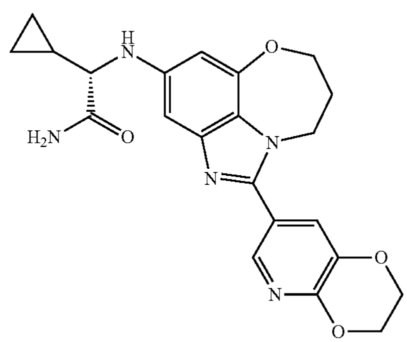 [SMILES: NC(=O)[C@@H](Nc1cc2c3c(c1)nc(-c1cnc4c(c1)OCCO4)n3CCCO2)C1CC1] | (S)-2-cyclopropyl-2-((1-(2,3-dihydro-[1,4]dioxino[2,3-b]pyridin-7-yl)-8,9-dihydro-7H-6-oxa-2,9a-diazabenzo[cd]azulen-4-yl)amino)acetamide | 0.059 | 422 |
| 149 | 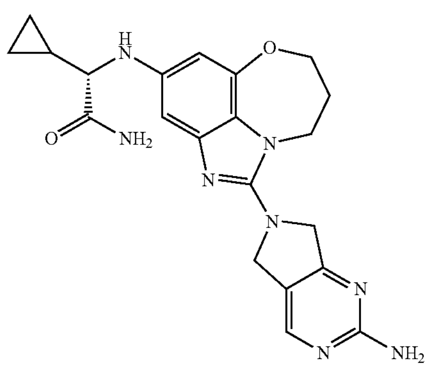 [SMILES: NC(=O)[C@@H](Nc1cc2c3c(c1)nc(N1Cc4cnc(N)nc4C1)n3CCCO2)C1CC1] | (S)-2-((1-(2-amino-5,7-dihydro-6H-pyrrolo[3,4-d]pyrimidin-6-yl)-8,9-dihydro-7H-6-oxa-2,9a-diazabenzo[cd]azulen-4-yl)amino)-2-cyclopropylacetamide | 0.0182 | 421 |
| 150 | 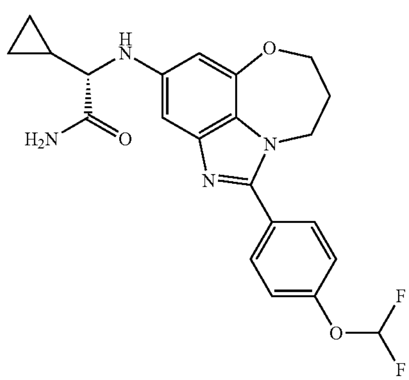 [SMILES: NC(=O)[C@@H](Nc1cc2c3c(c1)nc(-c1ccc(OC(F)F)cc1)n3CCCO2)C1CC1] | (S)-2-cyclopropyl-2-((1-(4-(difluoromethoxy)phenyl)-8,9-dihydro-7H-6-oxa-2,9a-diazabenzo[cd]azulen-4-yl)amino)acetamide | 0.49 | 429 |

TABLE 1-continued

| Compound No. | Structure | Name | PI3Kα-(alpha) ATP (Ki) micromolar (μM) | Mass Spec. M + H/1 (daltons) |
|---|---|---|---|---|
| 151 | 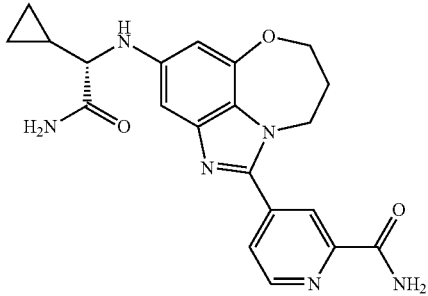 [SMILES: NC(=O)c1cc(-c2nc3cc(N[C@H](C(N)=O)C4CC4)cc4c3n2CCCO4)ccn1] | (S)-4-(4-((2-amino-1-cyclopropyl-2-oxoethyl)amino)-8,9-dihydro-7H-6-oxa-2,9a-diazabenzo[cd]azulen-1-yl)picolinamide | 0.0102 | 407 |
| 152 | 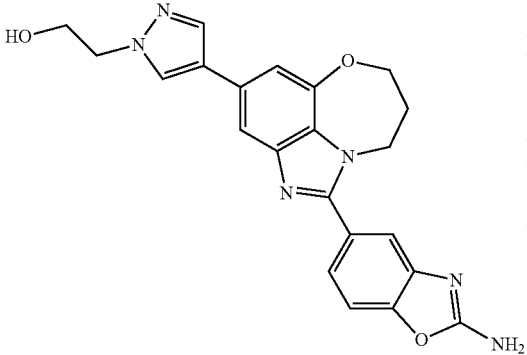 [SMILES: Nc1nc2cc(-c3nc4cc(-c5cnn(CCO)c5)cc5c4n3CCCO5)ccc2o1] | 2-(4-(1-(2-aminobenzo[d]oxazol-5-yl)-8,9-dihydro-7H-6-oxa-2,9a-diazabenzo[cd]azulen-4-yl)-1H-pyrazol-1-yl)ethan-1-ol | 0.000638 | 417 |
| 153 | 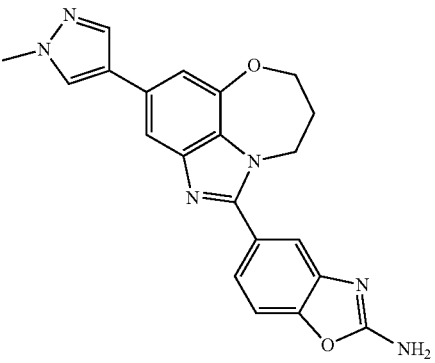 [SMILES: Cn1cc(-c2cc3c4c(c2)nc(-c2ccc5oc(N)nc5c2)n4CCCO3)cn1] | 5-(4-(1-methyl-1H-pyrazol-4-yl)-8,9-dihydro-7H-6-oxa-2,9a-diazabenzo[cd]azulen-1-yl)benzo[d]oxazol-2-amine | 0.00074 | 387 |
| 154 | 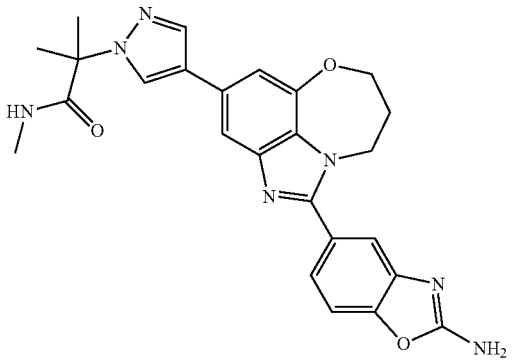 [SMILES: CNC(=O)C(C)(C)n1cc(-c2cc3c4c(c2)nc(-c2ccc5oc(N)nc5c2)n4CCCO3)cn1] | 2-(4-(1-(2-aminobenzo[d]oxazol-5-yl)-8,9-dihydro-7H-6-oxa-2,9a-diazabenzo[cd]azulen-4-yl)-1H-pyrazol-1-yl)-N,2-dimethylpropanamide | 0.000317 | 472 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 155 | 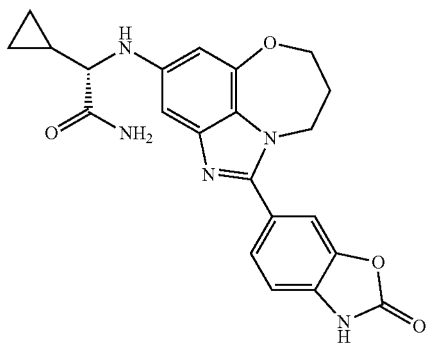 [SMILES: NC(=O)[C@@H](Nc1cc2c3c(c1)nc(-c1ccc4[nH]c(=O)oc4c1)n3CCCO2)C1CC1] | (S)-2-cyclopropyl-2-((1-(2-oxo-2,3-dihydrobenzo[d]oxazol-6-yl)-8,9-dihydro-7H-6-oxa-2,9a-diazabenzo[cd]azulen-4-yl)amino)acetamide | 0.078 | 420 |
| 156 | 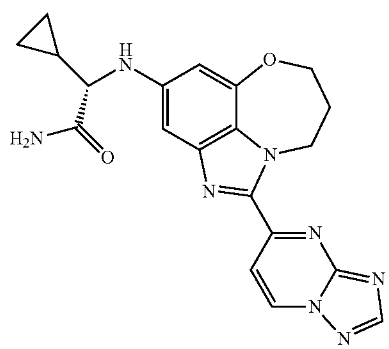 [SMILES: NC(=O)[C@@H](Nc1cc2c3c(c1)nc(-c1ccn4ncnc4n1)n3CCCO2)C1CC1] | (S)-2-((1-([1,2,4]triazolo[1,5-a]pyrimidin-5-yl)-8,9-dihydro-7H-6-oxa-2,9a-diazabenzo[cd]azulen-4-yl)amino)-2-cyclopropyl-acetamide | 0.000264 | 405.2 |
| 157 | 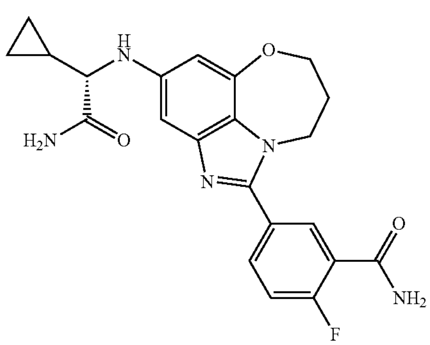 [SMILES: NC(=O)c1cc(-c2nc3cc(N[C@H](C(N)=O)C4CC4)cc4c3n2CCCO4)ccc1F] | (S)-5-(4-((2-amino-1-cyclopropyl-2-oxoethyl)amino)-8,9-dihydro-7H-6-oxa-2,9a-diazabenzo[cd]azulen-1-yl)-2-fluoro-benzamide | 0.0165 | 424 |
| 158 | 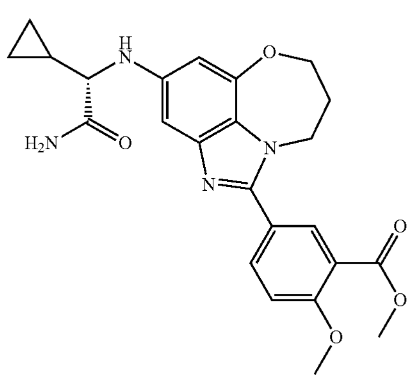 [SMILES: COC(=O)c1cc(-c2nc3cc(N[C@H](C(N)=O)C4CC4)cc4c3n2CCCO4)ccc1OC] | methyl (S)-5-(4-((2-amino-1-cyclopropyl-2-oxoethyl)amino)-8,9-dihydro-7H-6-oxa-2,9a-diazabenzo[cd]azulen-1-yl)-2-methoxy-benzoate | 0.206 | 451 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 159 | 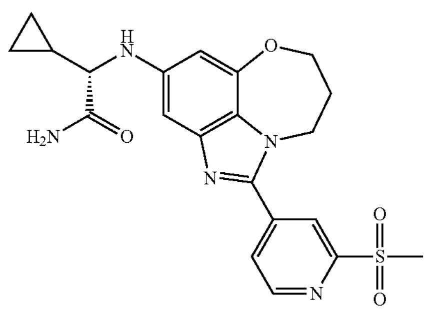 [SMILES: CS(=O)(=O)c1cc(-c2nc3cc(N[C@H](C(N)=O)C4CC4)cc4c3n2CCCO4)ccn1] | (S)-2-cyclopropyl-2-((1-(2-(methylsulfonyl)pyridin-4-yl)-8,9-dihydro-7H-6-oxa-2,9a-diazabenzo[cd]azulen-4-yl)amino)acetamide | 0.0872 | 442 |
| 160 | 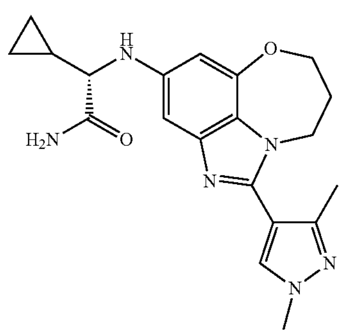 [SMILES: Cc1nn(C)cc1-c1nc2cc(N[C@H](C(N)=O)C3CC3)cc3c2n1CCCO3] | (S)-2-cyclopropyl-2-((1-(1,3-dimethyl-1H-pyrazol-4-yl)-8,9-dihydro-7H-6-oxa-2,9a-diazabenzo[cd]azulen-4-yl)amino)acetamide | 0.914 | 381.2 |
| 161 | 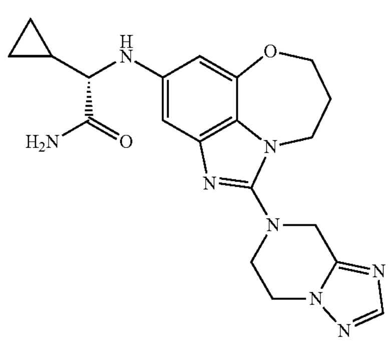 [SMILES: NC(=O)[C@@H](Nc1cc2c3c(c1)nc(N1CCn4ncnc4C1)n3CCCO2)C1CC1] | (S)-2-cyclopropyl-2-((1-(5,6-dihydro-[1,2,4]triazolo[1,5-a]pyrazin-7(8H)-yl)-8,9-dihydro-7H-6-oxa-2,9a-diazabenzo[cd]azulen-4-yl)amino)acetamide | 0.121 | 409 |
| 162 | 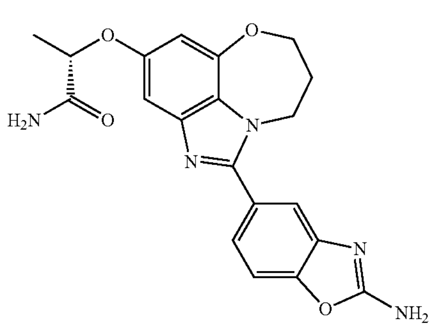 [SMILES: C[C@H](Oc1cc2c3c(c1)nc(-c1ccc4oc(N)nc4c1)n3CCCO2)C(N)=O] | (S)-2-((1-(2-aminobenzo[d]oxazol-5-yl)-8,9-dihydro-7H-6-oxa-2,9a-diazabenzo[cd]azulen-4-yl)oxy)propanamide | 0.000201 | 394 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 163 | 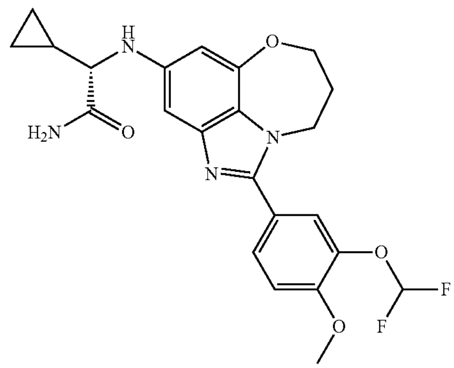 [SMILES: COc1ccc(-c2nc3cc(N[C@H](C(N)=O)C4CC4)cc4c3n2CCCO4)cc1OC(F)F] | (S)-2-cyclopropyl-2-((1-(3-(difluoromethoxy)-4-methoxyphenyl)-8,9-dihydro-7H-6-oxa-2,9a-diazabenzo[cd]azulen-4-yl)amino)acetamide | 0.0342 | 459 |
| 164 | 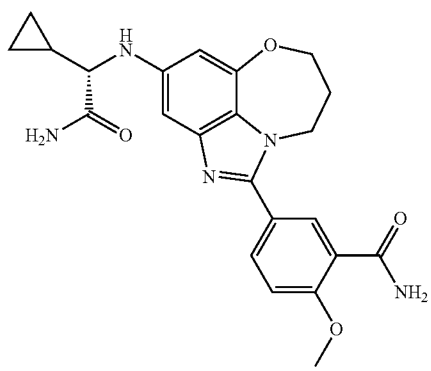 [SMILES: COc1ccc(-c2nc3cc(N[C@H](C(N)=O)C4CC4)cc4c3n2CCCO4)cc1C(N)=O] | (S)-5-(4-((2-amino-1-cyclopropyl-2-oxoethyl)amino)-8,9-dihydro-7H-6-oxa-2,9a-diazabenzo[cd]azulen-1-yl)-2-methoxybenzamide | 0.16 | 436 |
| 165 | 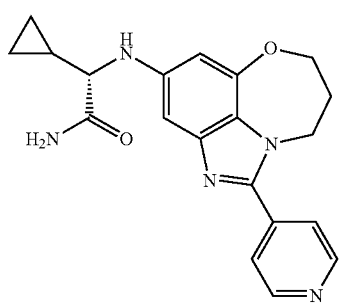 [SMILES: NC(=O)[C@@H](Nc1cc2c3c(c1)nc(-c1ccncc1)n3CCCO2)C1CC1] | (S)-2-cyclopropyl-2-((1-(pyridin-4-yl)-8,9-dihydro-7H-6-oxa-2,9a-diazabenzo[cd]azulen-4-yl)amino)acetamide | 0.108 | 364 |
| 166 | 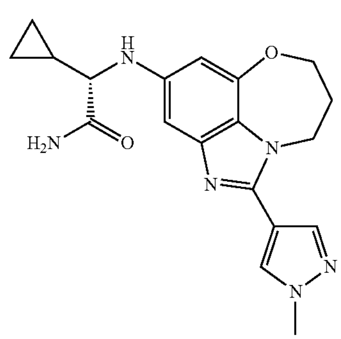 [SMILES: Cn1cc(-c2nc3cc(N[C@H](C(N)=O)C4CC4)cc4c3n2CCCO4)cn1] | (S)-2-cyclopropyl-2-((1-(1-methyl-1H-pyrazol-4-yl)-8,9-dihydro-7H-6-oxa-2,9a-diazabenzo[cd]azulen-4-yl)amino)acetamide | 0.359 | 380.2 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 167 | 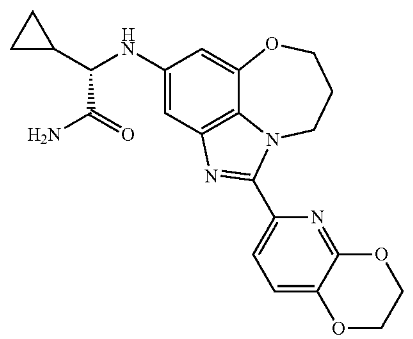 [SMILES: NC(=O)[C@@H](Nc1cc2c3c(c1)nc(-c1ccc4c(n1)OCCO4)n3CCCO2)C1CC1] | (S)-2-cyclopropyl-2-((1-(2,3-dihydro-[1,4]dioxino[2,3-b]pyridin-6-yl)-8,9-dihydro-7H-6-oxa-2,9a-diazabenzo[cd]azulen-4-yl)amino)acetamide | 0.0241 | 421 |
| 168 | 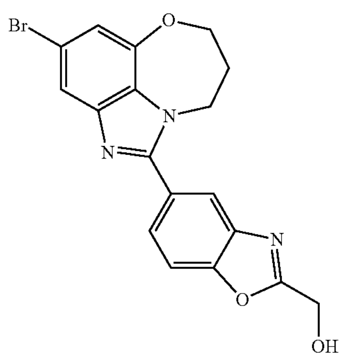 [SMILES: OCc1nc2cc(-c3nc4cc(Br)cc5c4n3CCCO5)ccc2o1] | (5-(4-bromo-8,9-dihydro-7H-6-oxa-2,9a-diazabenzo[cd]azulen-1-yl)benzo[d]oxazol-2-yl)methanol | 0.402 | 400.2 |
| 169 | 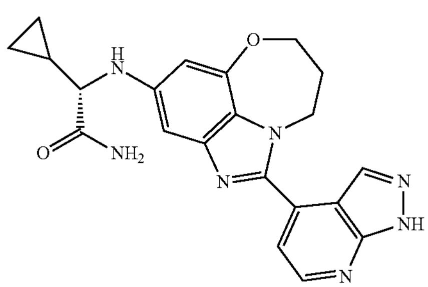 [SMILES: NC(=O)[C@@H](Nc1cc2c3c(c1)nc(-c1ccnc4[nH]ncc14)n3CCCO2)C1CC1] | (S)-2-((1-(1H-pyrazolo[3,4-b]pyridin-4-yl)-8,9-dihydro-7H-6-oxa-2,9a-diazabenzo[cd]azulen-4-yl)amino)-2-cyclopropylacetamide | 0.00392 | 404 |
| 170 | 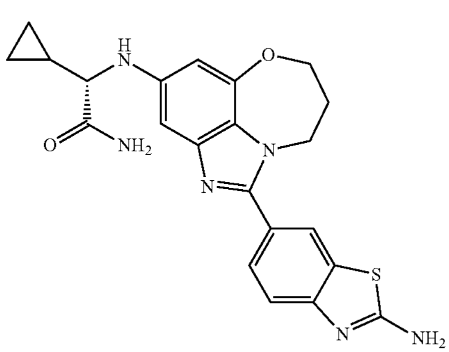 [SMILES: NC(=O)[C@@H](Nc1cc2c3c(c1)nc(-c1ccc4nc(N)sc4c1)n3CCCO2)C1CC1] | (S)-2-((1-(2-aminobenzo[d]thiazol-6-yl)-8,9-dihydro-7H-6-oxa-2,9a-diazabenzo[cd]azulen-4-yl)amino)-2-cyclopropylacetamide | 0.000614 | 435 |

TABLE 1-continued

| Compound No. | Structure | Name | PI3Kα-(alpha) ATP (Ki) micromolar (μM) | Mass Spec. M + H/1 (daltons) |
|---|---|---|---|---|
| 171 | 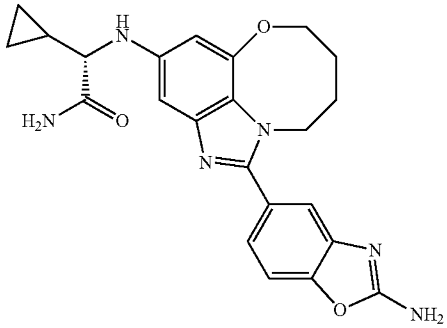 [SMILES: NC(=O)[C@@H](Nc1cc2c3c(c1)nc(-c1ccc4oc(N)nc4c1)n3CCCCO2)C1CC1] | (S)-2-((1-(2-aminobenzo[d]oxazol-5-yl)-7,8,9,10-tetrahydro-6-oxa-2,10a-diazacyclo-octa[cd]inden-4-yl)amino)-2-cyclopropyl-acetamide | <0.000020 | 433.2 |
| 172 | 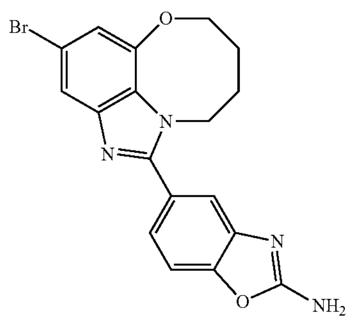 [SMILES: Nc1nc2cc(-c3nc4cc(Br)cc5c4n3CCCCO5)ccc2o1] | 5-(4-bromo-7,8,9,10-tetrahydro-6-oxa-2,10a-diazacyclo-octa[cd]inden-1-yl)benzo[d]oxazol-2-amine | 0.000501 | 399.1 |
| 173 | 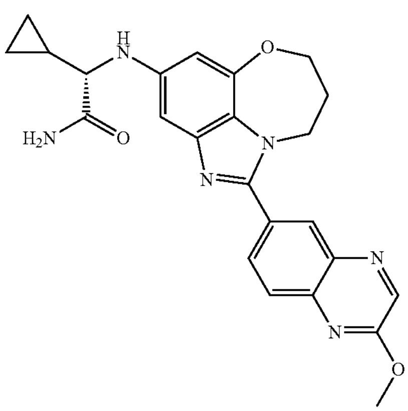 [SMILES: COc1cnc2cc(-c3nc4cc(N[C@H](C(N)=O)C5CC5)cc5c4n3CCCO5)ccc2n1] | (S)-2-cyclopropyl-2-((1-(2-methoxy-quinoxalin-6-yl)-8,9-dihydro-7H-6-oxa-2,9a-diazabenzo[cd]azulen-4-yl)amino)acetamide | 0.0465 | 445 |
| 174 | 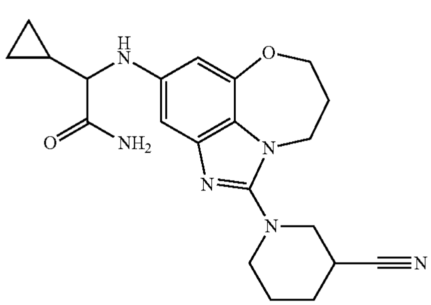 [SMILES: N#CC1CCCN(c2nc3cc(NC(C(N)=O)C4CC4)cc4c3n2CCCO4)C1] | 2-((1-(3-cyano-piperidin-1-yl)-8,9-dihydro-7H-6-oxa-2,9a-diazabenzo[cd]azulen-4-yl)amino)-2-cyclopropyl-acetamide | 0.262 | 395.2 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 175 | 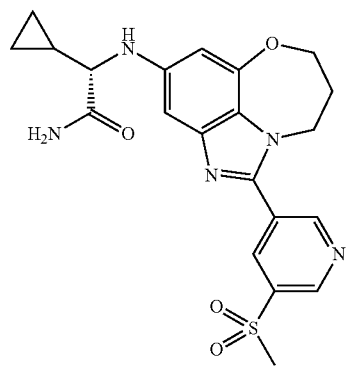 [SMILES: CS(=O)(=O)c1cncc(-c2nc3cc(N[C@H](C(N)=O)C4CC4)cc4c3n2CCCO4)c1] | (S)-2-cyclopropyl-2-((1-(5-(methylsulfonyl)pyridin-3-yl)-8,9-dihydro-7H-6-oxa-2,9a-diazabenzo[cd]azulen-4-yl)amino)acetamide | 0.026 | 442 |
| 176 | 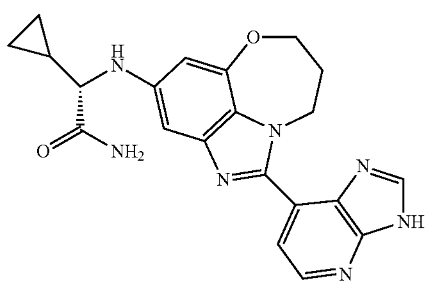 [SMILES: NC(=O)[C@@H](Nc1cc2c3c(c1)nc(-c1ccnc4[nH]cnc14)n3CCCO2)C1CC1] | (S)-2-((1-(3H-imidazo[4,5-b]pyridin-7-yl)-8,9-dihydro-7H-6-oxa-2,9a-diazabenzo[cd]azulen-4-yl)amino)-2-cyclopropylacetamide | 0.326 | 404 |
| 177 | 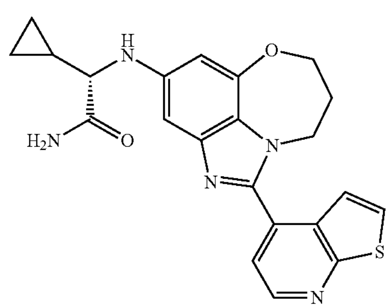 [SMILES: NC(=O)[C@@H](Nc1cc2c3c(c1)nc(-c1ccnc4sccc14)n3CCCO2)C1CC1] | (S)-2-cyclopropyl-2-((1-(thieno[2,3-b]pyridin-4-yl)-8,9-dihydro-7H-6-oxa-2,9a-diazabenzo[cd]azulen-4-yl)amino)acetamide | 0.234 | 420 |
| 178 | 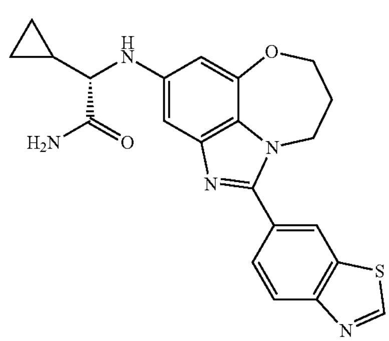 [SMILES: NC(=O)[C@@H](Nc1cc2c3c(c1)nc(-c1ccc4ncsc4c1)n3CCCO2)C1CC1] | (S)-2-((1-(benzo[d]thiazol-6-yl)-8,9-dihydro-7H-6-oxa-2,9a-diazabenzo[cd]azulen-4-yl)amino)-2-cyclopropylacetamide | 0.0322 | 420 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 179 | 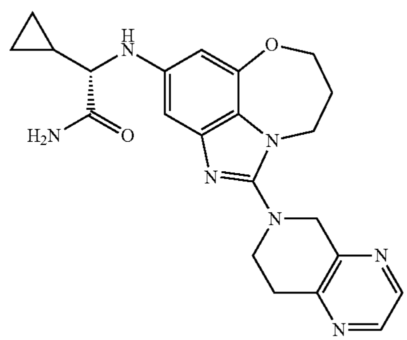 [SMILES: NC(=O)[C@@H](Nc1cc2c3c(c1)nc(N1CCc4nccnc4C1)n3CCCO2)C1CC1] | (S)-2-cyclo-propyl-2-((1-(7,8-dihydro-pyrido[3,4-b]pyrazin-6(5H)-yl)-8,9-dihydro-7H-6-oxa-2,9a-diazabenzo[cd]azulen-4-yl)amino)acetamide | 0.154 | 420 |
| 180 | 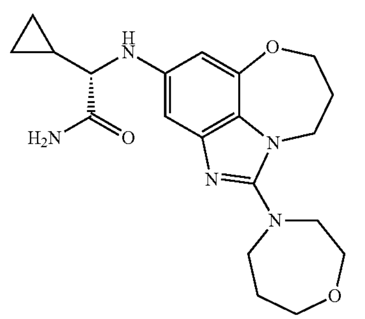 [SMILES: NC(=O)[C@@H](Nc1cc2c3c(c1)nc(N1CCCOCC1)n3CCCO2)C1CC1] | (S)-2-((1-(1,4-oxazepan-4-yl)-8,9-dihydro-7H-6-oxa-2,9a-diazabenzo[cd]azulen-4-yl)amino)-2-cyclopropyl-acetamide | 0.664 | 386 |
| 181 | 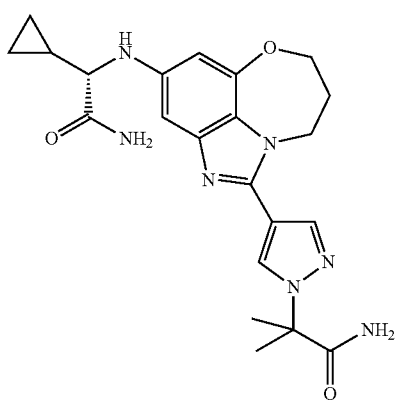 [SMILES: CC(C)(C(N)=O)n1cc(-c2nc3cc(N[C@H](C(N)=O)C4CC4)cc4c3n2CCCO4)cn1] | (S)-2-(4-(4-((2-amino-1-cyclo-propyl-2-oxoethyl)amino)-8,9-dihydro-7H-6-oxa-2,9a-diazabenzo[cd]azulen-1-yl)-1H-pyrazol-1-yl)-2-methyl-propanamide | 0.195 | 438.2 |
| 182 | 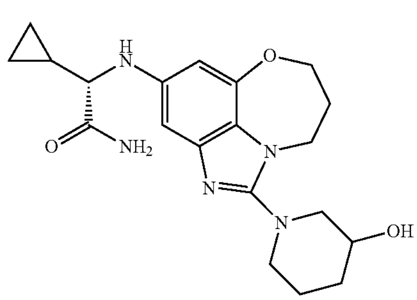 [SMILES: NC(=O)[C@@H](Nc1cc2c3c(c1)nc(N1CCCC(O)C1)n3CCCO2)C1CC1] | (S)-2-cyclo-propyl-2-((1-(3-hydroxy-piperidin-1-yl)-8,9-dihydro-7H-6-oxa-2,9a-diazabenzo[cd]azulen-4-yl)amino)acetamide | 0.398 | 386.2 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 183 | 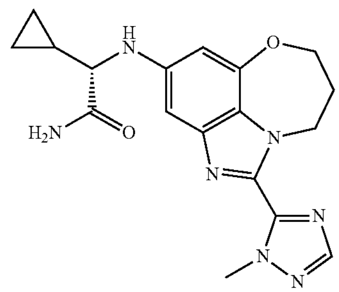 [SMILES: Cn1ncnc1-c1nc2cc(N[C@H](C(N)=O)C3CC3)cc3c2n1CCCO3] | (S)-2-cyclopropyl-2-((1-(1-methyl-1H-1,2,4-triazol-5-yl)-8,9-dihydro-7H-6-oxa-2,9a-diazabenzo[cd]azulen-4-yl)amino)acetamide | 0.396 | 386.2 |
| 184 | 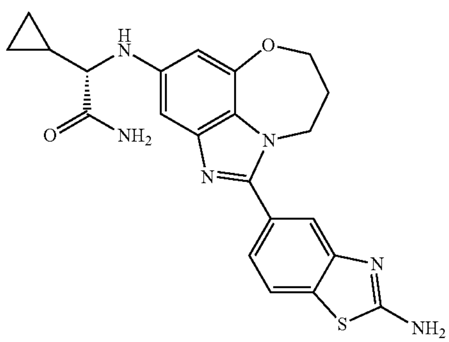 [SMILES: NC(=O)[C@@H](Nc1cc2c3c(c1)nc(-c1ccc4sc(N)nc4c1)n3CCCO2)C1CC1] | (S)-2-((1-(2-aminobenzo[d]thiazol-5-yl)-8,9-dihydro-7H-6-oxa-2,9a-diazabenzo[cd]azulen-4-yl)amino)-2-cyclopropylacetamide | 0.000491 | 435 |
| 185 | 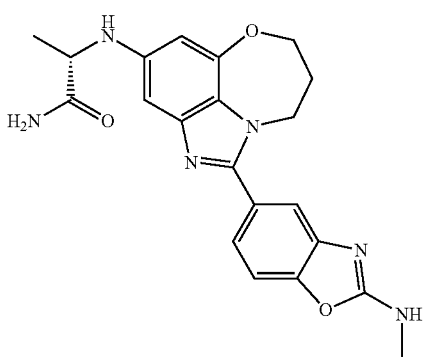 [SMILES: CNc1nc2cc(-c3nc4cc(N[C@@H](C)C(N)=O)cc5c4n3CCCO5)ccc2o1] | (S)-2-((1-(2-(methylamino)benzo[d]oxazol-5-yl)-8,9-dihydro-7H-6-oxa-2,9a-diazabenzo[cd]azulen-4-yl)amino)propanamide | 0.00201 | 407 |
| 186 | 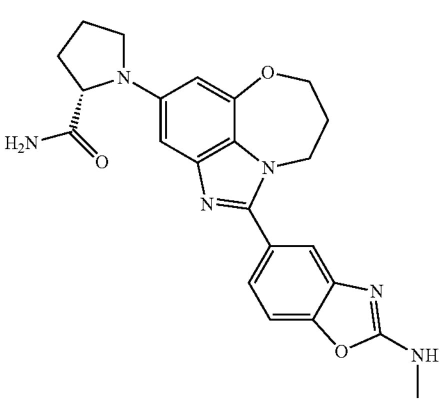 [SMILES: CNc1nc2cc(-c3nc4cc(N5CCC[C@H]5C(N)=O)cc5c4n3CCCO5)ccc2o1] | (S)-1-(1-(2-(methylamino)benzo[d]oxazol-5-yl)-8,9-dihydro-7H-6-oxa-2,9a-diazabenzo[cd]azulen-4-yl)pyrrolidine-2-carboxamide | 0.00693 | 433.2 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 187 | 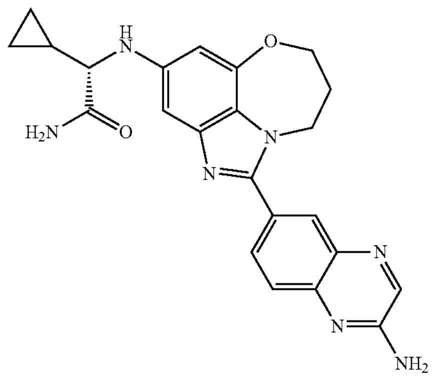 [SMILES: NC(=O)[C@@H](Nc1cc2c3c(c1)nc(-c1ccc4nc(N)cnc4c1)n3CCCO2)C1CC1] | (S)-2-((1-(2-amino-quinoxalin-6-yl)-8,9-dihydro-7H-6-oxa-2,9a-diazabenzo[cd]azulen-4-yl)amino)-2-cyclopropyl-acetamide | 0.000056 | 430 |
| 188 | 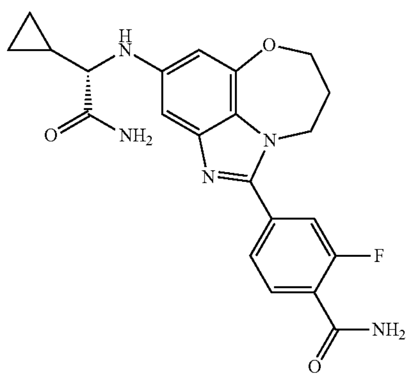 [SMILES: NC(=O)c1ccc(-c2nc3cc(N[C@H](C(N)=O)C4CC4)cc4c3n2CCCO4)cc1F] | (S)-4-(4-((2-amino-1-cyclopropyl-2-oxoethyl)amino)-8,9-dihydro-7H-6-oxa-2,9a-diazabenzo[cd]azulen-1-yl)-2-fluoro-benzamide | 0.0814 | 424 |
| 189 | 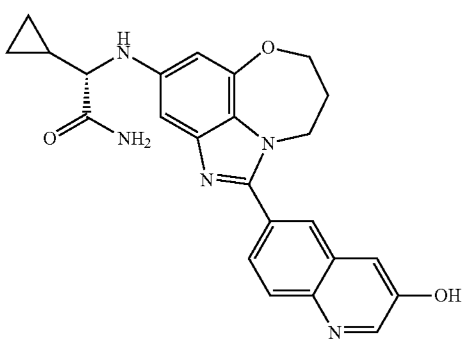 [SMILES: NC(=O)[C@@H](Nc1cc2c3c(c1)nc(-c1ccc4ncc(O)cc4c1)n3CCCO2)C1CC1] | (S)-2-cyclo-propyl-2-((1-(3-hydroxy-quinolin-6-yl)-8,9-dihydro-7H-6-oxa-2,9a-diazabenzo[cd]azulen-4-yl)amino)acetamide | 0.00612 | 430 |
| 190 | 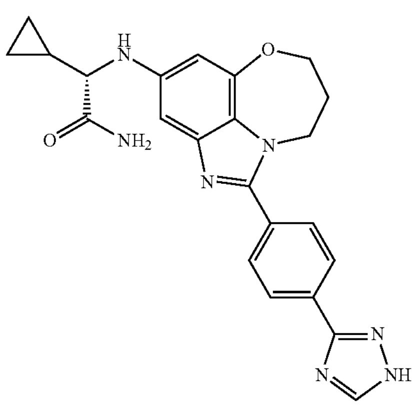 [SMILES: NC(=O)[C@@H](Nc1cc2c3c(c1)nc(-c1ccc(-c4nc[nH]n4)cc1)n3CCCO2)C1CC1] | (S)-2-((1-(4-(1H-1,2,4-triazol-3-yl)phenyl)-8,9-dihydro-7H-6-oxa-2,9a-diazabenzo[cd]azulen-4-yl)amino)-2-cyclopropyl-acetamide | 0.00015 | 430 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 191 | 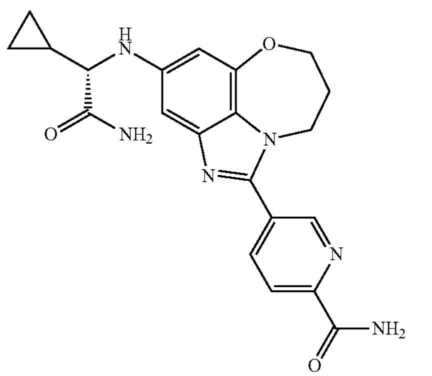 [SMILES: NC(=O)c1ccc(-c2nc3cc(N[C@H](C(N)=O)C4CC4)cc4c3n2CCCO4)cn1] | (S)-5-(4-((2-amino-1-cyclopropyl-2-oxoethyl)amino)-8,9-dihydro-7H-6-oxa-2,9a-diazabenzo[cd]azulen-1-yl)picolinamide | 0.105 | 407 |
| 192 | 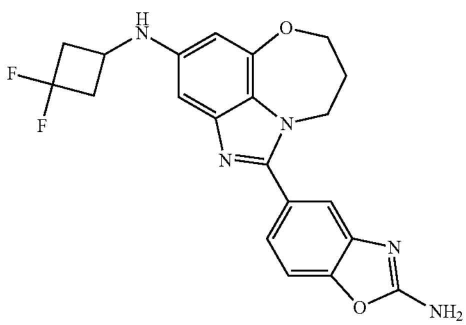 [SMILES: Nc1nc2cc(-c3nc4cc(NC5CC(F)(F)C5)cc5c4n3CCCO5)ccc2o1] | 1-(2-aminobenzo[d]oxazol-5-yl)-N-(3,3-difluorocyclobutyl)-8,9-dihydro-7H-6-oxa-2,9a-diazabenzo[cd]azulen-4-amine | 0.00164 | 412.1 |
| 193 | 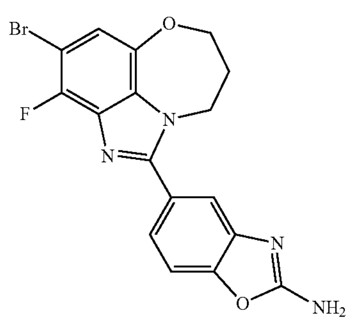 [SMILES: Nc1nc2cc(-c3nc4c(F)c(Br)cc5c4n3CCCO5)ccc2o1] | 5-(4-bromo-3-fluoro-8,9-dihydro-7H-6-oxa-2,9a-diazabenzo[cd]azulen-1-yl)benzo[d]oxazol-2-amine | 0.00517 | 403.1 |
| 194 | 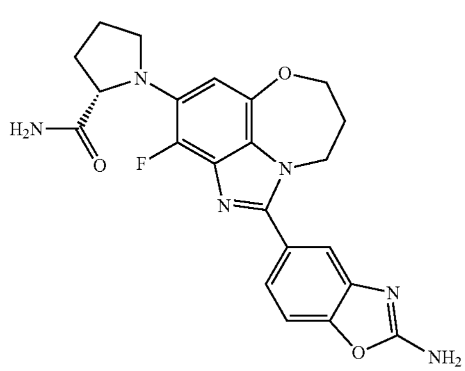 [SMILES: NC(=O)[C@@H]1CCCN1c1cc2c3c(nc(-c4ccc5oc(N)nc5c4)n3CCCO2)c1F] | (S)-1-(1-(2-aminobenzo[d]oxazol-5-yl)-3-fluoro-8,9-dihydro-7H-6-oxa-2,9a-diazabenzo[cd]azulen-4-yl)pyrrolidine-2-carboxamide | 0.000026 | 437 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 195 | 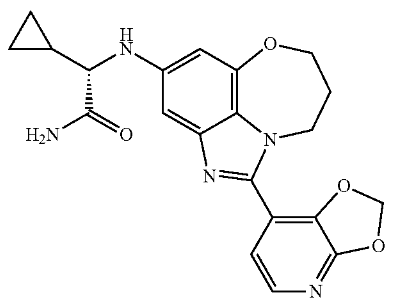 [SMILES: NC(=O)[C@@H](Nc1cc2c3c(c1)nc(-c1ccnc4c1OCO4)n3CCCO2)C1CC1] | (S)-2-((1-([1,3]dioxolo[4,5-b]pyridin-7-yl)-8,9-dihydro-7H-6-oxa-2,9a-diazabenzo[cd]azulen-4-yl)amino)-2-cyclopropyl-acetamide | 0.194 | 408.2 |
| 196 | 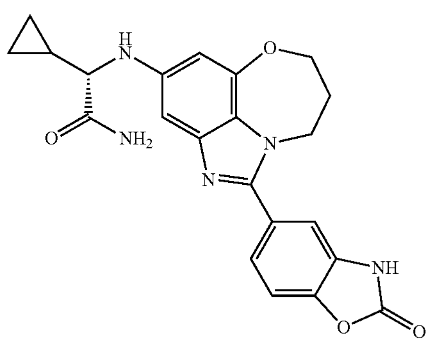 [SMILES: NC(=O)[C@@H](Nc1cc2c3c(c1)nc(-c1ccc4oc(=O)[nH]c4c1)n3CCCO2)C1CC1] | (S)-2-cyclopropyl-2-((1-(2-oxo-2,3-dihydrobenzo[d]oxazol-5-yl)-8,9-dihydro-7H-6-oxa-2,9a-diazabenzo[cd]azulen-4-yl)amino)acetamide | 0.314 | 420.2 |
| 197 | 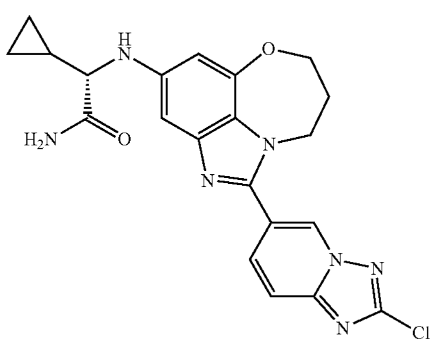 [SMILES: NC(=O)[C@@H](Nc1cc2c3c(c1)nc(-c1ccc4nc(Cl)nn4c1)n3CCCO2)C1CC1] | (S)-2-((1-(2-chloro-[1,2,4]triazolo[1,5-a]pyridin-6-yl)-8,9-dihydro-7H-6-oxa-2,9a-diazabenzo[cd]azulen-4-yl)amino)-2-cyclopropyl-acetamide | 0.0272 | 438.2 |
| 198 | 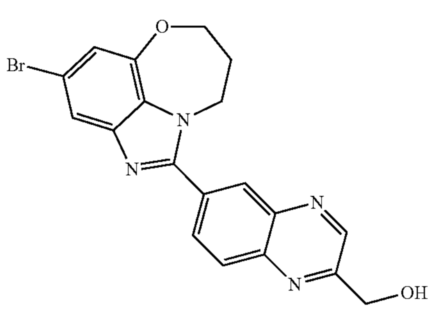 [SMILES: OCc1cnc2cc(-c3nc4cc(Br)cc5c4n3CCCO5)ccc2n1] | (6-(4-bromo-8,9-dihydro-7H-6-oxa-2,9a-diazabenzo[cd]azulen-1-yl)quinoxalin-2-yl)methanol | 0.677 | 411.1 |

TABLE 1-continued

| Compound No. | Structure | Name | PI3Kα-(alpha) ATP (Ki) micromolar (μM) | Mass Spec. M + H/1 (daltons) |
|---|---|---|---|---|
| 199 | 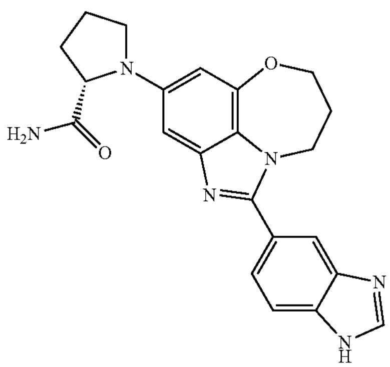 [SMILES: NC(=O)[C@@H]1CCCN1c1cc2c3c(c1)nc(-c1ccc4[nH]cnc4c1)n3CCCO2] | (S)-1-(1-(1H-benzo[d]imidazol-5-yl)-8,9-dihydro-7H-6-oxa-2,9a-diazabenzo[cd]azulen-4-yl)pyrrolidine-2-carboxamide | 0.0332 | 403 |
| 200 | 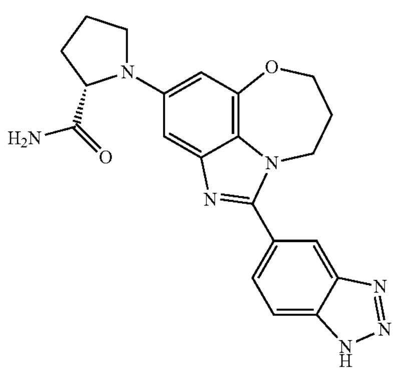 [SMILES: NC(=O)[C@@H]1CCCN1c1cc2c3c(c1)nc(-c1ccc4[nH]nnc4c1)n3CCCO2] | (S)-1-(1-(1H-benzo[d][1,2,3]triazol-5-yl)-8,9-dihydro-7H-6-oxa-2,9a-diazabenzo[cd]azulen-4-yl)pyrrolidine-2-carboxamide | 0.00459 | 404.2 |
| 201 | 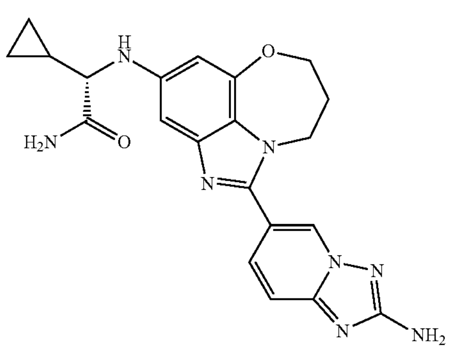 [SMILES: NC(=O)[C@@H](Nc1cc2c3c(c1)nc(-c1ccc4nc(N)nn4c1)n3CCCO2)C1CC1] | (S)-2-((1-(2-amino-[1,2,4]triazolo[1,5-a]pyridin-6-yl)-8,9-dihydro-7H-6-oxa-2,9a-diazabenzo[cd]azulen-4-yl)amino)-2-cyclopropylacetamide | 0.000717 | 419.2 |
| 202 | 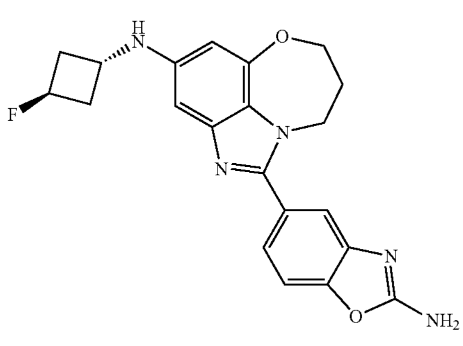 [SMILES: Nc1nc2cc(-c3nc4cc(N[C@H]5C[C@H](F)C5)cc5c4n3CCCO5)ccc2o1] | 1-(2-aminobenzo[d]oxazol-5-yl)-N-((1r,3r)-3-fluorocyclobutyl)-8,9-dihydro-7H-6-oxa-2,9a-diazabenzo[cd]azulen-4-amine | 0.000563 | 394.2 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 203 | 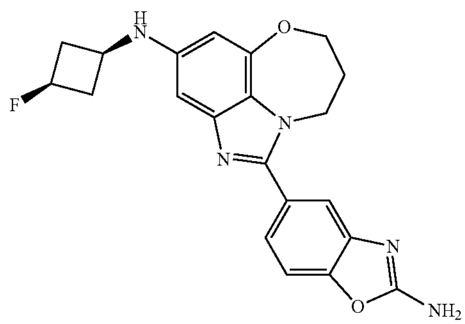 [SMILES: Nc1nc2cc(-c3nc4cc(N[C@H]5C[C@@H](F)C5)cc5c4n3CCCO5)ccc2o1] | 1-(2-aminobenzo[d]oxazol-5-yl)-N-((1s,3s)-3-fluorocyclobutyl)-8,9-dihydro-7H-6-oxa-2,9a-diazabenzo[cd]azulen-4-amine | 0.00137 | 394.2 |
| 204 | 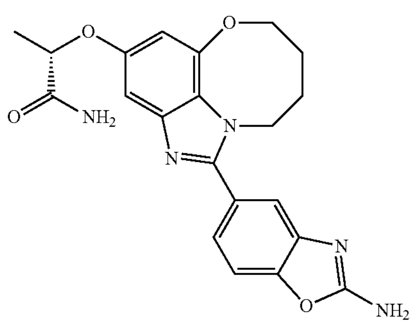 [SMILES: C[C@H](Oc1cc2c3c(c1)nc(-c1ccc4oc(N)nc4c1)n3CCCCO2)C(N)=O] | (S)-2-((1-(2-aminobenzo[d]oxazol-5-yl)-7,8,9,10-tetrahydro-6-oxa-2,10a-diazacycloocta[cd]inden-4-yl)oxy)propanamide | <0.000020 | 408 |
| 205 | 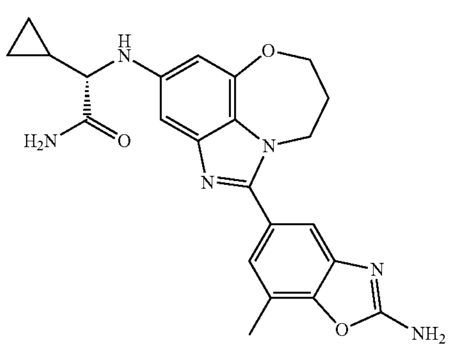 [SMILES: Cc1cc(-c2nc3cc(N[C@H](C(N)=O)C4CC4)cc4c3n2CCCO4)cc2nc(N)oc12] | (S)-2-((1-(2-amino-7-methylbenzo[d]oxazol-5-yl)-8,9-dihydro-7H-6-oxa-2,9a-diazabenzo[cd]azulen-4-yl)amino)-2-cyclopropyl-acetamide | 0.000191 | 433.2 |
| 206 | 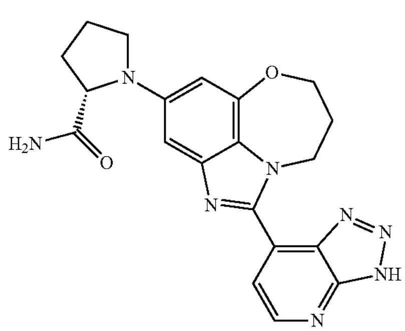 [SMILES: NC(=O)[C@@H]1CCCN1c1cc2c3c(c1)nc(-c1ccnc4[nH]nnc14)n3CCCO2] | (S)-1-(1-(3H-[1,2,3]triazolo[4,5-b]pyridin-7-yl)-8,9-dihydro-7H-6-oxa-2,9a-diazabenzo[cd]azulen-4-yl)pyrrolidine-2-carboxamide | 0.0259 | 405.2 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 207 | 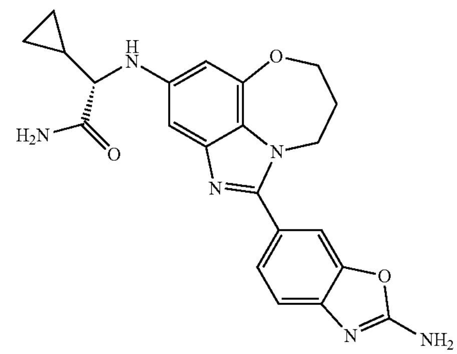 [SMILES: NC(=O)[C@@H](Nc1cc2c3c(c1)nc(-c1ccc4nc(N)oc4c1)n3CCCO2)C1CC1] | (S)-2-((1-(2-amino-benzo[d]oxazol-6-yl)-8,9-dihydro-7H-6-oxa-2,9a-diazabenzo[cd]azulen-4-yl)amino)-2-cyclopropyl-acetamide | 0.000988 | 419.2 |
| 208 | 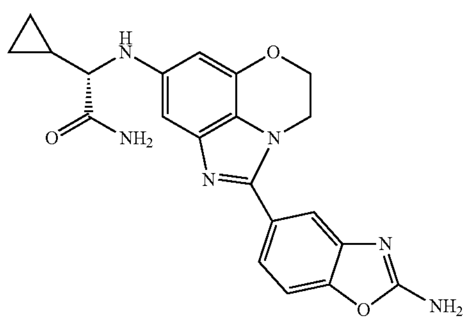 [SMILES: NC(=O)[C@@H](Nc1cc2c3c(c1)nc(-c1ccc4oc(N)nc4c1)n3CCO2)C1CC1] | (S)-2-((2-(2-aminobenzo[d]oxazol-5-yl)-3,4-dihydro-5-oxa-1,2a-diazaacenaphthylen-7-yl)amino)-2-cyclopropyl-acetamide | <0.000020 | 405.2 |
| 209 | 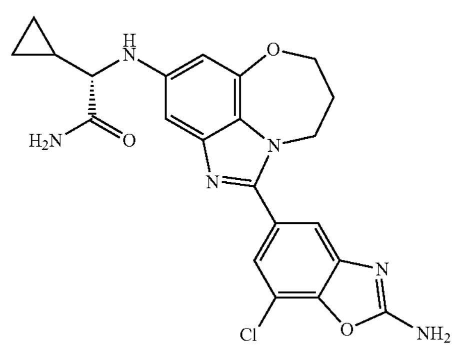 | (S)-2-((1-(2-amino-7-chloro-benzo[d]oxazol-5-yl)-8,9-dihydro-7H-6-oxa-2,9a-diazabenzo[cd]azulen-4-yl)amino)-2-cyclopropyl-acetamide | 0.000095 | 453.2 |
| 210 | 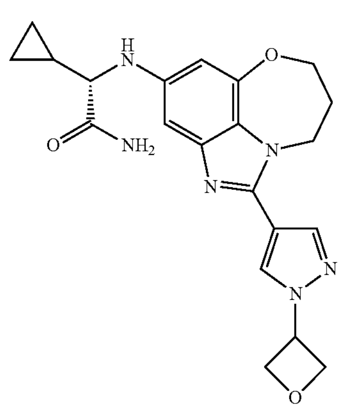 [SMILES: NC(=O)[C@@H](Nc1cc2c3c(c1)nc(-c1cnn(C4COC4)c1)n3CCCO2)C1CC1] | (S)-2-cyclopropyl-2-((1-(1-(oxetan-3-yl)-1H-pyrazol-4-yl)-8,9-dihydro-7H-6-oxa-2,9a-diazabenzo[cd]azulen-4-yl)amino)acetamide | 0.285 | 409 |

TABLE 1-continued

| Compound No. | Structure | Name | PI3Kα-(alpha) ATP (Ki) micromolar (μM) | Mass Spec. M + H/1 (daltons) |
|---|---|---|---|---|
| 211 | 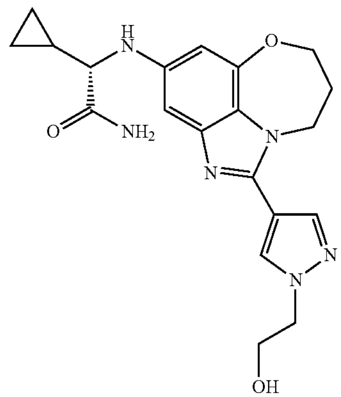 [SMILES: NC(=O)[C@@H](Nc1cc2c3c(c1)nc(-c1cnn(CCO)c1)n3CCCO2)C1CC1] | (S)-2-cyclopropyl-2-((1-(1-(2-hydroxyethyl)-1H-pyrazol-4-yl)-8,9-dihydro-7H-6-oxa-2,9a-diazabenzo[cd]azulen-4-yl)amino)acetamide | 0.815 | 443.2 |
| 212 | 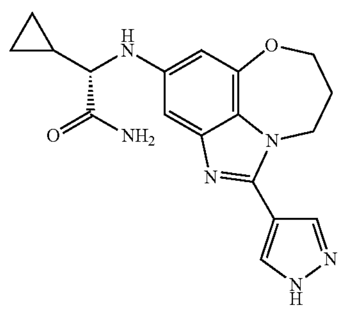 [SMILES: NC(=O)[C@@H](Nc1cc2c3c(c1)nc(-c1cn[nH]c1)n3CCCO2)C1CC1] | (S)-2-((1-(1H-pyrazol-4-yl)-8,9-dihydro-7H-6-oxa-2,9a-diazabenzo[cd]azulen-4-yl)amino)-2-cyclopropylacetamide | 0.148 | 399.2 |
| 213 | 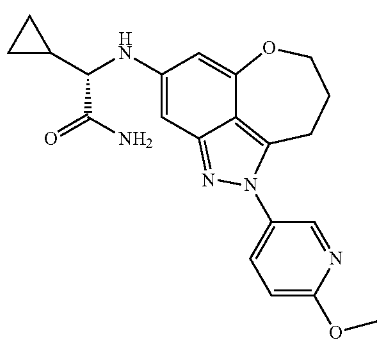 [SMILES: COc1ccc(-n2nc3cc(N[C@H](C(N)=O)C4CC4)cc4c3c2CCCO4)cn1] | (S)-2-cyclopropyl-2-((1-(6-methoxypyridin-3-yl)-1,7,8,9-tetrahydrooxepino[4,3,2-cd]indazol-4-yl)amino)acetamide | 0.0238 | 394.2 |
| 214 | 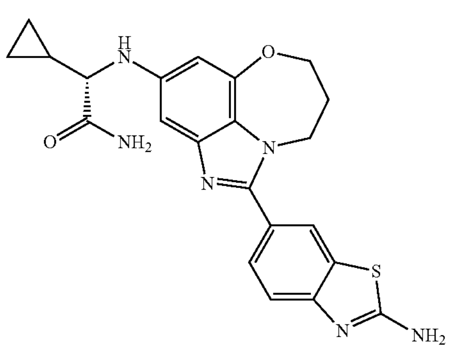 [SMILES: NC(=O)[C@@H](Nc1cc2c3c(c1)nc(-c1ccc4nc(N)sc4c1)n3CCCO2)C1CC1] | (S)-2-((1-(2-aminobenzo[d]thiazol-6-yl)-7,8,9,10-tetrahydro-6-oxa-2,10a-diazacycloocta[cd]inden-4-yl)amino)-2-cyclopropylacetamide | <0.000020 | 449.2 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 215 | 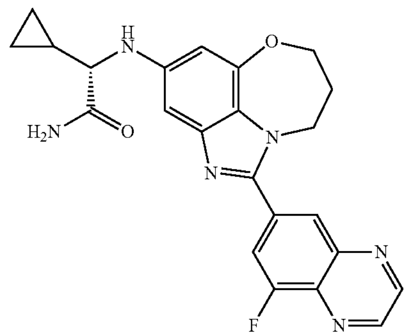 [SMILES: NC(=O)[C@@H](Nc1cc2c3c(c1)nc(-c1cc(F)c4nccnc4c1)n3CCCO2)C1CC1] | (S)-2-cyclopropyl-2-((1-(8-fluoroquinoxalin-6-yl)-8,9-dihydro-7H-6-oxa-2,9a-diazabenzo[cd]azulen-4-yl)amino)acetamide | 0.000424 | 433.2 |
| 216 | 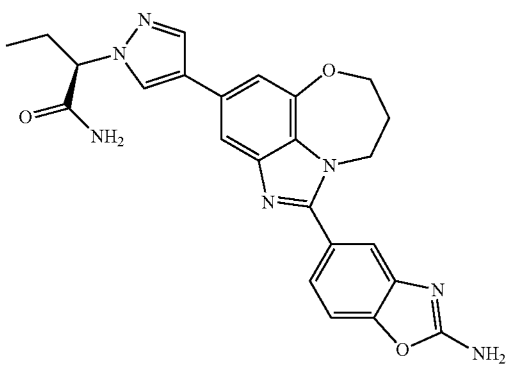 [SMILES: CC[C@H](C(N)=O)n1cc(-c2cc3c4c(c2)nc(-c2ccc5oc(N)nc5c2)n4CCCO3)cn1] | (R)-2-(4-(1-(2-aminobenzo[d]oxazol-5-yl)-8,9-dihydro-7H-6-oxa-2,9a-diazabenzo[cd]azulen-4-yl)-1H-pyrazol-1-yl)butanamide | 0.000214 | 458.2 |
| 217 | 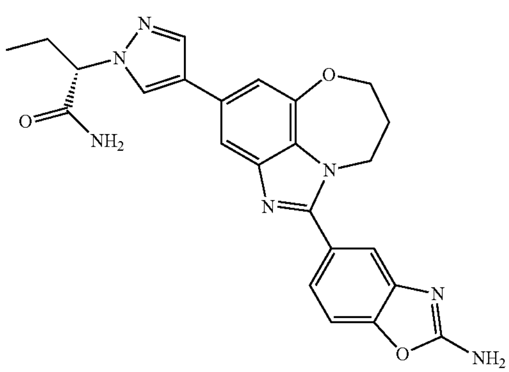 [SMILES: CC[C@@H](C(N)=O)n1cc(-c2cc3c4c(c2)nc(-c2ccc5oc(N)nc5c2)n4CCCO3)cn1] | (S)-2-(4-(1-(2-aminobenzo[d]oxazol-5-yl)-8,9-dihydro-7H-6-oxa-2,9a-diazabenzo[cd]azulen-4-yl)-1H-pyrazol-1-yl)butanamide | 0.000298 | 458.2 |
| 218 | 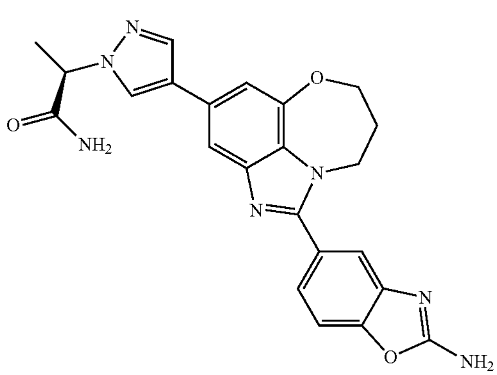 [SMILES: C[C@H](C(N)=O)n1cc(-c2cc3c4c(c2)nc(-c2ccc5oc(N)nc5c2)n4CCCO3)cn1] | (R)-2-(4-(1-(2-aminobenzo[d]oxazol-5-yl)-8,9-dihydro-7H-6-oxa-2,9a-diazabenzo[cd]azulen-4-yl)-1H-pyrazol-1-yl)propanamide | 0.000143 | 444.2 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 219 | 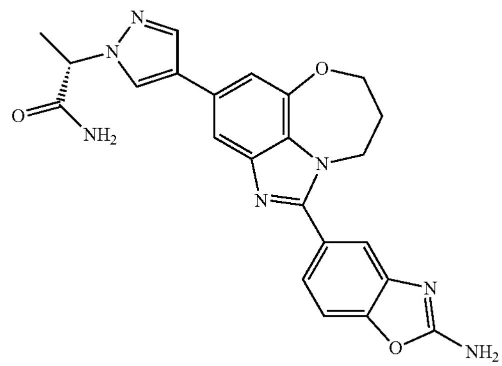 [SMILES: C[C@@H](C(N)=O)n1cc(-c2cc3c4c(c2)nc(-c2ccc5oc(N)nc5c2)n4CCCO3)cn1] | (S)-2-(4-(1-(2-amino-benzo[d]oxazol-5-yl)-8,9-dihydro-7H-6-oxa-2,9a-diazabenzo[cd]azulen-4-yl)-1H-pyrazol-1-yl)propanamide | 0.000242 | 444.2 |
| 220 | 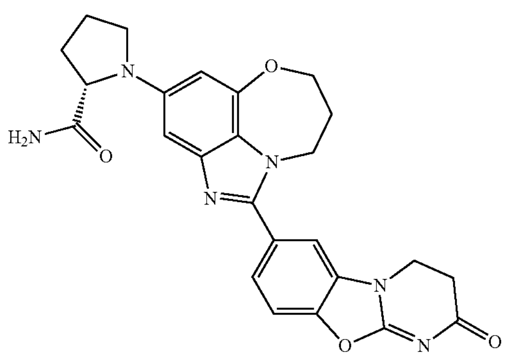 [SMILES: NC(=O)[C@@H]1CCCN1c1cc2c3c(c1)nc(-c1ccc4c(c1)N1CCC(=O)N=C1O4)n3CCCO2] | (S)-1-(1-(2-oxo-3,4-dihydro-2H-benzo[4,5]oxazolo[3,2-a]pyrimidin-7-yl)-8,9-dihydro-7H-6-oxa-2,9a-diazabenzo[cd]azulen-4-yl)pyrrolidine-2-carboxamide | 0.00292 | 473.2 |
| 221 | 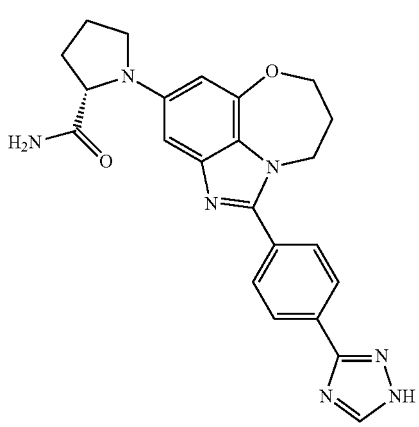 [SMILES: NC(=O)[C@@H]1CCCN1c1cc2c3c(c1)nc(-c1ccc(-c4nc[nH]n4)cc1)n3CCCO2] | (S)-1-(1-(4-(1H-1,2,4-triazol-3-yl)phenyl)-8,9-dihydro-7H-6-oxa-2,9a-diazabenzo[cd]azulen-4-yl)pyrrolidine-2-carboxamide | 0.000237 | 430.2 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 222 | 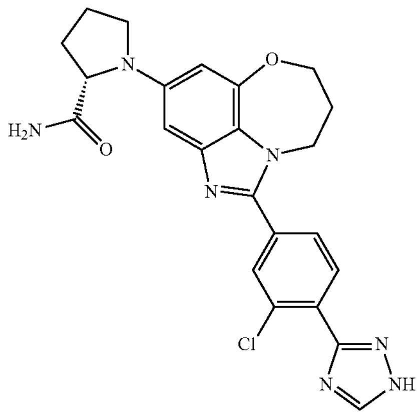 [SMILES: NC(=O)[C@@H]1CCCN1c1cc2c3c(c1)nc(-c1ccc(-c4nc[nH]n4)c(Cl)c1)n3CCCO2] | (S)-1-(1-(3-chloro-4-(1H-1,2,4-triazol-3-yl)phenyl)-8,9-dihydro-7H-6-oxa-2,9a-diazabenzo[cd]azulen-4-yl)pyrrolidine-2-carboxamide | 0.000261 | 464.2 |
| 223 | 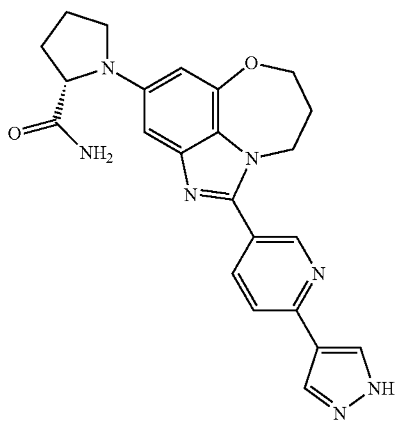 [SMILES: NC(=O)[C@@H]1CCCN1c1cc2c3c(c1)nc(-c1ccc(-c4cn[nH]c4)nc1)n3CCCO2] | (S)-1-(1-(6-(1H-pyrazol-4-yl)pyridin-3-yl)-8,9-dihydro-7H-6-oxa-2,9a-diazabenzo[cd]azulen-4-yl)pyrrolidine-2-carboxamide | 0.0746 | 430.2 |
| 224 | 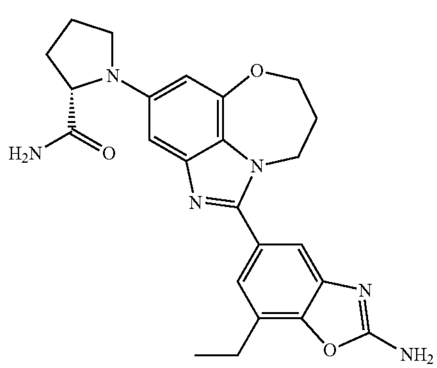 [SMILES: CCc1cc(-c2nc3cc(N4CCC[C@H]4C(N)=O)cc4c3n2CCCO4)cc2nc(N)oc12] | (S)-1-(1-(2-amino-7-ethylbenzo[d]oxazol-5-yl)-8,9-dihydro-7H-6-oxa-2,9a-diazabenzo[cd]azulen-4-yl)pyrrolidine-2-carboxamide | 0.00162 | 493.2 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 225 | 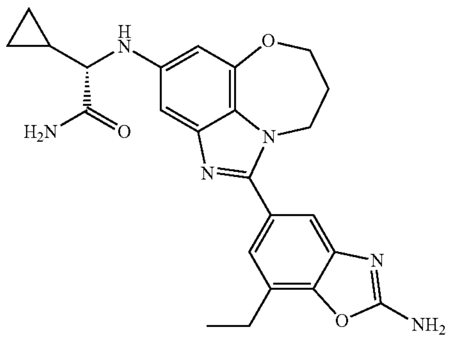 [SMILES: CCc1cc(-c2nc3cc(N[C@H](C(N)=O)C4CC4)cc4c3n2CCCO4)cc2nc(N)oc12] | (S)-2-((1-(2-amino-7-ethylbenzo[d]oxazol-5-yl)-8,9-dihydro-7H-6-oxa-2,9a-diazabenzo[cd]azulen-4-yl)amino)-2-cyclopropyl-acetamide | 0.000431 | 447 |
| 226 | 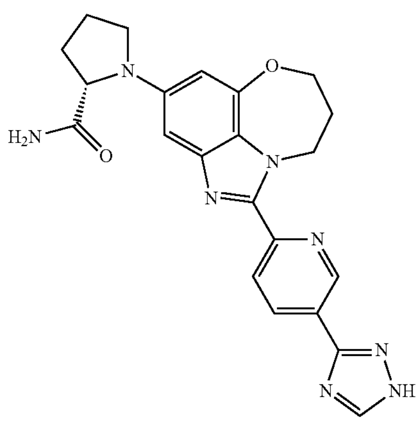 [SMILES: NC(=O)[C@@H]1CCCN1c1cc2c3c(c1)nc(-c1ccc(-c4nc[nH]n4)cn1)n3CCCO2] | (S)-1-(1-(5-(1H-1,2,4-triazol-3-yl)pyridin-2-yl)-8,9-dihydro-7H-6-oxa-2,9a-diazabenzo[cd]azulen-4-yl)pyrrolidine-2-carboxamide | 0.000393 | 431.2 |
| 227 | 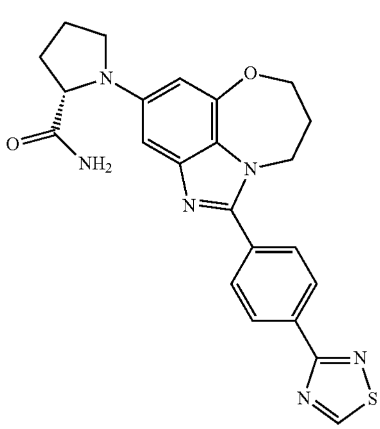 [SMILES: NC(=O)[C@@H]1CCCN1c1cc2c3c(c1)nc(-c1ccc(-c4ncsn4)cc1)n3CCCO2] | (S)-1-(1-(4-(1,2,4-thiadiazol-3-yl)phenyl)-8,9-dihydro-7H-6-oxa-2,9a-diazabenzo[cd]azulen-4-yl)pyrrolidine-2-carboxamide | 0.00821 | 447.2 |

TABLE 1-continued

Formula I compounds

| Compound No. | Structure | Name | PI3Kα-(alpha) ATP (Ki) micromolar (μM) | Mass Spec. M + H/1 (daltons) |
| --- | --- | --- | --- | --- |
| 228 | 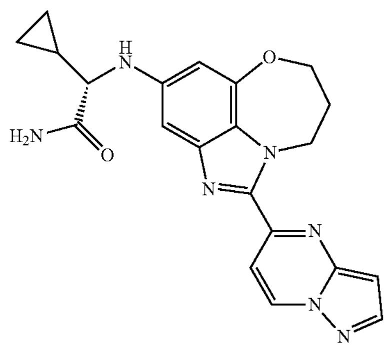 [SMILES: NC(=O)[C@@H](Nc1cc2c3c(c1)nc(-c1ccn4nccc4n1)n3CCCO2)C1CC1] | (S)-2-cyclopropyl-2-((1-(pyrazolo[1,5-a]pyrimidin-5-yl)-8,9-dihydro-7H-6-oxa-2,9a-diazabenzo[cd]azulen-4-yl)amino)acetamide | 0.00266 | 404.2 |
| 229 | 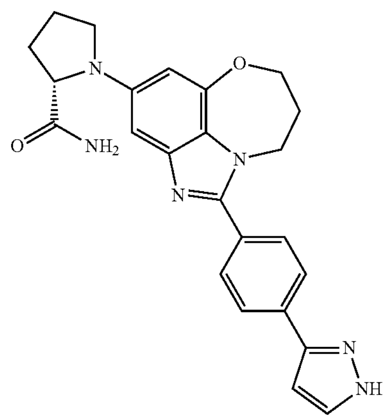 [SMILES: NC(=O)[C@@H]1CCCN1c1cc2c3c(c1)nc(-c1ccc(-c4cc[nH]n4)cc1)n3CCCO2] | (S)-1-(1-(4-(1H-pyrazol-3-yl)phenyl)-8,9-dihydro-7H-6-oxa-2,9a-diazabenzo[cd]azulen-4-yl)pyrrolidine-2-carboxamide | 0.00688 | 429.2 |
| 230 | 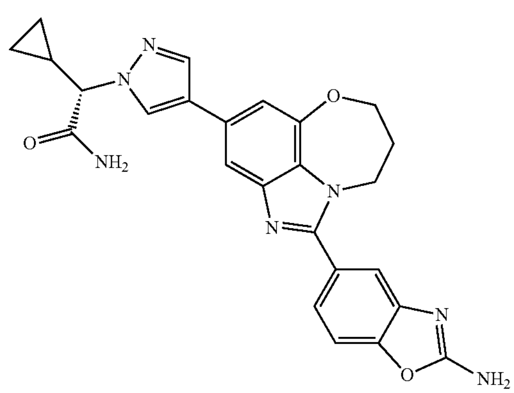 [SMILES: NC(=O)[C@H](C1CC1)n1cc(-c2cc3c4c(c2)nc(-c2ccc5oc(N)nc5c2)n4CCCO3)cn1] | (S)-2-(4-(1-(2-aminobenzo[d]oxazol-5-yl)-8,9-dihydro-7H-6-oxa-2,9a-diazabenzo[cd]azulen-4-yl)-1H-pyrazol-1-yl)-2-cyclopropylacetamide | 0.000309 | 470.2 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 231 | 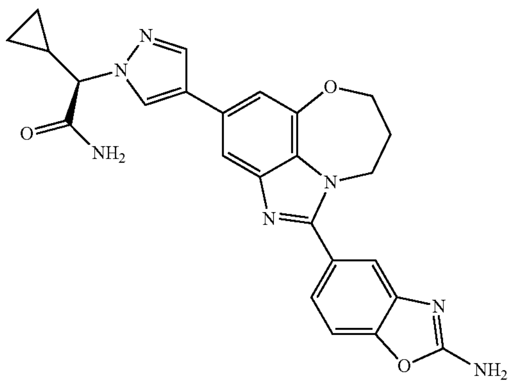 | (R)-2-(4-(1-(2-amino-benzo[d]oxazol-5-yl)-8,9-dihydro-7H-6-oxa-2,9a-diazabenzo[cd]azulen-4-yl)-1H-pyrazol-1-yl)-2-cyclopropyl-acetamide | 0.000437 | 470.2 |
| 232 | 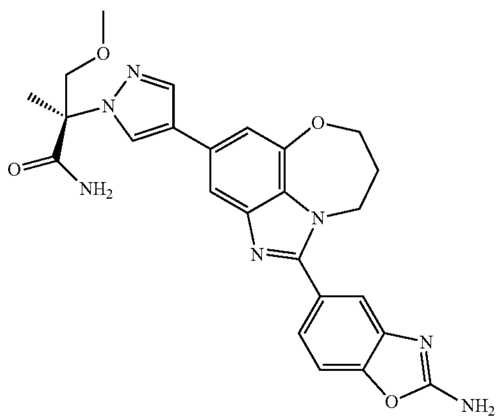 [SMILES: COC[C@](C)(C(N)=O)n1cc(-c2cc3c4c(c2)nc(-c2ccc5oc(N)nc5c2)n4CCCO3)cn1] | (R)-2-(4-(1-(2-amino-benzo[d]oxazol-5-yl)-8,9-dihydro-7H-6-oxa-2,9a-diazabenzo[cd]azulen-4-yl)-1H-pyrazol-1-yl)-3-methoxy-2-methyl-propanamide | 0.000311 | 488.2 |
| 233 | 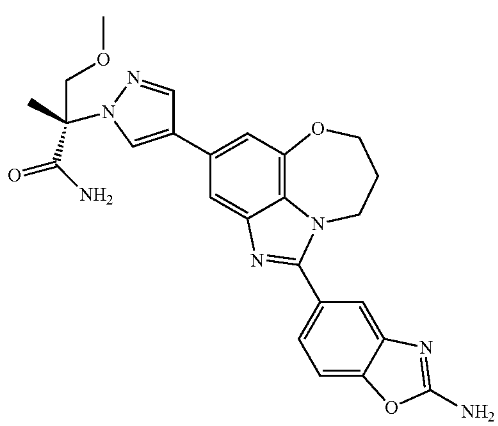 [SMILES: COC[C@@](C)(C(N)=O)n1cc(-c2cc3c4c(c2)nc(-c2ccc5oc(N)nc5c2)n4CCCO3)cn1] | (S)-2-(4-(1-(2-amino-benzo[d]oxazol-5-yl)-8,9-dihydro-7H-6-oxa-2,9a-diazabenzo[cd]azulen-4-yl)-1H-pyrazol-1-yl)-3-methoxy-2-methyl-propanamide | 0.000119 | 488.2 |

TABLE 1-continued

Formula I compounds

| Compound No. | Structure | Name | PI3Kα-(alpha) ATP (Ki) micromolar (μM) | Mass Spec. M + H/1 (daltons) |
|---|---|---|---|---|
| 234 | 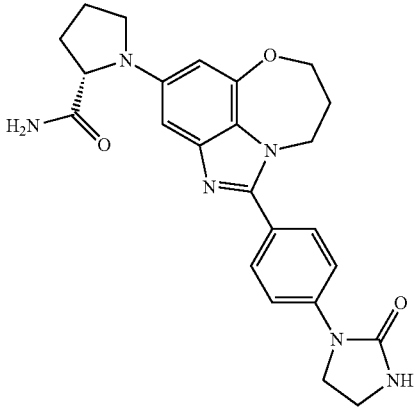 [SMILES: NC(=O)[C@@H]1CCCN1c1cc2c3c(c1)nc(-c1ccc(N4CCNC4=O)cc1)n3CCCO2] | (S)-1-(1-(4-(2-oxo-imidazolidin-1-yl) phenyl)-8,9-dihydro-7H-6-oxa-2,9a-diazabenzo[cd] azulen-4-yl) pyrrolidine-2-carboxamide | 0.0837 | 447.2 |
| 235 | 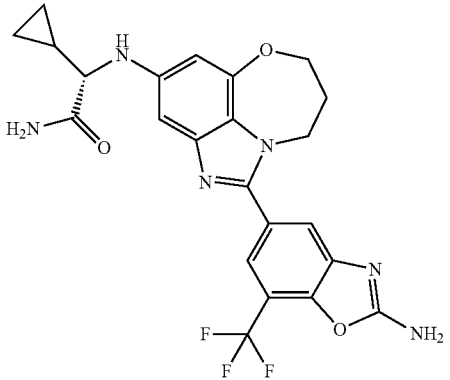 [SMILES: NC(=O)[C@@H](Nc1cc2c3c(c1)nc(-c1cc(C(F)(F)F)c4oc(N)nc4c1)n3CCCO2)C1CC1] | (S)-2-((1-(2-amino-7-(trifluoromethyl) benzo[d] oxazol-5-yl)-8,9-dihydro-7H-6-oxa-2,9a-diazabenzo[cd] azulen-4-yl) amino)-2-cyclopropyl-acetamide | 0.000209 | 487.2 |
| 236 | 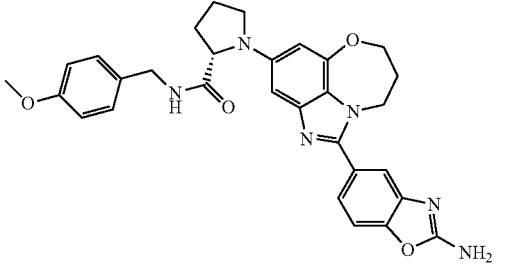 [SMILES: COc1ccc(CNC(=O)[C@@H]2CCCN2c2cc3c4c(c2)nc(-c2ccc5oc(N)nc5c2)n4CCCO3)cc1] | (S)-1-(1-(2-aminobenzo [d]oxazol-5-yl)-8,9-dihydro-7H-6-oxa-2,9a-diazabenzo[cd] azulen-4-yl)-N-(4-methoxybenzyl) pyrrolidine-2-carboxamide | 0.021 | 539.2 |
| 237 | 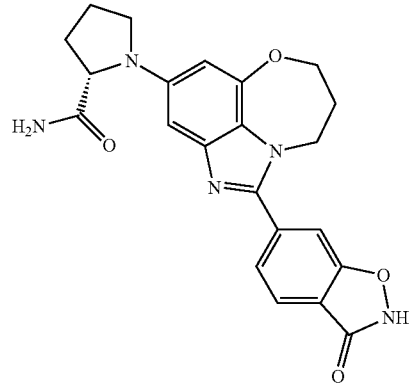 [SMILES: NC(=O)[C@@H]1CCCN1c1cc2c3c(c1)nc(-c1ccc4c(=O)[nH]oc4c1)n3CCCO2] | (S)-1-(1-(3-oxo-2,3-dihydrobenzo [d]isoxazol-6-yl)-8,9-dihydro-7H-6-oxa-2,9a-diazabenzo[cd] azulen-4-yl) pyrrolidine-2-carboxamide | 0.137 | 420.2 |

TABLE 1-continued

| Compound No. | Structure | Name | PI3Kα-(alpha) ATP (Ki) micromolar (μM) | Mass Spec. M + H/1 (daltons) |
|---|---|---|---|---|
| 238 | 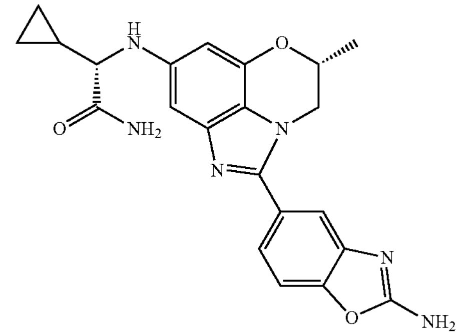 [SMILES: C[C@@H]1Cn2c(-c3ccc4oc(N)nc4c3)nc3cc(N[C@H](C(N)=O)C4CC4)cc(c32)O1] | (S)-2-(((R)-2-(2-amino-benzo[d]oxazol-5-yl)-4-methyl-3,4-dihydro-5-oxa-1,2a-diazaace-naphthylen-7-yl)amino)-2-cyclo-propyl-acetamide | 0.000045 | 419.2 |
| 239 | 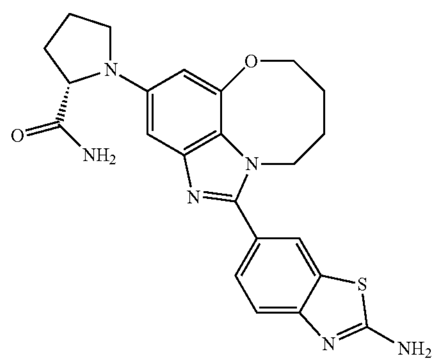 [SMILES: NC(=O)[C@@H]1CCCN1c1cc2c3c(c1)nc(-c1ccc4nc(N)sc4c1)n3CCCCO2] | (S)-1-(1-(2-aminobenzo[d]thiazol-6-yl)-7,8,9,10-tetrahydro-6-oxa-2,10a-diazacyclo-octa[cd]inden-4-yl)pyrrolidine-2-carboxamide | 0.000035 | 449.2 |
| 240 | 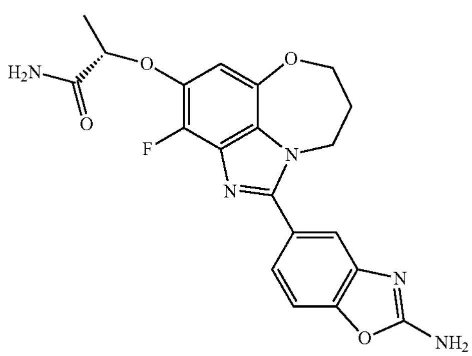 [SMILES: C[C@H](Oc1cc2c3c(nc(-c4ccc5oc(N)nc5c4)n3CCCO2)c1F)C(N)=O] | (S)-2-((1-(2-aminobenzo[d]oxazol-5-yl)-3-fluoro-8,9-dihydro-7H-6-oxa-2,9a-diazabenzo[cd]azulen-4-yl)oxy)propanamide | 0.00161 | 412.1 |
| 241 | 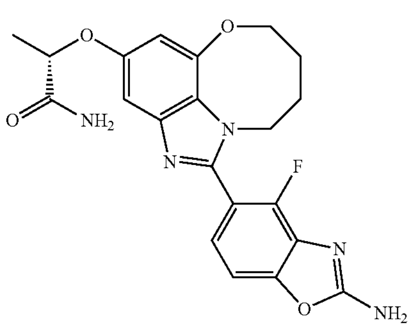 [SMILES: C[C@H](Oc1cc2c3c(c1)nc(-c1ccc4oc(N)nc4c1F)n3CCCCO2)C(N)=O] | (S)-2-((1-(2-amino-4-fluoro-benzo[d]oxazol-5-yl)-7,8,9,10-tetrahydro-6-oxa-2,10a-diazacyclo-octa[cd]inden-4-yl)oxy)propanamide | <0.000020 | 426.2 |

TABLE 1-continued

| Compound No. | Structure | Name | PI3Kα-(alpha) ATP (Ki) micromolar (μM) | Mass Spec. M + H/1 (daltons) |
|---|---|---|---|---|
| 242 | 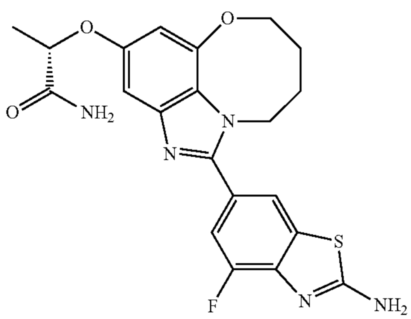 [SMILES: C[C@H](Oc1cc2c3c(c1)nc(-c1cc(F)c4nc(N)sc4c1)n3CCCCO2)C(N)=O] | (S)-2-((1-(2-amino-4-fluoro-benzo[d]thiazol-6-yl)-7,8,9,10-tetrahydro-6-oxa-2,10a-diazacyclo-octa[cd]inden-4-yl)oxy)propanamide | <0.000020 | 442.2 |
| 243 | 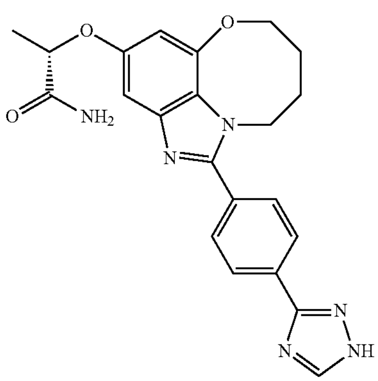 [SMILES: C[C@H](Oc1cc2c3c(c1)nc(-c1ccc(-c4nc[nH]n4)cc1)n3CCCCO2)C(N)=O] | (S)-2-((1-(4-(1H-1,2,4-triazol-3-yl)phenyl)-7,8,9,10-tetrahydro-6-oxa-2,10a-diazacyclo-octa[cd]inden-4-yl)oxy)propanamide | <0.000020 | 419.2 |
| 244 | 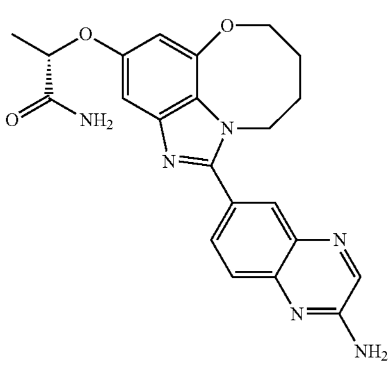 [SMILES: C[C@H](Oc1cc2c3c(c1)nc(-c1ccc4nc(N)cnc4c1)n3CCCCO2)C(N)=O] | (S)-2-((1-(2-amino-quinoxalin-6-yl)-7,8,9,10-tetrahydro-6-oxa-2,10a-diazacyclo-octa[cd]inden-4-yl)oxy)propanamide | <0.000020 | 419.2 |

TABLE 2

| | Formula I compounds | | | |
|---|---|---|---|---|
| No. | Structure | Name | PI3Kα- (alpha) ATP (Ki) micromolar (μM) | Mass Spec. M + H/1 (daltons) |
| 245 | | (R)-2-((1-(2-aminobenzo[d]oxazol-5-yl)-7,8,9,10-tetrahydro-6-oxa-2,10a-diazacycloocta[cd]inden-4-yl)oxy)propanamide | 0.000032 | 408 |
| 246 | | (S)-2-((1-(2-Aminobenzo[d]thiazol-5-yl)-7,8,9,10-tetrahydro-6-oxa-2,10a-diazacycloocta[cd]inden-4-yl)amino)-2-cyclopropylacetamide | <0.000020 | 449 |
| 247 | | (S)-1-(1-(2-aminobenzo[d]oxazol-5-yl)-3-fluoro-7,8,9,10-tetrahydro-6-oxa-2,10a-diazacycloocta[cd]inden-4-yl)pyrrolidine-2-carboxamide | 0.000024 | 450.74 |
| 248 | | (S)-2-((1-(2-aminobenzo[d]thiazol-6-yl)-7,8,9,10-tetrahydro-6-oxa-2,10a-diazacycloocta[cd]inden-4-yl)oxy)propanamide | 0.00003 | 424 |

TABLE 2-continued

Formula I compounds

| No. | Structure | Name | PI3Kα-(alpha) ATP (Ki) micromolar (μM) | Mass Spec. M + H/1 (daltons) |
|---|---|---|---|---|
| 249 | 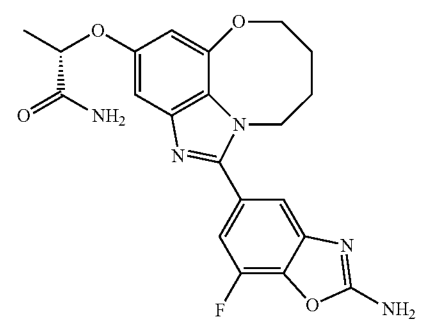 [SMILES: C[C@H](Oc1cc2c3c(c1)nc(-c1cc(F)c4oc(N)nc4c1)n3CCCCO2)C(N)=O] | (S)-2-((1-(2-amino-7-fluorobenzo[d]oxazol-5-yl)-7,8,9,10-tetrahydro-6-oxa-2,10a-diazacycloocta[cd]inden-4-yl)oxy)propanamide | <0.000020 | 426 |
| 250 | 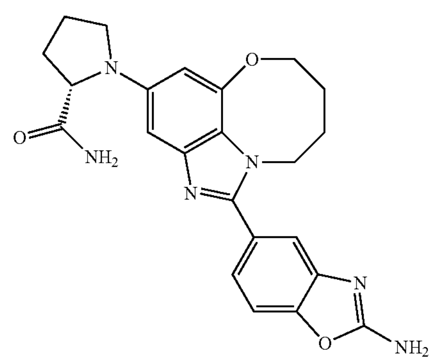 [SMILES: NC(=O)[C@@H]1CCCN1c1cc2c3c(c1)nc(-c1ccc4oc(N)nc4c1)n3CCCCO2] | (S)-1-(1-(2-aminobenzo[d]oxazol-5-yl)-7,8,9,10-tetrahydro-6-oxa-2,10a-diazacycloocta[cd]inden-4-yl)pyrrolidine-2-carboxamide | <0.000020 | 433 |
| 251 | 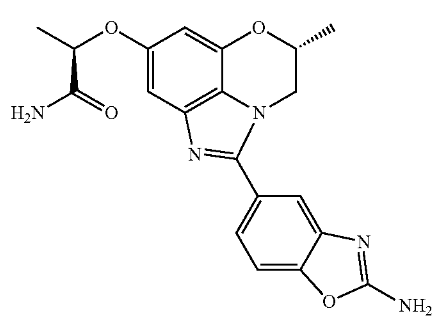 [SMILES: C[C@@H]1Cn2c(-c3ccc4oc(N)nc4c3)nc3cc(O[C@H](C)C(N)=O)cc(c32)O1] | (R)-2-(((R)-2-(2-aminobenzo[d]oxazol-5-yl)-4-methyl-3,4-dihydro-5-oxa-1,2a-diazaacenaphthylen-7-yl)oxy)propanamide | 0.00227 | 394 |
| 252 | 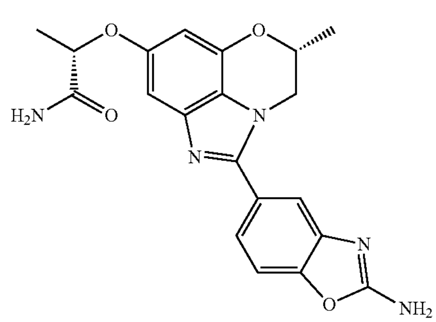 [SMILES: C[C@@H]1Cn2c(-c3ccc4oc(N)nc4c3)nc3cc(O[C@@H](C)C(N)=O)cc(c32)O1] | (S)-2-(((R)-2-(2-aminobenzo[d]oxazol-5-yl)-4-methyl-3,4-dihydro-5-oxa-1,2a-diazaacenaphthylen-7-yl)oxy)propanamide | 0.000221 | 394 |

TABLE 2-continued

Formula I compounds

| No. | Structure | Name | PI3Kα-(alpha) ATP (Ki) micromolar (μM) | Mass Spec. M + H/1 (daltons) |
|-----|-----------|------|-----------------------------------------|------------------------------|
| 253 | 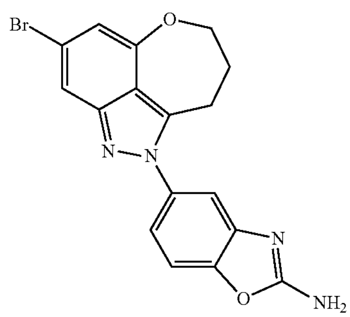 [SMILES: Nc1nc2cc(-n3nc4cc(Br)cc5c4c3CCCO5)ccc2o1] | 5-(4-bromo-8,9-dihydrooxepino[4,3,2-cd]indazol-1(7H)-yl)benzo[d]oxazol-2-amine | 0.0508 | 385/387 |
| 254 | 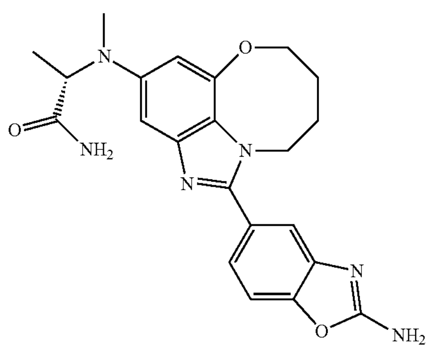 [SMILES: C[C@@H](C(N)=O)N(C)c1cc2c3c(c1)nc(-c1ccc4oc(N)nc4c1)n3CCCCO2] | (S)-2-((1-(2-aminobenzo[d]oxazol-5-yl)-7,8,9,10-tetrahydro-6-oxa-2,10a-diazacycloocta[cd]inden-4-yl)(methyl)amino)propanamide | <0.000020 | 420.46 |
| 255 | 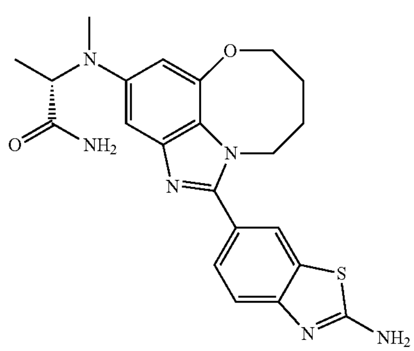 [SMILES: C[C@@H](C(N)=O)N(C)c1cc2c3c(c1)nc(-c1ccc4nc(N)sc4c1)n3CCCCO2] | (S)-2-((1-(2-aminobenzo[d]thiazol-6-yl)-7,8,9,10-tetrahydro-6-oxa-2,10a-diazacycloocta[cd]inden-4-yl)(methyl)amino)propanamide | 0.000149 | 436.53 |
| 256 | 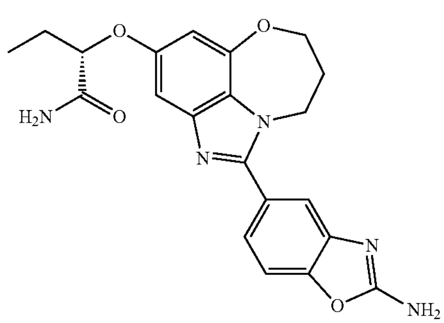 [SMILES: CC[C@H](Oc1cc2c3c(c1)nc(-c1ccc4oc(N)nc4c1)n3CCCO2)C(N)=O] | (S)-2-((1-(2-aminobenzo[d]oxazol-5-yl)-8,9-dihydro-7H-6-oxa-2,9a-diazabenzo[cd]azulen-4-yl)oxy)butanamide | 0.00027 | 407.42 |

TABLE 2-continued

Formula I compounds

| No. | Structure | Name | PI3Kα-(alpha) ATP (Ki) micromolar (μM) | Mass Spec. M + H/1 (daltons) |
|---|---|---|---|---|
| 257 | 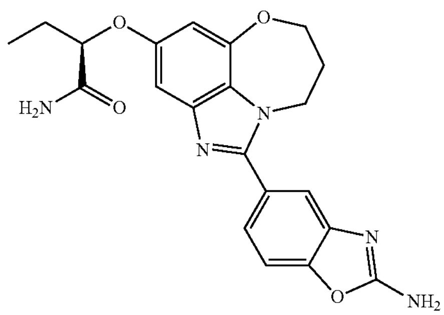 [SMILES: CC[C@@H](Oc1cc2c3c(c1)nc(-c1ccc4oc(N)nc4c1)n3CCCO2)C(N)=O] | (R)-2-((1-(2-aminobenzo[d]oxazol-5-yl)-8,9-dihydro-7H-6-oxa-2,9a-diazabenzo[cd]azulen-4-yl)oxy)butanamide | 0.00080 | 407.42 |
| 258 | 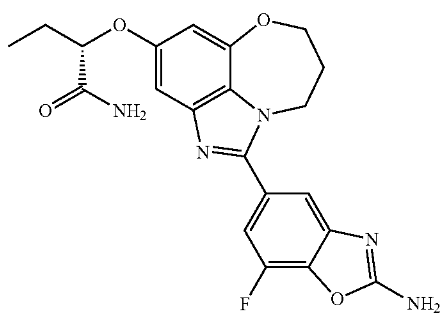 [SMILES: CC[C@H](Oc1cc2c3c(c1)nc(-c1cc(F)c4oc(N)nc4c1)n3CCCO2)C(N)=O] | (S)-2-((1-(2-amino-7-fluorobenzo[d]oxazol-5-yl)-8,9-dihydro-7H-6-oxa-2,9a-diazabenzo[cd]azulen-4-yl)oxy)propanamide | 0.00009 | 412 |
| 259 | 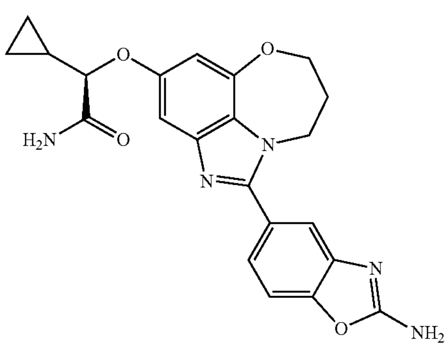 [SMILES: NC(=O)[C@H](Oc1cc2c3c(c1)nc(-c1ccc4oc(N)nc4c1)n3CCCO2)C1CC1] | (R)-2-((1-(2-aminobenzo[d]oxazol-5-yl)-8,9-dihydro-7H-6-oxa-2,9a-diazabenzo[cd]azulen-4-yl)oxy)-2-cyclopropylacetamide | 0.00274 | 420 |
| 260 | 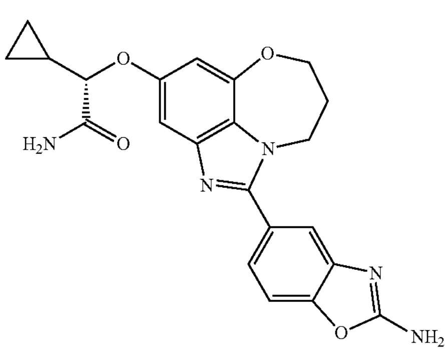 [SMILES: NC(=O)[C@@H](Oc1cc2c3c(c1)nc(-c1ccc4oc(N)nc4c1)n3CCCO2)C1CC1] | (S)-2-((1-(2-aminobenzo[d]oxazol-5-yl)-8,9-dihydro-7H-6-oxa-2,9a-diazabenzo[cd]azulen-4-yl)oxy)-2-cyclopropylacetamide | 0.000273 | 420 |

TABLE 2-continued

Formula I compounds

| No. | Structure | Name | PI3Kα-(alpha) ATP (Ki) micromolar (μM) | Mass Spec. M + H/1 (daltons) |
|---|---|---|---|---|
| 261 | 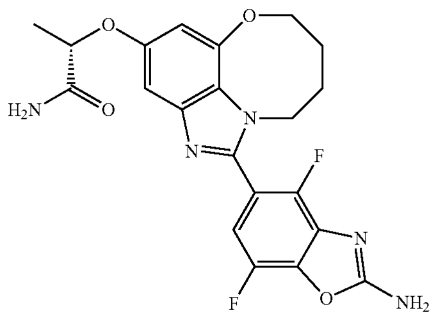 [SMILES: C[C@H](Oc1cc2c3c(c1)nc(-c1cc(F)c4oc(N)nc4c1F)n3CCCCO2)C(N)=O] | (S)-2-((1-(2-amino-4,7-difluorobenzo[d]oxazol-5-yl)-7,8,9,10-tetrahydro-6-oxa-2,10a-diazacycloocta[cd]inden-4-yl)oxy)propanamide | <0.000020 | 444 |
| 262 | 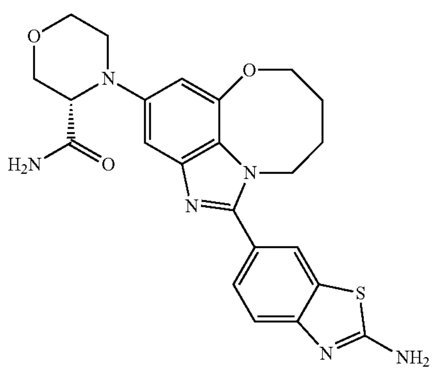 [SMILES: NC(=O)[C@@H]1COCCN1c1cc2c3c(c1)nc(-c1ccc4nc(N)sc4c1)n3CCCCO2] | (S)-4-(1-(2-aminobenzo[d]thiazol-6-yl)-7,8,9,10-tetrahydro-6-oxa-2,10a-diazacycloocta[cd]inden-4-yl)morpholine-3-carboxamide | 0.00195 | 465 |
| 263 | 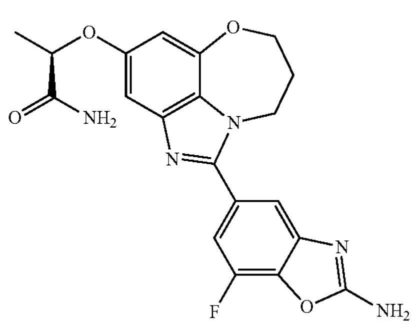 [SMILES: C[C@@H](Oc1cc2c3c(c1)nc(-c1cc(F)c4oc(N)nc4c1)n3CCCO2)C(N)=O] | (R)-2-((1-(2-Amino-7-fluorobenzo[d]oxazol-5-yl)-8,9-dihydro-7H-6-oxa-2,9a-diazabenzo[cd]azulen-4-yl)oxy)propanamide | 0.000346 | 412 |
| 264 | 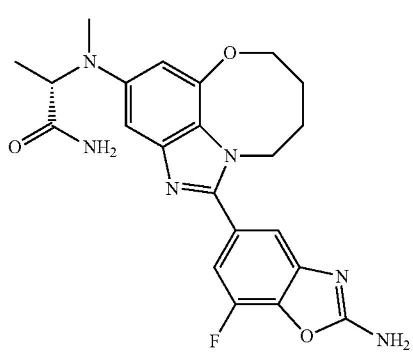 [SMILES: C[C@@H](C(N)=O)N(C)c1cc2c3c(c1)nc(-c1cc(F)c4oc(N)nc4c1)n3CCCCO2] | (S)-2-((1-(2-amino-7-fluorobenzo[d]oxazol-5-yl)-7,8,9,10-tetrahydro-6-oxa-2,10a-diazacycloocta[cd]inden-4-yl)(methyl)amino)propanamide | <0.000020 | 439 |

TABLE 2-continued

Formula I compounds

| No. | Structure | Name | PI3Kα-(alpha) ATP (Ki) micromolar (μM) | Mass Spec. M + H/1 (daltons) |
|---|---|---|---|---|
| 265 | 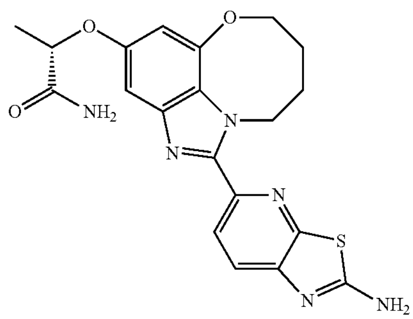 [SMILES: C[C@H](Oc1cc2c3c(c1)nc(-c1ccc4nc(N)sc4n1)n3CCCCO2)C(N)=O] | (S)-2-((1-(2-aminothiazolo[5,4-b]pyridin-5-yl)-7,8,9,10-tetrahydro-6-oxa-2,10a-diazacycloocta[cd]inden-4-yl)oxy)propanamide | <0.000020 | 425 |
| 266 | 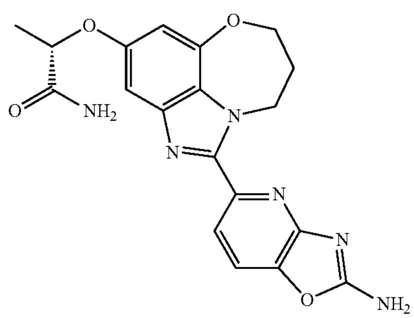 [SMILES: C[C@H](Oc1cc2c3c(c1)nc(-c1ccc4oc(N)nc4n1)n3CCCO2)C(N)=O] | (S)-2-((1-(2-aminooxazolo[4,5-b]pyridin-5-yl)-8,9-dihydro-7H-6-oxa-2,9a-diazabenzo[cd]azulen-4-yl)oxy)propanamide | 0.000108 | 395 |
| 267 | 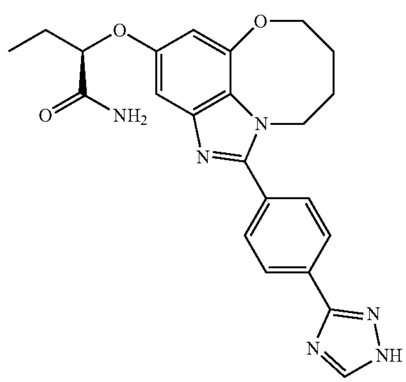 [SMILES: CC[C@@H](Oc1cc2c3c(c1)nc(-c1ccc(-c4nc[nH]n4)cc1)n3CCCCO2)C(N)=O] | (R)-2-((1-(4-(1H-1,2,4-triazol-3-yl)phenyl)-7,8,9,10-tetrahydro-6-oxa-2,10a-diazacycloocta[cd]inden-4-yl)oxy)butanamide | 0.00128 | 433 |
| 268 | 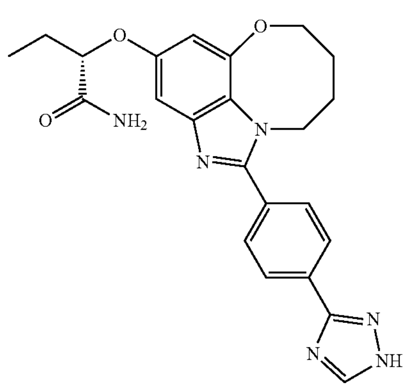 [SMILES: CC[C@H](Oc1cc2c3c(c1)nc(-c1ccc(-c4nc[nH]n4)cc1)n3CCCCO2)C(N)=O] | (S)-2-((1-(4-(1H-1,2,4-triazol-3-yl)phenyl)-7,8,9,10-tetrahydro-6-oxa-2,10a-diazacycloocta[cd]inden-4-yl)oxy)butanamide | 0.0000214 | 433 |

TABLE 2-continued

Formula I compounds

| No. | Structure | Name | PI3Kα-(alpha) ATP (Ki) micromolar (μM) | Mass Spec. M + H/1 (daltons) |
|---|---|---|---|---|
| 269 | 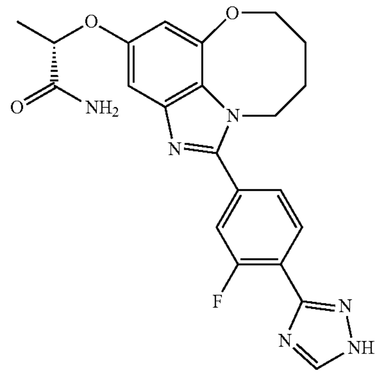 [SMILES: C[C@H](Oc1cc2c3c(c1)nc(-c1ccc(-c4nc[nH]n4)c(F)c1)n3CCCCO2)C(N)=O] | (S)-2-((1-(3-fluoro-4-(1H-1,2,4-triazol-3-yl)phenyl)-7,8,9,10-tetrahydro-6-oxa-2,10a-diazacycloocta[cd]inden-4-yl)oxy)propanamide | <0.000020 | 437 |
| 270 | 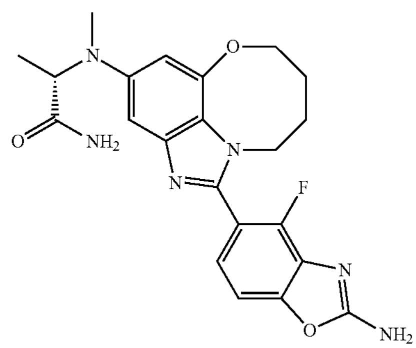 [SMILES: C[C@@H](C(N)=O)N(C)c1cc2c3c(c1)nc(-c1ccc4oc(N)nc4c1F)n3CCCCO2] | (S)-2-((1-(2-amino-4-fluorobenzo[d]oxazol-5-yl)-7,8,9,10-tetrahydro-6-oxa-2,10a-diazacycloocta[cd]inden-4-yl)(methyl)amino)propanamide | 0.00003 | 439 |
| 271 | 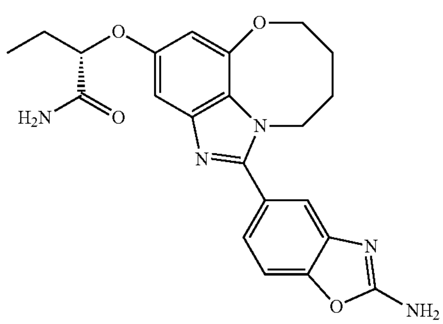 [SMILES: CC[C@H](Oc1cc2c3c(c1)nc(-c1ccc4oc(N)nc4c1)n3CCCCO2)C(N)=O] | (S)-2-((1-(2-aminobenzo[d]oxazol-5-yl)-7,8,9,10-tetrahydro-6-oxa-2,10a-diazacycloocta[cd]inden-4-yl)oxy)butanamide | <0.000020 | 422 |
| 272 | 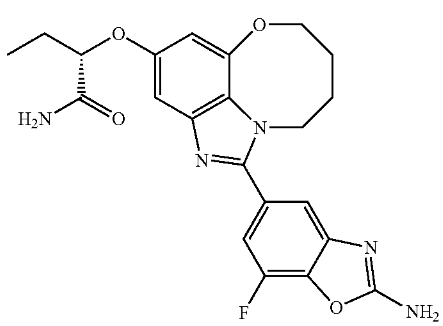 [SMILES: CC[C@H](Oc1cc2c3c(c1)nc(-c1cc(F)c4oc(N)nc4c1)n3CCCCO2)C(N)=O] | (S)-2-((1-(2-amino-7-fluorobenzo[d]oxazol-5-yl)-7,8,9,10-tetrahydro-6-oxa-2,10a-diazacycloocta[cd]inden-4-yl)oxy)butanamide | <0.000020 | 440 |

TABLE 2-continued

Formula I compounds

| No. | Structure | Name | PI3Kα-(alpha) ATP (Ki) micromolar (μM) | Mass Spec. M + H/1 (daltons) |
|---|---|---|---|---|
| 273 | 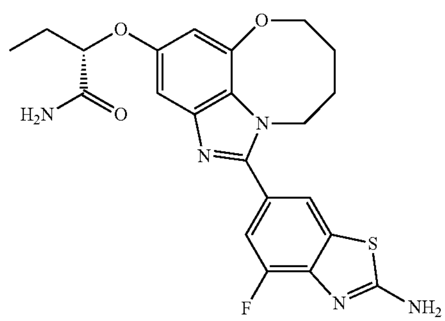 [SMILES: CC[C@H](Oc1cc2c3c(c1)nc(-c1cc(F)c4nc(N)sc4c1)n3CCCCO2)C(N)=O] | (S)-2-((1-(2-amino-4-fluorobenzo[d]thiazol-6-yl)-7,8,9,10-tetrahydro-6-oxa-2,10a-diazacycloocta[cd]inden-4-yl)oxy)butanamide | 0.0000494 | 456 |
| 274 | 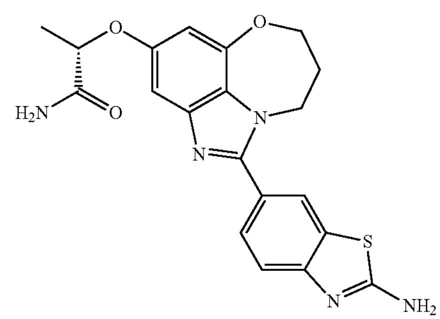 [SMILES: C[C@H](Oc1cc2c3c(c1)nc(-c1ccc4nc(N)sc4c1)n3CCCO2)C(N)=O] | (S)-2-((1-(2-aminobenzo[d]thiazol-6-yl)-8,9-dihydro-7H-6-oxa-2,9a-diazabenzo[cd]azulen-4-yl)oxy)propanamide | 0.0021 | 410.1 |
| 275 | 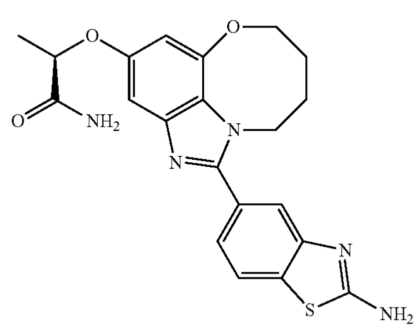 [SMILES: C[C@@H](Oc1cc2c3c(c1)nc(-c1ccc4sc(N)nc4c1)n3CCCCO2)C(N)=O] | (R)-2-((1-(2-aminobenzo[d]thiazol-5-yl)-7,8,9,10-tetrahydro-6-oxa-2,10a-diazacycloocta[cd]inden-4-yl)oxy)propanamide | 0.000754 | 424 |
| 276 | 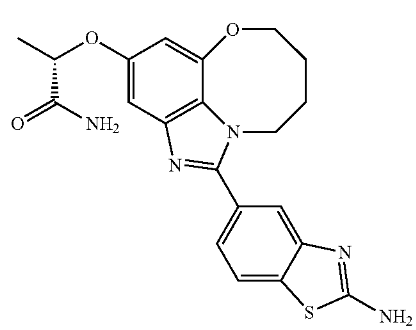 | (S)-2-((1-(2-aminobenzo[d]thiazol-5-yl)-7,8,9,10-tetrahydro-6-oxa-2,10a-diazacycloocta[cd]inden-4-yl)oxy)propanamide | 0.000113 | 424 |

TABLE 2-continued

Formula I compounds

| No. | Structure | Name | PI3Kα-(alpha) ATP (Ki) micromolar (μM) | Mass Spec. M + H/1 (daltons) |
|---|---|---|---|---|
| 277 | 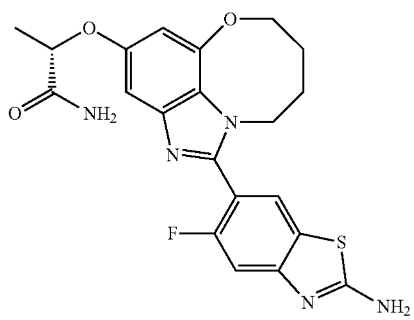 [SMILES: C[C@H](Oc1cc2c3c(c1)nc(-c1cc4sc(N)nc4cc1F)n3CCCCO2)C(N)=O] | (S)-2-((1-(2-amino-5-fluorobenzo[d]thiazol-6-yl)-7,8,9,10-tetrahydro-6-oxa-2,10a-diazacycloocta[cd]inden-4-yl)oxy)propanamide | 0.000208 | 442 |
| 278 | 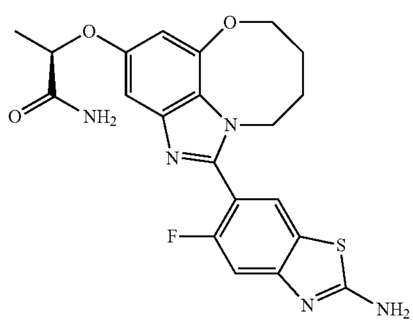 [SMILES: C[C@@H](Oc1cc2c3c(c1)nc(-c1cc4sc(N)nc4cc1F)n3CCCCO2)C(N)=O] | (R)-2-((1-(2-amino-5-fluorobenzo[d]thiazol-6-yl)-7,8,9,10-tetrahydro-6-oxa-2,10a-diazacycloocta[cd]inden-4-yl)oxy)propanamide | 0.0046 | 442 |
| 279 | 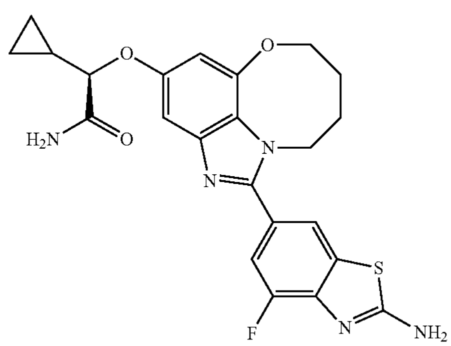 | (R)-2-((1-(2-amino-4-fluorobenzo[d]thiazol-6-yl)-7,8,9,10-tetrahydro-6-oxa-2,10a-diazacycloocta[cd]inden-4-yl)oxy)-2-cyclopropylacetamide | 0.00102 | 468 |
| 280 | 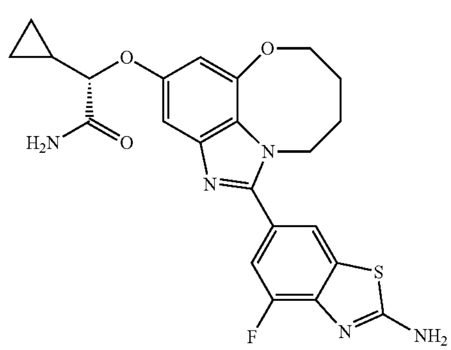 [SMILES: NC(=O)[C@@H](Oc1cc2c3c(c1)nc(-c1cc(F)c4nc(N)sc4c1)n3CCCCO2)C1CC1] | (S)-2-((1-(2-amino-4-fluorobenzo[d]thiazol-6-yl)-7,8,9,10-tetrahydro-6-oxa-2,10a-diazacycloocta[cd]inden-4-yl)oxy)-2-cyclopropylacetamide | <0.000020 | 468 |

TABLE 2-continued

Formula I compounds

| No. | Structure | Name | PI3Kα-(alpha) ATP (Ki) micromolar (μM) | Mass Spec. M + H/1 (daltons) |
|---|---|---|---|---|
| 281 | 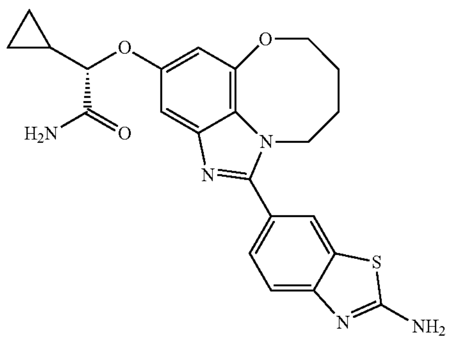 [SMILES: NC(=O)[C@@H](Oc1cc2c3c(c1)nc(-c1ccc4nc(N)sc4c1)n3CCCCO2)C1CC1] | (S)-2-((1-(2-aminobenzo[d]thiazol-6-yl)-7,8,9,10-tetrahydro-6-oxa-2,10a-diazacycloocta[cd]inden-4-yl)oxy)-2-cyclopropylacetamide | 0.000027 | 450 |
| 282 | 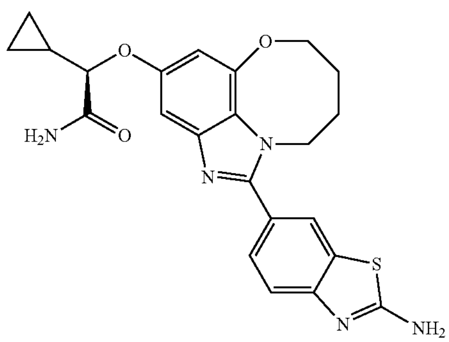 | (R)-2-((1-(2-aminobenzo[d]thiazol-6-yl)-7,8,9,10-tetrahydro-6-oxa-2,10a-diazacycloocta[cd]inden-4-yl)oxy)-2-cyclopropylacetamide | 0.00553 | 450 |
| 283 | 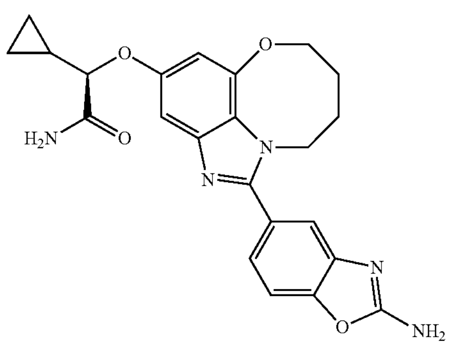 [SMILES: NC(=O)[C@H](Oc1cc2c3c(c1)nc(-c1ccc4oc(N)nc4c1)n3CCCCO2)C1CC1] | (R)-2-((1-(2-aminobenzo[d]oxazol-5-yl)-7,8,9,10-tetrahydro-6-oxa-2,10a-diazacycloocta[cd]inden-4-yl)oxy)-2-cyclopropylacetamide | 0.000104 | 434 |
| 284 | 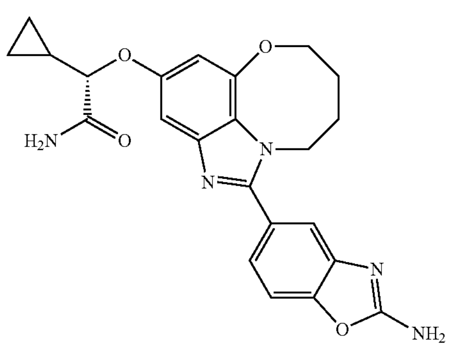 [SMILES: NC(=O)[C@@H](Oc1cc2c3c(c1)nc(-c1ccc4oc(N)nc4c1)n3CCCCO2)C1CC1] | (S)-2-((1-(2-aminobenzo[d]oxazol-5-yl)-7,8,9,10-tetrahydro-6-oxa-2,10a-diazacycloocta[cd]inden-4-yl)oxy)-2-cyclopropylacetamide | <0.000020 | 434 |

TABLE 2-continued

Formula I compounds

| No. | Structure | Name | PI3Kα-(alpha) ATP (Ki) micromolar (μM) | Mass Spec. M + H/1 (daltons) |
|---|---|---|---|---|
| 285 | 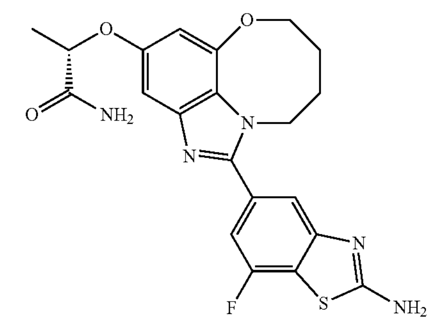 | (S)-2-((1-(2-amino-7-fluorobenzo[d]thiazol-5-yl)-7,8,9,10-tetrahydro-6-oxa-2,10a-diazacycloocta[cd]inden-4-yl)oxy)propanamide | 0.000062 | 442 |
| 286 | 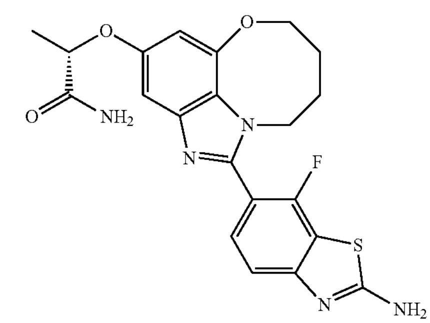 | (S)-2-((1-(2-amino-7-fluorobenzo[d]thiazol-6-yl)-7,8,9,10-tetrahydro-6-oxa-2,10a-diazacycloocta[cd]inden-4-yl)oxy)propanamide | 0.000072 | 442 |
| 287 | 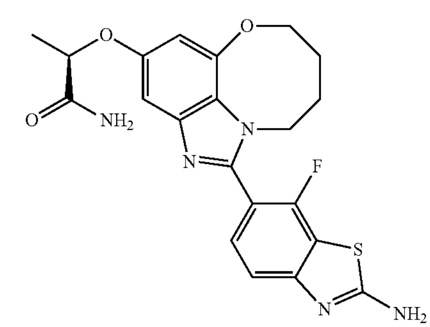 | (R)-2-((1-(2-amino-7-fluorobenzo[d]thiazol-6-yl)-7,8,9,10-tetrahydro-6-oxa-2,10a-diazacycloocta[cd]inden-4-yl)oxy)propanamide | 0.00171 | 442 |
| 288 | 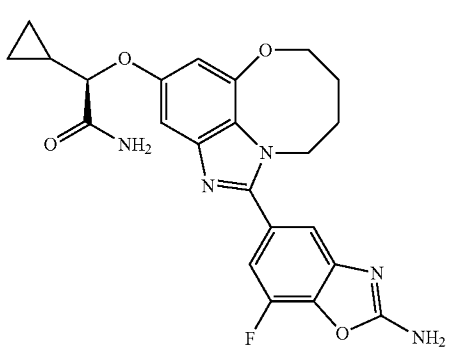 [SMILES: NC(=O)[C@H](Oc1cc2c3c(c1)nc(-c1cc(F)c4oc(N)nc4c1)n3CCCCO2)C1CC1] | (R)-2-((1-(2-amino-7-fluorobenzo[d]oxazol-5-yl)-7,8,9,10-tetrahydro-6-oxa-2,10a-diazacycloocta[cd]inden-4-yl)oxy)-2-cyclopropylacetamide | 0.00010 | 452 |

TABLE 2-continued

Formula I compounds

| No. | Structure | Name | PI3Kα-(alpha) ATP (Ki) micromolar (μM) | Mass Spec. M + H/1 (daltons) |
| --- | --- | --- | --- | --- |
| 289 | 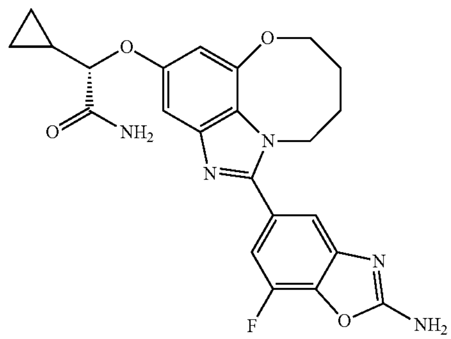 [SMILES: NC(=O)[C@@H](Oc1cc2c3c(c1)nc(-c1cc(F)c4oc(N)nc4c1)n3CCCCO2)C1CC1] | (S)-2-((1-(2-amino-7-fluorobenzo[d]oxazol-5-yl)-7,8,9,10-tetrahydro-6-oxa-2,10a-diazacycloocta[cd]inden-4-yl)oxy)-2-cyclopropylacetamide | <0.000020 | 452 |
| 290 | 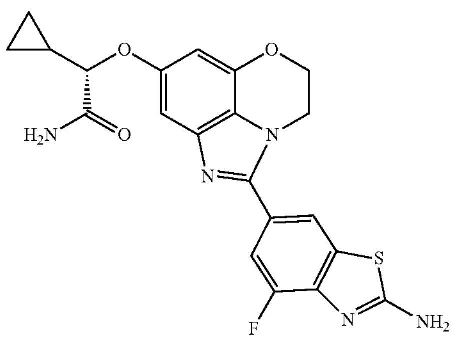 [SMILES: NC(=O)[C@@H](Oc1cc2c3c(c1)nc(-c1cc(F)c4nc(N)sc4c1)n3CCO2)C1CC1] | (S)-2-((2-(2-amino-4-fluorobenzo[d]thiazol-6-yl)-3,4-dihydro-5-oxa-1,2a-diazaacenaphthylen-7-yl)oxy)-2-cyclopropylacetamide | 0.000403 | 440 |
| 291 | 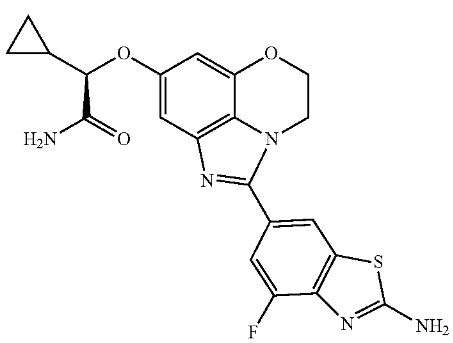 [SMILES: NC(=O)[C@H](Oc1cc2c3c(c1)nc(-c1cc(F)c4nc(N)sc4c1)n3CCO2)C1CC1] | (R)-2-((2-(2-amino-4-fluorobenzo[d]thiazol-6-yl)-3,4-dihydro-5-oxa-1,2a-diazaacenaphthylen-7-yl)oxy)-2-cyclopropylacetamide | 0.00762 | 440 |
| 292 | 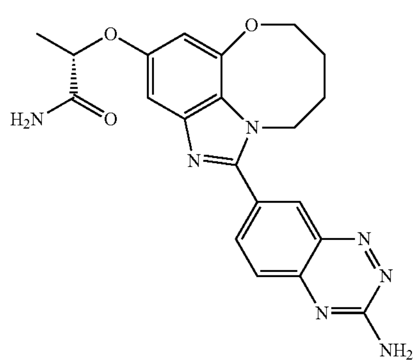 [SMILES: C[C@H](Oc1cc2c3c(c1)nc(-c1ccc4nc(N)nnc4c1)n3CCCCO2)C(N)=O] | (S)-2-((1-(3-aminobenzo[e][1,2,4]triazin-7-yl)-7,8,9,10-tetrahydro-6-oxa-2,10a-diazacycloocta[cd]inden-4-yl)oxy)propanamide | 0.000024 | 420 |

TABLE 2-continued

Formula I compounds

| No. | Structure | Name | PI3Kα-(alpha) ATP (Ki) micromolar (μM) | Mass Spec. M + H/1 (daltons) |
|---|---|---|---|---|
| 293 | 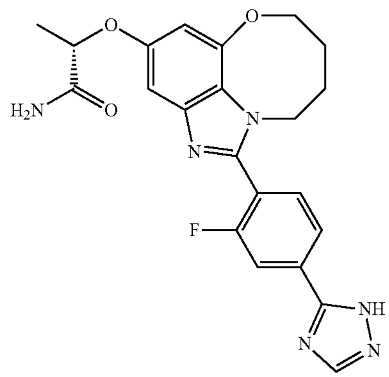 [SMILES: C[C@H](Oc1cc2c3c(c1)nc(-c1ccc(-c4ncn[nH]4)cc1F)n3CCCCO2)C(N)=O] | (S)-2-((1-(2-fluoro-4-(1H-1,2,4-triazol-5-yl)phenyl)-7,8,9,10-tetrahydro-6-oxa-2,10a-diazacycloocta[cd]inden-4-yl)oxy)propanamide | 0.0000222 | 437 |
| 294 | 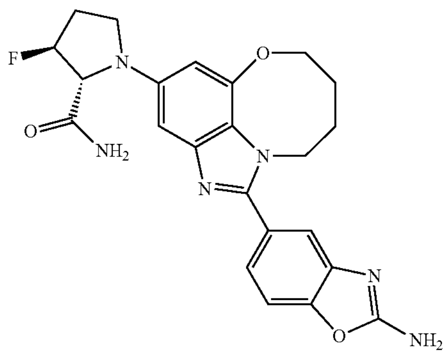 [SMILES: NC(=O)[C@@H]1[C@@H](F)CCN1c1cc2c3c(c1)nc(-c1ccc4oc(N)nc4c1)n3CCCCO2] | (2R,3S)-1-(1-(2-aminobenzo[d]oxazol-5-yl)-7,8,9,10-tetrahydro-6-oxa-2,10a-diazacycloocta[cd]inden-4-yl)-3-fluoropyrrolidine-2-carboxamide | <0.000020 | 451 |
| 295 | 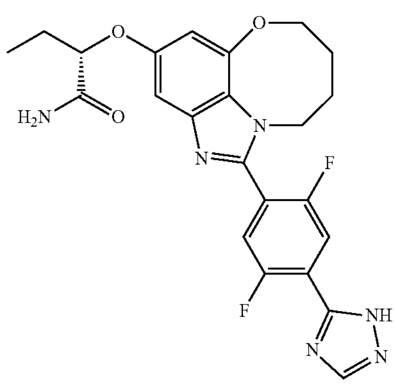 [SMILES: CC[C@H](Oc1cc2c3c(c1)nc(-c1cc(F)c(-c4ncn[nH]4)cc1F)n3CCCCO2)C(N)=O] | (S)-2-((1-(2,5-difluoro-4-(1H-1,2,4-triazol-5-yl)phenyl)-7,8,9,10-tetrahydro-6-oxa-2,10a-diazacycloocta[cd]inden-4-yl)oxy)butanamide | 0.000053 | 469 |
| 296 | 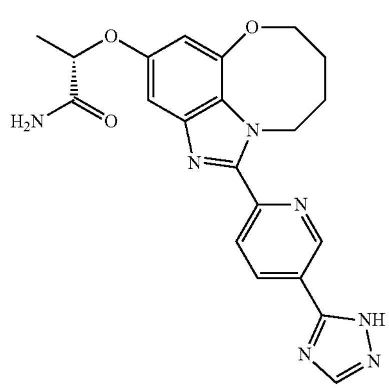 [SMILES: C[C@H](Oc1cc2c3c(c1)nc(-c1ccc(-c4ncn[nH]4)cn1)n3CCCCO2)C(N)=O] | (S)-2-((1-(5-(1H-1,2,4-triazol-5-yl)pyridin-2-yl)-7,8,9,10-tetrahydro-6-oxa-2,10a-diazacycloocta[cd]inden-4-yl)oxy)propanamide | <0.000020 | 420 |

TABLE 2-continued

Formula I compounds

| No. | Structure | Name | PI3Kα-(alpha) ATP (Ki) micromolar (μM) | Mass Spec. M + H/1 (daltons) |
|---|---|---|---|---|
| 297 | 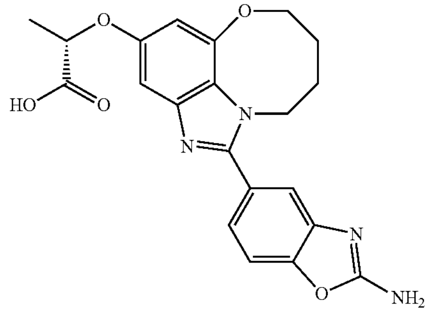 [SMILES: C[C@H](Oc1cc2c3c(c1)nc(-c1ccc4oc(N)nc4c1)n3CCCCO2)C(=O)O] | (S)-2-((1-(2-aminobenzo[d]oxazol-5-yl)-7,8,9,10-tetrahydro-6-oxa-2,10a-diazacycloocta[cd]inden-4-yl)oxy)propanoic acid | 0.002226 | 409 |
| 298 | 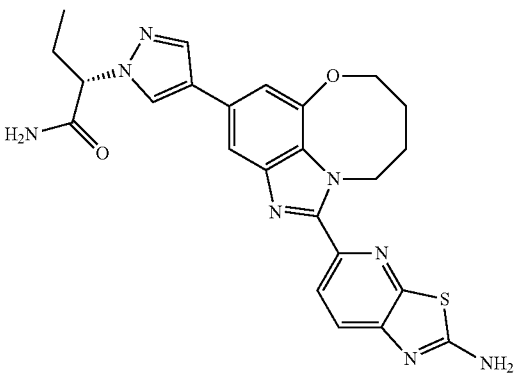 | (S)-2-(4-(1-(2-aminothiazolo[5,4-b]pyridin-5-yl)-7,8,9,10-tetrahydro-6-oxa-2,10a-diazacycloocta[cd]inden-4-yl)-1H-pyrazol-1-yl)butanamide | 0.000070 | 489 |
| 299 | 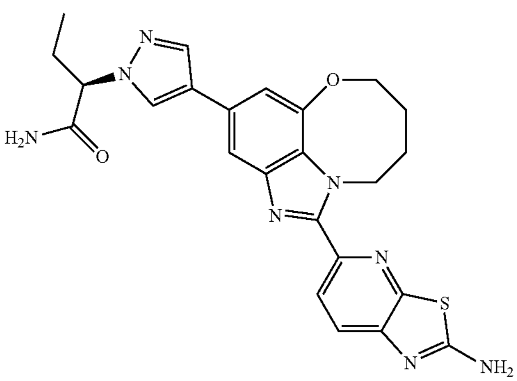 [SMILES: CC[C@H](C(N)=O)n1cc(-c2cc3c4c(c2)nc(-c2ccc5nc(N)sc5n2)n4CCCCO3)cn1] | (R)-2-(4-(1-(2-aminothiazolo[5,4-b]pyridin-5-yl)-7,8,9,10-tetrahydro-6-oxa-2,10a-diazacycloocta[cd]inden-4-yl)-1H-pyrazol-1-yl)butanamide | 0.000061 | 489 |
| 300 | 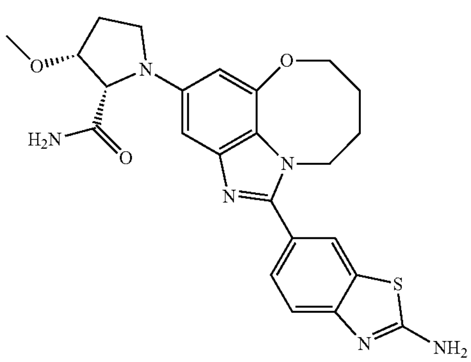 | (2S,3R)-1-(1-(2-aminobenzo[d]thiazol-6-yl)-7,8,9,10-tetrahydro-6-oxa-2,10a-diazacycloocta[cd]inden-4-yl)-3-methoxypyrrolidine-2-carboxamide | 0.000045 | 479 |

TABLE 2-continued

Formula I compounds

| No. | Structure | Name | PI3Kα-(alpha) ATP (Ki) micromolar (μM) | Mass Spec. M + H/1 (daltons) |
|---|---|---|---|---|
| 301 | 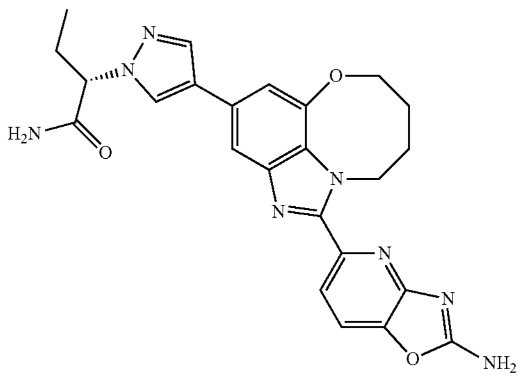 [SMILES: CC[C@@H](C(N)=O)n1cc(-c2cc3c4c(c2)nc(-c2ccc5oc(N)nc5n2)n4CCCCO3)cn1] | (S)-2-(4-(1-(2-aminooxazolo[4,5-b]pyridin-5-yl)-7,8,9,10-tetrahydro-6-oxa-2,10a-diazacycloocta[cd]inden-4-yl)-1H-pyrazol-1-yl)butanamide | 0.000038 | 473 |
| 302 | 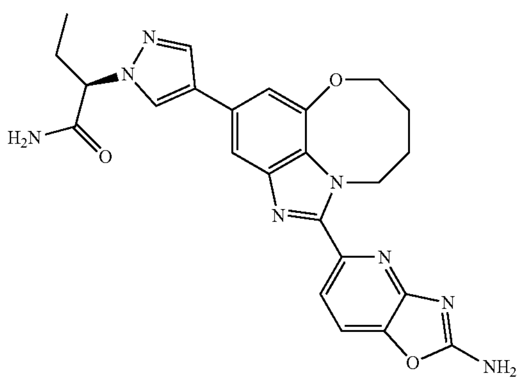 [SMILES: CC[C@H](C(N)=O)n1cc(-c2cc3c4c(c2)nc(-c2ccc5oc(N)nc5n2)n4CCCCO3)cn1] | (R)-2-(4-(1-(2-aminooxazolo[4,5-b]pyridin-5-yl)-7,8,9,10-tetrahydro-6-oxa-2,10a-diazacycloocta[cd]inden-4-yl)-1H-pyrazol-1-yl)butanamide | 0.000102 | 473 |
| 303 | 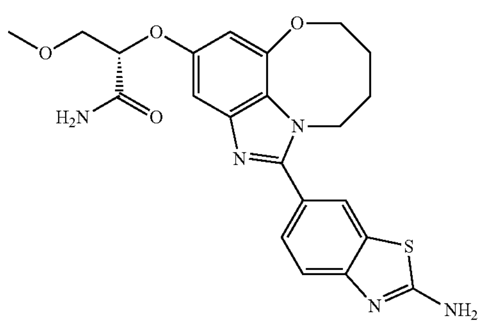 [SMILES: COC[C@H](Oc1cc2c3c(c1)nc(-c1ccc4nc(N)sc4c1)n3CCCCO2)C(N)=O] | (S)-2-((1-(2-aminobenzo[d]thiazol-6-yl)-7,8,9,10-tetrahydro-6-oxa-2,10a-diazacycloocta[cd]inden-4-yl)oxy)-3-methoxypropanamide | 0.00562 | 454 |
| 304 | 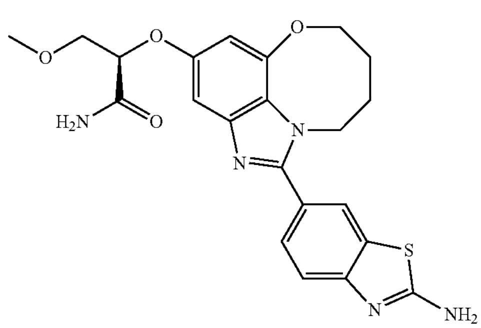 | (R)-2-((1-(2-aminobenzo[d]thiazol-6-yl)-7,8,9,10-tetrahydro-6-oxa-2,10a-diazacycloocta[cd]inden-4-yl)oxy)-3-methoxypropanamide | 0.000127 | 454 |

TABLE 2-continued

Formula I compounds

| No. | Structure | Name | PI3Kα-(alpha) ATP (Ki) micromolar (μM) | Mass Spec. M + H/1 (daltons) |
|---|---|---|---|---|
| 305 | 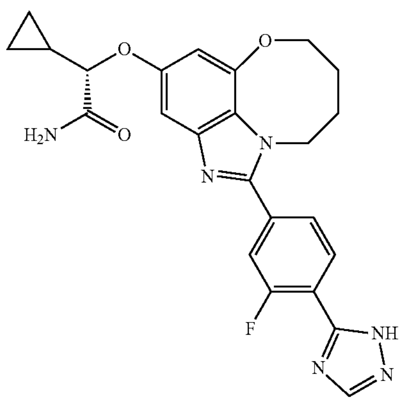 [SMILES: NC(=O)[C@@H](Oc1cc2c3c(c1)nc(-c1ccc(-c4ncn[nH]4)c(F)c1)n3CCCCO2)C1CC1] | (S)-2-cyclopropyl-2-((1-(3-fluoro-4-(1H-1,2,4-triazol-5-yl)phenyl)-7,8,9,10-tetrahydro-6-oxa-2,10a-diazacycloocta[cd]inden-4-yl)oxy)acetamide | <0.000020 | 463 |
| 306 | 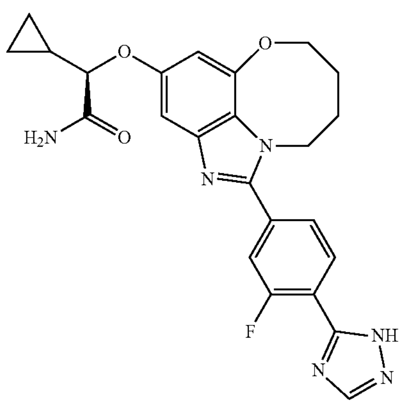 [SMILES: NC(=O)[C@H](Oc1cc2c3c(c1)nc(-c1ccc(-c4ncn[nH]4)c(F)c1)n3CCCCO2)C1CC1] | (R)-2-cyclopropyl-2-((1-(3-fluoro-4-(1H-1,2,4-triazol-5-yl)phenyl)-7,8,9,10-tetrahydro-6-oxa-2,10a-diazacycloocta[cd]inden-4-yl)oxy)acetamide | 0.00072 | 463 |
| 307 | 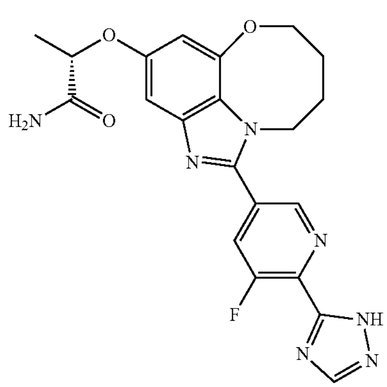 [SMILES: C[C@H](Oc1cc2c3c(c1)nc(-c1cnc(-c4ncn[nH]4)c(F)c1)n3CCCCO2)C(N)=O] | (S)-2-((1-(5-fluoro-6-(1H-1,2,4-triazol-5-yl)pyridin-3-yl)-7,8,9,10-tetrahydro-6-oxa-2,10a-diazacycloocta[cd]inden-4-yl)oxy)propanamide | <0.000020 | 438 |

TABLE 2-continued

Formula I compounds

| No. | Structure | Name | PI3Kα-(alpha) ATP (Ki) micromolar (μM) | Mass Spec. M + H/1 (daltons) |
|---|---|---|---|---|
| 308 | 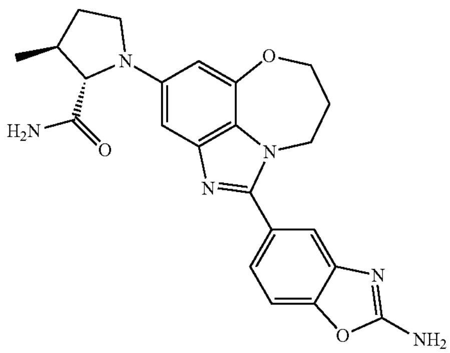 [SMILES: C[C@H]1CCN(c2cc3c4c(c2)nc(-c2ccc5oc(N)nc5c2)n4CCCO3)[C@@H]1C(N)=O] | (2S,3S)-1-(1-(2-aminobenzo[d]oxazol-5-yl)-8,9-dihydro-7H-6-oxa-2,9a-diazabenzo[cd]azulen-4-yl)-3-methylpyrrolidine-2-carboxamide | 0.000627 | 433 |
| 309 | 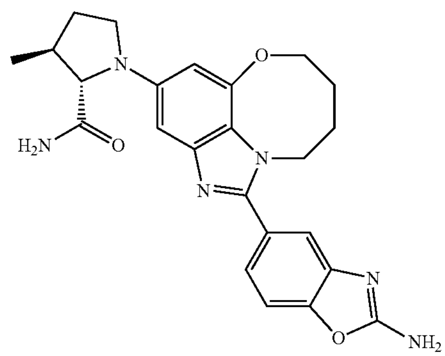 [SMILES: C[C@H]1CCN(c2cc3c4c(c2)nc(-c2ccc5oc(N)nc5c2)n4CCCCO3)[C@@H]1C(N)=O] | (2S,3S)-1-(1-(2-aminobenzo[d]oxazol-5-yl)-7,8,9,10-tetrahydro-6-oxa-2,10a-diazacycloocta[cd]inden-4-yl)-3-methylpyrrolidine-2-carboxamide | 0.000040 | 447 |
| 310 | 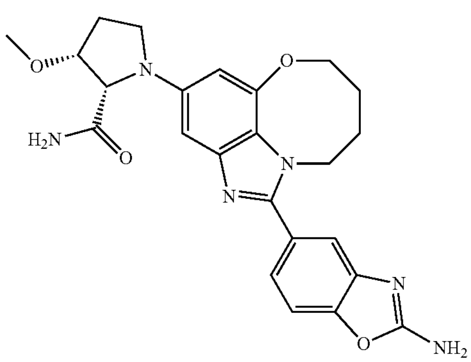 [SMILES: CO[C@@H]1CCN(c2cc3c4c(c2)nc(-c2ccc5oc(N)nc5c2)n4CCCCO3)[C@@H]1C(N)=O] | (2S,3R)-1-(1-(2-aminobenzo[d]oxazol-5-yl)-7,8,9,10-tetrahydro-6-oxa-2,10a-diazacycloocta[cd]inden-4-yl)-3-methoxypyrrolidine-2-carboxamide | 0.000171 | 463 |
| 311 | 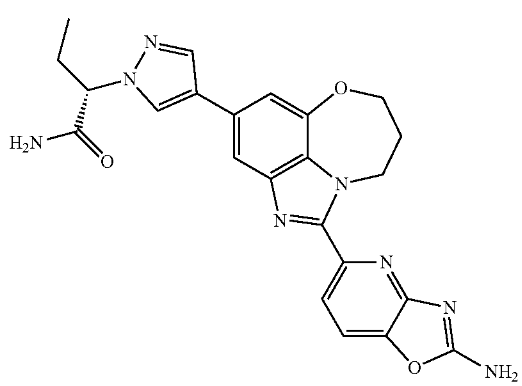 [SMILES: CC[C@@H](C(N)=O)n1cc(-c2cc3c4c(c2)nc(-c2ccc5oc(N)nc5n2)n4CCCO3)cn1] | (S)-2-(4-(1-(2-aminooxazolo[4,5-b]pyridin-5-yl)-8,9-dihydro-7H-6-oxa-2,9a-diazabenzo[cd]azulen-4-yl)-1H-pyrazol-1-yl)butanamide | 0.000031 | 459 |

TABLE 2-continued

Formula I compounds

| No. | Structure | Name | PI3Kα-(alpha) ATP (Ki) micromolar (μM) | Mass Spec. M + H/1 (daltons) |
|---|---|---|---|---|
| 312 | 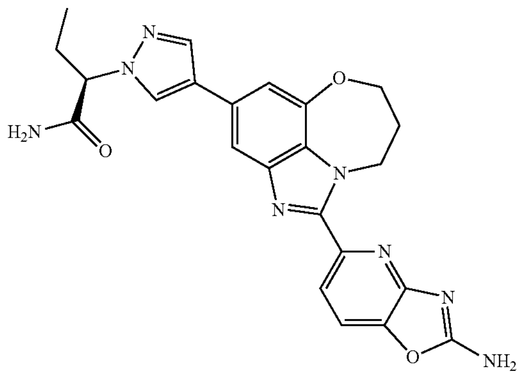 [SMILES: CC[C@H](C(N)=O)n1cc(-c2cc3c4c(c2)nc(-c2ccc5oc(N)nc5n2)n4CCCO3)cn1] | (R)-2-(4-(1-(2-aminooxazolo[4,5-b]pyridin-5-yl)-8,9-dihydro-7H-6-oxa-2,9a-diazabenzo[cd]azulen-4-yl)-1H-pyrazol-1-yl)butanamide | 0.000039 | 459 |
| 313 | 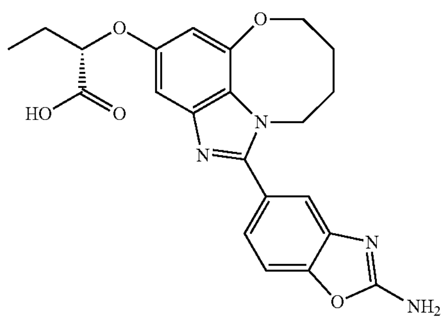 [SMILES: CC[C@H](Oc1cc2c3c(c1)nc(-c1ccc4oc(N)nc4c1)n3CCCCO2)C(=O)O] | (S)-2-((1-(2-aminobenzo[d]oxazol-5-yl)-7,8,9,10-tetrahydro-6-oxa-2,10a-diazacycloocta[cd]inden-4-yl)oxy)butanoic acid | 0.00209 | 423 |
| 314 | 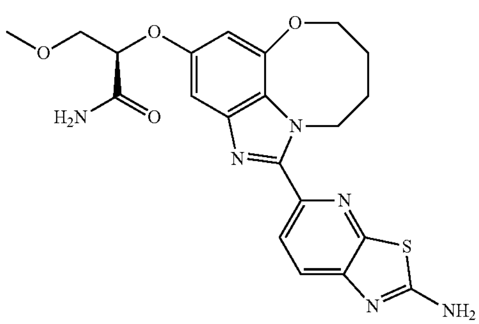 [SMILES: COC[C@@H](Oc1cc2c3c(c1)nc(-c1ccc4nc(N)sc4n1)n3CCCCO2)C(N)=O] | (R)-2-((1-(2-aminothiazolo[5,4-b]pyridin-5-yl)-7,8,9,10-tetrahydro-6-oxa-2,10a-diazacycloocta[cd]inden-4-yl)oxy)-3-methoxypropanamide | 0.000737 | 455 |
| 315 | 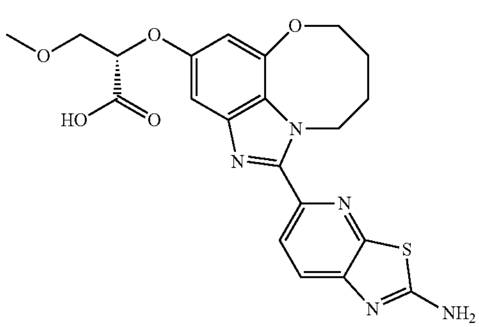 [SMILES: COC[C@H](Oc1cc2c3c(c1)nc(-c1ccc4nc(N)sc4n1)n3CCCCO2)C(=O)O] | (S)-2-((1-(2-aminothiazolo[5,4-b]pyridin-5-yl)-7,8,9,10-tetrahydro-6-oxa-2,10a-diazacycloocta[cd]inden-4-yl)oxy)-3-methoxypropanamide | <0.000020 | 455 |

Administration of Formula I Compounds

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 1 mg to about 1000 mg of Formula I compound. A typical dose may be about 10 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Formula I compounds of the present invention are useful for treating a human or animal patient suffering from a disease or disorder arising from abnormal cell growth, function or behavior associated with PI3K such as cancer, may thus be treated by a method comprising the administration thereto of a compound of the present invention as defined above. A human or animal patient suffering from cancer may also be treated by a method comprising the administration thereto of a compound of the present invention as defined above. The condition of the patient may thereby be improved or ameliorated.

Methods of the invention also include treating cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic myelogenous leukemia, lymphocytic leukemia, chronic lymphoid leukemia (CLL), myeloid leukemia, oral cavity and pharynx, non-Hodgkin lymphoma, melanoma, and villous colon adenoma.

Based on expression analysis, immunohistochemical analysis and on cell line profiling, malignancies of the colon, breast, cervix, stomach, lung, and multiple myeloma are most likely to respond to PI3K modulators or inhibitors.

Pharmaceutical Formulations

In order to use a compound of this invention for the therapeutic treatment of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs. The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with additional therapeutic agents for the treatment of a disease or disorder described herein, such as inflammation or a hyperproliferative disorder (e.g., cancer). In certain embodiments, a compound of Formula I is combined in a pharmaceutical combination formulation, or dosing regimen as combination therapy, with an additional, second therapeutic compound that has anti-inflammatory or anti-hyperproliferative properties or that is useful for treating an inflammation, immune-response disorder, or hyperproliferative disorder (e.g., cancer). The additional therapeutic may be a Bcl-2 inhibitor, a JAK inhibitor, an anti-inflammatory agent, an immunomodulatory agent, chemotherapeutic agent, an apoptosis-enhancer, a neurotropic factor, an agent for treating cardiovascular disease, an agent for treating liver disease, an anti-viral agent, an agent for treating blood disorders, an agent for treating diabetes, and an agent for treating immunodeficiency disorders. The second therapeutic agent may be an NSAID anti-inflammatory agent. The second therapeutic agent may be a chemotherapeutic agent. The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, or a stereoisomer, tautomer, solvate, metabolite, or pharmaceutically acceptable salt or prodrug thereof, in combination with a therapeutic agent such as an NSAID.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula I, or a stereoisomer, tautomer, solvate, metabolite, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I, or a stereoisomer, tautomer, solvate, metabolite, or pharmaceutically acceptable salt or prodrug thereof, and the use of at least one other cancer treatment method. The amounts of the compound(s) of Formula I and the other pharmaceutically active therapeutic agent(s) and the relative timings of administration will be selected in order to achieve the desired combined therapeutic effect.

Additional therapeutic agents employed in combination with a compound of Formula I include 5-FU, docetaxel, eribulin, gemcitabine, cobimetinib, ipatasertib, paclitaxel, tamoxifen, fulvestrant, GDC-0810, dexamethasone, palbociclib, bevacizumab, pertuzumab, trastuzumab emtansine, trastuzumab and letrozole.

Metabolites of Compounds of Formula I

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula I, or a stereoisomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Compounds of Formula I may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

The Examples provide exemplary methods for preparing Formula I compounds. Those skilled in the art will appreciate that other synthetic routes may be used to synthesize the Formula I compounds. Although specific starting materials and reagents are depicted and discussed in the Figures and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

In the methods of preparing Formula I compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Compounds of the invention were prepared as illustrated in general Schemes 1 through 10.

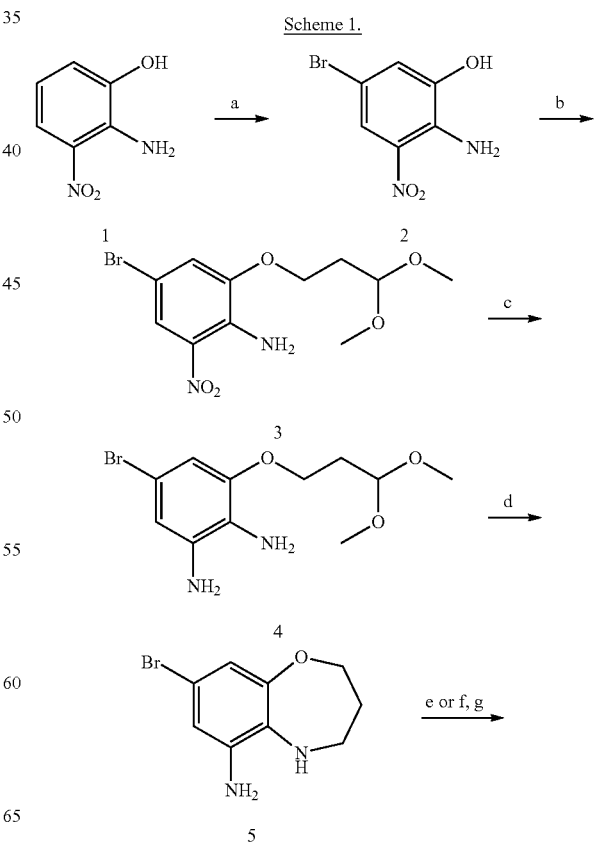

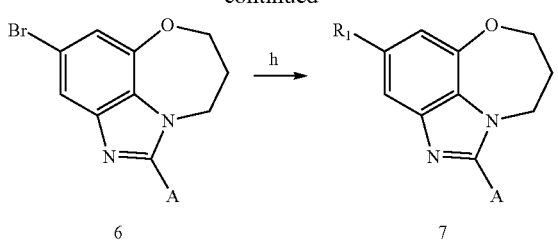

a) bromine, acetic acid; b) potassium carbonate, potassium iodide, 3-bromo-1,1-dimethoxypropane, 80° C.; c) ammonium chloride, iron powder, methanol, water, 90° C.; d) trifluoroacetic acid, triethylsilane, DCM 0-20° C.; e) A—COCl, triethylamine, THF; f) A—CO₂H, DIPEA, HATU, DMF; g) acetic acid, 90° C.; h) Ar—B(OR)₂, Pd(dppf)Cl₂, sodium carbonate, 1,4-dioxane, water, 100° C.

As shown in Scheme 1, bromination of 2-amino-3-nitrophenol provides compound 2. Alkylation provides compound 3. Reduction of the nitro group with iron followed by cyclization provides compound 5. Acylation of compound 5, followed by cyclization in acetic acid provides compound 6. Palladium-catalyzed cross-coupling with boronates provides compound 7.

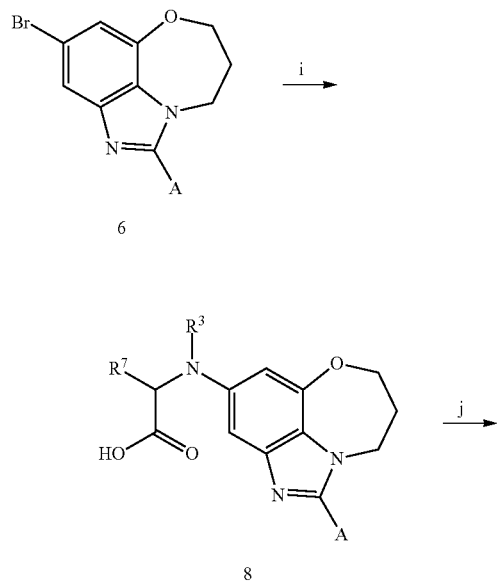

i) HNR³—CH(R⁷)—CO₂H, copper(I) iodide, potassium phosphate tribasic, DMSO, 100-120° C.; j) ammonium chloride, HATU, DIPEA, DMSO or DMF.

As shown in Scheme 2, compound 6 may be converted to compound 8 via copper-mediated cross coupling with amino acids. Conversion of acid 8 to primary amide 9 is achieved through reaction with ammonium chloride and HATU.

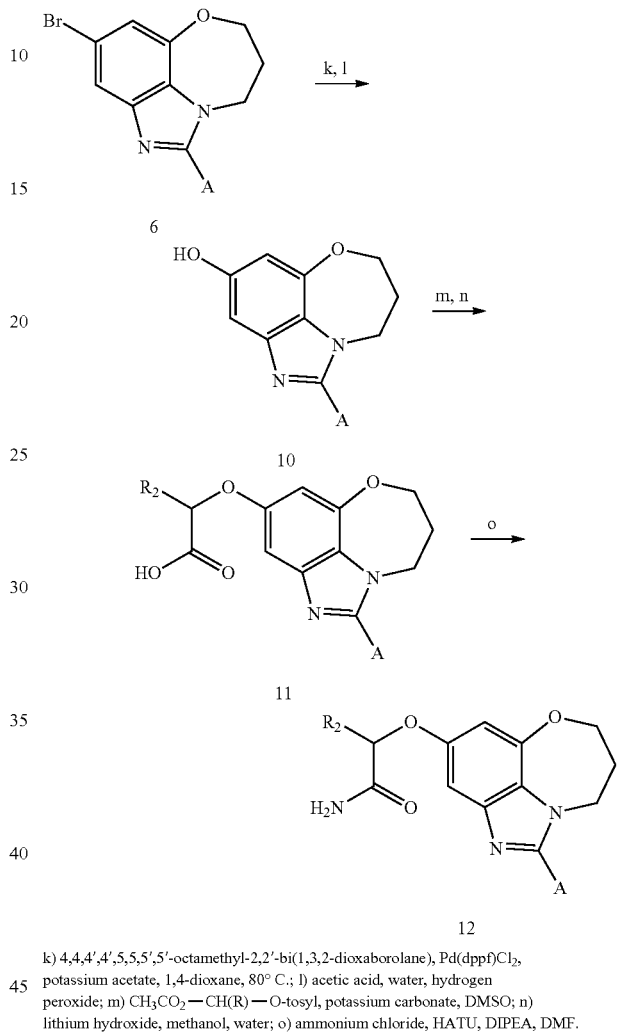

k) 4,4,4',4',5,5,5',5'-octamethyl-2,2'-bi(1,3,2-dioxaborolane), Pd(dppf)Cl₂, potassium acetate, 1,4-dioxane, 80° C.; l) acetic acid, water, hydrogen peroxide; m) CH₃CO₂—CH(R)—O-tosyl, potassium carbonate, DMSO; n) lithium hydroxide, methanol, water; o) ammonium chloride, HATU, DIPEA, DMF.

As shown in Scheme 3, conversion of the aryl-bromide 6 to the boronate pinacol ester, followed by oxidation provides compound 10. Alkylation with activated alpha-hydroxy esters, followed by ester hydrolysis, provides compound 11. Conversion of acid 11 to primary amide 12 is achieved through reaction with ammonium chloride and HATU.

Scheme 4.

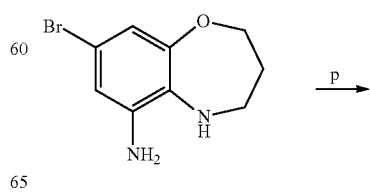

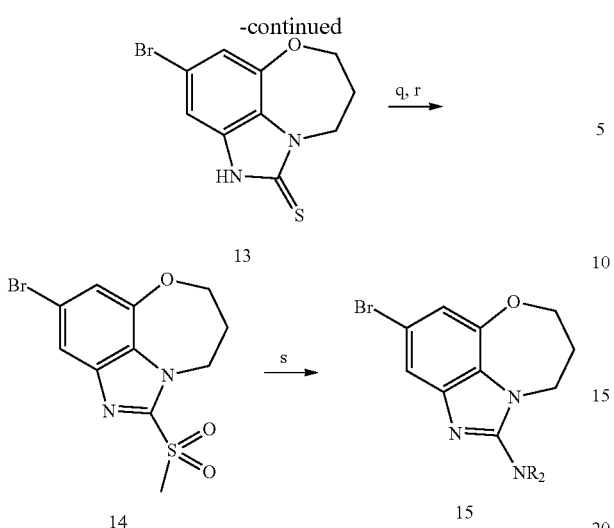

p) thiophosgene, triethylamine, THF, 0° C.; q) iodomethane, potassium carbonate, acetone; r) 3-chlorperoxybenzoic acid, DCM; s) HNR₂, DIPEA, 2-propanol, irr 150° C.

As shown in Scheme 4, cyclization of compound 5 may be effected with thiophosgene to provide compound 13. S-Methylation followed by oxidation to the sulfone provides compound 14. Reaction with amines under microwave heating provides compound 15.

Scheme 5.

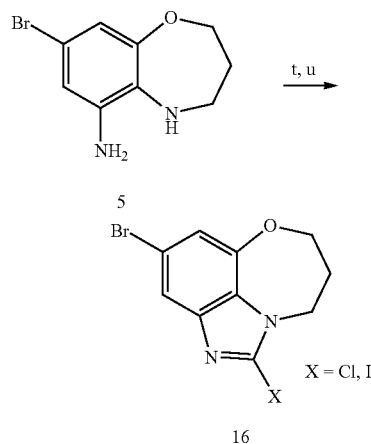

t) treithyl orthoformate, p-toluenesulfonic acid, 100° C.; u) lithium diisopropylamide, N-iodosuccinimide or N-chlorosuccinimide, THF, -78° C.; v) HNR₂, irr 140 C.; w) A—B(OR)₂, Pd(dppf)Cl₂, potassium acetate, sodium carbonate, water, acetonitrile, heat.

As shown in Scheme 5, compound 5 may be cyclized with triethyl orthoformate followed by halogenation to provide compound 16 as either the chloride or iodide. Heating with amines under microwave irradiation provides compound 6.

Alternatively, palladium-catalyzed Suzuki coupling with aryl boronates provides compound 6.

Scheme 6.

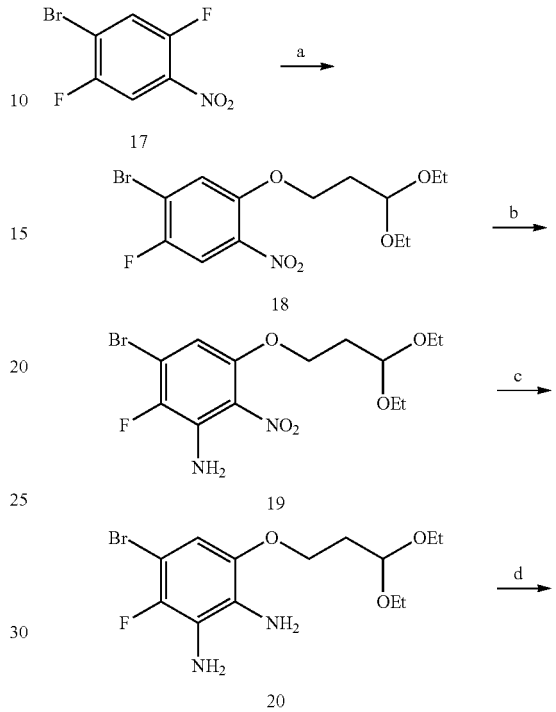

a) 3,3-diethoxypropanol, NaH, DMF; b) 1,1,1-trimethylhydrazinium iodide, KOtBu, DMSO; c) iron, ammonium chloride, methanol, water, 90° C.; d) TFA, triethylsilane, DCM; e) analogous steps as shown in Schemes 1-5

As shown in Scheme 6, a substituted alcohol may displace the fluorine atom of 17 to provide aryl ether 18. Amination may be effected using 1,1,1-trimethylhydrazinium iodide in the presence of base. Reduction of the nitro group with iron followed by cyclization under acidic conditions may provide compound 21. Conversion to general compound 22 may be effected using analogous steps as shown in Schemes 1-5.

Scheme 7.

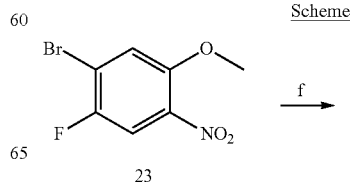

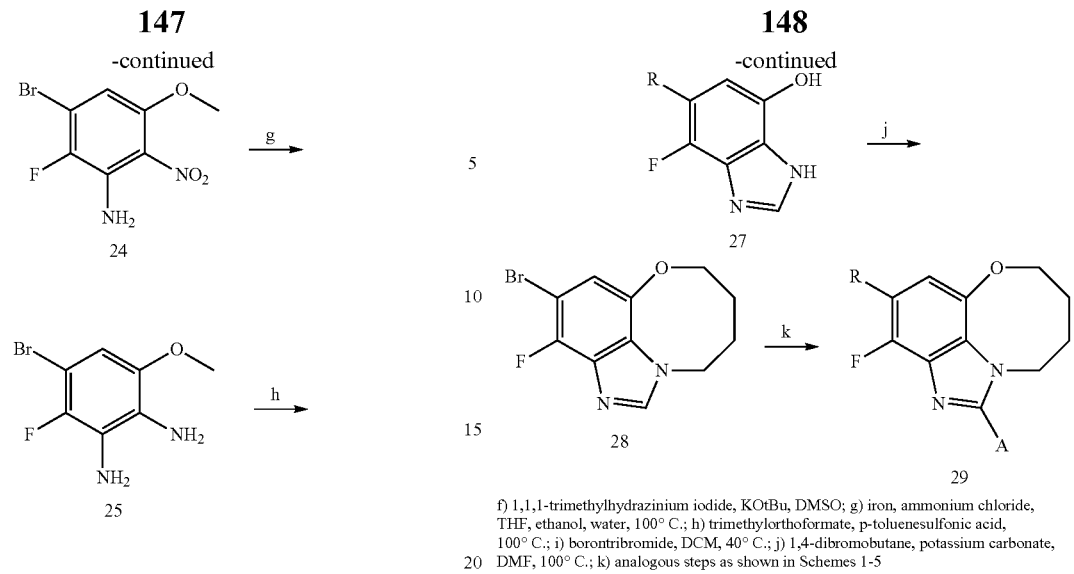

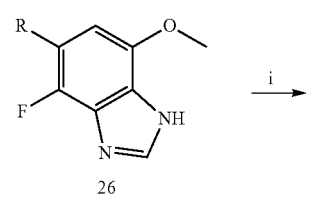

f) 1,1,1-trimethylhydrazinium iodide, KOtBu, DMSO; g) iron, ammonium chloride, THF, ethanol, water, 100° C.; h) trimethylorthoformate, p-toluenesulfonic acid, 100° C.; i) borontribromide, DCM, 40° C.; j) 1,4-dibromobutane, potassium carbonate, DMF, 100° C.; k) analogous steps as shown in Schemes 1-5

As shown in Scheme 7, amination of compound 23 may be effected using 1,1,1-trimethylhydrazinium iodide in the presence of base to afford compound 24. Reduction of the nitro group with iron followed by cyclization in trimethylorthoformate may provide compound 26. Demethylation using borontribromide followed by bis-alkylation with 1,4-dibromobutane may provide compound 28. Conversion to general compound 29 may be effected using analogous steps as shown in Schemes 1-5.

Scheme 8.

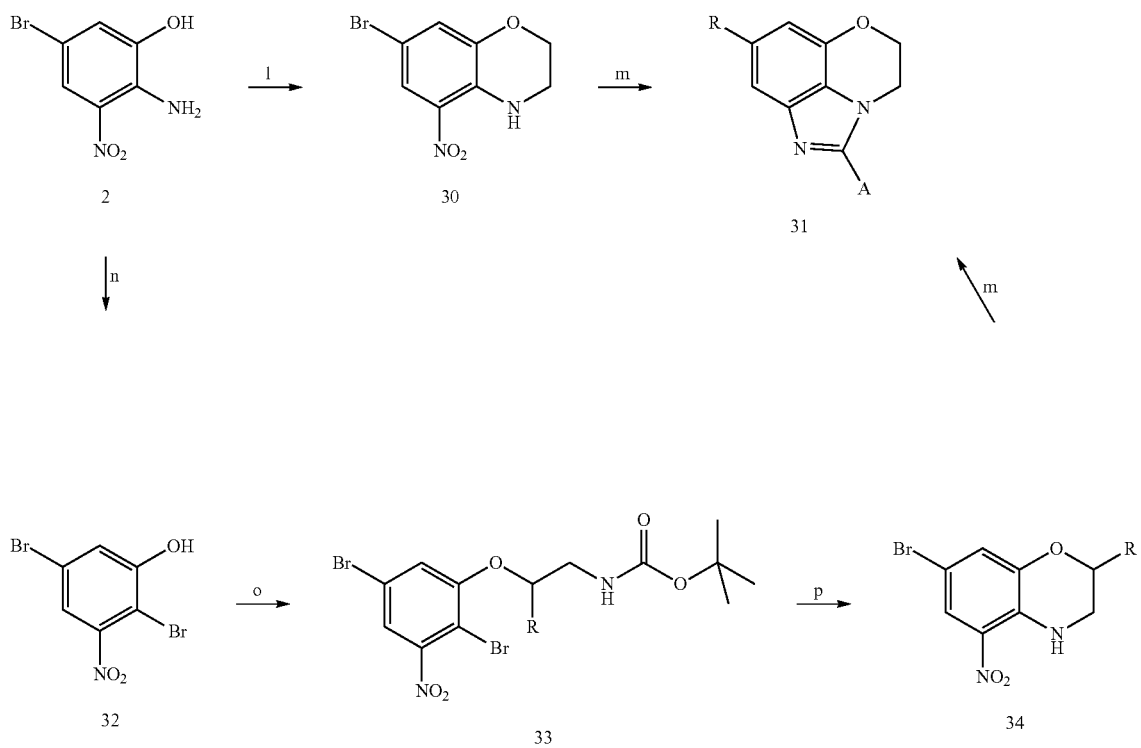

l) 1,2-dibromoethane, KOH, DMF, 140° C.; m) analogous steps as shown in Schemes 1-5; n) aq HBr, sodium nitrite, copper(II) bromide, 0-100° C.; o) substituted alcohol, triphenylphosphine, diisopropylazodicarboxylate, THF; p) i. HCl, dioxane, 50° C., ii. potassium carbonate, DMF, 90° C.

As shown in Scheme 8, compound 2 may be cyclized with 1,2-dibromoethane in the presence of base to afford compound 30. Conversion to general compound 31 may be effected using analogous steps as shown in Schemes 1-5. Alternatively, compound 2 may be converted to dibromo compound 32 using Sandmeyer conditions. Mitsunobu conditions allow alkylation of the phenol to produce compound 33 with defined stereochemistry. Boc deprotection and cyclization may provide compound 34, which can be converted to general compound 31 using analogous steps as shown in Schemes 1-5.

Scheme 10.

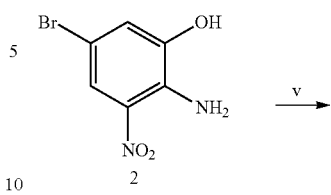

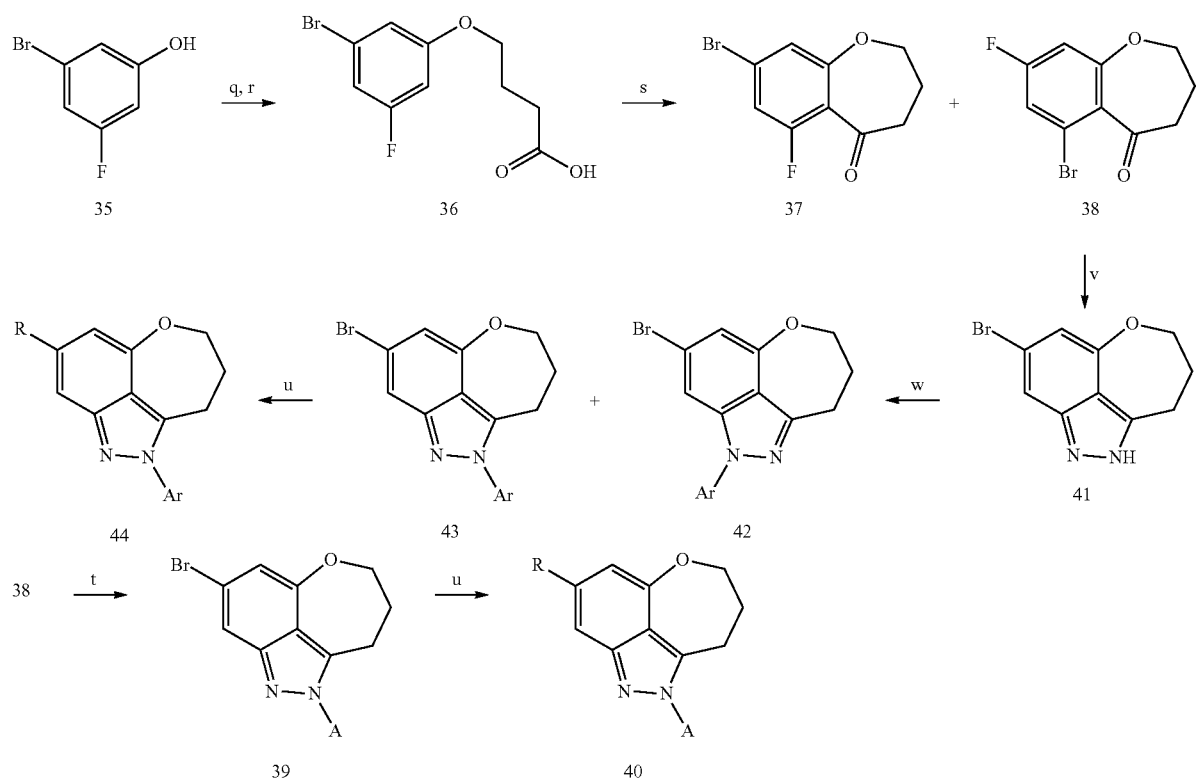

Scheme 9.

q) methyl 4-bromobutanate, potassium iodide, potassium carbonate, acetone, reflux; r) lithium hydroxide, methanol, water, 60° C.; s) i. thionyl chloride, DCM, ii. aluminum chloride, DCM, 0° C.; t) R—NHNH$_2$, pyridine, 60° C.; u) analogous steps from Schemes 1-5; v) hydrazine, diglyme, 120° C.; w) ArBr, copper(II) acetate, pyridine, 90° C.

As shown in Scheme 9, compound 35 may be alkylated and the methyl ester saponified to produce compound 36. Generation of the acid chloride followed by treatment with aluminum chloride may provide a mixture of compounds 37 and 38. Compound 37 may be treated with substituted hydrazines to afford compound 39, which may be carried forward to general compound 40 using analogous steps as shown in Schemes 1-5. Alternatively, compound 37 may be cyclized with hydrazine to afford compound 41. Copper-catalyzed coupling with aryl bromides may provide a mixture of compounds 42 and 43; when separated, compound 43 may be carried forward to general compound 44 using analogous steps as shown in Schemes 1-5.

-continued

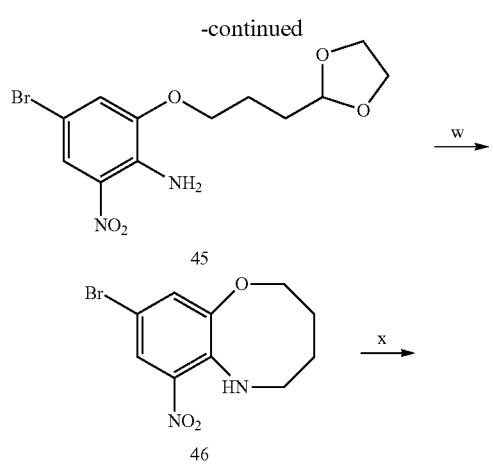

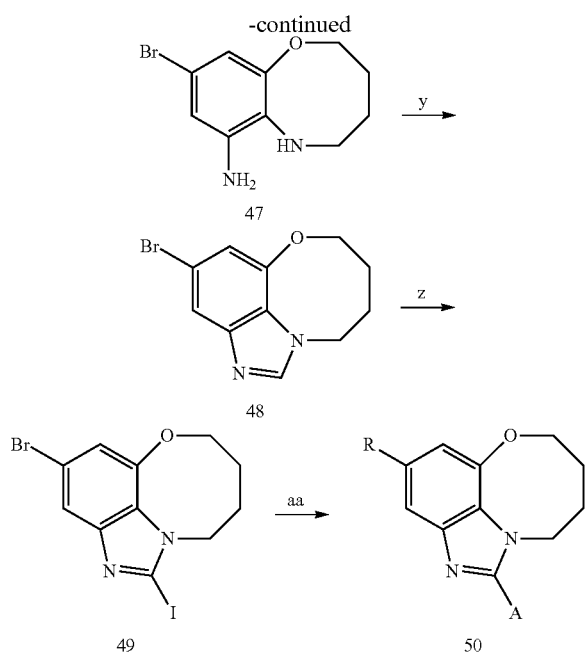

v) 2-(3-chloropropyl)-1,3-dioxolane, potassium carbonate, sodium iodide, DMF, 80° C.; w) TFA, triethylsilane, DCM, 0-25° C.; x) iron, ammonium chloride, methanol, water; y) trimethylorthoformate, p-toluenesulfonic acid, 100° C.; z) lithium diisopropylamide, N-iodosuccinimide, THF, -78° C.; aa) analogous steps from Schemes 1-5

As shown in Scheme 10, compound 2 may be alkylated to provide compound 45. Treatment with TFA and triethylsilane may afford compound 46. Reduction of the nitro group with iron followed by cyclization with trimethylorthoformate may provide compound 48. Treatment with lithium diisopropylamide followed by N-iodosuccinimide may afford compound 49. Conversion to general compound 50 may be effected using analogous steps as shown in Schemes 1-5.

EXAMPLES

Abbreviations

DCM dichloromethane
DIPEA N,N-diisopropylethylamine
DMF N,N-dimethylformamide
DMSO dimethyl sulfoxide
ESI electrospray ionization
h hour
HATU 1-[bis(dimethylamino)methylene]-1H-1,2,3-triazolo [4,5-b]pyridinium 3-oxid hexafluorophosphate
HPLC high pressure liquid chromatography
LCMS liquid chromatography mass spectrometry
LDA lithium diisopropyl amide
min minute
N Normal
NMR nuclear magnetic resonance
$R_T$ retention time
SFC super critical fluid chromatography
THF tetrahydrofuran
TFA trifluoroacetic acid
LCMS Methods LCMS Method A: Experiments performed on a Waters Micromass ZQ2000 quadrupole mass spectrometer linked to a Waters Acquity UPLC system with a PDA UV detector. The spectrometer has an electrospray source operating in positive and negative ion mode. This system uses an Acquity BEH C18 1.7 μm 100×2.1 mm column, maintained at 40° C. or an Acquity BEH Shield RP18 1.7 μm 100×2.1 mm column, maintained at 40° C. and a 0.4 mL/minute flow rate. The initial solvent system was 95% water containing 0.1% formic acid (solvent A) and 5% acetonitrile containing 0.1% formic acid (solvent B) for the first 0.4 minute followed by a gradient up to 5% solvent A and 95% solvent B over the next 5.6 minutes. This was maintained for 0.8 minutes before returning to 95% solvent A and 5% solvent B over the next 0.2 minutes. Total run time was 8 minutes.

LCMS Method B: Experiments performed on an Agilent 1100 HPLC coupled with Agilent MSD mass spectrometer using ESI as ionization source. The LC separation was using a Phenomenex XB-C18, 1.7 mm, 50×2.1 mm column with a 0.4 mL/minute flow rate. Solvent A is water with 0.1% formic acid and solvent B is acetonitrile with 0.1% formic acid. The gradient consisted with 2-98% solvent B over 7 minutes and hold 97% B for 1.5 minutes following equilibration for 1.5 minutes. LC column temperature is 40° C. UV absorbance was collected at 220 nm and 254 nm and mass spec full scan was applied to all experiments.

LCMS Method C: Experiments performed on an SHIMADZU 2020 HPLC coupled with SHIMADZU MSD mass spectrometer using ESI as ionization source. The LC separation was using a Shim-Pack XR-ODS-C18, 50×3.0 mm column with a 1 mL/minute flow rate. Solvent A is water with 0.05% TFA and solvent B is acetonitrile with 0.05% TFA. The gradient consisted with 5-100% solvent B over 2.2 minutes and hold 100% B for 1 minute. LC column temperature is 40° C. UV absorbance was collected from 190 nm to 400 nm and mass spec full scan was applied to all experiments.

LCMS Method D: Experiments performed on an SHIMADZU 2020 HPLC coupled with SHIMADZU MSD mass spectrometer using ESI as ionization source. The LC separation was conducted using a Gemini-NX 3μ C18 110A, 50×3.0 mm column with a 1.2 mL/minute flow rate. Solvent A is water with 0.4% $NH_4HCO_3$ and solvent B is acetonitrile. The gradient consisted with 10-50% solvent B over 4 minutes and hold 50% B for 1.2 minutes. LC column temperature is 40° C. UV absorbance was collected from 190 nm to 400 nm and mass spec full scan was applied to all experiments.

LCMS Method E: Experiments performed on an SHIMADZU UFLC-MS 2010EV coupled with SHIMADZU MSD mass spectrometer using ESI as ionization source. The LC separation was conducted using a Shim-pack XR-ODS-C18, 50×3.0 mm column with a 1 mL/minute flow rate. Solvent A is water with 0.05% TFA and solvent B is acetonitrile with 0.05% TFA. The gradient consisted with 5-100% solvent B over 2.2 minutes and hold 100% B for 1 minute. LC column temperature is 40° C. UV absorbance was collected from 190 nm to 400 nm and mass spec full scan was applied to all experiments.

LCMS Method F: Experiments performed on a Shimadzu LCMS-2020 coupled with SHIMADZU MSD mass spectrometer using ESI as ionization source. The LC separation was conducted on an Ascentis Express C18, 50×2.1 mm column with a 1 mL/minute flow rate. Solvent A is water with 0.05% TFA and solvent B is acetonitrile with 0.05% TFA. The gradient consisted with 5-95% solvent B over 2.0 minutes and hold 95% B for 0.7 minutes. LC column temperature is 40° C. UV absorbance was collected from 190 nm to 400 nm and mass spec full scan was applied to all experiments.

LCMS Method G: Experiments performed on a Shimadzu LCMS-2020 coupled with SHIMADZU MSD mass spectrometer using ESI as ionization source. The LC separation was using a Gemini-NX 3u C18 110A, 50×3.0 mm column with a 1.2 mL/minute flow rate. Solvent A is water with 0.05% $NH_4HCO_3$ and solvent B is acetonitrile. The gradient consisted with 95% solvent B over 2.2 minutes and hold 95% B for 1 minute. LC column temperature is 45° C. UV absorbance was collected from 190 nm to 400 nm and mass spec full scan was applied to all experiments.

Example 101 5-(4-Bromo-8,9-dihydro-7H-6-oxa-2, 9a-diazabenzo[cd]azulen-1-yl)benzo [d]oxazol 2-amine 101

Step 1: 2-Amino-5-bromo-3-nitrophenol

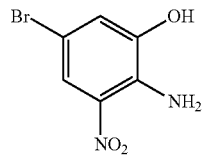 [SMILES: Nc1c(O)cc(Br)cc1[N+](=O)[O-]]

Bromine (51.9 g, 324 mmol) was added dropwise to a solution of 2-amino-3-nitrophenol (50.0 g, 324 mmol) in acetic acid at 25° C. and the reaction mixture was stirred at 25° C. overnight. The solids were collected by filtration to yield the crude title compound (84 g, 80% purity by LCMS, 89.1%) as a red solid which was used without further purification. LCMS (ESI): $[M+H]^+$=233/235.

Step 2: 4-Bromo-2-(3,3-dimethoxypropoxy)-6-nitrobenzenamine

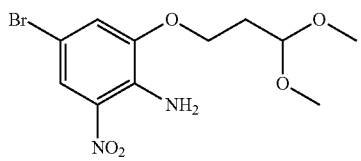 [SMILES: COC(CCOc1cc(Br)cc([N+](=O)[O-])c1N)OC]

A mixture of 2-amino-5-bromo-3-nitrophenol (93 g, 399 mmol), potassium carbonate (110 g, 797 mmol), potassium iodide (13.0 g, 78.3 mmol) and 3-bromo-1,1-dimethoxypropane (87.4 g, 478 mmol) in DMF (600 mL) was stirred for 4 h at 80° C. The reaction mixture was then cooled to room temperature and the resultant solid was filtered. The filtrate was diluted with water and extracted with ethyl acetate. The organic extracts were washed with brine then dried over anhydrous sodium sulfate and evaporated in vacuo. The resultant residue was purified via flash chromatography on silica gel (solvent gradient: 0-10% ethyl acetate in petroleum ether) to yield 110 g (82.7%) of the title compound as a yellow solid. $^1$H NMR (400 MHz, DMSO-$d_6$) δ 7.44 (d, J=2.4 Hz, 1H), 7.24 (s, 2H), 7.21 (d, J=2.0 Hz, 1H), 4.71-4.68 (m, 1H), 4.11-4.08 (m, 2H), 3.27 (s, 6H), 2.08-2.03 (m, 2H).

Step 3: 5-Bromo-3-(3, 3-dimethoxypropoxy)benzene-1,2-diamine

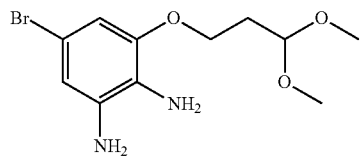

A mixture of 4-bromo-2-(3,3-dimethoxypropoxy)-6-nitrobenzenamine (30.0 g, 89.6 mmol), ammonium chloride (43.0 g, 811 mmol) and iron powder (30.0 g, 436 mmol) in methanol/water (150 mL/150 mL) was stirred for 2 h at 90° C. The solution was cooled to room temperature and the resultant solids were filtered. The filtrate was diluted with water and extracted with ethyl acetate. The organic extracts were combined, dried over anhydrous sodium sulfate and evaporated in vacuo. The residue was purified via flash chromatography on silica gel (solvent gradient: 0-50% ethyl acetate in petroleum ether) to yield 22 g (81.4%) of the title compound as a yellow solid. $^1$H NMR (400 MHz, DMSO-$d_6$) δ 6.40 (d, J=2.0 Hz, 1H), 6.32 (d, J=2.0 Hz, 1H), 4.79 (s, 2H), 4.66-4.63 (m, 1H), 4.13 (s, 2H), 3.92-3.89 (m, 2H), 3.26 (s, 6H), 1.99-1.94 (m, 2H).

Step 4: 8-Bromo-2,3,4,5-tetrahydrobenzo[b][1,4] oxazepin-6-amine

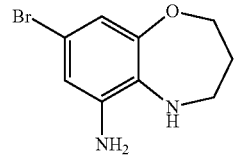

Trifluoroacetic acid (20 mL) and triethylsilane (3.20 g, 27.6 mmol) were added dropwise to a solution of 5-bromo-3-(3,3-dimethoxypropoxy)benzene-1,2-diamine (1.70 g, 5.57 mmol) in DCM (20 mL) at 0° C. while maintaining an inert atmosphere of nitrogen. The resulting solution was stirred for 10 min at 0° C. then a further 2 h at room temperature. The reaction mixture was evaporated in vacuo. The mixture was adjusted to pH 10 with aqueous sodium bicarbonate and then extracted with ethyl acetate. The organic extracts were combined, dried over anhydrous sodium sulfate and evaporated in vacuo. The residue was purified via flash chromatography on silica gel (solvent gradient: 0-20% ethyl acetate in petroleum ether) to yield 0.6 g (44.4%) of the title compound as an off-white solid. $^1$HNMR (300 MHz, DMSO-$d_6$) δ 6.46 (d, J=2.4 Hz, 1H), 6.26 (d, J=2.4 Hz, 1H), 5.01 (s, 2H), 4.37 (br, 1H), 3.98-3.94 (m, 2H), 3.09-3.04 (m, 2H), 1.87-1.79 (m, 2H).

Step 5: 4-Hydroxy-3-nitrobenzoyl chloride

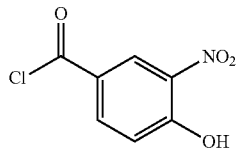 [SMILES: O=C(Cl)c1ccc(O)c([N+](=O)[O-])c1]

A mixture of 4-hydroxy-3-nitrobenzoic acid (1.83 g, 9.99 mmol) and thionyl chloride (1.1 mL, 15.2 mmol,) in 1,2-dimethoxyethane (20 mL) was stirred overnight at 80° C. The reaction mixture was evaporated in vacuo to yield the crude title compound which was used without further purification.

Step 6: N-(8-Bromo-2,3,4,5-tetrahydrobenzo[b][1,4]oxazepin-6-yl)-4-hydroxy-3-nitrobenzamide

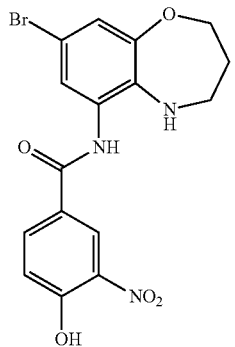 [SMILES: O=C(Nc1cc(Br)cc2c1NCCCO2)c1ccc(O)c([N+](=O)[O-])c1]

4-Hydroxy-3-nitrobenzoyl chloride (2.01 g crude) in THF (20 mL) was added dropwise to a solution of 8-bromo-2,3,4,5-tetrahydrobenzo[b][1,4]oxazepin-6-amine (2.42 g, 9.96 mmol) and triethylamine (1.21 g, 12.0 mmol) in THF (100 mL) at 0° C. The resulting solution was stirred for 1 h at room temperature then quenched by addition of water. The resulting solution was extracted with ethyl acetate and the organic layers combined and dried over anhydrous magnesium sulfate. The solids were filtered off, and the filtrate was evaporated in vacuo. The residue was purified via flash chromatography on silica gel (solvent gradient: 0-30% ethyl acetate in petroleum ether) to yield 3.0 g (73.8%) of the title compound as a yellow solid. LCMS (ESI): [M+H]$^+$=408/410.

Step 7: 4-(4-Bromo-8,9-dihydro-7H-6-oxa-2,9a-diazabenzo[cd]azulen-1-yl)-2-nitrophenol

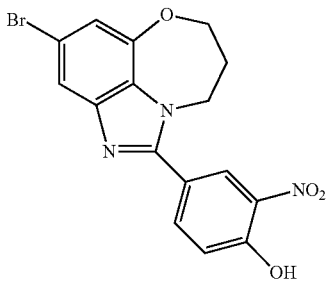 [SMILES: O=[N+]([O-])c1cc(-c2nc3cc(Br)cc4c3n2CCCO4)ccc1O]

A mixture of N-(8-bromo-2,3,4,5-tetrahydrobenzo[b][1,4]oxazepin-6-yl)-4-hydroxy-3-nitrobenzamide (3 g, 7.35 mmol) in acetic acid (50 mL) was stirred for 2 h at 90° C. The resulting mixture was evaporated in vacuo to yield 2.9 g of the crude title compound which was used without further purification. LCMS (ESI): [M+H]$^+$=390/392.

Step 8: 2-Amino-4-(4-bromo-8,9-dihydro-7H-6-oxa-2,9a-diazabenzo[cd]azulen-1-yl)phenol

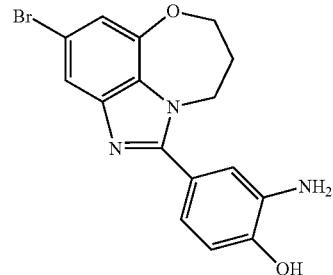 [SMILES: Nc1cc(-c2nc3cc(Br)cc4c3n2CCCO4)ccc1O]

A mixture of 4-(4-bromo-8,9-dihydro-7H-6-oxa-2,9a-diazabenzo[cd]azulen-1-yl)-2-nitrophenol (130 mg, 0.330 mmol) and iron powder (93.0 mg, 1.66 mmol) in AcOH (10 mL) was stirred for 2 h at 50° C. The resultant solids were removed by filtration. The filtrate was evaporated in vacuo to yield 250 mg of the crude title compound as a black solid which was used without further purification. LCMS (ESI): [M+H]$^+$=360/362.

Step 9: 5-(4-Bromo-8,9-dihydro-7H-6-oxa-2,9a-diazabenzo[cd]azulen-1-yl)benzo[d]oxazol-2-amine A mixture of 2-amino-4-(4-bromo-8,9-dihydro-7H-6-oxa-2,9a-diazabenzo[cd]azulen-1-yl) phenol (250 mg, crude) and cyanogen bromide (147 mg, 1.39 mmol) in methanol/water (15 mL/5 mL) was stirred for 2 h at room temperature. The reaction mixture was extracted with ethyl acetate. The organic extracts were combined, dried over anhydrous magnesium sulfate, and evaporated in vacuo. The residue was purified via flash chromatography on silica gel (solvent gradient: 0-5% methanol in DCM) to yield 98 mg (76.5% over two steps) of 101 as a yellow solid. LCMS (ESI): R$_T$ (min)=2.69, [M+H]$^+$=385/387, method=D; $^1$H NMR (300 MHz, DMSO-d$_6$) δ 7.59-7.57 (m, 3H), 7.51-7.36 (m, 3H), 6.89 (s, 1H), 4.45-4.42 (m, 2H), 4.33-4.29 (m, 2H), 2.38-2.25 (m, 2H).

Example 102 4-bromo-1-(2-methyloxazolo[4,5-b]pyridin-5-yl)-8,9-dihydro-7H-6-oxa-2,9a-diazabenzo[cd]azulene 102

Following the procedures herein, 102 was prepared. [M+H]$^+$=385.10

Example 103 1-(1-(2-methylbenzo[d]oxazol-5-yl)-8,9-dihydro-7H-6-oxa-2,9a-diazabenzo[cd]azulen-4-yl)pyrrolidine-2-carboxamide 103. [M+H]$^+$=418.18

Following the procedures herein, 103 was prepared. [M+H]$^+$=385

Example 104 (S)-1-(1-(2-Aminobenzo[d]oxazol-5-yl)-8,9-dihydro-7H-6-oxa-2,9a-diazabenzo[cd]azulen-4-yl)pyrrolidine-2-carboxamide 104

Step 1: (S)-1-(1-(2-Aminobenzo[d]oxazol-5-yl)-8,9-dihydro-7H-6-oxa-2,9a-diazabenzo[cd]azulen-4-yl)pyrrolidine-2-carboxylic acid

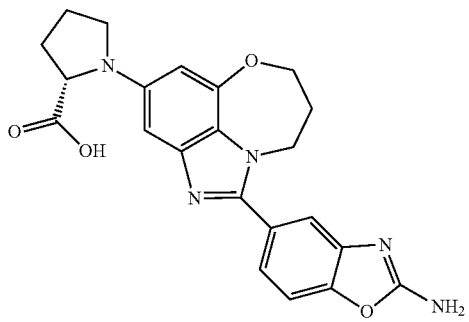 [SMILES: Nc1nc2cc(-c3nc4cc(N5CCC[C@H]5C(=O)O)cc5c4n3CCCO5)ccc2o1]

A mixture of 5-(4-bromo-8,9-dihydro-7H-6-oxa-2,9a-diazabenzo[cd]azulen-1-yl)benzo[d]oxazol-2-amine (50.0 mg, 0.130 mmol), (S)-pyrrolidine-2-carboxylic acid (75.0 mg, 0.651 mmol), copper(I) iodide (8.00 mg, 0.0420 mmol) and potassium phosphate tribasic (193 mg, 0.909 mmol) in DMSO (2 mL) was heated under microwave irradiation for 90 min at 120° C. The solids were removed by filtration and the brown filtrate was used without purification. LCMS (ESI): [M+H]$^+$=420.

Step 2: (S)-1-(1-(2-Aminobenzo[d]oxazol-5-yl)-8,9-dihydro-7H-6-oxa-2,9a-diazabenzo[cd]azulen-4-yl)pyrrolidine-2-carboxamide A mixture of (S)-1-(1-(2-aminobenzo[d]oxazol-5-yl)-8,9-dihydro-7H-6-oxa-2,9a-diazabenzo[cd]azulen-4-yl)pyrrolidine-2-carboxylic acid (crude), ammonium chloride (135 mg, 2.52 mmol), HATU (193 mg, 0.508 mmol) and DIPEA (707 mg, 5.47 mmol) in DMSO (2 mL) was stirred for 2 h at room temperature. The reaction solution was diluted with water, and then extracted with ethyl acetate. The organic extracts were combined and evaporated in vacuo. The resulting residue was purified via reverse-phase HPLC and lyophilized to yield 9.9 mg (18.2% over two steps) of 104 as a white solid. LCMS (ESI): R$_T$ (min)=2.00, [M+H]$^+$=419, method=C; $^1$H NMR (400 MHz, DMSO-d$_6$) δ 7.56-7.54 (m, 3H), 7.47 (d, J=8.0 Hz, 1H), 7.36 (d, J=8.4 Hz, 1H), 7.29 (s, 1H), 7.02 (s, 1H), 6.36 (s, 1H), 6.07 (s, 1H), 4.36-4.34 (m, 2H), 4.25-4.22 (m, 2H), 3.85-3.83 (m, 1H), 3.60-3.57 (m, 1H), 3.25-3.10 (m, 1H), 2.26-2.19 (m, 3H), 2.03-1.92 (m, 3H).

Example 105 (S)-2-((1-(2-Aminobenzo[d]oxazol-5-yl)-8,9-dihydro-7H-6-oxa-2,9a-diazabenzo[cd]azulen-4-yl)amino)propanamide 105

Step 1: (S)-2-((1-(2-Aminobenzo[d]oxazol-5-yl)-8,9-dihydro-7H-6-oxa-2,9a-diazabenzo[cd]azulen-4-yl)amino)propanoic acid and (R)-2-((1-(2-Aminobenzo[d]oxazol-5-yl)-8,9-dihydro-7H-6-oxa-2,9a-diazabenzo[cd]azulen-4-yl)amino)propanoic acid

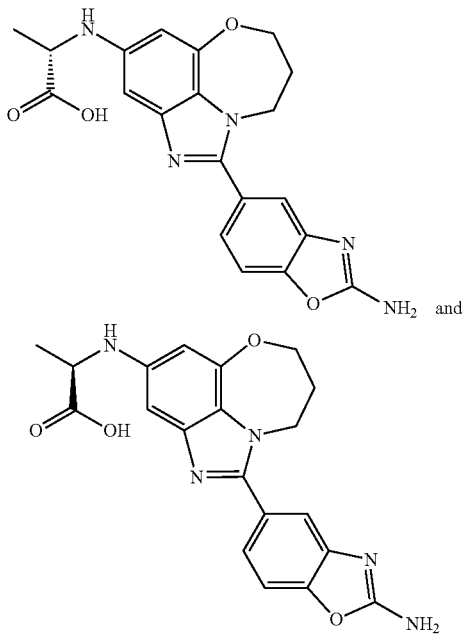

The title compounds 200 mg (crude) were generated as a mixture of major (S) and minor (R) stereoisomers from 5-(4-bromo-8,9-dihydro-7H-6-oxa-2,9a-diazabenzo[cd]azulen-1-yl)benzo[d]oxazol-2-amine from Example 101 (300 mg, 0.779 mmol) and (S)-2-aminopropanoic acid (347 mg, 3.89 mmol) following a procedure analogous to Example 104, step 1. LCMS (ESI): [M+H]$^+$=394.

Step 2: (S)-2-((1-(2-Aminobenzo[d]oxazol-5-yl)-8,9-dihydro-7H-6-oxa-2,9a-diazabenzo[cd]azulen-4-yl)amino)propanamide and (R)-2-((1-(2-Aminobenzo[d]oxazol-5-yl)-8,9-dihydro-7H-6-oxa-2,9a-diazabenzo[cd]azulen-4-yl)amino)propanamide The title compounds 95 mg (31% over two steps) of (S)-2-((1-(2-aminobenzo[d]oxazol-5-yl)-8,9-dihydro-7H-6-oxa-2,9a-diazabenzo[cd]azulen-4-yl)amino)propanamide 105 and 40 mg (13.1% over two steps) of (R)-2-((1-(2-aminobenzo[d]oxazol-5-yl)-8,9-dihydro-7H-6-oxa-2,9a-diazabenzo[cd]azulen-4-yl)amino) propanamide 107 (Example 107) were generated from (S)-2-((1-(2-aminobenzo[d]oxazol-5-yl)-8,9-dihydro-7H-6-oxa-2,9a-diazabenzo[cd]azulen-4-yl)amino)propanoic acid (200 mg crude) following a procedure analogous to Example 104, step 2 and the two stereoisomers were separated by chiral-HPLC. 105: LCMS (ESI): R$_T$ (min)=1.99, [M+H]$^+$=393, method=D; $^1$H NMR (300 MHz, DMSO-d$_6$) δ 7.55 (s, 2H), 7.51 (s, 1H), 7.45 (d, J=8.1 Hz, 1H), 7.32 (d, J=8.1 Hz, 1H), 7.29 (s, 1H), 6.94 (s, 1H), 6.37 (s, 1H), 6.20 (s, 1H), 5.42 (d, J=7.5 Hz, 1H), 4.33-4.31 (m, 2H), 4.21-4.18 (m, 2H), 3.75-3.70 (m, 1H), 2.17-2.32 (m, 2H), 1.31 (d, J=6.9 Hz, 3H).

Example 106 (S)-2-((1-phenyl-8,9-dihydro-7H-6-oxa-2,9a-diazabenzo[cd]azulen-4-yl)amino)propanamide 106

Step 1: (S)-2-(4-Amino-3-(3,3-dimethoxypropoxy)-5-nitrophenylamino)propanoic acid

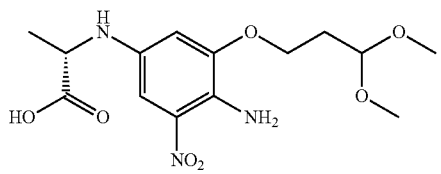 [SMILES: COC(CCOc1cc(N[C@@H](C)C(=O)O)cc([N+](=O)[O-])c1N)OC]

A mixture of 4-bromo-2-(3,3-dimethoxypropoxy)-6-nitrobenzenamine (2 g, 5.97 mmol), copper(I) iodide (340 mg, 1.79 mmol), potassium phosphate tribasic (7.59 g, 35.8 mmol) and (S)-2-aminopropanoic acid (2.66 g, 29.9 mmol) in DMSO (20 mL) was placed in a tube and the mixture degassed with nitrogen under sonication. The tube was sealed, and stirred for 16 h at 90° C. The resultant solids were filtered and the brown filtrate was used without purification. LCMS (ESI): [M+H]$^+$=344.

Step 2: (S)-2-(4-Amino-3-(3,3-dimethoxypropoxy)-5-nitrophenylamino)propanamide

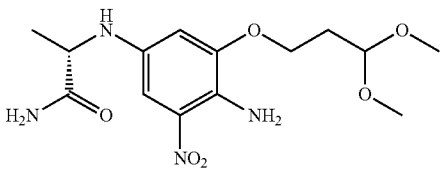 [SMILES: COC(CCOc1cc(N[C@@H](C)C(N)=O)cc([N+](=O)[O-])c1N)OC]

A mixture of (S)-2-(4-amino-3-(3,3-dimethoxypropoxy)-5-nitrophenylamino)propanoic acid (crude), ammonium chloride (4.62 g, 86.4 mmol), HATU (4.42 g, 11.6 mmol) and DIPEA (15.0 g, 116 mmol) in DMSO (20 mL) was stirred for 1 h at room temperature. The reaction mixture was diluted with water and extracted with ethyl acetate. The organic extracts were combined, washed with brine, and evaporated in vacuo. The residue was purified via flash chromatography on silica gel (solvent gradient: 0-5% methanol in DCM) to yield 800 mg (39.2% over two steps) of the title compound as a red solid. $^1$H NMR (400 MHz, DMSO-d$_6$) δ 7.39 (s, 1H), 6.99 (s, 1H), 6.73-6.69 (m, 3H), 6.53 (s, 1H), 5.57-5.55 (m, 1H), 4.69 (t, J=5.6 Hz, 1H), 4.01-3.98 (m, 2H), 3.71-3.68 (m, 1H), 3.28 (s, 6H), 2.09-2.05 (m, 2H), 1.27 (d, J=6.8 Hz, 3H).

Step 3: (S)-2-(6-Nitro-2,3,4,5-tetrahydrobenzo[b][1,4]oxazepin-8-ylamino) propanamide

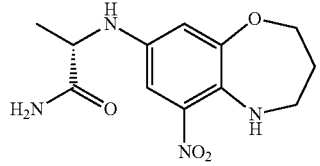

Trifluoroacetic acid (5 mL, 67.3 mmol) and triethylsilane (676 mg, 5.81 mmol) were added dropwise to a solution of (S)-2-(4-amino-3-(3,3-dimethoxypropoxy)-5-nitrophenylamino)propanamide (400 mg, 1.17 mmol) in DCM (20 mL) at 0° C. and the reaction mixture was stirred at 0° C. for 10 min. The mixture was evaporated in vacuo and the pH value was adjusted to 8 with aqueous sodium bicarbonate and the resulting solution was extracted with ethyl acetate. The organic extracts were combined, dried over anhydrous sodium sulfate and evaporated in vacuo to yield 140 mg of the crude title compound as a purple solid which was used without further purification. $^1$H NMR (300 MHz, DMSO-d$_6$) δ 7.48-7.46 (m, 1H), 7.39 (s, 1H), 6.99 (s, 1H), 6.78 (s, 1H), 6.65 (s, 1H), 5.74 (d, J=7.2 Hz, 1H), 4.17-4.06 (m, 2H), 3.68-3.52 (m, 1H), 3.49-3.32 (m, 2H), 2.03-1.95 (m, 2H), 1.25 (d, J=6.8 Hz, 3H).

Step 4: (S)-2-(6-Amino-2,3,4,5-tetrahydrobenzo[b][1,4]oxazepin-8-ylamino) propanamide

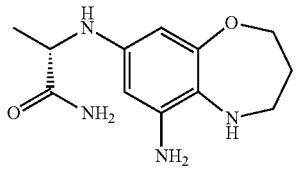 [SMILES: C[C@H](Nc1cc(N)c2c(c1)OCCCN2)C(N)=O]

Pd (10 mg, 10 wt % on carbon) was added to a solution of (S)-2-(6-nitro-2,3,4,5-tetrahydrobenzo[b][1,4] oxazepin-8-ylamino)propanamide (70.0 mg, 0.250 mmol) in ethanol (20 mL) and the reaction mixture was stirred under a balloon of hydrogen for 16 h at room temperature. The reaction mixture was filtered and the filtrate was evaporated in vacuo to yield 62 mg of the crude title compound which was used without further purification. LCMS (ESI): [M+H]$^+$=251.

Step 5: (S)—N-(8-(1-Amino-1-oxopropan-2-ylamino)-2,3,4,5-tetrahydrobenzo[b][1,4]oxazepin-6-yl)benzamide

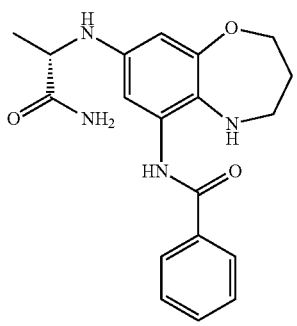 [SMILES: C[C@H](Nc1cc(NC(=O)c2ccccc2)c2c(c1)OCCCN2)C(N)=O]

Benzoyl chloride (34.8 mg, 0.248 mmol) in THF (1 mL) was added dropwise to a solution of crude (S)-2-(6-amino-2,3,4,5-tetrahydrobenzo[b][1,4]oxazepin-8-ylamino)propanamide (62 mg, 0.248 mmol) and triethylamine (74.8 mg, 0.739 mmol) in THF (20 mL) at 0° C. The reaction mixture stirred at 0° C. for 10 min, and then evaporated in vacuo to yield 87 mg of the crude title compound which was used without purification. LCMS (ESI): [M+H]$^+$=355.

Step 6: (S)-2-((1-Phenyl-8,9-dihydro-7H-6-oxa-2,9a-diazabenzo[cd]azulen-4-yl)amino)propanamide A mixture of crude (S)—N-(8-(1-amino-1-oxopropan-2-ylamino)-2,3,4,5-tetrahydrobenzo[b][1,4]oxazepin-6-yl)benzamide (87 mg) and acetic acid (5 mL) was stirred for 2 h at 90° C. The reaction mixture was evaporated in vacuo. The resulting residue was purified via reverse-phase HPLC and lyophilized to yield 13.8 mg (16.2% over three steps) of 106 as an off-white solid. LCMS (ESI): $R_T$ (min)=1.23, [M+H]$^+$=337, method=C; $^1$H NMR (300 MHz, DMSO-d$_6$) δ 7.76-7.73 (m, 2H), 7.57-7.49 (m, 3H), 7.28 (s, 1H), 6.94 (s, 1H), 6.38 (s, 1H), 6.22 (s, 1H), 5.45 (d, J=7.2 Hz, 1H), 4.33-4.31 (m, 2H), 4.22-4.19 (m, 2H), 3.77-3.68 (m, 1H), 2.30-2.17 (m, 2H), 1.32 (d, J=6.9 Hz, 3H).

Example 107 (R)-2-((1-(2-Aminobenzo[d]oxazol-5-yl)-8,9-dihydro-7H-6-oxa-2,9a-diazabenzo[cd]azulen-4-yl)amino)propanamide 107

Following the procedures of Example 105, 107 was prepared. LCMS (ESI): $R_T$ (min)=1.22, [M+H]$^+$=393, method=D; $^1$H NMR (300 MHz, DMSO-d$_6$) δ 7.55 (s, 2H), 7.51 (s, 1H), 7.45 (d, J=8.1 Hz, 1H), 7.32 (d, J=8.1 Hz, 1H), 7.29 (s, 1H), 6.94 (s, 1H), 6.37 (s, 1H), 6.20 (s, 1H), 5.42 (d, J=7.5 Hz, 1H), 4.33-4.31 (m, 2H), 4.21-4.18 (m, 2H), 3.75-3.70 (m, 1H), 2.17-2.32 (m, 2H), 1.31 (d, J=6.9 Hz, 3H).

Example 108 (S)-2-((1-(Pyridin-3-yl)-8,9-dihydro-7H-6-oxa-2,9a-diazabenzo[cd]azulen-4-yl)amino)propanamide 108

Following the procedures of Example 125, 108 was prepared. LCMS (ESI): $R_T$ (min)=1.83, [M+H]$^+$=338, method=G; $^1$H NMR (300 MHz, DMSO-d$_6$) δ 8.95 (s, 1H), 8.70 (d, J=4.9 Hz, 1H), 8.20-8.16 (m, 1H), 7.59-7.54 (m, 1H), 7.29 (s, 1H), 6.94 (s, 1H), 6.40 (d, J=2.0 Hz, 1H), 6.25 (d, J=2.0 Hz, 1H), 5.49 (d, J=4.5 Hz, 1H), 4.35-4.32 (m, 2H), 4.27-4.24 (m, 2H), 3.78-3.68 (m, 1H), 2.35-2.20 (m, 2H), 1.32 (d, J=6.8 Hz, 3H).

Example 109 (S)-2-((1-(pyrimidin-4-yl)-8,9-dihydro-7H-6-oxa-2,9a-diazabenzo[cd]azulen-4-yl)amino)propanamide 109

Following the procedures of Example 125, 109 was prepared. LCMS (ESI): $R_T$ (min)=1.79, [M+H]$^+$=339.1, method=D; $^1$H NMR (400 MHz, DMSO-d$_6$) δ 9.31 (s, 1H), 8.94 (d, J=5.2 Hz, 1H), 8.26 (d, J=6.8 Hz, 1H), 7.34 (s, 1H), 6.96 (s, 1H), 6.40 (s, 1H), 6.36 (s, 1H,), 5.66 (d, J=7.2 Hz, 1H), 4.87-4.76 (m, 2H), 4.44-4.35 (m, 2H), 3.77-3.73 (m, 1H), 2.20-2.40 (m, 2H), 1.32 (d, J=6.8 Hz, 3H).

Example 110 (S)-2-((1-(5-Cyanopyridin-2-yl)-8,9-dihydro-7H-6-oxa-2,9a-diazabenzo[cd]azulen-4-yl)amino)propanamide 110

Following the procedures of Example 125, 110 was prepared. LCMS (ESI): $R_T$ (min)=2.18, [M+H]$^+$=363.1, method=D; $^1$H NMR (400 MHz, DMSO-d$_6$) δ 9.21 (s, 1H), 8.44-8.39 (m, 2H), 7.33 (s, 1H), 6.96 (s, 1H), 6.44 (s, 1H), 6.40 (s, 1H), 5.64 (d, J=7.2 Hz, 1H), 4.81-4.78 (m, 2H), 4.45-4.36 (m, 2H), 3.78-3.71 (m, 1H), 2.20-2.40 (m, 2H), 1.33 (d, J=6.8 Hz, 3H)

Example 111 (S)-2-((1-(6-Methoxypyridin-3-yl)-8,9-dihydro-7H-6-oxa-2,9a-diazabenzo[cd]azulen-4-yl)amino)propanamide 111

Following the procedures of Example 125, 111 was prepared. LCMS (ESI): $R_T$ (min)=1.96, [M+H]$^+$=368, method=D; $^1$H NMR (400 MHz, DMSO-d$_6$) δ 8.55 (s, 1H), 8.09 (d, J=10.8 Hz, 1H), 7.28 (s, 1H), 6.99-6.93 (m, 2H), 6.37 (s, 1H), 6.22 (s, 1H), 5.45 (d, J=7.2 Hz, 1H), 4.33-4.31 (m, 2H), 4.27-4.17 (m, 2H), 3.93 (s, 3H), 3.75-3.69 (m, 1H), 2.15-2.35 (m, 2H), 1.31 (d, J=6.8 Hz, 3H)

Example 112 (S)-2-((1-(Pyridin-2-yl)-8,9-dihydro-7H-6-oxa-2,9a-diazabenzo[cd]azulen-4-yl)amino)propanamide 112

Following the procedures of Example 125, 112 was prepared. LCMS (ESI): $R_T$ (min)=1.13, [M+H]$^+$=338, method=E; $^1$H NMR (300 MHz, DMSO-d$_6$) δ 8.70 (d, J=4.2 Hz, 1H), 8.20 (d, J=7.8 Hz, 1H), 7.99-7.36 (m, 1H), 7.50-7.45 (m, 1H), 7.31 (s, 1H), 6.95 (s, 1H), 6.39 (d, J=2.1 Hz, 1H), 6.26 (d, J=1.8 Hz, 1H), 5.52 (d, J=7.2 Hz, 1H), 4.77-4.73 (m, 2H), 4.35-4.32 (m, 2H), 3.78-3.69 (m, 1H), 2.20-2.40 (m, 2H), 1.31 (d, J=6.9 Hz, 3H)

Example 113 (S)-2-Cyclopropyl-2-((1-(2,2-difluorobenzo[d][1,3]dioxol-5-yl)-8,9-dihydro-7H-6-oxa-2,9a-diazabenzo[cd]azulen-4-yl)amino)acetamide 113

Following the procedures of Example 125, 113 was prepared. LCMS (ESI): $R_T$ (min)=2.55, [M+H]$^+$=443, method=C; $^1$H NMR (400 MHz, DMSO-d$_6$) δ 7.82 (s, 1H), 7.66-7.54 (m, 2H), 7.34 (s, 1H), 6.96 (s, 1H), 6.38 (s, 1H), 6.27 (s, 1H), 5.51 (d, J=7.4 Hz, 1H), 4.34-4.31 (m, 2H), 4.23-4.20 (m, 2H), 3.16-3.12 (m, 1H), 2.15-2.35 (m, 2H), 1.13-1.08 (m, 1H), 0.58-0.42 (m, 3H), 0.36-0.26 (m, 1H)

Example 114 (S)-2-((1-(Benzo[d][1,3]dioxol-5-yl)-8,9-dihydro-7H-6-oxa-2,9a-diazabenzo[cd]azulen-4-yl)amino)-2-cyclopropylacetamide 114

Following the procedures of Example 125, 114 was prepared. LCMS (ESI): $R_T$ (min)=2.55, [M+H]$^+$=407, method=D; $^1$H NMR (400 MHz, DMSO-d$_6$) δ 7.33 (s, 1H), 7.29 (s, 1H), 7.25-7.22 (d, J=9.6 Hz, 1H), 7.07 (d, J=8.0 Hz, 1H), 6.96 (s, 1H), 6.36 (s, 1H), 6.23 (s, 1H), 6.13 (s, 2H), 5.45 (d, J=7.4 Hz, 1H), 4.32-4.30 (m, 2H), 4.20-4.17 (m, 2H), 3.16-3.12 (m, 1H), 2.15-2.30 (m, 2H), 1.13-1.08 (m, 1H), 0.52-0.46 (m, 3H), 0.32-0.29 (m, 1H)

Example 115 (S)-2-Cyclopropyl-2-((1-(3-oxoisoindolin-5-yl)-8,9-dihydro-7H-6-oxa-2,9a-diazabenzo[cd]azulen-4-yl)amino)acetamide 115

Following the procedures of Example 125, 115 was prepared. LCMS (ESI): $R_T$ (min)=1.16, [M+H]$^+$=418, method=E; $^1$H NMR (300 MHz, DMSO-d$_6$) δ 8.72 (s, 1H), 8.01-7.97 (m, 2H), 7.77-7.74 (d, J=8.4 Hz, 1H), 7.35 (s, 1H), 6.97 (s, 1H), 6.41 (d, J=1.8 Hz, 1H), 6.28 (d, J=2.1 Hz, 1H), 5.50 (d, J=7.5 Hz, 1H), 4.49 (s, 2H), 4.37-4.34 (m, 2H), 4.27-4.24 (m, 2H), 3.19-3.15 (m, 1H), 2.15-2.35 (m, 2H), 1.17-1.09 (m, 1H), 0.54-0.45 (m, 3H), 0.36-0.30 (m, 1H)

Example 116 (S)-2-Cyclopropyl-2-((1-(quinazolin-7-yl)-8,9-dihydro-7H-6-oxa-2,9a-diazabenzo [cd]azulen-4-yl)amino)acetamide 116

Step 1: Methyl quinazoline-7-carboxylate

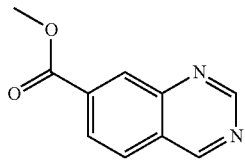

Carbon monoxide was passed into a solution of 7-bromoquinazoline (250 mg, 1.20 mmol), sodium carbonate (320 mg, 2.96 mmol) and [1,1'-bis(diphenylphosphino)ferrocene]palladium(II) chloride (90.0 mg, 0.120 mmol) in methanol (10 ml). The reaction mixture was stirred at 60° C. for 2.5 h, and then evaporated in vacuo. The residue was purified via flash chromatography on silica gel (solvent gradient: 0-10% methanol in DCM) to yield 180 mg (80%) of the title compound as an off-white solid. $^1$H NMR (300 MHz, DMSO-d$_6$) δ 9.78 (s, 1H), 9.44 (s, 1H), 8.55 (s, 1H), 8.35-8.32 (d, J=8.4 Hz, 1H), 8.25-8.22 (d, J=8.7 Hz, 1H), 3.98 (s, 3H).

Step 2: Quinazoline-7-carboxylic acid

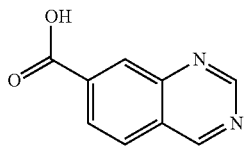 [SMILES: O=C(O)c1ccc2cncnc2c1]

A mixture of methyl quinazoline-7-carboxylate (180 mg, 0.900 mmol), lithium hydroxide (70.0 mg, 2.70 mmol), water (5 mL) and THF (15 mL) was stirred at room temperature for 2 h. The reaction mixture was evaporated in vacuo. The residue was dissolved in water (10 mL) and the pH was adjusted to 2 with acetic acid. The resulting precipitate was collected by filtration to yield 150 mg (98%) of the title compound as off-white solid. LCMS (ESI): [M−H]$^−$=173.

Step 3: N-(8-Bromo-2,3,4,5-tetrahydrobenzo[b][1,4]oxazepin-6-yl)quinazoline-7-carboxamide

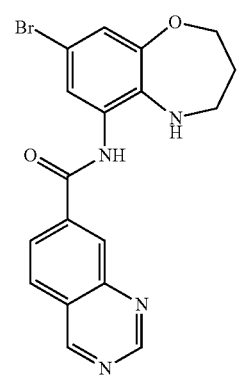 [SMILES: O=C(Nc1cc(Br)cc2c1NCCCO2)c1ccc2cncnc2c1]

The title compound (crude) was generated from 8-bromo-2,3,4,5-tetrahydrobenzo[b][1,4]oxazepin-6-amine from Example 101 (188 mg, 0.770 mmol) and quinazoline-7-carboxylic acid (150 mg, 0.860 mmol) following a procedure analogous to Example 125, step 1. LCMS (ESI): [M+H]$^+$=399/401.

Step 4: 4-Bromo-1-(quinazolin-7-yl)-8,9-dihydro-7H-6-oxa-2,9a-diazabenzo[cd]azulene

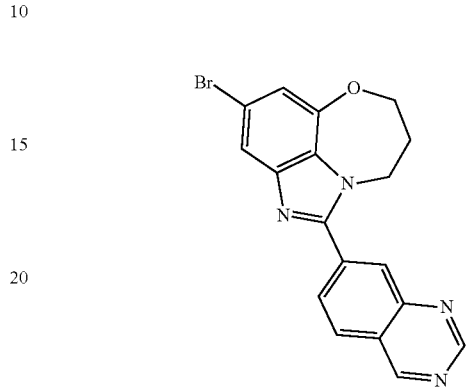

The title compound (160 mg, 54% yield over 2 steps) was generated from N-(8-bromo-2,3,4,5-tetrahydrobenzo[b][1,4]oxazepin-6-yl)quinazoline-7-carboxamide (crude) following a procedure analogous to Example 125, step 2. LCMS (ESI): [M+H]$^+$=381/383.

Step 5: (S)-2-Cyclopropyl-2-((1-(quinazolin-7-yl)-8,9-dihydro-7H-6-oxa-2,9a-diazabenzo[cd]azulen-4-yl)amino)acetamide The title compound (50.3 mg, 36% yield) was generated from 4-bromo-1-(quinazolin-7-yl)-8,9-dihydro-7H-6-oxa-2,9a-diazabenzo[cd]azulene (140 mg, 0.370 mmol) following a procedure analogous to Example 125, steps 3-4. 116: LCMS (ESI): R$_T$ (min)=1.98, [M+H]$^+$=415, method=D; $^1$H NMR (400 MHz, DMSO-d$_6$) δ 9.72 (s, 1H), 9.39 (s, 1H), 8.38 (s, 1H), 8.31 (d, J=8.4 Hz, 1H), 8.20 (d, J=8.0 Hz, 1H), 7.37 (s, 1H), 6.98 (s, 1H), 6.43 (s, 1H), 6.33 (s, 1H), 5.57 (d, J=7.2 Hz, 1H), 4.39-4.38 (m, 4H), 3.19-3.15 (m, 1H), 2.40-2.20 (m, 2H), 1.24-1.11 (m, 1H), 0.58-0.43 (m, 3H), 0.37-0.25 (m, 1H).

Example 117 (S)-2-Cyclopropyl-2-((1-(quinoxalin-6-yl)-8,9-dihydro-7H-6-oxa-2,9a-diazabenzo[cd]azulen-4-yl)amino)acetamide 117

Following the procedures of Example 125, 117 was prepared. LCMS (ESI): R$_T$ (min)=2.21, [M+H]$^+$=415, method=D; $^1$H NMR (300 MHz, DMSO-d$_6$) δ 9.05-9.03 (m, 2H), 8.47 (d, J=1.5 Hz, 1H), 8.30-8.22 (m, 2H), 7.36 (s, 1H), 6.98 (s, 1H), 6.43 (d, J=1.8 Hz, 1H), 6.31 (d, J=2.1 Hz, 1H), 5.55 (d, J=7.2 Hz, 1H), 4.39-4.36 (m, 4H), 3.19-3.19-3.14 (m, 1H), 2.20-2.40 (m, 2H), 1.15-1.08 (m, 1H), 0.54-0.50 (m, 3H), 0.36-0.27 (m, 1H)

Example 118 (S)-2-((1-(3-Cyanophenyl)-8,9-dihydro-7H-6-oxa-2,9a-diazabenzo[cd]azulen-4-yl)amino)-2-cyclopropylacetamide 118

Following the procedures of Example 125, 118 was prepared. LCMS (ESI): R$_T$ (min)=1.36, [M+H]$^+$=388, method=D; $^1$H NMR (400 MHz, DMSO-d$_6$) δ 8.24 (s, 1H), 8.12-8.10 (m, 1H), 8.01-7.98 (m, 1H), 7.78-7.74 (m, 1H), 7.35 (s, 1H), 6.97 (s, 1H), 6.39 (s, 1H), 6.29 (s, 1H), 5.54 (d, J=7.6 Hz, 1H), 4.35-4.32 (m, 2H), 4.27-4.23 (m, 3H), 3.17-3.13 (m, 1H), 2.29-2.26 (m, 2H), 1.13-1.10 (m, 1H), 0.52-0.47 (m, 3H), 0.33-0.30 (m, 1H)

Example 119 (S)-2-Cyclopropyl-2-((1-(quinazolin-6-yl)-8,9-dihydro-7H-6-oxa-2,9a-diazabenzo[cd]azulen-4-yl)amino)acetamide 119

Following the procedures of Example 116, 119 was prepared. LCMS (ESI): $R_T$ (min)=1.95, [M+H]$^+$=415, method=D; $^1$H NMR (300 MHz, DMSO-$d_6$) δ 9.73 (s, 1H), 9.38 (s, 1H), 8.62 (s, 1H), 8.46-8.43 (d, J=9.0 Hz, 1H), 8.15 (d, J=8.8 Hz, 1H), 7.36 (s, 1H), 6.98 (s, 1H), 6.42 (d, J=2.0 Hz, 1H), 6.30 (d, J=2.0 Hz, 1H), 5.55 (d, J=7.4 Hz, 1H), 4.45-4.30 (m, 4H), 3.18-3.13 (m, 1H), 2.31-2.30 (m, 2H), 1.16-1.09 (m, 1H), 0.60-0.40 (m, 3H), 0.34-0.29 (m, 1H)

Example 120 (S)-2-Cyclopropyl-2-((1-(quinazolin-6-yl)-8,9-dihydro-7H-6-oxa-2,9a-diazabenzo[cd]azulen-4-yl)amino)acetamide 120

Following the procedures of Example 116, 120 was prepared. LCMS (ESI): $R_T$ (min)=1.11, [M+H]$^+$=430, method=D; $^1$H NMR (300 MHz, DMSO-$d_6$) δ 9.21 (s, 1H), 8.22 (s, 1H), 8.07 (d, J=8.7 Hz, 1H), 7.51 (d, J=8.8 Hz, 1H), 7.34 (s, 1H), 7.07 (s, 2H), 6.96 (s, 1H), 6.38 (s, 1H), 6.25 (s, 1H), 5.49 (d, J=7.4 Hz, 1H), 4.36-4.30 (m, 4H), 3.17-3.11 (m, 1H), 2.38-2.20 (m, 2H), 1.12-1.10 (m, 1H), 0.53-0.47 (m, 3H), 0.33-0.31 (m, 1H)

Example 121 (S)-2-Cyclopropyl-2-((1-(2-methoxy-6-methylpyrimidin-4-yl)-8,9-dihydro-7H-6-oxa-2,9a-diazabenzo[cd]azulen-4-yl)amino)acetamide 121

Following the procedures of Example 125, 121 was prepared. LCMS (ESI): $R_T$ (min)=2.22, [M+H]$^+$=409, method=C; $^1$H NMR (300 MHz, DMSO-$d_6$): δ 7.80 (s, 1H), 7.36 (br, 1H), 6.97 (br, 1H), 6.38-6.35 (m, 2H), 5.65 (d, J=7.2 Hz, 1H), 4.86-4.82 (m, 2H), 4.39-4.30 (m, 2H), 3.97 (s, 3H), 3.15-3.10 (m, 1H), 2.49 (s, 3H), 2.34-2.30 (m, 2H), 1.16-1.08 (m, 1H), 0.58-0.41 (m, 3H), 0.37-0.24 (m, 1H)

Example 122 (S)-2-Cyclopropyl-2-((1-(4-methylpyridin-3-yl)-8,9-dihydro-7H-6-oxa-2,9a-diazabenzo[cd]azulen-4-yl)amino)acetamide 122

Following the procedures of Example 125, 122 was prepared. LCMS (ESI): $R_T$ (min)=1.15, [M+H]$^+$=378, method=D; $^1$H NMR (300 MHz, DMSO-$d_6$) δ 8.58-8.56 (m, 2H), 7.44 (d, J=5.1 Hz, 1H), 7.34 (s, 1H), 6.96 (s, 1H), 6.38 (d, J=1.9 Hz, 1H), 6.28 (d, J=1.9 Hz, 1H), 5.51 (d, J=7.4 Hz, 1H), 4.34-4.25 (m, 2H), 3.92-3.82 (m, 2H), 3.14-3.11 (m, 1H), 2.35-2.15 (m, 5H), 1.15-1.07 (m, 1H), 0.59-0.40 (m, 3H), 0.33-0.26 (m, 1H)

Example 123 (S)-2-Cyclopropyl-2-((1-(2-(hydroxymethyl)-6-methylpyrimidin-4-yl)-8,9-dihydro-7H-6-oxa-2,9a-diazabenzo[cd]azulen-4-yl)amino)acetamide 123

Step 1:
2-(Methoxymethyl)-6-methylpyrimidin-4(3H)-one

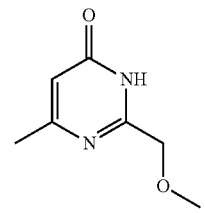

A mixture of sodium (1.84 g, 80.0 mmol) in ethanol (80 mL) was stirred until sodium disappeared under an inert atmosphere of nitrogen. Into the resulting mixture was added ethyl 3-oxobutanoate (5.20 g, 40.0 mmol) and 2-methoxyethanimidamide hydrochloride (5.00 g, 40.1 mmol). The resulting solution was stirred for 18 h at 80° C. and was then concentrated in vacuo. The residue was diluted with water and the pH was adjusted to 5 with concentrated hydrochloric acid (37%, 12 M) and extracted with ethyl acetate. The organic extracts were dried over anhydrous sodium sulfate and evaporated in vacuo to yield 2.8 g (45%) of the title compound as white solid. LCMS (ESI): [M+H]$^+$=155.

Step 2:
4-Chloro-2-(methoxymethyl)-6-methylpyrimidine

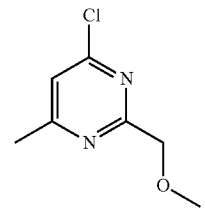

A mixture of 2-(methoxymethyl)-6-methylpyrimidin-4(3H)-one (2.80 g, 18.1 mmol) in phosphoryl trichloride (25 mL) was stirred for 1 h at 80° C. The reaction mixture was evaporated in vacuo then quenched with cold aqueous ammonia. The mixture was extracted with ethyl acetate. The combined organic layers were washed with brine, dried over anhydrous sodium sulfate and evaporated in vacuo to yield 1.9 g (crude) of the title compound as a red oil which was carried forward without purification. LCMS (ESI): [M+H]$^+$=173.

Step 3:
2-(Methoxymethyl)-6-methylpyrimidine-4-carboxylic acid

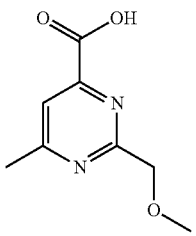

A mixture of 4-chloro-2-(methoxymethyl)-6-methylpyrimidine (500 mg, 3.15 mmol), [1,1'-bis(diphenylphosphino)ferrocene]palladium(II) dichloride (211 mg, 0.288 mmol) and sodium carbonate (766 mg, 7.23 mmol) in ethanol (20 mL) was stirred for 14 h at 80° C. while maintaining an atmosphere of carbon monoxide. The solids were filtered off, and the filtrate was evaporated in vacuo to yield 180 mg (crude) of the title compound as a red solid which was carried forward without purification. LCMS (ESI): [M+H]$^+$=183.

Step 4: N-(8-Bromo-2,3,4,5-tetrahydrobenzo[b][1,4]oxazepin-6-yl)-2-(methoxymethyl)-6-methylpyrimidine-4-carboxamide

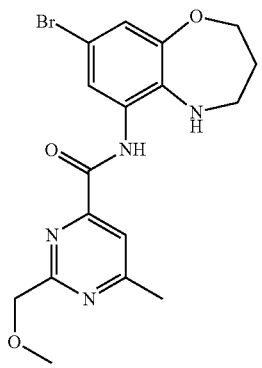 [SMILES: COCc1nc(C)cc(C(=O)Nc2cc(Br)cc3c2NCCCO3)n1]

The title compound (crude) was generated from 8-bromo-2,3,4,5-tetrahydrobenzo[b][1,4]oxazepin-6-amine from Example 101 (232 mg, 0.954 mmol) and 2-(methoxymethyl)-6-methylpyrimidine-4-carboxylic acid (350 mg, crude) following a procedure analogous to Example 125, step 1. The crude product was carried forward without purification. LCMS (ESI): [M+H]$^+$=407/409.

Step 5: 4-Bromo-1-(2-(methoxymethyl)-6-methylpyrimidin-4-yl)-8,9-dihydro-7H-6-oxa-2,9a-diazabenzo[cd]azulene

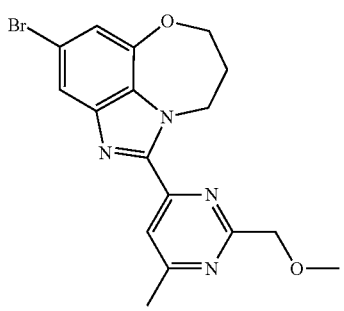 [SMILES: COCc1nc(C)cc(-c2nc3cc(Br)cc4c3n2CCCO4)n1]

The title compound (350 mg, 81%) was generated from N-(8-bromo-2,3,4,5-tetrahydrobenzo [b][1,4] oxazepin-6-yl)-2-(methoxymethyl)-6-methylpyrimidine-4-carboxamide (450 mg, 1.11 mmol) following a procedure analogous to Example 125, step 2. LCMS (ESI): [M+H]$^+$=389/391.

Step 6: (4-(4-Bromo-8,9-dihydro-7H-6-oxa-2,9a-diazabenzo[cd]azulen-1-yl)-6-methylpyrimidin-2-yl)methanol

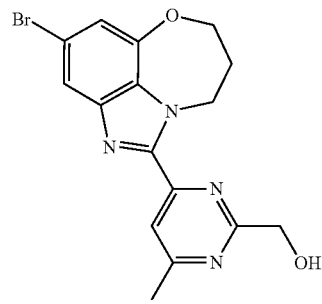 [SMILES: Cc1cc(-c2nc3cc(Br)cc4c3n2CCCO4)nc(CO)n1]

A mixture of 4-bromo-1-(2-(methoxymethyl)-6-methylpyrimidin-4-yl)-8,9-dihydro-7H-6-oxa-2,9a-diazabenzo[cd]azulene (350 mg, 0.899 mmol) in hydrobromic acid (48 w.t. % in water, 9 mL) was stirred for 3 h at 90° C. in an oil bath. The pH was adjusted to 8 with aqueous sodium bicarbonate. The resulting solution was extracted with DCM and the organic extracts were dried over anhydrous sodium sulfate and evaporated in vacuo. The residue was purified via flash chromatography on silica gel (solvent gradient: 0-10% methanol in DCM) to yield 269 mg (79.8%) of the title compound as a yellow solid. LCMS (ESI): [M+H]$^+$=375/377.

Step 7: (S)-2-Cyclopropyl-2-((1-(2-(hydroxymethyl)-6-methylpyrimidin-4-yl)-8,9-dihydro-7H-6-oxa-2,9a-diazabenzo[cd]azulen-4-yl)amino)acetic acid

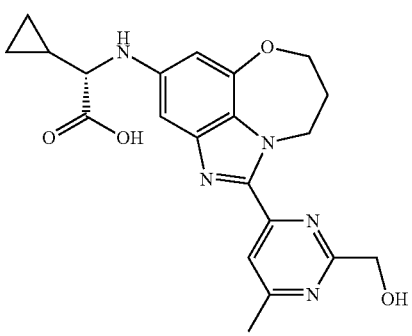 [SMILES: Cc1cc(-c2nc3cc(N[C@H](C(=O)O)C4CC4)cc4c3n2CCCO4)nc(CO)n1]

The title compound (60 mg, 21% yield) was generated from (4-(4-bromo-8,9-dihydro-7H-6-oxa-2,9a-diazabenzo[cd]azulen-1-yl)-6-methylpyrimidin-2-yl)methanol (260 mg, 0.693 mmol) and (S)-2-amino-2-cyclopropylacetic acid (399 mg, 3.47 mmol) following a procedure analogous to Example 125, step 3. LCMS (ESI): [M+H]$^+$=410.

Step 8: (S)-2-Cyclopropyl-2-((1-(2-(hydroxymethyl)-6-methylpyrimidin-4-yl)-8,9-dihydro-7H-6-oxa-2,9a-diazabenzo[cd]azulen-4-yl)amino)acetamide The title compound (16 mg, 27% yield) was generated from (S)-2-cyclopropyl-2-((1-(2-(hydroxymethyl)-6-methylpyrimidin-4-yl)-8,9-dihydro-7H-6-oxa-2,9a-diazabenzo[cd]azulen-4-yl)amino) acetic acid (60 mg, 0.147 mmol) following a procedure analogous to Example 125, step 4. 123: LCMS (ESI): $R_T$ (min)=1.83, $[M+H]^+$=409, method=D; $^1$H NMR (300 MHz, DMSO-$d_6$) δ 8.00 (s, 1H), 7.36 (s, 1H), 6.97 (s, 1H), 6.38-6.35 (m, 2H), 5.65 (d, J=7.2 Hz, 1H), 5.33 (br, 1H), 4.90-4.86 (m, 2H), 4.64 (s, 2H), 4.35-4.32 (m, 2H), 3.15-3.10 (m, 1H), 2.55 (s, 3H), 2.31-2.30 (m, 2H), 1.14-1.08 (m, 1H), 0.54-0.48 (m, 3H), 0.30-0.20 (m, 1H).

Example 124 2-(4-(1-(2-Aminobenzo[d]oxazol-5-yl)-8,9-dihydro-7H-6-oxa-2,9a-diazabenzo[cd]azulen-4-yl)-1H-pyrazol-1-yl)-2-methylpropanamide 124

Step 1: Methyl 2-methyl-2-(4-(4,4,5,5-tetramethyl-1,3,2-dioxaborolan-2-yl)-1H-pyrazol-1-yl)propanoate

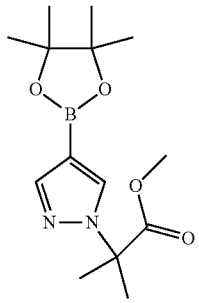 [SMILES: COC(=O)C(C)(C)n1cc(B2OC(C)(C)C(C)(C)O2)cn1]

A mixture of 4-(4,4,5,5-tetramethyl-1,3,2-dioxaborolan-2-yl)-1H-pyrazole (1.00 g, 5.15 mmol), methyl 2-bromo-2-methylpropanoate (1.12 g, 6.19 mmol) and potassium carbonate (2.14 g, 15.5 mmol) in DMF (10 mL) was stirred overnight at 90° C. The resulting solution was diluted with water and extracted with ethyl acetate. The organic extracts were combined, washed with brine, dried over anhydrous sodium sulfate and evaporated in vacuo. The residue was purified via flash chromatography on silica gel (solvent gradient: 0-20% ethyl acetate in petroleum ether) to yield the title compound 0.77 g (51%) as a white solid. LCMS (ESI): $[M+H]^+$=295.

Step 2: Methyl 2-(4-(1-(2-aminobenzo[d]oxazol-5-yl)-8,9-dihydro-7H-6-oxa-2,9a-diazabenzo[cd]azulen-4-yl)-1H-pyrazol-1-yl)-2-methylpropanoate

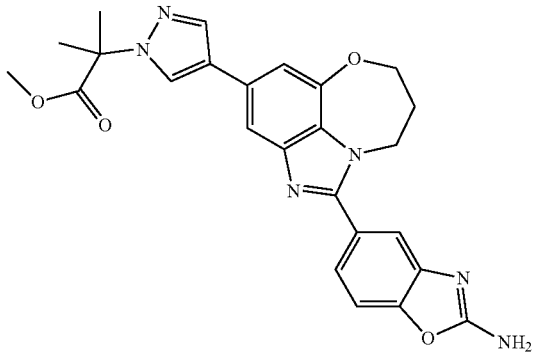 [SMILES: COC(=O)C(C)(C)n1cc(-c2cc3c4c(c2)nc(-c2ccc5oc(N)nc5c2)n4CCCO3)cn1]

A mixture of 5-(4-bromo-8,9-dihydro-7H-6-oxa-2,9a-diazabenzo[cd]azulen-1-yl)benzo[d]oxazol-2-amine from Example 101 (270 mg, 0.701 mmol), methyl 2-methyl-2-(4-(4,4,5,5-tetramethyl-1,3,2-dioxaborolan-2-yl)-1H-pyrazol-1-yl)propanoate (247 mg, 0.841 mmol), [1,1'-bis(diphenylphosphino)ferrocene] palladium(II) chloride (51.3 mg, 0.07 mmol), sodium carbonate (223 mg, 2.10 mmol), water (2 mL) and 1,4-dioxane (6 mL) was heated in a sealed tube under microwave irradiation at 100° C. for 1 h. The reaction mixture was diluted with water and extracted with DCM. The combined organic extracts were dried over anhydrous sodium sulfate, filtered and evaporated in vacuo. The residue was purified via flash chromatography on silica gel (solvent gradient: 0-3% methanol in DCM) to yield 240 mg (72%) of the title compound as a yellow solid. LCMS: $[M+H]^+$=473.

Step 3: 2-(4-(1-(2-Aminobenzo[d]oxazol-5-yl)-8,9-dihydro-7H-6-oxa-2,9a-diazabenzo[cd]azulen-4-yl)-1H-pyrazol-1-yl)-2-methylpropanamide A mixture of methyl 2-(4-(1-(2-aminobenzo[d]oxazol-5-yl)-8,9-dihydro-7H-6-oxa-2,9a-diazabenzo[cd]azulen-4-yl)-1H-pyrazol-1-yl)-2-methylpropanoate (200 mg, 0.423 mmol), formamide (0.500 mL, 11.1 mmol) and sodium methoxide (68.6 mg, 1.27 mmol) in DMF (2 mL) was heated under microwave irradiation for 30 min at 80° C. The solids were filtered off and the filtrate was purified via reverse-phase HPLC and lyophilized to yield 89.7 mg (46%) of 124 as an off-white solid. LCMS: $R_T$ (min)=1.25, $[M+H]^+$=458, method=D; $^1$H NMR (300 MHz, DMSO-$d_6$) δ 8.31 (s, 1H), 7.96 (s, 1H), 7.58-7.55 (m, 4H), 7.50 (d, J=8.1 Hz, 1H), 7.39 (d, J=8.4 Hz, 1H), 7.18 (s, 1H), 7.09 (s, 1H), 6.78 (s, 1H), 4.43-4.40 (m, 2H), 4.31-4.28 (m, 2H), 2.40-2.22 (m, 2H), 1.74 (s, 6H).

Example 125 (S)-2-Cyclopropyl-2-((1-(pyridazin-4-yl)-8,9-dihydro-7H-6-oxa-2,9a-diazabenzo [cd]azulen-4-yl)amino)acetamide 125

Step 1: N-(8-Bromo-2,3,4,5-tetrahydrobenzo[b][1,4]oxazepin-6-yl)pyridazine-4-carboxamide

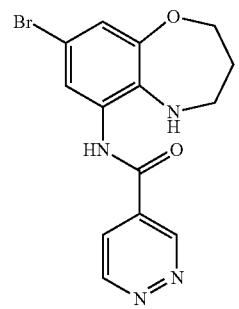 [SMILES: O=C(Nc1cc(Br)cc2c1NCCCO2)c1ccnnc1]

A mixture of 8-bromo-2,3,4,5-tetrahydrobenzo[b][1,4]oxazepin-6-amine from Example 101 (200 mg, 0.823 mmol), pyridazine-4-carboxylic acid (103 mg, 0.830 mmol), DIPEA (540 mg, 4.178 mmol) and HATU (628 mg, 1.65 mmol) in DMF (20 mL) was stirred at room temperature for 1 h. The reaction mixture was diluted with water and extracted with DCM. The organic extracts were washed with brine, dried over magnesium sulfate, and evaporated in vacuo to yield 520 mg of the crude title compound which was used without purification. LCMS (ESI): $[M+H]^+$=349/351.

Step 2: 4-Bromo-1-(pyridazin-4-yl)-8,9-dihydro-7H-6-oxa-2,9a-diazabenzo[cd]azulene

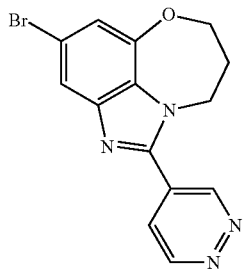 [SMILES: Brc1cc2c3c(c1)nc(-c1ccnnc1)n3CCCO2]

A mixture of crude N-(8-bromo-2,3,4,5-tetrahydrobenzo[b][1,4]oxazepin-6-yl)pyridazine-4-carboxamide (520 mg) and acetic acid (10 mL) was heated at 80° C. for 0.5 h. The reaction mixture was evaporated in vacuo. The resultant residue was purified via flash chromatography on silica gel (solvent gradient: 0-10% methanol in DCM) to yield 150 mg (55% over 2 steps) of the title compound as a light brown solid. LCMS (ESI): [M+H]$^+$=331/333.

Step 3: (S)-2-Cyclopropyl-2-((1-(pyridazin-4-yl)-8,9-dihydro-7H-6-oxa-2,9a-diazabenzo[cd]azulen-4-yl)amino)acetic acid

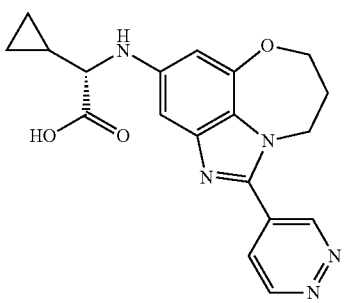 [SMILES: O=C(O)[C@@H](Nc1cc2c3c(c1)nc(-c1ccnnc1)n3CCCO2)C1CC1]

A mixture of 4-bromo-1-(pyridazin-4-yl)-8,9-dihydro-7H-6-oxa-2,9a-diazabenzo[cd]azulene (130 mg, 0.393 mmol), (S)-2-amino-2-cyclopropylacetic acid (240 mg, 2.09 mmol), copper(I) iodide (40 mg, 0.210 mmol) and potassium phosphate tribasic (430 mg, 2.03 mmol) in DMSO (10 mL) in a sealed tube was irradiated with microwave radiation at 120° C. for 1.5 h. The solids were removed by filtration and the brown filtrate was used without purification. LCMS (ESI): [M+H]$^+$=366.

Step 4: (S)-2-Cyclopropyl-2-((1-(pyridazin-4-yl)-8,9-dihydro-7H-6-oxa-2,9a-diazabenzo[cd]azulen-4-yl)amino)acetamide A mixture of (S)-2-cyclopropyl-2-((1-(pyridazin-4-yl)-8,9-dihydro-7H-6-oxa-2,9a-diazabenzo[cd]azulen-4-yl)amino)acetic acid (crude), DIPEA (1.20 g, 9.29 mmol), ammonium chloride (390 mg, 7.29 mmol) and HATU (276 mg, 0.726 mmol) in DMSO (10 mL) was stirred at room temperature for 1 h. The reaction mixture was diluted with water and extracted with DCM. The combined organic extracts were washed with brine, dried over sodium sulfate, and evaporated in vacuo. The residue was purified via reverse-phase HPLC and lyophilized to yield 14.0 mg (9.7% over 2 steps) of 125 as a yellow solid. LCMS (ESI): R$_T$ (min)=1.64, [M+H]$^+$=365, method=C; $^1$H NMR (400 MHz, DMSO-d$_6$) δ 9.66 (s, 1H), 9.40 (d, J=5.2 Hz, 1H), 8.11-8.09 (m, 1H), 7.37 (s, 1H), 6.98 (s, 1H), 6.41 (s, 1H), 6.36 (s, 1H), 5.64 (d, J=7.6 Hz, 1H), 4.41-4.37 (m, 4H), 3.18-3.14 (m, 1H), 2.31-2.30 (m, 2H), 1.15-1.08 (m, 1H), 0.54-0.48 (m, 3H), 0.35-0.25 (m, 1H).

Example 126 (S)-2-Cyclopropyl-2-[1-(4-hydroxymethylpiperidin-1-yl)-8,9-dihydro-7H-6-oxa-2,9a-diazabenzo[cd]azulen-4-ylamino]acetamide 126

Step 1: 4-Bromo-8,9-dihydro-2H,7H-6-oxa-2,9a-diazabenzo[cd]azulene-1-thione

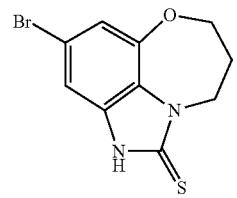 [SMILES: S=c1[nH]c2cc(Br)cc3c2n1CCCO3]

A solution of thiophosgene (0.74 mL, 20.1 mmol) in THF (5.0 mL) was added over 15 minutes to a solution of 8-bromo-2,3,4,5-tetrahydrobenzo[b][1,4]oxazepin-6-amine from Example 101 (1.97 g, 8.09 mmol) and triethylamine (2.8 mL, 20.1 mmol) in THF (40 mL) at 0° C. The reaction mixture was stirred at 0° C. for 15 min, then at room temperature for 30 min and then evaporated in vacuo. The residual solid was washed with water and then dried in a vacuum oven at 40° C. to give 2.35 g (quantitative) of the title compound as a white solid. $^1$H NMR (400 MHz, DMSO-d$_6$) δ 12.96 (br s, 1H), 6.91 (d, J=1.8 Hz, 1H), 6.86 (d, J=1.8 Hz, 1H), 4.39-4.37 (m, 2H), 4.12-4.09 (m, 2H), 2.34-2.28 (m, 2H).

Step 2: 4-Bromo-1-methyl sulfonyl-8,9-dihydro-7H-6-oxa-2,9a-diazabenzo[cd]azulene

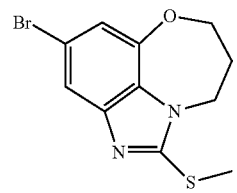 [SMILES: CSc1nc2cc(Br)cc3c2n1CCCO3]

Iodomethane (1.0 mL, 16.2 mmol) was added to a suspension of 4-bromo-8,9-dihydro-2H,7H-6-oxa-2,9a-diazabenzo[cd]azulene-1-thione (2.35 g, 8.09 mmol) and potassium carbonate (3.35 g, 24.3 mmol) in acetone (35 mL). The reaction mixture was stirred at room temperature for 16 h, then filtered through Celite® and the filtrate was evaporated in vacuo. The residue was purified via flash chromatography on silica gel (solvent gradient: 20-40% ethyl acetate in toluene) to yield 1.83 g (76%) of the title compound as a buff solid. $^1$H NMR (400 MHz, CDCl$_3$) δ 7.43 (d, J=1.7 Hz, 1H), 6.90 (d, J=1.7 Hz, 1H), 4.35-4.33 (m, 2H), 4.05-4.02 (m, 2H), 2.79 (s, 3H), 2.43-2.37 (m, 2H).

Step 3: 4-Bromo-1-methanesulfonyl-8,9-dihydro-7H-6-oxa-2,9a-diazabenzo[cd]azulene

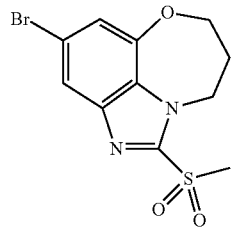 [SMILES: CS(=O)(=O)c1nc2cc(Br)cc3c2n1CCCO3]

A solution of 3-chloroperbenzoic acid (3.39 g, approximate 77% wt %, approximate 15.1 mmol) in DCM (20 mL) was added over 10 min to an ice-cooled solution of 4-bromo-1-methylsulfanyl-8,9-dihydro-7H-6-oxa-2,9a-diazabenzo[cd]azulene (1.81 g, 6.05 mmol) in DCM (50 mL). Stirring was continued at room temperature for 16 h. The reaction mixture was diluted with DCM and washed with aqueous sodium metabisulfite solution. The aqueous phase was extracted with more DCM and the combined organic extracts were washed with aqueous sodium bicarbonate solution, dried over sodium sulfate, filtered and evaporated in vacuo. The residue was purified via flash chromatography on silica gel (solvent gradient: 5-25% ethyl acetate in toluene) to yield 1.49 g (74%) of the title compound as a colorless foam. $^1$H NMR (400 MHz, CDCl$_3$) δ 7.58 (d, J=1.7 Hz, 1H), 7.13 (d, J=1.7 Hz, 1H), 4.69-4.66 (m, 2H), 4.42-4.40 (m, 2H), 3.57 (s, 3H), 2.49-2.44 (m, 2H).

Step 4: [1-(4-Bromo-8,9-dihydro-7H-6-oxa-2,9a-diazabenzo[cd]azulen-1-yl)piperidin-4-yl]methanol

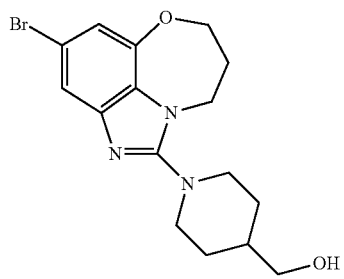 [SMILES: OCC1CCN(c2nc3cc(Br)cc4c3n2CCCO4)CC1]

A mixture of 4-bromo-1-methanesulfonyl-8,9-dihydro-7H-6-oxa-2,9a-diazabenzo[cd]azulene (0.35 g, 1.06 mmol), 4-(hydroxymethyl)piperidine (0.30 g, 2.64 mmol) and DIPEA (0.37 mL, 2.11 mmol) in propan-2-ol (2.0 mL) was heated in a sealed vial at 150° C. under microwave irradiation for 17 h. The reaction mixture was partitioned between ethyl acetate and aqueous sodium bicarbonate solution. The aqueous phase was further extracted with ethyl acetate and the combined organic extracts were washed with brine, dried over sodium sulfate, filtered and evaporated in vacuo. The residue was purified via flash chromatography on silica gel (solvent gradient: 25-100% ethyl acetate in toluene, then 50-100% methyl acetate in ethyl acetate) to yield 0.15 g (39%) of the title compound as a white solid. LCMS (ESI): [M+H]$^+$=366/368.

Step 5: (S)-Cyclopropyl-[1-(4-hydroxymethylpiperidin-1-yl)-8,9-dihydro-7H-6-oxa-2,9a-diazabenzo[cd]azulen-4-ylamino]acetic acid

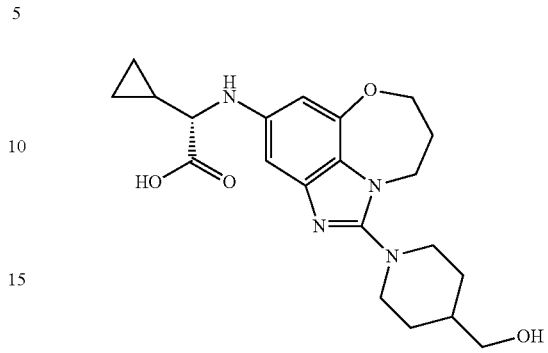

A mixture of [1-(4-bromo-8,9-dihydro-7H-6-oxa-2,9a-diazabenzo[cd]azulen-1-yl)piperidin-4-yl]methanol (40 mg, 0.11 mmol), L-cyclopropylglycine (31.5 mg, 0.27 mmol), cuprous iodide (4.2 mg, 0.022 mmol) and potassium phosphate tribasic (92.5 mg, 0.436 mmol) in DMSO (0.7 mL) was heated in a sealed vial at 100° C. for 16 h. The cooled reaction mixture was diluted with DCM (20 mL) and purified via flash chromatography on silica gel (solvent gradient: 5-50% 2 N ammonia/methanol in DCM) to yield 28.6 mg (66%) of the title compound as a buff solid. LCMS (ESI): [M+H]$^+$=401.

Step 6: (S)-2-Cyclopropyl-2-[1-(4-hydroxymethylpiperidin-1-yl)-8,9-dihydro-7H-6-oxa-2,9a-diazabenzo[cd]azulen-4-ylamino]acetamide To a mixture of (S)-cyclopropyl-[1-(4-hydroxymethylpiperidin-1-yl)-8,9-dihydro-7H-6-oxa-2,9a-diazabenzo[cd]azulen-4-ylamino]acetic acid (28.6 mg, 0.071 mmol), ammonium chloride (7.6 mg, 0.142 mmol) and DIPEA (50 µL, 0.285 mmol) in DMF (0.5 mL) was added HATU (54.3 mg, 0.142 mmol) portion-wise over 5 minutes, and the reaction mixture was stirred at room temperature for 10 min. The resulting mixture was diluted with DCM (10 mL) and purified via flash chromatography on silica gel (solvent gradient: 2-12% 2 N ammonia/methanol in DCM) to yield 11.8 mg (41%) of 126 as a colorless foam. LCMS (ESI): R$_T$=2.17, [M+H]$^+$=400.2, method=A; $^1$H NMR (400 MHz, DMSO-d$_6$) δ inter alia 7.27 (br s, 1H), 6.91 (br s, 1H), 6.21 (d, J=2.0 Hz, 1H), 6.02 (d, J=2.0 Hz, 1H), 5.24 (d, J=7.4 Hz, 1H), 4.49 (t, J=5.3 Hz, 1H), 4.25-4.23 (m, 2H), 3.89-3.86 (m, 2H), 3.46-3.42 (m, 2H), 3.07 (t, J=7.7 Hz, 1H), 2.82-2.75 (m, 2H), 2.20-2.15 (m, 2H), 1.76-1.72 (m, 2H), 1.59-1.49 (m, 1H), 1.36-1.26 (m, 2H), 1.12-1.04 (m, 1H), 0.50-0.42 (m, 3H), 0.30-0.25 (m, 1H).

Example 127 (S)-2-Cyclopropyl-2-(1-piperidin-1-yl-8,9-dihydro-7H-6-oxa-2,9a-diazabenzo[cd]azulen-4-ylamino)acetamide 127

Step 1: 4-Bromo-1-piperidin-1-yl-8,9-dihydro-7H-6-oxa-2,9a-diazabenzo[cd]azulene

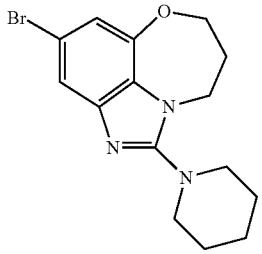 [SMILES: Brc1cc2c3c(c1)nc(N1CCCCC1)n3CCCO2]

A mixture of 4-bromo-1-methanesulfonyl-8,9-dihydro-7H-6-oxa-2,9a-diazabenzo[cd]azulene (0.35 g, 1.06 mmol) and piperidine (5.0 mL) was heated in a sealed vial at 150° C. under microwave irradiation for 5 h. The reaction mixture was evaporated in vacuo and the residue partitioned between ethyl acetate and aqueous sodium bicarbonate solution. The aqueous phase was further extracted with ethyl acetate and the combined organic extracts were washed with brine, dried over sodium sulfate, filtered and evaporated in vacuo. The residue was purified via flash chromatography on silica gel (solvent gradient: 10-40% ethyl acetate in toluene) to yield 0.27 g (77%) of the title compound as a colorless solid. LCMS (ESI): [M+H]$^+$=336/338.

Following the procedures of Example 126, 127 was prepared. LCMS (ESI): R$_T$ (min)=2.50, [M+H]$^+$=370.1, method=A; $^1$H NMR (400 MHz, DMSO-d$_6$) δ inter alia 7.27 (br s, 1H), 6.91 (br s, 1H), 6.21 (d, J=2.0 Hz, 1H), 6.02 (d, J=2.0 Hz, 1H), 5.24 (d, J=7.5 Hz, 1H), 4.25-4.23 (m, 2H), 3.89-3.87 (m, 2H), 3.10-3.07 (m, 4H), 2.20-2.15 (m, 2H), 1.67-1.62 (m, 4H), 1.59-1.53 (m, 2H), 1.12-1.04 (m, 1H), 0.50-0.42 (m, 3H), 0.30-0.25 (m, 1H)

Example 128 (S)-2-cyclopropyl-2-((1-(2-methoxypyrimidin-5-yl)-8,9-dihydro-7H-6-oxa-2,9a-diazabenzo[cd]azulen-4-yl)amino)acetamide 128

Following the procedures of Example 125, 128 was prepared. LCMS (ESI): R$_T$ (min)=2.55, [M+H]$^+$=395, method=B; $^1$H NMR (400 MHz, DMSO-d$_6$) δ 9.00 (s, 1H), 7.33 (s, 1H), 6.95 (s, 1H), 6.38 (d, J=2.0 Hz, 1H), 6.28 (d, J=1.9 Hz, 1H), 5.51 (d, J=7.4 Hz, 1H), 4.39-4.30 (m, 2H), 4.30-4.20 (m, 2H), 4.01 (s, 2H), 3.15 (t, J=7.7 Hz, 1H), 2.31-2.22 (m, 2H), 1.18-1.04 (m, 1H), 0.57-0.41 (m, 3H), 0.35-0.25 (m, 1H)

Example 129 (S)-2-Cyclopropyl-2-((1-(1-methyl-6-oxo-1,6-dihydropyridazin-3-yl)-8,9-dihydro-7H-6-oxa-2,9a-diazabenzo[cd]azulen-4-yl)amino)acetamide 129

Following the procedures of Example 125, 129 was prepared. LCMS (ESI): R$_T$ (min)=2.89, [M+H]$^+$=395, method=B; $^1$H NMR (400 MHz, DMSO-d$_6$) δ 8.15 (d, J=10.0 Hz, 1H), 7.34 (s, 1H), 7.06 (d, J=9.8 Hz, 1H), 6.95 (s, 1H), 6.34 (dd, J=21.7, 2.1 Hz, 2H), 5.59 (d, J=7.2 Hz, 1H), 4.59 (t, J=5.7 Hz, 2H), 4.34 (t, J=4.6 Hz, 2H), 3.76 (s, 3H), 3.13 (t, J=7.7 Hz, 1H), 2.34-2.25 (m, 2H), 1.18-1.04 (m, 1H), 0.57-0.43 (m, 3H), 0.40-0.25 (m, 1H)

Example 130 (S)-2-((1-(5-Chloro-6-methoxypyridin-3-yl)-8,9-dihydro-7H-6-oxa-2,9a-diazabenzo[cd]azulen-4-yl)amino)-2-cyclopropylacetamide 130

Following the procedures of Example 125, 130 was prepared. LCMS (ESI): R$_T$ (min)=3.15, [M+H]$^+$=428, method=B; $^1$H NMR (400 MHz, DMSO-d$_6$) δ 8.52 (d, J=2.1 Hz, 1H), 8.29 (d, J=2.4 Hz, 1H), 7.33 (s, 1H), 6.95 (s, 1H), 6.37 (d, J=2.0 Hz, 1H), 6.27 (d, J=1.9 Hz, 1H), 5.50 (d, J=7.4 Hz, 1H), 4.32 (t, J=4.7 Hz, 2H), 4.29-4.17 (m, 2H), 4.03 (s, 2H), 3.28 (s, 1H), 3.14 (t, J=7.7 Hz, 1H), 2.30-2.22 (m, 2H), 1.18-1.04 (m, 1H), 0.57-0.42 (m, 3H), 0.35-0.25 (m, 1H)

Example 131 (S)-2-Cyclopropyl-2-((1-(3-oxo-3,4-dihydro-2H-benzo[b][1,4]oxazin-6-yl)-8,9-dihydro-7H-6-oxa-2,9a-diazabenzo[cd]azulen-4-yl)amino)acetamide 131

Step 1: 4-Bromo-1-(2-(chloromethyl)benzo[d]oxazol-5-yl)-8,9-dihydro-7H-6-oxa-2,9a-diazabenzo[cd]azulene

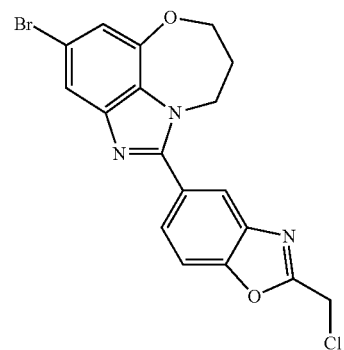 [SMILES: ClCc1nc2cc(-c3nc4cc(Br)cc5c4n3CCCO5)ccc2o1]

2-Chloro-1,1,1-triethoxyethane (0.53 g, 2.71 mmol) was added to a solution of 2-amino-4-(4-bromo-8,9-dihydro-7H-6-oxa-2,9a-diazabenzo[cd]azulen-1-yl)phenol (0.800 g, 2.22 mmol) in acetic acid (10 mL). The reaction mixture was heated at 120° C. for 3 h. The solids were filtered off, and the filtrate was evaporated in vacuo. The residue was dissolved in ethyl acetate and then diluted with petroleum ether. The precipitated solid was collected by filtration to yield the crude title compound which was carried forward without purification. $^1$H NMR (400 MHz, DMSO-d$_6$) δ 8.25 (s, 1H), 8.00 (d, J=8.3 Hz, 1H), 7.80 (d, J=8.5 Hz, 1H), 7.50 (s, 1H), 6.95 (s, 1H), 5.15 (s, 2H), 4.50-4.44 (m, 2H), 4.40-4.33 (m, 2H), 2.40-2.30 (m, 2H).

Step 2: 6-(4-Bromo-8,9-dihydro-7H-6-oxa-2,9a-diazabenzo[cd]azulen-1-yl)-2H-benzo[b][1,4]oxazin-3(4H)-one

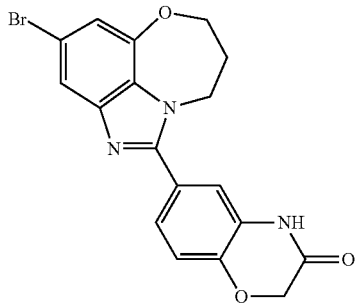 [SMILES: O=C1COc2ccc(-c3nc4cc(Br)cc5c4n3CCCO5)cc2N1]

Lithium hydroxide (0.040 g, 0.950 mmol) was added to a solution of 4-bromo-1-(2-(chloromethyl) benzo[d]oxazol-5-yl)-8,9-dihydro-7H-6-oxa-2,9a-diazabenzo[cd]azulene (200 mg, 0.480 mmol) in THF (10 mL) and water (2 mL). The resulting mixture was stirred at 25° C. for 16 h. The reaction mixture was diluted with water and extracted with DCM. The combined organic extracts were dried over anhydrous sodium sulfate, filtered and evaporated in vacuo. The residue was purified via flash chromatography on silica gel (solvent gradient: 0-10% methanol in DCM) to yield 80 mg (42%) of the title compound as a yellow solid. $^1$H NMR (400 MHz, DMSO-$d_6$) δ 10.89 (s, 1H), 7.43 (s, 1H), 7.38-7.33 (m, 2H), 7.11 (d, J=8.1 Hz, 1H), 6.90 (s, 1H), 4.68 (s, 2H), 4.45-4.42 (m, 2H), 4.31-4.27 (m, 2H), 2.31-2.20 (m, 2H).

Step 3 (S)-2-Cyclopropyl-2-((1-(3-oxo-3,4-dihydro-2H-benzo[b][1,4]oxazin-6-yl)-8,9-dihydro-7H-6-oxa-2,9a-diazabenzo[cd]azulen-4-yl)amino)acetamide 131

A mixture of 6-(4-bromo-8,9-dihydro-7H-6-oxa-2,9a-diazabenzo[cd]azulen-1-yl)-2H-benzo[b][1,4] oxazin-3(4H)-one (150 mg, 0.380 mmol), (S)-2-amino-2-cyclopropylacetic acid (216 mg, 1.88 mmol), copper(I) iodide (36.0 mg, 0.190 mmol) and potassium phosphate (477 mg, 2.25 mmol) in DMSO (6 mL) were degassed with nitrogen under sonication. The reaction mixture was heated at 100° C. for 2 hours then cooled to room temperature. The solids were removed by filtration and the filtrate was diluted with DMSO (2 mL). Ammonium chloride (370 mg, 6.92 mmol), HATU (263 mg, 0.690 mmol) and DIPEA (1.12 g, 8.63 mmol) were added and the mixture was stirred at room temperature for 30 min. The reaction mixture was diluted with water and extracted with DCM. The combined organic extracts were washed with brine, dried over anhydrous sodium sulfate, filtered and evaporated in vacuo. The crude product was purified via reverse-phase HPLC and lyophilized to yield 11.9 mg (8%) of 131 as a white solid. LCMS (ESI): $R_T$ (min)=1.23, [M+H]$^+$=434, method=D; $^1$H NMR (300 MHz, DMSO-$d_6$) δ 10.84 (s, 1H), 7.37-7.26 (m, 3H), 7.12-7.03 (m, 1H), 6.95 (d, J=2.3 Hz, 1H), 6.35 (d, J=2.0 Hz, 1H), 6.23 (d, J=2.0 Hz, 1H), 5.47 (d, J=7.4 Hz, 1H), 4.66 (s, 2H), 4.37-4.27 (m, 2H), 4.20-4.16 (m, 2H), 3.16-3.10 (m, 1H), 2.23-2.12 (m, 2H), 1.11-1.09 (m, 1H), 0.58-0.39 (m, 3H), 0.31-0.28 (m, 1H).

Example 132 (S)-2-((1-([1,2,4]Triazolo[1,5-a]pyridin-7-yl)-8,9-dihydro-7H-6-oxa-2,9a-diazabenzo[cd]azulen-4-yl)amino)-2-cyclopropylacetamide 132

Following the procedures of Example 116, 132 was prepared. LCMS (ESI): $R_T$ (min)=1.25, [M+H]$^+$=404, method=D; $^1$H NMR (400 MHz, DMSO-$d_6$) δ 9.09-9.07 (d, J=7.2 Hz, 1H), 8.62 (s, 1H), 8.24 (s, 1H), 7.61 (d, J=6.9 Hz, 1H), 7.35 (s, 1H), 6.96 (s, 1H), 6.41 (d, J=2.8 Hz, 1H), 6.32 (d, J=2.8 Hz, 1H), 5.57 (d, J=7.5 Hz, 1H), 4.40-4.35 (m, 4H), 3.19-3.14 (m, 1H), 2.40-2.20 (m, 2H), 1.19-1.02 (m, 1H), 0.52-0.47 (m, 3H), 0.31-0.30 (m, 1H)

Example 133 (S)-2-((1-(1H-Indazol-5-yl)-8,9-dihydro-7H-6-oxa-2,9a-diazabenzo[cd]azulen-4-yl)amino)-2-cyclopropylacetamide 133

Following the procedures of Example 125, 133 was prepared. LCMS (ESI): $R_T$ (min)=1.39, [M+H]$^+$=403, method=C; $^1$H NMR (300 MHz, DMSO-$d_6$) δ 13.33 (s, 1H), 8.20 (d, J=8.4 Hz, 2H), 7.76-7.67 (m, 2H), 7.36 (s, 1H), 6.98 (s, 1H), 6.38 (s, 1H), 6.27 (s, 1H), 5.59 (br, 1H), 4.45-4.30 (m, 2H), 4.29-4.15 (m, 2H), 3.17-3.12 (m, 1H), 2.35-2.18 (m, 2H), 1.14-1.08 (m, 1H), 0.51-0.44 (m, 3H), 0.35-0.25 (m, 1H)

Example 134 (S)-2-Cyclopropyl-2-((1-(pyrimidin-5-yl)-8,9-dihydro-7H-6-oxa-2,9a-diazabenzo[cd]azulen-4-yl)amino)acetamide 134

Following the procedures of Example 125, 134 was prepared. LCMS (ESI): $R_T$ (min)=1.59, [M+H]$^+$=365, method=C; $^1$H NMR (300 MHz, DMSO-$d_6$) δ 9.31 (s, 1H), 9.21 (s, 2H), 7.35 (s, 1H), 6.97 (s, 1H), 6.39 (d, J=2.0 Hz, 1H), 6.31 (d, J=2.0 Hz, 1H), 5.58 (d, J=7.4 Hz, 1H), 4.33-4.32 (m, 4H), 3.16-3.11 (m, 1H), 2.35-2.15 (m, 2H), 1.13-1.07 (m, 1H), 0.52-0.44 (m, 3H), 0.38-0.25 (m, 1H)

Example 135 (S)-2-((1-(2-Aminobenzo[d]oxazol-5-yl)-8,9-dihydro-7H-6-oxa-2,9a-diazabenzo[cd]azulen-4-yl)amino)-2-cyclopropylacetamide 135

Following the procedures of Example 104, 135 was prepared. LCMS (ESI): $R_T$ (min)=2.04, [M+H]$^+$=419, method=D; $^1$H NMR (300 MHz, DMSO-$d_6$) δ 7.55 (s, 2H), 7.51 (s, 1H), 7.45 (d, J=8.4 Hz, 1H), 7.34-7.30 (m, 2H), 6.96 (s, 1H), 6.36 (d, J=1.8 Hz, 1H), 6.22 (d, J=1.8 Hz, 1H), 5.44 (d, J=7.2 Hz, 1H), 4.33-4.30 (m, 2H), 4.20-4.10 (m, 2H), 3.16-3.11 (m, 1H), 2.35-2.15 (m, 2H), 1.13-1.08 (m, 1H), 0.52-0.46 (m, 3H), 0.40-0.25 (m, 1H)

Example 136 (S)-2-Cyclopropyl-2-((1-(thiazol-5-yl)-8,9-dihydro-7H-6-oxa-2,9a-diazabenzo[cd]azulen-4-yl)amino)acetamide 136

Following the procedures of Example 125, 136 was prepared. LCMS (ESI): $R_T$ (min)=1.83, [M+H]$^+$=370.0, method=D; $^1$H NMR (400 MHz, DMSO-$d_6$) δ 9.26 (s, 1H), 8.45 (s, 1H), 7.36 (s, 1H), 6.97 (s, 1H), 6.35 (s, 1H), 6.28 (s, 1H), 5.63 (br s, 1H), 4.45-4.43 (m, 2H), 4.37-4.34 (m, 2H), 3.20-3.11 (m, 1H), 2.40-2.30 (m, 2H), 1.18-1.05 (m, 1H), 0.58-0.43 (m, 3H), 0.33-0.28 (m, 1H)

Example 137 (S)-2-Cyclopropyl-2-((1-(4-(methyl-sulfonyl)phenyl)-8,9-dihydro-7H-6-oxa-2,9a-diaz-abenzo[cd]azulen-4-yl)amino)acetamide 137

Step 1: 4-Bromo-1-(4-(methylsulfonyl)phenyl)-8,9-dihydro-7H-6-oxa-2,9a-diazabenzo[cd]azulene

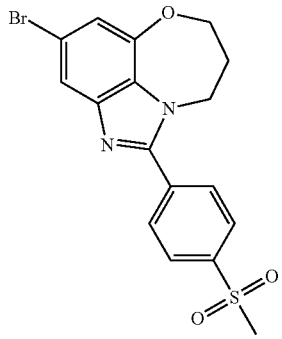 [SMILES: CS(=O)(=O)c1ccc(-c2nc3cc(Br)cc4c3n2CCCO4)cc1]

To a mixture of 8-bromo-2,3,4,5-tetrahydrobenzo[b][1,4]oxazepin-6-amine from Example 101 (176.7 mg, 0.7269 mmol), 4-methylsulfonylbenzoic acid (151.8 mg, 0.7582 mmol), DIPEA (0.35 mL, 2.0 mmol) and DMF (3.0 mL, 39 mmol) was added HATU (374.1 mg, 0.964 mmol). The reaction mixture was stirred at room temperature for 45 min. The reaction mixture was diluted with ethyl acetate, washed with water (3×) and brine, dried over magnesium sulfate, filtered, and evaporated in vacuo. The resulting residue was dissolved in acetic acid (2.0 mL, 35 mmol) and heated at 90° C. for 1 h. The reaction mixture was cooled to room temperature, and the acetic acid was removed under vacuum. The resulting residue was diluted with ethyl acetate, washed with saturated aqueous sodium bicarbonate and brine, dried over magnesium sulfate, filtered, and evaporated in vacuo to yield 243.6 mg (82%) of the title compound. LCMS (ESI): [M+H]$^+$=406.95; $^1$H NMR (400 MHz, DMSO-d$_6$) δ inter alia 8.19-8.04 (m, 4H), 7.51 (d, J=1.8 Hz, 1H), 6.96 (d, J=1.8 Hz, 1H), 4.53-4.42 (m, 2H), 4.40-4.32 (m, 2H), 2.39-2.28 (m, 2H).

Step 2: (S)-2-Cyclopropyl-2-((1-(4-(methylsulfonyl)phenyl)-8,9-dihydro-7H-6-oxa-2,9a-diazabenzo[cd]azulen-4-yl)amino)acetamide To a mixture of 4-bromo-1-(4-(methylsulfonyl)phenyl)-8,9-dihydro-7H-6-oxa-2,9a-diazabenzo[cd]azulene (242.6 mg, 0.5956 mmol), (2S)-2-amino-2-cyclopropyl-acetic acid (141 mg, 1.22 mmol), potassium phosphate tribasic (398 mg, 1.8375 mmol) and DMSO (2.0 mL, 28 mmol) was added copper(I) iodide (67.9 mg, 0.357 mmol). The reaction mixture was heated under microwave irradiation at 120° C. for 2 h. To the crude reaction mixture was added triethylamine (0.35 mL, 2.5 mmol), ammonium chloride (130.3 mg, 2.44 mmol) and HATU (933 mg, 2.40 mmol). This mixture was stirred at room temperature for 1 h. The reaction mixture was diluted with ethyl acetate, washed with water (2×) and brine, dried over magnesium sulfate, filtered, and evaporated in vacuo. The crude product was purified via flash chromatography on silica gel (12 g silica, solvent gradient: 0-10% methanol in DCM) and further purified via preparatory HPLC and lyophilized to yield 17.1 mg (6.5%) of 137. LCMS (ESI): R$_T$ (min)=2.74, [M+H]$^+$=441.2, method=B; $^1$HNMR (400 MHz, DMSO-d$_6$) δ 8.13-7.98 (m, 4H), 7.34 (d, J=2.5 Hz, 1H), 6.95 (d, J=2.4 Hz, 1H), 6.40 (d, J=2.0 Hz, 1H), 6.30 (d, J=2.0 Hz, 1H), 5.54 (d, J=7.4 Hz, 1H), 4.35 (t, J=4.7 Hz, 2H), 4.31-4.21 (m, 2H), 3.30 (s, 3H), 3.15 (t, J=7.8 Hz, 1H), 2.31-2.19 (m, 2H), 1.16-1.05 (m, 1H), 0.56-0.41 (m, 3H), 0.35-0.24 (m, 1H).

Example 138 (S)-2-Cyclopropyl-2-((1-(2,3-dihydrobenzo[b][1,4]dioxin-6-yl)-8,9-dihydro-7H-6-oxa-2,9a-diazabenzo[cd]azulen-4-yl)amino)acetamide 138

Step 1: 4-Bromo-1-(2,3-dihydrobenzo[b][1,4]dioxin-6-yl)-8,9-dihydro-7H-6-oxa-2,9a-diazabenzo[cd]azulene

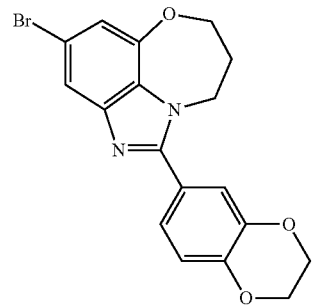 [SMILES: Brc1cc2c3c(c1)nc(-c1ccc4c(c1)OCCO4)n3CCCO2]

To a solution of 8-bromo-2,3,4,5-tetrahydro-1,5-benzoxazepin-6-amine (120.4 mg, 0.495 mmol), 2,3-dihydro-1,4-benzodioxine-6-carboxylic acid (80.0 mg, 0.431 mmol), DIPEA (111.3 mg, 0.861 mmol) in DMF (4 mL) was added HATU (334.2 mg, 0.861 mmol). The reaction was sealed in a vial under nitrogen and left to stir for 1.5 h at room temperature. The reaction mixture was diluted with water and extracted with DCM. The combined organic fractions were washed with brine, dried over sodium sulfate, filtered, and evaporated in vacuo. The resultant residue was purified via flash chromatography (solvent gradient: 0-80% ethyl acetate in heptane) to afford 120 mg (72%) of the title compound. LCMS (ESI): [M+H]$^+$=387.

Step 2: (S)-2-Cyclopropyl-2-((1-(2,3-dihydrobenzo[b][1,4]dioxin-6-yl)-8,9-dihydro-7H-6-oxa-2,9a-diazabenzo[cd]azulen-4-yl)amino)acetamide To a suspension of 4-bromo-1-(2,3-dihydrobenzo[b][1,4]dioxin-6-yl)-8,9-dihydro-7H-6-oxa-2,9a-diazabenzo[cd]azulene (42 mg, 0.109 mmol), potassium phosphate tribasic (118 mg, 0.54 mmol) and (2S)-2-amino-2-cyclopropyl-acetic acid (49.95 mg, 0.434 mmol) in DMSO (1.00 mL) was added cuprous iodide (12.4 mg, 0.065 mmol). The reaction was sealed in a vial under nitrogen and heated under microwave irradiation for 2 h at 120° C. The resulting mixture was treated with 5 mL DMSO, triethylamine (110 mg, 1.09 mmol), and ammonium chloride (58.0 mg, 1.09 mmol) followed by HATU (421 mg, 1.09 mmol). After stirring for 1 h at room temperature the reaction mixture was diluted with water and extracted with DCM. The combined organic fractions were washed with water followed by brine and then dried over magnesium sulfate, filtered, and evaporated in vacuo. The resultant crude residue was purified via flash chromatography on silica gel (solvent gradient: 0-10% methanol in DCM) to yield 9.2 mg (20%) of 138. LCMS (ESI): R$_T$ (min)=2.98, [M+H]$^+$=421.2, method=B; $^1$H NMR (400 MHz, DMSO-$d_6$) δ 7.31 (s, 1H), 7.25-7.17 (m, 2H), 6.99 (d, J=8.2 Hz, 1H), 6.94 (s, 1H), 6.34 (d, J=2.0 Hz, 1H), 6.22 (d, J=1.9 Hz, 1H), 5.43 (d, J=7.3 Hz, 1H), 4.36-4.26 (m, 6H), 4.24-4.12 (m, 2H), 3.13 (t, J=7.7 Hz, 1H), 2.28-2.18 (m, 2H), 1.17-1.04 (m, 1H), 0.56-0.41 (m, 3H), 0.35-0.24 (m, 1H).

Example 139 (S)-2-[1-((R)-3-Hydroxymethylpiperidin-1-yl)-8,9-dihydro-7H-6-oxa-2,9a-diazabenzo[cd]azulen-4-ylamino]propionamide 139

Step 1: [(R)-1-(4-Bromo-8,9-dihydro-7H-6-oxa-2,9a-diazabenzo[cd]azulen-1-yl)piperidin-3-yl]methanol

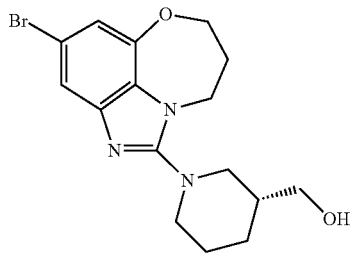 [SMILES: OC[C@@H]1CCCN(c2nc3cc(Br)cc4c3n2CCCO4)C1]

A mixture of 4-bromo-1-methanesulfonyl-8,9-dihydro-7H-6-oxa-2,9a-diazabenzo[cd]azulene (0.305 g, 0.92 mmol), (R)-1-piperidin-3-ylmethanol (0.212 g, 1.84 mmol) and N,N-diisopropylethylamine (0.319 mL, 1.84 mmol) in propan-2-ol (2.0 mL) was heated in a sealed vial at 150° C. under microwave irradiation for 17 hours. The reaction mixture was partitioned between ethyl acetate and aqueous sodium bicarbonate solution. The aqueous phase was further extracted with ethyl acetate and the combined organic extracts were washed with brine, dried over sodium sulfate, filtered and evaporated in vacuo. The residue was purified via flash chromatography on silica gel (solvent gradient: 25-100% ethyl acetate in toluene, then 50-100% methyl acetate in ethyl acetate) to yield 71 mg (21%) of the title compound as a white solid. LCMS (ESI): [M+H]$^+$=366/368.

Step 2: (S)-2-[1-((R)-3-Hydroxymethylpiperidin-1-yl)-8,9-dihydro-7H-6-oxa-2,9a-diazabenzo[cd]azulen-4-ylamino]propionic acid

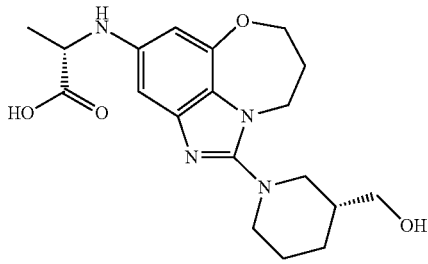 [SMILES: C[C@H](Nc1cc2c3c(c1)nc(N1CCC[C@@H](CO)C1)n3CCCO2)C(=O)O]

A mixture of [(R)-1-(4-bromo-8,9-dihydro-7H-6-oxa-2,9a-diazabenzo[cd]azulen-1-yl)piperidin-3-yl]methanol (51 mg, 0.139 mmol), L-alanine (31.1 mg, 0.349 mmol), cuprous iodide (5.4 mg, 0.028 mmol) and potassium phosphate tribasic (118 mg, 0.556 mmol) in dimethyl sulfoxide (0.5 mL) was heated in a sealed vial at 100° C. for 3 hours. The cooled reaction mixture was diluted with dichloromethane (10 mL) and purified via flash chromatography on silica gel (solvent gradient: 5-50% 2 N ammonia/methanol in dichloromethane) to yield the title compound (quantitative) as a buff solid. LCMS (ESI): [M+H]$^+$=375.

Step 3: (S)-2-[1-((R)-3-Hydroxymethylpiperidin-1-yl)-8,9-dihydro-7H-6-oxa-2,9a-diazabenzo[cd]azulen-4-ylamino]propionamide To a mixture of (S)-2-[1-((R)-3-hydroxymethylpiperidin-1-yl)-8,9-dihydro-7H-6-oxa-2,9a-diazabenzo[cd]azulen-4-ylamino]propionic acid (0.139 mmol), ammonium chloride (14.9 mg, 0.278 mmol) and N,N-diisopropylethylamine (96.4 µL, 0.556 mmol) in N,N-dimethylformamide (0.75 mL) was added 1-[bis(dimethylamino)methylene]-1H-1,2,3-triazolo[4,5-b]pyridinium 3-oxide hexafluorophosphate (105.6 mg, 0.278 mmol) portion-wise over 5 minutes, and the reaction mixture was stirred at room temperature for 10 minutes. The reaction mixture was diluted with dichloromethane (15 mL) and purified via flash chromatography on silica gel (solvent gradient: 2-12% 2 N ammonia/methanol in dichloromethane) to yield 39 mg (75%, 2 steps) of a colorless foam. This partially epimerised material was separated into the pure diastereomers by SFC on Amylose-C and methanol/$CO_2$ as eluents. The later eluting diastereomer was 139 (24.6 mg). LCMS (ESI): R$_T$(min)=2.01 [M+H]$^+$=374.2, Method=A; $^1$H NMR (400 MHz, DMSO-$d_6$) δ 7.22 (br s, 1H), 6.89 (br s, 1H), 6.21 (d, J=2.0 Hz, 1H), 6.00 (d, J=2.0 Hz, 1H), 5.23 (d, J=7.4 Hz, 1H), 4.53 (t, J=5.3 Hz, 1H), 4.26-4.24 (m, 2H), 3.94-3.84 (m, 2H), 3.65 (pent, J=7.1 Hz, 1H), 3.46-3.42 (m, 1H), 3.39-3.29 (m, 2H), 2.82-2.76 (m, 1H), 2.64-2.59 (m, 1H), 2.21-2.16 (m, 2H), 1.83-1.58 (m, 4H), 1.28 (d, J=6.9 Hz, 3H), 1.18-1.08 (m, 1H).

Example 140 (S)-2-[1-(4-Hydroxymethylpiperidin-1-yl)-8,9-dihydro-7H-6-oxa-2,9a-diazabenzo[cd]azulen-4-ylamino]propionamide 140

Following the procedures of Example 139, 140 was prepared. LCMS (ESI): R$_T$ (min)=1.94, [M+H]$^+$=374.2, method=A; $^1$H NMR (400 MHz, DMSO-$d_6$) δ inter alia 7.21 (br s, 1H), 6.89 (br s, 1H), 6.21 (d, J=2.0 Hz, 1H), 6.00 (d, J=2.0 Hz, 1H), 5.23 (d, J=7.4 Hz, 1H), 4.49 (t, J=5.3 Hz, 1H), 4.26-4.24 (m, 2H), 3.90-3.87 (m, 2H), 3.65 (pent, J=7.1 Hz, 1H), 3.47-3.42 (m, 2H), 2.83-2.75 (m, 2H), 2.21-2.16 (m, 2H), 1.76-1.71 (m, 2H), 1.60-1.50 (m, 1H), 1.36-1.27 (m, 1H), 1.28 (d, J=6.9 Hz, 3H)

Example 141 (S)-2-Cyclopropyl-2-((1-morpholino-8,9-dihydro-7H-6-oxa-2,9a-diazabenzo[cd]azulen-4-yl)amino)acetamide 141

Step 1: 4-Bromo-1-morpholino-8,9-dihydro-7H-6-oxa-2,9a-diazabenzo[cd]azulene

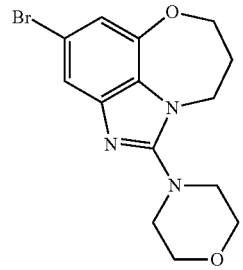 [SMILES: Brc1cc2c3c(c1)nc(N1CCOCC1)n3CCCO2]

A mixture of 4-bromo-1-iodo-8,9-dihydro-7H-6-oxa-2,9a-diazabenzo[cd]azulene (500 mg, 1.32 mmol) and morpholine (2.30 g, 26.39 mmol) in DMF (15 mL) in a sealed tube was heated under microwave irradiation at 140° C. for 2 h. The reaction mixture was diluted with water and extracted with DCM. The combined organic extracts were washed with brine, dried over sodium sulfate, filtered and the filtrate was evaporated in vacuo. The residue was purified via flash chromatography on silica gel (solvent gradient: 0-10% methanol in DCM) to yield 110 mg (25%) of the title compound as a yellow solid. LCMS (ESI): [M+H]$^+$=338/340.

Step 2: (S)-2-Cyclopropyl-2-((1-morpholino-8,9-dihydro-7H-6-oxa-2,9a-diazabenzo[cd]azulen-4-yl)amino)acetic acid

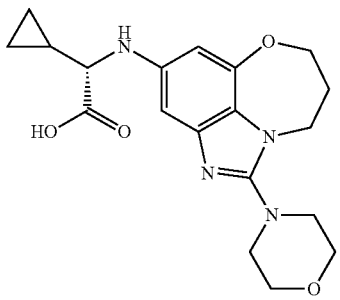 [SMILES: O=C(O)[C@@H](Nc1cc2c3c(c1)nc(N1CCOCC1)n3CCCO2)C1CC1]

The title compound (110 mg, 50%) was generated from 4-bromo-1-morpholino-8,9-dihydro-7H-6-oxa-2,9a-diazabenzo[cd]azulene (200 mg, 0.590 mmol) following a procedure analogous to Example 125, step 3. LCMS (ESI): [M+H]$^+$=373.

Step 3: (S)-2-Cyclopropyl-2-((1-morpholino-8,9-dihydro-7H-6-oxa-2,9a-diazabenzo[cd]azulen-4-yl)amino)acetamide The title compound (21.9 mg, 22%) was generated from (S)-2-cyclopropyl-2-((1-morpholino-8,9-dihydro-7H-6-oxa-2,9a-diazabenzo[cd]azulen-4-yl)amino)acetic acid (100 mg, 0.27 mmol) following a procedure analogous to Example 125, step 4. 141: LCMS (ESI): R$_T$ (min)=1.61, [M+H]$^+$=372, method=C; $^1$H NMR (300 MHz, DMSO-d$_6$) δ 7.29 (s, 1H), 6.93 (s, 1H), 6.23 (d, J=1.8 Hz, 1H), 6.05 (d, J=1.8 Hz, 1H), 5.29 (d, J=7.2 Hz, 1H), 4.27-4.24 (m, 2H), 3.95-3.91 (m, 2H), 3.75-3.72 (m, 4H), 3.14-3.05 (m, 5H), 2.22-2.10 (m, 2H), 1.11-1.05 (m, 1H), 0.51-0.44 (m, 3H), 0.39-0.19 (m, 1H).

Example 142 (S)-2-Cyclopropyl-2-((1-(oxazol-2-yl)-8,9-dihydro-7H-6-oxa-2,9a-diazabenzo[cd]azulen-4-yl)amino)acetamide 142

Following the procedures of Example 125, 142 was prepared. LCMS (ESI): R$_T$ (min)=2.16, [M+H]$^+$=354, method=C; $^1$H NMR (300 MHz, DMSO-d$_6$) δ 8.36 (s, 1H), 7.54 (s, 1H), 7.36 (s, 1H), 6.98 (s, 1H), 6.38-6.35 (m, 2H), 5.65 (d, J=7.2 Hz, 1H), 4.72-4.68 (m, 2H), 4.35-4.32 (m, 2H), 3.16-3.11 (m, 1H), 2.33-2.27 (m, 2H), 1.14-1.11 (m, 1H), 0.53-0.50 (m, 3H), 0.35-0.24 (m, 1H)

Example 143 (S)-2-Cyclopropyl-2-((1-(3-(difluoromethoxy)phenyl)-8,9-dihydro-7H-6-oxa-2,9a-diazabenzo[cd]azulen-4-yl)amino)acetamide 143

Following the procedures of Example 125, 143 was prepared. LCMS (ESI): R$_T$ (min)=1.54, [M+H]$^+$=429, method=D; $^1$H NMR (300 MHz, DMSO-d$_6$) δ 7.65-7.10 (m, 6H), 6.95 (s, 1H), 6.38 (d, J=1.8 Hz, 1H), 6.27 (d, J=1.8 Hz, 1H), 5.50 (d, J=7.5 Hz, 1H), 4.34-4.31 (m, 2H), 4.30-4.15 (m, 2H), 3.17-3.12 (m, 1H), 2.35-2.15 (m, 2H), 1.14-1.08 (m, 1H), 0.53-0.47 (m, 3H), 0.35-0.25 (m, 1H)

Example 144 (S)-2-Cyclopropyl-2-((1-(2-fluoro-4-methoxyphenyl)-8,9-dihydro-7H-6-oxa-2,9a-diazabenzo[cd]azulen-4-yl)amino)acetamide 144

Following the procedures of Example 125, 144 was prepared. LCMS (ESI): R$_T$ (min)=1.46, [M+H]$^+$=411, method=D; $^1$H NMR (400 MHz, DMSO-d$_6$) δ 7.54-7.52 (m, 1H), 7.34 (s, 1H), 7.06-7.02 (m, 1H), 6.97-6.95 (m, 2H), 6.38 (d, J=2.0 Hz, 1H), 6.27 (d, J=2.0 Hz, 1H), 5.49 (d, J=7.5 Hz, 1H), 4.35-4.28 (m, 2H), 4.01-3.93 (m, 2H), 3.86 (s, 3H), 3.17-3.13 (m, 1H), 2.23-2.22 (m, 2H), 1.15-1.09 (m, 1H), 0.53-0.45 (m, 3H), 0.34-0.30 (m, 1H)

Example 145 (S)-2-Cyclopropyl-2-((1-(2,4-difluorophenyl)-8,9-dihydro-7H-6-oxa-2,9a-diazabenzo[cd]azulen-4-yl)amino)acetamide 145

Following the procedures of Example 125, 145 was prepared. LCMS (ESI): R$_T$ (min)=2.78, [M+H]$^+$=399, method=D; $^1$H NMR (300 MHz, DMSO-d$_6$) δ 7.72-7.66 (m, 1H), 7.54-7.46 (m, 1H), 7.34-7.26 (m, 2H), 6.96 (s, 1H), 6.38 (d, J=1.8 Hz, 1H), 6.29 (d, J=2.1 Hz, 1H), 5.52 (d, J=7.5 Hz, 1H), 4.33-4.30 (m, 2H), 3.99-3.95 (m, 2H), 3.17-3.12 (m, 1H), 2.35-2.15 (m, 2H), 1.14-1.17 (m, 1H), 0.53-0.49 (m, 3H), 0.33-0.29 (m, 1H)

Example 146 (S)-3-(4-((2-Amino-1-cyclopropyl-2-oxoethyl)amino)-8,9-dihydro-7H-6-oxa-2,9a-diazabenzo[cd]azulen-1-yl)benzamide 146

Following the procedures of Example 125, 146 was prepared. LCMS (ESI): R$_T$ (min)=0.713, [M+H]$^+$=406, method=F; $^1$H NMR (300 MHz, DMSO-d$_6$) δ 8.24 (s, 1H), 8.13 (s, 1H), 8.04-8.01 (m, 1H), 7.93-7.90 (m, 1H), 7.66-7.61 (m, 1H), 7.50 (s, 1H), 7.35 (s, 1H), 6.97 (s, 1H), 6.40 (s, 1H), 6.28 (s, 1H), 5.50 (d, J=7.5 Hz, 1H), 4.36-4.34 (m, 2H), 4.29-4.24 (m, 2H), 3.19-3.14 (m, 1H), 2.27-2.25 (m, 2H), 1.16-1.07 (m, 1H), 0.55-0.45 (m, 3H), 0.33-0.31 (m, 1H)

Example 147 (S)-2-Cyclopropyl-2-((1-(1-methyl-6-oxo-1,6-dihydropyridin-3-yl)-8,9-dihydro-7H-6-oxa-2,9a-diazabenzo[cd]azulen-4-yl)amino)acetamide 147

Following the procedures of Example 125, 147 was prepared. LCMS (ESI): R$_T$ (min)=2.45, [M+H]$^+$=394, method=B; $^1$H NMR (400 MHz, DMSO-d$_6$) δ 8.12 (s, 1H), 7.67 (s, 1H), 7.32 (s, 1H), 6.95 (s, 1H), 6.37 (s, 1H), 6.26 (s, 1H), 5.50 (s, 1H), 4.52-4.45 (m, 2H), 4.36-4.26 (m, 4H), 4.26-4.15 (m, 2H), 3.14 (t, J=7.7 Hz, 1H), 2.30-2.20 (m, 2H), 1.18-1.04 (m, 1H), 0.57-0.41 (m, 3H), 0.35-0.25 (m, 1H)

Example 148 (S)-2-Cyclopropyl-2-((1-(2,3-dihydro-[1,4]dioxino[2,3-b]pyridin-7-yl)-8,9-dihydro-7H-6-oxa-2,9a-diazabenzo[cd]azulen-4-yl)amino)acetamide 148

Following the procedures of Example 125, 148 was prepared. LCMS (ESI): $R_T$ (min)=2.65, [M+H]$^+$=422, method=B; $^1$H NMR (400 MHz, DMSO-d$_6$) δ 8.12 (s, 1H), 7.67 (s, 1H), 7.32 (s, 1H), 6.95 (s, 1H), 6.37 (s, 1H), 6.26 (s, 1H), 5.50 (s, 1H), 4.52-4.45 (m, 2H), 4.36-4.26 (m, 4H), 4.26-4.15 (m, 2H), 3.14 (t, J=7.7 Hz, 1H), 2.30-2.20 (m, 2H), 1.18-1.04 (m, 1H), 0.57-0.41 (m, 3H), 0.35-0.25 (m, 1H)

Example 149 (S)-2-((1-(2-Amino-5H-pyrrolo[3,4-d]pyrimidin-6(7H)-yl)-8,9-dihydro-7H-6-oxa-2,9a-diazabenzo[cd]azulen-4-yl)amino)-2-cyclopropylacetamide 149

Following the procedures of Example 161, 149 was prepared. LCMS (ESI): $R_T$ (min)=1.89, [M+H]$^+$=421, method=D; $^1$H NMR (400 MHz, DMSO-d$_6$) δ 8.22 (s, 1H), 7.27 (s, 1H), 6.91 (s, 1H), 6.66 (s, 2H), 6.18 (s, 1H), 5.96 (s, 1H), 5.23-5.21 (d, J=7.2 Hz, 1H), 4.75 (s, 2H), 4.67 (s, 2H), 4.28-4.25 (m, 2H), 4.15-4.05 (m, 2H), 3.10-3.05 (m, 1H), 2.35-2.15 (m, 2H), 1.14-1.04 (m, 1H), 0.50-0.46 (m, 3H), 0.44-0.42 (m, 1H)

Example 150 (S)-2-Cyclopropyl-2-((1-(4-(difluoromethoxy)phenyl)-8,9-dihydro-7H-6-oxa-2,9a-diazabenzo[cd]azulen-4-yl)amino)acetamide 150

Step 1: 4-Bromo-8,9-dihydro-7H-6-oxa-2,9a-diazabenzo[cd]azulene

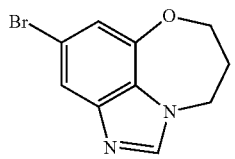 [SMILES: Brc1cc2c3c(c1)ncn3CCCO2]

4-methylbenzenesulfonic acid (354 mg, 2.06 mmol) was added to a solution of 8-bromo-2,3,4,5-tetrahydrobenzo[b][1,4]oxazepin-6-amine from Example 101 (5.00 g, 20.6 mmol) in triethyl orthoformate (60 mL) and the reaction mixture was heated at 100° C. for 16 h. The reaction mixture was evaporated in vacuo and the resultant residue was purified via flash chromatography on silica gel (solvent gradient: 0-10% methanol in DCM) to yield 4.20 g (81%) of the title compound as a yellow solid. LCMS (ESI): [M+H]$^+$=253/255; $^1$H NMR (300 MHz, DMSO-d$_6$) δ 8.27 (s, 1H), 7.43 (d, J=1.8 Hz, 1H), 6.89 (d, J=1.8 Hz, 1H), 4.40-4.31 (m, 4H), 2.35-2.28 (m, 2H).

Step 2: 4-Bromo-1-iodo-8,9-dihydro-7H-6-oxa-2,9a-diazabenzo[cd]azulene

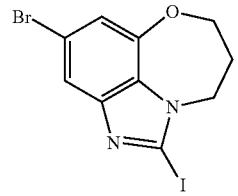

Lithium diisopropylamide (LDA) in anhydrous THF (2M, 16 mL, 32 mmol) was added dropwise to a solution of 4-bromo-8,9-dihydro-7H-6-oxa-2,9a-diazabenzo[cd]azulene (4.00 g, 15.8 mmol) in anhydrous THF at −78° C. and the reaction mixture stirred at −78° C. for 1 h. To this mixture was added N-iodosuccinimide (5.33 g, 23.7 mmol) at −78° C. and the resulting mixture was stirred at −78° C. for 1 h. The reaction mixture was diluted with water and extracted with DCM. The combined organic extracts were washed with brine, dried over sodium sulfate, filtered and the filtrate was evaporated in vacuo. The resultant residue was purified via flash chromatography on silica gel (solvent gradient: 0-25% ethyl acetate in petroleum ether) to yield 3.68 g (62%) of the title compound as a yellow solid. LCMS (ESI): [M+H]$^+$=379/381; $^1$H NMR (300 MHz, DMSO-d$_6$) δ 7.38-7.37 (d, J=1.8 Hz, 1H), 6.89 (d, J=1.8 Hz, 1H), 4.40-4.37 (m, 2H), 4.22-4.18 (m, 2H), 2.40-2.34 (m, 2H).

Step 3: 4-Bromo-1-(4-(difluoromethoxy)phenyl)-8,9-dihydro-7H-6-oxa-2,9a-diazabenzo[cd]azulene

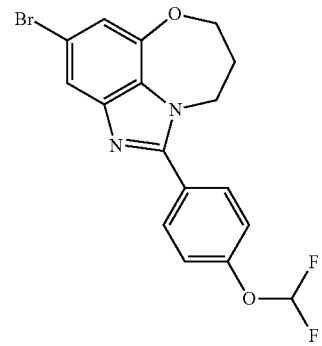 [SMILES: FC(F)Oc1ccc(-c2nc3cc(Br)cc4c3n2CCCO4)cc1]

A mixture of 4-bromo-1-iodo-8,9-dihydro-7H-6-oxa-2,9a-diazabenzo[cd]azulene (500 mg, 1.3 mmol), 4-(difluoromethoxy)phenylboronic acid (250 mg, 1.33 mmol), [1,1'-bis(diphenylphosphino)ferrocene] palladium(II) chloride (100 mg, 0.13 mmol), potassium acetate (2 M solution in water, 2.50 mL, 5.00 mmol) and sodium carbonate (2 M solution in water, 2.5 mL, 5.00 mmol) in acetonitrile (10 mL) was heated under microwave irradiation at 80° C. for 20 min. The reaction mixture was diluted with water and extracted with DCM. The combined organic extracts were dried over anhydrous sodium sulfate, filtered and evaporated in vacuo. The resultant residue was purified via flash chromatography on silica gel (solvent gradient: 0-10% methanol in DCM) to yield 160 mg (31%) of the title compound as an off-white solid. LCMS (ESI): [M+H]$^+$=395/397.

Step 4: (S)-2-Cyclopropyl-2-((1-(4-(difluoromethoxy)phenyl)-8,9-dihydro-7H-6-oxa-2,9a-diazabenzo[cd]azulen-4-yl)amino)acetamide The title compound (25.5 mg, 16%) was generated from 4-bromo-1-(4-(difluoromethoxy)phenyl)-8,9-dihydro-7H-6-oxa-2,9a-diazabenzo[cd]azulene (150 mg, 0.380 mmol) following a procedure analogous to Example 125, steps 3-4. 150: LCMS (ESI): $R_T$ (min)=1.65, [M+H]⁺=429, method=D; ¹H NMR (400 MHz, DMSO-$d_6$) δ 7.84-7.81 (m, 2H), 7.56-7.19 (m, 4H), 6.96 (s, 1H), 6.38 (d, J=2.0 Hz, 1H), 6.26 (d, J=2.0 Hz, 1H), 5.49 (d, J=7.4 Hz, 1H), 4.37-4.30 (m, 2H), 4.23-4.19 (m, 2H), 3.33-3.13 (m, 1H), 2.27-2.24 (m, 2H), 1.18-1.05 (m, 1H), 0.58-0.43 (m, 3H), 0.36-0.26 (m, 1H).

Example 151 (S)-4-(4-((2-Amino-1-cyclopropyl-2-oxoethyl)amino)-8,9-dihydro-7H-6-oxa-2,9a-diazabenzo[cd]azulen-1-yl)picolinamide 151

Following the procedures of Example 125, 151 was prepared. LCMS (ESI): $R_T$ (min)=1.12, [M+H]⁺=407, method=E; ¹H NMR (400 MHz, DMSO-$d_6$) δ 8.79 (d, J=5.2 Hz, 1H), 8.40 (s, 1H), 8.23 (s, 1H), 8.01-7.99 (d, J=5.2 Hz, 1H), 7.78 (s, 1H), 7.35 (s, 1H), 6.96 (s, 1H), 6.42 (d, J=2.0 Hz, 1H), 6.33 (d, J=2.0 Hz, 1H), 5.58 (d, J=7.2 Hz, 1H), 4.45-4.25 (m, 4H), 3.19-3.15 (m, 1H), 2.34-2.30 (m, 2H), 1.15-1.10 (m, 1H), 0.54-0.50 (m, 3H), 0.35-0.25 (m, 1H)

Example 152 2-(4-(1-(2-Aminobenzo[d]oxazol-5-yl)-8,9-dihydro-7H-6-oxa-2,9a-diazabenzo[cd]azulen-4-yl)-1H-pyrazol-1-yl)ethanol 152

Following the procedures of Example 124, 152 was prepared. LCMS (ESI): $R_T$ (min)=2.41, [M+H]⁺=417, method=C; ¹H NMR (300 MHz, DMSO-$d_6$) δ 8.14 (s, 1H), 7.88 (s, 1H), 7.58 (apparent s 3H), 7.51-7.47 (m, 2H), 7.40-7.37 (m, 1H), 7.00 (s, 1H), 4.93 (br, 1H), 4.50-4.35 (m, 2H), 4.31-4.28 (m, 2H), 4.17-4.13 (m, 2H), 3.79-3.76 (m, 2H), 2.40-2.25 (m, 2H)

Example 153 5-(4-(1-Methyl-1H-pyrazol-4-yl)-8,9-dihydro-7H-6-oxa-2,9a-diazabenzo[cd]azulen-1-yl)benzo[d]oxazol-2-amine 153

Following the procedures of Example 124, 153 was prepared. LCMS (ESI): $R_T$ (min)=2.38, [M+H]⁺=387, method=D; ¹H NMR (300 MHz, DMSO-$d_6$) δ 8.11 (s, 1H), 7.85 (s, 1H), 7.57 (apparent s, 3H), 7.50-7.45 (m, 2H), 7.39-7.37 (d, J=8.1 Hz, 1H), 6.99 (s, 1H), 4.42-4.39 (m, 2H), 4.30-4.27 (m, 2H), 3.85 (s, 3H), 2.37-2.24 (m, 2H)

Example 154 2-(4-(1-(2-Aminobenzo[d]oxazol-5-yl)-8,9-dihydro-7H-6-oxa-2,9a-diazabenzo[cd]azulen-4-yl)-1H-pyrazol-1-yl)-N,2-dimethylpropanamide 154

Following the procedures of Example 124, 154 was prepared. LCMS (ESI): $R_T$ (min)=1.34, [M+H]⁺=472, method=D; ¹H NMR (300 MHz, DMSO-$d_6$) δ 8.31 (s, 1H), 7.96 (s, 1H), 7.58-7.55 (m, 4H), 7.49 (d, J=8.4 Hz, 1H), 7.39 (d, J=8.1 Hz, 1H), 7.29-7.28 (m, 1H), 7.09 (s, 1H), 4.46-4.37 (m, 2H), 4.32-4.28 (m, 2H), 2.57 (d, J=4.5 Hz, 3H), 2.40-2.20 (m, 2H), 1.73 (s, 6H)

Example 155 (S)-2-Cyclopropyl-2-((1-(2-oxo-2,3-dihydrobenzo[d]oxazol-6-yl)-8,9-dihydro-7H-6-oxa-2,9a-diazabenzo[cd]azulen-4-yl)amino)acetamide 155

Following the procedures of Example 125, 155 was prepared. LCMS (ESI): $R_T$ (min)=1.74, [M+H]⁺=420, method=C; ¹H NMR (400 MHz, DMSO-$d_6$) δ 11.76 (br, 1H), 7.59 (s, 1H), 7.50-7.48 (m, 1H), 7.35 (s, 1H), 7.16 (d, J=8.1 Hz, 1H), 6.94 (s, 1H), 6.36 (d, J=2.0 Hz, 1H), 6.23 (d, J=2.0 Hz, 1H), 5.44 (d, J=7.4 Hz, 1H), 4.33-4.31 (m, 2H), 4.25-4.18 (m, 2H), 3.17-3.13 (m, 1H), 2.34-2.25 (m, 2H), 1.14-1.09 (m, 1H), 0.57-0.42 (m, 3H), 0.35-0.25 (m, 1H)

Example 157 (S)-5-(4-((2-Amino-1-cyclopropyl-2-oxoethyl)amino)-8,9-dihydro-7H-6-oxa-2,9a-diazabenzo[cd]azulen-1-yl)-2-fluorobenzamide 157

Following the procedures of Example 164, 157 was prepared. LCMS (ESI): $R_T$ (min)=1.24, [M+H]⁺=424, method=C; ¹H NMR (300 MHz, DMSO-$d_6$) δ 8.00-7.98 (m, 1H), 7.90-7.86 (m, 2H), 7.74 (s, 1H), 7.48-7.42 (m, 1H), 7.33 (s, 1H), 6.96 (s, 1H), 6.38 (d, J=1.8 Hz, 1H), 6.26 (d, J=2.1 Hz, 1H), 5.49 (d, J=7.2 Hz, 1H), 4.34-4.33 (m, 2H), 4.22-4.20 (m, 2H), 3.19-3.10 (m, 1H), 2.35-2.15 (m, 2H), 1.14-1.08 (m, 1H), 0.53-0.47 (m, 3H), 0.31-0.29 (m, 1H)

Example 158 (S)-Methyl 5-(4-((2-amino-1-cyclopropyl-2-oxoethyl)amino)-8,9-dihydro-7H-6-oxa-2,9a-diazabenzo[cd]azulen-1-yl)-2-methoxybenzoate 158

Step 1: Methyl 5-bromo-2-methoxybenzoate

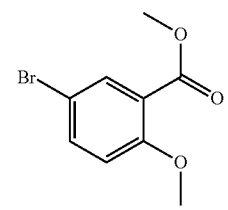

Trimethylsilyldiazomethane (2 M solution in hexane, 40 mL, 80.0 mmol) was added to a solution of 5-bromo-2-methoxybenzoic acid (5.00 g, 21.6 mmol) in methanol (100 mL) at 0° C., and the resulting solution was stirred at room temperature for 4 h. The reaction mixture was evaporated in vacuo and the residue was purified via flash chromatography on silica gel (solvent gradient: 0-20% ethyl acetate in petroleum ether) to yield 5.26 g (99%) of the title compound as a white solid. ¹H NMR (300 MHz, CDCl₃) δ 7.91 (s, 1H), 7.58-7.54 (d, J=9.0 Hz, 1H), 6.87 (d, J=9.0 Hz, 1H), 3.90 (s, 6H).

Step 2: Methyl 2-methoxy-5-(4,4,5,5-tetramethyl-1,3,2-dioxaborolan-2-yl)benzoate

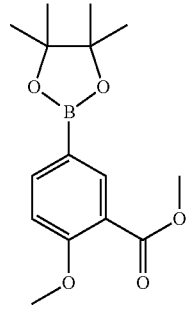

A mixture of methyl 5-bromo-2-methoxybenzoate (2.09 g, 8.53 mmol), 4,4,4',4',5,5,5',5'-octamethyl-2,2'-bi(1,3,2-dioxaborolane) (3.10 g, 12.2 mmol), potassium acetate (2.59 g, 26.4 mmol) and 1,1'-bis(diphenylphosphino)ferrocene palladium dichloride (600 mg, 0.820 mmol) in 1,4-dioxane (40 mL) was stirred at 80° C. for 2.5 h under nitrogen atmosphere. The reaction mixture was filtered and the filtrate was evaporated in vacuo. The residue was purified via flash chromatography on silica gel (solvent gradient: 0-10% ethyl acetate in petroleum ether) to yield 2.20 g (88.3%) of the title compound as a yellow solid. $^1$H NMR (300 MHz, CDCl$_3$) δ 8.23 (s, 1H), 7.91 (d, J=8.4 Hz, 1H), 6.98 (d, J=8.4 Hz, 1H), 3.94 (s, 3H), 3.89 (s, 3H), 1.35 (s, 12H).

Step 3: Methyl 5-(4-bromo-8,9-dihydro-7H-6-oxa-2,9a-diazabenzo[cd]azulen-1-yl)-2-methoxybenzoate

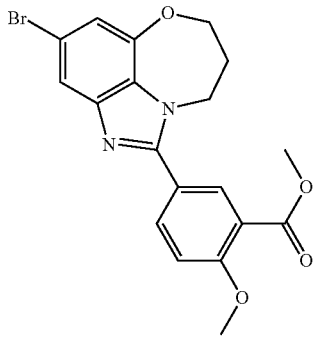 [SMILES: COC(=O)c1cc(-c2nc3cc(Br)cc4c3n2CCCO4)ccc1OC]

The title compound (241 mg, 49%) was generated from 4-bromo-1-iodo-8,9-dihydro-7H-6-oxa-2,9a-diazabenzo[cd]azulene (450 mg, 1.19 mmol) and methyl 2-methoxy-5-(4,4,5,5-tetramethyl-1,3,2-dioxaborolan-2-yl)benzoate (418 mg, 1.43 mmol) following a procedure analogous to Example 150, step 3. LCMS (ESI): [M+H]$^+$=417/419.

Step 4: (S)-2-Cyclopropyl-2-((1-(4-methoxy-3-(methoxycarbonyl)phenyl)-8,9-dihydro-7H-6-oxa-2,9a-diazabenzo[cd]azulen-4-yl)amino)acetic acid

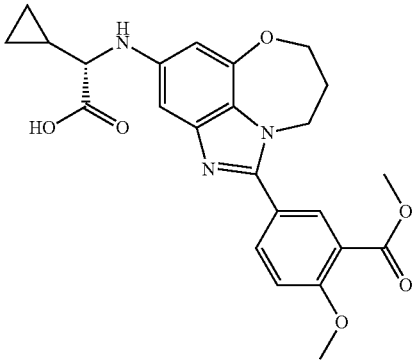 [SMILES: COC(=O)c1cc(-c2nc3cc(N[C@H](C(=O)O)C4CC4)cc4c3n2CCCO4)ccc1OC]

A mixture of methyl 5-(4-bromo-8,9-dihydro-7H-6-oxa-2,9a-diazabenzo[cd]azulen-1-yl)-2-methoxybenzoate (340 mg, 0.815 mmol), (S)-2-amino-2-cyclopropyl acetic acid (460 mg, 3.99 mmol), copper(I) iodide (193 mg, 1.01 mmol), potassium phosphate tribasic (1.02 g, 4.81 mmol) in DMSO (10 ml) in a sealed tube was heated under microwave irradiation at 110° C. for 2 h under nitrogen atmosphere. The reaction mixture was filtered and the filtrate was purified via reversed phase flash chromatography (solvent gradient: 0-100% methanol in water) to yield 310 mg (84.2%) of the title compound as a yellow solid. LCMS (ESI): [M+H]$^+$=452.

Step 5: (9-Methyl 5-(4-((2-amino-1-cyclopropyl-2-oxoethyl)amino)-8,9-dihydro-7H-6-oxa-2,9a-diazabenzo[cd]azulen-1-yl)-2-methoxybenzoate Ammonium chloride (729 mg, 13.6 mmol) was added to a solution of (S)-2-cyclopropyl-2-((1-(4-methoxy-3-(methoxycarbonyl)phenyl)-8,9-dihydro-7H-6-oxa-2,9a-diazabenzo[cd]azulen-4-yl)amino)acetic acid (310 mg, 0.687 mmol), DIPEA (2.22 g, 17.2 mmol) and HATU (522 mg, 1.373 mmol) in DMF (15 mL) and the resulting mixture was stirred at room temperature for 0.5 h. The reaction mixture was diluted with water and extracted with DCM. The combined organic extracts were washed with brine, dried over sodium sulfate, filtered and the filtrate was evaporated in vacuo. The residue was purified via reverse-phase HPLC and lyophilized to yield 9.0 mg (3%) of 158 as a white solid. LCMS (ESI): R$_T$(min)=2.378, [M+H]$^+$=451, method=C; $^1$H NMR (400 MHz, DMSO-d$_6$) δ 8.02 (s, 1H), 7.93 (d, J=8.4 Hz, 1H), 7.37-7.29 (m, 2H), 6.95 (s, 1H), 6.38 (d, J=2.0 Hz, 1H), 6.25 (d, J=2.0 Hz, 1H), 5.48 (d, J=7.4 Hz, 1H), 4.35-4.33 (m, 2H), 4.22-4.21 (m, 2H), 3.93 (s, 3H), 3.84 (s, 3H), 3.17-3.13 (m, 1H), 2.27-2.26 (m, 2H), 1.14-1.09 (m, 1H), 0.53-0.45 (m, 3H), 0.34-0.29 (m, 1H).

Example 159 (S)-2-Cyclopropyl-2-((1-(2-(methylsulfonyl)pyridin-4-yl)-8,9-dihydro-7H-6-oxa-2,9a-diazabenzo[cd]azulen-4-yl)amino)acetamide 159

Following the procedures of Example 125, 159 was prepared. LCMS (ESI): R$_T$ (min)=1.32, [M+H]$^+$=442, method=C; $^1$H NMR (400 MHz, DMSO-d$_6$) δ 8.95 (d, J=6.8 Hz, 1H), 8.41 (s, 1H), 8.17 (d, J=5.1 Hz, 1H), 7.37 (s, 1H), 6.98 (s, 1H), 6.43 (d, J=1.8 Hz, 1H), 6.36 (d, J=2.1 Hz, 1H), 5.63 (d, J=9.6 Hz, 1H), 4.43-4.37 (m, 4H), 3.37 (s, 3H), 3.20-3.15 (m, 1H), 2.40-2.25 (m, 2H), 1.16-1.10 (m, 1H), 0.55-0.46 (m, 3H), 0.33-0.32 (m, 1H)

Example 160 (S)-2-Cyclopropyl-2-[1-(1,3-dimethyl-1H-pyrazol-4-yl)-8,9-dihydro-7H-6-oxa-2,9a-diazabenzo[cd]azulen-4-ylamino]acetamide 160

Step 1: (6-Amino-8-bromo-3,4-dihydrobenzo[b][1,4]oxazepin-5(2H)-yl)(1,3-dimethyl-1H-pyrazol-4-yl)methanone and N-(8-bromo-2,3,4,5-tetrahydrobenzo[b][1,4]oxazepin-6-yl)-1,3-dimethyl-1H-pyrazole-4-carboxamide

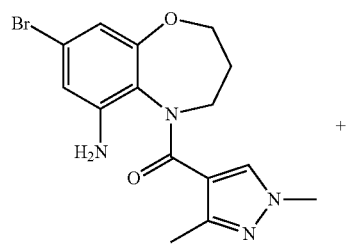

+

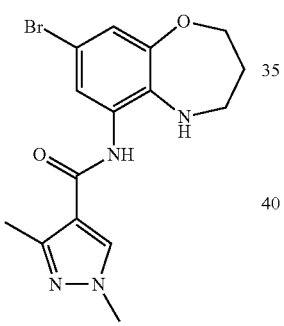

To a mixture of 1,3-dimethyl-1H-pyrazole-4-carboxylic acid (231 mg, 1.65 mmol) and DIPEA (0.32 mL, 1.82 mmol), in DCM (6.0 mL) was added methanesulfonyl chloride (0.14 mL, 1.82 mmol), under nitrogen, at 0° C. and the resultant mixture was stirred 0° C. for 15 min. A further portion of DIPEA (0.32 mL, 1.82 mmol) was added at 0° C. and the resultant mixture was then added to a solution of 8-bromo-2,3,4,5-tetrahydrobenzo[b][1,4]oxazepin-6-amine from Example 101 (365 mg, 1.50 mmol) in DCM (6.0 mL), at 0° C. under nitrogen. The reaction mixture was stirred at 0° C. for 30 min and was then diluted with water. The organic extracts were dried over magnesium sulfate, filtered and evaporated in vacuo. The crude residue was purified via flash chromatography on silica gel (solvent gradient: 0-5% methanol in DCM) to yield 458 mg (84%, ~2:1 mixture of isomers) of the title compounds as a beige foam. LCMS (ESI): [M+H]$^+$=365/367.

Step 2: 4-Bromo-1-(1,3-dimethyl-1H-pyrazol-4-yl)-8,9-dihydro-7H-6-oxa-2,9a-diazabenzo[cd]azulene

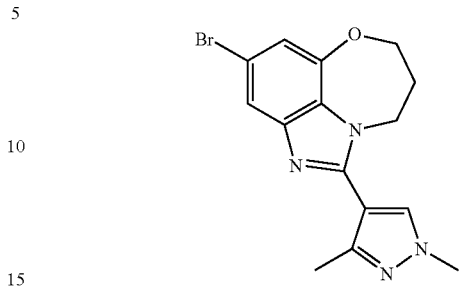

A mixture of (6-amino-8-bromo-3,4-dihydrobenzo[b][1,4]oxazepin-5(2H)-yl)(1,3-dimethyl-1H-pyrazol-4-yl) methanone and N-(8-bromo-2,3,4,5-tetrahydrobenzo[b][1,4]oxazepin-6-yl)-1,3-dimethyl-1H-pyrazole-4-carboxamide (348 mg, 0.95 mmol) in acetic acid (3.0 mL) was heated at 120° C., under microwave irradiation, for 15 min. The reaction mixture was evaporated in vacuo and the crude residue was purified via flash chromatography on silica gel (solvent gradient: 0-8% methanol in DCM) to yield 237 mg (72%) of the title compound as a white solid. LCMS (ESI): [M+H]$^+$=347/349.

Step 3: (S)-2-Cyclopropyl-2-[1-(1,3-dimethyl-1H-pyrazol-4-yl)-8,9-dihydro-7H-6-oxa-2,9a-diazabenzo[cd]azulen-4-ylamino]acetamide A mixture of 4-bromo-1-(1,3-dimethyl-1H-pyrazol-4-yl)-8,9-dihydro-7H-6-oxa-2,9a-diazabenzo[cd]azulene (100 mg, 0.58 mmol), L-cyclopropylglycine (66 mg, 0.58 mmol), cuprous iodide (11 mg, 0.06 mmol) and potassium phosphate tribasic (123 mg, 0.58 mmol) in DMSO (1.0 mL) was degassed with argon under sonication. The reaction mixture was heated at 100° C. for 18 h and then cooled to room temperature. To the resultant mixture was added ammonium chloride (93 mg, 1.16 mmol) and triethylamine (404 μL, 2.90 mmol) followed by portion-wise addition of HATU (441 mg, 1.16 mmol), and the reaction mixture was stirred at room temperature for 1 h. The resultant mixture was diluted with aqueous ammonium hydroxide solution and extracted with DCM. The combined organic extracts were dried over magnesium sulfate, filtered and evaporated in vacuo. The resultant residue was purified via flash chromatography on silica gel (solvent gradient: 0-15% methanol in DCM) to yield 20 mg (18%) of 160 as an off-white solid. LCMS (ESI): $R_T$ (min)=2.29, [M+H]$^+$=381.2, method=A; $^1$H NMR (400 MHz, DMSO-d$_6$) δ 8.12 (s, 1H), 7.32 (s, 1H), 6.94 (s, 1H), 6.33 (d, J=2.0 Hz, 1H), 6.19 (d, J=2.3 Hz, 1H), 5.40 (br s, 1H), 4.31 (t, J=4.5 Hz, 2H), 4.16 (t, J=5.4 Hz, 2H), 3.84 (s, 3H), 3.13 (t, J=7.7 Hz, 1H), 2.34 (s, 3H), 2.29-2.21 (m, 2H), 1.13-1.07 (m, 1H), 0.53-0.44 (m, 3H), 0.33-0.26 (m, 1H).

Example 161 (S)-2-Cyclopropyl-2-((1-(5,6-dihydro-[1,2,4]triazolo[1,5-a]pyrazin-7(8H)-yl)-8,9-dihydro-7H-6-oxa-2,9a-diazabenzo[cd]azulen-4-yl)amino)acetamide 161

Step 1: 4-Bromo-1-chloro-8,9-dihydro-7H-6-oxa-2,9a-diazabenzo[cd]azulene

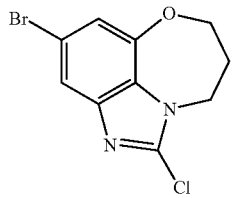 [SMILES: Clc1nc2cc(Br)cc3c2n1CCCO3]

LDA (2M in THF, 0.75 mL, 1.5 mmol) was added dropwise to a solution of 4-bromo-8,9-dihydro-7H-6-oxa-2,9a-diazabenzo[cd]azulene from Example 150 (200 mg, 0.790 mmol) in anhydrous THF (6 mL) at −78° C. and the mixture was stirred at −78° C. for 1 h. A solution of N-chlorosuccinimide (211 mg, 1.58 mmol) in THF was added dropwise at −78° C. The reaction mixture was allowed to warm to 20° C. and stirred for another 1 h. The reaction was then quenched by addition of aqueous ammonium chloride. The resulting solution was extracted with DCM and the organic extracts were combined and dried over anhydrous sodium sulfate and evaporated in vacuo. The residue was purified via flash chromatography on silica gel (solvent gradient: 0-5% methanol in DCM) to yield 100 mg (44%) of the title compound as a white solid. LCMS (ESI): $[M+H]^+$=287/289.

Step 2: 4-Bromo-1-(5,6-dihydro-[1,2,4]triazolo[1,5-a]pyrazin-7(8H)-yl)-8,9-dihydro-7H-6-oxa-2,9a-diazabenzo[cd]azulene

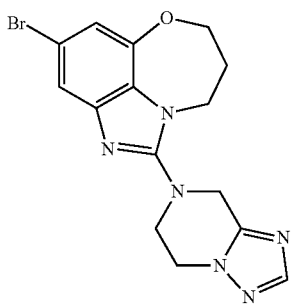 [SMILES: Brc1cc2c3c(c1)nc(N1CCn4ncnc4C1)n3CCCO2]

A mixture of 4-bromo-1-chloro-8,9-dihydro-7H-6-oxa-2,9a-diazabenzo[cd]azulene (200 mg, 0.696 mmol) and 5,6,7,7a-tetrahydro-4H-imidazo[4,5-c]pyridine (867 mg, 6.99 mmol) in DMSO (4 mL) was heated under microwave irradiation for 2 h at 140° C. The reaction mixture was purified by reverse phase flash chromatography (solvent gradient: 0-95% methanol in water) to yield 220 mg (84%) of the title compound as a yellow solid. LCMS (ESI): $[M+H]^+$=375/377.

Step 3: (S)-2-Cyclopropyl-2-((1-(5,6-dihydro-[1,2,4]triazolo[1,5-a]pyrazin-7(8H)-yl)-8,9-dihydro-7H-6-oxa-2,9a-diazabenzo[cd]azulen-4-yl)amino)acetic acid

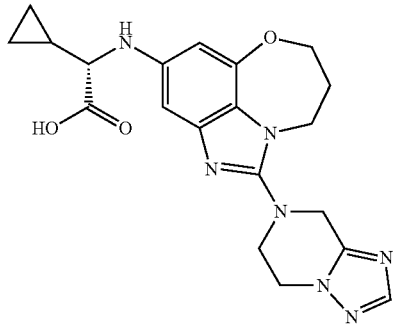 [SMILES: O=C(O)[C@@H](Nc1cc2c3c(c1)nc(N1CCn4ncnc4C1)n3CCCO2)C1CC1]

The title compound (240 mg, 69% yield) was generated from 4-bromo-1-(5,6-dihydro-[1,2,4]triazolo[1,5-a]pyrazin-7(8H)-yl)-8,9-dihydro-7H-6-oxa-2,9a-diazabenzo[cd]azulene (320 mg, 0.853 mmol) following a procedure analogous to Example 125, step 3. LCMS (ESI): $[M+H]^+$=410.

Step 4: (S)-2-Cyclopropyl-2-((1-(5,6-dihydro-[1,2,4]triazolo[1,5-a]pyrazin-7(8H)-yl)-8,9-dihydro-7H-6-oxa-2,9a-diazabenzo[cd]azulen-4-yl)amino)acetamide The title compound (130 mg, 57% yield) was generated from (S)-2-cyclopropyl-2-((1-(5,6-dihydro-[1,2,4]triazolo[1,5-c]pyrazin-7(8H)-yl)-8,9-dihydro-7H-6-oxa-2,9a-diazabenzo[cd]azulen-4-yl)amino) acetic acid (230 mg, 0.562 mmol) following a procedure analogous to Example 125, step 4. 161: LCMS (ESI): $R_T$ (min)=2.10, $[M+H]^+$=409, method=C; $^1$H NMR (400 MHz, DMSO-$d_6$) δ 7.98 (s, 1H), 7.29 (s, 1H), 6.92 (s, 1H), 6.24 (d, J=2.0 Hz, 1H), 6.10 (d, J=2.0 Hz, 1H), 5.33 (d, J=7.2 Hz, 1H), 4.55 (s, 2H), 4.39-4.22 (m, 4H), 4.12-3.92 (m, 2H), 3.82-3.64 (m, 2H), 3.17-3.01 (m, 1H), 2.23-2.15 (m, 2H), 1.13-1.04 (m, 1H), 0.52-0.40 (m, 3H), 0.32-0.21 (m, 1H).

Example 162 (S)-2-((1-(2-Aminobenzo[d]oxazol-5-yl)-8,9-dihydro-7H-6-oxa-2,9a-diazabenzo[cd]azulen-4-yl)oxy)propanamide 162

Step 1: 5-(4-(4,4,5,5-Tetramethyl-1,3,2-dioxaborolan-2-yl)-8,9-dihydro-7H-6-oxa-2,9a-diazabenzo[cd]azulen-1-yl)benzo[d]oxazol-2-amine

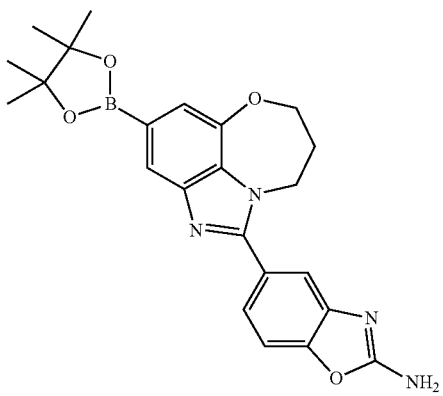 [SMILES: CC1(C)OB(c2cc3c4c(c2)nc(-c2ccc5oc(N)nc5c2)n4CCCO3)OC1(C)C]

A mixture of 5-(4-bromo-8,9-dihydro-7H-6-oxa-2,9a-diazabenzo[cd]azulen-1-yl)benzo[d]oxazol-2-amine from Example 101 (1.5 g, 3.89 mmol), 4,4,4',4',5,5,5',5'-octamethyl-2,2'-bi(1,3,2-dioxaborolane) (1.98 g, 7.80 mmol), 1,1'-bis(diphenylphosphino)ferrocenepalladiumdichloride dichloromethane complex (1.59 g, 1.95 mmol), potassium acetate (1.53 g, 15.6 mmol) and 1,4-dioxane (20 mL) were degassed with nitrogen under sonication. The resulting solution was stirred for 15 h at 80° C. The solids were filtered off, and the filtrate was evaporated in vacuo. The residue was purified via flash chromatography on silica gel (solvent gradient: 0-100% ethyl acetate in petroleum ether) to yield 750 mg (45%) of the title compound as a black solid. LCMS: [M+H]⁺=433.

Step 2: 1-(2-Aminobenzo[d]oxazol-5-yl)-8,9-dihydro-7H-6-oxa-2,9a-diazabenzo[cd]azulen-4-ol

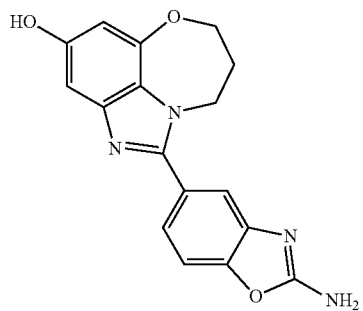 [SMILES: Nc1nc2cc(-c3nc4cc(O)cc5c4n3CCCO5)ccc2o1]

A mixture of 5-(4-(4,4,5,5-tetramethyl-1,3,2-dioxaborolan-2-yl)-8,9-dihydro-7H-6-oxa-2,9a-diazabenzo [cd]azulen-1-yl)benzo[d]oxazol-2-amine (800 mg, 1.85 mmol), acetic acid (3 mL), water (3 mL) and hydrogen peroxide (1.5 mL) was stirred for 1 h at 25° C. The reaction was quenched by the addition of aqueous sodium hydrogen sulfite. The precipitate was collected by filtration to yield 420 mg (70%) of the title compound as a yellow solid. ¹H NMR (400 MHz, DMSO-d₆) δ 9.54 (br, 1H), 7.69 (s, 2H), 7.63 (s, 1H), 7.54 (d, J=8.0 Hz, 1H), 7.43 (d, J=8.0 Hz, 1H), 6.66 (s, 1H), 6.41 (s, 1H), 4.46-4.40 (m, 2H), 4.36-4.30 (m, 2H), 2.40-2.25 (m, 2H).

Step 3: (S)-Methyl 2-((1-(2-aminobenzo[d]oxazol-5-yl)-8,9-dihydro-7H-6-oxa-2,9a-diazabenzo [cd]azulen-4-yl)oxy)propanoate

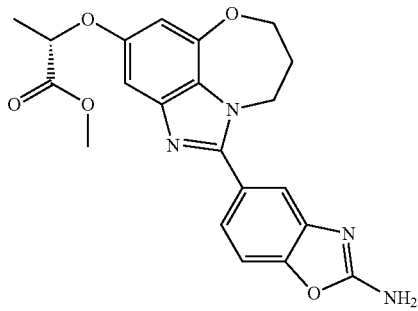 [SMILES: COC(=O)[C@H](C)Oc1cc2c3c(c1)nc(-c1ccc4oc(N)nc4c1)n3CCCO2]

A mixture of 1-(2-aminobenzo[d]oxazol-5-yl)-8,9-dihydro-7H-6-oxa-2,9a-diazabenzo[cd]azulen-4-ol (450 mg, 1.40 mmol), (R)-methyl 2-(tosyloxy)propanoate (540 mg, 2.09 mmol) and potassium carbonate (771 mg, 5.58 mmol) in DMSO (8 mL) was stirred for 24 h at 35° C. The solids were removed by filtration and the filtrate was purified via reverse phase flash chromatography (solvent gradient: 0-100% methanol in water) to yield 500 mg (88%) the title compound as a yellow solid. LCMS: [M+H]⁺=409.

Step 4: (S)-2-((1-(2-Aminobenzo[d]oxazol-5-yl)-8,9-dihydro-7H-6-oxa-2,9a-diazabenzo[cd]azulen-4-yl)oxy)propanoic acid

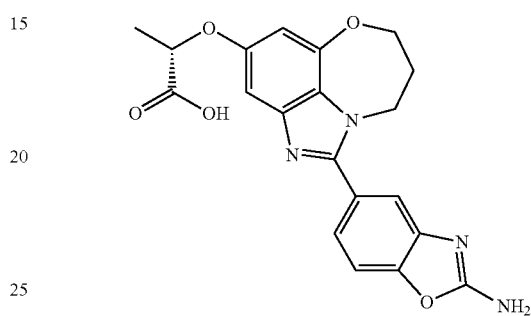

Lithium hydroxide (53.0 mg, 2.21 mmol) in water (2 mL) was added to a solution of (9-methyl 2-((1-(2-aminobenzo[d]oxazol-5-yl)-8,9-dihydro-7H-6-oxa-2,9a-diazabenzo [cd]azulen-4-yl)oxy)propanoate (600 mg, 1.47 mmol) in methanol (8 mL) and the resulting solution was stirred for 3 h at 25° C. The pH was adjusted to 5 with acetic acid and evaporated in vacuo. The residue was purified via reverse phase flash chromatography (solvent gradient: 0-95% methanol in water) to yield 350 mg (60%) of the title compound as a white solid. LCMS: [M+H]⁺=395.

Step 5: (S)-2-((1-(2-Aminobenzo[d]oxazol-5-yl)-8,9-dihydro-7H-6-oxa-2,9a-diazabenzo[cd]azulen-4-yl)oxy)propanamide A mixture of (S)-2-((1-(2-aminobenzo[d]oxazol-5-yl)-8,9-dihydro-7H-6-oxa-2,9a-diazabenzo[cd]azulen-4-yl)oxy) propanoic acid (330 mg, 0.837 mmol), DIPEA (3 mL, 38.765 mmol), ammonium chloride (452 mg, 8.45 mmol) and HATU (636 mg, 1.67 mmol) in DMF (3 mL) was stirred at room temperature for 20 min. The solids were filtered off, and the filtrate was purified via reverse-phase HPLC and lyophilized to yield 160 mg (49%) of 162 as a white solid. LCMS (ESI): R$_T$ (min)=2.41, [M+H]⁺=394, method=C; ¹H NMR (400 MHz, DMSO-d₆) δ 7.62-7.52 (m, 3H), 7.50-7.42 (m, 2H), 7.38-7.30 (m, 1H), 7.19 (s, 1H), 6.76 (s, 1H), 6.41 (s, 1H), 4.68-4.54 (m, 1H), 4.45-4.30 (m, 2H), 4.30-4.17 (m, 2H), 2.15-2.25 (m, 2H), 1.42 (d, J=6.8 Hz, 3H).

Example 163 (S)-2-Cyclopropyl-2-((1-(3-(difluoromethoxy)-4-methoxyphenyl)-8,9-dihydro-7H-6-oxa-2,9a-diazabenzo[cd]azulen-4-yl)amino)acetamide 163

Following the procedures of Example 125, 163 was prepared. LCMS (ESI): R$_T$ (min)=1.57, [M+H]⁺=459, method=G; ¹H NMR (400 MHz, DMSO-d₆) δ 7.64 (d, J=8.4 Hz, 1H), 7.58 (d, J=2.0 Hz, 1H), 7.40-7.00 (m, 3H), 6.96 (s, 1H), 6.37 (d, J=2.0 Hz, 1H), 6.24 (d, J=2.0 Hz, 1H), 5.47 (d, J=7.4 Hz, 1H), 4.34-4.32 (m, 2H), 4.25-4.21 (m, 2H), 3.92

(s, 3H), 3.16-3.12 (m, 1H), 2.35-2.20 (m, 2H), 1.12-1.09 (m, 1H), 0.58-0.42 (m, 3H), 0.36-0.26 (m, 1H)

Example 164 (S)-5-(4-((2-Amino-1-cyclopropyl-2-oxoethyl)amino)-8,9-dihydro-7H-6-oxa-2,9a-diazabenzo[cd]azulen-1-yl)-2-methoxybenzamide 164

A mixture of (S)-methyl 5-(4-((2-amino-1-cyclopropyl-2-oxoethyl)amino)-8,9-dihydro-7H-6-oxa-2,9a-diazabenzo[cd]azulen-1-yl)-2-methoxybenzoate from Example 158, 120 mg, 0.266 mmol) and saturated solution of ammonia in methanol (10 mL) in a sealed tube was stirred at room temperature for 24 h. The reaction mixture was evaporated in vacuo. The residue was purified via reverse-phase HPLC and lyophilized to yield 15.6 mg (13%) of 164 as a light yellow solid. LCMS (ESI): $R_T$ (min)=1.614, [M+H]$^+$=436, method=D; $^1$H NMR (400 MHz, DMSO-d$_6$) δ 8.18 (s, 1H), 7.89 (d, J=8.6 Hz, 1H), 7.74-7.68 (m, 2H), 7.37 (m, 2H), 6.99 (s, 1H), 6.33 (m, 2H), 5.76 (br, 1H), 4.50-4.35 (m, 2H), 4.32-4.15 (m, 2H), 3.98 (s, 3H), 3.19-3.15 (m, 1H), 2.29-2.27 (m, 2H), 1.13-1.11 (m, 1H), 0.52-0.48 (m, 3H), 0.35-0.27 (m, 1H).

Example 165 (S)-2-Cyclopropyl-2-((1-(pyridin-4-yl)-8,9-dihydro-7H-6-oxa-2,9a-diazabenzo[cd]azulen-4-yl)amino)acetamide 165

Following the procedures of Example 150, 165 was prepared. LCMS (ESI): $R_T$ (min)=1.17, [M+H]$^+$=364, method=D; $^1$H NMR (300 MHz, DMSO-d$_6$) δ 8.74 (d, J=4.5 Hz, 2H), 7.78 (d, J=4.5 Hz, 2H), 7.34 (s, 1H), 6.96 (s, 1H), 6.39 (d, J=2.0 Hz, 1H), 6.30 (d, J=2.0 Hz, 1H), 5.55 (d, J=7.4 Hz, 1H), 4.39-4.23 (m, 4H), 3.17-3.12 (m, 1H), 2.34-2.22 (m, 2H), 1.20-1.02 (m, 1H), 0.59-0.40 (m, 3H), 0.35-0.20 (m, 1H)

Example 166 (S)-2-Cyclopropyl-2-[1-(1-methyl-1H-pyrazol-4-yl)-8,9-dihydro-7H-6-oxa-2,9a-diazabenzo[cd]azulen-4-ylamino]acetamide 166

Following the procedures of Example 160, 166 was prepared. LCMS (ESI): $R_T$ (min)=2.22, [M+H]$^+$=380.2, method=A; $^1$H NMR (400 MHz, DMSO-d$_6$) δ 8.30 (s, 1H), 8.16 (s, 0.6H), 7.94 (d, J=0.8 Hz, 1H), 7.33 (d, J=2.2 Hz, 1H), 6.93 (d, J=2.0 Hz, 1H), 6.31 (d, J=2.0 Hz, 1H), 6.16 (d, J=2.0 Hz, 1H), 5.39 (br s, 1H), 4.34-4.24 (m, 4H), 3.92 (s, 3H), 3.11 (d, J=8.2 Hz, 1H), 2.34-2.25 (m, 2H), 1.14-1.04 (m, 1H), 0.53-0.41 (m, 3H), 0.33-0.22 (m, 1H)

Example 167 (S)-2-Cyclopropyl-2-((1-(2,3-dihydro-[1,4]dioxino[2,3-b]pyridin-6-yl)-8,9-dihydro-7H-6-oxa-2,9a-diazabenzo[cd]azulen-4-yl)amino)acetamide 167

Following the procedures of Example 125, 167 was prepared. LCMS (ESI): $R_T$ (min)=2.87, [M+H]$^+$=421, method=B; $^1$H NMR (400 MHz, DMSO-d6) δ 7.76 (d, J=8.0 Hz, 1H), 7.44 (d, J=8.3 Hz, 1H), 7.33 (br s, 1H), 6.95 (br s, 1H), 6.35 (d, J=2.0 Hz, 1H), 6.26 (d, J=2.0 Hz, 1H), 5.50 (d, J=7.3 Hz, 1H), 4.67 (t, J=5.6 Hz, 2H), 4.51-4.44 (m, 2H), 4.37-4.27 (m, 4H), 3.13 (t, J=7.7 Hz, 1H), 2.30-2.24 (m, 2H), 1.19-1.03 (m, 1H), 0.56-0.45 (m, 3H), 0.30 (dt, J=9.8, 4.2 Hz, 1H)

Example 168 (5-(4-Bromo-8,9-dihydro-7H-6-oxa-2,9a-diazabenzo[cd]azulen-1-yl)benzo[d]oxazol-2-yl)methanol 168

Step 1: (5-Bromobenzo[d]oxazol-2-yl)methyl acetate

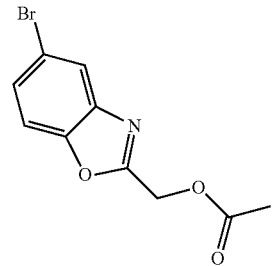

A mixture of 5-bromo-2-(chloromethyl)benzo[d]oxazole (1.40 g, 5.71 mmol), cesium acetate (2.20 g, 11.52 mmol) in DMF (30 mL) was stirred at room temperature for 10 hours, the reaction mixture was diluted with water and extracted with DCM. The combined organic extracts were dried over anhydrous sodium sulfate, filtered and evaporated in vacuo. The residue was purified via flash chromatography on silica gel (solvent gradient: 0-50% ethyl acetate in petroleum ether) to yield 1.2 g (78%) of the title compound as a off-white solid. $^1$H NMR (400 MHz, CDCl$_3$) δ 7.91 (s, 1H), 7.52 (d, J=8.0 Hz, 1H), 7.45 (d, J=8.7 Hz, 1H), 5.36 (s, 2H), 2.24 (s, 3H).

Step 2: (5-(4,4,5,5-Tetramethyl-1,3,2-dioxaborolan-2-yl)benzo[d]oxazol-2-yl)methyl acetate

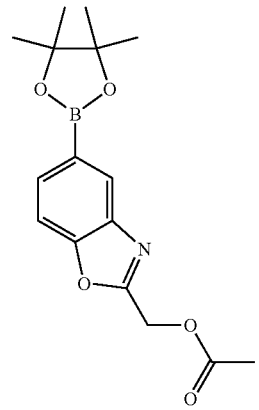 [SMILES: CC(=O)OCc1nc2cc(B3OC(C)(C)C(C)(C)O3)ccc2o1]

A mixture of (5-bromobenzo[d]oxazol-2-yl)methyl acetate (600 mg, 2.23 mmol), 4,4,4',4',5,5,5',5'-octamethyl-2,2'-bi(1,3,2-dioxaborolane) (678 mg, 2.66 mmol), [1,1'-bis(diphenylphosphino)ferrocene] palladium(II) chloride (100 mg, 0.130 mmol), and potassium acetate (652 mg, 6.66 mmol) in 1,4-dioxane (10 mL) in a sealed tube was heated under microwave irradiation at 80° C. for 30 min. The reaction mixture was diluted with water and extracted with DCM. The combined organic extracts were dried over anhydrous sodium sulfate, filtered and evaporated in vacuo. The residue was purified via flash chromatography on silica gel (solvent gradient: 0-50% ethyl acetate in petroleum ether) to yield 600 mg (85%) of the title compound as an off-white solid. LCMS (ESI): [M+H]⁺=318.

Step 3: (5-(4-Bromo-8,9-dihydro-7H-6-oxa-2,9a-diazabenzo[cd]azulen-1-yl)benzo[d]oxazol-2-yl) methyl acetate

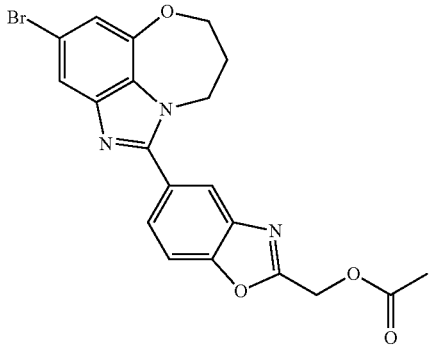 [SMILES: CC(=O)OCc1nc2cc(-c3nc4cc(Br)cc5c4n3CCCO5)ccc2o1]

A mixture of 4-bromo-1-iodo-8,9-dihydro-7H-6-oxa-2,9a-diazabenzo[cd]azulene (900 mg, 2.37 mmol), (5-(4,4,5,5-tetramethyl-1,3,2-dioxaborolan-2-yl) benzo [d]oxazol-2-yl) methyl acetate (600 mg, 1.89 mmol), [1,1'-bis(diphenylphosphino) ferrocene] palladium(II) chloride (138 mg, 0.190 mmol), potassium acetate (2N solution in water, 1.8 mL, 3.60 mmol) and sodium carbonate (2N solution in water, 1.8 mL, 3.60 mmol) in acetonitrile (7.2 mL) was heated under microwave irradiation at 80° C. for 20 min. The reaction mixture was diluted with water and extracted with DCM. The combined organic extracts were dried over anhydrous sodium sulfate, filtered and evaporated in vacuo. The residue was purified via flash chromatography on silica gel (solvent gradient: 0-10% methanol in DCM) to yield 201 mg (24%) of the title compound as an off-white solid. LCMS (ESI): [M+H]⁺=442/444; ¹H NMR (300 MHz, DMSO-d₆) δ 8.23-8.15 (m, 1H), 8.02-7.87 (m, 1H), 7.87-7.72 (m, 1H), 7.48 (d, J=1.8 Hz, 1H), 6.93 (d, J=1.8 Hz, 1H), 5.43 (d, J=2.8 Hz, 2H), 4.49-4.40 (m, 2H), 4.38-4.28 (m, 2H), 2.38-2.28 (m, 2H), 2.17 (s, 3H).

Step 4: (5-(4-Bromo-8,9-dihydro-7H-6-oxa-2,9a-diazabenzo[cd]azulen-1-yl)benzo[d]oxazol-2-yl) methanol A mixture of (5-(4-bromo-8,9-dihydro-7H-6-oxa-2,9a-diazabenzo[cd]azulen-1-yl)benzo[d]oxazol-2-yl)methyl acetate (150 mg, 0.340 mmol) and potassium carbonate (11.8 mg, 0.090 mmol) in methanol (2 mL) was stirred at room temperature for 2 h. The mixture was evaporated in vacuo, and the residue was purified via reverse-phase HPLC and lyophilized to yield 25.8 mg (19%) of 168 as a white solid. LCMS (ESI): R_T (min)=1.49, [M+H]⁺=400/402, method=D; ¹H NMR (300 MHz, DMSO-d₆) δ 8.15 (s, 1H), 7.93-7.90 (d, J=8.4 Hz, 1H), 7.83-7.80 (d, J=8.4 Hz, 1H), 7.47 (d, J=1.8 Hz, 1H), 6.92 (d, J=1.8 Hz, 1H), 5.97-5.92 (m, 1H), 4.76 (d, J=6.3 Hz, 2H), 4.46-4.32 (m, 2H), 4.39-4.28 (m, 2H), 2.33-2.07 (m, 2H).

Example 169 (S)-2-((1-(1H-Pyrazolo[3,4-b]pyridin-4-yl)-8,9-dihydro-7H-6-oxa-2,9a-diazabenzo[cd]azulen-4-yl)amino)-2-cyclopropylacetamide 169

Following the procedures of Example 164, 169 was prepared. LCMS (ESI): R_T (min)=1.65, [M+H]⁺=404, method=D; ¹H NMR (300 MHz, DMSO-d₆) δ 13.89 (br, 1H), 8.69 (d, J=4.8 Hz, 1H), 8.32 (s, 1H), 7.55 (d, J=4.8 Hz, 1H), 7.39 (s, 1H), 6.99 (s, 1H), 6.48 (d, J=1.9 Hz, 1H), 6.37 (d, J=2.0 Hz, 1H), 5.61 (d, J=7.4 Hz, 1H), 4.44-4.29 (m, 4H), 3.21-3.16 (m, 1H), 2.35-2.20 (m, 2H), 1.13-1.09 (m, 1H), 0.54-0.48 (m, 3H), 0.39-0.29 (m, 1H)

Example 170 (S)-2-((1-(2-Aminobenzo[d]thiazol-6-yl)-8,9-dihydro-7H-6-oxa-2,9a-diazabenzo[cd]azulen-4-yl)amino)-2-cyclopropylacetamide 170

Following the procedures of Example 164, 170 was prepared. LCMS (ESI): R_T (min)=1.25, [M+H]⁺=435, method=D; ¹H NMR (400 MHz, DMSO-d₆) δ 8.07 (s, 1H), 7.69 (s, 2H), 7.60 (d, J=8.2, 1H), 7.44 (d, J=8.3 Hz, 1H), 7.34 (s, 1H), 6.96 (s, 1H), 6.37 (d, J=2.0 Hz, 1H), 6.23 (d, J=2.0 Hz, 1H), 5.45 (d, J=7.3 Hz, 1H), 4.37-4.29 (m, 2H), 4.24-4.15 (m, 2H), 3.16-3.12 (m, 1H), 2.26-2.25 (m, 2H), 1.13-1.09 (m, 1H), 0.51-0.45 (m, 3H), 0.35-0.25 (m, 1H)

Example 173 (S)-2-Cyclopropyl-2-((1-(2-methoxyquinoxalin-6-yl)-8,9-dihydro-7H-6-oxa-2,9a-diazabenzo[cd]azulen-4-yl)amino)acetamide 173

Following the procedures of Example 164, 173 was prepared. LCMS (ESI): R_T (min)=2.47, [M+H]⁺=445, method=D; ¹H NMR (300 MHz, DMSO-d₆) δ 8.70 (s, 1H), 8.37 (s, 1H), 8.17-8.14 (d, J=8.4 Hz, 1H), 7.98 (d, J=8.7 Hz, 1H), 7.36 (s, 1H), 6.98 (s, 1H), 6.42 (s, 1H), 6.28 (s, 1H), 5.52 (d, J=7.2 Hz, 1H), 4.45-4.25 (m, 4H), 4.09 (s, 3H), 3.19-3.14 (m, 1H), 2.29-2.28 (m, 2H), 1.15-1.09 (m, 1H), 0.52-0.44 (m, 3H), 0.38-0.25 (m, 1H)

Example 174 (S)-2-[1-(3-Cyanopiperidin-1-yl)-8,9-dihydro-7H-6-oxa-2,9a-diazabenzo[cd]azulen-4-ylamino]-2-cyclopropylacetamide 174

Step 1: 1-(4-Bromo-8,9-dihydro-7H-6-oxa-2,9a-diazabenzo[cd]azulen-1-yl)piperidine-3-carboxylic acid

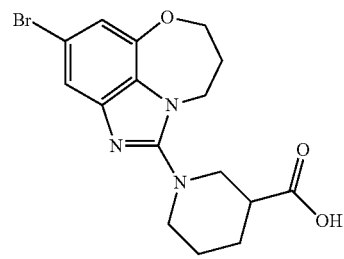 [SMILES: O=C(O)C1CCCN(c2nc3cc(Br)cc4c3n2CCCO4)C1]

A mixture of 4-bromo-1-iodo-8,9-dihydro-7H-6-oxa-2,9a-diazabenzo[cd]azulene (0.20 g, 0.53 mmol), nipecotic acid (88 mg, 0.68 mmol), cuprous iodide (20 mg, 0.11 mmol) and potassium phosphate tribasic (0.28 g, 1.32 mmol) in DMSO (2.0 mL) was heated in a sealed vial at 100° C. for 16 h. The reaction was mixture was cooled and diluted with DCM (40 mL) then purified via flash chromatography on silica gel (solvent gradient: 5-35% 2 N ammonia/methanol in DCM) to yield 0.17 g (86%) of the title compound as a cream solid. LCMS (ESI): [M+H]⁺=380/382.

Step 2: 1-(4-Bromo-8,9-dihydro-7H-6-oxa-2,9a-diazabenzo[cd]azulen-1-yl)piperidine-3-carboxylic acid amide

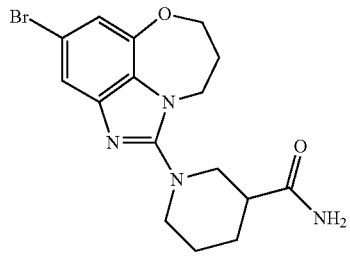 [SMILES: NC(=O)C1CCCN(c2nc3cc(Br)cc4c3n2CCCO4)C1]

To a mixture of 1-(4-bromo-8,9-dihydro-7H-6-oxa-2,9a-diazabenzo[cd]azulen-1-yl)piperidine-3-carboxylic acid (77.5 mg, 0.204 mmol), ammonium chloride (21.8 mg, 0.407 mmol) and DIPEA (0.14 mL, 0.82 mmol) in DMF (0.7 mL) was added HATU (155 mg, 0.41 mmol) portion-wise over 5 minutes, and the reaction mixture was stirred at room temperature for 10 min. The resulting mixture was diluted with DCM (20 mL) and purified via flash chromatography on silica gel (solvent gradient: 2-10% 2 N ammonia/methanol in DCM) to yield the title compound (quantitative) as a cream solid. LCMS (ESI): [M+H]$^+$=379/381.

Step 3: 1-(4-Bromo-8,9-dihydro-7H-6-oxa-2,9a-diazabenzo[cd]azulen-1-yl)piperidine-3-carbonitrile

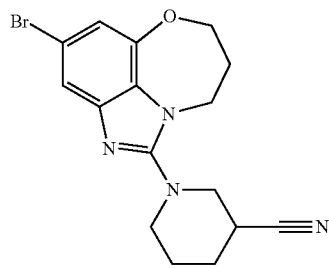 [SMILES: N#CC1CCCN(c2nc3cc(Br)cc4c3n2CCCO4)C1]

Trifluoroacetic anhydride (34 µL, 0.246 mmol) was added over 3 minutes to a mixture of 1-(4-bromo-8,9-dihydro-7H-6-oxa-2,9a-diazabenzo[cd]azulen-1-yl)piperidine-3-carboxylic acid amide (assumed 0.204 mmol) and pyridine (33 µL, 0.403 mmol) in THF (1.5 mL). The reaction mixture was stirred at room temperature for 30 min and then evaporated in vacuo. The residue was partitioned between DCM and saturated aqueous potassium carbonate. The aqueous phase was further extracted with DCM and the combined organic extracts were dried over sodium sulfate, filtered and evaporated in vacuo. The residue was purified via flash chromatography on silica gel (solvent gradient: 50-100% ethyl acetate in toluene) to yield 44 mg (60%, over 2 steps) of the title compound as a white solid. LCMS (ESI): [M+H]$^+$=361/363.

Step 4

Following the procedures of Example 126, 174 was prepared. LCMS (ESI): R$_T$ (min)=2.31, 2.33, [M+H]$^+$=395.2, method=A; $^1$H NMR (400 MHz, DMSO-d$_6$) δ inter alia 7.27 (br s, 1H), 6.91 (br s, 1H), 6.23 (d, J=2.0 Hz, 1H), 6.06 (d, J=2.0 Hz, 1H), 5.29 (d, J=7.4 Hz, 1H), 4.27-4.24 (m, 2H), 4.01-3.87 (m, 2H), 3.10-3.01 (m, 2H), 2.23-2.18 (m, 2H), 1.90-1.66 (m, 4H), 1.12-1.04 (m, 1H), 0.50-0.42 (m, 3H), 0.30-0.25 (m, 1H)

Example 175 (S)-2-Cyclopropyl-2-((1-(5-(methylsulfonyl)pyridin-3-yl)-8,9-dihydro-7H-6-oxa-2,9a-diazabenzo[cd]azulen-4-yl)amino)acetamide 175

Following the procedures of Example 125, 175 was prepared. LCMS (ESI): R$_T$ (min)=2.75, [M+H]$^+$=442, method=B; $^1$H NMR (400 MHz, DMSO-d6) δ 9.29 (d, J=2.0 Hz, 1H), 9.18 (d, J=1.8 Hz, 1H), 8.67 (t, J=2.1 Hz, 1H), 7.35 (br s, 1H), 6.96 (br s, 1H), 6.41 (d, J=2.0 Hz, 1H), 6.32 (d, J=1.9 Hz, 1H), 5.57 (d, J=7.2 Hz, 1H), 4.39-4.30 (m, 4H), 3.43 (s, 3H), 3.16 (t, J=7.7 Hz, 1H), 2.32-2.27 (m, 2H), 1.15-1.07 (m, 1H), 0.57-0.42 (m, 3H), 0.33-0.28 (m, 1H)

Example 176 (S)-2-((1-(3H-Imidazo[4,5-b]pyridin-7-yl)-8,9-dihydro-7H-6-oxa-2,9a-diazabenzo[cd]azulen-4-yl)amino)-2-cyclopropylacetamide 176

Following the procedures of Example 125, 176 was prepared. LCMS (ESI): R$_T$ (min)=1.08, [M+H]$^+$=404, method=D; $^1$H NMR (300 MHz, DMSO-d$_6$) δ 13.40 (s, 0.6H), 12.74 (s, 0.4H), 8.57-8.54 (m, 1H), 8.48-8.46 (m, 1H), 7.59-7.50 (m, 1H), 7.34 (s, 1H), 6.96 (s, 1H), 6.43 (d, J=10.2 Hz, 1H), 6.34 (d, J=11.4 Hz, 1H), 5.61-5.53 (m, 1H), 4.37-4.22 (m, 4H), 3.19-3.14 (m, 1H), 2.27-2.24 (m, 2H), 1.13 (m, 1H), 0.51 (m, 3H), 0.32 (m, 1H)

Example 177 (S)-2-Cyclopropyl-2-((1-(thieno[2,3-b]pyridin-4-yl)-8,9-dihydro-7H-6-oxa-2,9a-diazabenzo[cd]azulen-4-yl)amino)acetamide 177

Following the procedures of Example 158, 177 was prepared. LCMS (ESI): R$_T$ (min)=2.10, [M+H]$^+$=420, method=C; $^1$H NMR (300 MHz, DMSO-d$_6$) δ 8.73 (d, J=4.8 Hz, 1H), 7.99 (d, J=6.0 Hz, 1H), 7.72 (d, J=4.8 Hz, 1H), 7.58 (d, J=6.0 Hz, 1H), 7.37 (s, 1H), 6.98 (s, 1H), 6.44 (d, J=1.8 Hz, 1H), 6.35 (d, J=1.8 Hz, 1H), 5.59 (d, J=7.2 Hz, 1H), 4.36-4.33 (m, 2H), 4.18-4.14 (m, 2H), 3.19-3.14 (m, 1H), 2.27 (m, 2H), 1.14-1.11 (m, 1H), 0.52-0.48 (m, 3H), 0.31 (m, 1H)

Example 178 (S)-2-((1-(Benzo[d]thiazol-6-yl)-8,9-dihydro-7H-6-oxa-2,9a-diazabenzo[cd]azulen-4-yl)amino)-2-cyclopropylacetamide 178

Following the procedures of Example 158, 178 was prepared. LCMS (ESI): R$_T$ (min)=1.18, [M+H]$^+$=420, method=C; $^1$H NMR (400 MHz, DMSO-d$_6$) δ 9.52 (s, 1H), 8.61 (s, 1H), 8.22 (d, J=8.2 Hz, 1H), 7.94 (d, J=8.0 Hz, 1H), 7.34 (s, 1H), 6.97 (s, 1H), 6.41 (d, J=1.6 Hz, 1H), 6.28 (d, J=1.6 Hz, 1H), 5.50 (d, J=7.6 Hz, 1H), 4.36-4.34 (m, 2H), 4.32-4.28 (m, 2H), 3.18-3.14 (m, 1H), 2.28-2.27 (m, 2H), 1.14-1.11 (m, 1H), 0.52-0.46 (m, 3H), 0.33-0.31 (m, 1H)

Example 179 (S)-2-Cyclopropyl-2-((1-(7,8-dihydropyrido[3,4-b]pyrazin-6(5H)-yl)-8,9-dihydro-7H-6-oxa-2,9a-diazabenzo[cd]azulen-4-yl)amino)acetamide 179

Following the procedures of Example 161, 179 was prepared. LCMS (ESI): R$_T$ (min)=1.18, [M+H]$^+$=420, method=D; $^1$H NMR (300 MHz, DMSO-d$_6$) δ 8.49-8.46 (m, 2H), 7.27 (s, 1H), 6.90 (s, 1H), 6.23 (s, 1H), 6.07 (s, 1H), 5.29 (d, J=7.5 Hz, 1H), 4.48 (s, 2H), 4.29-4.28 (m, 2H), 4.03-4.00 (m, 2H), 3.62-3.58 (m, 2H), 3.13-3.05 (m, 3H), 2.26-2.22 (m, 2H), 1.09-1.06 (m, 1H), 0.48-0.43 (m, 3H), 0.28-0.27 (m, 1H)

Example 180 (S)-2-((1-(1,4-Oxazepan-4-yl)-8,9-dihydro-7H-6-oxa-2,9a-diazabenzo[cd]azulen-4-yl)amino)-2-cyclopropylacetamide 180

Following the procedures of Example 161, 180 was prepared. LCMS (ESI): $R_T$ (min)=1.71, [M+H]$^+$=386, method=D; $^1$H NMR (300 MHz, DMSO-d$_6$) δ 7.26 (s, 1H), 6.90 (s, 1H), 6.17 (d, J=2.0 Hz, 1H), 5.98 (d, J=2.0 Hz, 1H), 5.22 (d, J=7.4 Hz, 1H), 4.29-4.19 (m, 2H), 3.91-3.87 (m, 2H), 3.82-3.70 (m, 4H), 3.55-3.40 (m, 4H), 3.08-3.03 (m, 1H), 2.25-2.12 (m, 2H), 1.98-1.90 (m, 2H), 1.08-1.04 (m, 1H), 0.53-0.37 (m, 3H), 0.30-0.20 (m, 1H)

Example 181 2-(4-{4-[((S)-Carbamoylcyclopropylmethyl)amino]-8,9-dihydro-7H-6-oxa-2,9a-diazabenzo[cd]azulen-1-yl}pyrazol-1-yl)isobutyramide formic acid salt 181

Step 1: 4-(1-Amino-3-bromo-7,8-dihydro-6H-5-oxa-9-azabenzocycloheptene-9-carbonyl)-pyrazole-1-carboxylic acid tert-butyl ester and 4-(3-bromo-6,7,8,9-tetrahydro-5-oxa-9-azabenzocyclohepten-1-ylcarbamoyl)-pyrazole-1-carboxylic acid tert-butyl ester

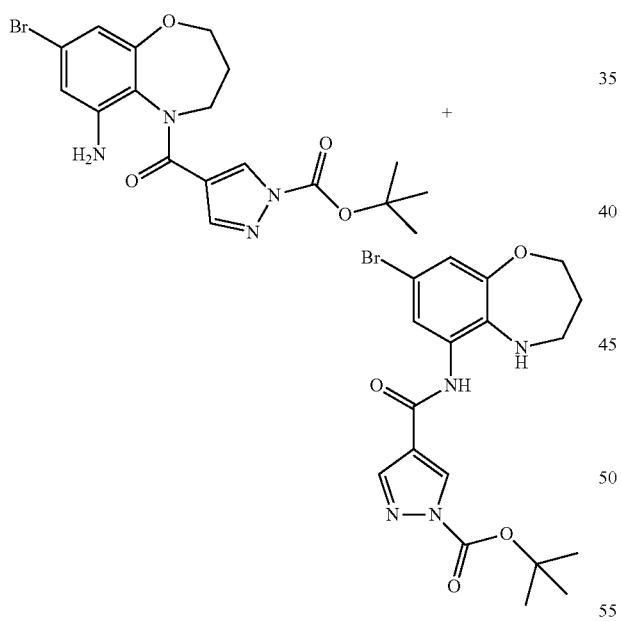

To a mixture of pyrazole-1,4-dicarboxylic acid 1-tert-butyl ester (865 mg, 4.07 mmol) and DIPEA (0.78 mL, 4.50 mmol) in DCM (10.0 mL) was added methanesulfonyl chloride (0.34 mL, 4.44 mmol), under nitrogen, at 0° C., and the resultant mixture was stirred 0° C. for 15 min. A further portion of DIPEA (0.32 mL, 1.82 mmol) was added at 0° C. and the resultant mixture was then added to a solution of 8-bromo-2,3,4,5-tetrahydrobenzo[b][1,4]oxazepin-6-amine from Example 101 (900 mg, 3.70 mmol) in DCM (10.0 mL), at 0° C., under nitrogen. The reaction mixture was stirred at 0° C. for 30 min and was then allowed to warm to room temperature and stirred at ambient temperature for 18 h. The resultant mixture was diluted with water. The organic extracts were dried over magnesium sulfate, filtered and evaporated in vacuo. The crude residue was purified via flash chromatography on silica gel (solvent gradient: 0-5% methanol in DCM) to yield 1.06 g (67%, ~1:1 mixture of isomers) of the title compounds as a white solid. LCMS (ESI): [M+H]$^+$=435/437.

Step 2: 4-Bromo-1-(1H-pyrazol-4-yl)-8,9-dihydro-7H-6-oxa-2,9a-diazabenzo[cd]azulene

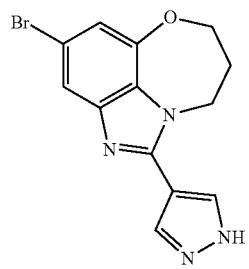 [SMILES: Brc1cc2c3c(c1)nc(-c1cn[nH]c1)n3CCCO2]

A mixture of 4-(1-amino-3-bromo-7,8-dihydro-6H-5-oxa-9-azabenzocycloheptene-9-carbonyl)pyrazole-1-carboxylic acid tert-butyl ester and 4-(3-bromo-6,7,8,9-tetrahydro-5-oxa-9-azabenzocyclohepten-1-ylcarbamoyl)pyrazole-1-carboxylic acid tert-butyl ester (1.08 g, 2.47 mmol) in acetic acid (20 mL) was heated at 90° C. for 2 h. The reaction mixture was evaporated in vacuo and the crude residue was purified via flash chromatography on silica gel (solvent gradient: 0-8% methanol in DCM) to yield 490 mg (63%) of the title compound as a white solid. LCMS (ESI): [M+H]$^+$=319/321.

Step 3: 2-[4-(4-Bromo-8,9-dihydro-7H-6-oxa-2,9a-diazabenzo[cd]azulen-1-yl)pyrazol-1-yl]-2-methylpropionic acid ethyl ester

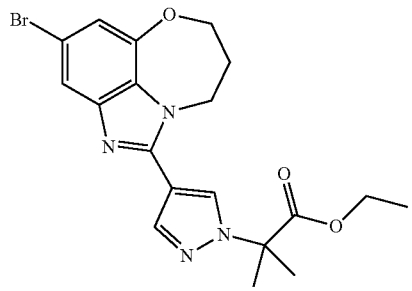 [SMILES: CCOC(=O)C(C)(C)n1cc(-c2nc3cc(Br)cc4c3n2CCCO4)cn1]

To a suspension of 4-bromo-1-(1H-pyrazol-4-yl)-8,9-dihydro-7H-6-oxa-2,9a-diazabenzo[cd]azulene (253 mg, 0.79 mmol) and cesium carbonate (388 mg, 1.19 mmol) in DMF (8.0 mL) was added 2-bromo-2-methylpropionic acid ethyl ester (240 mg, 1.19 mmol) and the reaction mixture was heated at 90° C. for 3 h. The resultant mixture was concentrated in vacuo and then partitioned between ethyl acetate and water. The organic layer was further washed with water then brine, dried over sodium sulfate, filtered and evaporated in vacuo to yield 300 mg (87%) of the title compound as a an off-white solid. LCMS (ESI): [M+H]$^+$=433/435.

Step 4: 2-(4-{4-[((S)-Carboxycyclopropylmethyl)amino]-8,9-dihydro-7H-6-oxa-2,9a-diazabenzo[cd]azulen-1-yl}pyrazol-1-yl)-2-methylpropionic acid

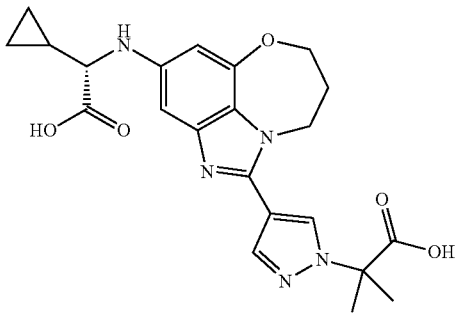 [SMILES: CC(C)(C(=O)O)n1cc(-c2nc3cc(N[C@H](C(=O)O)C4CC4)cc4c3n2CCCO4)cn1]

A mixture of 2-[4-(4-bromo-8,9-dihydro-7H-6-oxa-2,9a-diazabenzo[cd]azulen-1-yl)pyrazol-1-yl]-2-methylpropionic acid ethyl ester (300 mg, 0.69 mmol), L-cyclopropylglycine (203 mg, 1.73 mmol), cuprous iodide (27 mg, 0.138 mmol) and potassium phosphate tribasic (591 mg, 2.76 mmol) in DMSO (3.0 mL) was degassed with argon under sonication. The reaction mixture was heated at 100° C. for 18 h and then cooled to room temperature. DCM (60 mL) was added and the resultant grey solid was dried in vacuo to yield (>100%, assume 0.69 mmol) of the crude title compound which was used in the next step without further purification. LCMS (ESI): [M+H]$^+$=440.

Step 5: 2-(4-{4-[((S)-Carbamoylcyclopropylmethyl)amino]-8,9-dihydro-7H-6-oxa-2,9a-diazabenzo[cd]azulen-1-yl}pyrazol-1-yl)isobutyramide formic acid salt To a mixture of crude 2-(4-{4-[((S)-carboxycyclopropylmethyl)amino]-8,9-dihydro-7H-6-oxa-2,9a-diazabenzo[cd]azulen-1-yl}pyrazol-1-yl)-2-methylpropionic acid (assumed 0.69 mmol), ammonium chloride (230 mg, 4.10 mmol) and triethylamine (1.0 mL, 6.84 mmol) in DMF (5.0 mL) was added, portion-wise, HATU (1.60 g, 4.10 mmol) and the reaction mixture was stirred at room temperature for 1 h. The resultant mixture was evaporated in vacuo and the crude residue was purified via flash chromatography on silica gel [solvent gradient: 0-20% methanol (2 N ammonia) in DCM] followed by futher purification via reverse-phase HPLC to yield 17 mg (6%) of the formate salt of 181 as an off-white solid. LCMS (ESI): R$_T$=2.34, [M+H]$^+$=438.2, method=A; $^1$H NMR (400 MHz, DMSO-d$_6$) δ 8.34 (d, J=0.6 Hz, 1H), 8.21 (s, 0.6H), 8.02 (d, J=0.6 Hz, 1H), 7.33 (d, J=2.2 Hz, 1H), 7.23 (br s, 1H), 6.94 (s, 2H), 6.32 (d, J=1.9 Hz, 1H), 6.16 (d, J=2.1 Hz, 1H), 5.41 (br s, 1H), 4.37-4.28 (m, 4H), 3.10 (d, J=7.8 Hz, 1H), 2.34-2.26 (m, 2H), 1.77 (s, 6H), 1.15-1.05 (m, 1H), 0.54-0.44 (m, 3H), 0.32-0.26 (m, 1H).

Example 182 (S)-2-Cyclopropyl-2-[1-(3-hydroxypiperidin-1-yl)-8,9-dihydro-7H-6-oxa-2,9a-diazabenzo[cd]azulen-4-ylamino]acetamide 182

Step 1: 1-(4-Bromo-8,9-dihydro-7H-6-oxa-2,9a-diazabenzo[cd]azulen-1-yl)piperidin-3-ol

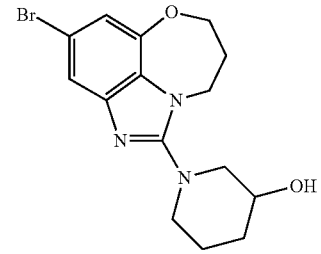 [SMILES: OC1CCCN(c2nc3cc(Br)cc4c3n2CCCO4)C1]

A mixture of 4-bromo-1-iodo-8,9-dihydro-7H-6-oxa-2,9a-diazabenzo[cd]azulene (50 mg, 0.132 mmol), 3-hydroxypiperidine (20.1 mg, 0.20 mmol), 3,4,7,8-tetramethyl-1,10-phenanthroline (6.2 mg, 0.026 mmol), Cu(OTf).PhMe (6.9 mg, 0.013 mmol), potassium phosphate tribasic (56 mg, 0.26 mmol) and 2-methylbutan-2-ol (0.75 ml) was heated in a sealed vial at 100° C. for 16 h. The cooled reaction mixture was partitioned between ethyl acetate and aqueous sodium bicarbonate. The aqueous phase was extracted with more ethyl acetate and the combined organic extracts were washed with brine, dried over sodium sulfate, filtered and evaporated in vacuo. The residue was purified via flash chromatography on silica gel (solvent gradient: 0-100% methyl acetate in ethyl acetate) to yield 14.3 mg (31%) of the title compound. LCMS (ESI): [M+H]$^+$=352/354.

Step 2: Following the procedures of Example 126, 182 was prepared. LCMS (ESI): R$_T$ (min)=2.20, [M+H]$^+$=386.2, method=A; $^1$H NMR (400 MHz, DMSO-d$_6$) δ inter alia 7.28 (br s, 1H), 6.91 (br s, 1H), 6.21 (d, J=2.0 Hz, 1H), 6.02 (d, J=2.0 Hz, 1H), 5.26 (d, J=7.4 Hz, 1H), 4.95-4.93 (m, 1H), 4.26-4.23 (m, 2H), 3.90-3.87 (m, 2H), 3.73-3.65 (m, 1H), 3.07 (t, J=7.7 Hz, 1H) 2.85-2.79 (m, 1H), 2.71-2.65 (m, 1H), 2.20-2.15 (m, 2H), 1.91-1.85 (m, 1H), 1.79-1.72 (m, 1H), 1.62-1.52 (m, 1H), 1.38-1.29 (m, 1H), 1.12-1.04 (m, 1H), 0.50-0.42 (m, 3H), 0.30-0.24 (m, 1H)

Example 183 (S)-2-cyclopropyl-2-((1-(1-methyl-1H-1,2,4-triazol-5-yl)-8,9-dihydro-7H-6-oxa-2,9a-diazabenzo[cd]azulen-4-yl)amino)acetamide 183

Following the procedures of Example 137, 183 was prepared. LCMS (ESI): R$_T$ (min)=3.10, [M+H]$^+$=386.2, method=B; $^1$H NMR (300 MHz, DMSO-d$_6$) δ 8.13 (s, 1H), 7.24 (s, 1H), 6.84 (s, 1H), 6.44 (d, J=2.0 Hz, 1H), 6.37 (d, J=2.0 Hz, 1H), 5.50 (d, J=7.3 Hz, 1H), 4.66-4.58 (m, 2H), 4.39-4.31 (m, 2H), 4.23 (s, 3H), 2.37-2.23 (m, 2H), 1.29-1.22 (m, 1H), 1.18-1.06 (m, 1H), 0.59-0.43 (m, 3H), 0.36-0.24 (m, 1H)

Example 184 (S)-2-((1-(2-Aminobenzo[d]thiazol-5-yl)-8,9-dihydro-7H-6-oxa-2,9a-diazabenzo[cd]azulen-4-yl)amino)-2-cyclopropylacetamide 184

Following the procedures of Example 158, 184 was prepared. LCMS (ESI): R$_T$ (min)=1.27, [M+H]$^+$=435, method=D; ¹H NMR (400 MHz, DMSO-d₆) δ 7.81 (d, J=8.1 Hz, 1H), 7.71-7.61 (m, 3H), 7.41-7.31 (m, 2H), 6.96 (s, 1H), 6.38 (d, J=2.0 Hz, 1H), 6.25 (d, J=2.0 Hz, 1H), 5.46 (d, J=7.3 Hz, 1H), 4.34-4.33 (m, 2H), 4.28-4.23 (m, 2H), 3.17-3.13 (m, 1H), 2.25-2.24 (m, 2H), 1.14-1.07 (m, 1H), 0.58-0.43 (m, 3H), 0.37-0.26 (m, 1H)

Example 185 (S)-2-((1-(2-(Methylamino)benzo[d]oxazol-5-yl)-8,9-dihydro-7H-6-oxa-2,9a-diazabenzo[cd]azulen-4-yl)amino)propanamide 185

Following the procedures of Example 186, 185 was prepared. LCMS (ESI): R_T (min)=1.18, [M+H]⁺=407, method=D; ¹H NMR (300 MHz, DMSO-d₆) δ 7.97-7.96 (m, 1H), 7.56 (s, 1H), 7.47 (d, J=8.2 Hz, 1H), 7.34 (d, J=8.4 Hz, 1H), 7.28 (s, 1H), 6.93 (s, 1H), 6.37 (d, J=2.0 Hz, 1H), 6.20 (d, J=2.0 Hz, 1H), 5.42 (d, J=7.3 Hz, 1H), 4.34-4.31 (m, 2H), 4.20-4.18 (m, 2H), 3.73-3.71 (m, 1H), 2.93 (d, J=4.7 Hz, 3H), 2.27-2.24 (m, 2H), 1.32-1.29 (d, J=6.9 Hz, 3H)

Example 187 (S)-2-((1-(2-Aminoquinoxalin-6-yl)-8,9-dihydro-7H-6-oxa-2,9a-diazabenzo[cd]azulen-4-yl)amino)-2-cyclopropylacetamide 187

Following the procedures of Example 158, 187 was prepared. LCMS (ESI): R_T (min)=1.75, [M+H]⁺=430, method=D; ¹H NMR (300 MHz, DMSO-d₆) δ 8.36 (s, 1H), 8.11 (s, 1H), 7.93 (d, J=8.4 Hz, 1H), 7.59 (d, J=8.7 Hz, 1H), 7.33 (s, 1H), 7.19 (s, 2H), 6.96 (s, 1H), 6.39 (d, J=1.8 Hz, 1H), 6.25 (d, J=1.8 Hz, 1H), 5.47 (d, J=7.5 Hz, 1H), 4.35-4.29 (m, 4H), 3.18-3.13 (m, 1H), 2.32-2.21 (m, 2H), 1.17-1.05 (m, 1H), 0.53-0.47 (m, 3H), 0.33-0.32 (m, 1H)

Example 188 (S)-4-(4-((2-Amino-1-cyclopropyl-2-oxoethyl)amino)-8,9-dihydro-7H-6-oxa-2,9a-diazabenzo[cd]azulen-1-yl)-2-fluorobenzamide 188

Following the procedures of Example 150, 188 was prepared. LCMS (ESI): R_T (min)=1.14, [M+H]⁺=424, method=C; ¹H NMR (300 MHz, DMSO-d₆) δ 7.82-7.65 (m, 5H), 7.33 (s, 1H), 6.96 (s, 1H), 6.38 (s, 1H), 6.28 (s, 1H), 5.52 (d, J=7.2 Hz, 1H), 4.34-4.32 (m, 2H), 4.28-4.17 (m, 2H), 3.17-3.12 (m, 1H), 2.27-2.26 (m, 2H), 1.14-1.08 (m, 1H), 0.53-0.46 (m, 3H), 0.35-2.22 (m, 1H)

Example 189 (S)-2-Cyclopropyl-2-((1-(3-hydroxyquinolin-6-yl)-8,9-dihydro-7H-6-oxa-2,9a-diazabenzo[cd]azulen-4-yl)amino)acetamide 189

Following the procedures of Example 158, 189 was prepared. LCMS (ESI): R_T (min)=0.83, [M+H]⁺=430, method=C; ¹H NMR (300 MHz, DMSO-d₆) δ 10.48 (br s, 1H), 8.66 (d, J=2.8 Hz, 1H), 8.24 (d, J=1.8 Hz, 1H), 8.03 (d, J=8.7 Hz, 1H), 7.87 (d, J=8.4 Hz, 1H), 7.65 (s, 1H), 7.37 (s, 1H), 6.99 (s, 1H), 6.42 (d, J=2.0 Hz, 1H), 6.29 (d, J=2.0 Hz, 1H), 5.53 (d, J=7.3 Hz, 1H), 4.42-4.26 (m, 4H), 3.20-3.08 (m, 1H), 2.35-2.24 (m, 2H), 1.15-1.02 (m, 1H), 0.60-0.43 (m, 3H), 0.35-0.25 (m, 1H)

Example 190 (S)-2-((1-(4-(1H-1,2,4-Triazol-3-yl)phenyl)-8,9-dihydro-7H-6-oxa-2,9a-diazabenzo[cd]azulen-4-yl)amino)-2-cyclopropylacetamide 190

Following the procedures of Example 158, 190 was prepared. LCMS (ESI): R_T (min)=1.15, [M+H]⁺=430, method=D; ¹H NMR (300 MHz, DMSO-d₆) δ 14.65 (s, 0.2H) 14.23 (s, 0.8H), 8.69 (s, 1H), 8.19-8.17 (m, 2H), 7.89-7.87 (m, 2H), 7.36 (s, 1H), 6.98 (s, 1H), 6.39 (s, 1H), 6.30 (s, 1H), 5.65 (br s, 1H), 4.49-4.18 (m, 4H), 3.18-3.08 (m, 1H), 2.33-2.18 (m, 2H), 1.21-1.06 (m, 1H), 0.52-0.48 (m, 3H), 0.32-0.30 (m, 1H)

Example 191 (S)-5-(4-((2-Amino-1-cyclopropyl-2-oxoethyl)amino)-8,9-dihydro-7H-6-oxa-2,9a-diazabenzo[cd]azulen-1-yl)picolinamide 191

Following the procedures of Example 150, 191 was prepared. LCMS (ESI): R_T (min)=1.08, [M+H]⁺=407, method=D; ¹H NMR (300 MHz, DMSO-d₆) δ 9.01 (s, 1H), 8.39-8.36 (d, J=8.1 Hz, 1H), 8.23 (s, 1H), 8.16 (d, J=8.4 Hz, 1H), 7.76 (s, 1H), 7.35 (s, 1H), 6.97 (s, 1H), 6.40 (d, J=1.5 Hz, 1H), 6.31 (d, J=2.1 Hz, 1H), 5.56 (d, J=7.5 Hz, 1H), 4.36-4.30 (m, 4H), 3.17-3.12 (m, 1H), 2.35-2.20 (m, 2H), 1.14-1.08 (m, 1H), 0.51-0.4 (m, 3H), 0.34-0.29 (m, 1H)

Example 192 1-(2-Aminobenzo[d]oxazol-5-yl)-N-(3,3-difluorocyclobutyl)-8,9-dihydro-7H-6-oxa-2,9a-diazabenzo[cd]azulen-4-amine 192

A mixture of 5-(4-bromo-8,9-dihydro-7H-6-oxa-2,9a-diazabenzo[cd]azulen-1-yl)benzo[d]oxazol-2-amine (Example 101, 200 mg, 0.519 mmol), 3,3-difluorocyclobutanamine hydrochloride (157 mg, 1.09 mmol), di-tert-butyl(2',4',6'-triisopropylbiphenyl-2-yl)phosphine (45.0 mg, 0.106 mmol), tris(dibenzylideneacetone)dipalladium(0) (93.0 mg, 0.117 mmol) and lithium bis(trimethylsilyl)amide (1 M solution in THF, 2.00 mL, 2.00 mmol) in THF (10.0 mL) was degassed with nitrogen. The reaction mixture was heated under microwave radiation for 2 h at 100° C. The reaction mixture was diluted with methanol and then filtered. The filtrate was evaporated in vacuo. The resultant residue was purified via reverse-phase HPLC and lyophilized to yield 17.5 mg (8%) of 192 as a light yellow solid. LCMS (ESI): R_T (min)=2.58, [M+H]⁺=412, method=C; ¹H NMR (300 MHz, DMSO-d₆) δ 7.56-7.46 (m, 4H), 7.35-7.32 (m, 1H), 6.35 (d, J=1.8 Hz, 1H), 6.14 (d, J=1.8 Hz, 1H), 5.81 (d, J=6.6 Hz, 1H), 4.35-4.32 (m, 2H), 4.23-4.20 (m, 2H), 3.81-3.74 (m, 1H), 3.14-2.93 (m, 2H), 2.49-2.30 (m, 2H), 2.27-2.20 (m, 2H).

Example 193 5-(4-Bromo-3-fluoro-8,9-dihydro-7H-6-oxa-2,9a-diazabenzo[cd]azulen-1-yl)benzo[d]oxazol-2-amine 193

Step 1: 1-Bromo-5-(3,3-diethoxypropoxy)-2-fluoro-4-nitrobenzene

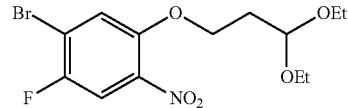 [SMILES: CCOC(CCOc1cc(Br)c(F)cc1[N+](=O)[O-])OCC]

To a solution of 1-bromo-2,5,-difluoro-4-nitrobenzene (6.1 g, 25.6 mmol) and 3,3-diethoxy-1-propanol (3.8 g, 25.6 mmol) in DMF (30 mL) was added sodium hydride (60% in mineral oil, 1.14 g, 28.1 mmol) portion wise over 10 min. The reaction mixture was stirred at 0° C. for 30 min, then allowed to warm to room temperature and was stirred for a further 30 min. The mixture was partitioned between ethyl acetate and 1 N hydrochloric acid and the phases were separated. The aqueous layer was extracted with ethyl acetate, the organic extracts were combined, washed with brine, dried over sodium sulfate and the solvent was evaporated. The residue was purified via flash chromatography on silica gel (solvent gradient: 5-20% ethyl acetate in cyclohexane) to yield 7.71 g (82%) of the title compound as a yellow oil. LCMS (ESI): [M+Na]$^+$=388/390.

Step 2: 3-Bromo-5-(3,3-diethoxypropoxy)-2-fluoro-6-nitroaniline

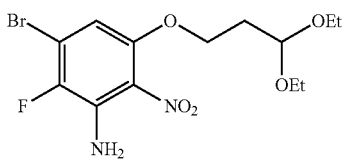 [SMILES: CCOC(CCOc1cc(Br)c(F)c(N)c1[N+](=O)[O-])OCC]

To a solution of 1-bromo-5-(3,3-diethoxypropoxy)-2-fluoro-4-nitrobenzene (3.50 g, 9.56 mmol) and 1,1,1-trimethylhydrazinium iodide (2.12 g, 10.5 mmol) in DMSO (35 mL) at 10° C. was added potassium tert-butoxide (2.57 g, 22.9 mmol). The mixture was allowed to warm to room temperature and was stirred for 1 h. The resulting mixture was partitioned between ethyl acetate and water and the phases separated. The aqueous layer was adjusted to ca. pH 3 with 1 N hydrochloric acid (ca. 20 mL) and then extracted with ethyl acetate. The organic extracts were combined, washed with brine, dried over sodium sulfate and the solvent was evaporated. This process was repeated and the two batches combined before the residue was purified via flash chromatography on silica gel (solvent gradient: 2-15% ethyl acetate in toluene) to yield 3.24 g (45%) of the title compound as a yellow solid. LCMS (ESI): [M+Na]$^+$=403/405.

Step 3: 4-Bromo-6-(3,3-diethoxypropoxy)-3-fluorobenzene-1,2-diamine

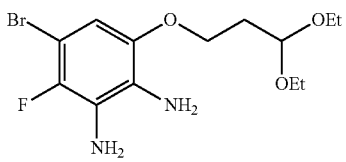 [SMILES: CCOC(CCOc1cc(Br)c(F)c(N)c1N)OCC]

To a suspension of 3-bromo-5-(3,3-diethoxypropoxy)-2-fluoro-6-nitroaniline (3.73 g, 9.77 mmol) in methanol (30 mL) was added a solution of ammonium chloride (4.72 g, 87.9 mmol) in water (20 mL) followed by iron powder (3.29 g, 58.6 mmol). The mixture was stirred at 90° C. for 30 min. The mixture was allowed to warm to room temperature and partitioned between ethyl acetate and water, before filtering through a celite pad. The filtrate was collected and the phases separated. The aqueous layer was extracted with ethyl acetate. The combined organic extracts were washed with brine, dried over sodium sulfate and the solvent was evaporated. The residue was purified via flash chromatography on silica gel (solvent gradient: 10-60% ethyl acetate in toluene) to yield 3.32 g (97%) of the title compound as a light brown oil. $^1$H NMR (400 MHz, CDCl$_3$) δ 6.50 (d, J=5.4 Hz, 1H), 4.74 (t, J=6.3 Hz, 1H), 4.03 (t, J=6.3 Hz, 2H), 3.72-3.64 (m, 2H), 3.58-3.42 (m, 6H), 2.10 (q, J=6.3 Hz, 2H), 1.22 (t, J=6.9 Hz, 6H).

Step 4: 8-Bromo-7-fluoro-2,3,4,5-tetrahydrobenzo[b][1,4]oxazepin-6-amine

To a solution of 4-bromo-6-(3,3-diethoxypropoxy)-3-fluorobenzene-1,2-diamine (3.32 g, 9.43 mmol) in DCM (33 mL) at 0° C. was added TFA (33 mL) then triethylsilane (7.4 mL, 47 mmol) dropwise over 5 min. The reaction mixture was stirred at 0° C. for 10 min, then allowed to warm to room temperature and stirred for a further 10 min. The solvent was removed, azeotroping with toluene. The residue was partitioned between ethyl acetate and saturated aqueous sodium hydrogen carbonate and the phases separated. The aqueous layer was further extracted with ethyl acetate. The organic extracts were combined, washed with brine, dried over sodium sulfate and the solvent was evaporated. The residue was purified via flash chromatography on silica gel (solvent gradient: 5-30% ethyl acetate in toluene) to yield 2.31 g (94%) of a 1:1 mixture of the title compound and 5-bromo-6-fluorochroman-7,8-diamine as a pale brown oil. LCMS (ESI): [M+H]$^+$=261/263.

Step 5: 4-Bromo-3-fluoro-8,9-dihydro-7H-6-oxa-2,9a-diazabenzo[cd]azulene

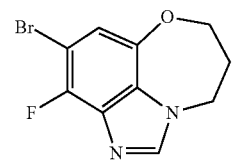 [SMILES: Fc1c(Br)cc2c3c1ncn3CCCO2]

A mixture of 8-bromo-7-fluoro-2,3,4,5-tetrahydrobenzo[b][1,4]oxazepin-6-amine and 5-bromo-6-fluorochroman-7,8-diamine (2.31 g, 8.86 mmol) and para-toluenesulfonic acid (150 mg, 0.87 mmol) in trimethylorthoformate (30 mL) was stirred at 105° C. for 16 h. The solvent was removed, azeotroping with toluene. The residue was purified via flash chromatography on silica gel (solvent gradient: 2-10% 2 N ammonia methanol in DCM) to yield 1.14 g (47%) of the title compound as a cream solid. LCMS (ESI): [M+H]$^+$=271/273.

Step 6: 4-Bromo-3-fluoro-1-iodo-8,9-dihydro-7H-6-oxa-2,9a-diazabenzo[cd]azulene

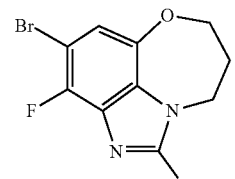

To a solution of diisopropylamine (0.58 mL, 4.10 mmol) in THF (20 mL) under nitrogen at −40° C. was dropwise added n-butyllithium (2.5 N in hexanes, 1.5 mL, 3.75 mmol). The mixture was allowed to warm to −20° C. over 10 min before cooling to −78° C. A solution of 4-bromo-3-fluoro-8,9-dihydro-7H-6-oxa-2,9a-diazabenzo[cd]azulene (926 mg, 3.42 mmol) in THF (8.0 mL) was added dropwise over 5 min. The mixture was stirred for a further 15 min before a solution of iodine (1.13 g, 4.45 mmol) in THF (5.0 mL) was added dropwise over 5 min. The mixture was stirred for a further 1 h, before quenching with saturated aqueous ammonium chloride. The mixture was partitioned between ethyl acetate and aqueous sodium thiosulfate and the phases separated. The aqueous layer was further extracted with ethyl acetate. The combined organic extracts were washed with brine before drying over sodium sulfate and evaporating to dryness. The residue was purified via flash chromatography on silica gel (solvent gradient: 1-3% methanol in DCM) to yield 1.04 g (77%) of the title compound as a cream solid. LCMS (ESI): [M+H]$^+$=397/399.

Step 7

To a suspension of 4-bromo-3-fluoro-1-iodo-8,9-dihydro-7H-6-oxa-2,9a-diazabenzo[cd]azulene (103 mg, 0.26 mmol), 5-(4,4,5,5-tetramethyl-[1,3,2]dioxaborolan-2-yl)-benzooxazol-2-ylamine (74 mg, 0.28 mmol) and 1,1'-bis(diphenylphosphino)ferrocenyl palladium (II) dichloride (21 mg, 0.026 mmol) in 1,2-dimethoxyethane (2.0 mL) was added 2 N aqueous sodium carbonate (0.52 mL, 1.04 mmol). The reaction mixture was stirred at 100° C. under nitrogen in a sealed vial for 5 h. The resulting mixture was allowed to warm to room temperature and partitioned between ethyl acetate and water and the aqueous layer was further extracted with ethyl acetate. The combined organic extracts were washed with brine, dried over sodium sulfate and evaporated. The crude residue was purified via flash chromatography on silica gel (solvent gradient: 2-10% methanol in DCM) to yield 78 mg (75%) of 193 as a buff solid. LCMS (ESI): R$_T$ (min)=4.02, [M+H]$^+$=403/405, method=A; $^1$H NMR (400 MHz, DMSO-d$_6$) δ 7.63 (s, 2H), 7.60 (d, J=1.3 Hz, 1H), 7.52 (d, J=8.1 Hz, 1H), 7.41 (dd, J=8.1, 1.3 Hz, 1H), 6.95 (d, J=5.2 Hz, 1H), 4.44-4.39 (m, 2H), 4.33 (t, J=5.2 Hz, 2H), 2.36-2.29 (m, 2H).

Example 194 (S)-1-(1-(2-Aminobenzo[d]oxazol-5-yl)-3-fluoro-8,9-dihydro-7H-6-oxa-2,9a-diazabenzo[cd]azulen-4-yl)pyrrolidine-2-carboxamide 194

Step 1: (1-(2-Aminobenzo[d]oxazol-5-yl)-3-fluoro-8,9-dihydro-7H-6-oxa-2,9a-diazabenzo[cd]azulen-4-yl)-L-proline

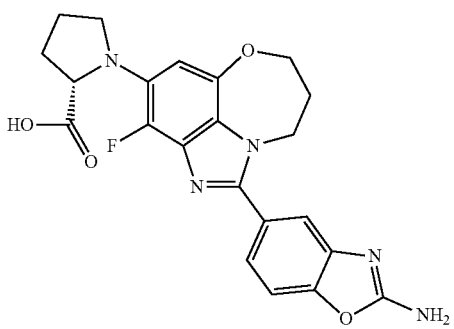 [SMILES: Nc1nc2cc(-c3nc4c(F)c(N5CCC[C@H]5C(=O)O)cc5c4n3CCCO5)ccc2o1]

5-(4-Bromo-3-fluoro-8,9-dihydro-7H-6-oxa-2,9a-diazabenzo[cd]azulen-1-yl)benzo[d]oxazol-2-amine (86 mg, 0.21 mmol), L-proline (99 mg, 0.84 mmol), copper (I) iodide (41 mg, 0.21 mmol) and potassium triphosphate tribasic (274 mg, 1.26 mmol) were suspended in DMSO (3.0 mL) and heated under microwave irradiation at 120° C. for 3.5 h. The crude reaction mixture was diluted with DCM (60 mL) and was purified via flash chromatography on silica gel (solvent gradient: 5-60% 2 N ammonia methanol in DCM) to yield 50 mg (53%) of the title compound as a grey solid. LCMS (ESI): [M+H]$^+$=438.

Step 2

To a solution of (1-(2-aminobenzo[d]oxazol-5-yl)-3-fluoro-8,9-dihydro-7H-6-oxa-2,9a-diazabenzo[cd]azulen-4-yl)-L-proline (107 mg, 0.24 mmol) in DMF (1.2 mL) was added ammonium chloride (26 mg, 0.49 mmol)) and DIPEA (169 0.98 mmol), followed by HATU (185 mg, 0.49 mmol) portion wise over 5 min and the reaction mixture was stirred at room temperature for 10 min. The resultant mixture was purified directly via flash chromatography on silica gel (solvent gradient: 2-14% 2 N ammonia methanol in DCM). The resulting residue was triturated with methanol to yield 53 mg (50%) of 194 as an off-white solid. LCMS (ESI): R$_T$ (min)=2.57, [M+H]$^+$=437, method=A; $^1$H NMR (400 MHz, DMSO-d$_6$) δ 7.58 (s, 2H), 7.56 (d, J=1.3 Hz, 1H), 7.49 (d, J=8.1 Hz, 1H), 7.37 (dd, J=8.1, 1.3 Hz, 1H), 7.23 (d, J=1.8 Hz, 1H), 6.93 (d, J=1.8 Hz, 1H), 6.22 (d, J=6.7 Hz, 1H), 4.35-4.31 (m, 2H), 4.27-4.21 (m, 2H), 4.10-4.04 (m, 1H), 3.76-3.69 (m, 1H), 3.31-3.24 (m, 1H), 2.30-2.15 (m, 3H), 1.96-1.84 (m, 3H).

Example 195: (S)-2-((1-([1,3]Dioxolo[4,5-b]pyridin-7-yl)-8,9-dihydro-7H-6-oxa-2,9a-diazabenzo[cd]azulen-4-yl)amino)-2-cyclopropylacetamide 195

Step 1: Ethyl [1,3]dioxolo[4,5-b]pyridine-7-carboxylate

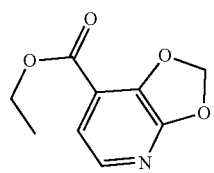

To a microwave vial was added 7-bromo-[1,3]dioxolo[4,5-b]pyridine (200 mg, 0.99 mmol), [1,1'-bis(diphenylphosphino)ferrocene]dichloropalladium (II) (73 mg, 0.099 mmol), potassium carbonate (205 mg, 1.49 mmol), ethanol (3 mL) and DMF (7.5 mL). The flask was purged of air and backfilled with carbon monoxide three times. The reaction was then heated to 70° C. and left to stir under a balloon containing carbon monoxide gas. After 16 h the reaction was cooled to room temperature and filtered through celite. The filtrate was diluted with water and extracted with isopropyl acetate. The organic layers were washed with brine and dried over magnesium sulfate. The crude product was purified by flash chromatography on silica gel (solvent gradient: 0-80% ethyl acetate/heptane) to yield 111 mg (58%) of the title compound. LCMS (ESI): [M+H]$^+$=195.1; $^1$H NMR (400

MHz, DMSO-d$_6$) δ 7.64 (d, J=5.7 Hz, 1H), 7.14 (d, J=6.0 Hz, 1H), 6.25 (s, 2H), 4.33 (q, J=7.1 Hz, 2H), 1.31 (t, J=7.1 Hz, 3H).

Step 2: [1,3]Dioxolo[4,5-b]pyridine-7-carboxylic acid

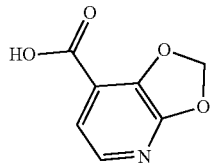

The title compound (143 mg, 88%) was prepared from 7-bromo-[1,3]dioxolo[4,5-b]pyridine following a procedure analogous to that of Example 116, step 2. LCMS (ESI): [M+H]$^+$=168; $^1$H NMR (400 MHz, DMSO-d$_6$) δ 7.43 (d, J=5.3 Hz, 1H), 7.00 (d, J=5.4 Hz, 1H), 6.02 (s, 2H).

Step 3: 1-([1,3]Dioxolo[4,5-b]pyridin-7-yl)-4-bromo-8,9-dihydro-7H-6-oxa-2,9a-diazabenzo[cd]azulene

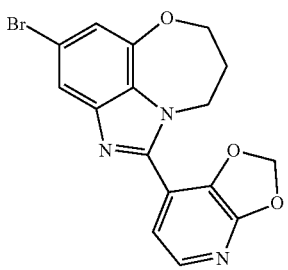 [SMILES: Brc1cc2c3c(c1)nc(-c1ccnc4c1OCO4)n3CCCO2]

The title compound (0.238 g, 51%) was prepared from 4-bromo-1-iodo-8,9-dihydro-7H-6-oxa-2,9a-diazabenzo[cd]azulene and [1,3]dioxolo[4,5-b]pyridine-7-carboxylic acid following procedures analogous to those of Example 125, steps 1-2. LCMS (ESI): [M+H]$^+$=374.

Step 4: 1-([1,3]Dioxolo[4,5-b]pyridin-7-yl)-4-bromo-8,9-dihydro-7H-6-oxa-2,9a-diazabenzo[cd]azulene

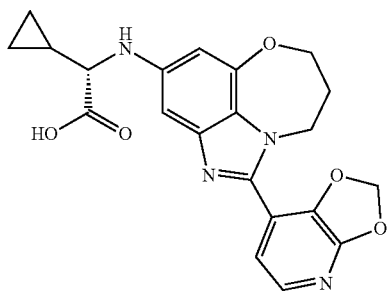 [SMILES: O=C(O)[C@@H](Nc1cc2c3c(c1)nc(-c1ccnc4c1OCO4)n3CCCO2)C1CC1]

The title compound (0.153 g, 99% yield) was prepared from 4-bromo-1-iodo-8,9-dihydro-7H-6-oxa-2,9a-diazabenzo[cd]azulene and (S)-2-amino-2-cyclopropylacetic acid following a procedure analogous to that of Example 125, step 3. LCMS (ESI): [M+H]$^+$=409.

Step 5

195 (18.5 mg, 12%) was prepared from (S)-2-((1-(benzo[d][1,3]dioxol-4-yl)-8,9-dihydro-7H-6-oxa-2,9a-diazabenzo[cd]azulen-4-yl)amino)-2-cyclopropylacetic acid following a procedure analogous to that of Example 125, step 4. LCMS (ESI): R$_T$(min)=2.69, [M+H]$^+$=409.1, method=B; $^1$H NMR (400 MHz, DMSO-d$_6$) δ 7.71 (d, J=5.6 Hz, 1H), 7.34 (d, J=2.7 Hz, 1H), 7.12 (d, J=5.5 Hz, 1H), 6.95 (d, J=2.6 Hz, 1H), 6.38 (d, J=1.9 Hz, 1H), 6.30 (d, J=1.9 Hz, 1H), 6.25 (d, J=2.8 Hz, 2H), 5.56 (d, J=7.3 Hz, 1H), 4.36-4.29 (m, 2H), 4.23-4.09 (m, 2H), 3.14 (t, J=7.8 Hz, 1H), 2.30-2.20 (m, 2H), 1.18-1.04 (m, 1H), 0.57-0.41 (m, 3H), 0.35-0.25 (m, 1H).

Example 196: (S)-2-Cyclopropyl-2-((1-(2-oxo-2,3-dihydrobenzo[d]oxazol-5-yl)-8,9-dihydro-7H-6-oxa-2,9a-diazabenzo[cd]azulen-4-yl)amino)acetamide 196

Step 1: 5-(4-Bromo-8,9-dihydro-7H-6-oxa-2,9a-diazabenzo[cd]azulen-1-yl)benzo[d]oxazol-2(3H)-one

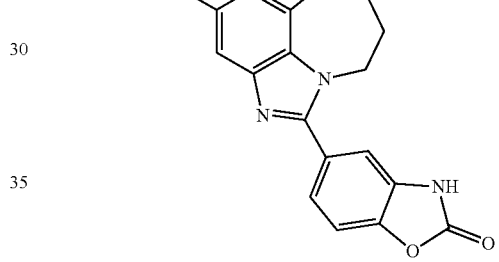

To a solution of 2-amino-4-(4-bromo-8,9-dihydro-7H-6-oxa-2,9a-diazabenzo[cd]azulen-1-yl)phenol (Example 101, step 8) (1.00 g, 2.77 mmol) in DCM (10 mL) was added 1,1'-carbonyldiimidazole (500 mg, 3.08 mmol). The reaction mixture was stirred at room temperature for 3 h and then evaporated in vacuo. The resultant residue was washed with ethyl acetate to yield 700 mg (crude) of the title compound as a brown solid. The solid was used in the next step without further purification. LCMS (ESI): [M+H]$^+$=386/388.

Step 2: 5-(4-Bromo-8,9-dihydro-7H-6-oxa-2,9a-diazabenzo[cd]azulen-1-yl)-3-((2-(trimethylsilyl)ethoxy)methyl)benzo[d]oxazol-2(3H)-one

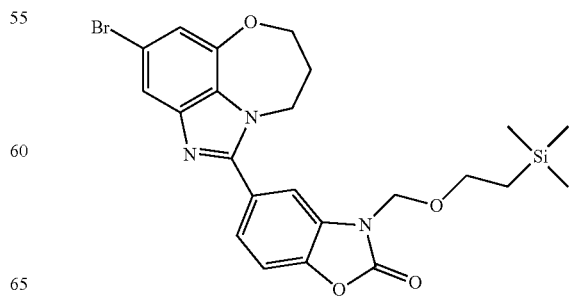

To a solution of 5-(4-bromo-8,9-dihydro-7H-6-oxa-2,9a-diazabenzo[cd]azulen-1-yl)benzo[d]oxazol-2(3H)-one (600 mg, 1.55 mmol) in DMF (10 mL) was added sodium hydride (72.0 mg, 3.08 mmol) at 0° C. The reaction mixture was stirred for 30 min and then (2-(chloromethoxy)ethyl)trimethylsilane (312 mg, 1.87 mmol) was added. The reaction mixture was stirred at room temperature for 2.5 h then quenched with water. The solid was collected by filtration and dried in vacuo to yield 680 mg (85%) of the title compound as an off-white solid. LCMS (ESI): [M+H]$^+$=516/518.

Step 3: (S)-2-Cyclopropyl-2-((1-(2-oxo-3-((2-(trimethylsilyl)ethoxy)methyl)-2,3-dihydrobenzo[d]oxazol-5-yl)-8,9-dihydro-7H-6-oxa-2,9a-diazabenzo[cd]azulen-4-yl)amino)acetic acid

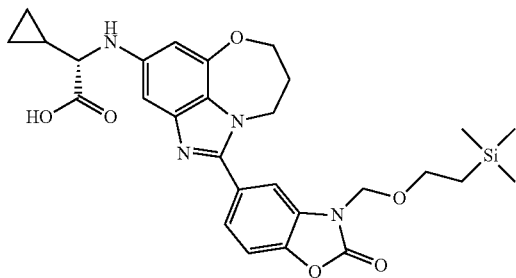 [SMILES: C[Si](C)(C)CCOCn1c(=O)oc2ccc(-c3nc4cc(N[C@H](C(=O)O)C5CC5)cc5c4n3CCCO5)cc21]

The title compound (100 mg, 16% yield) was generated from 5-(4-bromo-8,9-dihydro-7H-6-oxa-2,9a-diazabenzo[cd]azulen-1-yl)-3-((2-(trimethylsilyl)ethoxy)methyl)benzo[d]oxazol-2(3H)-one (600 mg, 1.16 mmol) and (S)-2-amino-2-cyclopropylacetic acid (700 mg, 6.00 mmol) following a procedure analogous to Example 104, step 1. LCMS (ESI): [M+H]$^+$=551.

Step 4: (S)-2-Cyclopropyl-2-((1-(2-oxo-3-((2-(trimethylsilyl)ethoxy)methyl)-2,3-dihydrobenzo[d]oxazol-5-yl)-8,9-dihydro-7H-6-oxa-2,9a-diazabenzo[cd]azulen-4-yl)amino)acetamide

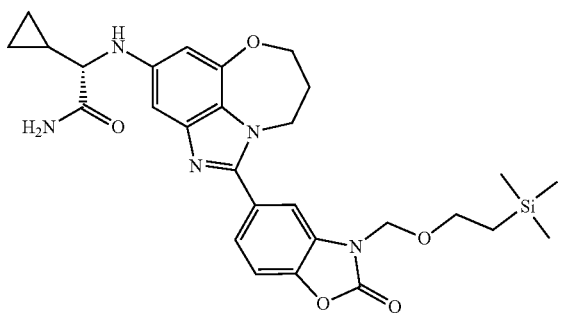 [SMILES: C[Si](C)(C)CCOCn1c(=O)oc2ccc(-c3nc4cc(N[C@H](C(N)=O)C5CC5)cc5c4n3CCCO5)cc21]

The title compound (45 mg, 45% yield) was generated from (S)-2-cyclopropyl-2-((1-(2-oxo-3-((2-(trimethylsilyl)ethoxy)methyl)-2,3-dihydrobenzo[d]oxazol-5-yl)-8,9-dihydro-7H-6-oxa-2,9a-diazabenzo[cd]azulen-4-yl)amino)acetic acid (100 mg, 1.18 mmol) and ammonium chloride (193 mg, 3.61 mmoll) following a procedure analogous to that of Example 104, step 2. LCMS (ESI): [M+H]$^+$=550.

Step 5

A solution of (S)-2-cyclopropyl-2-((1-(2-oxo-3-((2-(trimethylsilyl)ethoxy)methyl)-2,3-dihydrobenzo[d]oxazol-5-yl)-8,9-dihydro-7H-6-oxa-2,9a-diazabenzo[cd]azulen-4-yl)amino)acetamide (45 mg, 0.082 mmol) in TFA (2.0 mL) was stirred at room temperature for 1 h. The solvent was removed in vacuo. The residue was purified via flash chromatography on silica gel (solvent gradient: 10% methanol in dichloromethane) then chiral-SFC and lyophilized to yield 6.20 mg (18%) of 196 as a white solid. LCMS (ESI): R$_T$ (min)=2.11, [M+H]$^+$=420, method=D; $^1$H NMR (300 MHz, DMSO-d$_6$) δ 11.86 (s, 1H), 7.50-7.29 (m, 4H), 6.96 (s, 1H), 6.36 (d, J=2.0 Hz, 1H), 6.24 (d, J=2.0 Hz, 1H), 5.47 (d, J=7.4 Hz, 1H), 4.37-4.27 (m, 2H), 4.21-4.19 (m, 2H), 3.14-3.11 (m, 1H), 2.26-2.23 (m, 2H), 1.17-1.03 (m, 1H), 0.53-0.48 (m, 3H), 0.50-0.47 (m, 1H).

Example 197 (S)-2-((1-(2-Chloro-[1,2,4]triazolo[1,5-c]pyridin-6-yl)-8,9-dihydro-7H-6-oxa-2,9a-diazabenzo[cd]azulen-4-yl)amino)-2-cyclopropylacetamide 197

Step 1: 6-(4,4,5,5-Tetramethyl-1,3,2-dioxaborolan-2-yl)-[1,2,4]triazolo[1,5-a]pyridin-2-amine

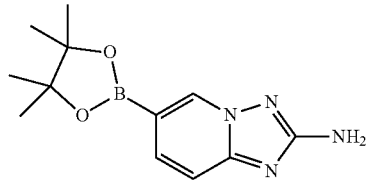 [SMILES: CC1(C)OB(c2ccc3nc(N)nn3c2)OC1(C)C]

A mixture of 6-bromo-[1,2,4]triazolo[1,5-a]pyridin-2-amine (2 g, 9.39 mmol), bis(pinacolato)diboron (2.82 g, 11.1 mmol), potassium acetate (2.77 g, 28.2 mmol) and 1,1'-bis(diphenylphosphino)ferrocenyl palladium (II) dichloride (768 mg, 1.05 mmol) in 1,4-dioxane (50 mL) was stirred at 120° C. for 16 h under an atmosphere of nitrogen. The resulting mixture was cooled down to room temperature and the solvent was evaporated in vacuo. The residue was washed with water and then washed with methanol to yield 1.2 g (49%) of the title compound as a brown solid. LCMS (ESI): [M+H]$^+$=261.

Step 2: 6-(4-Bromo-8,9-dihydro-7H-6-oxa-2,9a-diazabenzo[cd]azulen-1-yl)-[1,2,4]triazolo[1,5-a]pyridin-2-amine

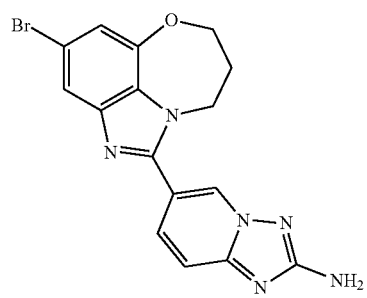 [SMILES: Nc1nc2ccc(-c3nc4cc(Br)cc5c4n3CCCO5)cn2n1]

The title compound (660 mg, 72% yield) was generated from 4-bromo-1-iodo-8,9-dihydro-7H-6-oxa-2,9a-diazabenzo[cd]azulene (Example 150, step 2) (900 mg, 2.38 mmol) and 6-(4,4,5,5-tetramethyl-1,3,2-dioxaborolan-2-yl)-[1,2,4]triazolo[1,5-a]pyridin-2-amine (750 mg, 2.88 mmol) following a procedure analogous to that of Example 150, step 3. LCMS (ESI): [M+H]$^+$=385/387.

Step 3: 4-Bromo-1-(2-chloro-[1,2,4]triazolo[1,5-a]pyridin-6-yl)-8,9-dihydro-7H-6-oxa-2,9a-diazabenzo[cd]azulene

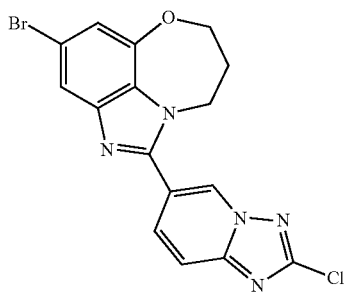 [SMILES: Clc1nc2ccc(-c3nc4cc(Br)cc5c4n3CCCO5)cn2n1]

6-(4-Bromo-8,9-dihydro-7H-6-oxa-2,9a-diazabenzo[cd]azulen-1-yl)-[1,2,4]triazolo[1,5-a]pyridin-2-amine (130 mg, 0.337 mmol), copper(II) chloride (90.0 mg, 0.669 mmol) and tert-butyl nitrite (70.0 mg, 0.679 mmol) were suspended in acetonitrile (5.0 mL) under an atmosphere of nitrogen and the reaction mixture was stirred at 70° C. for 3 h. The reaction mixture was diluted with water and extracted with DCM. The organic extracts were washed with brine, dried over magnesium sulfate and evaporated in vacuo. The resultant residue was purified via flash chromatography on silica gel (solvent gradient: 0-10% methanol in DCM) to yield 60 mg (44%) of the title compound as a brown solid. LCMS (ESI): [M+H]$^+$=404/406.

Step 4: (S)-2-((1-(2-Chloro-[1,2,4]triazolo[1,5-a]pyridin-6-yl)-8,9-dihydro-7H-6-oxa-2,9a-diazabenzo[cd]azulen-4-yl)amino)-2-cyclopropylacetic acid

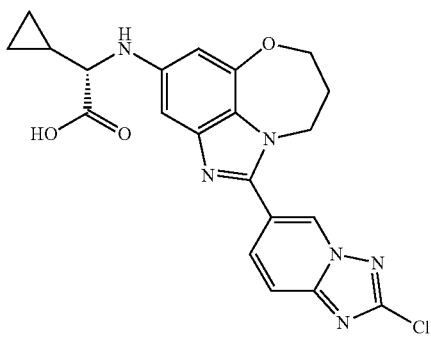 [SMILES: O=C(O)[C@@H](Nc1cc2c3c(c1)nc(-c1ccc4nc(Cl)nn4c1)n3CCCO2)C1CC1]

The title compound (30 mg, 46% yield) was generated from 4-bromo-1-(2-chloro-[1,2,4]triazolo[1,5-a]pyridin-6-yl)-8,9-dihydro-7H-6-oxa-2,9a-diazabenzo[cd]azulene (60.0 mg, 0.148 mmol) and (S)-2-amino-2-cyclopropylacetic acid (86.0 mg, 0.747 mmol) following a procedure analogous to that of Example 104, step 1. LCMS (ESI): [M+H]$^+$=439.

Step 5

197 (10.3 mg, 17% yield) was generated from (S)-2-((1-(2-chloro-[1,2,4]triazolo[1,5-a]pyridin-6-yl)-8,9-dihydro-7H-6-oxa-2,9a-diazabenzo[cd]azulen-4-yl)amino)-2-cyclopropylacetic acid (60 mg, 0.137 mmol) and ammonium chloride (145 mg, 2.71 mmol) following a procedure analogous to Example 104, step 2. LCMS (ESI): R$_T$ (min)=2.12, [M+H]$^+$=438, method=D; $^1$H NMR (400 MHz, DMSO-d$_6$) 9.38 (d, J=0.6 Hz, 1H), 8.15-8.11 (m, 1H), 7.98-7.95 (m, 1H), 7.36 (s, 1H), 6.98 (s, 1H), 6.39 (d, J=1.8 Hz, 1H), 6.30 (d, J=2.1 Hz, 1H), 5.57 (d, J=7.5 Hz, 1H), 4.34-4.32 (m, 4H), 3.17-3.12 (m, 1H), 2.28-2.27 (m, 2H), 1.14-1.08 (m, 1H), 0.53-0.44 (m, 3H), 0.35-0.28 (m, 1H).

Example 198 (6-(4-Bromo-8,9-dihydro-7H-6-oxa-2,9a-diazabenzo[cd]azulen-1-yl)quinoxalin-2-yl)methanol 198

Step 1: 6-Bromo-2-vinylquinoxaline

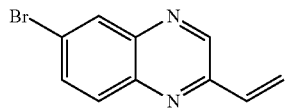

A mixture of 6-bromo-2-chloroquinoxaline (5.00 g, 20.5 mmol), potassium trimethyl (vinyl)borate (2.50 g, 18.7 mmol), 1,1'-bis(diphenylphosphino)ferrocenyl palladium (II) dichloride (1.60 g, 2.19 mmol) and triethylamine (7.50 mL, 54.0 mmol) in 1,4-dioxane (100 mL) was degassed with nitrogen. The reaction mixture was stirred for 4 h at 80° C. and then filtered. The filtrate was evaporated in vacuo. The resultant residue was purified via flash chromatography on silica gel (solvent gradient, 0-10% ethyl acetate in petroleum ether) to yield 2.00 g (41%) of the title compound as a yellow solid. LCMS (ESI): [M+H]$^+$=235/237.

Step 2: 6-Bromoquinoxaline-2-carboxylic acid

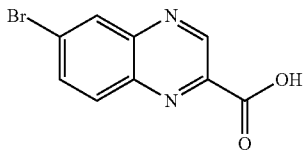 [SMILES: O=C(O)c1cnc2cc(Br)ccc2n1]

To a solution of 6-bromo-2-vinylquinoxaline (2.00 g, 8.51 mmol) in THF (60 mL) and water (20 mL) was added potassium osmate (1.60 g, 4.34 mmol) and sodium periodate (4.75 g, 22.2 mmol). The resulting mixture was stirred for 16 h at room temperature and then diluted with water. The resultant mixture was extracted with DCM and the organic phase was discarded. The aqueous layer was adjusted to ca. pH 5 with acetic acid, and the resulting solids were collected by filtration to yield 3 g of the crude title compound as a light yellow solid. LCMS (ESI): [M+H]$^+$=253/255. $^1$H NMR (300 MHz, DMSO-d$_6$) δ 13.96 (s, 1H), 9.38 (s, 1H), 8.44 (d, J=2.3 Hz, 1H), 8.22-8.04 (m, 2H).

Step 3: Methyl 6-bromoquinoxaline-2-carboxylate

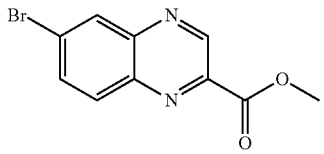

To a solution of 6-bromoquinoxaline-2-carboxylic acid (3.00 g, 11.8 mmol) in methanol (60.0 mL) was added (diazomethyl)trimethylsilane (40.0 mL, 2 mol/L solution in hexane) dropwise with stirring at room temperature. The reaction mixture was stirred for 4 h at room temperature, and then evaporated in vacuo. The resultant residue was purified via flash chromatography on silica gel (solvent gradient, 0-20% ethyl acetate in petroleum ether) to yield 1.6 g (53%) of the title compound as a yellow solid. LCMS (ESI): [M+H]$^+$=267/269. $^1$H NMR (300 MHz, DMSO-d$_6$) δ 9.45 (s, 1H), 8.47 (d, J=2.1 Hz, 1H), 8.25-8.08 (m, 2H), 4.00 (s, 3H).

Step 4: (6-Bromoquinoxalin-2-yl) methanol

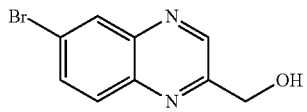 [SMILES: OCc1cnc2cc(Br)ccc2n1]

To a solution of methyl 6-bromoquinoxaline-2-carboxylate (1.60 g, 5.99 mmol) in DCM (10.0 mL) and methanol (20.0 mL) was added NaBH$_4$ (737 mg, 19.5 mmol) portionwise at 10° C. The reaction mixture was stirred for 1 h at 10° C. and then quenched with water. The resultant mixture was extracted with DCM, washed with brine, dried over anhydrous sodium sulfate and evaporated in vacuo. The resultant residue was purified via flash chromatography on silica gel (solvent gradient: 0-50% ethyl acetate in petroleum ether) to yield 600 mg (42%) of the title compound as a light yellow solid. LCMS (ESI): [M+H]$^+$=239/241. $^1$H NMR (300 MHz, DMSO-d$_6$) δ 9.07 (s, 1H), 8.34 (d, J=1.3 Hz, 1H), 8.05-7.93 (m, 2H), 5.81-5.77 (m, 1H), 4.80 (d, J=5.9 Hz, 2H).

Step 5: (6-(4,4,5,5-Tetramethyl-1,3,2-dioxaborolan-2-yl)quinoxalin-2-yl)methanol

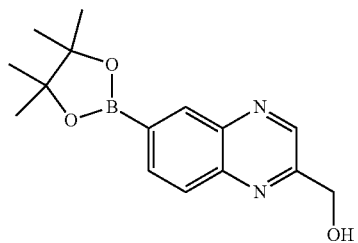 [SMILES: CC1(C)OB(c2ccc3nc(CO)cnc3c2)OC1(C)C]

A mixture of (6-bromoquinoxalin-2-yl) methanol (207 mg, 0.864 mmol), 4,4,4',4',5,5,5',5'-octamethyl-2,2'-bi(1,3,2-dioxaborolane) (483 mg, 1.90 mmol), 1,1'-bis(diphenylphosphino)ferrocenyl palladium (II) dichloride (85.5 mg, 0.117 mmol), and potassium acetate (315 mg, 3.21 mmol) in 1,4-dioxane (12 mL) was degassed with nitrogen. The reaction mixture was heated at 90° C. for 4 h. The reaction mixture was filtered and the filtrate was evaporated in vacuo. The resultant residue was purified via flash chromatography on silica gel (solvent gradient: 0-60% ethyl acetate in petroleum ether) to afford 88 mg (36%) of the title compound as brown oil. LCMS (ESI): [M+H]$^+$=287.

Step 6

198 (50 mg, 21% yield) was generated from 4-bromo-1-iodo-8,9-dihydro-7H-6-oxa-2,9a-diazabenzo[cd]azulene (Example 150, step 2) (220 mg, 0.580 mmol) and (6-(4,4,5,5-tetramethyl-1,3,2-dioxaborolan-2-yl)quinoxalin-2-yl)methanol (160 mg, 0.559 mmol) following a procedure analogous to Example 150, step 3. LCMS (ESI): R$_T$ (min)=2.510, [M+H]$^+$=411, method=C; $^1$H NMR (400 MHz, DMSO-d$_6$) δ 9.16 (s, 1H), 8.54 (d, J=1.6 Hz, 1H), 8.29-8.27 (m, 1H), 8.22 (d, J=8.4 Hz, 1H), 7.55 (d, J=1.6 Hz, 1H), 6.98 (d, J=1.6 Hz, 1H), 5.88-5.85 (m, 1H), 4.88 (d, J=5.6 Hz, 2H), 4.53-4.45 (m, 4H), 2.43-2.33 (m, 2H).

Example 199 (S)-1-(1-(1H-Benzo[d]imidazol-5-yl)-8,9-dihydro-7H-6-oxa-2,9a-diazabenzo[cd]azulen-4-yl)pyrrolidine-2-carboxamide 199

199 was prepared following procedures analogous to those of Example 150. LCMS (ESI): R$_T$ (min)=1.75, [M+H]$^+$=403, method=C; $^1$H NMR (300 MHz, DMSO-d$_6$) δ 12.68 (s, 1H), 8.34 (s, 1H), 8.02 (d, J=9.3 Hz, 1H), 7.75-7.69 (m, 2H), 7.28 (s, 1H), 7.01 (s, 1H), 6.36 (s, 1H), 6.07 (s, 1H), 4.39-4.27 (m, 4H), 3.90-3.85 (m, 1H), 3.69-3.59 (m, 1H), 3.25-3.16 (m, 1H), 2.27-2.26 (m, 3H), 1.96 (br s, 3H).

Example 200 (S)-1-(1-(1H-Benzo[d][1,2,3]triazol-5-yl)-8,9-dihydro-7H-6-oxa-2,9a-diazabenzo[cd]azulen-4-yl)pyrrolidine-2-carboxamide 200

200 was prepared following procedures analogous to those of Example 125. LCMS (ESI): R$_T$ (min)=1.19, [M+H]$^+$=404, method=C; $^1$H NMR (300 MHz, DMSO-d$_6$) δ 8.31 (s, 1H), 8.03 (d, J=8.7 Hz, 1H), 7.85 (d, J=8.4 Hz, 1H), 7.30 (s, 1H), 7.02 (s, 1H), 6.38 (d, J=2.1 Hz, 1H), 6.10 (d, J=2.1 Hz, 1H), 4.39-4.27 (m, 4H), 3.85 (d, J=7.5 Hz, 1H), 3.70-3.30 (m, 1H), 3.21-3.18 (m, 1H), 2.40-2.15 (m, 3H), 2.10-1.85 (m, 3H).

Example 201 (S)-2-((1-(2-Amino-[1,2,4]triazolo[1,5-c]pyridin-6-yl)-8,9-dihydro-7H-6-oxa-2,9a-diazabenzo[cd]azulen-4-yl)amino)-2-cyclopropylacetamide 201

201 was prepared following procedures analogous to those of Example 197. LCMS (ESI): R$_T$ (min)=1.06, [M+H]$^+$=419, method=D; $^1$H NMR (400 MHz, DMSO-d$_6$) δ 8.93 (d, J=0.6 Hz, 1H), 7.81-7.78 (m, 1H), 7.49-7.46 (m, 1H), 7.35 (d, J=2.0 Hz, 1H), 6.97 (d, J=2.0 Hz, 1H), 6.38 (d, J=2.0 Hz, 1H), 6.27 (d, J=2.0 Hz, 1H), 6.20 (s, 1H), 5.52 (d, J=7.6 Hz 1H), 4.35-4.28 (m, 4H), 3.17-3.12 (m, 1H), 2.28-2.27 (m, 2H), 1.14-1.08 (m, 1H), 0.52-0.48 (m, 3H), 0.35-0.26 (m, 1H).

Examples 202 and 203 1-(2-Aminobenzo[d]oxazol-5-yl)-N-((1r,3r)-3-fluorocyclobutyl)-8,9-dihydro-7H-6-oxa-2,9a-diazabenzo[cd]azulen-4-amine 202 and 1-(2-Aminobenzo[d]oxazol-5-yl)-N-((1s,3s)-3-fluorocyclobutyl)-8,9-dihydro-7H-6-oxa-2,9a-diazabenzo[cd]azulen-4-amine 203

The title compounds were prepared each as a single unknown stereoisomer following procedures analogous to those of Example 192 followed by chiral HPLC separation.

202 (7.5 mg): LCMS: $R_T$ (min)=3.5 min, [M+H]$^+$=394, method=C; $^1$H NMR (300 MHz, DMSO-d$_6$) δ 7.56-7.51 (m, 3H), 7.48-7.34 (m, 1H), 7.34-7.31 (m, 1H), 6.26 (d, J=1.8 Hz, 1H), 6.11 (d, J=1.8 Hz, 1H), 5.65 (d, J=5.7 Hz, 1H), 5.35-5.18 (m, 1H), 4.34-4.31 (m, 2H), 4.22-4.18 (m, 2H), 3.98-3.95 (m, 1H), 2.50-2.49 (m, 2H), 2.30-2.23 (m, 4H).

203 (22 mg): LCMS: $R_T$ (min)=3.5 min, [M+H]$^+$=394, method=C; $^1$H NMR (300 MHz, DMSO-d$_6$) δ 7.56-7.51 (m, 2H), 7.48-7.45 (m, 2H), 7.34-7.31 (m, 1H), 6.34 (d, J=1.8 Hz, 1H), 6.13 (d, J=1.8 Hz, 1H), 5.62 (d, J=7.5 Hz, 1H), 4.99-4.80 (m, 1H), 4.33-4.31 (m, 2H), 4.22-4.18 (m, 2H), 3.39 (d, J=6.9 Hz, 1H), 2.89-2.83 (m, 2H), 2.24 (s, 2H), 2.09-1.98 (m, 2H).

Example 204 (S)-2-((1-(2-Aminobenzo[d]oxazol-5-yl)-7,8,9,10-tetrahydro-6-oxa-2,10a-diazacycloocta[cd]inden-4-yl)oxy)propanamide 204

Step 1: 2-Amino-5-bromo-3-nitrophenol hydrobromide

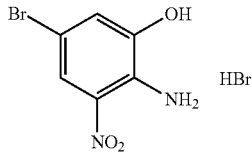

To a suspension of 2-amino-3-nitrophenol (192 g, 1.25 mol) in dioxane (4 L) at 10° C. was dropwise added bromine (239 g, 1.50 mol). The reaction mixture was stirred at 10° C. for 15 min then at 25° C. for 3 h. The mixture was filtered and the filter cake was washed with dioxane to yield 408.4 g (crude) of the title compound as a yellow solid. This material was carried forward without further purification. LCMS (ESI): [M+H]$^+$=233/235.

Step 2: 2-(3-(1,3-Dioxolan-2-yl)propoxy)-4-bromo-6-nitrobenzenamine

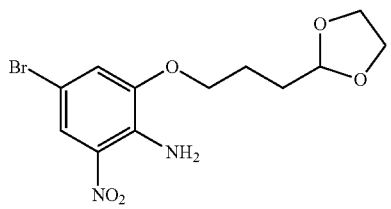 [SMILES: Nc1c(OCCCC2OCCO2)cc(Br)cc1[N+](=O)[O-]]

A mixture of 2-amino-5-bromo-3-nitrophenol hydrobromide (300 g, 0.955 mol), 2-(3-chloropropyl)-1,3-dioxolane (143 g, 0.955 mol), potassium carbonate (396 g, 2.87 mol) and sodium iodide (43.0 g, 0.287 mol) in DMF (3.5 L) was stirred at 80° C. for 16 h. The reaction mixture was diluted with water and extracted with ethyl acetate. The organic extracts were washed with brine, dried over magnesium sulfate and evaporated in vacuo to yield 288 g (crude) of the title compound as a brown solid. This material was carried forward without further purification. LCMC (ESI): [M+H]$^+$=347/349.

Step 3: 9-Bromo-7-nitro-3,4,5,6-tetrahydro-2H-benzo[b][1,4]oxazocine

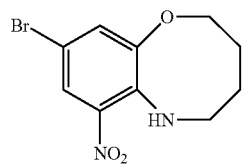

To a solution of 2-(3-(1,3-dioxolan-2-yl)propoxy)-4-bromo-6-nitrobenzenamine (390 g, 1.12 mol) in DCM (2 L) at 0° C. was added dropwise TFA (1 L, 13.5 mol). The reaction mixture was stirred at 0° C. for 15 min then triethylsilane (372 g, 3.20 mol) was added dropwise and the reaction mixture was stirred at 0° C. for 15 min and then at 25° C. for 16 h. The reaction mixture was diluted with water and adjusted the pH to 8 with saturated aqueous sodium hydrogen carbonate and extracted with DCM. The organic extracts were washed with brine, dried over magnesium sulfate and evaporated in vacuo to yield 433 g (crude) of the title compound as a red solid. This material was carried forward without further purification. LCMS (ESI): [M+H]$^+$=287/289.

Step 4: 9-Bromo-3,4,5,6-tetrahydro-2H-benzo[b][1,4]oxazocin-7-amine

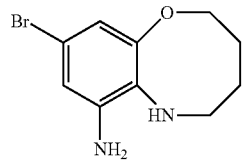 [SMILES: O=[N+]([O-])c1cc(Br)cc2c1NCCCCO2]

To a suspension of 9-bromo-7-nitro-3,4,5,6-tetrahydro-2H-benzo[b][1,4]oxazocine (433 g, 1.51 mol) and ammonium chloride (410 g, 7.67 mol) in methanol (2.5 L) and water (2.5 L) was added in portions iron powder (280 g, 5.01 mol) at 55° C. and the reaction mixture stirred at 70° C. in a sealed vessel for 2 h. The resulting mixture was filtered and the solids thoroughly washed with ethyl acetate. The filtrate was extracted with ethyl acetate and the combined organic extracts were washed with brine, dried over magnesium sulfate and evaporated in vacuo to yield 242 g (crude) of the title compound as brown oil. This material was carried forward without further purification. LCMS (ESI): [M+H]$^+$=257/259.

Step 5: 4-Bromo-7,8,9,10-tetrahydro-6-oxa-2,10a-diazacycloocta[cd]indene

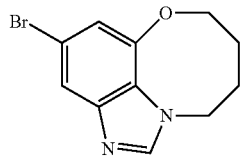 [SMILES: Brc1cc2c3c(c1)ncn3CCCCO2]

9-Bromo-3,4,5,6-tetrahydro-2H-benzo[b][1,4]oxazocin-7-amine (180 g, 700 mmol) and 4-methylbenzenesulfonic acid (18 g, 105 mmol) was dissolved in trimethylorthoformate (2 L) and the reaction mixture was stirred at 100° C. for 16 h. The resulting mixture was evaporated in vacuo and the product purified via flash chromatography on silica gel (solvent gradient: 0-50% ethyl acetate in petroleum ether) to yield 126 g (67%) of the title compound as a brown solid. LCMS (ESI): [M+H]$^+$=267/269.

Step 6: 4-Bromo-1-iodo-7,8,9,10-tetrahydro-6-oxa-2,10a-diazacycloocta[cd]indene

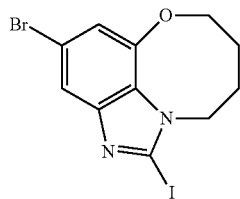

To a solution of 4-bromo-7,8,9,10-tetrahydro-6-oxa-2,10a-diazacycloocta[cd]indene (12 g, 44.9 mmol) in THF (1.5 L) at −78° C. was added dropwise LDA (2 N solution in THF, 45 mL, 90.0 mmol) and the reaction mixture stirred at −78° C. for 1 h. A solution of 1-iodopyrrolidine-2,5-dione (20.2 g, 89.8 mmol) in THF (200 mL) was added dropwise at −78° C. and the reaction mixture was stirred at −78° C. for 2 h. The resulting mixture was quenched with water and extracted with DCM. The combined organic extracts were washed with brine, dried over magnesium sulfate and evaporated in vacuo. The residue was purified via flash chromatography on silica gel (solvent gradient: 0-10% methanol in DCM) to yield 8.8 g (50%) of the title compound as a yellow solid. LCMS (ESI): [M+H]$^+$=393/395; $^1$H NMR (300 MHz, DMSO-$d_6$): δ 7.59 (d, J=1.8 Hz, 1H), 7.05 (d, J=1.5 Hz, 1H), 4.45-4.41 (m, 2H), 4.27-4.23 (m, 2H), 1.99-1.92 (m, 2H), 1.54-1.48 (m, 2H).

Step 7: 5-(4,4,5,5-Tetramethyl-1,3,2-dioxaborolan-2-yl)benzo[d]oxazol-2-amine

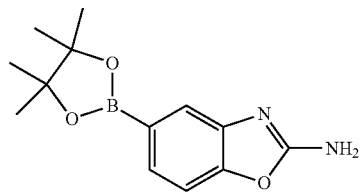 [SMILES: CC1(C)OB(c2ccc3oc(N)nc3c2)OC1(C)C]

A mixture of 5-bromobenzo[d]oxazol-2-amine (20.0 g, 93.9 mmol), 4,4,4',4',5,5,5',5'-octamethyl-2,2'-bi(1,3,2-dioxaborolane) (28.6 g, 113 mmol), 1,1'-bis(diphenylphosphino)ferrocenyl palladium (II) dichloride (6.87 g, 9.39 mmol) and potassium acetate (27.6 g, 282 mmol) in DMF (200 mL) was stirred at 80° C. for 6 h under nitrogen. The resulting solution was diluted with water and extracted with ethyl acetate. The organic layers were combined and dried over anhydrous sodium sulfate and concentrated in vacuo. The residue was purified via flash chromatography on silica gel (solvent gradient: 0-50% ethyl acetate in petroleum ether) to yield 10.5 g (43%) of the title compound as a brown solid. LCMS (ESI): [M+H]$^+$=261.

Step 8: 5-(4-Bromo-7,8,9,10-tetrahydro-6-oxa-2,10a-diazacycloocta[cd]inden-1-yl)benzo[d]oxazol-2-amine

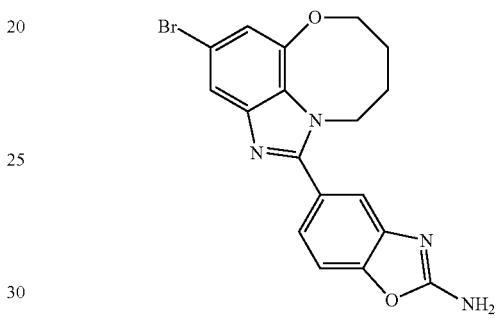

A mixture of 4-bromo-1-iodo-7,8,9,10-tetrahydro-6-oxa-2,10a-diazacycloocta[cd]indene (1.20 g, 3.05 mmol), 5-(4,4,5,5-tetramethyl-1,3,2-dioxaborolan-2-yl)benzo[d]oxazol-2-amine (790 mg, 3.04 mmol), 1,1'-bis(diphenylphosphino)ferrocenyl palladium (II) dichloride (220 mg, 0.301 mmol) and sodium carbonate (2 M solution in water, 3 mL, 6 mmol) in DMF (15 mL) was heated under microwave irradiation at 80° C. for 45 min. The resulting solution was diluted with water and extracted with DCM. The organic layers combined and dried over anhydrous sodium sulfate and concentrated in vacuo. The residue was purified via flash chromatography on silica gel (solvent gradient, 0-10% methanol in DCM) to yield 660 mg (54%) of the title compound as a yellow solid. LCMS (ESI): [M+H]$^+$=399/401.

Step 9: 5-(4-(4,4,5,5-Tetramethyl-1,3,2-dioxaborolan-2-yl)-7,8,9,10-tetrahydro-6-oxa-2,10a-diazacycloocta[cd]inden-1-yl)benzo[d]oxazol-2-amine

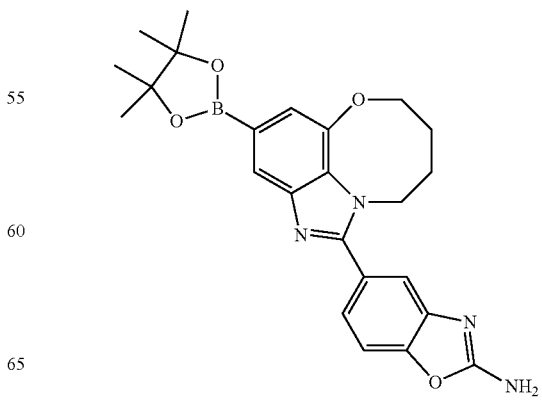

The title compound (400 mg, 41% yield) was generated from 5-(4-bromo-7,8,9,10-tetrahydro-6-oxa-2,10a-diazacycloocta[cd]inden-1-yl)benzo[d]oxazol-2-amine (700 mg, 1.75 mmol) and 4,4,4',4',5,5,5',5'-octamethyl-2,2'-bi(1,3,2-dioxaborolane) (891 mg, 3.51 mmol) following a procedure analogous to Example 162, Step 1. LCMS (ESI): [M+H]⁺=447.

Step 10: 1-(2-Aminobenzo[d]oxazol-5-yl)-7,8,9,10-tetrahydro-6-oxa-2,10a-diazacycloocta[cd]inden-4-ol

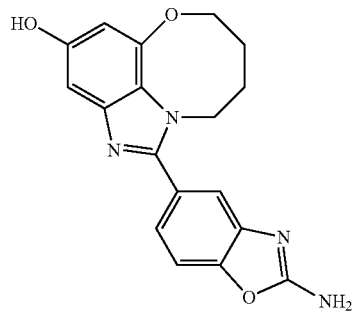 [SMILES: Nc1nc2cc(-c3nc4cc(O)cc5c4n3CCCCO5)ccc2o1]

The title compound (281 mg, 98% yield) was generated from 5-(4-(4,4,5,5-tetramethyl-1,3,2-dioxaborolan-2-yl)-7,8,9,10-tetrahydro-6-oxa-2,10a-diazacycloocta[cd]inden-1-yl)benzo[d]oxazol-2-amine (380 mg, 0.851 mmol) following a procedure analogous to Example 162, step 2. LCMS (ESI): [M+H]⁺=337.

Step 11: (9-Methyl 2-((1-(2-aminobenzo[d]oxazol-5-yl)-7,8,9,10-tetrahydro-6-oxa-2,10a-diazacycloocta[cd]inden-4-yl)oxy)propanoate

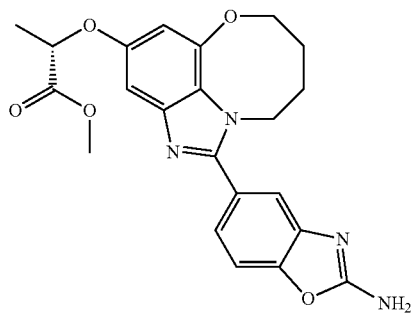 [SMILES: COC(=O)[C@H](C)Oc1cc2c3c(c1)nc(-c1ccc4oc(N)nc4c1)n3CCCCO2]

The title compound (700 mg, 56% yield) was generated from 1-(2-aminobenzo[d]oxazol-5-yl)-7,8,9,10-tetrahydro-6-oxa-2,10a-diazacycloocta[cd]inden-4-ol (1.00 g, 2.97 mmol) and (R)-methyl 2-(tosyloxy)propanoate (1.15 g, 4.45 mmol) following a procedure analogous to Example 162, step 3. LCMS (ESI): [M+H]⁺=423.

Step 12

A reaction vessel was charged with (S)-methyl 2-((1-(2-aminobenzo[d]oxazol-5-yl)-7,8,9,10-tetrahydro-6-oxa-2,10a-diazacycloocta[cd]inden-4-yl)oxy)propanoate (600 mg, 1.42 mmol) and 7 N ammonia in methanol (6 mL). The reaction mixture was stirred at room temperature for 16 h. The resulting mixture was concentrated in vacuo. The residue was purified via flash chromatography on silica gel (solvent gradient: 5-10% methanol in DCM), then by chiral-SFC and lyophilized to yield 309 mg (55%) of 204 as a light yellow solid. LCMS (ESI): R$_T$ (min)=1.47, [M+H]⁺=408, method=D; ¹H NMR (300 MHz, DMSO-d$_6$) δ 7.61-7.44 (m, 5H), 7.29-7.26 (m, 2H), 6.92 (d, J=2.1 Hz, 1H), 6.59 (d, J=2.1 Hz, 1H), 4.66-4.59 (m, 1H), 4.39-4.35 (m, 2H), 4.26-4.23 (m, 2H), 2.11 (apparent s, 2H), 1.69 (apparent s, 2H), 1.45 (d, J=8.8 Hz, 3H).

Example 205 (S)-2-((1-(2-Amino-7-methylbenzo[d]oxazol-5-yl)-8,9-dihydro-7H-6-oxa-2,9a-diazabenzo[cd]azulen-4-yl)amino)-2-cyclopropylacetamide 205

Step 1: 5-(4-Bromo-8,9-dihydro-7H-6-oxa-2,9a-diazabenzo[cd]azulen-1-yl)-7-methylbenzo[d]oxazol-2-amine

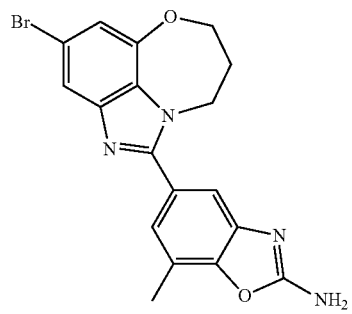 [SMILES: Cc1cc(-c2nc3cc(Br)cc4c3n2CCCO4)cc2nc(N)oc12]

A reaction vessel was charged with 5-bromo-7-methylbenzo[d]oxazol-2-amine (200 mg, 0.88 mmol), bis(pinacolato)diboron (268 mg, 1.06 mmol), 1,1'-bis(diphenylphosphino)ferrocene palladium dichloride dichloromethane complex (71.9 mg, 0.09 mmol), potassium acetate (259 mg, 2.64 mmol) and solvated in 1,4-dioxane (2.6 mL). The reaction mixture was degassed under argon and then stirred at 110° C. for 2 h. The resultant mixture was allowed to cool to room temperature then 4-bromo-1-iodo-8,9-dihydro-7H-6-oxa-2,9a-diazabenzo[cd]azulene (334 mg, 0.88 mmol), 1,1'-bis(diphenylphosphino)ferrocenepalladiumdichloride dichloromethane complex (71.9 mg, 0.088 mmol) and 2 N aqueous sodium carbonate (1.75 mL, 3.52 mmol) were added. The reaction mixture was degassed under argon and stirred at 100° C. for 24 h. The resultant mixture was allowed to cool to room temperature and partitioned between DCM and distilled water. The organic layer was separated, dried over magnesium sulfate and evaporated in vacuo. The residue was purified via flash chromatography on silica (solvent gradient: 0-5% methanol in ethyl acetate) to afford 128 mg (36%) of the title compound as an off white solid. LCMS (ESI): [M+H]⁺=399/401.

Step 2: (S)-2-((1-(2-Amino-7-methylbenzo[d]ox-azol-5-yl)-8,9-dihydro-7H-6-oxa-2,9a-diazabenzo[cd]azulen-4-yl)amino)-2-cyclopropylacetic acid

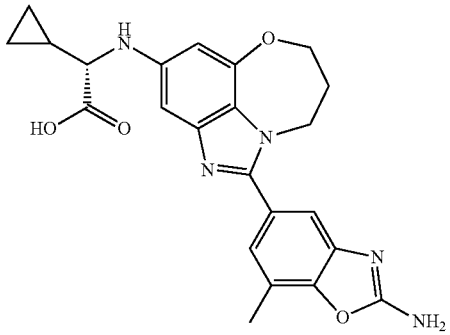 [SMILES: Cc1cc(-c2nc3cc(N[C@H](C(=O)O)C4CC4)cc4c3n2CCCO4)cc2nc(N)oc12]

The title compound (148 mg, 58% yield) was generated from 5-(4-bromo-8,9-dihydro-7H-6-oxa-2,9a-diazabenzo[cd]azulen-1-yl)-7-methylbenzo[d]oxazol-2-amine (235 mg, 0.59 mmol) and (S)-2-amino-2-cyclopropylacetic acid (135 mg, 1.17 mmol) following a procedure analogous to Example 125, step 3. LCMS (ESI): [M+H]$^+$=434.

Step 3

205 (24.3 mg, 16% yield) was generated from (S)-2-((1-(2-amino-7-methylbenzo[d]oxazol-5-yl)-8,9-dihydro-7H-6-oxa-2,9a-diazabenzo[cd]azulen-4-yl)amino)-2-cyclopropylacetic acid (148 mg, 0.34 mmol) following a procedure analogous to Example 125, step 4. LCMS (ESI): R$_T$ (min)=2.52, [M+H]$^+$=433, method=A; $^1$H NMR (400 MHz, DMSO-d$_6$) δ 7.51 (br s, 2H), 7.33-7.32 (m, 2H), 7.18-7.17 (m, 1H), 6.96-6.95 (m, 1H), 6.36 (d, J=2.0 Hz, 1H), 6.22 (d, J=2.0 Hz, 1H), 5.44 (d, J=7.4 Hz, 1H), 4.32-4.14 (m, 4H), 3.14 (t, J=7.4 Hz, 1H), 2.42 (s, 3H), 2.26-2.20 (m, 2H), 1.15-1.06 (m, 1H), 0.54-0.44 (m, 3H), 0.34-0.28 (m, 1H).

Example 206 (S)-1-(1-(3H-[1,2,3]Triazolo[4,5-b]pyridin-7-yl)-8,9-dihydro-7H-6-oxa-2,9a-diazabenzo[cd]azulen-4-yl)pyrrolidine-2-carboxamide 206

Step 1: 7-Chloro-3-(4-methoxybenzyl)-3H-[1,2,3]triazolo[4,5-b]pyridine

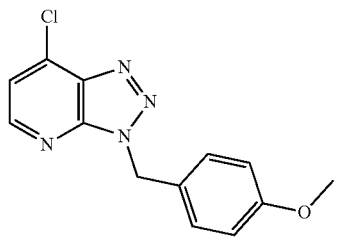 [SMILES: COc1ccc(Cn2nnc3c(Cl)ccnc32)cc1]

A mixture of 7-chloro-3H-[1,2,3]triazolo[4,5-b]pyridine (1.00 g, 6.47 mmol), cesium carbonate (4.22 g, 12.9 mmol), 1-(chloromethyl)-4-methoxybenzene (1.22 g, 7.79 mmol) in DMF (15 mL) was stirred at 25° C. for 3 h. The resultant mixture was diluted with water and extracted with DCM. The organic extracts was washed with brine, dried over sodium sulfate and concentrated in vacuo. The residue was purified via flash chromatography on silica gel (solvent gradient: 0-50% ethyl acetate in petroleum ether) to yield 900 mg (51%) of the title compound as a white solid. LCMS: [M+H]$^+$=275.

Step 2: 3-(4-Methoxybenzyl)-7-(4,4,5,5-tetramethyl-1,3,2-dioxaborolan-2-yl)-3H-[1,2,3]triazolo[4,5-b]pyridine

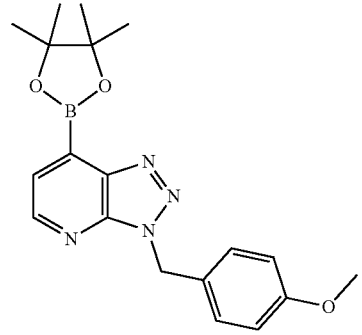

A mixture of 7-chloro-3-(4-methoxybenzyl)-3H-[1,2,3]triazolo[4,5-b]pyridine (1.50 g, 5.46 mmol), 1,1'-bis(diphenylphosphino)ferrocenyl palladium (II) dichloride (400 mg, 0.547 mmol), 4,4,4',4',5,5,5',5'-octamethyl-2,2'-bi(1,3,2-dioxaborolane) (1.66 g, 6.54 mmol) and potassium acetate (1.07 g, 10.9 mmol) in 1,4-dioxane (20 mL) was stirred at 100° C. for 16 h. The resulting mixture was cooled to room temperature. The solids were filtered out and the solvent was evaporated in vacuo. The residue was purified via flash chromatography on silica gel (solvent gradient: 0-50% ethyl acetate in petroleum ether) to yield 1.00 g (50%) of the title compound as a yellow solid. LCMS (53): [M+H]$^+$=367.

Step 3: 4-Bromo-1-(3-(4-methoxybenzyl)-3H-[1,2,3]triazolo[4,5-b]pyridin-7-yl)-8,9-dihydro-7H-6-oxa-2,9a-diazabenzo[cd]azulene

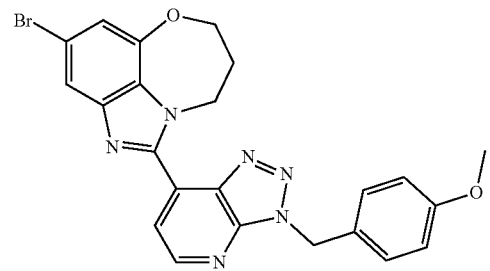 [SMILES: COc1ccc(Cn2nnc3c(-c4nc5cc(Br)cc6c5n4CCCO6)ccnc32)cc1]

The title compound (300 mg, 22% yield) was generated from 4-bromo-1-iodo-8,9-dihydro-7H-6-oxa-2,9a-diazabenzo[cd]azulene (Example 150, step 2) (1.03 g, 2.72 mmol) and 3-(4-methoxybenzyl)-7-(4,4,5,5-tetramethyl-1,3,2-dioxaborolan-2-yl)-3H-[1,2,3]triazolo[4,5-b]pyridine (1.00 g, 2.73 mmol) following a procedure analogous to Example 150, step 3. LCMS (ESI): [M+H]$^+$=491/493.

Step 4: (S)-1-(1-(3-(4-Methoxybenzyl)-3H-[1,2,3]triazolo[4,5-b]pyridin-7-yl)-8,9-dihydro-7H-6-oxa-2,9a-diazabenzo[cd]azulen-4-yl)pyrrolidine-2-carboxamide

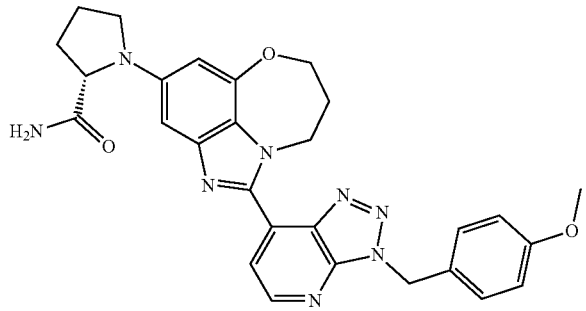 [SMILES: COc1ccc(Cn2nnc3c(-c4nc5cc(N6CCC[C@H]6C(N)=O)cc6c5n4CCCO6)ccnc32)cc1]

The title compound (150 mg, 40% yield over two steps) was generated from 4-bromo-1-(3-(4-methoxybenzyl)-3H-[1,2,3]triazolo[4,5-b]pyridin-7-yl)-8,9-dihydro-7H-6-oxa-2,9a-diazabenzo[cd]azulene (350 mg, 3.04 mmol) following procedures analogous to those of Example 104, steps 1-2. LCMS (ESI): [M+H]$^+$=525.

Step 5

A mixture of (S)-1-(1-(3-(4-methoxybenzyl)-3H-[1,2,3]triazolo[4,5-b])pyridin-7-yl)-8,9-dihydro-7H-6-oxa-2,9a-diazabenzo[cd]azulen-4-yl)pyrrolidine-2-carboxamide in TFA was stirred at 80° C. for 4 h. The resultant mixture was diluted with water and extracted with DCM. The combined organic extracts were washed with brine, dried over anhydrous sodium sulfate and evaporated in vacuo. The resultant residue was purified via flash chromatography on silica gel (solvent gradient: 0-10% methanol in DCM) to yield 13.1 mg (11%) of 206 as a yellow solid. LCMS: R$_T$ (min)=4.5, [M+H]$^+$=405, method=D; $^1$H NMR (300 MHz, DMSO-d$_6$) δ 16.44 (s, 1H), 8.84 (d, J=4.8 Hz, 1H), 7.85 (d, J=4.5 Hz, 1H), 7.36 (s, 1H), 7.05 (s, 1H), 6.47 (d, J=2.1 Hz, 1H), 6.22 (d, J=2.1 Hz, 1H), 4.42 (d, J=3.9 Hz, 4H), 3.90-3.87 (m, 1H), 3.64-3.59 (m, 1H), 3.26-3.21 (m, 1H), 2.33-2.28 (m, 3H), 2.27-2.21 (m, 3H).

Example 207 (S)-2-((1-(2-Aminobenzo[d]oxazol-6-yl)-8,9-dihydro-7H-6-oxa-2,9a-diazabenzo[cd]azulen-4-yl)amino)-2-cyclopropylacetamide 207

Step 1: 6-(4-Bromo-8,9-dihydro-7H-6-oxa-2,9a-diazabenzo[cd]azulen-1-yl)benzo[d]oxazol-2-amine

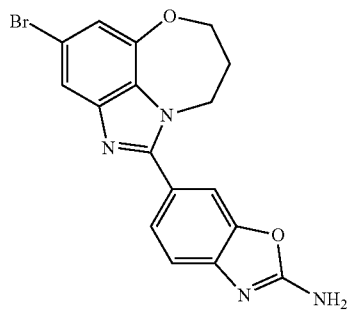 [SMILES: Nc1nc2ccc(-c3nc4cc(Br)cc5c4n3CCCO5)cc2o1]

The title compound (720 mg, 32% yield) was generated from 6-(4,4,5,5-tetramethyl-1,3,2-dioxaborolan-2-yl)benzo[d]oxazol-2-amine (1.50 g, 5.77 mmol), and 4-bromo-1-iodo-8,9-dihydro-7H-6-oxa-2,9a-diazabenzo[cd]azulene (Example 150, step 2) (2.70 g, 7.12 mmol) following a procedure analogous to Example 204, step 8. LCMS (ESI): [M+H]$^+$=385/387.

Step 2

207 (40.3 mg, 11.2% yield over two steps) was generated from 6-(4-bromo-8,9-dihydro-7H-6-oxa-2,9a-diazabenzo[cd]azulen-1-yl)benzo[d]oxazol-2-amine (220 mg, 0.571 mmol) and (2S)-2-amino-2-cyclopropylacetic acid (330 mg, 2.87 mmol) following procedures analogous to those of Example 104, steps 1-2. LCMS (ESI): R$_T$ (min)=1.16, [M+H]$^+$=419, Method=D; $^1$H NMR (300 MHz, DMSO-d$_6$) δ 7.71-7.76 (m, 3H), 7.51-7.48 (m, 1H), 7.35-7.29 (m, 2H), 6.98 (s, 1H), 6.36 (d, J=2.1 Hz, 1H), 6.28 (d, J=2.1 Hz, 1H), 5.46 (d, J=7.2 Hz, 1H), 4.34-4.23 (m, 4H), 3.16-3.11 (m, 1H), 2.24 (d, J=3.9 Hz, 2H), 1.14-1.08 (m, 1H), 0.51-0.47 (m, 3H), 0.31-0.29 (m, 1H).

Example 208 (S)-2-((2-(2-Aminobenzo[d]oxazol-5-yl)-3,4-dihydro-5-oxa-1,2a-diazaacenaphthylen-7-yl)amino)-2-cyclopropylacetamide 208

Step 1: 7-Bromo-5-nitro-3,4-dihydro-2H-benzo[b][1,4]oxazine

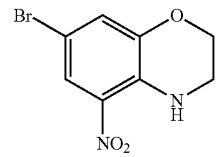 [SMILES: O=[N+]([O-])c1cc(Br)cc2c1NCCO2]

To a solution of 2-amino-5-bromo-3-nitrophenol (7.5 g, 32.2 mmol) and 1,2-dibromoethane (16.6 mL, 193 mmol) in DMF (40 mL) was added potassium hydroxide (3.61 g, 64.4 mmol) and the reaction mixture stirred at 140° C. for 10 h. The reaction mixture was diluted with water and extracted with ethyl acetate. The combined organic fractions were washed with brine, dried over magnesium sulfate and concentrated in vacuo. The residue was triturated with methanol to yield a first batch of product as a red solid. The mother liquors were purified via flash chromatography on silica gel (solvent gradient, 0-70% ethyl acetate in cyclohexane). The product obtained was combined with the first batch to provide 4.24 g (51%) of the title compound as a red solid. $^1$H NMR (400 MHz, DMSO-d$_6$) δ 8.48 (br s, 1H), 7.75 (d, J=2.3 Hz, 1H), 7.19 (dd, J=2.3, 0.8 Hz, 1H), 4.21 (t, J=9.2 Hz, 2H), 3.57-3.51 (m, 2H).

Step 2: 7-Bromo-3,4-dihydro-2H-benzo[b][1,4]oxazin-5-amine

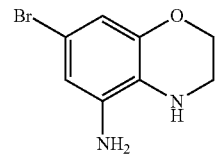 [SMILES: Nc1cc(Br)cc2c1NCCO2]

To a suspension of 7-bromo-5-nitro-3,4-dihydro-2H-benzo[b][1,4]oxazine (4.24 g, 16.4 mmol) and ammonium chloride (7.88 g, 147 mmol) in methanol (75 mL) and water (75 mL) was added iron powder (5.48 g, 98.2 mmol) and the reaction mixture heated at 55° C. for 2 h. The reaction mixture was filtered through celite and concentrated in vacuo to remove the methanol. The aqueous residue was extracted with ethyl acetate. The combined organic fractions were washed with brine, dried over magnesium sulfate and concentrated in vacuo to yield 3.69 g (75%) of the crude title compound as a brown oil. $^1$H NMR (400 MHz, CDCl$_3$) δ 6.52 (d, J=2.3 Hz, 1H), 6.46 (d, J=2.3 Hz, 1H), 4.17-4.14 (m, 2H), 3.41-3.36 (m, 2H).

Step 3:
7-Bromo-3,4-dihydro-5-oxa-1,2a-diazaacenaphthylene

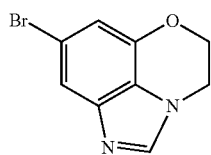

A solution of 7-bromo-3,4-dihydro-2H-benzo[b][1,4]oxazin-5-amine (3.20 g, 13.9 mmol) and p-toluenesulfonic acid (0.04 g, 0.2 mmol) in trimethylorthoformate (10 mL, 91.4 mmol) was heated under reflux for 1 h. The reaction mixture was dry loaded onto diatomaceous earth and purified via flash chromatography on silica gel (solvent gradient: 0-5% methanol in DCM) to yield 2.70 g (81%) of the title compound as a beige solid. LCMS (ESI): [M+H]$^+$=239/241.

Step 4: 7-Bromo-2-iodo-3,4-dihydro-5-oxa-1,2a-diazaacenaphthylene

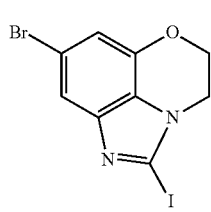 [SMILES: Brc1cc2c3c(c1)nc(I)n3CCO2]

To a solution of diisopropylamine (2.5 mL, 18.1 mmol) in THF (30 mL) at −40° C. was added dropwise n-butyllithium (6.32 mL, 2.5 N in hexanes, 15.8 mmol) and the reaction mixture allowed to warm to −20° C. The reaction mixture was cooled to −78° C. and a solution of 7-bromo-3,4-dihydro-5-oxa-1,2a-diazaacenaphthylene (2.70 g, 11.3 mmol) in THF (20 mL) was added. The reaction mixture was stirred at −78° C. for 2 h. A solution of iodine (4.01 g, 15.8 mmol) in THF (12 mL) was added dropwise and the reaction mixture stirred at −78° C. for 2 h. The resultant mixture was diluted with saturated aqueous ammonium chloride and extracted with ethyl acetate. The combined organic extracts were washed with brine, dried over magnesium sulfate and evaporated in vacuo. The resultant residue was purified via flash chromatography on silica gel (solvent gradient: 0-100% ethyl acetate in cyclohexane) to yield 2.55 g (62%) of the title compound as a brown solid. LCMS (ESI): [M+H]$^+$=365/367.

Step 5: 5-(7-Bromo-3,4-dihydro-5-oxa-1,2a-diazaacenaphthylen-2-yl)benzo[d]oxazol-2-amine

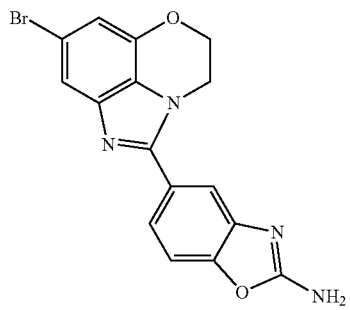 [SMILES: Nc1nc2cc(-c3nc4cc(Br)cc5c4n3CCO5)ccc2o1]

A mixture of 7-bromo-2-iodo-3,4-dihydro-5-oxa-1,2a-diazaacenaphthylene (200 mg, 0.55 mmol), 5-(4,4,5,5-tetramethyl-[1,3,2]dioxaborolan-2-yl)-benzooxazol-2-ylamine (214 mg, 0.83 mmol), cesium carbonate (303 mg, 0.93 mmol) and tetrakis(triphenylphosphine)palladium(0) (63 mg, 0.05 mmol) in 1,4-dioxane (5.0 mL) and water (0.5 mL) was degassed with argon. The reaction mixture was heated at 100° C. for 16 h. The reaction mixture was diluted with water and extracted with ethyl acetate. The organic extracts were washed with brine, dried over magnesium sulfate and evaporated in vacuo. The resultant residue was purified via flash chromatography on silica gel (solvent gradient: 0-100% ethyl acetate in cyclohexane) to yield 80 mg (40%) of the title compound as a beige solid. LCMS (ESI): [M+H]$^+$=371/373.

Step 6: (S)-2-((2-(2-Aminobenzo[d]oxazol-5-yl)-3,4-dihydro-5-oxa-1,2a-diazaacenaphthylen-7-yl)amino)-2-cyclopropylacetic acid

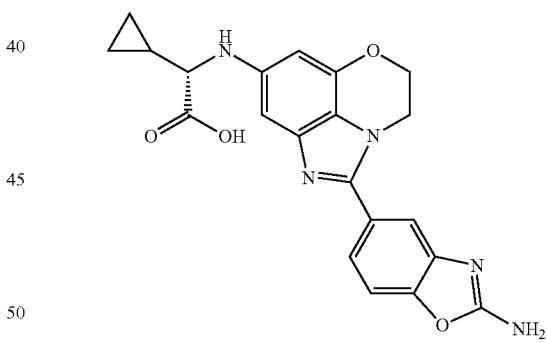

A mixture of 5-(7-bromo-3,4-dihydro-5-oxa-1,2a-diazaacenaphthylen-2-yl)benzo[d]oxazol-2-amine (80 mg, 0.22 mmol), (S)-aminocyclopropylacetic acid (50 mg, 0.43 mmol), copper (I) iodide (8 mg, 0.04 mmol) and potassium phosphate tribasic (91 mg, 0.43 mmol) was dissolved in DMSO (1.2 mL) and the mixture degassed with argon. The reaction mixture was heated at 100° C. for 16 h. The reaction mixture was purified via flash chromatography on silica gel (solvent gradient: 0-50% 2 N ammonia methanol in DCM) to yield 63 mg (72%) of the title compound as a brown solid. LCMS (ESI): [M+H]$^+$=406.

Step 7

To a solution of (S)-2-((2-(2-aminobenzo[d]oxazol-5-yl)-3,4-dihydro-5-oxa-1,2a-diazaacenaphthylen-7-yl)amino)-2- cyclopropylacetic acid (63 mg, 0.16 mmol), ammonium chloride (17 mg, 0.31 mmol) and triethylamine (65 μL, 0.47 mmol) in DMF (2.0 mL) was added HATU (89 mg, 0.23 mmol) and the reaction stirred at room temperature for 1.5 h. The reaction mixture was purified on silica (solvent gradient: 0-15% ammonia methanol in DCM) then purified by via reverse-phase HPLC to yield 16 mg (25%) of 208 as a white solid. LCMS (ESI): $R_T$ (min)=2.28, [M+H]$^+$=405, method=A; $^1$H NMR (400 MHz, DMSO-d$_6$) δ 7.68 (d, J=1.6 Hz, 1H), 7.56 (br, s, 2H), 7.53 (dd, J=8.4, 1.6 Hz, 1H), 7.46 (d, J=8.4 Hz, 1H), 7.35 (d, J=2.1 Hz, 1H), 6.97 (d, J=2.1 Hz, 1H), 6.28 (d, J=1.6 Hz, 1H), 6.23 (d, J=1.6 Hz, 1H), 5.49 (d, J=7.3 Hz, 1H), 4.59-4.49 (m, 2H), 4.44-4.36 (m, 2H), 3.13 (t, J=7.8 Hz, 1H), 1.17-1.05 (m, 1H), 0.56-0.44 (m, 3H), 0.36-0.27 (m, 1H).

Example 209 (S)-2-((1-(2-Amino-7-chlorobenzo[d]oxazol-5-yl)-8,9-dihydro-7H-6-oxa-2,9a-diazabenzo[cd]azulen-4-yl)amino)-2-cyclopropylacetamide 209

Step 1: 5-(4-Bromo-8,9-dihydro-7H-6-oxa-2,9a-diazabenzo[cd]azulen-1-yl)-7-chlorobenzo[d]oxazol-2-amine

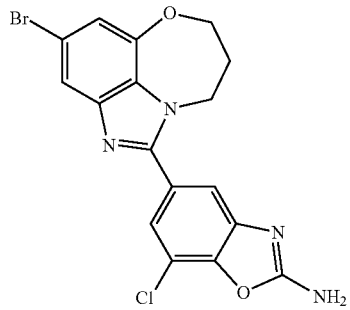 [SMILES: Nc1nc2cc(-c3nc4cc(Br)cc5c4n3CCCO5)cc(Cl)c2o1]

The title compound (180 mg, 28% yield) was generated from 5-bromo-7-chlorobenzo[d]oxazol-2-amine (370 mg, 1.50 mmol) following a procedure analogous to Example 205, step 1. LCMS (ESI): [M+H]$^+$=418/420.

Step 2: (S)-2-((1-(2-Amino-7-chlorobenzo[d]oxazol-5-yl)-8,9-dihydro-7H-6-oxa-2,9a-diazabenzo[cd]azulen-4-yl)amino)-2-cyclopropylacetic acid

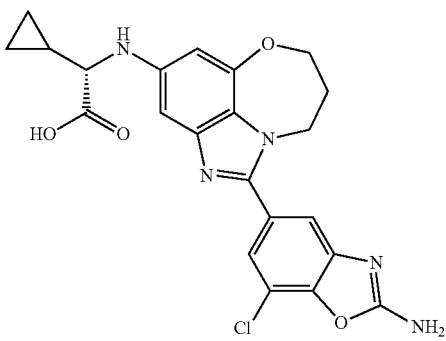 [SMILES: Nc1nc2cc(-c3nc4cc(N[C@H](C(=O)O)C5CC5)cc5c4n3CCCO5)cc(Cl)c2o1]

The title compound (72.9 mg, 37% yield) was generated 5-(4-bromo-8,9-dihydro-7H-6-oxa-2,9a-diazabenzo[cd]azulen-1-yl)-7-chlorobenzo[d]oxazol-2-amine (180 mg, 0.428 mmol) and (S)-2-amino-2-cyclopropylacetic acid (98.6 mg, 0.856 mmol) following a procedure analogous to Example 125, step 3. LCMS (ESI): [M+H]$^+$=454.

Step 3

209 (4.1 mg, 6% yield) was generated from (S)-2-((1-(2-amino-7-chlorobenzo[d]oxazol-5-yl)-8,9-dihydro-7H-6-oxa-2,9a-diazabenzo[cd]azulen-4-yl)amino)-2-cyclopropylacetic acid (72.9 mg, 0.161 mmol) following a procedure analogous to Example 125, step 4. LCMS (ESI): $R_T$ (min)=2.62, [M+H]$^+$=453, method=A; $^1$H NMR (400 MHz, DMSO-d$_6$) δ 7.88 (br s, 2H), 7.45 (d, J=1.4 Hz, 1H), 7.40 (d, J=1.4 Hz, 1H), 7.33 (d, J=2.0 Hz, 1H), 6.96 (d, J=2.0 Hz, 1H), 6.36 (d, J=2.0 Hz, 1H), 6.25 (d, J=2.0 Hz, 1H), 5.47 (d, J=6.0 Hz, 1H), 4.32-4.17 (m, 4H), 3.14 (t, J=6.0 Hz, 1H), 2.27-2.22 (m, 2H), 1.15-1.06 (m, 1H), 0.54-0.43 (m, 3H), 0.33-0.27 (m, 1H).

Example 210 (S)-2-Cyclopropyl-2-((1-(1-(oxetan-3-yl)-1H-pyrazol-4-yl)-8,9-dihydro-7H-6-oxa-2,9a-diazabenzo[cd]azulen-4-yl)amino)acetamide 210

Step 1: 4-Bromo-1-(1H-pyrazol-4-yl)-8,9-dihydro-7H-6-oxa-2,9a-diazabenzo[cd]azulene

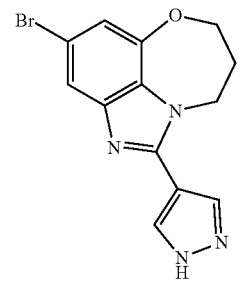 [SMILES: Brc1cc2c3c(c1)nc(-c1cn[nH]c1)n3CCCO2]

The title compound (490 mg, 42% yield) was prepared from 8-bromo-2,3,4,5-tetrahydrobenzo[b][1,4]oxazepin-6-amine (900 mg, 3.70 mmol) and pyrazole-1,4-dicarboxylic acid 1-tert-butyl ester (865 mg, 4.07 mmol) following a procedure analogous to Example 160, steps 1 and 2. LCMS (ESI): [M+H]$^+$=319/321.

Step 2: 4-Bromo-1-(1-(oxetan-3-yl)-1H-pyrazol-4-yl)-8,9-dihydro-7H-6-oxa-2,9a-diazabenzo[cd]azulene

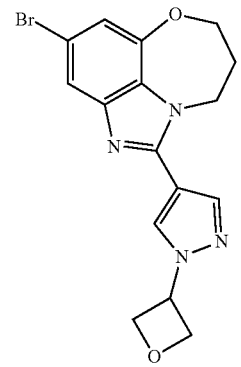 [SMILES: Brc1cc2c3c(c1)nc(-c1cnn(C4COC4)c1)n3CCCO2]

To a solution of 4-bromo-1-(1H-pyrazol-4-yl)-8,9-dihydro-7H-6-oxa-2,9a-diazabenzo[cd]azulene (270 mg, 0.85 mmol) in DMF (11 mL) was added cesium carbonate (414 mg, 1.27 mmol) then 3-bromooxetane (105 μL, 1.27 mmol) and the reaction mixture was stirred at 90° C. for 3 h. The resultant mixture was allowed to cool to room temperature and filtered. The solid was collected, washed with water and dried to yield 190 mg (60%) of the title compound. LCMS (ESI): [M+H]$^+$=375/377.

Step 3

4-Bromo-1-(1-(oxetan-3-yl)-1H-pyrazol-4-yl)-8,9-dihydro-7H-6-oxa-2,9a-diazabenzo[cd]azulene (190 mg, 0.51 mmol), (S)-aminocyclopropylacetic acid (152 mg, 1.28 mmol), copper (I) iodide (21 mg, 0.10 mmol) and potassium triphosphate tribasic (435 mg, 2.04 mmol) were suspended in DMSO (2.0 mL) and degassed with nitrogen. The reaction mixture was heated at 100° C. for 16 h and was then allowed to cool to room temperature. To this mixture was added ammonium chloride (172 mg, 3.06 mmol), triethylamine (0.761 mL, 5.1 mmol) and then HATU (1.2 g, 3.06 mmol) portionwise. The reaction mixture was stirred at room temperature for 1 h. The resultant mixture was purified via flash chromatography on silica gel (solvent gradient, 0-30% 2 N ammonia in methanol, in DCM) and then further purified on HPLC (solvent gradient: 10-40% acetonitrile in water with 0.1% formic acid) to yield 70 mg (34%) of 210. LCMS (ESI): R$_T$ (min)=2.26, [M+H]$^+$=409, method=A; $^1$H NMR (400 MHz, DMSO-d$_6$) δ 8.48 (s, 1H), 8.12 (s, 1H), 7.32 (br s, 1H), 6.95 (br s, 1H), 6.32 (d, J=1.9 Hz, 1H), 6.17 (d, J=1.9 Hz, 1H), 5.67 (quint, J=6.4 Hz, 1H), 5.42 (br s, 1H), 4.96 (d, J=7.0 Hz, 4H), 4.34-4.28 (m, 4H), 3.13-3.08 (m, 1H), 2.33-2.27 (m, 2H), 1.15-1.05 (m, 1H), 0.53-0.45 (m, 3H), 0.32-0.26 (m, 1H).

Example 211 (S)-2-Cyclopropyl-2-((1-(1-(2-hydroxyethyl)-1H-pyrazol-4-yl)-8,9-dihydro-7H-6-oxa-2,9a-diazabenzo[cd]azulen-4-yl)amino)acetamide 211

Step 1: 4-Bromo-1-(1-(2-((tetrahydro-2H-pyran-2-yl)oxy)ethyl)-1H-pyrazol-4-yl)-8,9-dihydro-7H-6-oxa-2,9a-diazabenzo[cd]azulene

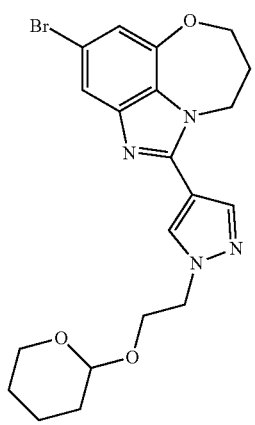 [SMILES: Brc1cc2c3c(c1)nc(-c1cnn(CCOC4CCCCO4)c1)n3CCCO2]

The title compound (350 mg, 100%) was prepared from 4-bromo-1-(1H-pyrazol-4-yl)-8,9-dihydro-7H-6-oxa-2,9a-diazabenzo[cd]azulene (250 mg, 0.78 mmol) and 2-(2-bromo-ethoxy)-tetrahydropyran (177 μL, 1.17 mmol) following a procedure analogous to Example 210, Step 2. LCMS (ESI): [M+H]$^+$=447/449.

Step 2: (2S)-2-Cyclopropyl-2-((1-(1-(2-((tetrahydro-2H-pyran-2-yl)oxy)ethyl)-1H-pyrazol-4-yl)-8,9-dihydro-7H-6-oxa-2,9a-diazabenzo[cd]azulen-4-yl)amino)acetamide

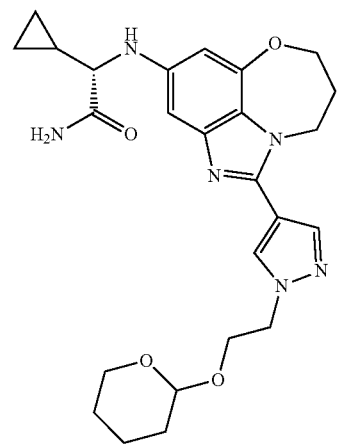 [SMILES: NC(=O)[C@@H](Nc1cc2c3c(c1)nc(-c1cnn(CCOC4CCCCO4)c1)n3CCCO2)C1CC1]

The title compound (380 mg, 100%) was prepared from 4-bromo-1-(1-(2-((tetrahydro-2H-pyran-2-yl)oxy)ethyl)-1H-pyrazol-4-yl)-8,9-dihydro-7H-6-oxa-2,9a-diazabenzo[cd]azulene (350 mg, 0.78 mmol) following a procedure analogous to Example 210, Step 3. LCMS (ESI): [M+H]$^+$=482.

Step 3: (S)-2-Cyclopropyl-2-((1-(1-(2-hydroxyethyl)-1H-pyrazol-4-yl)-8,9-dihydro-7H-6-oxa-2,9a-diazabenzo[cd]azulen-4-yl)amino)acetamide To a solution of (2S)-2-cyclopropyl-2-((1-(1-(2-((tetrahydro-2H-pyran-2-yl)oxy)ethyl)-1H-pyrazol-4-yl)-8,9-dihydro-7H-6-oxa-2,9a-diazabenzo[cd]azulen-4-yl)amino)acetamide (376 mg, 0.78 mmol) in DCM (8.0 mL) was added trifluoroacetic acid (2 mL) dropwise and the reaction mixture was stirred at room temperature for 30 min. The resultant mixture was poured onto a 10 g SCX-2 cartridge. The cartridge was washed with acetonitrile, then methanol and then eluted with 2 N ammonia in methanol. The eluent was collected and the solvent was evaporated. The residue was purified via reverse-phase HPLC to yield 34 mg (11%) of 211. LCMS (ESI): R$_T$ (min)=2.14, [M+H]$^+$=397, method=A; $^1$H NMR (400 MHz, DMSO-d$_6$) δ 8.30 (s, 1H), 7.97 (s, 1H), 7.32 (br s, 1H), 6.94 (br s, 1H), 6.31 (d, J=1.9 Hz, 1H), 6.16 (d, J=1.9 Hz, 1H), 5.42 (br s, 1H), 4.95 (t, J=5.0 Hz, 1H), 4.34-4.27 (m, 4H), 4.23 (t, J=5.3 Hz, 2H), 3.79 (q, J=5.3 Hz, 2H), 3.11 (d, J=7.6 Hz, 1H), 2.33-2.27 (m, 2H), 1.15-1.05 (m, 1H), 0.54-0.43 (m, 3H), 0.32-0.26 (m, 1H).

Example 212 (S)-2-((1-(1H-Pyrazol-4-yl)-8,9-dihydro-7H-6-oxa-2,9a-diazabenzo[cd]azulen-4-yl)amino)-2-cyclopropylacetamide 212

Step 1: 4-Bromo-1-(1-(tetrahydro-2H-pyran-2-yl)-1H-pyrazol-4-yl)-8,9-dihydro-7H-6-oxa-2,9a-diazabenzo[cd]azulene

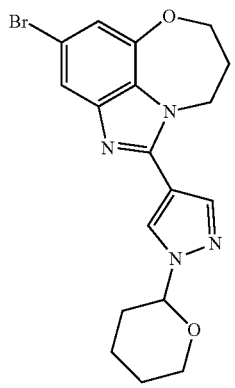 [SMILES: Brc1cc2c3c(c1)nc(-c1cnn(C4CCCCO4)c1)n3CCCO2]

To a suspension of 4-bromo-1-(1H-pyrazol-4-yl)-8,9-dihydro-7H-6-oxa-2,9a-diazabenzo[cd]azulene (250 mg, 0.78 mmol) in toluene (5.0 mL) was added trifluoroacetic acid (10 μL) followed by dihydropyran (107 μL, 1.18 mmol) and the mixture stirred at 80° C. for 16 h. The reaction mixture was allowed to cool to room temperature and the solvent was removed under reduced pressure. The residue was partitioned between ethyl acetate and saturated aqueous sodium hydrogen carbonate and the aqueous layer was further extracted with ethyl acetate. The combined organic extracts were washed with brine, dried over sodium sulfate and the solvent evaporated to yield 310 mg (98%) of the title compound. LCMS (ESI): [M+H]⁺=403/405.

Step 2: (2S)-2-Cyclopropyl-2-((1-(1-(tetrahydro-2H-pyran-2-yl)-1H-pyrazol-4-yl)-8,9-dihydro-7H-6-oxa-2,9a-diazabenzo[cd]azulen-4-yl)amino)acetamide

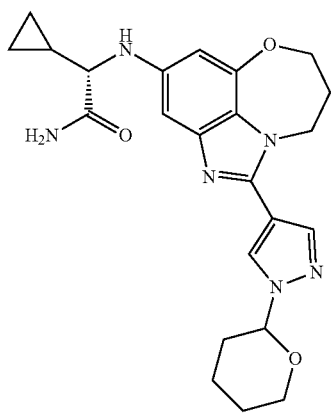 [SMILES: NC(=O)[C@@H](Nc1cc2c3c(c1)nc(-c1cnn(C4CCCCO4)c1)n3CCCO2)C1CC1]

The title compound (320 mg, 100% yield) was prepared from 4-bromo-1-(1-(tetrahydro-2H-pyran-2-yl)-1H-pyrazol-4-yl)-8,9-dihydro-7H-6-oxa-2,9a-diazabenzo[cd]azulene (300 mg, 0.74 mmol) following a procedure analogous to Example 210, Step 3. LCMS (ESI): [M+H]⁺=438.

Step 3

212 (70 mg, 27% yield) was prepared from (2S)-2-cyclopropyl-2-((1-(1-(tetrahydro-2H-pyran-2-yl)-1H-pyrazol-4-yl)-8,9-dihydro-7H-6-oxa-2,9a-diazabenzo[cd]azulen-4-yl)amino)acetamide (320 mg, 0.74 mmol) following a procedure analogous to Example 211, Step 3. LCMS (ESI): $R_T$ (min)=2.16, [M+H]⁺=353, method=A; ¹H NMR (400 MHz, DMSO-d₆) δ 13.3 (br s, 1H), 8.27 (br s, 1H), 8.07 (br s, 1H), 7.32 (s, 1H), 6.95 (s, 1H), 6.32 (d, J=1.9 Hz, 1H), 6.17 (d, J=1.9 Hz, 1H), 5.45 (br s, 1H), 4.35-4.27 (m, 4H), 3.11 (d, J=7.6 Hz, 1H), 2.34-2.25 (m, 2H), 1.15-1.05 (m, 1H), 0.54-0.43 (m, 3H), 0.32-0.26 (m, 1H).

Example 213 (S)-2-Cyclopropyl-2-((1-(6-methoxypyridin-3-yl)-1,7,8,9-tetrahydrooxepino[4,3,2-cd]indazol-4-yl)amino)acetamide 213

Step 1: Methyl 4-(3-bromo-5-fluorophenoxy)butanoate

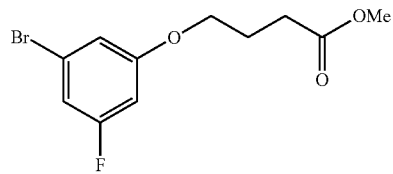 [SMILES: COC(=O)CCCOc1cc(F)cc(Br)c1]

To a solution of 3-bromo-5-fluoro-phenol (5.24 mmol, 1.0 g) in acetone (20 mL) was added potassium iodide (0.26 mmol, 43 mg), potassium carbonate (5.76 mmol, 800 mg) and methyl 4-bromobutanoate (5.76 mmol, 0.73 mL). The reaction was heated at reflux overnight. The mixture was partitioned between ethyl acetate and water and the phases were separated. The aqueous layer was extracted with ethyl acetate, the organic extracts were combined, washed with brine, dried over sodium sulfate and the solvent was evaporated. The residue was purified by silica gel chromatography (solvent gradient: 0-30% ethyl acetate in heptanes) to afford 1370 mg (90%) of the title compound.

Step 2: 4-(3-Bromo-5-fluorophenoxy)butanoic acid

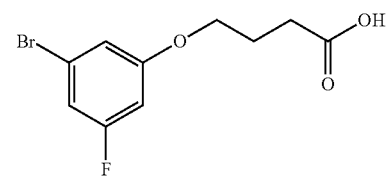 [SMILES: O=C(O)CCCOc1cc(F)cc(Br)c1]

To a solution of methyl 4-(3-bromo-5-fluoro-phenoxy)butanoate (4.71 mmol, 1370 mg) in methanol (10 mL) and water (1 mL) was added lithium hydroxide (9.41 mmol, 225 mg), and the reaction mixture was heated at 60° C. overnight. After overnight, methanol was removed in vacuo. The mixture was partitioned between DCM and water and the phases were separated. The aqueous layer was extracted with DCM, the organic extracts were combined, washed with brine, dried over sodium sulfate and the solvent was evaporated to provide the title compound (1300 mg, 99% yield) which was directed used in the next step.

Step 3: 8-Bromo-6-fluoro-3,4-dihydrobenzo[b]ox-epin-5(2H)-one and 6-Bromo-8-fluoro-3,4-dihyd-robenzo[b]oxepin-5(2H)-one

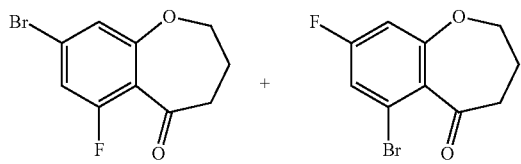 [SMILES: O=C1CCCOc2cc(Br)cc(F)c21 ; O=C1CCCOc2cc(F)cc(Br)c21]

To a solution of 4-(3-bromo-5-fluoro-phenoxy)butanoic acid (1.80 mmol, 500 mg) in DCM (10 mL) was added thionyl chloride (3.61 mmol, 0.263 mL) dropwise. The reaction was stirred at 50° C. for 4 hours. After 4 hours, the solvent was removed. To the resulting residue was added DCM (10 mL), and then aluminium chloride (2.71 mmol, 361 mg) at 0° C.

The reaction mixture was stirred overnight at room temperature and then carefully quenched with water. The mixture was partitioned between DCM and water and the phases were separated. The aqueous layer was extracted with DCM, the organic extracts were combined, washed with brine, dried over sodium sulfate and the solvent was evaporated. The residue was purified by silica gel chromatography (solvent gradient: 0-30% ethyl acetate in heptanes) to afford the title compounds (220 mg, 47% combined yield) as a 1:1 mixture of the two regioisomers. LCMS (ESI): [M+H]$^+$= 259/261.

Step 4: 4-Bromo-1-(6-methoxypyridin-3-yl)-1,7,8,9-tetrahydrooxepino[4,3,2-cd]indazole

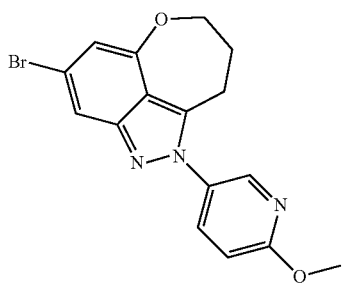 [SMILES: COc1ccc(-n2nc3cc(Br)cc4c3c2CCCO4)cn1]

To a solution of a mixture of 8-bromo-6-fluoro-3,4-dihydro-2H-1-benzoxepin-5-one (0.386 mmol, 100 mg) and 6-bromo-8-fluoro-3,4-dihydro-2H-1-benzoxepin-5-one (100 mg) in pyridine (5 mL) was added (6-methoxy-3-pyridyl)hydrazine dihydrochloride (0.772 mmol, 164 mg). The reaction mixture was heated at 60° C. The mixture was partitioned between DCM and water and the phases were separated. The aqueous layer was extracted with DCM, the organic extracts were combined, washed with brine, dried over sodium sulfate and the solvent was evaporated. The residue was purified by silica gel chromatography (solvent gradient: 0-80% (isopropylacetate/methanol (3:1) in heptanes) to afford 8-bromo-6-[2-(6-methoxy-3-pyridyl)hydrazino]-3,4-dihydro-2H-1-benzoxepin-5-one (100 mg). To this residue was added methanol (1 mL), then zinc (0.529 mmol, 35 mg) and ammonium chloride (0.793 mmol, 42 mg). The reaction mixture was stirred at room temperature for 20 min. The resulting slurry was diluted with water and filtered. The filter liquor was then extracted with DCM and dried over magnesium sulfate. Then the solvent was evaporated under reduced pressure. The residue was purified by silica gel chromatography (solvent gradient: 0-40% (isopropylacetate/methanol (3:1) in heptanes) to afford the desired product (60 mg). LCMS (ESI): [M+H]$^+$=360.

Step 5

(S)-2-Cyclopropyl-2-((1-(6-methoxypyridin-3-yl)-1,7,8,9-tetrahydrooxepino[4,3,2-cd]indazol-4-yl)amino)acetic acid was generated from 4-bromo-1-(6-methoxypyridin-3-yl)-1,7,8,9-tetrahydrooxepino[4,3,2-cd]indazole (45 mg, 0.125 mmol) and (S)-2-amino-2-cyclopropylacetic acid following a procedure analogous to Example 125, step 3. LCMS (ESI): [M+H]+=395. The crude was directly used in the next step and 213 (5.9 mg) was generated following a procedure analogous to Example 125, step 4. LCMS (ESI): R$_T$ (min)=4.17, [M+H]$^+$=394.1, method=B; $^1$H NMR (400 MHz, DMSO-d$_6$) δ 8.40 (dd, J=2.8, 0.7 Hz, 1H), 7.92 (dd, J=8.9, 2.8 Hz, 1H), 7.36 (d, J=2.3 Hz, 1H), 6.99 (d, J=0.6 Hz, 1H), 6.97 (d, J=0.6 Hz, 1H), 6.20 (d, J=1.6 Hz, 1H), 6.16 (d, J=7.0 Hz, 1H), 6.09 (d, J=1.6 Hz, 1H), 4.31-4.33 (m, 2H), 3.92 (s, 3H), 3.21-3.12 (m, 1H), 3.00 (t, J=6.2 Hz, 2H), 2.17-2.11 (m, 2H), 1.16-1.03 (m, 1H), 0.57-0.41 (m, 3H), 0.33-0.23 (m, 1H).

Example 214 (S)-2-((1-(2-Aminobenzo[d]thiazol-6-yl)-7,8,9,10-tetrahydro-6-oxa-2,10a-diazacycloocta[cd]inden-4-yl)amino)-2-cyclopropylacetamide 214

Step 1: tert-Butyl 6-bromobenzo[d]thiazol-2-ylcarbamate

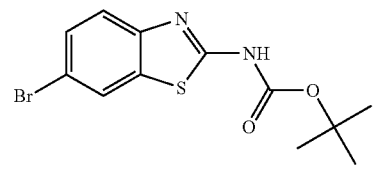 [SMILES: CC(C)(C)OC(=O)Nc1nc2ccc(Br)cc2s1]

A mixture of 6-bromobenzo[d]thiazol-2-amine (14.7 g, 64.2 mmol), di-tert-butyl dicarbonate (14.0 g, 64.1 mmol) and N,N-dimethylpyridin-4-amine (40.0 mg, 0.327 mmol) in DCM (200 mL) was stirred at room temperature for 24 h and then filtered. The filtrate was evaporated in vacuo. The resultant residue was purified via flash chromatography on silica gel (solvent gradient: 0-10% ethyl acetate in petroleum ether) to yield 7.26 g (34%) of the title compound as a yellow solid. LCMS (ESI): [M+H]$^+$=329/331.

Step 2: tert-Butyl 6-(4,4,5,5-tetramethyl-1,3,2-di-oxaborolan-2-yl)benzo[d]thiazol-2-ylcarbamate

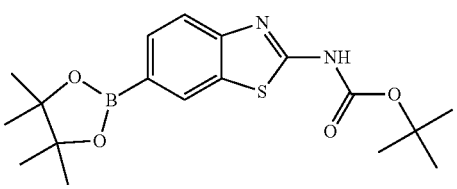 [SMILES: CC(C)(C)OC(=O)Nc1nc2ccc(B3OC(C)(C)C(C)(C)O3)cc2s1]

A mixture of tert-butyl 6-bromobenzo[d]thiazol-2-ylcarbamate (2.00 g, 6.07 mmol), 4,4,4',4',5,5,5',5'-octamethyl-2,2'-bi(1,3,2-dioxaborolane) (2.32 g, 9.12 mmol), 1,1'-bis(diphenylphosphino)ferrocenyl palladium (II) dichloride (444 mg, 0.607 mmol), and potassium acetate (1.78 g, 18.2 mmol) in 1,4-dioxane (60.0 mL) was degassed with argon. The reaction mixture was heated at 100° C. for 16 h. The reaction mixture was filtered and the filtrate was evaporated in vacuo. The resultant residue was purified via flash chromatography on silica gel (solvent gradient: 0-10% ethyl acetate in petroleum ether) to yield 1.17 g (51%) of the title compound as a yellow solid. LCMS (ESI): [M+H]$^+$=377.

Step 3: tert-Butyl (6-(4-bromo-7,8,9,10-tetrahydro-6-oxa-2,10a-diazacycloocta[cd]inden-1-yl)benzo[d]thiazol-2-yl)carbamate

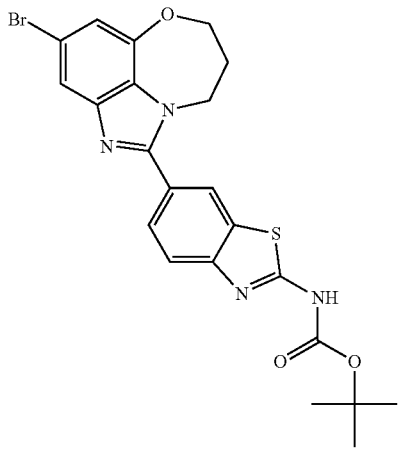 [SMILES: CC(C)(C)OC(=O)Nc1nc2ccc(-c3nc4cc(Br)cc5c4n3CCCO5)cc2s1]

The title compound (768 mg, 48% yield) was generated from tert-butyl 6-(4,4,5,5-tetramethyl-1,3,2-dioxaborolan-2-yl)benzo[d]thiazol-2-ylcarbamate (1.17 g, 3.12 mmol) and 4-bromo-1-iodo-7,8,9,10-tetrahydro-6-oxa-2,10a-diazacycloocta[cd]indene (Example 204, step 6) (1.47 g, 3.75 mmol) following a procedure analogous to Example 204, step 8. LCMS (ESI): [M+H]$^+$=515/517.

Step 4: (S)-tert-Butyl (6-(4-((2-amino-1-cyclopropyl-2-oxoethyl) amino)-7,8,9,10-tetrahydro-6-oxa-2,10a-diazacycloocta[cd]inden-1-yl)benzo[d]thiazol-2-yl)carbamate

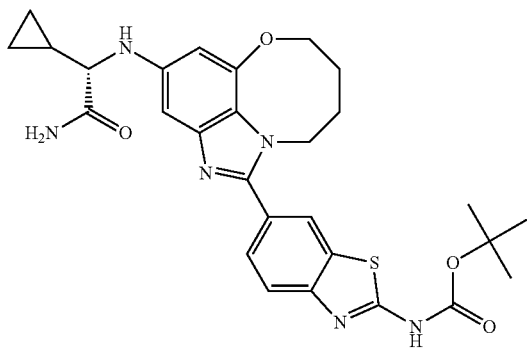 [SMILES: CC(C)(C)OC(=O)Nc1nc2ccc(-c3nc4cc(N[C@H](C(N)=O)C5CC5)cc5c4n3CCCCO5)cc2s1]

The title compound (380 mg, crude) was generated from tert-butyl (6-(4-bromo-7,8,9,10-tetrahydro-6-oxa-2,10a-diazacycloocta[cd]inden-1-yl)benzo[d]thiazol-2-yl)carbamate (380 mg, 0.737 mmol) and (S)-2-amino-2-cyclopropylacetic acid (420 mg, 3.64 mmol) following a procedure analogous to Example 104, steps 1-2. LCMS (ESI): [M+H]$^+$=549.

Step 5

To a solution of (S)-tert-butyl (6-(4-((2-amino-1-cyclopropyl-2-oxoethyl)amino)-7,8,9,10-tetrahydro-6-oxa-2,10a-diazacycloocta[cd]inden-1-yl)benzo[d]thiazol-2-yl)carbamate (380 mg crude) in DCM (5 mL) was added TFA (10 mL) at room temperature. The reaction mixture was stirred for 30 min at room temperature. The pH value of the reaction mixture was adjusted to 7 with sodium bicarbonate (1 mol/L aqueous) and then extracted with DCM. The organic portion was washed with brine, dried over anhydrous sodium sulfate and evaporated in vacuo. The resultant residue was purified via flash chromatography on silica gel (solvent gradient: 0-50% methanol in DCM) then purified via reverse-phase HPLC and lyophilized to yield 42.5 mg (14%) of 214 as a white solid. LCMS (ESI): R$_T$ (min)=1.22, [M+H]$^+$=449, method=E; $^1$H NMR (300 MHz, DMSO-d$_6$) δ 7.96 (d, J=1.2 Hz, 1H), 7.70 (s, 2H), 7.60-7.45 (m, 3H), 7.00 (s, 1H), 6.43 (d, J=1.8 Hz, 1H), 6.37 (d, J=1.8 Hz, 1H), 5.58 (d, J=7.2 Hz, 1H), 4.38-4.28 (m, 2H), 4.23-4.15 (m, 2H), 3.17-3.07 (m, 1H), 2.14-2.08 (m, 2H), 1.71-1.65 (m, 2H), 1.17-1.05 (m, 1H), 0.55-0.42 (m, 3H), 0.37-0.27 (m, 1H).

Example 215 (S)-2-Cyclopropyl-2-((1-(8-fluoroquinoxalin-6-yl)-8,9-dihydro-7H-6-oxa-2,9a-diazabenzo[cd]azulen-4-yl)amino)acetamide 215

Following the procedures of Example 158, 215 were prepared. LCMS: R$_T$ (min)=4.50, [M+H]$^+$=433, method=D; $^1$H NMR (300 MHz, DMSO-d$_6$) δ 9.10 (m, 2H), 8.33 (m, 1H), 8.14 (m, 1H), 7.37 (d, J=2.7 Hz, 1H), 6.99 (d, J=2.3 Hz, 1H), 6.41 (d, J=1.9 Hz, 1H), 6.32 (d, J=2.0 Hz, 1H), 5.59 (d, J=7.3 Hz, 1H), 4.48-4.32 (m, 4H), 3.20-3.05 (m, 1H), 2.40-2.15 (m, 2H), 1.20-1.00 (m, 1H), 0.60-0.40 (m, 3H), 0.35-0.20 (m, 1H).

Examples 216 and 217 (R)-2-(4-(1-(2-Aminobenzo[d]oxazol-5-yl)-8,9-dihydro-7H-6-oxa-2,9a-diazabenzo[cd]azulen-4-yl)-1H-pyrazol-1-yl)butanamide 216 and (S)-2-(4-(1-(2-Aminobenzo[d]oxazol-5-yl)-8,9-dihydro-7H-6-oxa-2,9a-diazabenzo[cd]azulen-4-yl)-1H-pyrazol-1-yl)butanamide 217

216 and 217 were prepared each as a single unknown isomer following procedures analogous to those of Examples 230 and 231.

216 (31.0 mg): LCMS (ESI): R$_T$ (min)=2.53, [M+H]$^+$=458, method=A; $^1$H NMR (400 MHz, DMSO-d$_6$) δ 8.24 (s, 1H), 7.91 (s, 1H), 7.58 (br s, 3H), 7.53 (br s, 1H), 7.51 (d, J=1.5 Hz, 1H), 7.50 (d, J=8.1 Hz, 1H), 7.40 (dd, J=8.1, 1.5 Hz, 1H), 7.27 (br s, 1H), 7.04 (d, J=1.5 Hz, 1H), 4.75 (t, J=7.8 Hz, 1H), 4.44-4.40 (m, 2H), 4.30 (t, J=5.2 Hz, 2H), 2.35-2.29 (m, 2H), 2.08 (apparent quintet, J=7.3 Hz, 2H), 0.85 (t, J=7.8 Hz, 3H).

217 (34.6 mg): LCMS (ESI): R$_T$ (min)=2.53, [M+H]$^+$=458, method=A; $^1$H NMR (400 MHz, DMSO-d$_6$) δ 8.24 (s, 1H), 7.91 (s, 1H), 7.58 (br s, 3H), 7.53 (br s, 1H), 7.51 (d, J=1.5 Hz, 1H), 7.50 (d, J=8.1 Hz, 1H), 7.40 (dd, J=8.1, 1.5 Hz, 1H), 7.27 (br s, 1H), 7.04 (d, J=1.5 Hz, 1H), 4.75 (t, J=7.8 Hz, 1H), 4.44-4.40 (m, 2H), 4.30 (t, J=5.2 Hz, 2H), 2.35-2.29 (m, 2H), 2.08 (apparent quintet, J=7.3 Hz, 2H), 0.85 (t, J=7.8 Hz, 3H).

Example 218 and 219 (R)-2-(4-(1-(2-Aminobenzo[d]oxazol-5-yl)-8,9-dihydro-7H-6-oxa-2,9a-diazabenzo[cd]azulen-4-yl)-1H-pyrazol-1-yl)propanamide 218 and (S)-2-(4-(1-(2-Aminobenzo[d]oxazol-5-yl)-8,9-dihydro-7H-6-oxa-2,9a-diazabenzo[cd]azulen-4-yl)-1H-pyrazol-1-yl)propanamide 219

The title compounds were prepared each as a single unknown isomer following procedures analogous to those of Examples 230 and 231.

218 (45.2 mg): LCMS (ESI): $R_T$ (min)=2.35, [M+H]$^+$=444, method=A; $^1$H NMR (400 MHz, DMSO-d$_6$) δ 8.24 (s, 1H), 7.91 (s, 1H), 7.58 (br s, 3H), 7.52 (d, J=1.5 Hz, 1H), 7.50 (d, J=8.1 Hz, 1H), 7.46 (br s, 1H), 7.39 (dd, J=8.1, 1.5 Hz, 1H), 7.24 (br s, 1H), 7.05 (d, J=1.5 Hz, 1H), 4.96 (q, J=7.4 Hz, 1H), 4.44-4.40 (m, 2H), 4.30 (t, J=5.2 Hz, 2H), 2.35-2.29 (m, 2H), 1.65 (d, J=7.4 Hz, 3H).

219 (42.5 mg): LCMS (ESI): $R_T$ (min)=2.35, [M+H]$^+$=444, method=A; $^1$H NMR (400 MHz, DMSO-d$_6$) δ 8.24 (s, 1H), 7.91 (s, 1H), 7.58 (br s, 3H), 7.52 (d, J=1.5 Hz, 1H), 7.50 (d, J=8.1 Hz, 1H), 7.46 (br s, 1H), 7.39 (dd, J=8.1, 1.5 Hz, 1H), 7.24 (br s, 1H), 7.05 (d, J=1.5 Hz, 1H), 4.96 (q, J=7.4 Hz, 1H), 4.44-4.40 (m, 2H), 4.30 (t, J=5.2 Hz, 2H), 2.35-2.29 (m, 2H), 1.65 (d, J=7.4 Hz, 3H).

Example 220 (S)-1-(1-(2-Oxo-3,4-dihydro-2H-benzo[4,5]oxazolo[3,2-a]pyrimidin-7-yl)-8,9-dihydro-7H-6-oxa-2,9a-diazabenzo[cd]azulen-4-yl)pyrrolidine-2-carboxamide 220

A mixture of (S)-1-(1-(2-aminobenzo[d]oxazol-5-yl)-8,9-dihydro-7H-6-oxa-2,9a-diazabenzo[cd]azulen-4-yl)pyrrolidine-2-carboxamide from Example 104 (150 mg, 0.358 mmol), 3-bromopropanoic acid (83.4 mg, 0.545 mmol), HATU (307 mg, 0.808 mmol) and DIPEA (0.400 mL) in DMF (12.0 mL) was heated at 60° C. for 6 h. This reaction was repeated separately at the same scale. The two reaction mixtures were combined, diluted with water, extracted with DCM, washed with brine, dried over anhydrous sodium sulfate and evaporated in vacuo. The resultant residue was purified via flash chromatography on silica gel (solvent gradient: 0-13% methanol in DCM) to yield the crude product. The crude product was triturated with DMF and DMSO. The solid was collected to yield 58.9 mg (35%) of 220 as an off-white solid. LCMS (ESI): $R_T$ (min)=2.34 min, [M+H]$^+$: 473, method=C; $^1$H NMR (300 MHz, DMSO-d$_6$): δ 7.86 (s, 1H), 7.73 (d, J=8.4 Hz, 1H), 7.65 (d, J=8.4 Hz, 1H), 7.32 (s, 1H), 7.03 (s, 1H), 6.35 (d, J=1.5 Hz, 1H), 6.10 (d, J=1.2 Hz, 1H), 4.37-4.23 (m, 6H), 3.86-3.83 (m, 1H), 3.60-3.58 (m, 1H), 3.20-3.10 (m, 1H), 2.76-2.70 (m, 2H), 2.28-2.19 (m, 3H), 2.08-1.97 (m, 3H).

Example 221 (S)-1-(1-(4-(1H-1,2,4-Triazol-3-yl)phenyl)-8,9-dihydro-7H-6-oxa-2,9a-diazabenzo[cd]azulen-4-yl)pyrrolidine-2-carboxamide 221

221 was prepared using commercially available 3-(4-bromophenyl)-1H-1,2,4-triazole and following procedures analogous to those of Example 158. LCMS: $R_T$ (min)=3.00, [M+H]$^+$=430, method=C; $^1$H NMR (300 MHz, DMSO-d$_6$) δ 14.22 (s, 1H), 8.68 (s, 1H), 8.17 (d, J=8.1 Hz, 2H), 7.90 (d, J=7.8 Hz, 2H), 7.31 (d, J=2.3 Hz, 1H), 7.03 (s, 1H), 6.37 (d, J=2.1 Hz, 1H), 6.09 (d, J=2.1 Hz, 1H), 4.37-4.29 (m, 4H), 3.90-3.80 (m, 1H), 3.70-3.60 (m, 1H), 3.30-3.08 (m, 1H), 2.35-2.15 (m, 3H), 2.09-1.87 (m, 3H).

Example 222 (S)-1-(1-(3-Chloro-4-(1H-1,2,4-triazol-3-yl)phenyl)-8,9-dihydro-7H-6-oxa-2,9a-diazabenzo[cd]azulen-4-yl)pyrrolidine-2-carboxamide 222

Step 1: 4-Bromo-2-chlorobenzamide

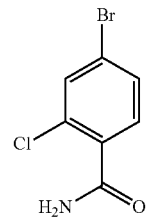 [SMILES: NC(=O)c1ccc(Br)cc1Cl]

To a solution of 4-bromo-2-chlorobenzoic acid (10.0 g, 42.5 mmol) in DCM (100 mL) at 0° C. was added oxalyl chloride (21.5 g, 0.169 mol) portionwise over 10 min, followed by the addition of DMF (1 mL). The reaction mixture was stirred at room temperature for 60 min after which the solvent was removed in vacuo. The residue was dissolved in THF (400 mL), then ammonium hydroxide (312 mL of a 25-28% aqueous solution) was added dropwise at 0° C. The reaction mixture was allowed to warm to room temperature and was stirred for a further 60 min. The THF was removed in vacuo and the residue was filtered. The solid was collected, washed with water and dried to yield 8.66 g (87%) of the title compound. LCMS (ESI): [M+H]$^+$=234/236.

Step 2: 3-(4-Bromo-2-chlorophenyl)-1-(4-methoxybenzyl)-1H-1,2,4-triazole

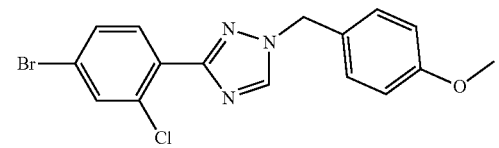 [SMILES: COc1ccc(Cn2cnc(-c3ccc(Br)cc3Cl)n2)cc1]

4-Bromo-2-chlorobenzamide (8.00 g, 34.1 mmol) was dissolved by N,N-dimethylformamide dimethyl acetal (50 mL). The resulting mixture was stirred at 130° C. for 120 min and then the solvent was removed in vacuo. The residue was dissolved in acetic acid (100 mL), then (4-methoxybenzyl)hydrazine (7.10 g, 0.046 mol) was added. The reaction mixture was stirred at 100° C. for 60 min. The solvent was removed in vacuo. The residue was purified via flash chromatography on silica gel (solvent gradient: 50% ethyl acetate in petroleum ether) to yield 3.5 g (27%) of the title compound as yellow oil. LCMS (ESI): [M+H]$^+$=378/380.

Step 3: 3-(2-Chloro-4-(4,4,5,5-tetramethyl-1,3,2-dioxaborolan-2-yl)phenyl)-1-(4-methoxybenzyl)-1H-1,2,4-triazole

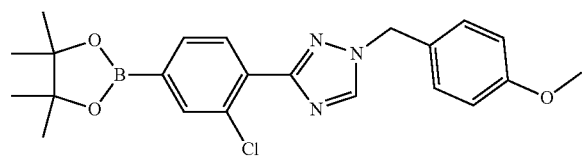

The title compound (2.2 g, 98% yield) was generated from 3-(4-bromo-2-chlorophenyl)-1-(4-methoxybenzyl)-1H-1,2,4-triazole (2.00 g, 5.28 mmol) and 4,4,4',4',5,5,5',5'-octamethyl-2,2'-bi(1,3,2-dioxaborolane) (1.6 g, 6.30 mmol) following a procedure analogous to Example 158, step 2. LCMS (ESI): [M+H]⁺=426.

Step 4: 4-Bromo-1-(3-chloro-4-(1-(4-methoxybenzyl)-1H-1,2,4-triazol-3-yl)phenyl)-8,9-dihydro-7H-6-oxa-2,9a-diazabenzo[cd]azulene

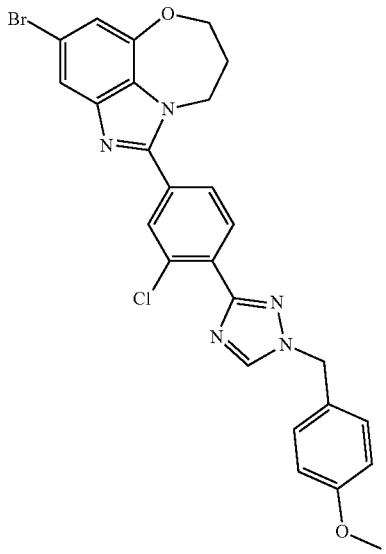 [SMILES: COc1ccc(Cn2cnc(-c3ccc(-c4nc5cc(Br)cc6c5n4CCCO6)cc3Cl)n2)cc1]

The title compound (700 mg, 24% yield) was generated from 4-bromo-1-iodo-8,9-dihydro-7H-6-oxa-2,9a-diazabenzo[cd]azulene (2.00 g, 5.28 mmol) and 3-(2-chloro-4-(4,4,5,5-tetramethyl-1,3,2-dioxaborolan-2-yl)phenyl)-1-(4-methoxybenzyl)-1H-1,2,4-triazole (2.69 g, 6.32 mmol) following a procedure analogous to Example 150, step 3. LCMS (ESI): [M+H]⁺=550/552.

Step 5: (S)-1-(1-(3-Chloro-4-(1-(4-methoxybenzyl)-1H-1,2,4-triazol-3-yl)phenyl)-8,9-dihydro-7H-6-oxa-2,9a-diazabenzo[cd]azulen-4-yl)pyrrolidine-2-carboxamide

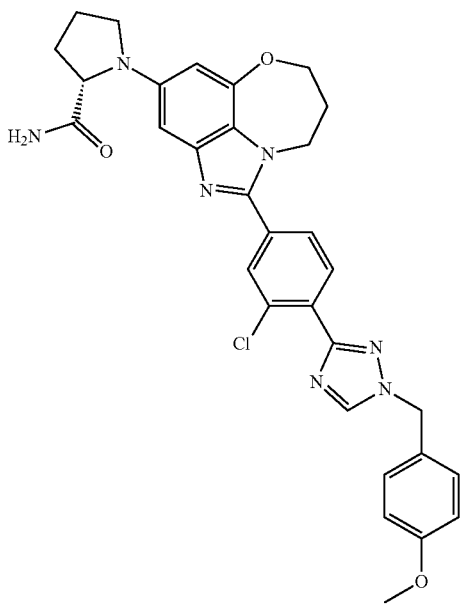 [SMILES: COc1ccc(Cn2cnc(-c3ccc(-c4nc5cc(N6CCC[C@H]6C(N)=O)cc6c5n4CCCO6)cc3Cl)n2)cc1]

The title compound (200 mg, 36% yield) was generated from 4-bromo-1-(3-chloro-4-(1-(4-methoxybenzyl)-1H-1,2,4-triazol-3-yl)phenyl)-8,9-dihydro-7H-6-oxa-2,9a-diazabenzo[cd]azulene (600 mg, 1.09 mmol) following a procedure analogous to Example 104, steps 1-2. LCMS (ESI): [M+H]⁺=584.

Step 6

A mixture of (S)-1-(1-(3-chloro-4-(1-(4-methoxybenzyl)-1H-1,2,4-triazol-3-yl)phenyl)-8,9-dihydro-7H-6-oxa-2,9a-diazabenzo[cd]azulen-4-yl)pyrrolidine-2-carboxamide (200 mg, 0.341 mmol) in TFA (5.00 mL) was stirred at 80° C. for 2 h. The solvent was removed in vacuo. The residue was purified via flash chromatography on silica gel (solvent gradient: 10% methanol in dichloromethane), and then by chiral SFC and lyophilized to yield 47.6 mg (30% yield) of 222 as a yellow solid. LCMS: R$_T$ (min)=0.92, [M+H]⁺=464, method=C; ¹H NMR (300 MHz, DMSO-d$_6$): δ 14.47-14.37 (m, 1H), 8.75 (s, 1H), 8.18-7.87 (m, 3H), 7.35 (s, 1H), 7.05 (s, 1H), 6.39 (d, J=2.1 Hz, 1H), 6.13 (d, J=2.2 Hz, 1H), 4.40-4.35 (m, 4H), 3.88-3.85 (m, 1H), 3.61-3.58 (m, 1H), 3.23-3.17 (m, 1H), 2.36-2.16 (m, 3H), 2.11-1.90 (m, 3H).

Example 223 (S)-1-(1-(6-(1H-Pyrazol-4-yl)pyridin-3-yl)-8,9-dihydro-7H-6-oxa-2,9a-diazabenzo[cd]azulen-4-yl)pyrrolidine-2-carboxamide 223

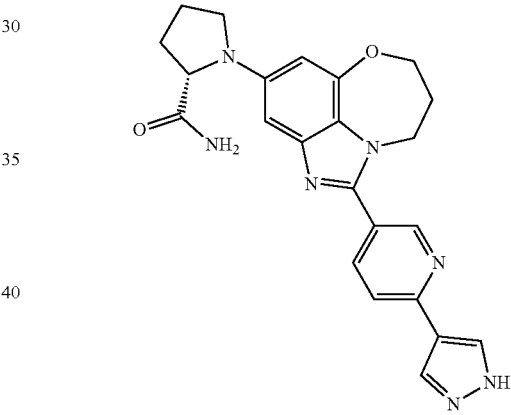

Step 1: Methyl 6-(1H-pyrazol-4-yl)nicotinate

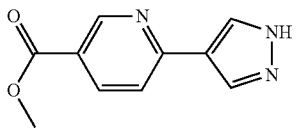

A mixture of methyl 6-bromonicotinate (4.80 g, 22.2 mmol), tert-butyl 4-(4,4,5,5-tetramethyl-1,3,2-dioxaborolan-2-yl)-1H-pyrazole-1-carboxylate (7.20 g, 24.4 mmol), potassium carbonate (10 mL, 2 N solution in water) and 1,1'-bis(diphenylphosphino)ferrocenyl palladium (II) dichloride (1.63 g, 2.23 mmol) in 1.4-dioxane under an atmosphere of nitrogen was stirred at 100° C. for 16 h. The resultant mixture was allowed to cool to room temperature and diluted with water. The resulting solid was collected via filtration and dried in vacuo to yield 3.1 g (crude) of the title compound as a brown solid. The solid was used next step directly without further purification. LCMS (ESI): [M+H]⁺=204.

Step 2: Methyl 6-(1-(4-methoxybenzyl)-1H-pyrazol-4-yl)nicotinate

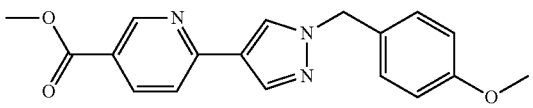

To a solution of methyl 6-(1H-pyrazol-4-yl)nicotinate (3.00 g, 14.8 mmol) and cesium carbonate (10.5 g, 32.2 mmol) in DMF (35 mL) was added 1-(chloromethyl)-4-methoxybenzene (2.50 g, 15.9 mmol). The reaction mixture was stirred at 25° C. for 2 h, then diluted with water. The resulting solid was collected via filtration and dried in vacuo to yield 4.05 g (crude) of the title compound as a brown solid. The solid was used next step directly without further purification. LCMS (ESI): [M+H]$^+$=324.

Step 3: 6-(1-(4-Methoxybenzyl)-1H-pyrazol-4-yl)nicotinic acid

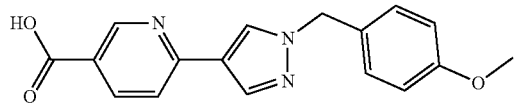 [SMILES: COc1ccc(Cn2cc(-c3ccc(C(=O)O)cn3)cn2)cc1]

A mixture of methyl 6-(1-(4-methoxybenzyl)-1H-pyrazol-4-yl)nicotinate (4.00 g, 12.4 mmol) and potassium hydroxide (2.40 g, 42.8 mmol) in THF (35 mL) and water (35 mL) was stirred for 12 h at 25° C. The THF was removed in vacuo and the mixture adjusted to pH 6 with a 1 N aqueous solution of hydrogen chloride. The resulting solid was collected via filtration and dried in vacuo to yield 3.5 g (91%) of the title compound as a white solid. LCMS (ESI): [M+H]$^+$=309.

Step 4: (S)-1-(1-(6-(1-(4-Methoxybenzyl)-1H-pyrazol-4-yl)pyridin-3-yl)-8,9-dihydro-7H-6-oxa-2,9a-diazabenzo[cd]azulen-4-yl)pyrrolidine-2-carboxamide

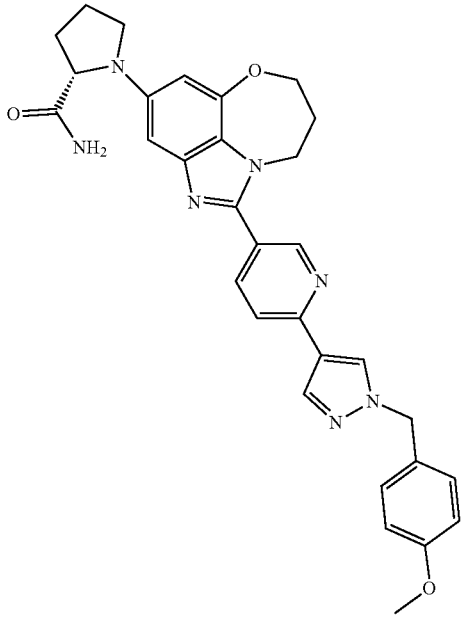 [SMILES: COc1ccc(Cn2cc(-c3ccc(-c4nc5cc(N6CCC[C@H]6C(N)=O)cc6c5n4CCCO6)cn3)cn2)cc1]

The title compound (550 mg, 40% yield over four steps) was generated from 6-(1-(4-methoxybenzyl)-1H-pyrazol-4-yl)nicotinic acid (770 mg, 2.49 mmol) following procedures analogous to those of Example 125. LCMS (ESI): [M+H]$^+$= 550.

Step 5

A solution of (S)-1-(1-(6-(1-(4-methoxybenzyl)-1H-pyrazol-4-yl)pyridin-3-yl)-8,9-dihydro-7H-6-oxa-2,9a-diazabenzo[cd]azulen-4-yl)pyrrolidine-2-carboxamide (500 mg, 0.910 mmol) in TFA (4 mL) was stirred at 80° C. for 4 h. The solvent was evaporated in vacuo and the crude product was purified via prep-HPLC then lyophilized to yield 32.8 mg (8%) of 223 as a yellow solid. LCMS (ESI): R$_T$ (min)=1.18, [M+H]$^+$=430, method=D; $^1$H NMR (300 MHz, DMSO-d$_6$) δ 13.18 (m, 1H), 8.92-8.91 (m, 1H), 8.45-8.39 (m, 1H), 8.19-8.16 (m, 2H), 7.87-7.84 (m, 1H), 7.32 (s, 1H), 7.03 (s, 1H), 6.38 (m, 1H), 6.10-6.09 (m, 1H), 4.38-4.31 (m, 4H), 3.87-3.84 (m, 1H), 3.61-3.56 (m, 1H), 3.23-3.15 (m, 1H), 2.30-2.20 (m, 3H), 2.08-2.01 (m, 3H).

Example 224 (S)-1-(1-(2-Amino-7-ethylbenzo[d]oxazol-5-yl)-8,9-dihydro-7H-6-oxa-2,9a-diazabenzo[cd]azulen-4-yl)pyrrolidine-2-carboxamide 224

Step 1: (1-(2-Amino-7-ethylbenzo[d]oxazol-5-yl)-8,9-dihydro-7H-6-oxa-2,9a-diazabenzo[cd]azulen-4-yl)-L-proline

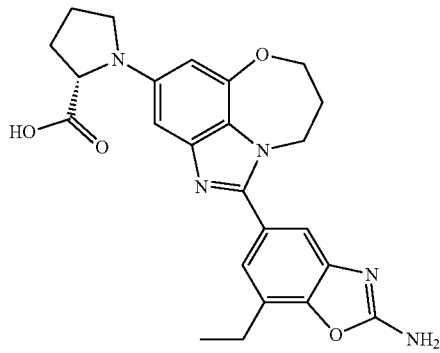 [SMILES: CCc1cc(-c2nc3cc(N4CCC[C@H]4C(=O)O)cc4c3n2CCCO4)cc2nc(N)oc12]

The title compound (116 mg, 39% yield) was generated from 5-(4-bromo-8,9-dihydro-7H-6-oxa-2,9a-diazabenzo[cd]azulen-1-yl)-7-ethylbenzooxazol-2-ylamine (275 mg, 0.666 mmol) and (S)-pyrrolidine-2-carboxylic acid (153 mg, 1.33 mmol) following a procedure analogous to Example 104, step 1. LCMS (ESI): [M+H]$^+$=448.

Step 2: (S)-1-(1-(2-Amino-7-ethylbenzo[d]oxazol-5-yl)-8,9-dihydro-7H-6-oxa-2,9a-diazabenzo[cd]azulen-4-yl)pyrrolidine-2-carboxamide 224 (10.0 mg, 9% yield) was generated from (1-(2-amino-7-ethylbenzo[d]oxazol-5-yl)-8,9-dihydro-7H-6-oxa-2,9a-diazabenzo[cd]azulen-4-yl)-L-proline (116.5 mg, 0.260 mmol) following a procedure analogous to Example 104, step 2. LCMS (ESI): R$_T$ (min)=2.76, [M+H]$^+$=447, method=A; $^1$H NMR (400 MHz, DMSO-d$_6$) δ 7.52 (br s, 2H), 7.38 (d, J=1.6 Hz, 1H), 7.29 (d, J=2.1 Hz, 1H), 7.23 (d, J=1.6 Hz, 1H), 7.01 (d, J=2.1 Hz, 1H), 6.35 (d, J=2.0 Hz, 1H), 6.06 (d, J=2.0 Hz, 1H), 4.35 (t, J=4.6 Hz, 2H), 4.24 (t, J=5.2 Hz, 2H), 3.84-3.82 (m, 1H), 3.60-3.56 (m, 1H), 3.21-3.15 (m, 1H), 2.81 (q, J=7.7 Hz, 2H), 2.30-2.17 (m, 3H), 2.05-1.91 (m, 3H), 1.29 (t, J=7.7 Hz, 3H).

Example 225 (S)-2-((1-(2-Amino-7-ethylbenzo[d] oxazol-5-yl)-8,9-dihydro-7H-6-oxa-2,9a-diazabenzo [cd]azulen-4-yl)amino)-2-cyclopropylacetamide 225

Step 1: 5-(4-Bromo-8,9-dihydro-7H-6-oxa-2,9a-diazabenzo[cd]azulen-1-yl)-'7-ethylbenzo[d]oxazol-2-amine

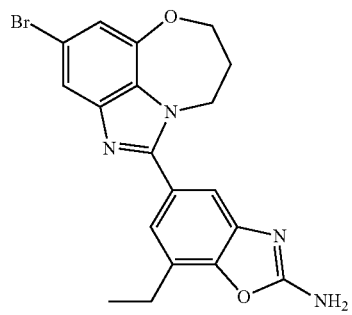 [SMILES: CCc1cc(-c2nc3cc(Br)cc4c3n2CCCO4)cc2nc(N)oc12]

The title compound (139 mg, 35% yield) was generated from 5-bromo-7-ethylbenzo[d]oxazol-2-amine (232 mg, 0.962 mmol) following a procedure analogous to Example 205, step 1. LCMS (ESI): [M+H]⁺=413/415.

Step 2: (S)-2-((1-(2-Amino-7-ethylbenzo[d]oxazol-5-yl)-8,9-dihydro-7H-6-oxa-2,9a-diazabenzo[cd] azulen-4-yl)amino)-2-cyclopropylacetic acid

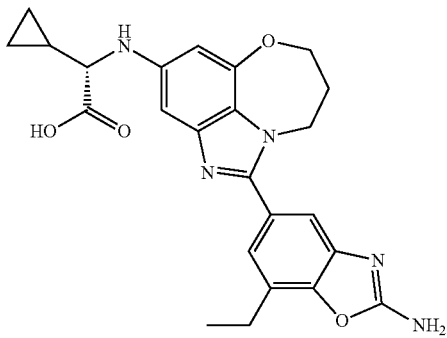

The title compound (148 mg, 58% yield) was generated from 5-(4-bromo-8,9-dihydro-7H-6-oxa-2,9a-diazabenzo [cd]azulen-1-yl)-7-ethylbenzo[d]oxazol-2-amine (139 mg, 0.336 mmol) and (S)-2-amino-2-cyclopropylacetic acid (77.3 mg, 0.67 mmol) following a procedure analogous to Example 125, step 3. LCMS (ESI): [M+H]⁺=448.

Step 3: (S)-2-((1-(2-Amino-7-ethylbenzo[d]oxazol-5-yl)-8,9-dihydro-7H-6-oxa-2,9a-diazabenzo[cd] azulen-4-yl)amino)-2-cyclopropylacetamide 225 (26.6 mg, 27% yield) was generated (S)-2-((1-(2-amino-7-ethylbenzo[d]oxazol-5-yl)-8,9-dihydro-7H-6-oxa-2,9a-diazabenzo[cd]azulen-4-yl)amino)-2-cyclopropylacetic acid (97.5 mg, 0.218 mmol) following a procedure analogous to Example 125, step 4. LCMS (ESI): R$_T$ (min)= 2.71, [M+H]⁺=447, method=A; ¹H NMR (400 MHz, DMSO-d₆) δ 7.51 (br s, 2H), 7.35 (d, J=1.5 Hz, 1H), 7.33 (d, J=2.1 Hz, 1H), 7.19 (d, J=1.5 Hz, 1H), 6.96 (d, J=2.1 Hz, 1H), 6.36 (d, J=2.0 Hz, 1H), 6.22 (d, J=2.0 Hz, 1H), 5.44 (d, J=7.2 Hz, 1H), 4.33-4.15 (m, 4H), 3.14 (t, J=7.2 Hz, 1H), 2.81 (q, J=7.5 Hz, 2H), 2.26-2.21 (m, 2H), 1.29 (t, J=7.5 Hz, 3H), 1.15-1.06 (m, 1H), 0.54-0.44 (m, 3H), 0.34-0.28 (m, 1H).

Example 227 (S)-1-(1-(5-(1H-1,2,4-Triazol-3-yl) pyridin-2-yl)-8,9-dihydro-7H-6-oxa-2,9a-diazabenzo [cd]azulen-4-yl)pyrrolidine-2-carboxamide 227

Step 1: 3-Bromo-1-(4-methoxybenzyl)-1H-1,2,4-triazole

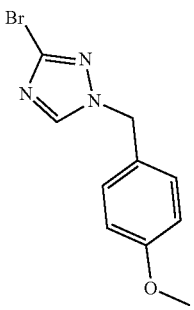

A mixture of 3-bromo-1H-1,2,4-triazole (10.0 g, 67.6 mmol), 1-(chloromethyl)-4-methoxybenzene (10.6 g, 67.6 mmol), DIPEA (17.5 g, 135 mmol) and potassium iodide (5.61 g, 33.8 mmol) in acetonitrile (300 mL) was stirred at 65° C. for 120 min. The solvent was evaporated in vacuo and the residue was purified via flash chromatography on silica gel (solvent gradient: 0-30% ethyl acetate in petroleum ether) to yield 12.9 g (71%) of the title compound as a white solid. LCMS (ESI): [M+H]⁺=268/270.

Step 2: 5-(1-(4-Methoxybenzyl)-1H-1,2,4-triazol-3-yl)picolinic acid

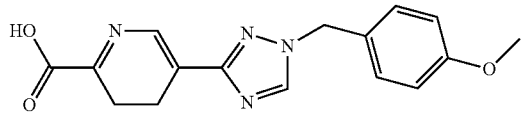 [SMILES: COc1ccc(Cn2cnc(C3=CN=C(C(=O)O)CC3)n2)cc1]

A mixture of 3-bromo-1-(4-methoxybenzyl)-1H-1,2,4-triazole (500 mg, 1.86 mmol), methyl 5-(4,4,5,5-tetramethyl-1,3,2-dioxaborolan-2-yl)picolinate (520 mg, 1.98 mmol), tetrakis(triphenylphosphine)palladium (220 mg, 0.190 mmol) and sodium carbonate (590 mg, 5.57 mmol) in water (1 mL) and dioxane (9 mL) was heated under microwave irradiation at 140° C. for 30 min. This procedure was repeated separately ten times. The ten reaction mixtures were combined, diluted with water (100 mL) and extracted with ethyl acetate. The pH of the aqueous layer was adjusted to pH 6 with a 0.5 N aqueous solution of hydrogen chloride and the resulting solid was collected via filtration and dried in vacuo to yield 636 mg (11%) the title compound as an off-white solid. LCMS (ESI): [M+H]⁺=311.

Step 3: (S)-1-(1-(5-(1-(4-Methoxybenzyl)-1H-1,2,4-triazol-3-yl)pyridin-2-yl)-8,9-dihydro-7H-6-oxa-2,9a-diazabenzo[cd]azulen-4-yl)pyrrolidine-2-carboxamide

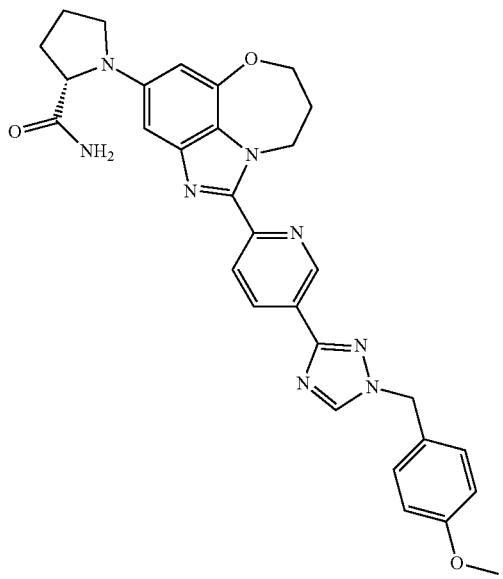 [SMILES: COc1ccc(Cn2cnc(-c3ccc(-c4nc5cc(N6CCC[C@H]6C(N)=O)cc6c5n4CCCO6)nc3)n2)cc1]

The title compound (287 mg, 27% yield over 4 steps) was generated from 5-(1-(4-methoxybenzyl)-1H-1,2,4-triazol-3-yl)picolinic acid (600 mg, 1.94 mmol) following procedures analogous to those of Example 125. LCMS (ESI): [M+H]$^+$= 551.

Step 4

A solution of (S)-1-(1-(5-(1-(4-methoxybenzyl)-1H-1,2,4-triazol-3-yl)pyridin-2-yl)-8,9-dihydro-7H-6-oxa-2,9a-diazabenzo[cd]azulen-4-yl)pyrrolidine-2-carboxamide (140 mg, 0.254 mmol) in TFA (6 mL) was stirred at 80° C. for 6 h. The solvent was evaporated in vacuo and the crude was purified by preparatory reverse-phase HPLC then lyophilized to yield 2.4 mg (2%) of 226 as a white solid. LCMS (ESI): R$_T$ (min)=1.21, [M+H]$^+$=431, method=E; $^1$H NMR (300 MHz, DMSO-d$_6$) δ 9.29 (s, 1H), 8.65 (s, 1H), 8.51-8.48 (m, 1H), 8.37-8.34 (m, 1H), 7.35 (s, 1H), 7.03 (s, 1H), 6.39 (s, 1H), 6.14 (s, 1H), 4.85-4.81 (m, 2H), 4.40-4.30 (m, 2H), 3.87-3.84 (m, 1H), 3.61-3.58 (m, 1H), 3.24-3.16 (m, 1H), 2.26-2.19 (m, 3H), 2.03-1.97 (m, 3H).

Example 227 (S)-1-(1-(4-(1,2,4-Thiadiazol-3-yl)phenyl)-8,9-dihydro-7H-6-oxa-2,9a-diazabenzo[cd]azulen-4-yl)pyrrolidine-2-carboxamide 227

Step 1: 5-(4-Bromophenyl)-1,3,4-oxathiazol-2-one

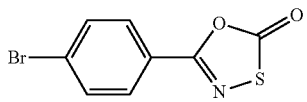

To a solution of 4-bromobenzamide (11.0 g, 55.0 mmol) in toluene (150 mL) was added carbonochloridic hypochlorous thioanhydride (14.3 g, 110 mmol), The reaction mixture was stirred at 100° C. for 180 min, and the solvent was evaporated in vacuo to yield 12.8 g (90%) of the title compound as brown solid. LCMS (ESI): [M+H]$^+$=258/260.

Step 2: Ethyl 3-(4-bromophenyl)-1,2,4-thiadiazole-5-carboxylate

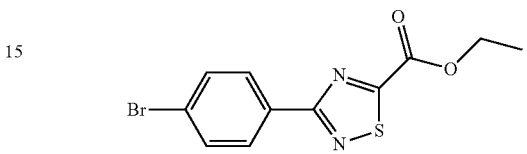

To a solution of 5-(4-bromophenyl)-1,3,4-oxathiazol-2-one (9.00 g, 34.9 mmol) in dodecane (100 mL) was added ethyl carbonocyanidate (13.8 g, 140 mmol). The reaction mixture was stirred at 160° C. for 180 min, and the solvent was evaporated in vacuo to yield 8.1 g (74%) of the title compound as off-white solid. LCMS (ESI): [M+H]$^+$=313/315.

Step 3: 3-(4-Bromophenyl)-1,2,4-thiadiazole

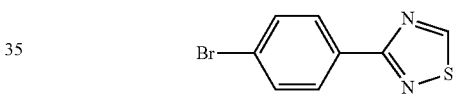

To a solution of ethyl 3-(4-bromophenyl)-1,2,4-thiadiazole-5-carboxylate (8.00 g, 25.5 mmol) in ethanol (100 mL) and water (60 mL) was added sodium hydroxide (1.13 g, 28.2 mmol). The reaction mixture was stirred at 100° C. for 120 min then cooled to room temperature, and concentrated aqueous hydrogen chloride (7 mL) was added. The reaction mixture was stirred at 100° C. for 180 min. The reaction mixture was adjusted to ca. pH 3 with 2 N sodium bicarbonate and then extracted with ethyl acetate. The organic extracts were combined, washed with brine, dried over sodium sulfate and the solvent was removed in vacuo to yield 6.1 g (99%) of the title compound as an off-white solid. LCMS (ESI): [M+H]$^+$=241/243.

Step 4

227 (41.3 mg, 9.5% yield) was generated from 4-bromo-1-iodo-8,9-dihydro-7H-6-oxa-2,9a-diazabenzo[cd]azulene (Example 150, step 2) (400 mg, 0.971 mmol) following a procedure analogous to Example 158, steps 2-5. LCMS: R$_T$ (min)=2.15, [M+H]$^+$=447, method=C; $^1$H NMR (300 MHz, DMSO-d$_6$) δ 10.41 (s, 1H), 8.40 (d, J=8.4, 2H), 7.98 (d, J=8.4, 2H), 7.32 (s, 1H), 7.03 (s, 1H), 6.38 (d, J=2.1 Hz, 1H), 6.10 (d, J=2.1 Hz, 1H), 4.38-4.31 (m, 4H), 3.90-3.80 (m, 1H), 3.59 (d, J=7.8 Hz, 1H), 3.19 (d, J=8.2 Hz, 1H), 2.33-2.25 (m, 3H), 2.10-1.87 (m, 3H).

Example 228 (S)-2-Cyclopropyl-2-((1-(pyrazolo[1,5-c]pyrimidin-5-yl)-8,9-dihydro-7H-6-oxa-2,9a-diazabenzo[cd]azulen-4-yl)amino)acetamide 228

228 was prepared following procedures analogous to those of Example 125. LCMS (ESI): $R_T$ (min)=1.05, [M+H]$^+$=404, method=D. $^1$H NMR (300 MHz, DMSO-d$_6$) δ 9.17 (d, J=7.2 Hz, 1H), 8.29 (s, 1H), 7.82 (d, J=7.2 Hz, 1H), 7.38 (s, 1H), 6.99 (s, 1H), 6.84 (s, 1H), 6.40-6.37 (m, 2H), 5.68 (d, J=7.2 Hz, 1H), 4.91-4.88 (m, 2H), 4.37-4.35 (m, 2H), 3.17-3.12 (m, 1H), 2.40-2.20 (m, 2H), 1.13-1.11 (m, 1H), 0.54-0.48 (m, 3H), 0.32-0.30 (m, 1H).

Example 229 (S)-1-(1-(4-(1H-Pyrazol-3-yl)phenyl)-8,9-dihydro-7H-6-oxa-2,9a-diazabenzo[cd]azulen-4-yl)pyrrolidine-2-carboxamide 229

Step 1: 4-Bromo-1-(4-(1-(tetrahydro-2H-pyran-2-yl)-1H-pyrazol-5-yl)phenyl)-8,9-dihydro-7H-6-oxa-2,9a-diazabenzo[cd]azulene

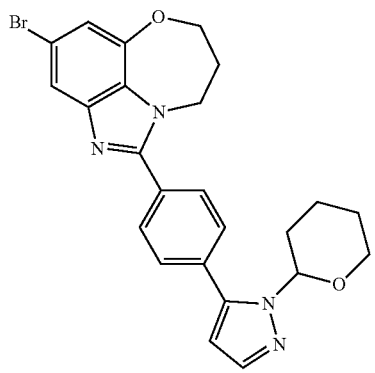 [SMILES: Brc1cc2c3c(c1)nc(-c1ccc(-c4ccnn4C4CCCCO4)cc1)n3CCCO2]

A mixture of 4-bromo-1-(4-iodophenyl)-8,9-dihydro-7H-6-oxa-2,9a-diazabenzo[cd]azulene (Example 235, step 1) (1.00 g, 2.20 mmol), 1-(tetrahydro-2H-pyran-2-yl)-5-(4,4,5,5-tetramethyl-1,3,2-dioxaborolan-2-yl)-1H-pyrazole (610 mg, 2.19 mmol), 1,1'-bis(diphenylphosphino)ferrocenyl palladium (II) dichloride (160 mg, 0.219 mmol) and sodium carbonate (2 M aqueous solution, 10 mL) in DMF (20 mL) was stirred at 60° C. for 3 h. The reaction mixture was quenched by water, extracted with DCM, the organic layers combined and dried over anhydrous sodium sulfate and evaporated in vacuo. The residue was purified via flash chromatography on silica gel (solvent gradient: 10% ethyl acetate in hexane) to yield 737 mg (70%) of the title compound as a yellow solid. LCMS (ESI): [M+H]$^+$=479/481.

Step 2: (2S)-1-(1-(4-(1-(Tetrahydro-2H-pyran-2-yl)-1H-pyrazol-5-yl)phenyl)-8,9-dihydro-7H-6-oxa-2,9a-diazabenzo[cd]azulen-4-yl)pyrrolidine-2-carboxamide

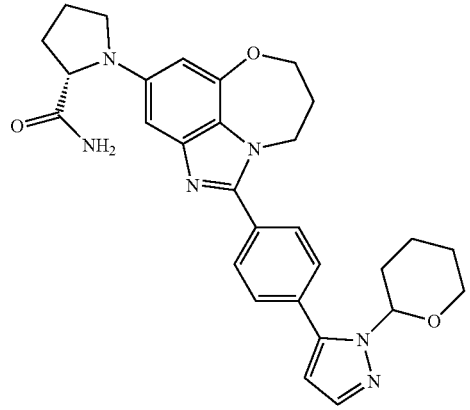 [SMILES: NC(=O)[C@@H]1CCCN1c1cc2c3c(c1)nc(-c1ccc(-c4ccnn4C4CCCCO4)cc1)n3CCCO2]

The title compound (320 mg, 44% yield) was generated from 4-bromo-1-(4-(1-(tetrahydro-2H-pyran-2-yl)-1H-pyrazol-5-yl)phenyl)-8,9-dihydro-7H-6-oxa-2,9a-diazabenzo[cd]azulene (680 mg, 1.42 mmol) following procedures analogous to those of Example 104. LCMS (ESI): [M+H]$^+$=513.

Step 3: (S)-1-(1-(4-(1H-Pyrazol-3-yl)phenyl)-8,9-dihydro-7H-6-oxa-2,9a-diazabenzo[cd]azulen-4-yl)pyrrolidine-2-carboxamide A solution of (2S)-1-(1-(4-(1-(tetrahydro-2H-pyran-2-yl)-1H-pyrazol-5-yl)phenyl)-8,9-dihydro-7H-6-oxa-2,9a-diazabenzo[cd]azulen-4-yl)pyrrolidine-2-carboxamide (270 mg, 0.527 mmol) in TFA (3 mL) and DCM (6 mL) was stirred at 20° C. for 30 min. The solvent was evaporated in vacuo and the crude product was purified by preparatory reverse-phase HPLC and lyophilized to yield 18.5 mg (8%) of 229 as a white solid. LCMS (ESI): $R_T$ (min)=0.97, [M+H]$^+$=429, method=C; $^1$H NMR (300 MHz, DMSO-d$_6$) δ 13.02 (br, 1H), 7.98-7.95 (m, 2H), 7.84-7.77 (m, 3H), 7.30 (s, 1H), 7.02 (s, 1H), 6.82 (d, J=2.4 Hz, 1H), 6.36 (s, 1H), 6.08 (s, 1H), 4.37-4.28 (m, 4H), 3.85-3.82 (m, 1H), 3.75-3.45 (m, 1H), 3.20-3.17 (m, 1H), 2.40-2.10 (m, 3H), 2.05-1.85 (m, 3H).

Examples 230 and 231 (S)-2-(4-(1-(2-Aminobenzo[d]oxazol-5-yl)-8,9-dihydro-7H-6-oxa-2,9a-diazabenzo[cd]azulen-4-yl)-1H-pyrazol-1-yl)-2-cyclopropylacetamide 230 and (R)-2-(4-(1-(2-Aminobenzo[d]oxazol-5-yl)-8,9-dihydro-7H-6-oxa-2,9a-diazabenzo[cd]azulen-4-yl)-1H-pyrazol-1-yl)-2-cyclopropylacetamide 231

Step 1: Ethyl 2-cyclopropyl-2-(1H-pyrazol-1-yl)acetate

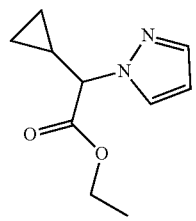

A mixture of pyrazole (110 mg, 1.61 mmol), ethyl 2-bromo-2-cyclopropylacetate (0.33 g, 1.61 mmol) and cesium carbonate (576 mg, 1.77 mmol) in DMF (3.0 mL) was stirred at 60° C. for 16 h. The reaction mixture was partitioned between ethyl acetate and water and the phases separated. The aqueous layer was further extracted with ethyl acetate. The combined organic extracts were washed with brine, dried over sodium sulfate and the solvent evaporated. The residue was purified via flash chromatography on silica gel (solvent gradient: 10-50% ethyl acetate in cyclohexane) to yield 186 mg (60%) of the title compound as a colorless oil. LCMS (ESI): [M+H]$^+$=195.

Step 2: Ethyl 2-(4-bromo-1H-pyrazol-1-yl)-2-cyclopropylacetate

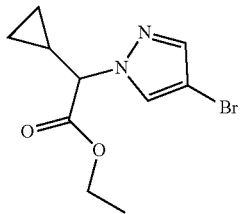

To a solution of ethyl 2-cyclopropyl-2-(1H-pyrazol-1-yl) acetate (186 mg, 0.96 mmol) in THF (3.0 mL) was added N-bromosuccinimide (188 mg, 1.06 mmol) and the reaction mixture stirred at room temperature for 2.5 h. The solvent was evaporated, azeotroping with toluene, and the residue was purified via flash chromatography on silica gel (solvent gradient: 5-20% ethyl acetate in cyclohexane) to yield 253 mg (97%) of the title compound as a colorless oil. LCMS (ESI): [M+H]$^+$=273/275.

Step 3: Ethyl 2-cyclopropyl-2-(4-(4,4,5,5-tetramethyl-1,3,2-dioxaborolan-2-yl)-1H-pyrazol-1-yl) acetate

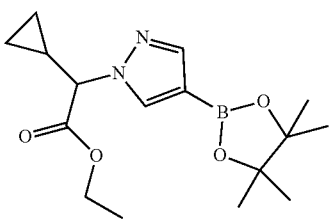 [SMILES: CCOC(=O)C(C1CC1)n1cc(B2OC(C)(C)C(C)(C)O2)cn1]

Ethyl 2-(4-bromo-1H-pyrazol-1-yl)-2-cyclopropylacetate (253 mg, 0.93 mmol), bis(pinacolato)diboron (283 mg, 1.11 mmol), potassium acetate (270 mg, 2.8 mmol) and 1,1'-bis(diphenylphosphino)ferrocenyl palladium (II) dichloride (75 mg, 0.093 mmol) were suspended in 1,4-dioxane (2.0 mL) under an atmosphere of nitrogen and the reaction mixture was stirred at 110° C. for 6.5 h. The resulting mixture was allowed to warm to room temperature and the solvent was evaporated, azeotroping with toluene. The crude residue was purified via flash chromatography on silica gel (solvent gradient: 2-25% ethyl acetate in toluene) to yield 169 mg (57%) of the title compound as a colorless oil. LCMS (ESI): [M+H]$^+$=321.

Step 4: 2-(4-(1-(2-Aminobenzo[d]oxazol-5-yl)-8,9-dihydro-7H-6-oxa-2,9a-diazabenzo[cd]azulen-4-yl)-1H-pyrazol-1-yl)-2-cyclopropylacetic acid

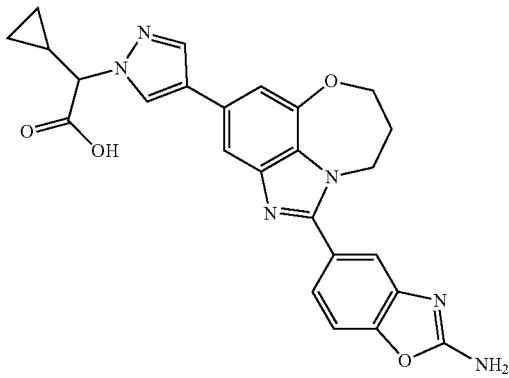 [SMILES: Nc1nc2cc(-c3nc4cc(-c5cnn(C(C(=O)O)C6CC6)c5)cc5c4n3CCCO5)ccc2o1]

5-(4-bromo-8,9-dihydro-7H-6-oxa-2,9a-diazabenzo[cd]azulen-1-yl)benzo[d]oxazol-2-amine from Example 101 (84 mg, 0.218 mmol), ethyl 2-cyclopropyl-2-(4-(4,4,5,5-tetramethyl-1,3,2-dioxaborolan-2-yl)-1H-pyrazol-1-yl)acetate (168 mg, 0.436 mmol), [1,1'-bis(diphenylphosphino)ferrocene] palladium(II) chloride (18 mg, 0.022 mmol), 2 N aqueous sodium carbonate (0.4 mL, 0.80 mmol) and 1,2-dimethoxyethane (1.5 mL) was heated in a sealed vial under nitrogen at 100° C. for 16 h. The reaction mixture was cooled to 45° C. and methanol (1.0 mL) and a solution of lithium hydroxide (37 mg, 0.872 mmol) in water (1.0 mL) were added to the resultant mixture and stirred for a further 1.5 h. The reaction mixture was allowed to warm to room temperature and 1 N HCl (5 mL) was added and the mixture was poured onto a 10 g SCX-2 cartridge. The cartridge was washed with methanol and then eluted with 2 N ammonia in methanol. The eluent was collected and the solvent evaporated. The residue was purified via flash chromatography on silica gel (solvent gradient: 5-50% (2 N ammonia in methanol) in DCM) to yield 97 mg (95%) of the title compound as a grey solid. LCMS (ESI): [M+H]$^+$=471.

Step 5

To a mixture of 2-(4-(1-(2-aminobenzo[d]oxazol-5-yl)-8,9-dihydro-7H-6-oxa-2,9a-diazabenzo[cd]azulen-4-yl)-1H-pyrazol-1-yl)-2-cyclopropylacetic acid (97 mg, 0.21 mmol), ammonium chloride (22 mg, 0.42 mmol) and DIPEA (143 0.84 mmol) in DMF (1.0 mL) was added HATU (157 mg, 0.42 mmol) portion-wise over 5 min and stirred for a further 10 min. The mixture was purified via flash chromatography on silica gel (solvent gradient: 2-14% 2 N ammonia methanol in DCM) and the resulting residue was dissolved in methanol and loaded onto a 2 g SCX-2 cartridge. The cartridge was washed with methanol and then eluted with 2N ammonia in methanol. The eluent was collected and the solvent removed to yield a racemic mixture 74 mg (76%) of the title compounds as an off white solid. The two stereoisomers were separated by chiral SFC to yield 230 and 231 each as a single unknown stereoisomer, as off-white solids.

Example 230 (30 mg, 31% yield): LCMS (ESI): R$_T$ (min)=2.54 min, [M+H]$^+$: 470, method=A; $^1$H NMR (400 MHz, DMSO-d$_6$): δ 8.35 (s, 1H), 7.90 (s, 1H), 7.58 (br s, 3H), 7.53 (d, J=1.3 Hz, 1H), 7.50 (d, J=8.1 Hz, 1H), 7.39 (dd, J=8.1, 1.3 Hz, 1H), 7.28 (br s, 1H), 7.06 (d, J=1.3 Hz, 1H), 4.46-4.40 (m, 2H), 4.20 (t, J=5.1 Hz, 2H), 4.11 (d, J=10.2 Hz, 1H), 2.36-2.29 (m, 2H), 1.68-1.58 (m, 1H), 0.75-0.62 (m, 3H), 0.37-0.29 (m, 1H).

Example 231 (31 mg, 32% yield): LCMS (ESI): $R_T$ (min)=2.54 min, [M+H]$^+$: 470, method=A; $^1$H NMR (400 MHz, DMSO-d$_6$): δ 8.35 (s, 1H), 7.90 (s, 1H), 7.58 (br s, 3H), 7.53 (d, J=1.3 Hz, 1H), 7.50 (d, J=8.1 Hz, 1H), 7.39 (dd, J=8.1, 1.3 Hz, 1H), 7.28 (br s, 1H), 7.06 (d, J=1.3 Hz, 1H), 4.46-4.40 (m, 2H), 4.20 (t, J=5.1 Hz, 2H), 4.11 (d, J=10.2 Hz, 1H), 2.36-2.29 (m, 2H), 1.68-1.58 (m, 1H), 0.75-0.62 (m, 3H), 0.37-0.29 (m, 1H).

Examples 232 and 233 (R)-2-(4-(1-(2-Aminobenzo[d]oxazol-5-yl)-8,9-dihydro-7H-6-oxa-2,9a-diazabenzo[cd]azulen-4-yl)-1H-pyrazol-1-yl)-3-methoxy-2-methylpropanamide 232 and (S)-2-(4-(1-(2-Aminobenzo[d]oxazol-5-yl)-8,9-dihydro-7H-6-oxa-2,9a-diazabenzo[cd]azulen-4-yl)-1H-pyrazol-1-yl)-3-methoxy-2-methylpropanamide 233

Step 1: Diethyl 2-methyl-2-(1H-pyrazol-1-yl)malonate

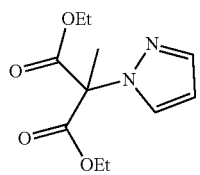 [SMILES: CCOC(=O)C(C)(C(=O)OCC)n1cccn1]

A mixture of pyrazole (1.34 g, 19.75 mmol), diethyl 3-bromo-2-methylmalonate (5.0 g, 19.75 mmol) and cesium carbonate (7.08 g, 21.73 mmol) in DMF (35 mL) was stirred at 60° C. for 2 h. The reaction mixture was partitioned between ethyl acetate and water and the phases separated. The aqueous layer was further extracted with ethyl acetate. The combined organic extracts were washed with brine, dried over sodium sulfate and the solvent evaporated. The residue was purified via flash chromatography on silica gel (solvent gradient: 5-25% ethyl acetate in cyclohexane) to yield 4.06 g (86%) of the title compound as a colorless oil. LCMS (ESI): [M+H]$^+$=241.

Step 2: Ethyl 3-hydroxy-2-methyl-2-(1H-pyrazol-1-yl)propanoate

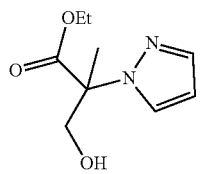

To a solution of diethyl 2-methyl-2-(1H-pyrazol-1-yl)malonate (480 mg, 2.0 mmol) in THF (5.0 mL) was added lithium tri-tert-butoxyaluminium hydride (1 N in THF, 4.5 mL, 4.5 mmol) dropwise over 2 min. The reaction mixture was then refluxed for 30 min. The resulting mixture was cooled to 0° C. and quenched with 10% aqueous sodium bisulfate (30 mL), then extracted twice with ethyl acetate. The combined organic extracts were washed with brine, dried over sodium sulfate and the solvent evaporated. The residue was purified via flash chromatography on silica gel (solvent gradient: 30-60% ethyl acetate in cyclohexane) to yield 235 mg (59%) of the title compound as a colorless oil. LCMS (ESI): [M+H]$^+$=199.

Step 3: Ethyl 3-methoxy-2-methyl-2-(1H-pyrazol-1-yl)propanoate

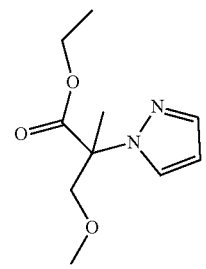

To a solution of ethyl 3-hydroxy-2-methyl-2-(1H-pyrazol-1-yl)propanoate (235 mg, 1.19 mmol) in THF (5.0 mL) was added methyl iodide (148 μL, 2.37 mmol), followed by sodium hydride (60% in mineral oil, 57 mg, 1.42 mmol) portion wise over 3 min. The reaction mixture was stirred at room temperature for 45 min. The resulting mixture was quenched with saturated aqueous ammonium chloride then extracted twice with ethyl acetate. The combined organic extracts were washed with brine, dried over sodium sulfate and the solvent evaporated. The residue was purified via flash chromatography on silica gel (solvent gradient: 10-40% ethyl acetate in cyclohexane) to yield 168 mg (67%) of the title compound as a colorless oil. LCMS (ESI): [M+H]$^+$=213.

Step 4: Ethyl 2-(4-bromo-1H-pyrazol-1-yl)-3-methoxy-2-methylpropanoate

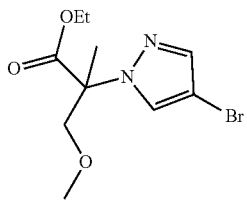 [SMILES: CCOC(=O)C(C)(COC)n1cc(Br)cn1]

To a solution of ethyl 3-methoxy-2-methyl-2-(1H-pyrazol-1-yl)propanoate (168 mg, 0.79 mmol) in THF (3.0 mL) was added N-bromosuccinimide (155 mg, 0.87 mmol) and the reaction mixture stirred at room temperature for 1 h. The solvent was evaporated, azeotroping with toluene, and the residue was purified via flash chromatography on silica gel (solvent gradient: 5-20% ethyl acetate in cyclohexane) to yield 219 mg (95%) of the title compound as a colorless oil. LCMS (ESI): [M+H]$^+$=291/293.

Step 5: Ethyl 3-methoxy-2-methyl-2-(4-(4,4,5,5-tetramethyl-1,3,2-dioxaborolan-2-yl)-1H-pyrazol-1-yl)propanoate

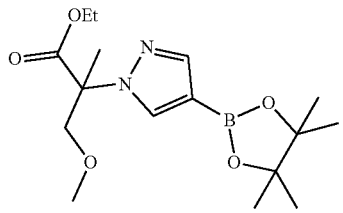 [SMILES: CCOC(=O)C(C)(COC)n1cc(B2OC(C)(C)C(C)(C)O2)cn1]

Ethyl 2-(4-bromo-1H-pyrazol-1-yl)-3-methoxy-2-methylpropanoate (219 mg, 0.75 mmol), bis(pinacolato)diboron (230 mg, 0.90 mmol), potassium acetate (219 mg, 2.25 mmol) and 1,1'-bis(diphenylphosphino)ferrocenyl palladium (II) dichloride (75 mg, 0.075 mmol) were suspended in 1,4-dioxane (1.75 mL) under an atmosphere of nitrogen and stirred at 110° C. for 5 h, then allowed to room temperature. The solvent was removed under reduced pressure, azeotroping with toluene, and the residue was purified via flash chromatography on silica gel (solvent gradient: 5-30% ethyl acetate in toluene) to yield 125 mg (49%) of the title compound as a colorless oil. LCMS (ESI): [M+H]$^+$=339.

Step 6: 2-(4-(1-(2-Aminobenzo[d]oxazol-5-yl)-8,9-dihydro-7H-6-oxa-2,9a-diazabenzo[cd]azulen-4-yl)-1H-pyrazol-1-yl)-3-methoxy-2-methylpropanoic acid

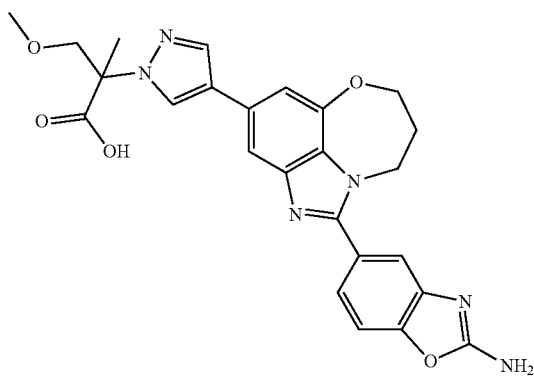 [SMILES: COCC(C)(C(=O)O)n1cc(-c2cc3c4c(c2)nc(-c2ccc5oc(N)nc5c2)n4CCCO3)cn1]

5-(4-Bromo-8,9-dihydro-7H-6-oxa-2,9a-diazabenzo[cd]azulen-1-yl)benzo[d]oxazol-2-amine from Example 101 (99 mg, 0.257 mmol), ethyl 3-methoxy-2-methyl-2-(4-(4,4,5,5-tetramethyl-1,3,2-dioxaborolan-2-yl)-1H-pyrazol-1-yl)propanoate (124 mg, 0.257 mmol), [1,1'-bis(diphenylphosphino)ferrocene] palladium(II) chloride (21 mg, 0.026 mmol), 2 N aqueous sodium carbonate (0.5 mL, 1.0 mmol) and 1,2-dimethoxyethane (1.8 mL) was heated in a sealed vial under nitrogen at 100° C. for 3 h. The reaction mixture was cooled to 45° C. and methanol (3 mL) and a solution of lithium hydroxide (42 mg, 1.0 mmol) in water (2 mL) were added to the resulting mixture which was stirred for a further 1.5 h. The reaction mixture was allowed to room temperature and 1 N HCl (5 mL) was added and the mixture was poured onto a 10 g SCX-2 cartridge. The cartridge was washed with methanol and then eluted with 2 N ammonia in methanol. The eluent was collected and the solvent evaporated. The residue was purified via flash chromatography on silica gel (solvent gradient: 10-60% 2 N ammonia in methanol, in DCM) to yield 84 mg (67%) of the title compound as a grey solid. LCMS (ESI): [M+H]$^+$=489.

Step 7

To a mixture of racemic 2-(4-(1-(2-aminobenzo[d]oxazol-5-yl)-8,9-dihydro-7H-6-oxa-2,9a-diazabenzo[cd]azulen-4-yl)-1H-pyrazol-1-yl)-3-methoxy-2-methylpropanoic acid (84 mg, 0.17 mmol), ammonium chloride (18 mg, 0.35 mmol) and DIPEA (120 µL, 0.69 mmol) in DMF (1.0 mL) was added HATU (132 mg, 0.35 mmol) portion-wise over 5 min and stirred for a further 10 min. The reaction mixture was directly purified via flash chromatography on silica gel (solvent gradient: 2-14% 2 N ammonia in methanol, in DCM) and the resulting residue was dissolved in methanol and loaded onto a 2 g SCX-2 cartridge. The cartridge was washed with methanol and then eluted with 2 N ammonia in methanol. The eluent was collected and the solvent evaporated to yield a racemic mixture 73 mg (86%) of the title compounds as an off-white solid. The two stereoisomers were separated by chiral SFC to yield 232 and 233 each as a single unknown stereoisomer, as off-white solids.

Example 232 (20 mg, 24% yield): LCMS (ESI): R$_T$ (min)=2.63 min, [M+H]$^+$: 470, method=A; $^1$H NMR (400 MHz, DMSO-d$_6$): δ 8.25 (s, 1H), 7.97 (s, 1H), 7.58 (br s, 3H), 7.55 (d, J=1.3 Hz, 1H), 7.50 (d, J=8.1 Hz, 1H), 7.39 (dd, J=8.1, 1.3 Hz, 1H), 7.29 (br s, 1H), 7.08 (d, J=1.5 Hz, 1H), 6.86 (br s, 1H), 4.44-4.40 (m, 2H), 4.30 (t, J=5.3 Hz, 2H), 4.00 (d, J=10.0 Hz, 1H), 3.86 (d, J=10.0 Hz, 1H), 3.25 (s, 3H), 2.36-2.28 (m, 2H), 1.77 (s, 3H).

Example 233 (23 mg, 27% yield): LCMS (ESI): R$_T$ (min)=2.63 min, [M+H]$^+$: 470, method=A; $^1$H NMR (400 MHz, DMSO-d$_6$): δ 8.25 (s, 1H), 7.97 (s, 1H), 7.58 (br s, 3H), 7.55 (d, J=1.3 Hz, 1H), 7.50 (d, J=8.1 Hz, 1H), 7.39 (dd, J=8.1, 1.3 Hz, 1H), 7.29 (br s, 1H), 7.08 (d, J=1.5 Hz, 1H), 6.86 (br s, 1H), 4.44-4.40 (m, 2H), 4.30 (t, J=5.3 Hz, 2H), 4.00 (d, J=10.0 Hz, 1H), 3.86 (d, J=10.0 Hz, 1H), 3.25 (s, 3H), 2.36-2.28 (m, 2H), 1.77 (s, 3H).

Example 234 (S)-1-(1-(4-(2-Oxoimidazolidin-1-yl)phenyl)-8,9-dihydro-7H-6-oxa-2,9a-diazabenzo[cd]azulen-4-yl)pyrrolidine-2-carboxamide 234

Step 1: 4-Bromo-1-(4-iodophenyl)-8,9-dihydro-7H-6-oxa-2,9a-diazabenzo[cd]azulene

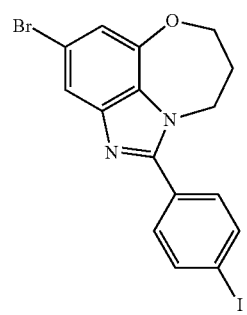 [SMILES: Brc1cc2c3c(c1)nc(-c1ccc(I)cc1)n3CCCO2]

The title compound (5.8 g, 31% yield over two steps) was generated from 8-bromo-2,3,4,5-tetrahydrobenzo[b][1,4]oxazepin-6-amine (9.8 g, 40.3 mmol) following procedures analogous to those of Example 125, steps 1-2. LCMS (ESI): [M+H]⁺=455/457.

Step 2: 1-(4-(4-Bromo-8,9-dihydro-7H-6-oxa-2,9a-diazabenzo[cd]azulen-1-yl)phenyl)imidazolidin-2-one

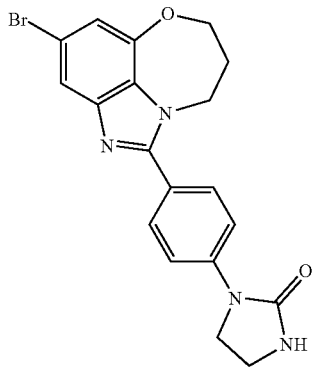 [SMILES: O=C1NCCN1c1ccc(-c2nc3cc(Br)cc4c3n2CCCO4)cc1]

A mixture of 4-bromo-1-(4-iodophenyl)-8,9-dihydro-7H-6-oxa-2,9a-diazabenzo[cd]azulene (500 mg, 1.10 mmol), imidazolidin-2-one (760 mg, 8.83 mmol), copper(I) iodide (40 mg, 0.210 mmol), $N^1,N^2$-dimethylethane-1,2-diamine (60 mg, 0.681 mmol) and potassium triphosphate tribasic (700 mg, 3.30 mmol) in DMF (11 mL) was heated under microwave irradiation at 130° C. for 1 h. The crude reaction mixture was diluted with water and extracted with DCM. The organic layers were combined and dried over anhydrous sodium sulfate and evaporated in vacuo. The residue was purified via flash chromatography on silica gel (solvent gradient: 10% methanol in DCM) to yield 330 mg (73%) of the title compound as a yellow solid. LCMS (ESI): [M+H]⁺=413/415.

Step 3

234 (33.4 mg, 6.1% yield over two steps) was generated from 1-(4-(4-bromo-8,9-dihydro-7H-6-oxa-2,9a-diazabenzo[cd]azulen-1-yl)phenyl)imidazolidin-2-one (500 mg, 1.21 mmol) following procedures analogous to those of Example 104, steps 1-2. LCMS (ESI): $R_T$ (min)=1.24, [M+H]⁺=447, method=D; ¹H NMR (300 MHz, DMSO-$d_6$) δ 7.72 (s, 4H), 7.30 (s, 1H), 7.11 (s, 1H), 7.02 (s, 1H), 6.34 (d, J=1.8 Hz, 1H), 6.05 (d, J=1.8 Hz, 1H), 4.35-4.27 (m, 2H), 4.25-4.23 (m, 2H), 3.94-3.81 (m, 3H), 3.65-3.50 (m, 1H), 3.47-3.41 (m, 2H), 3.25-3.05 (m, 1H), 2.35-2.10 (m, 3H), 2.08-1.85 (m, 3H).

Example 235 (S)-2-((1-(2-Amino-7-(trifluoromethyl)benzo[d]oxazol-5-yl)-8,9-dihydro-7H-6-oxa-2,9a-diazabenzo[cd]azulen-4-yl)amino)-2-cyclopropylacetamide 235

Step 1: 5-Bromo-7-(trifluoromethyl)benzo[d]oxazol-2-amine

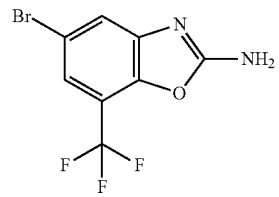 [SMILES: Nc1nc2cc(Br)cc(C(F)(F)F)c2o1]

A reaction vessel was charged with 2-amino-4-bromo-6-(trifluoromethyl)phenol (0.37 g, 1.44 mmol), cyanic bromide (184 mg, 1.74 mmol) and methanol (10 mL) and the reaction mixture was stirred at 35° C. for 16 h. The resulting mixture was cooled to room temperature and further cyanic bromide (62 mg, 0.59 mmol) was added. The reaction mixture was stirred at 35° C. for 2 h. The resultant mixture was quenched with saturated aqueous sodium carbonate (10 mL) and the solvent was concentrated in vacuo. The mixture was partitioned between ethyl acetate and water and the phases separated. The aqueous phase was further extracted with ethyl acetate. The combined organic extracts were washed with brine, dried over magnesium sulfate and evaporated in vacuo to yield 350 mg (86%) of the title compound. The residue was used without further purification. LCMS (ESI): [M+H]⁺282.

Step 2: 5-(4-Bromo-8,9-dihydro-7H-6-oxa-2,9a-diazabenzo[cd]azulen-1-yl)-7-(trifluoromethyl)benzo[d]oxazol-2-amine

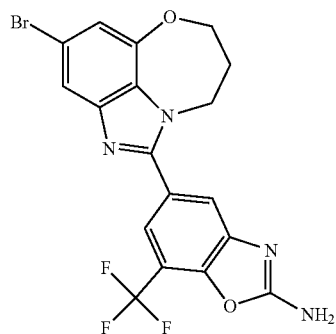 [SMILES: Nc1nc2cc(-c3nc4cc(Br)cc5c4n3CCCO5)cc(C(F)(F)F)c2o1]

The title compound (105 mg, 19% yield) was obtained from 4-bromo-1-iodo-8,9-dihydro-7H-6-oxa-2,9a-diazabenzo[cd]azulene (472 mg, 1.25 mmol) and 5-bromo-7-(trifluoromethyl)benzo[d]oxazol-2-amine (350 mg, 1.25 mmol) following a procedure analogous to Example 205 LCMS (ESI): [M+H]⁺=453.

Step 3: (S)-2-((1-(2-Amino-7-(trifluoromethyl) benzo[d]oxazol-5-yl)-8,9-dihydro-7H-6-oxa-2,9a-diazabenzo[cd]azulen-4-yl)amino)-2-cyclopropylacetic acid

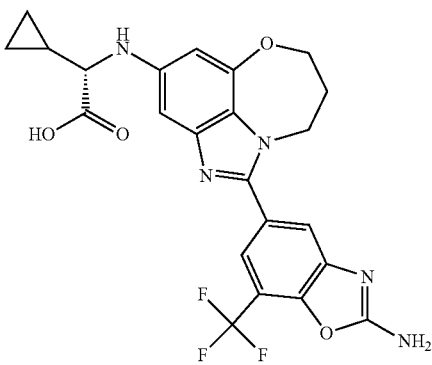 [SMILES: Nc1nc2cc(-c3nc4cc(N[C@H](C(=O)O)C5CC5)cc5c4n3CCCO5)cc(C(F)(F)F)c2o1]

The title compound was generated from 5-(4-bromo-8,9-dihydro-7H-6-oxa-2,9a-diazabenzo[cd]azulen-1-yl)-7-(trifluoromethyl)benzo[d]oxazol-2-amine (105 mg, 0.23 mmol) and (S)-2-amino-2-cyclopropylacetic acid (66.7 mg, 0.58 mmol) following a procedure analogous to Example 125, step 3. LCMS (ESI): [M+H]$^+$=488.

Step 4

235 (3.0 mg, 2.3% yield) was generated from (S)-2-((1-(2-amino-7-(trifluoromethyl)benzo[d]oxazol-5-yl)-8,9-dihydro-7H-6-oxa-2,9a-diazabenzo[cd]azulen-4-yl)amino)-2-cyclopropylacetic acid (129 mg, 0.265 mmol) following a procedure analogous to Example 125, step 4. LCMS (ESI): $R_T$ (min)=2.89 min, [M+H]$^+$: 487, method=A; $^1$H NMR (400 MHz, MeOD-d$_4$): δ 7.75 (s, 1H), 7.61 (s, 1H), 6.50 (d, J=2.0 Hz, 1H), 6.34 (d, J=2.0 Hz, 1H), 4.42-4.36 (m, 2H), 4.26 (t, J=2.0 Hz, 2H), 3.14 (d, J=8.6 Hz, 1H), 2.37-2.30 (m, 2H), 1.23-1.13 (m, 1H), 0.69-0.57 (m, 3H), 0.45-0.37 (m, 1H).

Example 236 (S)-1-(1-(2-Aminobenzo[d]oxazol-5-yl)-8,9-dihydro-7H-6-oxa-2,9a-diazabenzo[cd]azulen-4-yl)-N-(4-methoxybenzyl)pyrrolidine-2-carboxamide 236

236 was prepared from (S)-1-(1-(2-aminobenzo[d]oxazol-5-yl)-8,9-dihydro-7H-6-oxa-2,9a-diazabenzo[cd]azulen-4-yl)pyrrolidine-2-carboxylic acid following a procedure analogous to Example 104, step 2 using 4-methoxybenzylamine. LCMS (ESI): $R_T$ (min)=3.539, [M+H]$^+$=539.3, method=B; $^1$H NMR (400 MHz, DMSO-d$_6$) δ 8.35 (t, J=6.2 Hz, 1H), 7.60-7.51 (m, 3H), 7.48 (d, J=8.2 Hz, 1H), 7.36 (dd, J=8.2, 1.7 Hz, 1H), 7.17-7.09 (m, 2H), 6.85-6.76 (m, 2H), 6.40 (d, J=2.1 Hz, 1H), 6.09 (d, J=2.1 Hz, 1H), 4.41-4.32 (m, 2H), 4.29-4.23 (m, 2H), 4.20 (d, J=6.2 Hz, 2H), 3.97 (dd, J=9.3, 2.3 Hz, 1H), 3.69 (s, 3H), 3.66-3.58 (m, 1H), 3.25-3.15 (m, 1H), 2.34-2.18 (m, 3H), 2.06-1.88 (m, 3H).

Example 237 (S)-1-(1-(3-Oxo-2,3-dihydrobenzo[d]isoxazol-6-yl)-8,9-dihydro-7H-6-oxa-2,9a-diazabenzo[cd]azulen-4-yl)pyrrolidine-2-carboxamide 237

237 was prepared following procedures analogous to those of Example 158. LCMS (ESI): $R_T$ (min)=1.22,

[M+H]$^+$=420, Method=C; $^1$H NMR (300 MHz, DMSO-d$_6$) δ 11.89-11.80 (m, 1H), 7.70-7.69 (m, 1H), 7.58-7.55 (m, 1H), 7.30 (s, 1H), 7.24-7.21 (m, 1H), 7.03 (s, 1H), 6.35-6.34 (m, 1H), 6.07 (d, J=2.1 Hz, 1H), 4.46-4.34 (m, 2H), 4.26-4.18 (m, 2H), 3.84-3.82 (m, 1H), 3.68-3.57 (m, 1H), 3.19-3.16 (m, 1H), 2.26-2.15 (m, 3H), 2.08-1.96 (m, 3H).

Example 238 (S)-2-(((R)-2-(2-Aminobenzo[d]oxazol-5-yl)-4-methyl-3,4-dihydro-5-oxa-1,2a-diazaacenaphthylen-7-yl)amino)-2-cyclopropylacetamide 238

Step 1: 2,5-Dibromo-3-nitrophenol

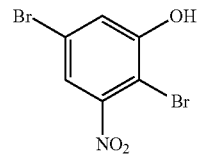 [SMILES: O=[N+]([O-])c1cc(Br)cc(O)c1Br]

To a suspension of 2-amino-5-bromo-3-nitrophenol (10.0 g, 42.9 mmol) in 48% aqueous hydrobromic acid (20 mL) at 0° C. was added dropwise a solution of sodium nitrite (3.15 g, 45.1 mmol) in water (20 mL). The reaction mixture was stirred at 0° C. for 15 min. Copper(II) bromide (4.79 g, 21.5 mmol) in 48% aqueous hydrobromic acid (20 mL) was then added dropwise and the reaction mixture was stirred at 0° C. for 15 min and then at 100° C. for 2 h. The resultant mixture was diluted with water and extracted with ethyl acetate. The combined organic extracts were washed with brine, dried over magnesium sulfate and concentrated in vacuo. The product was purified via flash chromatography on silica gel (solvent gradient, 0-100% ethyl acetate in cyclohexane) to yield 6.28 g (49%) of the title compound as an orange solid. $^1$H NMR (400 MHz, CDCl$_3$) δ 7.62 (d, J=2.2 Hz, 1H), 7.42 (d, J=2.2 Hz, 1H), 6.17 (br s, 1H).

Step 2: tert-Butyl (R)-(2-(2,5-dibromo-3-nitrophenoxy)propyl)carbamate

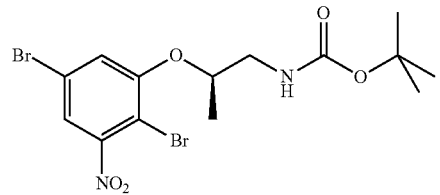 [SMILES: C[C@H](CNC(=O)OC(C)(C)C)Oc1cc(Br)cc([N+](=O)[O-])c1Br]

To a solution of 2,5-dibromo-3-nitrophenol (1.0 g, 3.40 mmol), N-Boc-(S)-1-amino-2-propanol (708 mg, 4.0 mmol) and triphenylphosphine (1.24 g, 4.70 mmol) in THF (6.0 mL) at room temperature was added dropwise, diisopropylazodicarboxylate (0.86 mL, 4.4 mmol) and the reaction mixture was stirred at room temperature for 1 h. The resultant mixture was concentrated in vacuo and the residue purified via flash chromatography on silica gel (solvent gradient, 0-50% ethyl acetate in cyclohexane) to yield 1.61 g (>100%) of the title compound as a yellow oil. LCMS (ESI): [M+H-100]$^+$=353/355/357.

Step 3: (R)-7-Bromo-2-methyl-5-nitro-3,4-dihydro-2H-benzo[b][1,4]oxazine

tert-Butyl (R)-(2-(2,5-dibromo-3-nitrophenoxy)propyl)carbamate (1.61 g, 3.60 mmol) was dissolved in hydrochloric acid (4 N in 1,4-dioxane, 12 mL, 48 mmol) and the reaction mixture was stirred at 50° C. for 1 h. The resulting mixture was concentrated in vacuo and the residue dissolved in DMF (7.0 mL). Potassium carbonate (1.23 g, 8.9 mmol) was added and the reaction mixture stirred at 90° C. for 2 h. The resulting mixture was diluted with water and extracted with ethyl acetate. The combined organic extracts were washed with brine, dried over magnesium sulfate and evaporated in vacuo to yield 1.19 g (>100%) of the title product as a bright red solid. This material was carried forward without purification. $^1$H NMR (400 MHz, CDCl$_3$) δ 7.90 (d, J=2.0 Hz, 1H), 7.88 (br s, 1H), 7.09 (dd, J=2.3, 0.6 Hz, 1H), 4.23-4.14 (m, 1H), 3.60 (ddd, J=12.5, 4.4, 2.7 Hz, 1H), 3.29 (ddd, J=12.6, 8.3, 1.3 Hz, 1H), 1.42 (d, J=6.1 Hz, 3H).

Step 4: (R)-7-Bromo-2-methyl-3,4-dihydro-2H-benzo[b][1,4]oxazin-5-amine

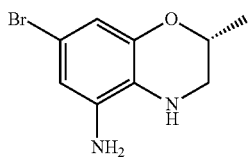

To a suspension of (R)-7-bromo-2-methyl-5-nitro-3,4-dihydro-2H-benzo[b][1,4]oxazine (968 mg, 3.50 mmol) in methanol (10 mL) and water (10 mL) was added iron powder (1.12 g, 21.3 mmol) and ammonium chloride (1.7 g, 31.9 mmol) and the reaction mixture stirred at 80° C. for 30 min. The resulting mixture was filtered and the solids thoroughly washed with ethyl acetate. The filtrate was extracted with ethyl acetate and the combined organic extracts were washed with brine, dried over magnesium sulfate and concentrated in vacuo to yield 860 mg (99%) of the title compound as a brown oil. This material was carried forward without purification. $^1$H NMR (400 MHz, CDCl$_3$) δ 6.52 (d, J=2.1 Hz, 1H), 6.45 (d, J=2.1 Hz, 1H), 4.13-4.05 (m, 1H), 3.37 (dd, J=12.4, 2.2 Hz, 1H), 2.99 (dd, J=12.4, 8.1 Hz, 1H), 1.34 (d, J=6.2 Hz, 3H).

Step 5: (R)-7-Bromo-4-methyl-3,4-dihydro-5-oxa-1,2a-diazaacenaphthylene

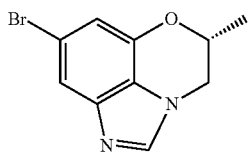

(R)-7-Bromo-2-methyl-3,4-dihydro-2H-benzo[b][1,4]oxazin-5-amine (861 mg, 3.54 mmol) was dissolved in trimethylorthoformate (5.0 mL, 45.7 mmol) and the reaction mixture was heated at 100° C. for 30 min. The resulting mixture was loaded directly onto diatomaceous earth and the product purified via flash chromatography on silica gel (solvent gradient, 0-5% methanol in DCM) to yield 735 mg (82%) of the title compound as an off-white solid. LCMS (ESI): [M+H]$^+$=253/255.

Step 6: (R)-7-Bromo-2-iodo-4-methyl-3,4-dihydro-5-oxa-1,2a-diazaacenaphthylene

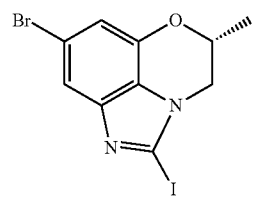

To a solution of diisopropylamine (0.65 mL, 4.65 mmol) in THF (3.0 mL) at −40° C. was added, dropwise n-butyllithium (0.58 mL, 2.5 N in hexanes, 1.46 mmol). The reaction mixture was allowed to warm to −20° C. and then cooled to −78° C. A solution of (R)-7-bromo-4-methyl-3,4-dihydro-5-oxa-1,2a-diazaacenaphthylene (735 mg, 2.9 mmol) in THF (6.0 mL) was added dropwise and the reaction mixture stirred at −78° C. for 2 h. A solution of iodine (1.03 g, 4.1 mmol) in THF (6.0 mL) was added and the reaction mixture was stirred at −78° C. for 3 h. The resulting mixture was quenched with water and extracted with ethyl acetate. The combined organic extracts were washed with brine, dried over magnesium sulfate and evaporated in vacuo. The residue was purified via flash chromatography on silica gel (solvent gradient, 0-100% ethyl acetate in cyclohexane) to yield 378 mg (34%) of the title compound as a beige solid. $^1$H NMR (400 MHz, CDCl$_3$) δ 7.46 (d, J=1.2 Hz, 1H), 6.87 (d, J=1.2 Hz, 1H), 4.51-4.41 (m, 1H), 4.19 (dd, J=12.7, 2.9 Hz, 1H), 3.83 (dd, J=12.7, 9.2 Hz, 1H), 1.61 (d, J=6.4 Hz, 3H).

Step 7: (R)-5-(7-Bromo-4-methyl-3,4-dihydro-5-oxa-1,2a-diazaacenaphthylen-2-yl)benzo[d]oxazol-2-amine

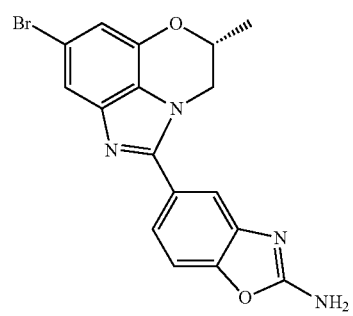 [SMILES: C[C@@H]1Cn2c(-c3ccc4oc(N)nc4c3)nc3cc(Br)cc(c32)O1]

A mixture of tetrakis(triphenylphosphine)palladium(0) (32 mg, 0.03 mmol), cesium carbonate (180 mg, 0.55 mmol), 5-(4,4,5,5-tetramethyl-1,3,2-dioxaborolan-2-yl)-1, 3-benzoxazol-2-amine (154 mg, 0.60 mmol) and (R)-7-bromo-2-iodo-4-methyl-3,4-dihydro-5-oxa-1,2a-diazaacenaphthylene (150 mg, 0.40 mmol) in 1,4-dioxane (2.5 mL) and water (0.5 mL) were sealed in a vial and degassed with argon and the reaction mixture was heated at 100° C. for 16 h. The resultant mixture was diluted with water and extracted with ethyl acetate. The organic extracts were washed with brine, dried over magnesium sulfate and evaporated in vacuo. The resultant residue was purified via flash chromatography on silica gel (solvent gradient, 0-7% methanol in DCM) to yield 50 mg (30%) of the title compound as an off white solid. LCMS (ESI): [M+H]$^+$=385/387.

Step 8: (S)-2-(((R)-2-(2-Aminobenzo[d]oxazol-5-yl)-4-methyl-3,4-dihydro-5-oxa-1,2a-diazaacenaphthylen-7-yl)amino)-2-cyclopropylacetic acid

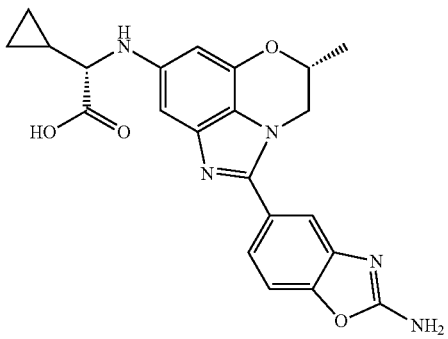 [SMILES: C[C@@H]1Cn2c(-c3ccc4oc(N)nc4c3)nc3cc(N[C@H](C(=O)O)C4CC4)cc(c32)O1]

A mixture of (R)-5-(7-bromo-4-methyl-3,4-dihydro-5-oxa-1,2a-diazaacenaphthylen-2-yl)benzo[d]oxazol-2-amine (145 mg, 0.38 mmol), (2S)-2-amino-2-cyclopropylacetic acid (87 mg, 0.75 mmol), copper (I) iodide (14 mg, 0.08 mmol) and potassium phosphate tribasic (160 mg, 0.75 mmol) in DMSO (2.0 mL) were degassed with argon and the reaction mixture was heated at 110° C. for 16 h. The resultant mixture was diluted with DCM (40 mL) and purified directly via flash chromatography on silica gel (solvent gradient, 0-50% 2 N ammonia in methanol, in DCM) to yield 168 mg (106%) of the title compound as a yellow oil. LCMS (ESI): [M+H]$^+$=420.

Step 9

To a mixture of (S)-2-(((R)-2-(2-aminobenzo[d]oxazol-5-yl)-4-methyl-3,4-dihydro-5-oxa-1,2a-diazaacenaphthylen-7-yl)amino)-2-cyclopropylacetic acid (164 mg, 0.39 mmol), ammonium chloride (42 mg, 0.78 mmol) and triethylamine (0.16 mL, 1.17 mmol) in DMF (3.0 mL) was added HATU (223 mg, 0.59 mmol) and the reaction mixture stirred at room temperature for 30 min. The reaction mixture was diluted with water and extracted with ethyl acetate. The combined organic extracts were washed with brine, dried over magnesium sulfate and concentrated in vacuo. The residue was purified by via reverse-phase HPLC to yield 9 mg (6%) of 238 as a white solid. LCMS (ESI): R$_T$ (min)= 2.50 min, [M+H]$^+$: 419, method=A; $^1$H NMR (400 MHz, DMSO-d$_6$): δ 8.17 (s, 1H), 7.68 (d, J=1.2 Hz, 1H), 7.56 (br s, 2H), 7.53 (dd, J=8.1, 1.8 Hz, 1H), 7.46 (d, J=8.1 Hz, 1H), 7.36 (d, J=1.8 Hz, 1H), 6.97 (d, J=1.7 Hz, 1H), 6.27 (d, J=1.4 Hz, 1H), 6.21 (d, J=1.4 Hz, 1H), 4.64 (dd, J=12.6, 2.8 Hz, 1H), 4.42-4.33 (m, 1H), 4.19 (dd, J=12.7, 9.2 Hz, 1H), 3.13 (d, J=8.3 Hz, 1H), 1.47 (d, J=6.2 Hz, 3H).

Example 239 (S)-1-(1-(2-Aminobenzo[d]thiazol-6-yl)-7,8,9,10-tetrahydro-6-oxa-2,10a-diazacycloocta[cd]inden-4-yl)pyrrolidine-2-carboxamide 239

239 was prepared following procedures analogous to those of Example 214. LCMS (ESI): R$_T$ (min)=4.5, [M+H]$^+$= 449, method=D; $^1$H NMR (300 MHz, DMSO-d$_6$) δ 8.00 (d, J=1.6 Hz, 1H), 7.74 (s, 2H), 7.62-7.43 (m, 2H), 7.43-7.32 (m, 1H), 7.21-7.01 (m, 1H), 6.46 (d, J=1.9 Hz, 1H), 6.23 (d, J=2.0 Hz, 1H), 4.39 (d, J=6.2 Hz, 2H), 4.23-4.20 (m, 2H), 4.00-3.76 (m, 1H), 3.69-3.52 (m, 1H), 3.19 (d, J=9.0 Hz, 1H), 2.25-2.11 (m, 3H), 2.03-1.88 (m, 3H), 1.70 (s, 2H).

Example 240 (S)-2-((1-(2-Aminobenzo[d]oxazol-5-yl)-3-fluoro-8,9-dihydro-7H-6-oxa-2,9a-diazabenzo[cd]azulen-4-yl)oxy)propanamide 240

Step 1: 5-(3-Fluoro-4-(4,4,5,5-tetramethyl-1,3,2-dioxaborolan-2-yl)-8,9-dihydro-7H-6-oxa-2,9a-diazabenzo[cd]azulen-1-yl)benzo[d]oxazol-2-amine

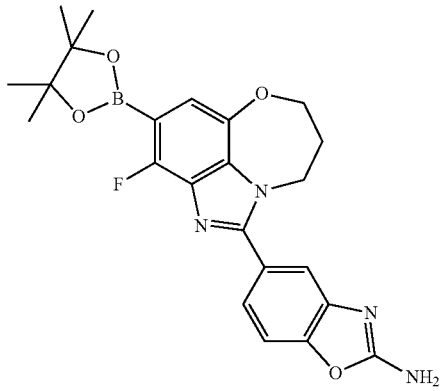 [SMILES: CC1(C)OB(c2cc3c4c(nc(-c5ccc6oc(N)nc6c5)n4CCCO3)c2F)OC1(C)C]

5-(4-Bromo-3-fluoro-8,9-dihydro-7H-6-oxa-2,9a-diazabenzo[cd]azulen-1-yl)benzo[d]oxazol-2-amine (530 mg, 1.30 mmol), bis(pinacolato)diboron (495 mg, 1.95 mmol), potassium acetate (382 mg, 3.90 mmol) and 1,1'-bis(diphenylphosphino)ferrocenyl palladium (II) dichloride (106 mg, 0.13 mmol) were suspended in 1,4-dioxane (10 mL) under an atmosphere of nitrogen and the reaction was stirred at 110° C. for 6 h. The resultant mixture was allowed to warm to room temperature, the solvent was evaporated and the residue was partitioned between ethyl acetate and water, filtered through a celite pad. The organic phase was washed with brine, dried over sodium sulfate and the solvent was evaporated. The residue was used directly in the next step without further purification. LCMS (ESI): [M+H]$^+$=450/451/452.

Step 2: 1-(2-Aminobenzo[d]oxazol-5-yl)-3-fluoro-8,9-dihydro-7H-6-oxa-2,9a-diazabenzo[cd]azulen-4-ol

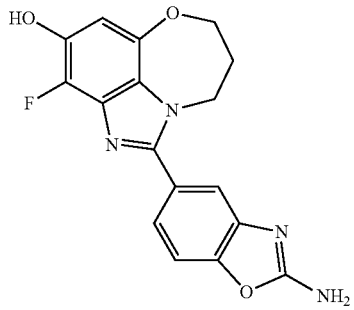 [SMILES: Nc1nc2cc(-c3nc4c(F)c(O)cc5c4n3CCCO5)ccc2o1]

To a solution of 5-(3-fluoro-4-(4,4,5,5-tetramethyl-1,3,2-dioxaborolan-2-yl)-8,9-dihydro-7H-6-oxa-2,9a-diazabenzo[cd]azulen-1-yl)benzo[d]oxazol-2-amine (crude, assume 1.30 mmol) in ethanol (15 mL) was added hydroxylamine hydrochloride (271 mg, 3.90 mmol) and sodium hydroxide (208 mg, 5.20 mmol) and the reaction mixture was stirred at room temperature for 18 h. The resulting mixture was diluted with methanol, acidified with 1 N hydrochloric acid and then loaded onto a 10 g SCX-2 cartridge. The cartridge was washed thoroughly with methanol and then eluted with 2 N ammonia in methanol. The eluent was collected and the solvent evaporated. The residue was purified via flash chromatography on silica gel (solvent gradient: 5-10% 2 N ammonia in methanol, in DCM) to yield 152 mg (34% over 2 steps) of the title compound as a light brown solid. LCMS (ESI): [M+H]$^+$=341.

Step 3

To a solution of 1-(2-aminobenzo[d]oxazol-5-yl)-3-fluoro-8,9-dihydro-7H-6-oxa-2,9a-diazabenzo[cd]azulen-4-ol (159 mg, 0.47 mmol) in DMF (5.0 mL) was added potassium carbonate (105 mg, 0.75 mmol) and toluene-4-sulfonic acid (R)-1-carbamoylethyl ester (135 mg, 0.55 mmol) and the reaction mixture was stirred at 80° C. for 6 h. Further potassium carbonate (42 mg, 0.3 mmol) and toluene-4-sulfonic acid (R)-1-carbamoylethyl ester (34 mg, 0.14 mmol) were added and the reaction was stirred at 80° C. for a further 18 h. The resultant mixture was allowed to warm to room temperature and partitioned between ethyl acetate and water. The aqueous layer was further extracted with ethyl acetate. The combined organic extracts were washed with brine, dried over sodium sulfate and evaporated. The residue was purified via reverse-phase HPLC, then by chiral SFC and lyophilized to yield 38 mg (25% yield) of 240 as a white solid. LCMS (ESI): R$_T$ (min)=2.56, [M+H]$^+$=412, method=A; $^1$H NMR (400 MHz, DMSO-d$_6$) δ 7.60 (s, 2H), 7.57 (d, J=1.3 Hz, 1H), 7.50 (d, J=8.1 Hz, 1H), 7.49 (s, 1H), 7.38 (dd, J=8.1, 1.3 Hz, 1H), 7.27 (s, 1H), 6.57 (d, J=6.3 Hz, 1H), 4.57 (q, J=6.8 Hz, 1H), 4.39-4.34 (m, 2H), 4.28 (t, J=5.5 Hz, 2H), 2.32-2.25 (m, 2H), 1.44 (d, J=6.8 Hz, 3H).

Example 241 (S)-2-((1-(2-Amino-4-fluorobenzo[d]oxazol-5-yl)-'7,8,9,10-tetrahydro-6-oxa-2,10a-diazacycloocta[cd]inden-4-yl)oxy)propanamide 241

241 was prepared following procedures analogous to those of Example 249. LCMS (ESI): R$_T$ (min)=1.17, [M+H]$^+$=426, method=D; $^1$H NMR (300 MHz, DMSO-d$_6$) δ 7.81 (s, 2H), 7.54 (s, 1H), 7.38 (d, J=8.4 Hz, 1H), 7.25 (s, 1H), 7.17-7.12 (m, 1H), 6.94 (d, J=2.1 Hz, 1H), 6.63 (d, J=2.1 Hz, 1H), 4.66-4.60 (m, 1H), 4.22-4.21 (m, 4H), 2.05-1.85 (m, 2H), 1.70-1.55 (m, 2H), 1.45 (d, J=6.6 Hz, 3H).

Example 242 (S)-2-((1-(2-Amino-4-fluorobenzo[d]thiazol-6-yl)-7,8,9,10-tetrahydro-6-oxa-2,10a-diazacycloocta[cd]inden-4-yl)oxy)propanamide 242

Step 1: 6-Bromo-4-fluorobenzo[d]thiazol-2-amine

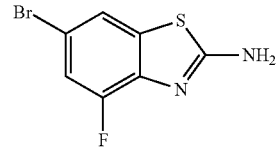

A mixture of 4-bromo-2-fluorobenzenamine (144 g, 758 mmol), acetic acid (1000 mL) and potassium thiocyanate (243 g, 2.50 mol) was stirred for 15 min at room temperature. Then a solution of bromine (243 g, 1.52 mol) in acetic acid (200 mL) was added dropwise to the mixture. The reaction mixture was stirred for 16 h at room temperature then diluted with water. The mixture was adjusted to ca. pH 7 with aqueous sodium hydroxide. The mixture was extracted ethyl acetate, washed with brine, dried over anhydrous sodium sulfate and evaporated in vacuo. The resultant residue was purified via flash chromatography on silica gel (solvent gradient: 0-20% ethyl acetate in petroleum ether) to yield 46.7 g (25%) of the title compound as an off-white solid. LCMS (ESI): [M+H]$^+$=247/249. $^1$H NMR (300 MHz, DMSO-d$_6$) δ 7.87 (s, 2H), 7.78 (d, J=2.0 Hz, 1H), 7.38-7.34 (m, 1H).

Step 2: 6-Bromo-4-fluoro-N,N-bis(4-methoxybenzyl)benzo[d]thiazol-2-amine

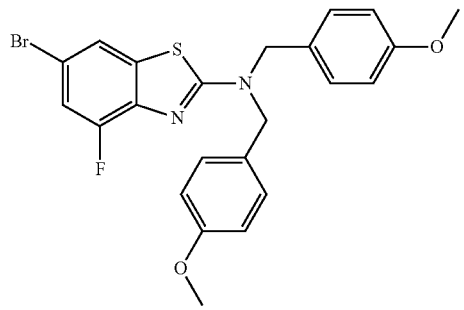 [SMILES: COc1ccc(CN(Cc2ccc(OC)cc2)c2nc3c(F)cc(Br)cc3s2)cc1]

A mixture of 6-bromo-4-fluorobenzo[d]thiazol-2-amine (16.2 g, 65.5 mmol), potassium carbonate (33.8 g, 244 mmol), and 1-(chloromethyl)-4-methoxybenzene (33.0 g, 210 mmol) in DMF (350 mL) was heated at 60° C. for 16 h. The reaction mixture was diluted with water, extracted with ethyl acetate, washed with brine, dried over anhydrous sodium sulfate and evaporated in vacuo. The resultant residue was purified via flash chromatography on silica gel (solvent gradient: 0-10% ethyl acetate in petroleum ether) to yield 20.2 g (51%) of the title compound as a light yellow solid. LCMS (ESI): [M+H]⁺=487/489. ¹H NMR (300 MHz, DMSO-d₆) δ 7.87-7.84 (m, 1H), 7.46-7.41 (m, 1H), 7.26-7.22 (m, 4H), 6.94-6.84 (m, 4H), 4.69 (s, 4H), 3.73 (s, 6H).

Step 3: 4-Fluoro-N, N-bis(4-methoxybenzyl)-6-(4,4,5,5-tetramethyl-1,3,2-dioxaborolan-2-yl)benzo[d]thiazol-2-amine

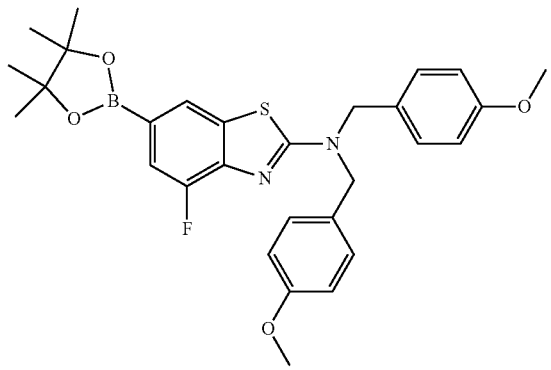

The title compound (14.2 g, 64% yield) was generated from 6-bromo-4-fluoro-N,N-bis(4-methoxybenzyl)benzo[d]thiazol-2-amine (20.2 g, 41.4 mmol) following a procedure analogous to Example 204, Step 7. LCMS (ESI): [M+H]⁺= 535. ¹H NMR (400 MHz, DMSO-d₆) δ 7.86 (s, 1H), 7.33-7.20 (m, 5H), 6.91 (d, J=8.5 Hz, 4H), 4.70 (s, 4H), 3.73 (s, 6H), 1.29 (s, 12H).

Step 4: 6-(4-Bromo-7,8,9,10-tetrahydro-6-oxa-2,10a-diazacycloocta[cd]inden-1-yl)-4-fluoro-N,N-bis(4-methoxybenzyl)benzo[d]thiazol-2-amine

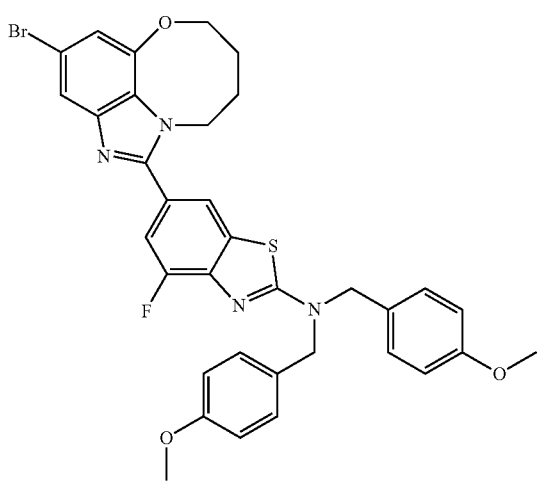 [SMILES: COc1ccc(CN(Cc2ccc(OC)cc2)c2nc3c(F)cc(-c4nc5cc(Br)cc6c5n4CCCCO6)cc3s2)cc1]

A mixture of 4-bromo-1-iodo-7,8,9,10-tetrahydro-6-oxa-2,10a-diazacycloocta[cd]indene (Example 204, step 6) (320 mg, 0.814 mmol), 4-fluoro-N,N-bis(4-methoxybenzyl)-6-(4,4,5,5-tetramethyl-1,3,2-dioxaborolan-2-yl)benzo[d]thiazol-2-amine (430 mg, 0.805 mmol), 1,1'-bis(diphenylphosphino)ferrocenyl palladium (II) dichloride (116 mg, 0.159 mmol), and cesium carbonate (767 mg, 2.35 mmol) in 1,4-dioxane (10 mL) and water (2 mL) was degassed with nitrogen. The reaction mixture was heated under microwave irradiation for 1 h at 100° C. This procedure was repeated separately 29 times. The separate reaction mixtures were combined, diluted with water, extracted with DCM, washed with brine, dried over anhydrous sodium sulfate and evaporated in vacuo. The resultant residue was purified via flash chromatography on silica gel (solvent gradient: 0-30% ethyl acetate in petroleum ether) to yield 11.5 g (69.9%) of the title compound as a yellow solid. LCMS (ESI): [M+H]⁺=673/675.

Step 5: (S)-2-((1-(2-(Bis(4-methoxybenzyl)amino)-4-fluorobenzo[d]thiazol-6-yl)-7,8,9,10-tetrahydro-6-oxa-2,10a-diazacycloocta[cd]inden-4-yl)oxy)propanamide

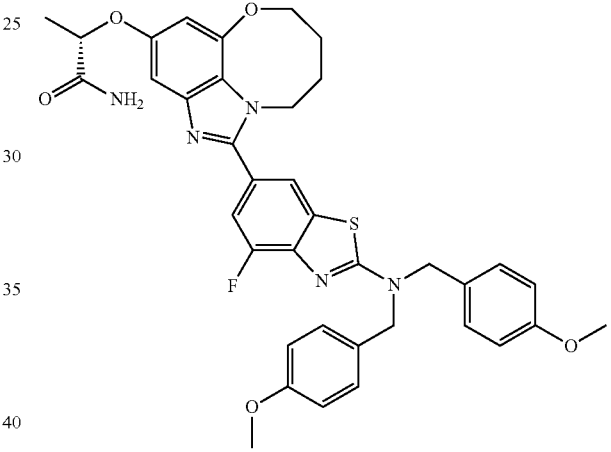

The title compound (1.3 g, 43.3% yield over four steps) was generated from 6-(4-bromo-7,8,9,10-tetrahydro-6-oxa-2,10a-diazacycloocta[cd]inden-1-yl)-4-fluoro-N,N-bis(4-methoxybenzyl)benzo[d]thiazol-2-amine (3 g, 4.45 mmol) following procedures analogous to those of Example 204, steps 9-12. LCMS (ESI): [M+H]⁺=682.

Step 6

A solution of (S)-2-((1-(2-(bis(4-methoxybenzyl)amino)-4-fluorobenzo[d]thiazol-6-yl)-7,8,9,10-tetrahydro-6-oxa-2,10a-diazacycloocta[cd]inden-4-yl)oxy)propanamide (1.30 g, 1.91 mmol) in TFA (20 mL) was heated at 90° C. for 2 h. The reaction mixture was evaporated in vacuo. The resultant residue was purified via flash chromatography on silica gel (solvent gradient: 0-10% methanol in DCM) followed by chiral-HPLC to yield 177.8 mg (21% yield) of 242 as a white solid. LCMS (ESI): R$_T$ (min)=1.26, [M+H]⁺=442, method D; ¹H NMR (300 MHz, DMSO-d₆) δ 7.94 (s, 2H), 7.84 (s, 1H), 7.50 (s, 1H), 7.39 (d, J=11.4 Hz, 1H), 7.22 (s, 1H), 6.92 (d, J=1.2 Hz, 1H), 6.59 (d, J=1.2 Hz, 1H), 4.66-4.59 (m, 1H), 4.47-4.36 (m, 2H), 4.29-4.20 (m, 2H), 2.19-2.06 (m, 2H), 1.75-1.60 (m, 2H), 1.45 (d, J=6.6 Hz, 3H).

Example 243 (S)-2-((1-(4-(1H-1,2,4-Triazol-3-yl)phenyl)-7,8,9,10-tetrahydro-6-oxa-2,10a-diazacycloocta[cd]inden-4-yl)oxy)propanamide 243

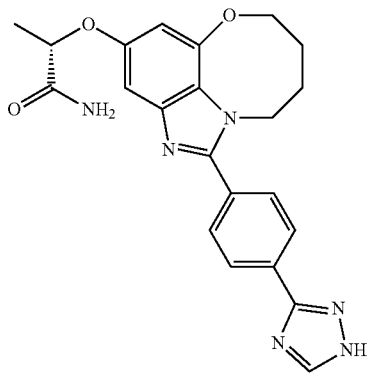 [SMILES: C[C@H](Oc1cc2c3c(c1)nc(-c1ccc(-c4nc[nH]n4)cc1)n3CCCCO2)C(N)=O]

243 was prepared using commercially available 3-(4-bromophenyl)-1H-1,2,4-triazole and following procedures analogous to those of Example 242. LCMS (ESI): $R_T$ (min)=1.02, [M+H]$^+$=419, method=F; $^1$H NMR (300 MHz, DMSO-d$_6$) δ 12.28 (br, 1H), 8.53 (s, 1H), 8.20 (d, J=8.4 Hz, 2H), 7.82 (d, J=8.4 Hz, 2H), 7.55 (s, 1H), 7.25 (s, 1H), 6.94 (d, J=2.1 Hz, 1H), 6.62 (d, J=2.1 Hz, 1H), 4.67-4.60 (m, 1H), 4.44-4.40 (m, 2H), 4.27-4.24 (m, 2H), 2.20-2.00 (m, 2H), 1.80-1.55 (m, 2H), 1.45 (d, J=6.6 Hz, 3H).

Example 244 (S)-2-((1-(2-Aminoquinoxalin-6-yl)-7,8,9,10-tetrahydro-6-oxa-2,10a-diazacycloocta[cd]inden-4-yl)oxy)propanamide 244

244 was prepared following procedures analogous to those of Example 204. LCMS (ESI): $R_T$ (min)=1.79, [M+H]$^+$=419, method=C; $^1$H NMR (300 MHz, DMSO-d$_6$) δ 8.37 (s, 1H), 8.01 (d, J=2.1 Hz, 1H), 7.89-7.86 (m, 1H), 7.65-7.62 (m, 1H), 7.54 (s, 1H), 7.25 (s, 3H), 6.95-6.94 (m, 1H), 6.61-6.60 (m, 1H), 4.66-4.60 (m, 1H), 4.47-4.43 (m, 2H), 4.42-4.27 (m, 2H), 2.17 (s, 2H), 1.72-1.71 (m, 2H), 1.45 (d, J=6.6 Hz, 3H).

Example 245 (R)-2-((1-(2-Aminobenzo[d]oxazol-5-yl)-7,8,9,10-tetrahydro-6-oxa-2,10a-diazacycloocta[cd]inden-4-yl)oxy)propanamide 245

245 was isolated as a minor epimer of Example 204 through chiral SFC. LCMS (ESI): $R_T$ (min)=1.47, [M+H]$^+$=408, method=D; $^1$H NMR (300 MHz, DMSO-d$_6$) δ 7.61-7.44 (m, 5H), 7.29-7.26 (m, 2H), 6.92 (d, J=2.1 Hz, 1H), 6.59 (d, J=2.1 Hz, 1H), 4.66-4.59 (m, 1H), 4.39-4.35 (m, 2H), 4.26-4.23 (m, 2H), 2.11 (apparent s, 2H), 1.69 (apparent s, 2H), 1.45 (d, J=8.8 Hz, 3H).

Example 246 (S)-2-((1-(2-Aminobenzo[d]thiazol-5-yl)-7,8,9,10-tetrahydro-6-oxa-2,10a-diazacycloocta[cd]inden-4-yl)amino)-2-cyclopropylacetamide 246

246 was prepared following procedures analogous to those of Example 214. LCMS (ESI): $R_T$ (min)=1.24, [M+H]$^+$=449, method=E; $^1$H NMR (300 MHz, DMSO-d$_6$) δ 7.81 (d, J=8.1 Hz, 1H), 7.66 (s, 2H), 7.54 (d, J=1.2 Hz, 1H), 7.41 (d, J=1.8 Hz, 1H), 7.29-7.25 (m, 1H), 7.01 (s, 1H), 6.46-6.39 (m, 2H), 5.59 (d, J=7.2 Hz, 1H), 4.37-4.27 (m, 2H), 4.23-4.14 (m, 2H), 3.15-3.09 (m, 1H), 2.15-2.05 (m, 2H), 1.75-1.63 (m, 2H), 1.15-1.08 (m, 1H), 0.58-0.42 (m, 3H), 0.40-0.28 (m, 1H).

Example 247 (S)-1-(1-(2-Aminobenzo[d]oxazol-5-yl)-3-fluoro-7,8,9,10-tetrahydro-6-oxa-2,10a-diazacycloocta[cd]inden-4-yl)pyrrolidine-2-carboxamide 247

Step 1: 3-Bromo-2-fluoro-5-methoxy-6-nitroaniline

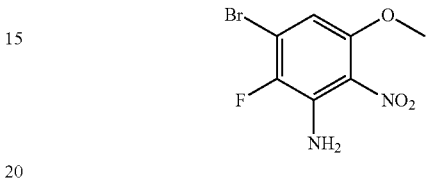

A solution of 1-bromo-2-fluoro-5-methoxy-4-nitrobenzene (10.0 g, 40 mmol) and 1,1,1-trimethylhydrazinium iodide (8.89 g, 44 mmol) in DMSO (50 mL) was added dropwise over 15 min to a solution of potassium tert-butoxide (10.77 g, 96.0 mmol) in DMSO (150 mL) cooled in an ice-water bath. The water bath was removed after the addition was complete and the reaction mixture was stirred at room temperature for 2 h. The reaction mixture was poured onto a mixture of 1 N hydrochloric acid (200 mL) and 30 g of ice and then extracted twice with ethyl acetate. The combined organic extracts were dried over sodium sulfate and the solvent was evaporated. The residue was purified via flash chromatography on silica gel (solvent gradient: 0-20% ethyl acetate in cyclohexane) to yield 1.73 g (16%) of the title compound as a bright yellow solid. $^1$H NMR (400 MHz, CDCl$_3$) δ 6.43 (d, J=5.4 Hz, 1H), 5.31 (br s, 2H), 3.87 (s, 3H).

Step 2: 4-Bromo-3-fluoro-6-methoxybenzene-1,2-diamine

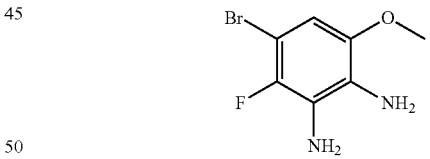

To a suspension of 3-bromo-2-fluoro-5-methoxy-6-nitroaniline (1.73 g, 6.53 mmol) in ethanol (21 mL) and THF (7.0 mL) was added a solution of ammonium chloride (3.14 g, 58.8 mmol) in water (14 mL) followed by iron powder (2.19 g, 39.2 mmol). The reaction was stirred at 100° C. for 1 h and then allowed to warm to room temperature. The reaction mixture was diluted with ethyl acetate and water, then filtered through a celite pad, eluting with ethyl acetate. The filtrate was collected, the phases separated and the organic extracts washed with brine, dried over sodium sulfate and the solvent evaporated. The residue was purified via flash chromatography on silica gel (solvent gradient: 30% ethyl acetate in cyclohexane) to yield 1.34 g (88%) of the title compound as an off-white solid. LCMS (ESI): [M+H]$^+$=235/237.

Step 3: 5-Bromo-4-fluoro-7-methoxy-1H-benzo[d]imidazole

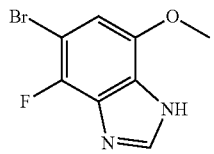

To a solution of 4-bromo-3-fluoro-6-methoxybenzene-1,2-diamine (1.34 g, 5.70 mmol) in trimethylorthoformate (40 mL) was added p-toluenesulfonic acid (49 mg, 0.29 mmol). The reaction mixture was stirred at 100° C. for 1 h and the allowed to cool to room temperature. The solvent was evaporated and the residue was triturated with DCM/methanol, filtered and dried to yield 1.18 g (84%) of the title compound as a white solid. LCMS (ESI): [M+H]$^+$=245/247.

Step 4: 5-Bromo-4-fluoro-1H-benzo[d]imidazol-7-ol

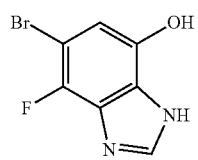 [SMILES: Oc1cc(Br)c(F)c2nc[nH]c12]

To a solution of 5-bromo-4-fluoro-7-methoxy-1H-benzo[d]imidazole (2.00 g, 8.16 mmol) in DCM (75 mL) at 20° C. was added boron tribromide (1 N in DCM) (32.6 mL, 32.6 mmol) and the reaction mixture was stirred at 40° C. Further boron tribromide (8.20 mmol) was added after 16 h and additional boron tribromide (8.20 mmol) was added after 40 h. After 64 h the mixture was cooled in an ice bath, then cautiously quenched with methanol. The resulting mixture was washed twice with brine. The combined aqueous extracts were treated with 1 N sodium hydroxide (50 ml) to reach ca. pH 5, then treated with saturated aqueous sodium hydrogen carbonate. A precipitate formed and the mixture was filtered and the solid collected. The aqueous layer was further extracted twice with DCM and the organic extracts combined and the solvent removed. The residue from the extraction was combined with filtered precipitate and dried to yield 1.22 g (65%) of the title compound as an off-white solid. LCMS (ESI): [M+H]$^+$=231/233.

Step 5: 4-Bromo-3-fluoro-7,8,9,10-tetrahydro-6-oxa-2,10a-diazacycloocta[cd]indene

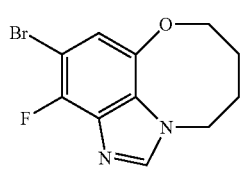 [SMILES: Fc1c(Br)cc2c3c1ncn3CCCCO2]

To a solution of 5-bromo-4-fluoro-1H-benzo[d]imidazol-7-ol (1.22 g, 5.28 mmol) in DMF (50 mL) was added potassium carbonate (1.85 g, 13.2 mmol) then 1,4-dibromobutane (0.69 mL, 5.81 mmol) under nitrogen and the mixture was stirred at 100° C. for 16 h. The resulting mixture was allowed to cool to room temperature, the solvent was evaporated and the residue was partitioned between ethyl acetate and water. The aqueous phase was further extracted with ethyl acetate. The combined organic extracts were washed with brine, dried over sodium sulfate and the solvent evaporated. The residue was purified via flash chromatography on silica gel (solvent gradient: 60-70% ethyl acetate in cyclohexane) to yield 728 mg (48%) of the title compound as a white solid. LCMS (ESI): [M+H]$^+$=285/287.

Step 6: 4-Bromo-3-fluoro-1-iodo-7,8,9,10-tetrahydro-6-oxa-2,10a-diazacycloocta[cd]indene

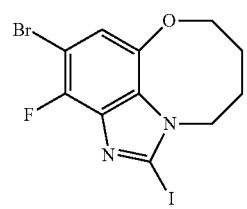 [SMILES: Fc1c(Br)cc2c3c1nc(I)n3CCCCO2]

To a solution of diisopropylethylamine (0.56 mL, 4.03 mmol) in THF (4.0 mL) at −20° C. was added n-butyllithium (1.6 N in hexanes, 2.52 mL, 4.03 mmol) under nitrogen and the reaction mixture was stirred at −20° C. for 30 min before cooling to −50° C. To this solution, was added dropwise, a solution of 4-bromo-3-fluoro-7,8,9,10-tetrahydro-6-oxa-2,10a-diazacycloocta[cd]indene (718 mg, 2.52 mmol) in THF (16 mL). The mixture was stirred at −50° C. for 1 h and allowed to warm to −25° C. and then aged at −25° C. for 3 h. The reaction mixture was cooled to −50° C. and a solution of iodine (1.11 g, 4.41 mmol) in THF (8.0 mL) was added dropwise and the reaction mixture was stirred at −50° C. for 30 min, then allowed to warm to room temperature and stirred for 1 h. The resultant mixture was quenched with aqueous sodium thiosulfate and diluted with ethyl acetate. The organic extracts were washed with brine, dried over sodium sulfate and the solvent was evaporated. The residue was purified via flash chromatography on silica gel (solvent gradient: 20-50% ethyl acetate in cyclohexane). The residue was triturated with cyclohexane to yield 378 mg (37%) of the title compound as a beige solid. LCMS (ESI): [M+H]$^+$=411/413.

Step 7: 5-(4-Bromo-3-fluoro-7,8,9,10-tetrahydro-6-oxa-2,10a-diazacycloocta[cd]inden-1-yl)benzo[d]oxazol-2-amine

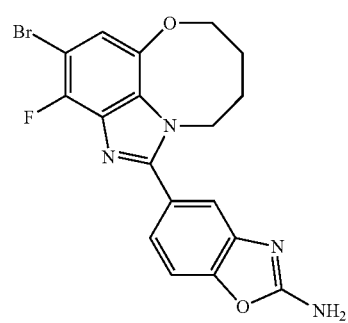 [SMILES: Nc1nc2cc(-c3nc4c(F)c(Br)cc5c4n3CCCCO5)ccc2o1]

4-Bromo-3-fluoro-1-iodo-7,8,9,10-tetrahydro-6-oxa-2, 10a-diazacycloocta[cd]indene (324 mg, 0.79 mmol), 5-(4,4,5,5-tetramethyl-1,3,2-dioxaborolan-2-yl)benzo[d]oxazol-2-amine (246 mg, 0.95 mmol) and 1,1'-bis(diphenylphosphino)ferrocenyl palladium (II) dichloride (96.8 mg, 0.12 mmol) were dissolved in DMF (5.0 mL). The flask was evacuated and flushed with nitrogen, then 2 N aqueous sodium carbonate (1.18 mL, 2.36 mmol) was added and the reaction mixture was stirred at 70° C. for 4 h. Further 1,1'-bis(diphenylphosphino)ferrocenyl palladium (II) dichloride (96.8 mg, 0.12 mmol) was then added and the reaction mixture was stirred for a further 1.5 h at 70° C., then allowed to cool to room temperature. The resulting mixture was partitioned between ethyl acetate and water and the aqueous layer was extracted with ethyl acetate. The combined organic extracts were washed with brine, dried over sodium sulfate and the solvent evaporated. The residue was purified via flash chromatography on silica gel (solvent gradient: 4% methanol in DCM) to yield 159 mg (43%) of the title compound as a light brown solid. LCMS (ESI): [M+H]$^+$=417/419.

Step 8

5-(4-Bromo-3-fluoro-7,8,9,10-tetrahydro-6-oxa-2,10a-diazacycloocta[cd]inden-1-yl)benzo[d]oxazol-2-amine (155 mg, 0.37 mmol), (2S)-pyrrolidine-2-carboxylic acid (171 mg, 1.49 mmol), copper (I) iodide (71 mg, 0.37 mmol) and potassium phosphate tribasic (473 mg, 2.23 mmol) were suspended in DMSO (4.0 mL) in a microwave vial. The vial was sealed, evacuated and flushed with nitrogen twice. The reaction mixture was heated in a microwave reactor at 120° C. for 2 h. The crude reaction mixture was allowed to cool to ambient temperature and was diluted with DMSO (2.0 mL). Triethylamine (0.52 mL, 3.71 mmol), ammonium chloride (79 mg, 1.48 mmol) and HATU (846 mg, 2.23 mmol) were added and the reaction mixture was stirred at 20° C. for 3 h. The resulting mixture was partitioned between ethyl acetate and water. A precipitate formed, so the mixture was filtered and the solid collected. The filtrate was also collected and the aqueous layer was extracted with ethyl acetate. The combined organic extracts were washed with brine, dried over sodium sulfate and the solvent was evaporated. The resultant residue and precipitate above were combined and purified via flash chromatography on silica gel (solvent gradient: 6-8% 2 N ammonia in methanol, in DCM) then re-purified via flash chromatography on silica gel (solvent: 7% 2 N ammonia in methanol, in DCM) to yield 36 mg (22%) of 247 as a beige solid. LCMS (ESI): R$_T$ (min)=2.58, [M+H]$^+$=451, method=A; $^1$H NMR (400 MHz, DMSO-d$_6$) δ 7.60 (s, 2H), 7.50 (d, J=8.1 Hz, 1H), 7.44 (d, J=1.3 Hz, 1H), 7.29 (dd, J=8.1, 1.3 Hz, 1H), 7.26 (br s, 1H), 6.96 (br s, 1H), 6.44 (d, J=6.5 Hz, 1H), 4.35 (t, J=5.5 Hz, 2H), 4.20 (t, J=5.5 Hz, 2H), 4.13-4.08 (m, 1H), 3.75-3.68 (m, 1H), 3.31-3.24 (m, 1H), 2.25-2.16 (m, 1H), 2.13-2.06 (m, 2H), 1.95-1.86 (m, 3H), 1.72-1.65 (m, 2H).

Example 248 (S)-2-((1-(2-Aminobenzo[d]thiazol-6-yl)-7,8,9,10-tetrahydro-6-oxa-2,10a-diazacycloocta[cd]inden-4-yl)oxy)propanamide 248

Step 1: (S)-tert-Butyl (6-(4-((1-amino-1-oxopropan-2-yl)oxy)-7,8,9,10-tetrahydro-6-oxa-2,10a-diazacycloocta[cd]inden-1-yl)benzo[d]thiazol-2-yl)carbamate

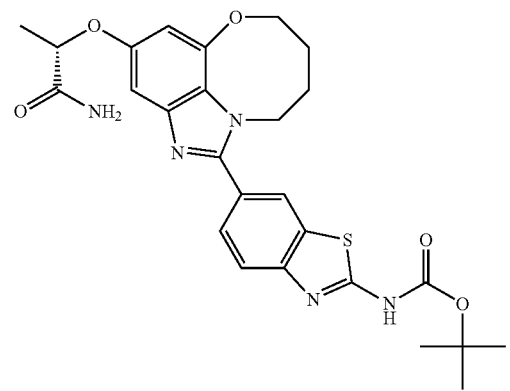 [SMILES: C[C@H](Oc1cc2c3c(c1)nc(-c1ccc4nc(NC(=O)OC(C)(C)C)sc4c1)n3CCCCO2)C(N)=O]

The title compound (42 mg, 5% yield over four steps) was generated from tert-butyl (6-(4-bromo-7,8,9,10-tetrahydro-6-oxa-2,10a-diazacycloocta[cd]inden-1-yl)benzo[d]thiazol-2-yl)carbamate (Example 214, step 3) (826 mg, 1.60 mmol) following procedures analogous to Example 204, steps 9-12. LCMS (ESI): [M+H]$^+$=524.

Step 2: (S)-2-((1-(2-Aminobenzo[d]thiazol-6-yl)-7,8,9,10-tetrahydro-6-oxa-2,10a-diazacycloocta[cd]inden-4-yl)oxy)propanamide A mixture of (S)-tert-butyl (6-(4-((1-amino-1-oxopropan-2-yl)oxy)-7,8,9,10-tetrahydro-6-oxa-2,10a-diazacycloocta[cd]inden-1-yl)benzo[d]thiazol-2-yl)carbamate (45.0 mg, 0.086 mmol) and TFA (0.3 mL) in DCM was stirred at room temperature for 30 min. The resultant mixture was evaporated in vacuo. The crude product was purified by chiral HPLC to yield 11.5 mg (32%) of the title compound as a white solid. LCMS (ESI): R$_T$ (min)=3.50, [M+H]$^+$=424, method=D; $^1$H NMR (300 MHz, DMSO-d$_6$) δ 8.02 (d, J=1.6 Hz, 1H), 7.76 (s, 2H), 7.63-7.39 (m, 3H), 7.28 (s, 1H), 6.92 (d, J=2.2 Hz, 1H), 6.60 (d, J=2.1 Hz, 1H), 4.63 (d, J=6.7 Hz, 1H), 4.41 (m, 2H), 4.33-4.17 (m, 2H), 2.15 (d, J=7.2 Hz, 2H), 1.68 (d, J=9.4 Hz, 2H), 1.46 (d, J=6.6 Hz, 3H).

Example 249 (S)-2-((1-(2-Amino-7-fluorobenzo[d]oxazol-5-yl)-7,8,9,10-tetrahydro-6-oxa-2,10a-diazacycloocta[cd]inden-4-yl)oxy)propanamide 249

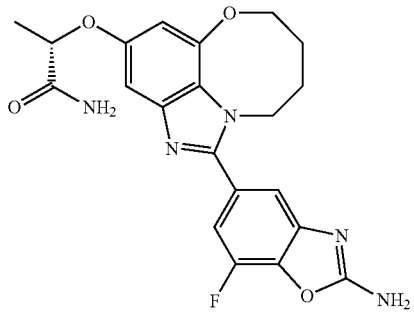

Step 1: 5-Bromo-7-fluorobenzo[d]oxazol-2-amine

To a solution of 2-amino-4-bromo-6-fluorophenol (18.0 g, 87.4 mmol) in methanol (180 mL) was added cyanogen bromide (18.4 g, 174 mmol). The reaction mixture was heated at 35° C. for 16 h and then allowed to cool to room temperature. The resultant mixture was quenched with aqueous sodium carbonate and extracted with ethyl acetate. The organic extracts were washed with brine, dried over sodium sulfate and the solvent was evaporated in vacuo. The residue was purified via flash chromatography on silica gel (solvent gradient: 20-70% ethyl acetate in petroleum ether) to yield 18 g (89%) of the title compound as a brown solid. LCMS (ESI): [M+H]$^+$=231/233.

Step 2: 7-Fluoro-5-(4,4,5,5-tetramethyl-1,3,2-dioxaborolan-2-yl)benzo[d]oxazol-2-amine

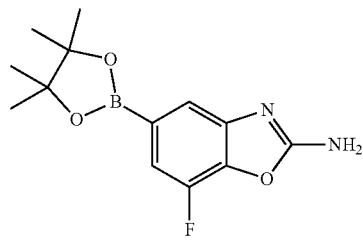 [SMILES: CC1(C)OB(c2cc(F)c3oc(N)nc3c2)OC1(C)C]

5-Bromo-7-fluorobenzo[d]oxazol-2-amine (5.85 g, 25.3 mmol), 4,4,4',4',5,5,5',5'-octamethyl-2,2'-bi(1,3,2-dioxaborolane) (7.84 g, 30.9 mmol), potassium acetate (7.80 g, 79.5 mmol) and 1,1'-bis(diphenylphosphino)ferrocenyl palladium (II) dichloride (1.92 g, 2.62 mmol) were suspended in DMF (100 mL) under an atmosphere of nitrogen and the reaction mixture was stirred at 100° C. for 3 h. The resulting mixture was partitioned between ethyl acetate and distilled water. The organic layer was dried over sodium sulfate and the solvent was evaporated. The residue was purified via flash chromatography on silica gel (solvent gradient: 30-70% ethyl acetate in petroleum ether) to yield 3.5 g (50%) of the title compound as a white solid. LCMS (ESI): [M+H]$^+$=279.

Step 3: 5-(4-Bromo-7,8,9,10-tetrahydro-6-oxa-2,10a-diazacycloocta[cd]inden-1-yl)-7-fluorobenzo[d]oxazol-2-amine

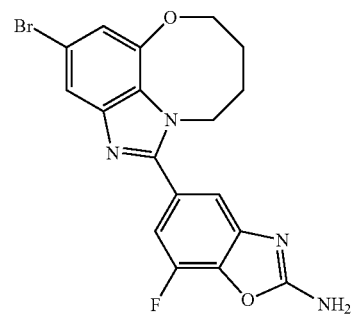 [SMILES: Nc1nc2cc(-c3nc4cc(Br)cc5c4n3CCCCO5)cc(F)c2o1]

To a suspension of 4-bromo-1-iodo-7,8,9,10-tetrahydro-6-oxa-2,10a-diazacycloocta[cd]indene (Example 204, step 6) (320 mg, 0.814 mmol), 7-fluoro-5-(4,4,5,5-tetramethyl-1,3,2-dioxaborolan-2-yl)benzo[d]oxazol-2-amine (279 mg, 1.00 mmol) and 1,1'-bis(diphenylphosphino)ferrocenyl palladium (II) dichloride (124 mg, 0.169 mmol) in tetrahydrofuran (9.00 mL) was added 2 N aqueous sodium carbonate (1.60 mL, 3.20 mmol). The reaction mixture was stirred at 80° C. for 5 h. The resulting mixture was partitioned between DCM and water and the aqueous layer was further extracted with DCM. The combined organic extracts were washed with brine, dried over sodium sulfate and evaporated in vacuo. The crude residue was purified via flash chromatography on silica gel (solvent gradient: 2-10% methanol in DCM) to yield 150 mg (44.3% yield) of the title compound as a light yellow solid. LCMS (ESI): [M+H]$^+$=417/419.

Step 4: 7-Fluoro-5-(4-(4,4,5,5-tetramethyl-1,3,2-dioxaborolan-2-yl)-7,8,9,10-tetrahydro-6-oxa-2,10a-diazacycloocta[cd]inden-1-yl)benzo[d]oxazol-2-amine

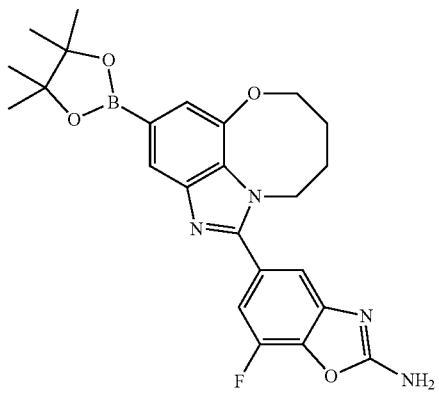 [SMILES: CC1(C)OB(c2cc3c4c(c2)nc(-c2cc(F)c5oc(N)nc5c2)n4CCCCO3)OC1(C)C]

5-(4-bromo-7,8,9,10-tetrahydro-6-oxa-2,10a-diazacycloocta[cd]inden-1-yl)-7-fluorobenzo[d]oxazol-2-amine (300 mg, 0.719 mmol), 4,4,4',4',5,5,5',5'-octamethyl-2,2'-bi(1,3,2-dioxaborolane) (389 mg, 1.53 mmol), potassium acetate (253 mg, 2.58 mmol) and 1,1'-bis(diphenylphosphino)ferrocenyl palladium (II) dichloride (107 mg, 0.146 mmol) were suspended in 1,4-dioxane (12 mL) under an atmosphere of nitrogen and the reaction mixture was stirred at 100° C. for 16 h. The resulting mixture was allowed to cool to room temperature and partitioned between DCM and distilled water. The organic layer was dried over sodium sulfate and the solvent was evaporated. The residue was purified via flash chromatography on silica gel (solvent gradient: 2-10% methanol in DCM) to yield 490 mg (73.5% yield) of the title compound as a yellow solid. LCMS (ESI): [M+H]$^+$=465.

Step 5: 1-(2-Amino-7-fluorobenzo[d]oxazol-5-yl)-7,8,9,10-tetrahydro-6-oxa-2,10a-diazacycloocta[cd]inden-4-ol

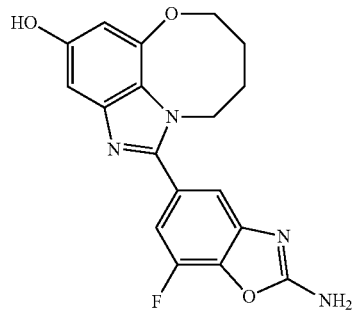 [SMILES: Nc1nc2cc(-c3nc4cc(O)cc5c4n3CCCCO5)cc(F)c2o1]

A reaction vessel was charged with 7-fluoro-5-(4-(4,4,5,5-tetramethyl-1,3,2-dioxaborolan-2-yl)-7,8,9,10-tetrahydro-6-oxa-2,10a-diazacycloocta[cd]inden-1-yl)benzo[d]oxazol-2-amine, acetic acid (4.00 mL) and water (4.00 mL). Hydrogen peroxide (30%, 2 mL) was added and the reaction mixture was stirred at room temperature for 1 h. The resultant mixture was quenched with aqueous sodium hydrogensulfite and the solvent was evaporated in vacuo. The residue was purified via flash chromatography on reversed phase silica gel (solvent gradient: 0-100% methanol in water) to yield 345 mg (63.0%) of the title compound as a light yellow solid. LCMS (ESI): [M+H]$^+$=355.

Step 6: (9-Methyl 2-((1-(2-amino-7-fluorobenzo[d]oxazol-5-yl)-7,8,9,10-tetrahydro-6-oxa-2,10a-diazacycloocta[cd]inden-4-yl)oxy)propanoate

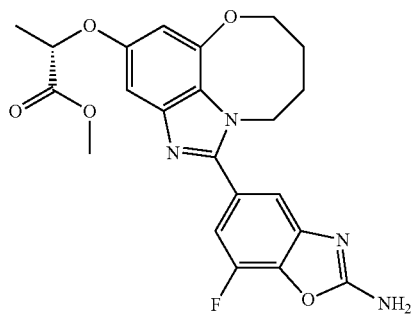 [SMILES: COC(=O)[C@H](C)Oc1cc2c3c(c1)nc(-c1cc(F)c4oc(N)nc4c1)n3CCCCO2]

The title compound (900 mg, 72.0% yield) was generated from 1-(2-amino-7-fluorobenzo[d]oxazol-5-yl)-7,8,9,10-tetrahydro-6-oxa-2,10a-diazacycloocta[cd]inden-4-ol (1.00 g, 2.82 mmol) and (R)-methyl 2-(tosyloxy)propanoate (1.09 g, 4.22 mmol) following a procedure analogous to Example 204, step 11. LCMS (ESI): [M+H]$^+$=441.

Step 7

249 (322 mg, 37.0% yield) was generated from (9-methyl 2-((1-(2-amino-7-fluorobenzo[d]oxazol-5-yl)-7,8,9,10-tetrahydro-6-oxa-2,10a-diazacycloocta[cd]inden-4-yl)oxy)propanoate following a procedure analogous to Example 204, step 12. LCMS (ESI): R$_T$ (min)=1.03, [M+H]$^+$=426, method=D; $^1$H NMR (300 MHz, DMSO-d$_6$) δ 7.89 (s, 2H), 7.55 (s, 1H), 7.29-7.19 (m, 3H), 6.93 (d, J=2.1 Hz, 1H), 6.60 (d, J=2.1 Hz, 1H), 4.68-4.55 (s, 1H), 4.40-4.36 (m, 2H), 4.26-4.23 (m, 2H), 2.10 (s, 2H), 1.68 (s, 2H), 1.45 (d, J=6.6 Hz, 3H).

Example 250 (S)-1-(1-(2-Aminobenzo[d]oxazol-5-yl)-7,8,9,10-tetrahydro-6-oxa-2,10a-diazacycloocta[cd]inden-4-yl)pyrrolidine-2-carboxamide 250

250 was prepared following procedures analogous to those of Examples 104 and 204. LCMS (ESI): R$_T$ (min)=1.23, [M+H]$^+$=433, method=D; $^1$H NMR (400 MHz, DMSO-d$_6$) δ 7.60 (s, 2H), 7.49 (d, J=8.4 Hz, 1H), 7.43 (d, J=1.2 Hz, 1H), 7.38 (s, 1H), 7.28-7.26 (m, 1H), 7.07 (s, 1H), 6.45 (d, J=2.0 Hz, 1H), 6.23 (d, J=1.6 Hz, 1H), 4.36-4.33 (m, 2H), 4.24-4.21 (m, 2H), 3.87-3.84 (m, 1H), 3.62-3.58 (m, 1H), 3.31-3.19 (m, 1H), 2.24-2.20 (m, 1H), 2.14-2.06 (m, 2H), 2.03-1.95 (m, 3H), 1.71-1.69 (m, 2H).

Examples 251 and 252 (R)-2-(((R)-2-(2-Aminobenzo[d]oxazol-5-yl)-4-methyl-3,4-dihydro-5-oxa-1,2a-diazaacenaphthylen-7-yl)oxy)propanamide 251 and (S)-2-(((R)-2-(2-Aminobenzo[d]oxazol-5-yl)-4-methyl-3,4-dihydro-5-oxa-1,2a-diazaacenaphthylen-7-yl)oxy)propanamide 252

Step 1: (R)-5-(4-Methyl-7-(4,4,5,5-tetramethyl-1,3,2-dioxaborolan-2-yl)-3,4-dihydro-5-oxa-1,2a-diazaacenaphthylen-2-yl)benzo[d]oxazol-2-amine

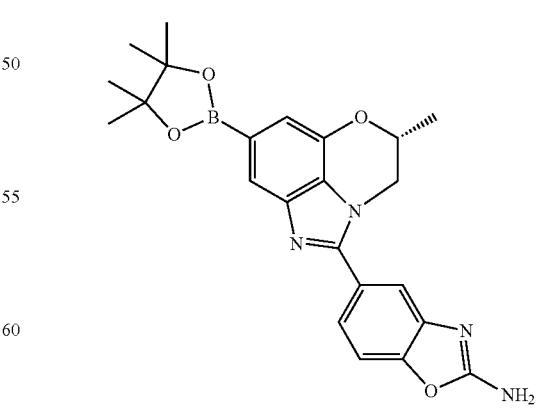

The title compound (282 mg, 100% yield) was prepared from (R)-5-(7-bromo-4-methyl-3,4-dihydro-5-oxa-1,2a-diazaacenaphthylen-2-yl)benzo[d]oxazol-2-amine (251 mg, 0.65 mmol) following a procedure analogous to Example 162, step 1. LCMS (ESI): [M+H]⁺=433.

Step 2: (R)-2-(2-Aminobenzo[d]oxazol-5-yl)-4-methyl-3,4-dihydro-5-oxa-1,2a-diazaacenaphthylen-7-ol

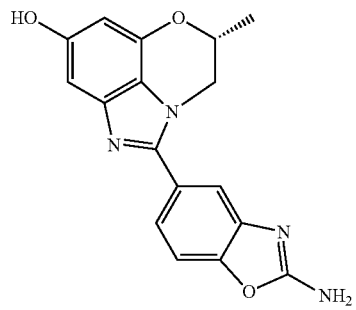 [SMILES: C[C@@H]1Cn2c(-c3ccc4oc(N)nc4c3)nc3cc(O)cc(c32)O1]

A reaction vessel was charged with (R)-5-(4-methyl-7-(4,4,5,5-tetramethyl-1,3,2-dioxaborolan-2-yl)-3,4-dihydro-5-oxa-1,2a-diazaacenaphthylen-2-yl)benzo[d]oxazol-2-amine (282 mg, 0.65 mmol) and THF (5.0 mL). Hydrogen peroxide (30%, 222 µL) was added and the reaction mixture was stirred at room temperature for 6.5 h. The mixture was loaded directly onto an SCX-2 cartridge, washed with methanol, eluted with 2 N ammonia in methanol. Fractions containing the title compound were evaporated in vacuo. The residue was further purified via flash chromatography (solvent gradient: 0-5% methanol in ethyl acetate) to yield 96 mg (46%) of the title compound. LCMS (ESI): [M+H]⁺=323.

Step 3: Methyl (S)-2-(((R)-2-(2-aminobenzo[d]oxazol-5-yl)-4-methyl-3,4-dihydro-5-oxa-1,2a-diazaacenaphthylen-7-yl)oxy)propanoate

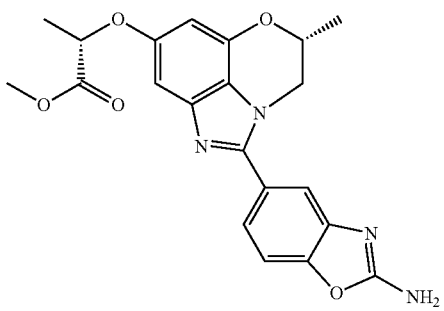 [SMILES: COC(=O)[C@H](C)Oc1cc2c3c(c1)nc(-c1ccc4oc(N)nc4c1)n3C[C@@H](C)O2]

A reaction vessel was charged with (R)-2-(2-aminobenzo[d]oxazol-5-yl)-4-methyl-3,4-dihydro-5-oxa-1,2a-diazaacenaphthylen-7-ol (96 mg, 0.30 mmol), (R)-2-methanesulfonyloxypropionic acid methyl ester (65.1 mg, 1.20 mmol), potassium carbonate (53.5 mg, 0.39 mmol) and DMSO (2.0 mL). The reaction mixture was heated at 35° C. for 24 h. The resulting mixture was then cooled to room temperature and additional (R)-2-methanesulfonyloxypropionic acid methyl ester (65.1 mg, 1.20 mmol) and potassium carbonate (53.5 mg, 0.39 mmol) were added. The reaction mixture was heated for an additional 24 h at 35° C. The resulting mixture was allowed to cool to room temperature and partitioned between ethyl acetate and distilled water. The organic layer was dried over magnesium sulfate and concentrated in vacuo to yield 122 mg of the title compound (undetermined ee). LCMS (ESI): [M+H]⁺=409.

Step 4: (R)-2-(((R)-2-(2-Aminobenzo[d]oxazol-5-yl)-4-methyl-3,4-dihydro-5-oxa-1,2a-diazaacenaphthylen-7-yl)oxy)propanamide and (S)-2-(((R)-2-(2-Aminobenzo[d]oxazol-5-yl)-4-methyl-3,4-dihydro-5-oxa-1,2a-diazaacenaphthylen-7-yl)oxy)propanamide A reaction vessel was charged with (S)-2-[(R)-2-(2-aminobenzooxazol-5-yl)-4-methyl-3,4-dihydro-5-oxa-1,2a-diazaacenaphthylen-7-yloxy]propionic acid methyl ester (122 mg, 0.3 mmol) and 7 N ammonia in methanol (10 mL). The reaction mixture was stirred at room temperature for 24 h. The resulting mixture was concentrated in vacuo and triturated with DCM. The solid was filtered to afford a mixture of the title compounds 40 mg (34%, 31% de). The filtrate was concentrated in vacuo and the residue was purified via flash chromatography (solvent gradient: 0-10% methanol in ethyl acetate) to afford a mixture of the title compounds 30 mg (26%, 88% de). The above filtered solid and the material recovered from flash chromatography were combined and resolved by chiral SFC to yield the title compounds.

251 (minor stereoisomer): LCMS (ESI): $R_T$ (min)=2.37, [M+H]⁺=394 method=A; ¹H NMR (400 MHz, DMSO-d₆) δ 7.71 (d, J=1.5 Hz, 1H), 7.59 (br s, 2H), 7.56 (dd, J=8.2 Hz, 1H), 7.49 (d, J=8.2 Hz, 1H), 7.48 (br s, 1H), 7.22 (br s, 1H), 6.75 (d, J=1.8 Hz, 1H), 6.43 (d, J=1.8 Hz, 1H), 4.69 (dd, J=12.7, 2.6 Hz, 1H), 4.61 (q, J=6.5 Hz, 1H), 4.48-4.39 (m, 1H), 4.28 (dd, J=12.7, 9.2 Hz, 1H), 1.50 (d, J=6.3 Hz, 3H), 1.44 (d, J=6.5 Hz, 3H).

252 (major stereoisomer). LCMS (ESI): $R_T$ (min)=2.32, [M+H]⁺=394, method=A; ¹H NMR (400 MHz, DMSO-d₆) δ 7.71 (d, J=1.5 Hz, 1H), 7.59 (br s, 2H), 7.56 (dd, J=8.1, 1.5 Hz, 1H), 7.49 (d, J=8.1 Hz, 1H), 7.48 (s, 1H), 7.22 (s, 1H), 6.75 (d, J=1.7 Hz, 1H), 6.42 (d, J=1.7 Hz, 1H), 4.70 (dd, J=12.5, 3.0 Hz, 1H), 4.60 (q, J=6.0 Hz, 1H), 4.49-4.40 (m, 1H), 4.27 (dd, J=12.5, 9.0 Hz, 1H), 1.50 (d, J=6.0 Hz, 3H), 1.44 (d, J=6.0 Hz, 3H).

Example 253 5-(4-Bromo-8,9-dihydrooxepino[4,3,2-cd]indazol-1(7H)-yl)benzo[d]oxazol-2-amine 253

Step 1: 5-Bromo-N,N-bis(4-methoxybenzyl)benzo[d]oxazol-2-amine

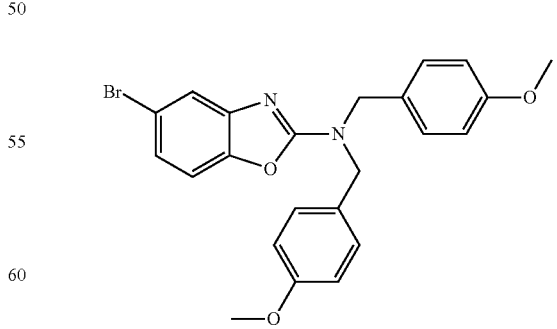

The title compound (3.07 g, 47% yield) was generated from 5-bromobenzo[d]oxazol-2-amine (3.10 g, 14.5 mmol) following a procedure analogous to Example 242, step 2. LCMS (ESI): [M+H]⁺=453/455.

Step 2: N,N-Bis(4-methoxybenzyl)-5-(4,4,5,5-tetramethyl-1,3,2-dioxaborolan-2-yl)benzo[d]oxazol-2-amine

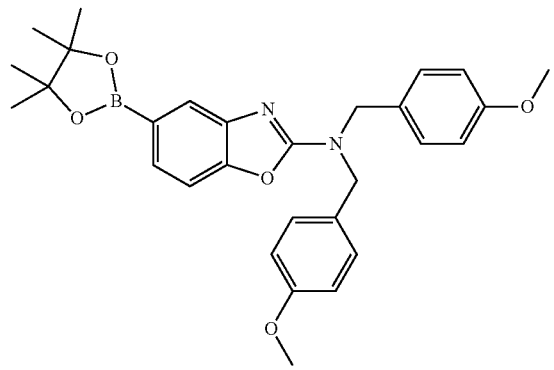

The title compound (1.06 g, 94% yield) was generated from 5-bromo-N,N-bis(4-methoxybenzyl)benzo[d]oxazol-2-amine (1.02 g, 2.25 mmol) following a procedure analogous to Example 204, step 7. LCMS (ESI): [M+H]$^+$=501.

Step 3: 4-Bromo-2,7,8,9-tetrahydrooxepino[4,3,2-cd]indazole

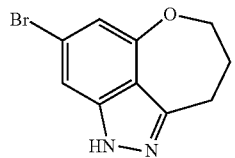 [SMILES: Brc1cc2c3c(n[nH]c3c1)CCCO2]

A mixture of 8-bromo-6-fluoro-3,4-dihydrobenzo[b]oxepin-5(2H)-one and 6-bromo-8-fluoro-3,4-dihydrobenzo[b]oxepin-5(2H)-one (Example 213, step 3) (500 mg, 1.93 mmol) and hydrazine (8 mL, 80%) in ethylene glycol dimethyl ether (7.00 mL, 72.3 mmol) was heated under microwave irradiation for 90 min at 120° C. This reaction was repeated separately five times. The five reaction mixtures were combined, diluted with water, extracted with ethyl acetate, washed with brine, dried over anhydrous sodium sulfate and evaporated in vacuo. The resultant residue was purified via flash chromatography on silica gel (solvent gradient: 0-50% ethyl acetate in petroleum ether) to yield 1.40 g (55%) of the title compound as a white solid. LCMS (ESI): [M+H]$^+$=253/255.

Step 4: 5-(4-Bromo-8,9-dihydrooxepino[4,3,2-cd]indazol-1(7H)-yl)-N,N-bis(4-methoxybenzyl)benzo[d]oxazol-2-amine and 5-(4-Bromo-8,9-dihydrooxepino[4,3,2-cd]indazol-2(7H)-yl)-N,N-bis(4-methoxybenzyl)benzo[d]oxazol-2-amine

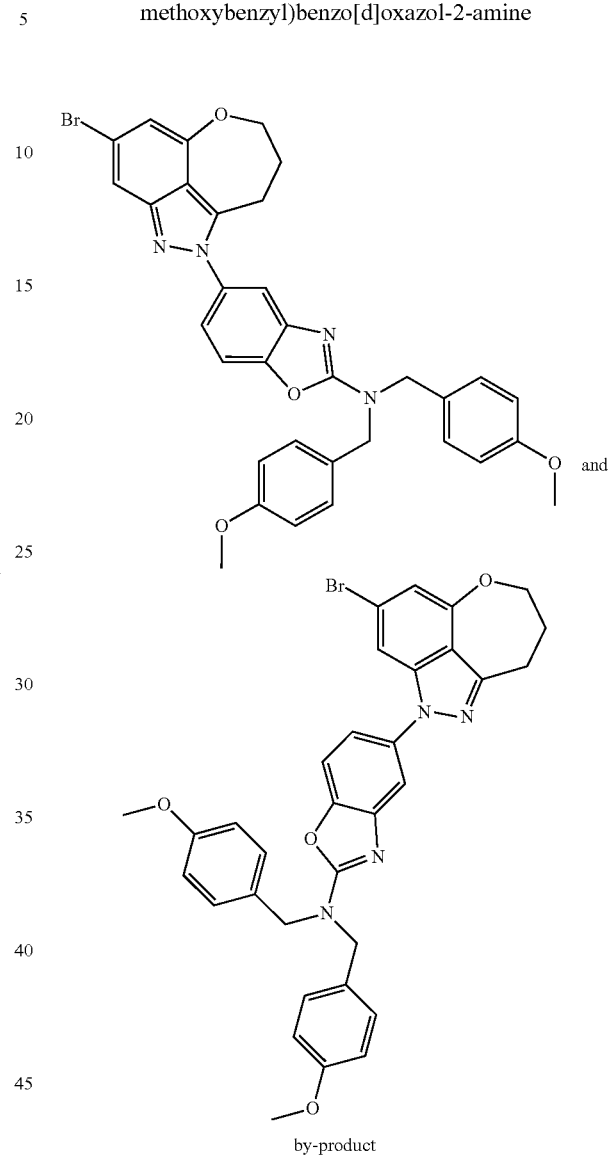

by-product

A mixture of 4-bromo-2,7,8,9-tetrahydrooxepino[4,3,2-cd]indazole (312 mg, 1.23 mmol), N,N-bis(4-methoxybenzyl)-5-(4,4,5,5-tetramethyl-1,3,2-dioxaborolan-2-yl)benzo[d]oxazol-2-amine (720 mg, 1.43 mmol), copper(II) acetate (152 mg, 0.840 mmol) and 4A molecular sieves (100 mg) in pyridine (15.0 mL) was degassed with oxygen. The reaction mixture was heated at 90° C. for 16 h. The mixture was cooled to room temperature and then filtered. The filtrate was evaporated in vacuo. The resultant residue was purified via flash chromatography on silica gel (solvent gradient: 0-50% ethyl acetate in petroleum ether) to yield a mixture of the two title compounds (620 mg) as a yellow solid, which was carried forward without further purification. LCMS (ESI): [M+H]$^+$=625/627.

Step 8

A mixture of 5-(4-bromo-8,9-dihydrooxepino[4,3,2-cd]indazol-1(7H)-yl)-N,N-bis(4-methoxybenzyl)benzo[d]oxazol-2-amine and 5-(4-bromo-8,9-dihydroooxepino[4,3,2-cd] indazol-2(7H)-yl)-N,N-bis(4-methoxybenzyl)benzo[d] oxazol-2-amine (620 mg, 0.990 mmol) in TFA (20 mL) was heated at 80° C. for 24 h. The reaction mixture was diluted with water. The aqueous layer was adjusted to ca. pH 8 with aqueous sodium bicarbonate. The mixture was extracted with DCM, washed with brine, dried over anhydrous sodium sulfate and evaporated in vacuo. The resultant residue was purified via reverse-phase HPLC and lyophilized to yield 253 as the minor regioisomer (2.5 mg, 1% yield). LCMS (ESI): $R_T$ (min)=1.83, [M+H]$^+$=385/387, method=C; $^1$H NMR (300 MHz, DMSO-$d_6$) δ 7.69 (s, 2H), 7.52 (d, J=8.4 Hz, 1H), 7.46 (d, J=2.1 Hz, 1H), 7.39 (d, J=1.2 Hz, 1H), 7.25-7.21 (m, 1H), 6.51 (d, J=1.5 Hz, 1H), 4.44-4.41 (m, 2H), 3.14-3.09 (m, 2H), 2.30-2.10 (m, 2H).

Example 254 (S)-2-((1-(2-Aminobenzo[d]oxazol-5-yl)-7,8,9,10-tetrahydro-6-oxa-2,10a-diazacycloocta[cd]inden-4-yl)(methyl)amino)propanamide 254

254 was prepared following procedures analogous to those of Example 104. LCMS (ESI): $R_T$ (min)=1.21, [M+H]$^+$=421, method=D; $^1$H NMR (300 MHz, DMSO-$d_6$) δ 7.59 (s, 2H), 7.49 (d, J=8.4 Hz, 1H), 7.43 (d, J=1.5 Hz, 1H), 7.36 (s, 1H), 7.28-7.25 (m, 1H), 7.08 (s, 1H), 6.78 (d, J=1.8 Hz, 1H), 6.57 (d, J=2.1 Hz, 1H), 4.37-4.21 (m, 5H), 2.80 (s, 3H) 2.18-2.02 (m, 2H), 1.76-1.64 (m, 2H), 1.22 (d, J=6.9 Hz, 3H).

Example 255 (S)-2-((1-(2-Aminobenzo[d]thiazol-6-yl)-7,8,9,10-tetrahydro-6-oxa-2,10a-diazacycloocta[cd]inden-4-yl)(methyl)amino)propanamide 255

255 was prepared following procedures analogous to those of Example 214. LCMS (ESI): $R_T$ (min)=3.50, [M+H]$^+$=437, method=D; $^1$H NMR (300 MHz, DMSO-$d_6$) δ 8.00 (s, 1H), 7.74 (s, 2H), 7.52-7.44 (m, 2H), 7.38 (s, 1H), 7.09 (s, 1H), 6.76 (s, 1H), 6.56 (s, 1H), 4.37-4.23 (m, 5H), 2.79 (s, 3H), 2.23-2.15 (m, 2H), 1.80-1.60 (m, 2H), 1.22 (d, J=6.7 Hz, 3H).

Examples 256 and 257: (S)-2-((1-(2-Aminobenzo[d]oxazol-5-yl)-8,9-dihydro-7H-6-oxa-2,9a-diazabenzo[cd]azulen-4-yl)oxy)butanamide 256 and (R)-2-((1-(2-aminobenzo[d]oxazol-5-yl)-8,9-dihydro-7H-6-oxa-2,9a-diazabenzo[cd]azulen-4-yl)oxy)butanamide 257

To a suspension of 1-(2-aminobenzo[d]oxazol-5-yl)-8,9-dihydro-7H-6-oxa-2,9a-diazabenzo[cd]azulen-4-ol (Example 162, step 2) (178 mg, 0.552 mmol) and potassium carbonate (305 mg, 2.21 mmol) in acetone (2.7 mL) was added 2-bromobutanamide (145 mg, 0.828 mmol). The reaction was sealed in a vial under nitrogen and heated to 60° C. After stirring for 1 h the temperature was increased to 70° C. and the reaction was left to stir overnight. After 18 h the reaction was diluted with methanol and filtered. The filtrate was evaporated in vacuo and the crude product was purified via flash chromatography on silica gel (solvent gradient: 0-20% methanol in DCM), followed by chiral SFC separation to afford the two title compounds each as a single unknown stereoisomer.

256 (8.5 mg): LCMS (ESI): $R_T$ (min)=2.82, [M+H]$^+$=408.1, method=B; $^1$H NMR (400 MHz, DMSO-$d_6$) δ 7.59-7.52 (m, 3H), 7.53-7.42 (m, 2H), 7.36 (dd, J=8.2, 1.7 Hz, 1H), 7.22 (d, J=2.1 Hz, 1H), 6.78 (d, J=2.2 Hz, 1H), 6.44 (d, J=2.2 Hz, 1H), 4.45-4.35 (m, 3H), 4.26 (t, J=5.5 Hz, 2H), 2.33-2.26 (m, 2H), 1.88-1.76 (m, 2H), 0.98 (t, J=7.3 Hz, 3H).

257 (7.2 mg): LCMS (ESI): $R_T$ (min)=2.83, [M+H]$^+$=408.1, method=B; $^1$H NMR (400 MHz, DMSO-$d_6$) δ 7.59-7.52 (m, 3H), 7.52-7.42 (m, 2H), 7.36 (dd, J=8.2, 1.7 Hz, 1H), 7.22 (d, J=2.1 Hz, 1H), 6.79 (d, J=2.3 Hz, 1H), 6.44 (d, J=2.1 Hz, 1H), 4.45-4.35 (m, 3H), 4.26 (t, J=5.6 Hz, 2H), 2.33-2.24 (m, 2H), 1.88-1.76 (m, 2H), 0.98 (t, J=7.4 Hz, 3H).

Example 258 (S)-2-((1-(2-Amino-7-fluorobenzo[d]oxazol-5-yl)-8,9-dihydro-7H-6-oxa-2,9a-diazabenzo[cd]azulen-4-yl)oxy)propanamide 258

Step 1: 5-(4-Bromo-8,9-dihydro-7H-6-oxa-2,9a-diazabenzo[cd]azulen-1-yl)-'7-fluorobenzo[d]oxazol-2-amine

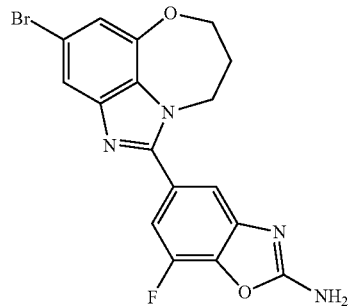

The title compound (456 mg, 19% yield) was generated from 5-bromo-7-fluorobenzoooxazol-2-ylamine (1.38 g, 5.97 mmol) following a procedure analogous to Example 205, step 1. LCMS (ESI): [M+H]$^+$=404/406.

Step 2: 7-Fluoro-5-(4-(4,4,5,5-tetramethyl-1,3,2-dioxaborolan-2-yl)-8,9-dihydro-7H-6-oxa-2,9a-diazabenzo[cd]azulen-1-yl)benzo[d]oxazol-2-amine

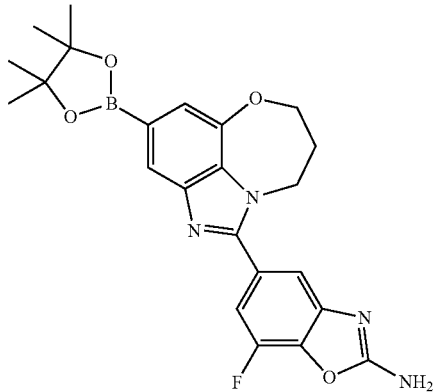 [SMILES: CC1(C)OB(c2cc3c4c(c2)nc(-c2cc(F)c5oc(N)nc5c2)n4CCCO3)OC1(C)C]

The title compound (509 mg, quantitative yield) was generated from 5-(4-bromo-8,9-dihydro-7H-6-oxa-2,9a-diazabenzo[cd]azulen-1-yl)-7-fluorobenzo[d]oxazol-2-amine (456 mg, 1.13 mmol) following a procedure analogous to Example 162, step 1. LCMS (ESI): [M+H]$^+$=451.

Step 3: 1-(2-Amino-7-fluorobenzo[d]oxazol-5-yl)-8,9-dihydro-7H-6-oxa-2,9a-diazabenzo[cd]azulen-4-ol

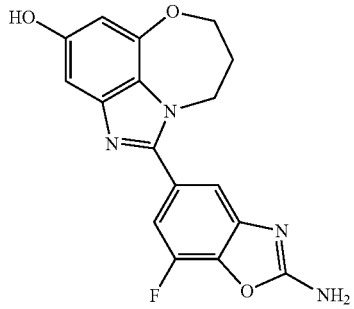 [SMILES: Nc1nc2cc(-c3nc4cc(O)cc5c4n3CCCO5)cc(F)c2o1]

The title compound (161 mg, 41% yield) was generated from 7-fluoro-5-(4-(4,4,5,5-tetramethyl-1,3,2-dioxaborolan-2-yl)-8,9-dihydro-7H-6-oxa-2,9a-diazabenzo[cd]azulen-1-yl)benzo[d]oxazol-2-amine (509 mg, 1.13 mmol) following a procedure analogous to Examples 251 and 252, step 2. LCMS (ESI): [M+H]$^+$=451.

Step 4: Methyl (S)-2-((1-(2-amino-7-fluorobenzo[d]oxazol-5-yl)-8,9-dihydro-7H-6-oxa-2,9a-diazabenzo[cd]azulen-4-yl)oxy)propanoate

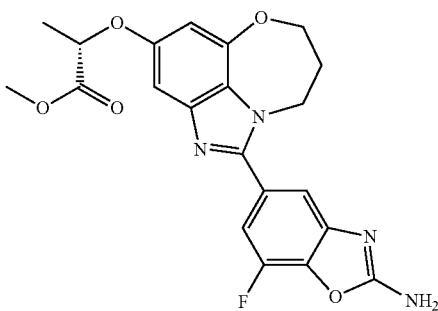 [SMILES: COC(=O)[C@H](C)Oc1cc2c3c(c1)nc(-c1cc(F)c4oc(N)nc4c1)n3CCCO2]

The title compound (202 mg, 100% yield) was generated from 1-(2-amino-7-fluorobenzo[d]oxazol-5-yl)-8,9-dihydro-7H-6-oxa-2,9a-diazabenzo[cd]azulen-4-ol (161 mg, 0.47 mmol) following a procedure analogous to Examples 251 and 252, step 3. LCMS (ESI): [M+H]$^+$=427.

Step 5

258 (31.8 mg, 27% yield) was generated from methyl (S)-2-((1-(2-amino-7-fluorobenzo[d]oxazol-5-yl)-8,9-dihydro-7H-6-oxa-2,9a-diazabenzo[cd]azulen-4-yl)oxy)propanoate (202 mg, 0.47 mmol) following a procedure analogous to Examples 251 and 252, step 4. LCMS (ESI): R$_T$ (min)=2.45, [M+H]$^+$=412, method=A; $^1$H NMR (400 MHz, DMSO-d$_6$) δ 7.86 (br s, 2H), 7.47 (s, 1H), 7.43 (d, J=1.4, 1H), 7.32 (dd, J=10.7, 1.4 Hz, 1H), 7.21 (s, 1H), 6.78 (d, J=2.1 Hz, 1H), 6.44 (d, J=2.1 Hz, 1H), 4.60 (q, J=6.5 Hz, 1H), 4.42-4.36 (m, 2H), 4.32-4.26 (m, 2H), 2.34-2.25 (m, 2H), 1.44 (d, J=6.5 Hz, 3H).

Examples 259 and 260 (R)-2-((1-(2-Aminobenzo[d]oxazol-5-yl)-8,9-dihydro-7H-6-oxa-2,9a-diazabenzo[cd]azulen-4-yl)oxy)-2-cyclopropylacetamide 259 and (S)-2-((1-(2-Aminobenzo[d]oxazol-5-yl)-8,9-dihydro-7H-6-oxa-2,9a-diazabenzo[cd]azulen-4-yl)oxy)-2-cyclopropylacetamide 260

Step 1: Methyl 2-((1-(2-aminobenzo[d]oxazol-5-yl)-8,9-dihydro-7H-6-oxa-2,9a-diazabenzo[cd]azulen-4-yl)oxy)-2-cyclopropylacetate

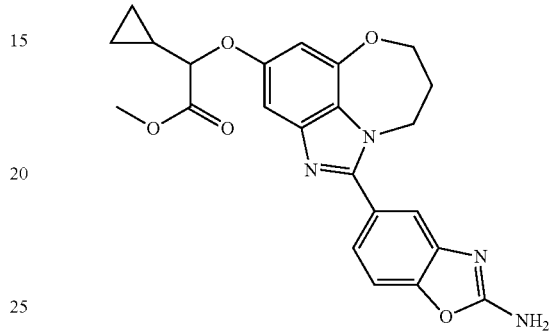

To a suspension of 1-(2-aminobenzo[d]oxazol-5-yl)-8,9-dihydro-7H-6-oxa-2,9a-diazabenzo[cd]azulen-4-ol (0.5895 mmol, 190 mg) and potassium carbonate (3.537 mmol, 488.9 mg) in acetone (3 mL) was added ethyl 2-bromo-2-cyclopropylacetate (0.728 mmol, 157 mg). The reaction was sealed in a vial under nitrogen and heated to 70° C. After 2 h an additional 3 equivalents of potassium carbonate and 0.5 equivalents of ethyl 2-bromo-2-cyclopropylacetate were added and the reaction mixture heated at 40° C. overnight. To the reaction were then added 3.0 mL DMF and 70 mg ethyl 2-bromo-2-cyclopropylacetate and the reaction mixture heated at 35° C. for 3 days. The reaction mixture was evaporated onto celite and the crude product was purified via flash chromatography on silica gel (12 g silica, solvent gradient: 0-5% methanol in DCM) to yield 42.4 mg (17%) of the title compound. LCMS (ESI): [M+H]$^+$=435; $^1$H NMR (400 MHz, DMSO-d$_6$) δ 7.56 (s, 1H), 7.54 (d, J=1.7 Hz, 1H), 7.48 (d, J=8.2 Hz, 1H), 7.35 (dd, J=8.2, 1.7 Hz, 1H), 6.67 (d, J=2.3 Hz, 1H), 6.38 (d, J=2.3 Hz, 1H), 4.45-4.35 (m, 2H), 4.31-4.22 (m, 3H), 3.67 (s, 3H), 2.28 (t, J=6.0 Hz, 2H), 1.35-1.26 (m, 1H), 0.68-0.50 (m, 4H).

Step 2: (R)-2-((1-(2-Aminobenzo[d]oxazol-5-yl)-8,9-dihydro-7H-6-oxa-2,9a-diazabenzo[cd]azulen-4-yl)oxy)-2-cyclopropylacetamide and (S)-2-((1-(2-Aminobenzo[d]oxazol-5-yl)-8,9-dihydro-7H-6-oxa-2,9a-diazabenzo[cd]azulen-4-yl)oxy)-2-cyclopropylacetamide A mixture of methyl 2-((1-(2-aminobenzo[d]oxazol-5-yl)-8,9-dihydro-7H-6-oxa-2,9a-diazabenzo[cd]azulen-4-yl)oxy)-2-cyclopropylacetate (42 mg, 0.10 mmol) and ammonia (7M solution in methanol, 3.0 mL, 21 mmol) was heated in a sealed tube at 50° C. for 48 h. The reaction mixture was then evaporated in vacuo and purified by reverse-phase HPLC and resolved by chiral SFC to afford the title compounds each as a single unknown stereoisomer.

259 (9.7 mg): LCMS (ESI): R$_T$ (min)=2.839, [M+H]$^+$=420.1, method=B; $^1$H NMR (400 MHz, DMSO-d$_6$) δ 7.56 (s, 2H), 7.54 (d, J=1.7 Hz, 1H), 7.50-7.44 (m, 2H), 7.35 (dd, J=8.2, 1.7 Hz, 1H), 7.17 (s, 1H), 6.73 (d, J=2.3 Hz, 1H), 6.41 (d, J=2.3 Hz, 1H), 4.44-4.34 (m, 2H), 4.31-4.21 (m, 2H), 3.93 (d, J=8.0 Hz, 1H), 2.36-2.19 (m, 2H), 1.33-1.20 (m, 1H), 0.62-0.52 (m, 3H), 0.48-0.38 (m, 1H).

260 (9.5 mg): LCMS (ESI): $R_T$ (min)=2.849, [M+H]$^+$= 420.1, method=B; $^1$H NMR (400 MHz, DMSO-d$_6$) δ 7.56 (s, 2H), 7.54 (d, J=1.7, 1H), 7.50-7.45 (m, 2H), 7.35 (dd, J=8.2, 1.7 Hz, 1H), 7.17 (d, J=2.0 Hz, 1H), 6.73 (d, J=2.3 Hz, 1H), 6.41 (d, J=2.3 Hz, 1H), 4.44-4.34 (m, 2H), 4.30-4.19 (m, 2H), 3.93 (d, J=8.0 Hz, 1H), 2.33-2.22 (m, 2H), 1.32-1.20 (m, 1H), 0.63-0.52 (m, 3H), 0.49-0.39 (m, 1H).

Example 261 (S)-2-((1-(2-Amino-4,7-difluorobenzo [d]oxazol-5-yl)-7,8,9,10-tetrahydro-6-oxa-2,10a-diazacycloocta[cd]inden-4-yl)oxy)propanamide 261

Step 1: 4-Bromo-3,6-difluoro-2-nitrophenol

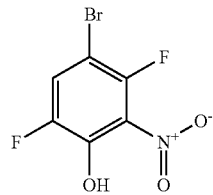

A solution of 4-bromo-2,5-difluoro-phenol (21.09 g, 100.9 mmol) in acetic acid (50.0 mL, 872 mmol) was cooled in an ice bath. Nitric acid (6.00 mL, 120 mmol) was added and the reaction mixture stirred at room temperature. After 3 h, the reaction mixture was transferred to a separating funnel with 500 mL EtOAc and 250 mL water. The organic phase was separated, dried over brine and magnesium sulfate, filtered, and evaporated in vacuo. The crude product was purified via flash chromatography on silica gel (330 g silica, solvent gradient: 0-100% ethyl acetate in heptanes) to yield 11.43 g (44%) of the title compound. LCMS (ESI): [M−H]$^-$=252; $^1$H NMR (400 MHz, DMSO-d$_6$) δ 8.03 (dd, J=10.4, 6.6 Hz, 1H).

Step 2: 2-Amino-4-bromo-3,6-difluorophenol

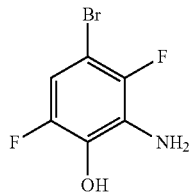

A mixture of 4-bromo-3,6-difluoro-2-nitro-phenol (11.43 g, 45.00 mmol), iron powder (325 mesh) (13.03 g, 226.3 mmol), ammonium chloride (9.68 g, 181 mmol), ethanol (25 mL) and water (25 mL) was heated at 60° C. for 1 h. The reaction mixture was cooled to room temperature, diluted with ethyl acetate (300 mL) and water (200 mL) and filtered through celite. Brine (100 mL) was added and the layers were separated. The organic layer was dried over magnesium sulfate, filtered, and evaporated in vacuo. The crude product was purified via flash chromatography on silica gel (125 g silica, solvent gradient: 0-40% ethyl acetate in heptanes) to yield 5.92 g (59%) of the title compound as a peach colored solid. LCMS (ESI): [M+H]$^+$=224; $^1$H NMR (400 MHz, DMSO-d$_6$) δ 9.71 (s, 1H), 6.72 (dd, J=9.9, 6.2 Hz, 1H), 5.12 (s, 2H).

Step 3: 5-Bromo-4,7-difluorobenzo[d]oxazol-2-amine

A mixture of 2-amino-4-bromo-3,6-difluoro-phenol (5.92 g, 26.4 mmol), methanol (30.0 mL,) and cyanogen bromide (8.40 g, 79.3 mmol) was heated at 35° C. for 15 h. The reaction mixture was evaporated under reduced pressure to remove the majority of solvent, and then partitioned between 200 mL DCM and 150 mL saturated aqueous sodium bicarbonate. The aqueous layer was extracted with an additional 3×150 mL DCM. The combined organic layers were dried over magnesium sulfate, filtered, and evaporated in vacuo. The crude product was purified via flash chromatography on silica gel (80 g silica, solvent gradient: 0-20% ethyl acetate in DCM) to yield 4.43 g (67%) of the title compound as a peach solid. LCMS (ESI): [M+H]$^+$=249; $^1$H NMR (400 MHz, DMSO-d$_6$) δ 8.06 (s, 2H), 7.34 (dd, J=9.3, 4.9 Hz, 1H).

Step 4: 4,7-Difluoro-5-(4,4,5,5-tetramethyl-1,3,2-dioxaborolan-2-yl)benzo[d]oxazol-2-amine

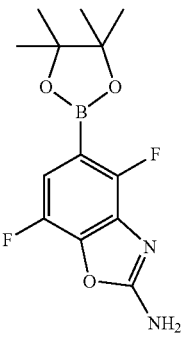 [SMILES: CC1(C)OB(c2cc(F)c3oc(N)nc3c2F)OC1(C)C]

A 200 mL flask was charged with 5-bromo-4,7-difluorobenzo[d]oxazol-2-amine (4.43 g, 17.8 mmol), tris(dibenzylideneacetone)dipalladium(0) (163 mg, 0.178 mmol), 2-(dicyclohexylphosphino)-2',4',6'-triisopropylbiphenyl (342 mg, 0.703 mmol), bis(pinacolato)diboron (9.30 g, 36.6 mmol), and potassium acetate (5.48 g, 55.8 mmol). The flask was evacuated and backfilled with nitrogen twice. 1,4-Dioxane (75 mL) was then added by syringe. The mixture was heated at 100° C. under a nitrogen atmosphere for 2 h. The reaction mixture was evaporated onto celite. The crude product was purified via flash chromatography on silica gel (80 g silica, solvent gradient: 20-60% ethyl acetate in heptanes) to yield 4.31 g (82%) of the title compound. LCMS (ESI): [M+H]$^+$=297.0; $^1$H NMR (400 MHz, DMSO-d$_6$) δ 7.89 (s, 2H), 6.99 (dd, J=9.8, 3.3 Hz, 1H), 1.17 (s, 12H).

Step 5: 5-(4-Bromo-7,8,9,10-tetrahydro-6-oxa-2,10a-diazacycloocta[cd]inden-1-yl)-4,7-difluorobenzo[d]oxazol-2-amine

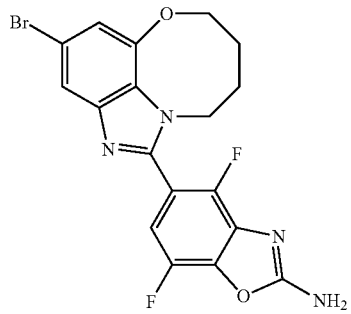

A 100 mL flask charged with 4-bromo-1-iodo-7,8,9,10-tetrahydro-6-oxa-2,10a-diazacycloocta[cd]indene (1.046 g, 2.66 mmol), 4,7-difluoro-5-(4,4,5,5-tetramethyl-1,3,2-dioxaborolan-2-yl)benzo[d]oxazol-2-amine (887 mg, 3.00 mmol), [1,1'-bis(diphenylphosphino)ferrocene]palladium(II) chloride, complex with dichloromethane (1:1) (444 mg, 0.54 mmol) and sodium carbonate (592 mg, 5.53 mmol) was evacuated and backfilled with nitrogen. DMF (10 mL) and water (1 mL) were added and the flask was then heated under a nitrogen balloon at 90° C. for 7 h. To the reaction was added 4,7-difluoro-5-(4,4,5,5-tetramethyl-1,3,2-dioxaborolan-2-yl)benzo[d]oxazol-2-amine (309 mg), [1,1'-bis(diphenylphosphino)ferrocene]palladium(II) chloride, complex with dichloromethane (1:1) (201 mg, 1.04 mmol), and a 2 M solution of sodium carbonate in water (1.5 mL, 3.0 mmol) and the reaction mixture heated at 80° C. overnight. The reaction mixture was diluted with ethyl acetate, filtered through celite, washed with water and brine, and evaporated in vacuo. The crude product was purified via flash chromatography on silica gel (40 g silica, solvent gradient: 0-100% ethyl acetate in DCM) to yield 0.44 g (38%) of the title compound. LCMS (ESI): [M+H]⁺=434.9; ¹H NMR (400 MHz, DMSO-d₆) δ 8.10 (s, 2H), 7.70 (d, J=1.7 Hz, 1H), 7.19 (dd, J=9.8, 4.7 Hz, 1H), 7.14 (d, J=1.7 Hz, 1H), 4.28 (t, J=5.5 Hz, 4H), 2.03-1.94 (m, 2H), 1.69-1.58 (m, 2H).

Step 6: 4,7-Difluoro-5-(4-(4,4,5,5-tetramethyl-1,3,2-dioxaborolan-2-yl)-7,8,9,10-tetrahydro-6-oxa-2,10a-diazacycloocta[cd]inden-1-yl)benzo[d]oxazol-2-amine

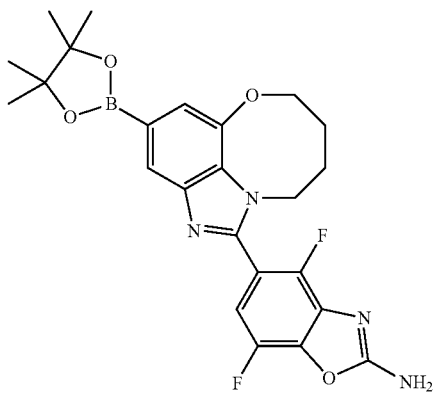 [SMILES: CC1(C)OB(c2cc3c4c(c2)nc(-c2cc(F)c5oc(N)nc5c2F)n4CCCCO3)OC1(C)C]

The title compound (256 mg, 52% yield) was prepared from 5-(4-bromo-7,8,9,10-tetrahydro-6-oxa-2,10a-diazacycloocta[cd]inden-1-yl)-4,7-difluorobenzo[d]oxazol-2-amine following a procedure analogous to Example 162, step 1. LCMS (ESI): [M+H]⁺=483.1.

Step 7: 1-(2-Amino-4,7-difluorobenzo[d]oxazol-5-yl)-7,8,9,10-tetrahydro-6-oxa-2,10a-diazacycloocta[cd]inden-4-ol

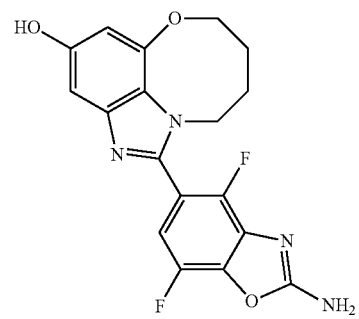 [SMILES: Nc1nc2c(F)c(-c3nc4cc(O)cc5c4n3CCCCO5)cc(F)c2o1]

The title compound (47.9 mg, 58% yield) was prepared from 4,7-difluoro-5-(4-(4,4,5,5-tetramethyl-1,3,2-dioxaborolan-2-yl)-7,8,9,10-tetrahydro-6-oxa-2,10a-w diazacycloocta[cd]inden-1-yl)benzo[d]oxazol-2-amine following a procedure analogous to Example 162, step 2. LCMS (ESI): [M+H]⁺=372.95; ¹H NMR (400 MHz, DMSO-d₆) δ 9.17 (s, 1H), 8.06 (s, 2H), 7.13 (dd, J=9.8, 4.7 Hz, 1H), 6.77 (d, J=2.1 Hz, 1H), 6.44 (d, J=2.1 Hz, 1H), 4.20 (t, J=5.6 Hz, 4H), 2.00-1.90 (m, 2H), 1.67-1.57 (m, 2H).

Step 8: Methyl (S)-2-((1-(2-amino-4,7-difluorobenzo[d]oxazol-5-yl)-7,8,9,10-tetrahydro-6-oxa-2,10a-diazacycloocta[cd]inden-4-yl)oxy)propanoate

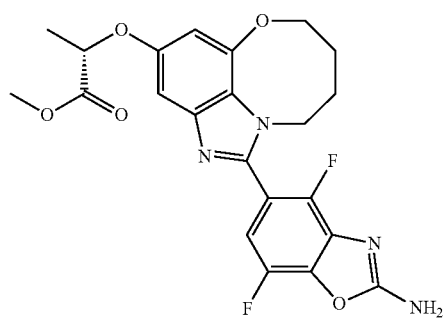 [SMILES: COC(=O)[C@H](C)Oc1cc2c3c(c1)nc(-c1cc(F)c4oc(N)nc4c1F)n3CCCCO2]

The title compound (36.1 mg, 22%) was prepared from 1-(2-amino-4,7-difluorobenzo[d]oxazol-5-yl)-7,8,9,10-tetrahydro-6-oxa-2,10a-diazacycloocta[cd]inden-4-ol following a procedure analogous to Example 162, step 3. LCMS (ESI): [M+H]⁺=459.0; ¹H NMR (400 MHz, DMSO-d₆) δ 8.08 (s, 2H), 7.15 (dd, J=9.8, 4.6 Hz, 1H), 6.90 (d, J=2.2 Hz, 1H), 6.61 (d, J=2.2 Hz, 1H), 5.00 (q, J=6.7 Hz, 1H), 4.28-4.20 (m, 4H), 3.70 (s, 3H), 2.01-1.94 (m, 2H), 1.68-1.61 (m, 2H), 1.53 (d, J=6.7 Hz, 3H).

Step 9

A mixture of methyl (S)-2-((1-(2-amino-4,7-difluorobenzo[d]oxazol-5-yl)-'7,8,9,10-tetrahydro-6-oxa-2,10a- diazacycloocta[cd]inden-4-yl)oxy)propanoate (36 mg, 0.07853 mmol) and ammonia (7M solution in methanol) (3.0 mL, 21 mmol) was stirred in a sealed tube at room temperature for 21 h. The reaction mixture was evaporated in vacuo, and the crude product was purified via reverse-phase HPLC followed by chiral SFC to remove the minor epimer, yielding 20.7 mg (58%) of 261. LCMS (ESI): $R_T$ (min)=3.22, [M+H]$^+$=444.1, method=B; $^1$H NMR (400 MHz, DMSO-d$_6$) δ 8.08 (s, 2H), 7.53 (s, 1H), 7.23 (s, 1H), 7.15 (dd, J=9.8, 4.7 Hz, 1H), 6.94 (d, J=2.2 Hz, 1H), 6.64 (d, J=2.1 Hz, 1H), 4.63 (q, J=6.6 Hz, 1H), 4.30-4.15 (m, 4H), 2.03-1.90 (m, 2H), 1.71-1.59 (m, 2H), 1.45 (d, J=6.6 Hz, 3H).

Example 262 (S)-4-(1-(2-Aminobenzo[d]thiazol-6-yl)-7,8,9,10-tetrahydro-6-oxa-2,10a-diazacycloocta[cd]inden-4-yl)morpholine-3-carboxamide 262

Step 1: tert-Butyl (6-(4,4,5,5-tetramethyl-1,3,2-dioxaborolan-2-yl)benzo[d]thiazol-2-yl)carbamate

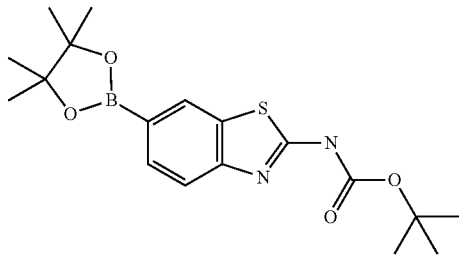 [SMILES: CC(C)(C)OC(=O)Nc1nc2ccc(B3OC(C)(C)C(C)(C)O3)cc2s1]

A 100 mL flask charged with 2-amino-6-bromobenzothiazole (2.52 g, 10.77 mmol), bis(pinacolato)diboron (5.45 g, 21.24 mmol), potassium acetate (3.28 g, 33.09 mmol), 2-(dicyclohexylphosphino)-2',4',6'-triisopropylbiphenyl (212.2 mg, 0.436 mmol), and tris(dibenylideneacetone)dipalladium chloroform complex (117.9 mg, 0.110 mmol) was evacuated and backfilled with nitrogen. 1,4-Dioxane (20.0 mL, 233 mmol) was added and the reaction mixture stirred under a nitrogen balloon at 100° C. for 1 h. To the reaction was then added [1,1'-bis(diphenylphosphino)ferrocene]palladium(II) chloride, complex with DCM (1:1) (285.9 mg, 0.350 mmol). After an additional 17 h the reaction mixture was cooled to room temperature, filtered through celite, rinsing with ethyl acetate, and then evaporated to dry on celite. The crude product was purified via flash chromatography on silica gel (80 g silica, solvent gradient: 0-100% isopropyl acetate in heptanes) to yield 2.85 g. Of this material, 2.64 g was combined with di-tert-butyl dicarbonate (2.58 g, 11.45 mmol), 4-dimethylaminopyridine (79.9 mg, 0.654 mmol) and DCM (20.0 mL, 312 mmol) and stirred at room temperature for 2 h. The mixture was evaporated in vacuo and the crude product was purified via flash chromatography on silica gel (40 g silica, solvent gradient: 0-50% ethyl acetate in heptane) to yield 2.24 g of the title compound. LCMS (ESI): [M+H]$^+$=377.

Step 2: tert-Butyl (6-(4-bromo-7,8,9,10-tetrahydro-6-oxa-2,10a-diazacycloocta[cd]inden-1-yl)benzo[d]thiazol-2-yl)carbamate

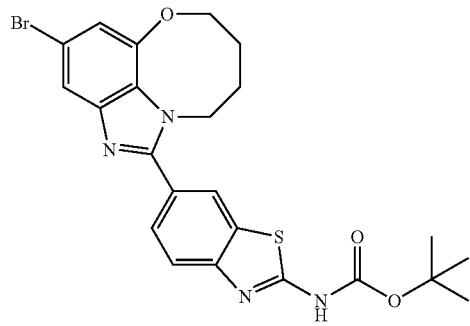 [SMILES: CC(C)(C)OC(=O)Nc1nc2ccc(-c3nc4cc(Br)cc5c4n3CCCCO5)cc2s1]

A mixture of 4-bromo-1-iodo-7,8,9,10-tetrahydro-6-oxa-2,10a-diazacycloocta[cd]indene (1.0323 g, 2.6266 mmol), tert-butyl (6-(4,4,5,5-tetramethyl-1,3,2-dioxaborolan-2-yl)benzo[d]thiazol-2-yl)carbamate (2.031 g, 3.239 mmol), [1,1'-bis(diphenylphosphino)ferrocene]palladium(II) chloride, complex with DCM (1:1) (324.8 mg, 0.3977 mmol), sodium carbonate (847.5 mg, 7.92 mmol), water (3.0 mL, 170 mmol) and THF (9.0 mL, 110 mmol) was heated in a sealed vessel under nitrogen at 80° C. for 20 h. The reaction mixture was degassed by bubbling through nitrogen for 10 minutes, additional [1,1'-bis(diphenylphosphino)ferrocene]palladium(II) chloride, complex with DCM (1:1) (523 mg) was added, and the mixture heated at 80° C. for 6 h. The reaction mixture was cooled to room temperature, diluted with ethyl acetate, filtered, washed with water and brine, and evaporated in vacuo. The crude product was purified via flash chromatography on silica gel (40 g silica, solvent gradient: 0-100% ethyl acetate in dichloromethane) to yield 0.4242 g (31%) of the title compound as a yellow solid. LCMS (ESI): [M+H]$^+$=514.95; $^1$H NMR (400 MHz, DMSO-d$_6$) δ 11.94 (s, 1H), 8.32 (d, J=1.2 Hz, 1H), 7.84 (d, J=8.4 Hz, 1H), 7.72 (dd, J=8.3, 1.7 Hz, 1H), 7.69-7.64 (m, 1H), 7.12-7.06 (m, 1H), 4.52-4.41 (m, 2H), 4.36-4.26 (m, 2H), 2.24-2.11 (m, 2H), 1.78-1.63 (m, 2H), 1.53 (s, 9H).

Step 3: tert-Butyl (S)-(6-(4-(3-carbamoylmorpholino)-7,8,9,10-tetrahydro-6-oxa-2,10a-diazacycloocta[cd]inden-1-yl)benzo[d]thiazol-2-yl)carbamate

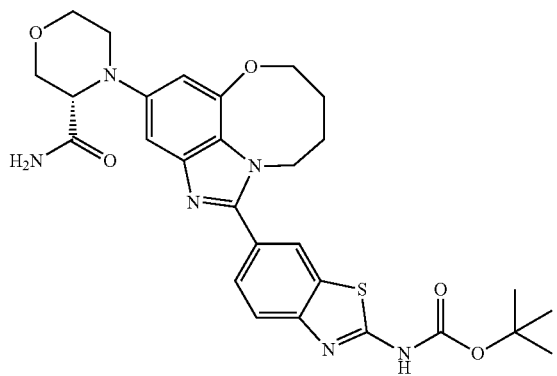 [SMILES: CC(C)(C)OC(=O)Nc1nc2ccc(-c3nc4cc(N5CCOC[C@H]5C(N)=O)cc5c4n3CCCCO5)cc2s1]

The title compound was prepared from tert-butyl (6-(4-bromo-7,8,9,10-tetrahydro-6-oxa-2,10a-diazacycloocta[cd]inden-1-yl)benzo[d]thiazol-2-yl)carbamate following procedures analogous to Example 104, steps 1-2. LCMS (ESI): [M+H]$^+$=565.1.

Step 4

To a solution of tert-butyl (S)-(6-(4-(3-carbamoylmorpholino)-7,8,9,10-tetrahydro-6-oxa-2,10a-diazacycloocta[cd]inden-1-yl)benzo[d]thiazol-2-yl)carbamate (0.2072 mmol, 0.2072 mmol) in DCM (3.0 mL, 47 mmol) was added hydrogen chloride (4.0 mol/L in dioxane, 0.50 mL, 2.0 mmol) and methanol (0.5 mL). The reaction mixture was stirred at room temperature for 3 h and then heated at 35° C. overnight, followed by an additional 4 h at 50° C. The reaction mixture was evaporated in vacuo and the crude product purified by reverse-phase HPLC and achiral SFC to yield 6.3 mg (6%) of 262. LCMS (ESI): R$_T$ (min)=2.74, [M+H]$^+$=465.1, method=B; $^1$H NMR (400 MHz, DMSO-d$_6$) δ 7.98 (d, J=1.7 Hz, 1H), 7.70 (s, 2H), 7.51 (dd, J=8.3, 1.8 Hz, 1H), 7.45 (d, J=8.3 Hz, 1H), 7.19 (d, J=1.9 Hz, 1H), 7.02 (s, 1H), 6.84 (d, J=2.1 Hz, 1H), 6.60 (d, J=2.1 Hz, 1H), 4.37 (t, J=6.1 Hz, 2H), 4.22 (t, J=5.4 Hz, 2H), 4.11-3.98 (m, 2H), 3.92-3.79 (m, 2H), 3.70-3.53 (m, 2H), 3.21-3.15 (m, 1H), 2.19-2.08 (m, 2H), 1.75-1.65 (m, 2H).

Example 263 (R)-2-((1-(2-Amino-7-fluorobenzo[d]oxazol-5-yl)-8,9-dihydro-7H-6-oxa-2,9a-diazabenzo[cd]azulen-4-yl)oxy)propanamide 263

263 was isolated via chiral SFC as a minor epimer produced during the preparation of Example 258. LCMS (ESI): R$_T$ (min) 2.44, [M+H]$^+$412, method A; $^1$H NMR (400 MHz, DMSO-d$_6$) δ 7.86 (br s, 2H), 7.47 (s, 1H), 7.43 (d, J=1.4, 1H), 7.32 (dd, J=10.7, 1.4 Hz, 1H), 7.21 (s, 1H), 6.78 (d, J=2.1 Hz, 1H), 6.44 (d, J=2.1 Hz, 1H), 4.60 (q, J=6.5 Hz, 1H), 4.42-4.36 (m, 2H), 4.32-4.26 (m, 2H), 2.34-2.25 (m, 2H), 1.44 (d, J=6.5 Hz, 3H).

Example 264 (S)-2-((1-(2-Amino-7-fluorobenzo[d]oxazol-5-yl)-7,8,9,10-tetrahydro-6-oxa-2,10a-diazacycloocta[cd]inden-4-yl)(methyl)amino)propanamide 264

264 (99.5 mg, 9.4% yield) was generated from 5-(4-bromo-7,8,9,10-tetrahydro-6-oxa-2,10a-diazacycloocta[cd]inden-1-yl)-7-fluorobenzo[d]oxazol-2-amine (Example 249, step 3) (1.00 g, 2.40 mmol) following a procedure analogous to Example 104. LCMS (ESI): R$_T$(min)=3.50, [M+H]$^+$=439, method=D; $^1$H NMR (300 MHz, DMSO-d$_6$) δ 7.86 (s, 2H), 7.36 (s, 1H), 7.29 (s, 1H), 7.19 (d, J=10.8 Hz, 1H), 7.06 (s, 1H), 6.83 (s, 1H), 6.59 (s, 1H), 4.36-4.23 (m, 5H), 2.79 (s, 3H), 2.20-2.02 (m, 2H), 1.80-1.55 (m, 2H), 1.22 (d, J=6.9 Hz, 3H).

Example 265 (S)-2-((1-(2-Aminothiazolo[5,4-b]pyridin-5-yl)-7,8,9,10-tetrahydro-6-oxa-2,10a-diazacycloocta[cd]inden-4-yl)oxy)propanamide 265

Step 1: 5-Bromothiazolo[5,4-b]pyridin-2-amine

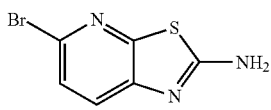 [SMILES: Nc1nc2ccc(Br)nc2s1]

To a suspension of 6-bromopyridin-3-amine (20.0 g, 115 mmol) and potassium thiocyanate (56.0 g, 576 mmol) in acetic acid (250 mL) was added dropwise a solution of bromine (23.88 g, 149 mmol) in acetic acid (100 mL) at room temperature. The reaction mixture was stirred at room temperature for 15 h. The solids were filtered out, and then the resulting solution was extracted with ethyl acetate and the organic layers combined and dried over anhydrous sodium sulfate, filtered and the filtrate was evaporated in vacuo. The crude product was purified via flash chromatography on silica gel (solvent gradient: 0-10% methanol in DCM) to yield 18 g (68%) of the title compound. LCMS (ESI): [M+H]$^+$=230/232.

Step 2: tert-Butyl 5-bromothiazolo[5,4-b]pyridin-2-ylcarbamate

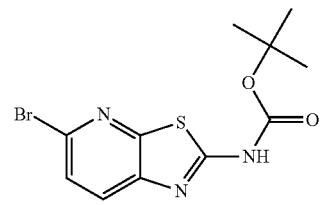 [SMILES: CC(C)(C)OC(=O)Nc1nc2ccc(Br)nc2s1]

To a suspension of 5-bromothiazolo[5,4-b]pyridin-2-amine (15.0 g, 65.1 mmol) in DCM (300 mL) was added di-tert butyl dicarbonate (21.0 g, 96.2 mmol) and 4-dimethylaminopyridine (8 g, 65.5 mmol). The reaction mixture stirred at room temperature for 2 h and evaporated in vacuo. The residue was purified via flash chromatography on silica gel (solvent gradient: 0-50% ethyl acetate in petroleum ether) to yield 13 g (60%) of the title compound as a white solid. LCMS (ESI): [M+H]$^+$=330/332.

Step 3: Methyl 2-(tert-butoxycarbonylamino)thiazolo[5,4-b]pyridine-5-carboxylate

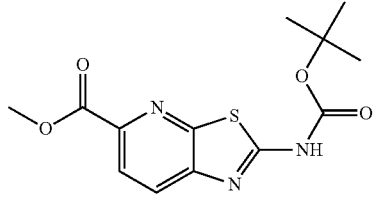 [SMILES: COC(=O)c1ccc2nc(NC(=O)OC(C)(C)C)sc2n1]

A mixture of tert-butyl 5-bromothiazolo[5,4-b]pyridin-2-ylcarbamate (14.0 g, 42.4 mmol), potassium carbonate (17 g, 123 mmol), palladium (II) acetate (2.80 g, 12.5 mmol) and [3-(diphenylphosphanyl)propyl]diphenylphosphane (4.2 g, 10.1 mmol) in methanol (300 mL) and DMF (150 mL) was saturated with carbon monoxide gas and stirred at 60° C. for 6 h. The resulting mixture was cooled to room temperature and evaporated in vacuo. The residue was partitioned between ethyl acetate and water and then filtered through celite. The aqueous layer was extracted with ethyl acetate and the combined organic extracts were washed with brine, dried over magnesium sulfate and evaporated in vacuo. The crude product was purified via flash chromatography on silica gel (solvent gradient, 0-5% methanol in DCM) to yield 8 g (61%) of the title compound as a white solid. LCMS (ESI): [M+H]$^+$=310.

Step 4: 2-(tert-Butoxycarbonylamino)thiazolo[5,4-b]pyridine-5-carboxylic acid

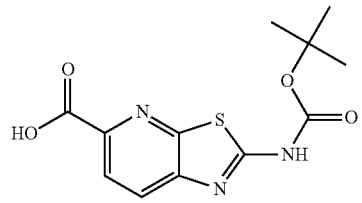 [SMILES: CC(C)(C)OC(=O)Nc1nc2ccc(C(=O)O)nc2s1]

To a suspension of methyl 2-(tert-butoxycarbonylamino)thiazolo[5,4-b]pyridine-5-carboxylate (8.00 g, 25.8 mmol) in THF (100 mL) was added lithium hydroxide (1 N aqueous, 140 mL, 133 mmol) and the mixture was stirred at room temperature for 4 h. The pH value of the solution was adjusted to 6 with hydrogen chloride. The solvent was evaporated and the crude product used directly in the next step without further purification. LCMS (ESI): [M+H]$^+$= 296.

Step 5: tert-Butyl (5-(4-bromo-7,8,9,10-tetrahydro-6-oxa-2,10a-diazacycloocta[cd]inden-1-yl)thiazolo[5,4-b]pyridin-2-yl)carbamate

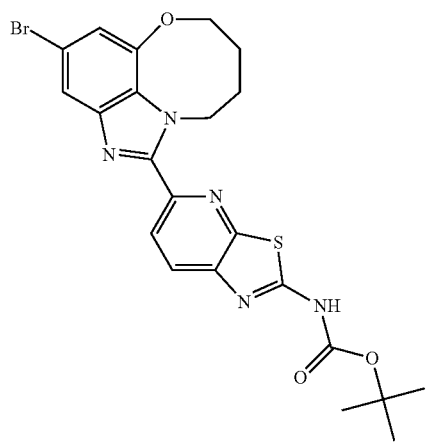 [SMILES: CC(C)(C)OC(=O)Nc1nc2ccc(-c3nc4cc(Br)cc5c4n3CCCCO5)nc2s1]

The title compound (3.1 g, 67.4% yield over two steps) was generated from 9-bromo-3,4,5,6-tetrahydro-2H-benzo[b][1,4]oxazocin-7-amine (Example 204, step 4) (2.3 g, 8.94 mmol) and 2-(tert-butoxycarbonylamino)thiazolo[5,4-b]pyridine-5-carboxylic acid (3.40 g, 11.5 mmol) following procedures analogous to those of Example 125, steps 1-2. LCMS (ESI): [M+H]$^+$=516/518.

Step 6: tert-Butyl (5-(4-(4,4,5,5-tetramethyl-1,3,2-dioxaborolan-2-yl)-7,8,9,10-tetrahydro-6-oxa-2,10a-diazacycloocta[cd]inden-1-yl)thiazolo[5,4-b]pyridin-2-yl)carbamate

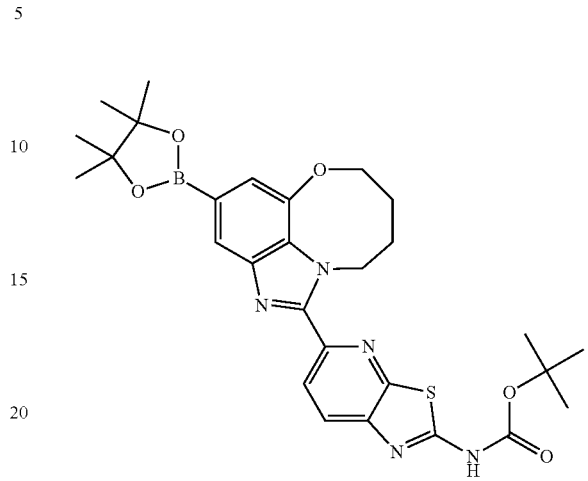

tert-Butyl (5-(4-bromo-7,8,9,10-tetrahydro-6-oxa-2,10a-diazacycloocta[cd]inden-1-yl)thiazolo[5,4-b]pyridin-2-yl)carbamate (3.00 g, 5.81 mmol,), 4,4,4',4',5,5,5',5'-octamethyl-2,2'-bi(1,3,2-dioxaborolane) (1.80 g, 7.09 mmol), potassium acetate (1.80 g, 18.3 mmol) and 1,1'-bis(diphenylphosphino)ferrocenyl palladium (II) dichloride (700 mg, 0.957 mmol) were suspended in DMF (100 mL) under an atmosphere of nitrogen and the reaction was heated at 90° C. for 16 h. The resultant mixture was cooled to room temperature and diluted with water. The mixture was extracted with DCM, dried over magnesium sulfate and evaporated in vacuo. The crude product was purified via flash chromatography on silica gel (solvent gradient, 0-10% methanol in DCM) to yield 1.3 g (40%) of the title compound as a light yellow solid. LCMS (ESI): [M+H]$^+$=564.

Step 7: tert-Butyl (5-(4-hydroxy-7,8,9,10-tetrahydro-6-oxa-2,10a-diazacycloocta[cd]inden-1-yl)thiazolo[5,4-b]pyridin-2-yl)carbamate

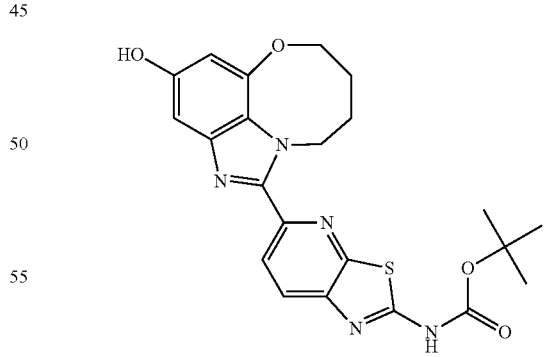

To a solution of tert-butyl (5-(4-(4,4,5,5-tetramethyl-1,3,2-dioxaborolan-2-yl)-7,8,9,10-tetrahydro-6-oxa-2,10a-diazacycloocta[cd]inden-1-yl)thiazolo[5,4-b]pyridin-2-yl)carbamate (1.30 g, 2.31 mmol) in acetic acid (10 mL) and water (10 mL) was added hydrogen peroxide (5 mL, 30% aqueous solution) and the reaction mixture was stirred at room temperature for 2 h. The resulting mixture was quenched by the addition of sodium bisulfite. The solids were collected by filtration and dried in vacuo obtained the crude product, which was used directly in the next step without further purification. LCMS (ESI): [M+H]⁺=454.

Step 8: 1-(2-Aminothiazolo[5,4-b]pyridin-5-yl)-7,8,9,10-tetrahydro-6-oxa-2,10a-diazacycloocta[cd]inden-4-ol

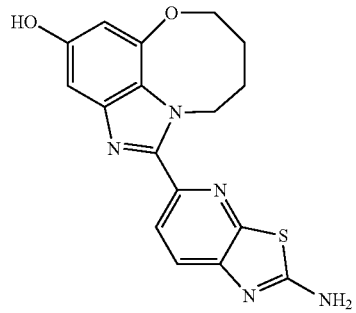

tert-Butyl (5-(4-hydroxy-7,8,9,10-tetrahydro-6-oxa-2,10a-diazacycloocta[cd]inden-1-yl)thiazolo[5,4-b]pyridin-2-yl)carbamate (900 mg, 1.99 mmol) was dissolved in hydrochloric acid (20 mL, 4 M solution in dioxane) and stirred at room temperature for 2 h and then the solvent was evaporated in vacuo. The solids were collected and used directly in the next step without further purification. LCMS (ESI): [M+H]⁺=354.

Step 9: (S)-Methyl 2-((1-(2-aminothiazolo[5,4-b]pyridin-5-yl)-7,8,9,10-tetrahydro-6-oxa-2,10a-diazacycloocta[cd]inden-4-yl)oxy)propanoate

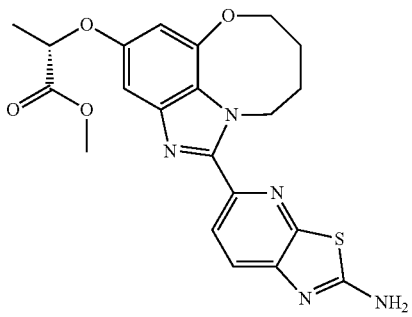 [SMILES: COC(=O)[C@H](C)Oc1cc2c3c(c1)nc(-c1ccc4nc(N)sc4n1)n3CCCCO2]

A reaction vessel was charged with 1-(2-aminothiazolo[5,4-b]pyridin-5-yl)-7,8,9,10-tetrahydro-6-oxa-2,10a-diazacycloocta[cd]inden-4-ol (900 mg, 2.55 mmol), (9-methyl 2-(tosyloxy)propanoate (1.00 g, 3.88 mmol 1), potassium carbonate (1.20 g, 8.68 mmol) and DMSO (15 mL). The reaction mixture was heated at 40° C. for 20 h. The resulting mixture was allowed to cool to room temperature and partitioned between DCM and water. The organic layer was washed with brine, dried over magnesium sulfate and evaporated in vacuo. The crude product was purified via flash chromatography on silica gel (solvent gradient: 0-10% methanol in DCM) to yield 150 mg (13%) of the title compound as a yellow solid. LCMS (ESI): [M+H]⁺=440.

Step 10

A reaction vessel was charged with (9-methyl 2-((1-(2-aminothiazolo[5,4-b]pyridin-5-yl)-7,8,9,10-tetrahydro-6-oxa-2,10a-diazacycloocta[cd]inden-4-yl)oxy)propanoate (180 mg, 0.410 mmol) and 7 N ammonia in methanol (10 mL). The reaction mixture was stirred at room temperature for 6 h. The resulting mixture was concentrated in vacuo. The crude product was purified via chiral-SFC to yield 34.2 mg (20%) of 265 as a light yellow solid. LCMS (ESI): R$_T$ (min)=1.20, [M+H]⁺=425, method=D; ¹H NMR (300 MHz, DMSO-d$_6$) δ 8.11-8.06 (m, 3H), 7.76-7.73 (m, 1H), 7.54 (s, 1H), 7.25 (s, 1H), 6.92-6.91 (m, 1H), 6.59-6.58 (m, 1H), 4.95-4.91 (m, 2H), 4.65-4.58 (m, 1H), 4.26-4.22 (m, 2H), 2.14-2.12 (m, 2H), 1.59 (s, 2H), 1.45-1.43 (m, 3H).

Example 266 (S)-2-((1-(2-Aminooxazolo[4,5-b]pyridin-5-yl)-8,9-dihydro-7H-6-oxa-2,9a-diazabenzo[cd]azulen-4-yl)oxy)propanamide 266

Step 1: 5-Bromooxazolo[4,5-b]pyridin-2-amine

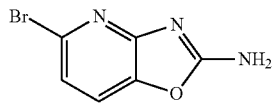

The title compound (1.45 g, 64% yield) was generated from 2-amino-6-bromopyridin-3-ol (2.0 g, 10.6 mmol) following a procedure analogous to Example 235, step 1. LCMS (ESI): [M+1-1]⁺=214/216.

Step 2: tert-Butyl (5-bromooxazolo[4,5-b]pyridin-2-yl)carbamate

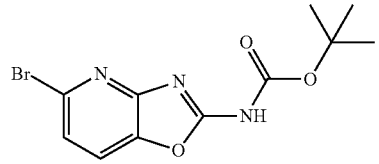 [SMILES: CC(C)(C)OC(=O)Nc1nc2nc(Br)ccc2o1]

To a suspension of 5-bromooxazolo[4,5-b]pyridin-2-amine (1.10 g, 5.12 mmol) in DCM (20 mL) was added triethylamine (2.14 mL, 15.4 mmol) and di-tert butyl dicarbonate (2.46 g, 11.3 mmol) followed by catalytic 4-dimethylaminopyridine and the reaction mixture stirred at room temperature for 16 h. The resulting mixture was diluted with water and extracted with ethyl acetate. The combined organic extracts were washed with brine, dried over magnesium sulfate and evaporated in vacuo to yield 2.24 g (66%) of the title compound as a yellow solid. The crude residue was used without further purification. LCMS (ESI): [M+Na]⁺=336/338.

Step 3: Methyl 2-((tert-butoxycarbonyl)amino)oxazolo[4,5-b]pyridine-5-carboxylate

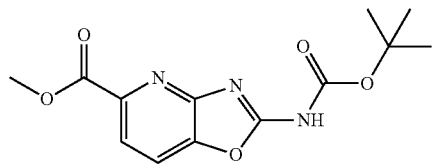 [SMILES: COC(=O)c1ccc2oc(NC(=O)OC(C)(C)C)nc2n1]

A mixture of tert-butyl (5-bromooxazolo[4,5-b]pyridin-2-yl)carbamate (2.00 g, 6.37 mmol), triethylamine (30 mL, 23.4 mmol), palladium (II) acetate (71.4 mg, 0.32 mmol) and Xantphos (195 mg, 0.34 mmol) in methanol (10 mL) was thoroughly degassed with argon. This resulting mixture was saturated with carbon monoxide gas for 10 min under stirring and the reaction mixture was heated at 65° C. for 24 h. The resulting mixture was cooled to room temperature and evaporated in vacuo. The residue was partitioned between ethyl acetate and water and then filtered through celite. The aqueous layer was washed with ethyl acetate and the combined organic extracts were washed with brine, dried over magnesium sulfate and evaporated in vacuo. The crude product was purified via flash chromatography on silica gel (solvent gradient, 0-5% methanol in DCM) to yield 650 mg (35%) of the title compound as a pale red solid. LCMS (ESI): [M+H]$^+$=294.

Step 4: 2-((tert-Butoxycarbonyl)amino)oxazolo[4,5-b]pyridine-5-carboxylic acid

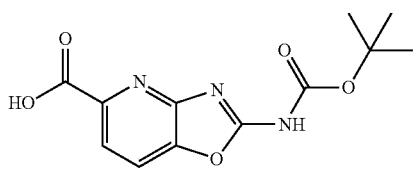 [SMILES: CC(C)(C)OC(=O)Nc1nc2nc(C(=O)O)ccc2o1]

To a suspension of methyl 2-((tert-butoxycarbonyl)amino)oxazolo[4,5-b]pyridine-5-carboxylate (650 mg, 2.22 mmol) in THF (10 mL) was added lithium hydroxide (1 N aqueous, 2.5 mL, 2.50 mmol) and the mixture was stirred at room temperature for 16 h. Further lithium hydroxide (1 N aqueous, 1.7 mL, 1.70 mmol) was added and the reaction mixture was stirred for an additional 30 min. The solvent was evaporated and the crude product used directly in the next step without further purification. LCMS (ESI): [M+Na]$^+$=302.

Step 5: tert-Butyl (5-((8-bromo-2,3,4,5-tetrahydrobenzo[b][1,4]oxazepin-6-yl)carbamoyl)oxazolo[4,5-b]pyridin-2-yl)carbamate

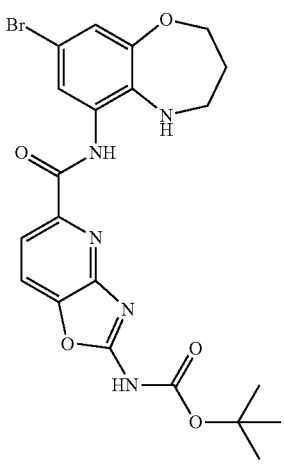 [SMILES: CC(C)(C)OC(=O)Nc1nc2nc(C(=O)Nc3cc(Br)cc4c3NCCCO4)ccc2o1]

To a solution of 2-((tert-butoxycarbonyl)amino)oxazolo[4,5-b]pyridine-5-carboxylic acid (614 mg, 2.22 mmol) in DMF (10 mL) was added DIPEA (0.77 mL, 4.40 mmol) and then HATU (1.25 g, 3.30 mmol). The resulting mixture was stirred at room temperature for 5 min then 8-bromo-2,3,4,5-tetrahydrobenzo[b][1,4]oxazepin-6-amine (534 mg, 2.20 mmol) was added and the reaction mixture was stirred at room temperature for 1.5 h. The resulting mixture was partitioned between ethyl acetate and water and the aqueous phase was extracted with ethyl acetate. The combined organic extracts were washed with brine, dried over sodium sulfate and the solvent was evaporated. The crude residue was used directly in the next step without further purification. LCMS (ESI): [M+H]$^+$=504/506.

Step 6: 5-(4-Bromo-8,9-dihydro-7H-6-oxa-2,9a-diazabenzo[cd]azulen-1-yl)oxazolo[4,5-b]pyridin-2-amine

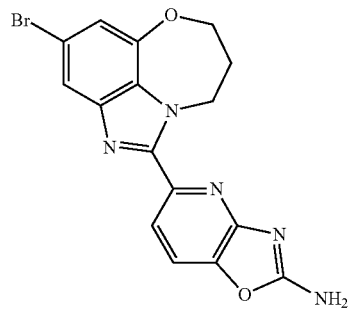 [SMILES: Nc1nc2nc(-c3nc4cc(Br)cc5c4n3CCCO5)ccc2o1]

tert-Butyl (5-((8-bromo-2,3,4,5-tetrahydrobenzo[b][1,4]oxazepin-6-yl)carbamoyl)oxazolo[4,5-b]pyridin-2-yl)carbamate (crude, assume 2.22 mmol) was dissolved in acetic acid (10 mL) and stirred at 90° C. for 2 h and was then allowed to cool to room temperature. The solvent was removed under reduced pressure, the residue was suspended in DCM and then washed with saturated aqueous sodium hydrogen carbonate. The resulting precipitate was filtered and the solid collected. The organic phase of the filtrate was washed with brine and the solvent removed in vacuo. The resulting residue was combined with the filtered solid and triturated with DCM, filtered and the solid dried in vacuo to yield 622 mg (73%, over 3 steps) of the title compound as a beige solid. LCMS (ESI): [M+H]$^+$=386/388.

Step 7: 1-(2-Aminooxazolo[4,5-b]pyridin-5-yl)-8,9-dihydro-7H-6-oxa-2,9a-diazabenzo[cd]azulen-4-ol

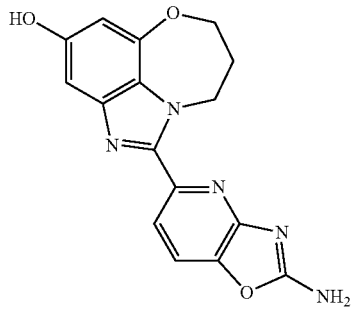 [SMILES: Nc1nc2nc(-c3nc4cc(O)cc5c4n3CCCO5)ccc2o1]

The title compound (128 mg, 54% yield over 2 steps) was generated from 5-(4-bromo-8,9-dihydro-7H-6-oxa-2,9a-diazabenzo[cd]azulen-1-yl)oxazolo[4,5-b]pyridin-2-amine (282 mg, 0.73 mmol) following procedures analogous to Example 240, Steps 1-2. LCMS (ESI): [M+H]$^+$=324.

Step 8

266 (16 mg, 10% yield over 2 steps) was generated from 1-(2-aminooxazolo[4,5-b]pyridin-5-yl)-8,9-dihydro-7H-6-oxa-2,9a-diazabenzo[cd]azulen-4-ol (125 mg, 0.39 mmol) following procedures analogous to Example 251 and 252, Steps 3-4. LCMS (ESI): $R_T$ (min)=2.24, [M+H]$^+$=395, method=A; $^1$H NMR (400 MHz, DMSO-d$_6$) δ 8.09 (s, 2H), 7.83 (d, J=8.1 Hz, 1H), 7.80 (d, J=8.1 Hz, 1H), 7.49 (s, 1H), 7.21 (s, 1H), 6.79 (d, J=2.2 Hz, 1H), 6.45 (d, J=2.2 Hz, 1H), 4.75 (t, J=5.5 Hz, 2H), 4.61 (q, J=6.5 Hz, 1H), 4.42-4.37 (m, 2H), 2.37-2.30 (m, 2H), 1.44 (d, J=6.5 Hz, 3H).

Examples 267 and 268 (R)-2-((1-(4-(1H-1,2,4-Triazol-3-yl)phenyl)-7,8,9,10-tetrahydro-6-oxa-2,10a-diazacycloocta[cd]inden-4-yl)oxy)butanamide 267 and (S)-2-((1-(4-(1H-1,2,4-Triazol-3-yl)phenyl)-7,8,9,10-tetrahydro-6-oxa-2,10a-diazacycloocta[cd]inden-4-yl)oxy)butanamide 268

Step 1: 3-(4-Bromophenyl)-1-(4-methoxybenzyl)-1H-1,2,4-triazole

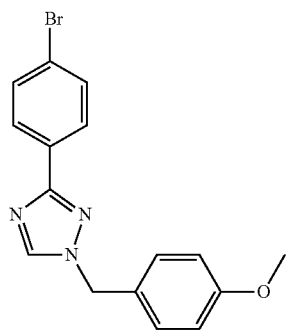 [SMILES: COc1ccc(Cn2cnc(-c3ccc(Br)cc3)n2)cc1]

A mixture of 3-(4-bromophenyl)-1H-1,2,4-triazole (5 g, 22.3 mmol), 1-(chloromethyl)-4-methoxybenzene (4.19 g, 26.8 mmol) and cesium carbonate (14.6 g, 44.9 mmol) in DMF (100 mL) was stirred at room temperature for 16 h. The resulting solution was diluted with water and extracted with ethyl acetate. The organic layers were combined and concentrated in vacuo. The crude product was purified via flash chromatography on silica gel (solvent gradient, 0-5% ethyl acetate in petroleum ether) to yield 6 g (78%) of the title compound as a white solid. LCMS (ESI): [M+H]$^+$=344/346.

Step 2: 4-Bromo-1-(4-(1-(4-methoxybenzyl)-1H-1,2,4-triazol-3-yl)phenyl)-7,8,9,10-tetrahydro-6-oxa-2,10a-diazacycloocta[cd]indene

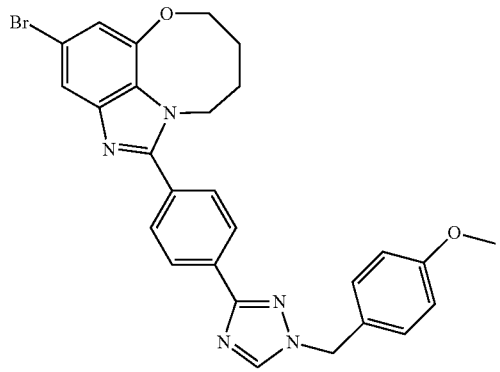 [SMILES: COc1ccc(Cn2cnc(-c3ccc(-c4nc5cc(Br)cc6c5n4CCCCO6)cc3)n2)cc1]

The title compound (2.2 g, 47% yield over two steps) was generated from 4-bromo-1-iodo-7,8,9,10-tetrahydro-6-oxa-2,10a-diazacycloocta[cd]indene (Example 204, step 6) (3.46 g, 8.80 mmol) and 3-(4-bromophenyl)-1-(4-methoxybenzyl)-1H-1,2,4-triazole (3.64 g, 9.30 mmol) following procedures analogous to Example 158, steps 2-3. LCMS (ESI): [M+H]$^+$=530/532.

Step 3: 1-(4-(1-(4-Methoxybenzyl)-1H-1,2,4-triazol-3-yl)phenyl)-7,8,9,10-tetrahydro-6-oxa-2,10a-diazacycloocta[cd]inden-4-ol

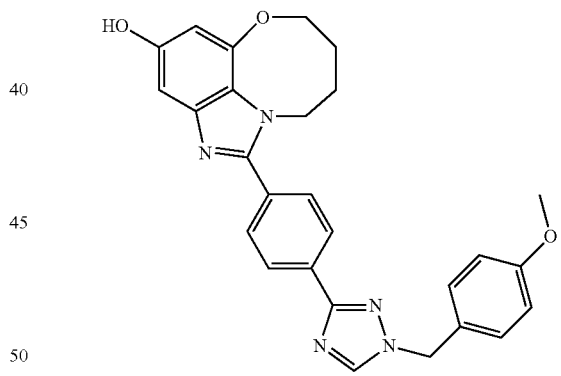

4-Bromo-1-(4-(1-(4-methoxybenzyl)-1H-1,2,4-triazol-3-yl)phenyl)-7,8,9,10-tetrahydro-6-oxa-2,10a-diazacycloocta[cd]indene (1.3 g, 3.31 mmol), 2-di-t-butylphosphino-2',4',6'-tri-i-propyl-1,1'-biphenyl (150 mg, 0.353 mmol), tris(dibenzylideneacetone)dipalladium(0) (170 mg, 0.186 mmol), and potassium hydroxide (270 mg, 4.81 mmol) were suspended in 1,4-dioxane (15 mL) and water (1.5 mL) under an atmosphere of nitrogen and the mixture was heated at 100° C. for 7 h. The reaction system was diluted with water and extracted with DCM. The organic phase was dried over magnesium sulfate and evaporated in vacuo. The crude product was purified via flash chromatography on silica gel (solvent gradient: 0-10% methanol in DCM) to yield 760 mg (67%) of the title compound as a yellow solid. LCMS (ESI): [M+H]$^+$=468.

Step 4: Methyl 2-((1-(4-(1-(4-methoxybenzyl)-1H-1,2,4-triazol-3-yl)phenyl)-7,8,9,10-tetrahydro-6-oxa-2,10a-diazacycloocta[cd]inden-4-yl)oxy)butanoate

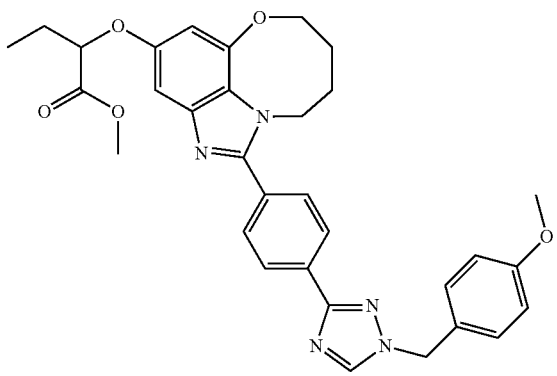 [SMILES: CCC(Oc1cc2c3c(c1)nc(-c1ccc(-c4ncn(Cc5ccc(OC)cc5)n4)cc1)n3CCCCO2)C(=O)OC]

A reaction vessel was charged with 1-(4-(1-(4-methoxybenzyl)-1H-1,2,4-triazol-3-yl)phenyl)-7,8,9,10-tetrahydro-6-oxa-2,10a-diazacycloocta[cd]inden-4-ol (700 mg, 1.50 mmol), methyl 2-bromobutanoate (400 mg, 2.21 mmol), potassium carbonate (1.20 g, 8.68 mmol) and DMSO (15.0 mL). The reaction mixture was stirred at room temperature for 1 h. The resulting mixture was partitioned between DCM and water. The organic layer was washed with brine, dried over magnesium sulfate and evaporated in vacuo. The crude product was purified via flash chromatography on silica gel (solvent gradient: 0-10% methanol in DCM) to yield 620 mg (73%) of the title compound as a grey solid. LCMS (ESI): [M+H]$^+$=568.

Step 5: 2-((1-(4-(1-(4-Methoxybenzyl)-1H-1,2,4-triazol-3-yl)phenyl)-7,8,9,10-tetrahydro-6-oxa-2,10a-diazacycloocta[cd]inden-4-yl)oxy)butanamide

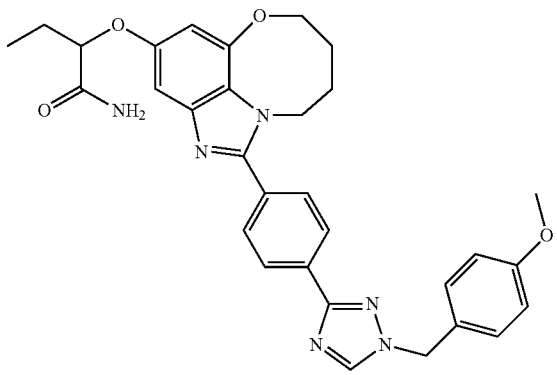 [SMILES: CCC(Oc1cc2c3c(c1)nc(-c1ccc(-c4ncn(Cc5ccc(OC)cc5)n4)cc1)n3CCCCO2)C(N)=O]

A mixture of methyl 2-((1-(4-(1-(4-methoxybenzyl)-1H-1,2,4-triazol-3-yl)phenyl)-7,8,9,10-tetrahydro-6-oxa-2,10a-diazacycloocta[cd]inden-4-yl)oxy)butanoate (650 mg, 1.15 mmol) and ammonia (20 mL, 7 M solution in methanol) was stirred at room temperature for 48 h. The resulting mixture was evaporated in vacuo to yield 600 mg (crude) of the title compound as a yellow solid. LCMS (ESI): [M+H]$^+$=553.

Step 6

A solution of 2-((1-(4-(1-(4-methoxybenzyl)-1H-1,2,4-triazol-3-yl)phenyl)-7,8,9,10-tetrahydro-6-oxa-2,10a-diazacycloocta[cd]inden-4-yl)oxy)butanamide (600 mg, 1.08 mmol) in TFA (20 mL) was heated at 90° C. for 4 h. The reaction mixture was evaporated in vacuo. The resultant residue was purified via flash chromatography on silica gel (solvent gradient: 0-10% methanol in DCM) to yield 350 mg of a racemic mixture of 267 and 268 as a yellow solid. The two stereoisomers were separated by chiral SFC to yield the title compounds each as a single unknown stereoisomer.

267 (102.4 mg, 21% yield): LCMS (ESI): R$_T$ (min)=1.99, [M+H]$^+$=433, method=C; $^1$H NMR (300 MHz, DMSO-d$_6$) δ 14.23 (s, 1H), 8.69 (s, 1H), 8.22-8.11 (m, 2H), 7.91-7.80 (m, 1H), 7.53 (s, 1H), 7.27 (s, 1H), 6.96 (d, J=1.8 Hz, 1H), 6.64 (d, J=2.8 Hz, 1H), 4.47-4.41 (m, 3H), 4.28-4.25 (m, 2H), 2.17 (s, 2H), 1.89-1.79 (m, 2H), 1.71 (s, 2H), 1.07-0.98 (m, 3H).

268 (90.2 mg, 19% yield): LCMS (ESI): R$_T$ (min)=1.99, [M+H]$^+$=433, method=C; $^1$H NMR (300 MHz, DMSO-d$_6$) δ 14.23 (s, 1H), 8.69 (s, 1H), 8.22-8.11 (m, 2H), 7.91-7.80 (m, 1H), 7.53 (s, 1H), 7.27 (s, 1H), 6.96 (d, J=1.8 Hz, 1H), 6.64 (d, J=2.8 Hz, 1H), 4.47-4.41 (m, 3H), 4.28-4.25 (m, 2H), 2.17 (s, 2H), 1.89-1.79 (m, 2H), 1.71 (s, 2H), 1.07-0.98 (m, 3H).

Example 269 (S)-2-((1-(3-Fluoro-4-(1H-1,2,4-triazol-3-yl)phenyl)-7,8,9,10-tetrahydro-6-oxa-2,10a-diazacycloocta[cd]inden-4-yl)oxy)propanamide 269

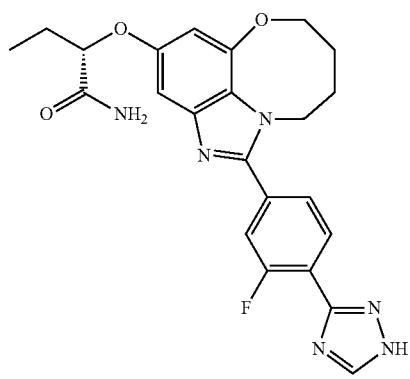 [SMILES: CC[C@H](Oc1cc2c3c(c1)nc(-c1ccc(-c4nc[nH]n4)c(F)c1)n3CCCCO2)C(N)=O]

Step 1: (9-Methyl 2-((1-(3-fluoro-4-(1-(4-methoxybenzyl)-1H-1,2,4-triazol-3-yl)phenyl)-7,8,9,10-tetrahydro-6-oxa-2,10a-diazacycloocta[cd]inden-4-yl)oxy)propanoate

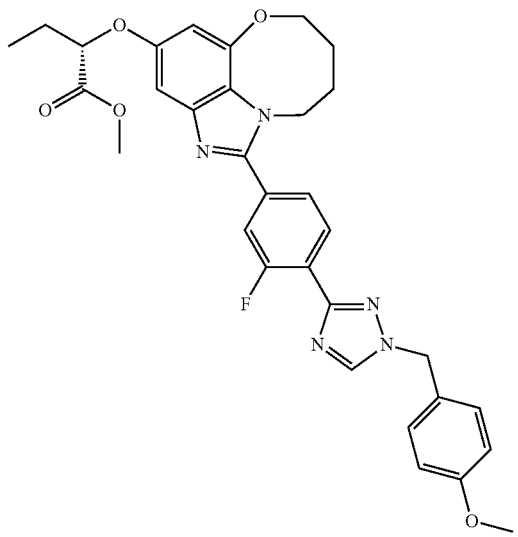 [SMILES: CC[C@H](Oc1cc2c3c(c1)nc(-c1ccc(-c4ncn(Cc5ccc(OC)cc5)n4)c(F)c1)n3CCCCO2)C(=O)OC]

The title compound (1.00 g, 85% yield) was generated from 1-(3-fluoro-4-(1-(4-methoxybenzyl)-1H-1,2,4-triazol-3-yl)phenyl)-7,8,9,10-tetrahydro-6-oxa-2,10a-diazacycloocta[cd]inden-4-ol (Example 305, step 7) (1.00 g, 2.06 mmol) following a procedure analogous to Example 162, step 3. LCMS: [M+H]$^+$=572.

Step 2: (S)-2-((1-(3-Fluoro-4-(1-(4-methoxybenzyl)-1H-1,2,4-triazol-3-yl)phenyl)-7,8,9,10-tetrahydro-6-oxa-2,10a-diazacycloocta[cd]inden-4-yl)oxy)propanamide

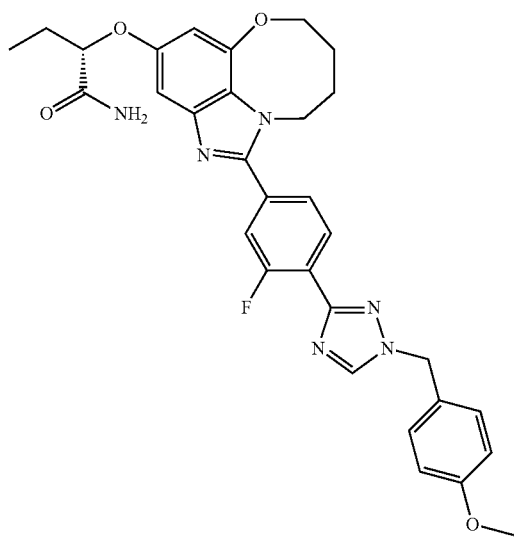 [SMILES: CC[C@H](Oc1cc2c3c(c1)nc(-c1ccc(-c4ncn(Cc5ccc(OC)cc5)n4)c(F)c1)n3CCCCO2)C(N)=O]

The title compound (0.5 g, 64% yield) was generated from (9-methyl 2-((1-(3-fluoro-4-(1-(4-methoxybenzyl)-1H-1,2,4-triazol-3-yl)phenyl)-7,8,9,10-tetrahydro-6-oxa-2,10a-diazacycloocta[cd]inden-4-yl)oxy)propanoate (800 mg, 1.40 mmol) following a procedure analogous to Example 267, step 5. LCMS: [M+H]$^+$=557.

Step 4

269 (165 mg, 23% yield) was generated from (S)-2-((1-(3-fluoro-4-(1-(4-methoxybenzyl)-1H-1,2,4-triazol-3-yl)phenyl)-7,8,9,10-tetrahydro-6-oxa-2,10a-diazacycloocta[cd]inden-4-yl)oxy)propanamide (900 mg, 1.61 mmol) following a procedure analogous to Example 267, step 6. LCMS: R$_T$ (min)=3.50, [M+H]$^+$=437, method=C; $^1$H NMR (300 MHz, DMSO-d$_6$) δ 14.38 (s, 1H), 8.67-8.43 (m, 1H), 8.31-8.19 (m, 1H), 7.69-7.64 (m, 3H), 7.32-7.26 (s, 1H), 6.96-6.91 (m, 1H), 6.64-6.63 (m, 1H), 4.67-4.61 (m, 1H), 4.45 (d, J=6.3 Hz, 2H), 4.27-4.25 (m, 2H), 2.15-2.14 (m, 2H), 1.69-1.65 (m, 2H), 1.47-1.23 (m, 3H).

Example 270 (S)-2-((1-(2-Amino-4-fluorobenzo[d]oxazol-5-yl)-7,8,9,10-tetrahydro-6-oxa-2,10a-diazacycloocta[cd]inden-4-yl)(methyl)amino)propanamide 270

Step 1:
1-Bromo-2-fluoro-4-methoxy-3-nitrobenzene

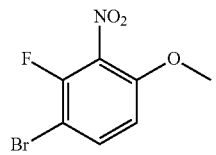

To a solution of 1-fluoro-3-methoxy-2-nitrobenzene (45.0 g, 0.263 mol) in acetic acid (300 mL) was added bromine (54.0 g, 0.338 mol) dropwise with stirring. The reaction mixture was stirred at 55° C. for 17 h. The resulting mixture was evaporated in vacuo to yield 63.8 g (97%) of the title compound as a yellow solid.

Step 2: 3-Bromo-2-fluoro-6-methoxybenzenamine

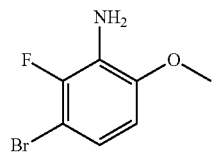

To a solution of 1-bromo-2-fluoro-4-methoxy-3-nitrobenzene (65.5 g, 0.262 mol) and ammonium chloride (56.7 g, 1.06 mol) in methanol (720 mL) and water (720 mL) at room temperature was added iron powder (44.1 g, 0.790 mol). The mixture was stirred at 60° C. for 2 h then filtered. The solvent was evaporated in vacuo to yield 54.1 g (94%) of the title compound as an orange solid. LCMS (ESI): [M+H]$^+$= 220/222.

Step 3: 2-Amino-4-bromo-3-fluorophenol

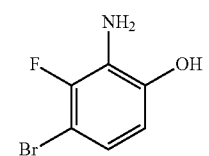

To a suspension of 3-bromo-2-fluoro-6-methoxybenzenamine (30.0 g, 0.136 mmol) in DCM (950 mL) was added tribromoborane (330 mL, 1 M solution in DCM) dropwise with stirring at 0° C. The resulting solution was stirred for 16 h at room temperature, and then quenched by the addition of aqueous sodium bicarbonate. The aqueous layer was extracted with DCM, and the organic portion was dried over sodium sulfate and evaporated in vacuo to yield 27.5 g (98%) of the title compound as an orange solid. LCMS (ESI): [M+H]$^+$=206/208.

Step 4: 5-Bromo-4-fluorobenzo[d]oxazol-2-amine

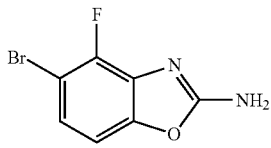

To a solution of 2-amino-4-bromo-3-fluorophenol (22.0 g, 0.107 mol) in methanol (120 mL) was added cyanic bromide (22.0 g, 208 mol). The reaction mixture was stirred at 35° C. for 16 h, The reaction was then quenched by the addition of saturated aqueous sodium bicarbonate. The methanol was removed under reduced pressure. The residue was partitioned between ethyl acetate and saturated aqueous sodium hydrogen carbonate and the phases separated. The aqueous layer was further extracted with ethyl acetate. The organic extracts were combined, washed with brine, dried over sodium sulfate and evaporated in vacuo. The residue was purified via flash chromatography on silica gel (solvent gradient: 5-33% ethyl acetate in petroleum ether) to yield 22.3 g (90%) of the title compound as a yellow solid. LCMS (ESI): [M+H]$^+$=231/233.

Step 5: 5-(4-Bromo-7,8,9,10-tetrahydro-6-oxa-2,10a-diazacycloocta[cd]inden-1-yl)-4-fluorobenzo[d]oxazol-2-amine

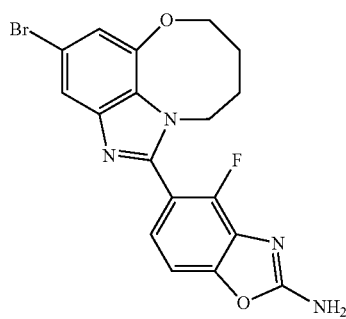 [SMILES: Nc1nc2c(F)c(-c3nc4cc(Br)cc5c4n3CCCCO5)ccc2o1]

The title compound (870 mg, 29% yield over two steps) was generated from 4-bromo-1-iodo-7,8,9,10-tetrahydro-6-oxa-2,10a-diazacycloocta[cd]indene (Example 204, step 6) (2.80 g, 7.12 mmol) following procedures analogous to Example 204, steps 7-8. LCMS (ESI): [M+H]$^+$=206/208.

Step 6: (S)-2-((1-(2-Amino-4-fluorobenzo[d]oxazol-5-yl)-7,8,9,10-tetrahydro-6-oxa-2,10a-diazacycloocta[cd]inden-4-yl)(methyl)amino)propanamide 270 (75.9 mg, 14.4% yield over two steps) was generated from 5-(4-bromo-7,8,9,10-tetrahydro-6-oxa-2,10a-diazacycloocta[cd]inden-1-yl)-4-fluorobenzo[d]oxazol-2-amine (500 mg, 1.20 mmol) following procedures analogous to those of Example 264. LCMS (ESI): R$_T$ (min)=1.18, [M+H]$^+$: 439, method=D; $^1$H NMR (400 MHz, DMSO-d$_6$): δ 7.81 (s, 2H), 7.40-7.35 (m, 2H), 7.16-7.07 (m, 2H), 6.79 (d, J=2.0 Hz, 1H), 6.20 (d, J=2.0 Hz, 1H), 4.33-4.27 (m, 1H), 4.23-4.17 (m, 4H), 2.81 (s, 3H), 2.00-1.94 (m, 2H), 1.68-1.63 (m, 2H), 1.23 (d, J=6.8 Hz, 3H).

Example 271: (S)-2-((1-(2-Aminobenzo[d]oxazol-5-yl)-7,8,9,10-tetrahydro-6-oxa-2,10a-diazacycloocta[cd]inden-4-yl)oxy)butanamide 271

Step 1: Methyl (S)-2-((1-(2-aminobenzo[d]oxazol-5-yl)-7,8,9,10-tetrahydro-6-oxa-2,10a-diazacycloocta[cd]inden-4-yl)oxy)butanoate

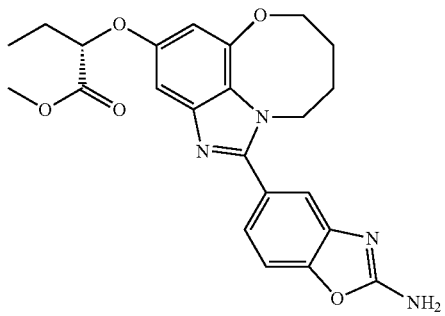 [SMILES: CC[C@H](Oc1cc2c3c(c1)nc(-c1ccc4oc(N)nc4c1)n3CCCCO2)C(=O)OC]

The title compound (27 mg, 35%) was prepared from 1-(2-aminobenzo[d]oxazol-5-yl)-7,8,9,10-tetrahydro-6-oxa-2,10a-diazacycloocta[cd]inden-4-ol and methyl (2R)-2-(p-tosylsulfonyloxy)butanoate following a procedure analogous to that of Example 204. LCMS (ESI) [M+H]$^+$=437.

Step 2

271 (12.9 mg, 12% yield) was prepared from methyl (S)-2-((1-(2-aminobenzo[d]oxazol-5-yl)-7,8,9,10-tetrahydro-6-oxa-2,10a-diazacycloocta[cd]inden-4-yl)oxy)butanoate following a procedure analogous to that of Example 261, step 9. LCMS (ESI): R$_T$ (min)=3.03, [M+H]$^+$=422.2, method=B; $^1$H NMR (400 MHz, DMSO-d$_6$) δ 7.58 (s, 2H), 7.54-7.47 (m, 2H), 7.44 (d, J=1.7 Hz, 1H), 7.31-7.22 (m, 2H), 6.93 (d, J=2.2 Hz, 1H), 6.59 (d, J=2.2 Hz, 1H), 4.43 (t, J=6.1 Hz, 1H), 4.37 (t, J=6.2 Hz, 2H), 4.24 (t, J=5.3 Hz, 2H), 2.16-2.05 (m, 2H), 1.90-1.77 (m, 2H), 1.75-1.65 (m, 2H), 0.99 (t, J=7.4 Hz, 3H).

Example 272 (S)-2-((1-(2-Amino-7-fluorobenzo[d]oxazol-5-yl)-7,8,9,10-tetrahydro-6-oxa-2,10a-diazacycloocta[cd]inden-4-yl)oxy)butanamide 272

272 was prepared following procedures analogous to those of Example 249. LCMS (ESI): R$_T$ (min)=1.12, [M+H]$^+$=440, method=D; $^1$H NMR (300 MHz, DMSO-d$_6$) δ 7.88 (s, 2H), 7.53 (s, 1H), 7.29-7.19 (m, 3H), 6.93 (d, J=1.8 Hz, 1H), 6.61 (d, J=2.1 Hz, 1H), 4.46-4.38 (m, 3H), 4.26-4.23 (m, 2H), 2.10 (s, 2H), 1.88-1.79 (m, 2H), 1.68 (s, 2H), 1.02-0.97 (m, 3H).

Example 273 (S)-2-((1-(2-Amino-4-fluorobenzo[d]thiazol-6-yl)-7,8,9,10-tetrahydro-6-oxa-2,10a-diazacycloocta[cd]inden-4-yl)oxy)butanamide 273

273 was prepared following procedures analogous to those of Example 242. LCMS (ESI): R$_T$ (min)=1.11, [M+H]$^+$=456, method=D; $^1$H NMR (300 MHz, DMSO-d$_6$): δ 7.97 (s, 2H), 7.84 (d, J=1.5 Hz, 1H), 7.53 (s, 1H), 7.41-7.36 (m, 1H), 7.27 (s, 1H), 6.92 (d, J=2.1 Hz, 1H), 6.60 (d, J=2.1 Hz, 1H), 4.45-4.39 (m, 3H), 4.26-4.23 (m, 2H), 2.20-2.09 (m, 2H), 1.88-1.79 (m, 2H), 1.74-1.61 (m, 2H), 1.01-0.96 (m, 3H).

Example 274 (S)-2-((1-(2-Aminobenzo[d]thiazol-6-yl)-8,9-dihydro-7H-6-oxa-2,9a-diazabenzo[cd]azulen-4-yl)oxy)propanamide 274

Step 1: tert-Butyl (6-(4-bromo-8,9-dihydro-7H-6-oxa-2,9a-diazabenzo[cd]azulen-1-yl)benzo[d]thiazol-2-yl)carbamate

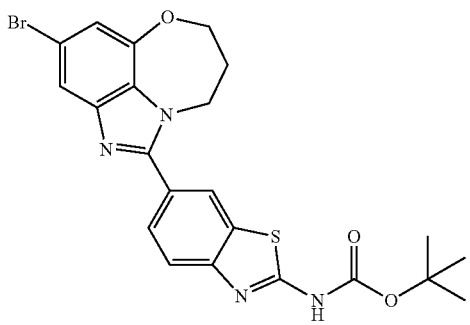 [SMILES: CC(C)(C)OC(=O)Nc1nc2ccc(-c3nc4cc(Br)cc5c4n3CCCO5)cc2s1]

The title compound (883.9 mg, 44% yield) was generated from 4-bromo-1-iodo-8,9-dihydro-7H-6-oxa-2,9a-diazabenzo[cd]azulene following a procedure analogous to Example 261, step 5. LCMS (ESI): [M+H]$^+$=500.9; $^1$H NMR (400 MHz, DMSO-d$_6$) δ 11.94 (s, 1H), 8.40 (s, 1H), 7.85-7.80 (m, 2H), 7.46 (d, J=1.8 Hz, 1H), 6.92 (d, J=1.8 Hz, 1H), 4.53-4.42 (m, 2H), 4.42-4.33 (m, 2H), 2.39-2.27 (m, 2H), 1.53 (s, 9H).

Step 2: tert-Butyl (6-(4-(4,4,5,5-tetramethyl-1,3,2-dioxaborolan-2-yl)-8,9-dihydro-7H-6-oxa-2,9a-diazabenzo[cd]azulen-1-yl)benzo[d]thiazol-2-yl)carbamate

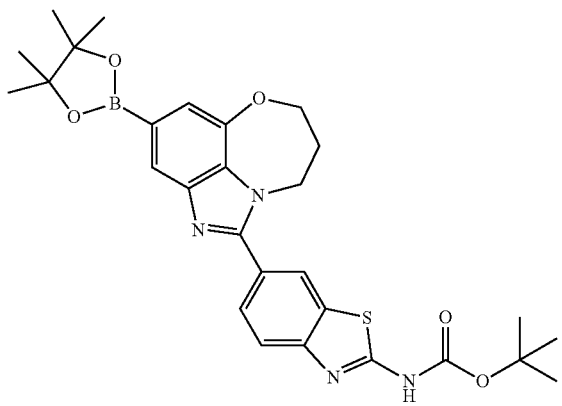 [SMILES: CC(C)(C)OC(=O)Nc1nc2ccc(-c3nc4cc(B5OC(C)(C)C(C)(C)O5)cc5c4n3CCCO5)cc2s1]

The title compound (491.9 mg, 51% yield) was prepared from tert-butyl (6-(4-bromo-8,9-dihydro-7H-6-oxa-2,9a-diazabenzo[cd]azulen-1-yl)benzo[d]thiazol-2-yl)carbamate following a procedure analogous to Example 162, step 1. LCMS (ESI): [M+H]$^+$=549; $^1$H NMR (400 MHz, DMSO-d$_6$) δ 11.93 (s, 1H), 8.40 (s, 1H), 7.82 (s, 2H), 7.58 (d, J=0.9 Hz, 1H), 7.03 (d, J=0.9 Hz, 1H), 4.46-4.33 (m, 4H), 2.39-2.29 (m, 2H), 1.31 (s, 9H), 1.07 (s, 12H).

Step 3: tert-Butyl (6-(4-hydroxy-8,9-dihydro-7H-6-oxa-2,9a-diazabenzo[cd]azulen-1-yl)benzo[d]thiazol-2-yl)carbamate

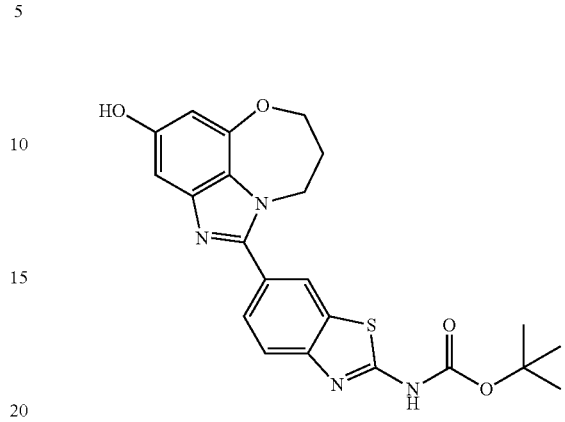

The title compound (205.5 mg, 47% yield) was prepared from tert-butyl (6-(4-(4,4,5,5-tetramethyl-1,3,2-dioxaborolan-2-yl)-8,9-dihydro-7H-6-oxa-2,9a-diazabenzo[cd]azulen-1-yl)benzo[d]thiazol-2-yl)carbamate following a procedure analogous to Example 162, step 2. LCMS (ESI): [M+H]$^+$=439.

Step 4: 1-(2-Aminobenzo[d]thiazol-6-yl)-8,9-dihydro-7H-6-oxa-2,9a-diazabenzo[cd]azulen-4-ol

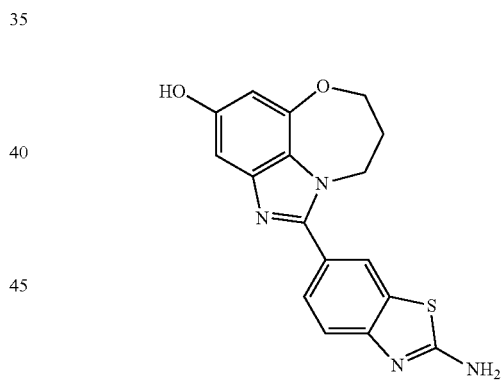

To a suspension tert-butyl (6-(4-hydroxy-8,9-dihydro-7H-6-oxa-2,9a-diazabenzo[cd]azulen-1-yl)benzo[d]thiazol-2-yl)carbamate (205.5 mg, 0.42 mmol) in DCM (4.0 mL, 62 mmol) was added methanol (1.0 mL, 20 mmol) and hydrogen chloride (4.0 mol/L in dioxane, 2.0 mL, 8.0 mmol). The resulting mixture was stirred at room temperature for 18 h. Solvent was removed under reduced pressure, and the resulting residue suspended in DCM (4.0 mL) with hydrogen chloride (4.0 mol/L in dioxane, 4.0 mL, 16.0 mmol). The reaction mixture was stirred at room temperature for 2 h and then evaporated in vacuo, and carried forward without purification as the HCl salt. LCMS (ESI): [M+H]$^+$=338.95.

Step 5: Methyl (S)-2-((1-(2-aminobenzo[d]thiazol-6-yl)-8,9-dihydro-7H-6-oxa-2,9a-diazabenzo[cd]azulen-4-yl)oxy)propanoate

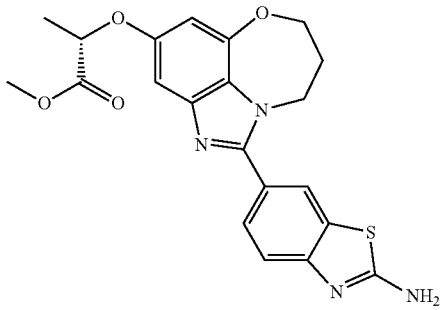 [SMILES: COC(=O)[C@H](C)Oc1cc2c3c(c1)nc(-c1ccc4nc(N)sc4c1)n3CCCO2]

The title compound (37.7 mg, 26%) was prepared from 1-(2-aminobenzo[d]thiazol-6-yl)-8,9-dihydro-7H-6-oxa-2,9a-diazabenzo[cd]azulen-4-ol following a procedure analogous to Example 162, step 3. LCMS (ESI): [M+H]$^+$=425.0.

Step 6

274 (9.8 mg, 27.5%) was prepared from methyl (S)-2-((1-(2-aminobenzo[d]thiazol-6-yl)-8,9-dihydro-7H-6-oxa-2,9a-diazabenzo[cd]azulen-4-yl)oxy)propanoate following a procedure analogous to Example 261, step 9. LCMS (ESI): R$_T$ (min)=2.77, [M+H]$^+$=410.1, method=B; $^1$H NMR (400 MHz, DMSO-d$_6$) δ 8.09 (d, J=1.7 Hz, 1H), 7.71 (s, 2H), 7.62 (dd, J=8.4, 1.8 Hz, 1H), 7.50-7.42 (m, 2H), 7.20 (s, 1H), 6.77 (d, J=2.2 Hz, 1H), 6.42 (d, J=2.2 Hz, 1H), 4.60 (q, J=6.7 Hz, 1H), 4.43-4.35 (m, 2H), 4.30 (t, J=5.3 Hz, 2H), 2.35-2.25 (m, 2H), 1.44 (d, J=6.6 Hz, 3H).

Examples 275 and 276 (R)-2-((1-(2-Aminobenzo[d]thiazol-5-yl)-7,8,9,10-tetrahydro-6-oxa-2,10a-diazacycloocta[cd]inden-4-yl)oxy)propanamide 275 and (S)-2-((1-(2-Aminobenzo[d]thiazol-5-yl)-'7,8,9,10-tetrahydro-6-oxa-2,10a-diazacycloocta[cd]inden-4-yl)oxy)propanamide 276

Step 1: tert-Butyl 5-bromobenzo[d]thiazol-2-ylcarbamate

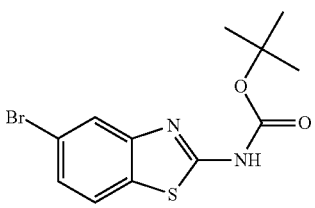 [SMILES: CC(C)(C)OC(=O)Nc1nc2cc(Br)ccc2s1]

The title compound (25.1 g, 94% yield) was generated from 5-bromobenzo[d]thiazol-2-amine (18.4 g, 80.3 mmol) following a procedure analogous to Example 214, step 1. LCMS (ESI): [M+H]$^+$=329/331.

Step 2: tert-Butyl 5-(4,4,5,5-tetramethyl-1,3,2-dioxaborolan-2-yl)benzo[d]thiazol-2-ylcarbamate

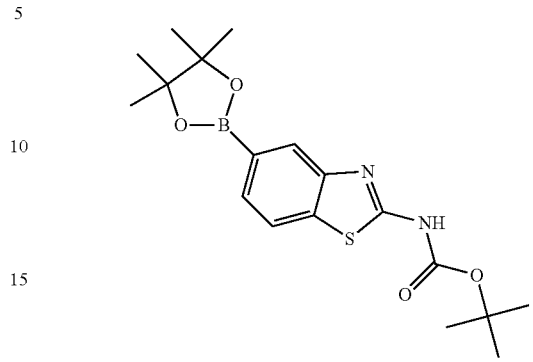

The title compound (7.1 g, 56% yield) was generated from tert-butyl 5-bromobenzo[d]thiazol-2-ylcarbamate (11 g, 33.4 mmol) following a procedure analogous to Example 214, step 2. LCMS (ESI): [M+H]$^+$=377.

Step 3: tert-Butyl (5-(4-bromo-7,8,9,10-tetrahydro-6-oxa-2,10a-diazacycloocta[cd]inden-1-yl)benzo[d]thiazol-2-yl)carbamate

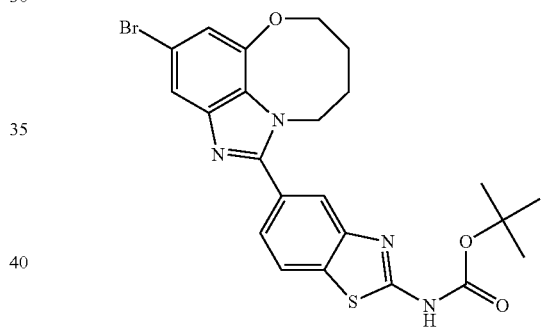

A mixture of tert-butyl 5-(4,4,5,5-tetramethyl-1,3,2-dioxaborolan-2-yl)benzo[d]thiazol-2-ylcarbamate (6.00 g, 15.9 mmol), 4-bromo-1-iodo-7,8,9,10-tetrahydro-6-oxa-2,10a-diazacycloocta[cd]indene (6.00 g, 15.2 mmol), 1,1'-bis(diphenylphosphino)ferrocenyl palladium (II) dichloride (360 mg, 0.492 mmol), potassium acetate (2 M solution in water, 35 mL, 70.0 mmol) and sodium carbonate (2 M solution in water, 35 mL, 70.0 mmol) in acetonitrile (140 mL) was stirred at 90° C. for 3 h in atmosphere of nitrogen. The resultant mixture was diluted with water and extracted with DCM. The organic phase was dried over magnesium sulfate and evaporated in vacuo. The crude product was purified via flash chromatography on silica gel (solvent gradient: 0-10% methanol in DCM) to yield 6 g (73%) of the title compound as a yellow solid. LCMS (ESI): [M+H]$^+$= 515/517.

Step 4

275 and 276 were generated each as a single unknown stereoisomer from tert-butyl (5-(4-bromo-7,8,9,10-tetrahydro-6-oxa-2,10a-diazacycloocta[cd]inden-1-yl)benzo[d]thiazol-2-yl)carbamate (3 g, 5.83 mmol) following procedures analogous to those of Example 265, steps 6-10, followed by chiral-HPLC separation.

275 (13.0 mg, 5.3% yield over five steps): LCMS (ESI): R$_T$ (min)=1.95 min, [M+H]$^+$=424, method=C; $^1$H NMR (300 MHz, DMSO-d$_6$) δ 7.85-7.83 (m, 1H), 7.68 (s, 2H), 7.58-7.54 (m, 2H), 7.31-7.25 (m, 2H), 6.93 (d, J=1.5 Hz, 1H), 6.59 (d, J=1.2 Hz, 1H), 4.65-4.60 (m, 1H), 4.41-4.36 (m, 2H), 4.26-4.23 (m, 2H), 2.12-2.11 (m, 2H), 1.69 (s, 2H), 1.46-1.44 (m, 3H).

276 (16.2 mg, 6.5% yield over five steps): LCMS (ESI): R$_T$ (min)=1.95 min, [M+H]$^+$=424, method=C; $^1$H NMR (300 MHz, DMSO-d$_6$) δ 7.85-7.83 (m, 1H), 7.68 (s, 2H), 7.58-7.54 (m, 2H), 7.31-7.25 (m, 2H), 6.93 (d, J=1.5 Hz, 1H), 6.59 (d, J=1.2 Hz, 1H), 4.65-4.60 (m, 1H), 4.41-4.36 (m, 2H), 4.26-4.23 (m, 2H), 2.12-2.11 (m, 2H), 1.69 (s, 2H), 1.46-1.44 (m, 3H).

Examples 277 and 278 (S)-2-((1-(2-Amino-5-fluorobenzo[d]thiazol-6-yl)-7,8,9,10-tetrahydro-6-oxa-2,10a-diazacycloocta[cd]inden-4-yl)oxy)propanamide 277 and (R)-2-((1-(2-Amino-5-fluorobenzo[d]thiazol-6-yl)-7,8,9,10-tetrahydro-6-oxa-2,10a-diazacycloocta[cd]inden-4-yl)oxy)propanamide 278

Following procedures analogous to those of Example 265, followed by chiral-SFC separation, the title compounds were prepared each as a single unknown stereoisomer.

277 (45.3 mg): LCMS (ESI): R$_T$ (min)=1.14, [M+H]$^+$=442, method=D; $^1$H NMR (300 MHz, DMSO-d$_6$) δ 7.91-7.87 (m, 3H), 7.54 (s, 1H), 7.34-7.30 (d, J=12 Hz, 1H), 7.25 (s, 1H), 6.93-6.92 (m, 1H), 6.62-6.61 (m, 1H), 4.66-4.64 (m, 1H), 4.22 (br s, 4H), 1.98 (s, 2H), 1.63 (s, 2H), 1.46-1.44 (m, 3H).

278 (21.7 mg): LCMS (ESI): R$_T$ (min)=1.14, [M+H]$^+$=442, method=D; $^1$H NMR (300 MHz, DMSO-d$_6$) δ 7.91-7.87 (m, 3H), 7.54 (s, 1H), 7.32 (d, J=12 Hz, 1H), 7.25 (s, 1H), 6.93-6.92 (m, 1H), 6.62-6.61 (m, 1H), 4.66-4.64 (m, 1H), 4.22 (br s, 4H), 1.98 (s, 2H), 1.63 (s, 2H), 1.46-1.44 (m, 3H).

Examples 279 and 280 (R)-2-((1-(2-Amino-4-fluorobenzo[d]thiazol-6-yl)-7,8,9,10-tetrahydro-6-oxa-2,10a-diazacycloocta[cd]inden-4-yl)oxy)-2-cyclopropylacetamide 279 and (S)-2-((1-(2-Amino-4-fluorobenzo[d]thiazol-6-yl)-7,8,9,10-tetrahydro-6-oxa-2,10a-diazacycloocta[cd]inden-4-yl)oxy)-2-cyclopropylacetamide 280

Step 1: Ethyl 2-((1-(2-(bis(4-methoxybenzyl)amino)-4-fluorobenzo[d]thiazol-6-yl)-7,8,9,10-tetrahydro-6-oxa-2,10a-diazacycloocta[cd]inden-4-yl)oxy)-2-cyclopropylacetate

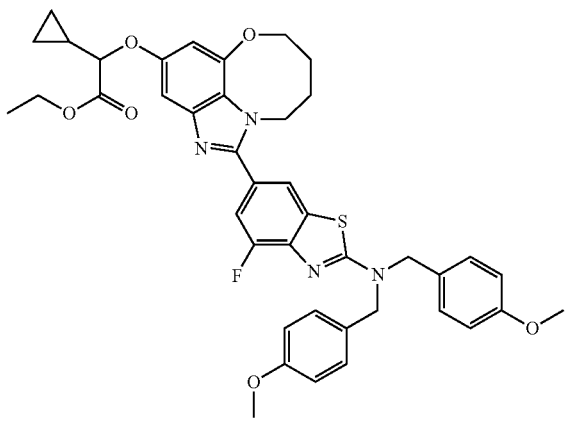 [SMILES: CCOC(=O)C(Oc1cc2c3c(c1)nc(-c1cc(F)c4nc(N(Cc5ccc(OC)cc5)Cc5ccc(OC)cc5)sc4c1)n3CCCCO2)C1CC1]

A mixture of 1-(2-(bis(4-methoxybenzyl)amino)-4-fluorobenzo[d]thiazol-6-yl)-7,8,9,10-tetrahydro-6-oxa-2,10a-diazacycloocta[cd]inden-4-ol (Example 242, step 4) (800 mg, 1.31 mmol), ethyl 2-bromo-2-cyclopropylacetate (410 mg, 1.98 mmol) and potassium carbonate (730 mg, 5.28 mmol) in DMSO (15 mL) was stirred at 35° C. for 16 h. The reaction mixture was diluted with water and extracted with DCM. The organic portion was washed with brine, dried over magnesium sulfate and evaporated in vacuo. The resultant mixture was purified via flash chromatography on silica gel (solvent gradient: 0-50% ethyl acetate in petroleum ether) to yield 600 mg (62%) of the title compound as a white solid LCMS (ESI): [M+H]$^+$=737.

Step 2: 2-((1-(2-(Bis(4-methoxybenzyl)amino)-4-fluorobenzo[d]thiazol-6-yl)-7,8,9,10-tetrahydro-6-oxa-2,10a-diazacycloocta[cd]inden-4-yl)oxy)-2-cyclopropylacetamide

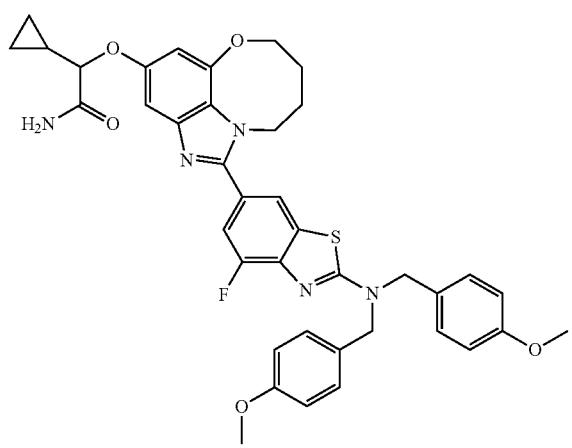 [SMILES: COc1ccc(CN(Cc2ccc(OC)cc2)c2nc3c(F)cc(-c4nc5cc(OC(C(N)=O)C6CC6)cc6c5n4CCCCO6)cc3s2)cc1]

A mixture of ethyl 2-((1-(2-(bis(4-methoxybenzyl)amino)-4-fluorobenzo[d]thiazol-6-yl)-7,8,9,10-tetrahydro-6-oxa-2,10a-diazacycloocta[cd]inden-4-yl)oxy)-2-cyclopropylacetate (520 mg, 0.706 mmol) and ammonia (7 M solution in methanol, 20 mL) was stirred in a sealed vessel at 55° C. for 48 h. The reaction mixture was evaporated in vacuo to yield 480 mg (96%) of the title compound as a white solid LCMS (ESI): [M+H]$^+$=708.

Step 3

A racemic mixture of 2-((1-(2-(bis(4-methoxybenzyl)amino)-4-fluorobenzo[d]thiazol-6-yl)-7,8,9,10-tetrahydro-6-oxa-2,10a-diazacycloocta[cd]inden-4-yl)oxy)-2-cyclopropylacetamide (420 mg, 0.593 mmol) in TFA (10 mL) was stirred at 80° C. for 2.5 h. The reaction mixture was diluted with water and treated with saturated aqueous sodium hydrogen carbonate to reach ca. pH 8, then extracted with DCM. The organic portion was washed with brine, dried over magnesium sulfate and evaporated in vacuo. The resultant mixture was purified via flash chromatography on silica gel (solvent gradient: 0-10% methanol in DCM) and the two stereoisomers were separated by chiral SFC to yield 279 and 280 each as a single unknown stereoisomer, as off-white solids.

279 (62 mg, 22% yield): LCMS (ESI): R$_T$ (min)=1.11, [M+H]$^+$=468, method=D; $^1$H NMR (300 MHz, DMSO-d$_6$): δ 7.97 (s, 2H), 7.84 (d, J=1.5 Hz, 1H), 7.54 (s, 1H), 7.40-7.36 (m, 1H), 7.23 (s, 1H), 6.86 (d, J=2.1 Hz, 1H), 6.57 (d, J=2.1 Hz, 1H), 4.42-4.35 (m, 2H), 4.26-4.22 (m, 2H), 3.93 (d, J=8.1 Hz, 1H), 2.22-2.05 (m, 2H), 1.73-1.62 (m, 2H), 1.33-1.28 (m, 1H), 0.59-0.57 (m, 3H), 0.48-0.39 (m, 1H).

280 (20.7 mg, 7% yield) LCMS (ESI): $R_T$ (min)=2.07, [M+H]$^+$=468, method=C; $^1$H NMR (300 MHz, DMSO-d$_6$): δ 7.97 (s, 2H), 7.84 (d, J=1.5 Hz, 1H), 7.54 (s, 1H), 7.40-7.36 (m, 1H), 7.23 (s, 1H), 6.86 (d, J=2.1 Hz, 1H), 6.57 (d, J=2.1 Hz, 1H), 4.50 (br, 2H), 4.24 (br, 2H), 3.95 (d, J=7.8 Hz, 1H), 2.14 (br, 2H), 1.67 (br, 2H), 1.35 (br, 1H), 0.59-0.57 (m, 3H), 0.45-0.44 (m, 1H).

Examples 281 and 282: (S)-2-((1-(2-Aminobenzo [d]thiazol-6-yl)-7,8,9,10-tetrahydro-6-oxa-2,10a-diazacycloocta[cd]inden-4-yl)oxy)-2-cyclopropylacetamide 281 and (R)-2-((1-(2-aminobenzo[d] thiazol-6-yl)-7,8,9,10-tetrahydro-6-oxa-2,10a-diazacycloocta[cd]inden-4-yl)oxy)-2-cyclopropylacetamide 282

Step 1: 1-(2-Aminobenzo[d]thiazol-6-yl)-7,8,9,10-tetrahydro-6-oxa-2,10a-diazacycloocta[cd]inden-4-ol

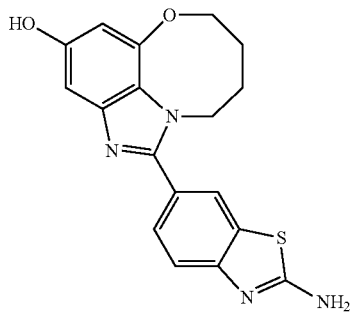 [SMILES: Nc1nc2ccc(-c3nc4cc(O)cc5c4n3CCCCO5)cc2s1]

The title compound was prepared from tert-butyl (6-(4-bromo-7,8,9,10-tetrahydro-6-oxa-2,10a-diazacycloocta[cd] inden-1-yl)benzo[d]thiazol-2-yl)carbamate (Example 214, step 3) following procedures analogous to those of Example 265, steps 6-8. LCMS (ESI): [M+H]$^+$=353.

Step 2: Ethyl 2-((1-(2-aminobenzo[d]thiazol-6-yl)-7,8,9,10-tetrahydro-6-oxa-2,10a-diazacycloocta[cd] inden-4-yl)oxy)-2-cyclopropylacetate

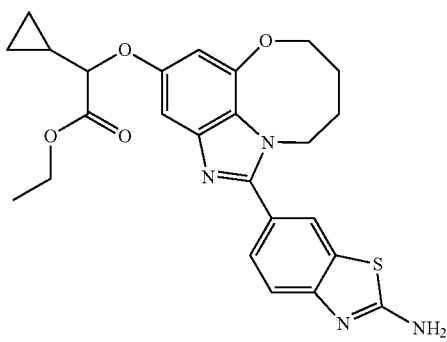 [SMILES: CCOC(=O)C(Oc1cc2c3c(c1)nc(-c1ccc4nc(N)sc4c1)n3CCCCO2)C1CC1]

The title compound (117, 43% yield) was prepared from 1-(2-aminobenzo[d]thiazol-6-yl)-7,8,9,10-tetrahydro-6-oxa-2,10a-diazacycloocta[cd]inden-4-ol and ethyl 2-bromo-2-cyclopropylacetate following a procedure analogous to Example 279, Step 1. LCMS (ESI): [M+H]$^+$=479.

Step 3: (S)-2-((1-(2-Aminobenzo[d]thiazol-6-yl)-7, 8,9,10-tetrahydro-6-oxa-2,10a-diazacycloocta[cd] inden-4-yl)oxy)-2-cyclopropylacetamide and (R)-2-((1-(2-aminobenzo[d]thiazol-6-yl)-7,8,9,10-tetrahydro-6-oxa-2,10a-diazacycloocta[cd]inden-4-yl)oxy)-2-cyclopropylacetamide The title compounds were prepared each as a single unknown stereoisomer from methyl 2-((1-(2-aminobenzo[d] oxazol-5-yl)-7,8,9,10-tetrahydro-6-oxa-2,10a-diazacycloocta[cd]inden-4-yl)oxy)-2-cyclopropylacetate following a procedure analogous to that of Example 261, step 9, followed by chiral SFC separation.

281 (28.3 mg, 25% yield): LCMS (ESI): $R_T$ (min)=3.20, [M+H]$^+$=450, method=B; $^1$H NMR (400 MHz, DMSO-d$_6$) δ 10.34 (s, 1H), 8.13 (d, J=8.8 Hz, 1H), 7.74-7.67 (m, 1H), 7.49-7.31 (m, 4H), 6.94 (d, J=2.5 Hz, 1H), 6.66 (d, J=5.0 Hz, 1H), 6.03 (d, J=5.1 Hz, 1H), 3.10 (d, J=16.4 Hz, 1H), 2.99 (d, J=16.6 Hz, 1H), 2.49-2.44 (m, 4H), 1.56 (t, J=6.1 Hz, 4H), 1.38 (d, J=6.5 Hz, 2H).

282 (28.3 mg, 25% yield): LCMS (ESI): $R_T$ (min)=3.19, [M+H]$^+$=450, method=B; $^1$H NMR (400 MHz, DMSO-d$_6$) δ 10.33 (s, 1H), 8.13 (d, J=8.8 Hz, 1H), 7.74-7.67 (m, 1H), 7.49-7.31 (m, 4H), 6.94 (d, J=2.5 Hz, 1H), 6.66 (d, J=5.1 Hz, 1H), 6.03 (d, J=5.0 Hz, 1H), 3.10 (d, J=16.4 Hz, 1H), 2.99 (d, J=16.5 Hz, 1H), 2.49-2.44 (m, 4H), 1.56 (t, J=6.1 Hz, 4H), 1.38 (d, J=6.2 Hz, 2H).

Examples 283 and 284: (R)-2-((1-(2-aminobenzo[d] oxazol-5-yl)-7,8,9,10-tetrahydro-6-oxa-2,10a-diazacycloocta[cd]inden-4-yl)oxy)-2-cyclopropylacetamide 283 and (S)-2-((1-(2-aminobenzo[d]oxazol-5-yl)-7,8,9,10-tetrahydro-6-oxa-2,10a-diazacycloocta [cd]inden-4-yl)oxy)-2-cyclopropylacetamide 284

Step 1: Methyl 2-((1-(2-aminobenzo[d]oxazol-5-yl)-7,8,9,10-tetrahydro-6-oxa-2,10a-diazacycloocta[cd] inden-4-yl)oxy)-2-cyclopropylacetate

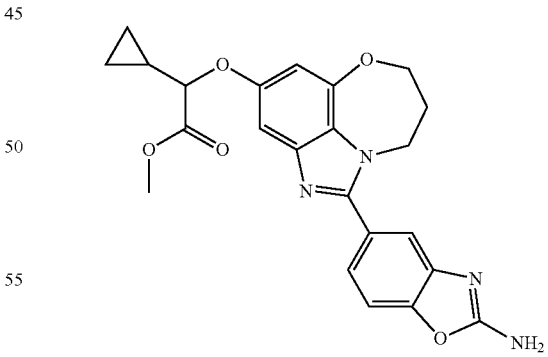

To a suspension of 1-(2-aminobenzo[d]oxazol-5-yl)-7,8, 9,10-tetrahydro-6-oxa-2,10a-diazacycloocta[cd]inden-4-ol (Example 204, step 10) (250 mg) in DMSO (1.5 mL) was added potassium carbonate (321 mg, 2.3 mmol) followed by ethyl 2-bromo-2-cyclopropylacetate (201 mg, 0.93 mmol). The vial was purged with nitrogen, sealed, and left to stir at room temperature for 16 h. The reaction mixture was diluted with water and extracted with DCM. The combined organic layers were washed with brine, dried over magnesium sulfate, filtered and evaporated in vacuo. The crude product was purified via flash chromatography on silica gel (solvent gradient: 0-15% methanol in DCM) yield 0.243 g (70%) of the title compound. LCMS (ESI): [M+H]$^+$=449.

Step 2

283 and 284 were prepared each as a single unknown stereoisomer from methyl 2-((1-(2-aminobenzo[d]oxazol-5-yl)-7,8,9,10-tetrahydro-6-oxa-2,10a-diazacycloocta[cd]inden-4-yl)oxy)-2-cyclopropylacetate following a procedure analogous to that of Example 261, step 9, followed by chiral-SFC separation.

283 (67.2 mg, 28% yield): LCMS (ESI): R$_T$ (min)=3.10, [M+H]$^+$=434.2, method=B; $^1$H NMR (400 MHz, DMSO-d$_6$) δ 7.61-7.46 (m, 4H), 7.43 (d, J=1.7 Hz, 1H), 7.26 (dd, J=8.1, 1.7 Hz, 1H), 7.21 (d, J=2.0 Hz, 1H), 6.87 (d, J=2.2 Hz, 1H), 6.56 (d, J=2.1 Hz, 1H), 4.36 (t, J=6.2 Hz, 2H), 4.24 (t, J=5.2 Hz, 2H), 3.95 (d, J=8.0 Hz, 1H), 2.16-2.05 (m, 2H), 1.76-1.59 (m, 2H), 1.34-1.21 (m, 1H), 0.65-0.51 (m, 3H), 0.50-0.40 (m, 1H).

284 (67.6 mg, 28% yield): LCMS (ESI): R$_T$ (min)=3.09, [M+H]$^+$=434.2, method=B; $^1$H NMR (400 MHz, DMSO-d$_6$) δ 7.61-7.46 (m, 4H), 7.43 (d, J=1.8 Hz, 1H), 7.26 (dd, J=8.1, 1.7 Hz, 1H), 7.21 (d, J=2.0 Hz, 1H), 6.87 (d, J=2.2 Hz, 1H), 6.56 (d, J=2.1 Hz, 1H), 4.36 (t, J=6.1 Hz, 2H), 4.24 (t, J=5.4 Hz, 2H), 3.95 (d, J=8.0 Hz, 1H), 2.16-2.04 (m, 2H), 1.74-1.63 (m, 2H), 1.34-1.21 (m, 1H), 0.65-0.51 (m, 3H), 0.50-0.40 (m, 1H).

Example 285 (S)-2-((1-(2-Amino-7-fluorobenzo[d]thiazol-5-yl)-7,8,9,10-tetrahydro-6-oxa-2,10a-diazacycloocta[cd]inden-4-yl)oxy)propanamide 285

Step 1: 4-Bromo-2-fluoro-6-nitrobenzenamine

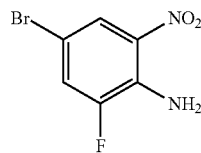 [SMILES: Nc1c(F)cc(Br)cc1[N+](=O)[O-]]

A mixture of 5-bromo-1,2-difluoro-3-nitrobenzene (20.0 g, 84.0 mmol), ammonium carbonate (8.40 g, 87.4 mmol) and triethylamine (25.6 g, 0.252 mol) in DMF (200 mL) was stirred at room temperature for 16 hours. The reaction mixture was diluted with water. The solids were collected by filtration, washed with water and dried in vacuo to yield 16.7 g (85%) of the title compound as a yellow solid. LCMS (ESI): [M+1]$^+$=235/237.

Step 2: 5-Bromo-1-fluoro-3-nitro-2-thiocyanatobenzene

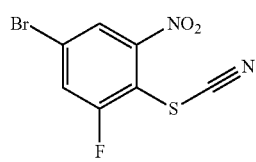 [SMILES: N#CSc1c(F)cc(Br)cc1[N+](=O)[O-]]

4-Bromo-2-fluoro-6-nitrobenzenamine (10.0 g, 42.0 mmol) was suspended in sulfuric acid (100 mL) and water (100 mL). The reaction mixture was stirred at 60° C. for 1 h then cooled to −5° C. and then a solution of sodium nitrite (3.2 g, 46.0 mmol) in water (10 mL) was added dropwise. The reaction system was stirred for 1 h at −5° C. and then the solution was added to a mixture of thiocyanatocopper (12.7 g, 104 mmol) and potassium thiocyanate (1.00 g, 10.0 mmol) in water (50 mL). The reaction mixture was stirred at room temperature for 0.5 h and then extracted with ethyl acetate. The combined organic extracts were washed with brine, dried over anhydrous sodium sulfate, filtered and evaporated in vacuo to yield 10.1 g of the title compound as a brown solid, which was used in the next step directly without purification.

Step 3: 5-Bromo-7-fluorobenzo[d]thiazol-2-amine

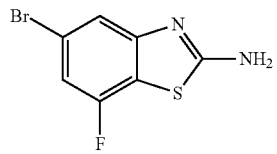

A mixture of 5-bromo-1-fluoro-3-nitro-2-thiocyanatobenzene (10.0 g, 36.0 mmol), ammonium chloride (9.60 g, 179 mmol) and iron powder (16.1 g, 0.310 mol) in ethanol (50.0 mL) and water (50.0 mL) was stirred for 1 h at 90° C. The reaction mixture was filtered and filter cake was washed with ethyl acetate. The organic phase was dried over anhydrous sodium sulfate, filtered and evaporated in vacuo to yield 5.5 g (62%) of the title compound as a brown solid. LCMS (ESI): [M+H]$^+$=247/249.

Step 4: 5-Bromo-7-fluoro-N,N-bis(4-methoxybenzyl)benzo[d]thiazol-2-amine

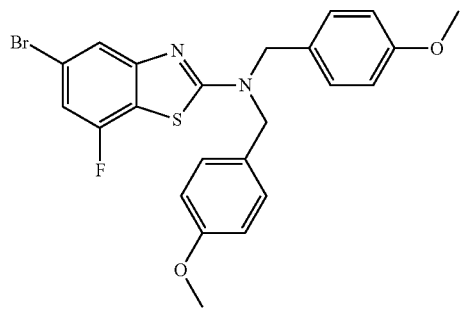

To a solution of 5-bromo-7-fluorobenzo[d]thiazol-2-amine (5.50 g, 22.2 mmol) and potassium carbonate (9.10 g, 66.0 mmol) in DMF (100 mL) was added 1-(chloromethyl)-4-methoxybenzene (10.3 g, 66.0 mmol). The reaction mixture was stirred for 6 h at 60° C., diluted with water and extracted with ethyl acetate. The combined organic extracts were washed with brine, dried over anhydrous sodium sulfate, filtered and evaporated in vacuo. The resultant residue was purified via flash chromatography on silica gel (solvent gradient: 20% ethyl acetate in petroleum ether) to yield 5.00 g (46%) of the title compound as an off-white solid. LCMS (ESI): [M+H]$^+$=487/489.

Step 5: 7-Fluoro-N,N-bis(4-methoxybenzyl)-5-(4,4,5,5-tetramethyl-1,3,2-dioxaborolan-2-yl)benzo[d]thiazol-2-amine

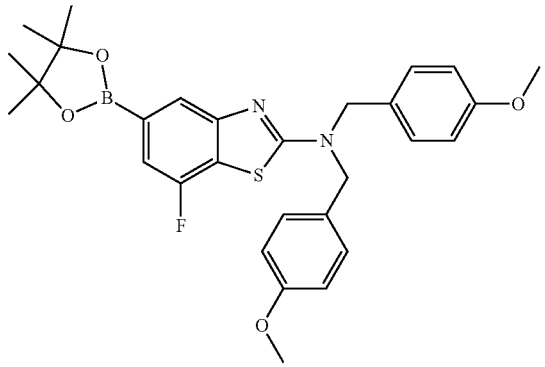

A mixture of 5-bromo-7-fluoro-N,N-bis(4-methoxybenzyl)benzo[d]thiazol-2-amine (5.0 g, 10.0 mmol), 4,4,4',4',5,5,5',5'-octamethyl-2,2'-bi(1,3,2-dioxaborolane) (0.730 g, 20.0 mmol), potassium acetate (2.94 g, 30.0 mmol) and 1,1'-bis(diphenylphosphino)ferrocenyl palladium (II) dichloride (730 mg, 1 mmol) in DMF (100 mL) was stirred at 90° C. for 2 h under an atmosphere of nitrogen. The resultant mixture was allowed to cool to room temperature, diluted with water and extracted with ethyl acetate. The combined organic extracts were dried over anhydrous sodium sulfate, filtered and evaporated in vacuo. The resultant residue was purified via flash chromatography on silica gel (solvent: 20% ethyl acetate in petroleum ether) to yield 2.84 g (52%) of the title compound as an off-white solid. LCMS (ESI): [M+H]$^+$=535.

Step 6: 5-(4-Bromo-7,8,9,10-tetrahydro-6-oxa-2,10a-diazacycloocta[cd]inden-1-yl)-7-fluoro-N,N-bis(4-methoxybenzyl)benzo[d]thiazol-2-amine

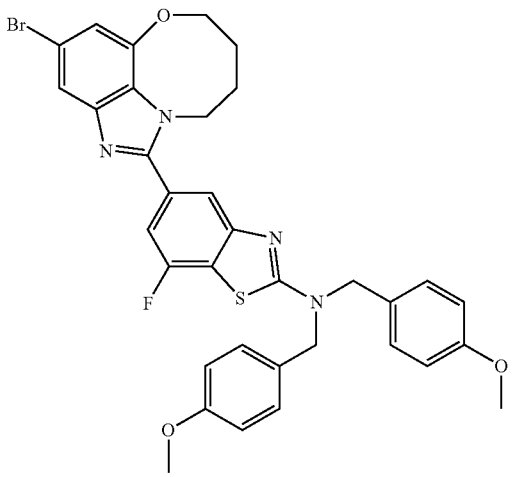 [SMILES: COc1ccc(CN(Cc2ccc(OC)cc2)c2nc3cc(-c4nc5cc(Br)cc6c5n4CCCCO6)cc(F)c3s2)cc1]

The title compound (2.0 g, 58% yield) was obtained from 4-bromo-1-iodo-7,8,9,10-tetrahydro-6-oxa-2,10a-diazacycloocta[cd]indene (Example 204, step 6) (2.0 g, 5.10 mmol) following a procedure analogous to Example 242, step 4. LCMS (ESI): [M+H]$^+$=673/675.

Step 7: (S)-2-((1-(2-(Bis(4-methoxybenzyl)amino)-7-fluorobenzo[d]thiazol-5-yl)-7,8,9,10-tetrahydro-6-oxa-2,10a-diazacycloocta[cd]inden-4-yl)oxy)propanamide

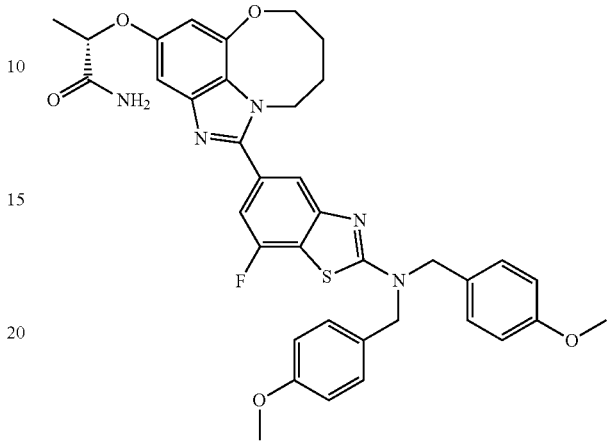

The title compound (1.1 g, 57% yield) was obtained from 5-(4-bromo-7,8,9,10-tetrahydro-6-oxa-2,10a-diazacycloocta[cd]inden-1-yl)-7-fluoro-N,N-bis(4-methoxybenzyl)benzo[d]thiazol-2-amine (1.9 g, 2.8 mmol) following a procedure analogous to Example 242, step 5. LCMS (ESI): [M+H]$^+$=682.

Step 8

A solution of (S)-2-((1-(2-(bis(4-methoxybenzyl)amino)-7-fluorobenzo[d]thiazol-5-yl)-'7,8,9,10-tetrahydro-6-oxa-2,10a-diazacycloocta[cd]inden-4-yl)oxy)propanamide (1.1 g, 1.61 mmol) in TFA (10.0 mL) was stirred at 90° C. for 4 h. The solvent was removed in vacuo. The residue was purified via flash chromatography on silica gel (solvent gradient: 10% methanol in dichloromethane), and then by chiral SFC to yield 191.7 mg (26.9% yield) of 285 as an off-white solid. LCMS: R$_T$ (min)=1.33, [M+H]$^+$=442, method=C; $^1$H NMR (300 MHz, DMSO-d$_6$) δ 7.96 (s, 2H), 7.54 (d, J=2.2 Hz, 1H), 7.45 (d, J=1.3 Hz, 1H), 7.29-7.15 (m, 2H), 6.95 (d, J=2.1 Hz, 1H), 6.62 (d, J=2.1 Hz, 1H), 4.66-4.60 (m, 1H), 4.48-4.41 (m, 2H), 4.25-4.23 (m, 2H), 2.15-2.05 (m, 2H), 1.72-1.62 (m, 2H), 1.46 (d, J=6.5 Hz, 3H).

Examples 286 and 287 (S)-2-((1-(2-Amino-7-fluorobenzo[d]thiazol-6-yl)-7,8,9,10-tetrahydro-6-oxa-2,10a-diazacycloocta[cd]inden-4-yl)oxy)propanamide 286 and (R)-2-((1-(2-Amino-7-fluorobenzo[d]thiazol-6-yl)-7,8,9,10-tetrahydro-6-oxa-2,10a-diazacycloocta[cd]inden-4-yl)oxy)propanamide 287

Following procedures analogous to those of Example 285, the title compounds were prepared each as a single unknown stereoisomer.

286 (96.6 mg): LCMS: R$_T$ (min)=1.28, [M+H]$^+$=442, method=C; $^1$H NMR (400 MHz, DMSO-d$_6$) δ 8.01 (s, 2H), 7.54 (d, J=1.9 Hz, 1H), 7.44-7.40 (m, 1H), 7.35-7.33 (m, 1H), 7.25 (d, J=2.0 Hz, 1H), 6.94 (d, J=2.2 Hz, 1H), 6.63 (d, J=2.2 Hz, 1H), 4.66-4.61 (m, 1H), 4.28-4.18 (m, 4H), 2.01-1.97 (m, 2H), 1.68-1.62 (m, 2H), 1.46 (d, J=6.6 Hz, 3H).

287 (49.9 mg): LCMS: $R_T$ (min)=1.28, [M+H]$^+$=442, method=C; $^1$H NMR (400 MHz, DMSO-d$_6$) δ 8.01 (s, 2H), 7.54 (d, J=1.9 Hz, 1H), 7.44-7.40 (m, 1H), 7.35-7.33 (m, 1H), 7.25 (d, J=2.0 Hz, 1H), 6.94 (d, J=2.2 Hz, 1H), 6.63 (d, J=2.2 Hz, 1H), 4.66-4.61 (m, 1H), 4.28-4.18 (m, 4H), 2.01-1.97 (m, 2H), 1.68-1.62 (m, 2H), 1.46 (d, J=6.6 Hz, 3H).

Examples 288 and 289 (R)-2-((1-(2-Amino-7-fluorobenzo[d]oxazol-5-yl)-7,8,9,10-tetrahydro-6-oxa-2,10a-diazacycloocta[cd]inden-4-yl)oxy)-2-cyclopropylacetamide 288 and (S)-2-((1-(2-Amino-7-fluorobenzo[d]oxazol-5-yl)-7,8,9,10-tetrahydro-6-oxa-2,10a-diazacycloocta[cd]inden-4-yl)oxy)-2-cyclopropylacetamide 289

From 1-(2-amino-7-fluorobenzo[d]oxazol-5-yl)-7,8,9,10-tetrahydro-6-oxa-2,10a-diazacycloocta[cd]inden-4-ol (Example 249, step 5) (900 mg, 2.54 mmol), and following procedures analogous to those of Examples 279 and 280, steps 1-2, the title compounds were generated each as a single unknown stereoisomer.

288 (246 mg, 21% yield): LCMS (ESI): $R_T$ (min)=2.12, [M+H]$^+$=452, method=C; $^1$H NMR (300 MHz, DMSO-d$_6$) δ 7.87 (s, 2H), 7.53 (s, 1H), 7.28-7.15 (m, 3H), 6.87 (d, J=1.8 Hz, 1H), 6.58 (d, J=2.1 Hz, 1H), 4.44-4.34 (m, 2H), 4.30-4.18 (s, 2H), 3.95 (d, J=8.1 Hz, 1H), 2.09 (s, 2H), 1.68 (s, 2H), 1.31-1.24 (m, 1H), 0.59-0.57 (m, 3H), 0.53-0.44 (m, 1H).

289 (231 mg, 20% yield): LCMS (ESI): $R_T$ (min)=2.12, [M+H]$^+$=452, method=C; $^1$H NMR (300 MHz, DMSO-d$_6$) δ 7.87 (s, 2H), 7.53 (s, 1H), 7.28-7.15 (m, 3H), 6.87 (d, J=1.8 Hz, 1H), 6.58 (d, J=2.1 Hz, 1H), 4.44-4.34 (m, 2H), 4.30-4.18 (s, 2H), 3.95 (d, J=8.1 Hz, 1H), 2.09 (s, 2H), 1.68 (s, 2H), 1.31-1.24 (m, 1H), 0.59-0.57 (m, 3H), 0.53-0.44 (m, 1H).

Examples 290 and 291 (S)-2-((2-(2-Amino-4-fluorobenzo[d]thiazol-6-yl)-3,4-dihydro-5-oxa-1,2a-diazaacenaphthylen-7-yl)oxy)-2-cyclopropylacetamide 290 and (R)-2-((2-(2-Amino-4-fluorobenzo[d]thiazol-6-yl)-3,4-dihydro-5-oxa-1,2a-diazaacenaphthylen-7-yl)oxy)-2-cyclopropylacetamide 291

Following procedures analogous to those of Examples 208, 279 and 280, the title compounds were prepared each as a single unknown stereoisomer.

290: LCMS: $R_T$ (min)=4.5, [M+H]$^+$=440, method=D; $^1$H NMR (300 MHz, DMSO-d$_6$) δ 8.12 (s, 1H), 7.97 (s, 2H), 7.68-7.64 (m, 1H), 7.49 (s, 1H), 7.20 (s, 1H), 6.69 (s, 1H), 6.42 (s, 1H), 4.64-4.60 (m, 2H), 4.49-4.48 (m, 2H), 3.92 (d, J=8.1 Hz, 1H), 1.29-1.23 (m, 1H), 0.58-0.52 (m, 3H), 0.45-0.42 (m, 1H).

291: LCMS: $R_T$ (min)=4.5, [M+H]$^+$=440, method=D; $^1$H NMR (300 MHz, DMSO-d$_6$) δ 8.12 (s, 1H), 7.97 (s, 2H), 7.68-7.64 (m, 1H), 7.49 (s, 1H), 7.20 (s, 1H), 6.69 (s, 1H), 6.42 (s, 1H), 4.64-4.60 (m, 2H), 4.49-4.48 (m, 2H), 3.92 (d, J=8.1 Hz, 1H), 1.29-1.23 (m, 1H), 0.58-0.52 (m, 3H), 0.45-0.42 (m, 1H).

Example 292 (S)-2-((1-(3-Aminobenzo[e][1,2,4]triazin-7-yl)-7,8,9,10-tetrahydro-6-oxa-2,10a-diazacycloocta[cd]inden-4-yl)oxy)propanamide 292

292 was prepared following procedures analogous to those of Example 265. LCMS: $R_T$ (min)=1.91, [M+H]$^+$=420, method=C; $^1$H NMR (300 MHz, DMSO-d$_6$) δ 8.41 (s, 1H), 8.14 (d, J=9 Hz, 1H), 7.91 (br s, 2H), 7.68 (d, J=8.7 Hz, 1H), 7.55 (s, 1H), 7.26 (s, 1H), 6.97 (s, 1H), 6.64 (s, 2H), 4.68-4.61 (m, 1H), 4.52-4.48 (m, 2H), 4.29-4.26 (m, 2H), 2.30-2.12 (m, 2H), 1.80-1.65 (m, 2H), 1.46 (d, J=6.6 Hz, 3H).

Example 293 (S)-2-((1-(2-Fluoro-4-(1H-1,2,4-triazol-3-yl)phenyl)-7,8,9,10-tetrahydro-6-oxa-2,10a-diazacycloocta[cd]inden-4-yl)oxy)propanamide 293

293 was prepared following procedures analogous to those of Example 269. LCMS (ESI): $R_T$ (min)=0.63, [M+H]$^+$=437, method=F; $^1$H NMR (400 MHz, DMSO-d$_6$): δ 14.36 (s, 1H), 8.56 (s, 1H), 8.05-8.03 (m, 1H), 7.97-7.94 (m, 1H), 7.76-7.72 (m, 1H), 7.57-7.56 (m, 1H), 7.27-7.26 (m, 1H), 6.97 (d, J=2.0 Hz, 1H), 6.66 (d, J=2.0 Hz, 1H), 4.68-4.63 (m, 1H), 4.31-4.25 (m, 4H), 2.04-1.98 (m, 2H), 1.67-1.63 (m, 2H), 1.46 (d, J=6.8 Hz, 3H).

Example 294 (2R,3S)-1-(1-(2-Aminobenzo[d]oxazol-5-yl)-7,8,9,10-tetrahydro-6-oxa-2,10a-diazacycloocta[cd]inden-4-yl)-3-fluoropyrrolidine-2-carboxamide 294

Step 1: 5-(4-Bromo-7,8,9,10-tetrahydro-6-oxa-2,10a-diazacycloocta[cd]inden-1-yl)-N,N-bis(4-methoxybenzyl)benzo[d]oxazol-2-amine

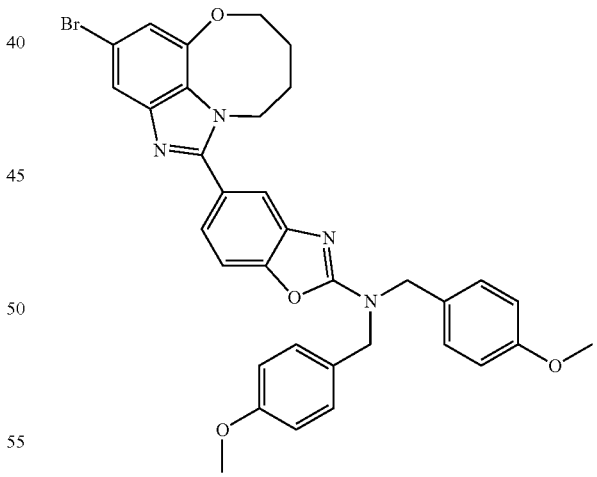

The title compound (3.5 g, 41% yield) was generated from 4-bromo-1-iodo-7,8,9,10-tetrahydro-6-oxa-2,10a-diazacycloocta[cd]indene (Example 204, step 6) (5.26 g, 13.4 mmol) and N,N-bis(4-methoxybenzyl)-5-(4,4,5,5-tetramethyl-1,3,2-dioxaborolan-2-yl)benzo[d]oxazol-2-amine (Example 253, step 2) (6.80 g, 13.6 mmol) following procedures analogous to those of Example 242, steps 2-4. LCMS (ESI): [M+H]$^+$=639/641.

Step 2: (2S,3R)-Methyl 1-(1-(2-(bis(4-methoxybenzyl)amino)benzo[d]oxazol-5-yl)-7,8,9,10-tetrahydro-6-oxa-2,10a-diazacycloocta[cd]inden-4-yl)-3-hydroxypyrrolidine-2-carboxylate

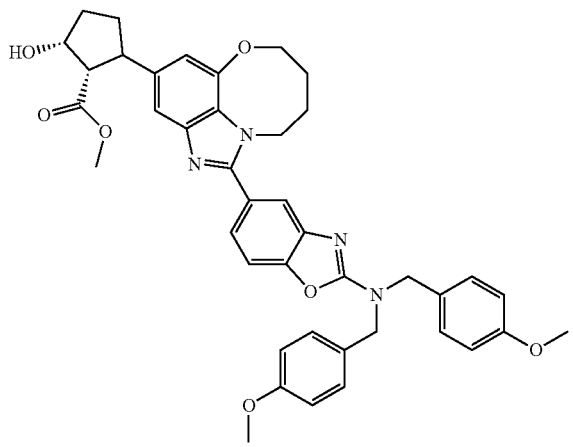 [SMILES: COC(=O)[C@H]1C(c2cc3c4c(c2)nc(-c2ccc5oc(N(Cc6ccc(OC)cc6)Cc6ccc(OC)cc6)nc5c2)n4CCCCO3)CC[C@H]1O]

A mixture of 5-(4-bromo-7,8,9,10-tetrahydro-6-oxa-2,10a-diazacycloocta[cd]inden-1-yl)-N,N-bis(4-methoxybenzyl)benzo[d]oxazol-2-amine (348 mg, 0.544 mmol), (2S,3R)-3-hydroxypyrrolidine-2-carboxylic acid (234 mg, 1.78 mmol), copper(I) iodide (101 mg, 0.534 mmol) and potassium phosphate (509 mg, 2.40 mmol) in DMSO (12.0 mL) was degassed with nitrogen. The reaction mixture was heated under microwave irradiation for 2 h at 100° C. The reaction mixture was filtered. The filtrate was diluted with ethyl acetate (15.0 mL) and treated with (diazomethyl)trimethylsilane (40.0 mL, 2 mol/L solution in hexane) dropwise with stirring at room temperature. The reaction mixture was stirred for 6 h at room temperature and diluted with water, extracted with ethyl acetate, washed with brine and evaporated in vacuo. The resultant residue was purified via flash chromatography on silica gel (solvent gradient, 0-100% ethyl acetate in petroleum ether) to yield 160 mg (52%) of the title compound as a yellow solid. LCMS (ESI): [M+H]$^+$=704.

Step 3: (2R,3S)-Methyl 1-(1-(2-(bis(4-methoxybenzyl)amino)benzo[d]oxazol-5-yl)-7,8,9,10-tetrahydro-6-oxa-2,10a-diazacycloocta[cd]inden-4-yl)-3-fluoropyrrolidine-2-carboxylate

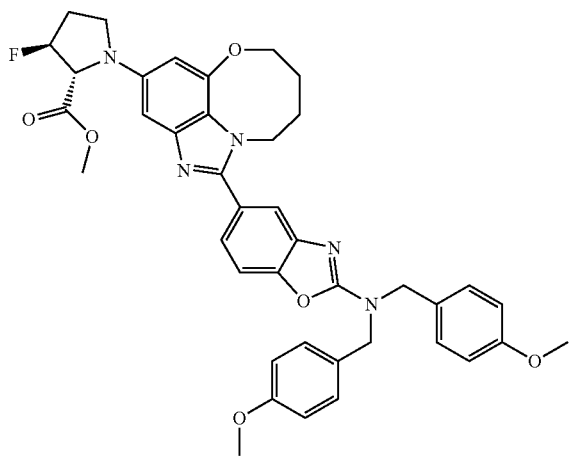 [SMILES: COC(=O)[C@@H]1[C@@H](F)CCN1c1cc2c3c(c1)nc(-c1ccc4oc(N(Cc5ccc(OC)cc5)Cc5ccc(OC)cc5)nc4c1)n3CCCCO2]

To a solution of (2S,3R)-methyl 1-(1-(2-(bis(4-methoxybenzyl)amino)benzo[d]oxazol-5-yl)-'7,8,9,10-tetrahydro-6-oxa-2,10a-diazacycloocta[cd]inden-4-yl)-3-hydroxypyrrolidine-2-carboxylate (405 mg, 0.575 mmol) in DCM (10.0 mL) was added diethylaminosulfurtrifluoride (DAST) (1.00 mL) dropwise with stirring at −40° C. The reaction mixture was allowed to warm to 15° C. and was stirred for 8 h, then quenched by aqueous sodium bicarbonate solution, diluted with water, extracted with DCM, washed with brine, dried over anhydrous sodium sulfate and evaporated in vacuo. The resultant residue was purified via flash chromatography on silica gel (solvent gradient: 0-30% ethyl acetate in petroleum ether) to yield 230 mg (57%) of the title compound as a yellow solid. LCMS (ESI): [M+H]+=706.

Step 4: (2R,3S)-1-(1-(2-(Bis(4-methoxybenzyl)amino)benzo[d]oxazol-5-yl)-7,8,9,10-tetrahydro-6-oxa-2,10a-diazacycloocta[cd]inden-4-yl)-3-fluoropyrrolidine-2-carboxamide

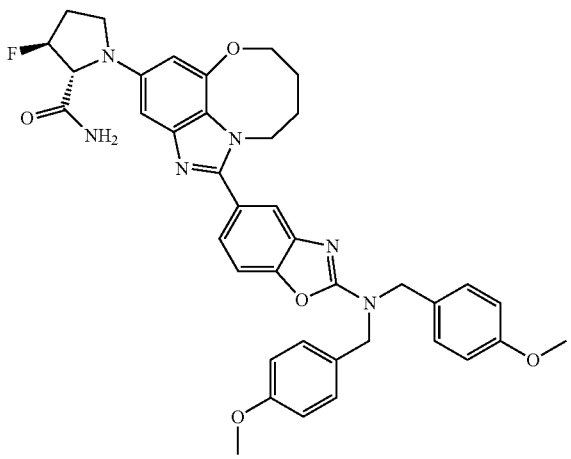 [SMILES: COc1ccc(CN(Cc2ccc(OC)cc2)c2nc3cc(-c4nc5cc(N6CC[C@H](F)[C@H]6C(N)=O)cc6c5n4CCCCO6)ccc3o2)cc1]

A mixture of (2R,3S)-methyl 1-(1-(2-(bis(4-methoxybenzyl)amino)benzo[d]oxazol-5-yl)-7,8,9,10-tetrahydro-6-oxa-2,10a-diazacycloocta[cd]inden-4-yl)-3-fluoropyrrolidine-2-carboxylate (110 mg, 0.156 mmol) and ammonia (7 M solution in methanol, 20 mL) was stirred at 25° C. for 48 h. The reaction mixture was evaporated in vacuo. The resultant residue was purified via flash chromatography on silica gel (solvent gradient: 0-100% ethyl acetate in petroleum ether) to yield 69 mg (64%) of the title compound as a light yellow solid. LCMS (ESI): [M+H]$^+$=691.

Step 6

A solution of (2R,3S)-methyl 1-(1-(2-(bis(4-methoxybenzyl)amino)benzo[d]oxazol-5-yl)-7,8,9,10-tetrahydro-6-oxa-2,10a-diazacycloocta[cd]inden-4-yl)-3-fluoropyrrolidine-2-carboxylate (40.0 mg, 0.058 mmol) in TFA (8.00 mL) was heated at 80° C. for 24 h. The reaction mixture was diluted with water. The pH value of the mixture was adjusted to 7-8 with aqueous sodium bicarbonate solution and extracted with DCM. The organic portion was washed with brine, dried over anhydrous sodium sulfate and evaporated in vacuo. The resultant residue was purified via prep-HPLC and lyophilized to yield 11.9 mg (46%) of 294 as an off-white solid. LCMS (ESI): R$_T$ (min)=2.36, [M+H]$^+$=451, method=C; $^1$H NMR (300 MHz, DMSO-d$_6$) δ 7.74 (s, 1H), 7.58 (s, 2H), 7.49 (d, J=8.1 Hz, 1H), 7.43 (d, J=1.5 Hz, 1H), 7.37 (s, 1H), 7.29-7.25 (m, 1H), 6.50 (d, J=2.1 Hz, 1H), 6.25 (d, J=1.8 Hz, 1H), 5.35-5.17 (m, 1H), 4.37-4.30 (m, 2H), 4.25-4.20 (m, 2H), 4.09 (d, J=26.4 Hz, 1H), 3.72-3.65 (m, 1H), 3.41-3.32 (m, 1H), 2.30-2.07 (m, 4H), 1.80-1.65 (m, 2H).

Example 295 (S)-2-((1-(2,5-Difluoro-4-(1H-1,2,4-triazol-5-yl)phenyl)-7,8,9,10-tetrahydro-6-oxa-2,10a-diazacycloocta[cd]inden-4-yl)oxy)butanamide 295

295 was prepared following procedures analogous to those of Example 269. LCMS (ESI): R$_T$ (min)=1.19 min, [M+H]$^+$=469, method=D; $^1$H NMR (400 MHz, DMSO-d$_6$): δ14.14 (s, 1H), 8.78 (s, 1H), 8.21-7.97 (m, 1H), 7.82-7.64 (m, 1H), 7.54-7.53 (m, 1H), 7.27-7.26 (m, 1H), 6.97 (d, J=2.0 Hz, 1H), 6.67 (d, J=2.0 Hz, 1H), 4.48-4.45 (m, 1H), 4.30-4.23 (m, 4H), 2.04-1.99 (m, 2H), 1.88-1.81 (m, 2H), 1.68-1.63 (m, 2H), 1.02-0.98 (m, 3H).

Example 296 (S)-2-((1-(5-(1H-1,2,4-Triazol-5-yl)pyridin-2-yl)-7,8,9,10-tetrahydro-6-oxa-2,10a-diazacycloocta[cd]inden-4-yl)oxy)propanamide 296

Step 1: 6-Chloronicotinamide

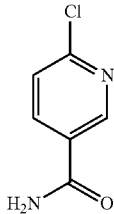

To a solution of 6-bromopyridine-3-carboxylic acid (50 g, 247 mmol) in DCM (1 L) and DMF (3 mL) at room temperature was dropwise added oxalyl dichloride (80 mL). The mixture was stirred for 30 min at room temperature. The solvent was removed under reduced pressure and ammonia (1 L, 25-28% aqueous solution) was added dropwise. The resulting mixture was stirred for a further 1 h at room temperature. The solvent was evaporated in vacuo to yield 43 g of the crude product, which was used directly in the next step without further purification. LCMS (ESI): [M+H]$^+$=157/159.

Step 2: (Z)-6-Chloro-N-((dimethylamino)methylene)nicotinamide

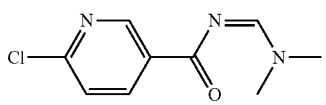

6-Chloronicotinamide (43 g, 274 mmol) was dissolved in dimethoxy-N, N-dimethylmethanamine (1 L) and stirred at 100° C. for 3 h. The solvent was evaporated in vacuo, and the residue was triturated with hexane and the solid was collected by filtration. The crude product (40 g, 69% yield) was used directly in the next step without further purification. LCMS (ESI): [M+H]$^+$=212.

Step 3: 2-Chloro-5-(2H-1,2,4-triazol-3-yl)pyridine

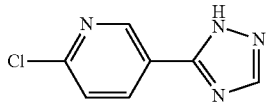 [SMILES: Clc1ccc(-c2ncn[nH]2)cn1]

To a solution of (Z)-6-chloro-N-((dimethylamino)methylene)nicotinamide (40 g, 188 mmol) in acetic acid (1 L) was added hydrazine acetate (40 g, 434 mmol). The resulting mixture was stirred at 90° C. for 3 h. The solvent was evaporated in vacuo. The pH value of the solution was adjusted to 8 with sodium bicarbonate. The solid was collected by filtration to yield 38 g (69%) of the crude product, which was used directly in the next step without further purification. LCMS (ESI): [M+H]$^+$=181.

Step 4: 2-Chloro-5-(1-(4-methoxybenzyl)-1H-1,2,4-triazol-3-yl)pyridine

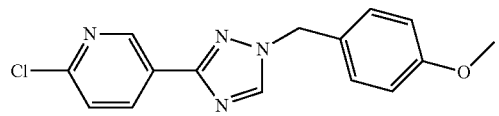 [SMILES: COc1ccc(Cn2cnc(-c3ccc(Cl)nc3)n2)cc1]

To a solution of 2-chloro-5-(2H-1,2,4-triazol-3-yl)pyridine (20 g, 110 mmol) and cesium carbonate (72 g, 220 mmol) in DMF (1 L) was added 1-(chloromethyl)-4-methoxybenzene (20.3 g, 129 mmol). The reaction mixture was stirred at 25° C. for 16 h and diluted with water, filtered, and the solids were collected and dried to yield 20 g (60%) of the title compound as a white solid. LCMS (ESI): [M+H]$^+$=301.

Step 5: 5-(1-(4-Methoxybenzyl)-1H-1,2,4-triazol-3-yl) picolinic acid

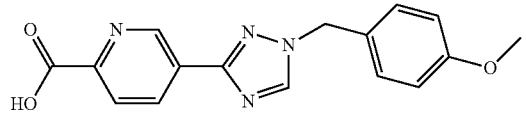 [SMILES: COc1ccc(Cn2cnc(-c3ccc(C(=O)O)nc3)n2)cc1]

A mixture of 2-chloro-5-(1-(4-methoxybenzyl)-1H-1,2,4-triazol-3-yl)pyridine (20 g, 67 mmol), sodium carbonate (22 g, 207 mmol), and bis(diphenylphosphino)ferrocenyl palladium (II) dichloride (7.3 g, 9.98 mmol) in methanol (300 mL) and water (18 mL) was charged with carbon monoxide and heated at 60° C. for 18 h. The resulting mixture was cooled to room temperature and evaporated in vacuo. The residue was partitioned between DCM and water. The pH of water layer was adjusted to 6 with hydrogen chloride. The solvent was evaporated and the crude product 10 g (48%) was used directly in the next step without further purification. LCMS (ESI): [M+H]$^+$=311.

Step 6: 4-Bromo-1-(5-(1-(4-methoxybenzyl)-1H-1,2,4-triazol-3-yl)pyridin-2-yl)-'7,8,9,10-tetrahydro-6-oxa-2,10a-diazacycloocta[cd]indene

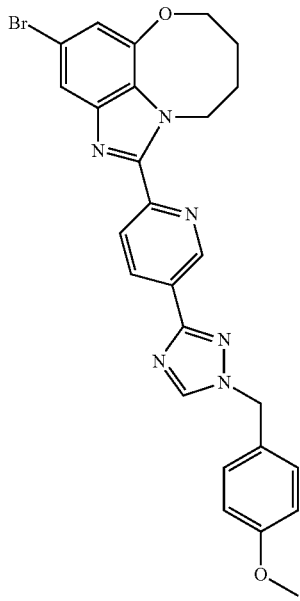 [SMILES: COc1ccc(Cn2cnc(-c3ccc(-c4nc5cc(Br)cc6c5n4CCCCO6)nc3)n2)cc1]

The title compound (8.5 g, 63% yield over two steps) was generated from 9-bromo-3,4,5,6-tetrahydro-2H-benzo[b][1,4]oxazocin-7-amine (Example 204, step 4) (6.5 g, 25.3 mmol) following procedures analogous to Example 125, steps 1-2. LCMS (ESI): [M+H]$^+$=531/533.

Step 7

296 (251 mg, 16% yield over five steps) was generated from 4-bromo-1-(5-(1-(4-methoxybenzyl)-1H-1,2,4-triazol-3-yl)pyridin-2-yl)-7,8,9,10-tetrahydro-6-oxa-2,10a-diazacycloocta[cd]indene (2 g, 3.77 mmol) following procedures analogous to those of Example 269. LCMS (ESI): R$_T$ (min)=1.07, [M+H]$^+$=420, method=D; $^1$H NMR (300 MHz, DMSO-d$_6$) δ 14.38 (s, 1H), 9.31-9.30 (m, 1H), 8.75 (s, 1H), 8.53-8.50 (m, 1H), 8.37 (d, J=6 Hz, 1H), 7.59-7.52 (m, 1H), 7.25 (s, 1H), 6.96 (d, J=3 Hz, 1H), 6.65 (d, J=3 Hz, 1H), 5.08-5.04 (m, 2H), 4.68-4.61 (m, 1H), 4.31-4.21 (m, 2H), 2.16-2.14 (m, 2H), 1.60-1.58 (m, 2H), 1.47-1.45 (m, 3H).

Example 297 (S)-2-((1-(2-Aminobenzo[d]oxazol-5-yl)-7,8,9,10-tetrahydro-6-oxa-2,10a-diazacycloocta[cd]inden-4-yl)oxy)propanoic acid 297

To a solution of (S)-methyl 2-((1-(2-aminobenzo[d]oxazol-5-yl)-7,8,9,10-tetrahydro-6-oxa-2,10a-diazacycloocta[cd]inden-4-yl)oxy)propanoate (Example 204, step 11) (521 mg, 1.23 mmol) in THF (10 mL) and water (5 mL) was added lithium hydroxide hydrate (148 mg, 3.53 mmol) at room temperature. The reaction mixture was stirred for 1 h at room temperature, and then evaporated in vacuo. The resultant residue was purified via reverse phase flash chromatography (solvent gradient: 0-60% methanol in water) then chiral-SFC to yield 48.4 mg (10%) of 297 as a white solid. LCMS (ESI): R$_T$ (min)=1.27, [M+H]$^+$=409, method=C; $^1$H NMR (300 MHz, DMSO-d$_6$) δ 13.11 (s, 1H), 7.59 (s, 2H), 7.50 (d, J=8.4 Hz, 1H), 7.43 (d, J=1.5 Hz, 1H), 7.28-7.25 (m, 1H), 6.84 (d, J=2.1 Hz, 1H), 6.53 (d, J=2.1 Hz, 1H), 4.78-4.73 (m, 1H), 4.39-4.34 (m, 2H), 4.25-4.22 (m, 2H), 2.15-2.06 (m, 2H), 1.75-1.65 (m, 2H), 1.50 (d, J=6.9 Hz, 3H).

Examples 298 and 299 (S)-2-(4-(1-(2-Aminothiazolo[5,4-b]pyridin-5-yl)-7,8,9,10-tetrahydro-6-oxa-2,10a-diazacycloocta[cd]inden-4-yl)-1H-pyrazol-1-yl)butanamide 298 and (R)-2-(4-(1-(2-Aminothiazolo[5,4-b]pyridin-5-yl)-7,8,9,10-tetrahydro-6-oxa-2,10a-diazacycloocta[cd]inden-4-yl)-1H-pyrazol-1-yl)butanamide 299

Step 1: Methyl 2-(4-(4,4,5,5-tetramethyl-1,3,2-dioxaborolan-2-yl)-1H-pyrazol-1-yl)butanoate

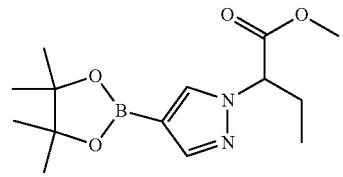

A mixture of 4-(4,4,5,5-tetramethyl-1,3,2-dioxaborolan-2-yl)-1H-pyrazole (22 g, 113 mmol), methyl 2-bromobutanoate (24.5 g, 135 mmol) and cesium carbonate (55.3 g, 170 mmol) in acetonitrile (650 mL) was stirred at 60° C. for 16 h. The resulting solution was diluted with DCM. The solids were filtered off. The filtrate was evaporated in vacuo and purified via flash chromatography on silica gel (solvent gradient: 0-50% ethyl acetate in petroleum ether) to yield 32.5 g (97%) of the title compound as yellow oil. LCMS (ESI): [M+H]$^+$=295.

Step 2: Methyl 2-(4-(1-(2-((tert-butoxycarbonyl)amino)thiazolo[5,4-b]pyridin-5-yl)-7,8,9,10-tetrahydro-6-oxa-2,10a-diazacycloocta[cd]inden-4-yl)-1H-pyrazol-1-yl)butanoate

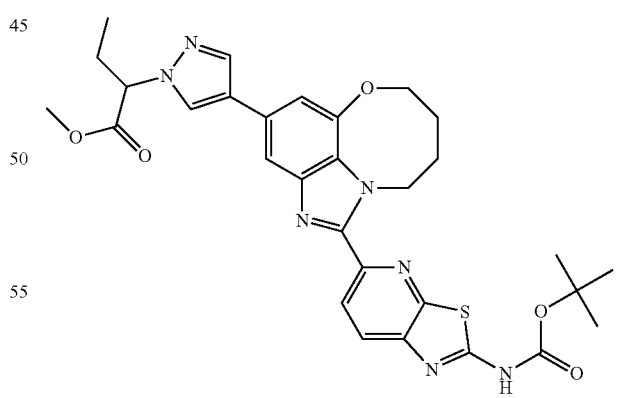

A mixture of tert-butyl (5-(4-bromo-7,8,9,10-tetrahydro-6-oxa-2,10a-diazacycloocta[cd]inden-1-yl)thiazolo[5,4-b]pyridin-2-yl)carbamate (Example 265, step 5) (1 g, 1.94 mmol), methyl 2-(4-(4,4,5,5-tetramethyl-1,3,2-dioxaborolan-2-yl)-1H-pyrazol-1-yl)butanoate (860 mg, 2.92 mmol), 1,1'-bis(diphenylphosphino)ferrocenyl palladium (II) dichloride (280 mg, 0.383 mmol) and sodium carbonate (620 mg, 5.850 mmol) in dioxane (10 mL) and water (1 mL) was stirred at 80° C. for 1 h. The reaction mixture was diluted with water and extracted with ethyl acetate. The organic extracts were washed with brine, dried over magnesium sulfate and evaporated in vacuo. The resultant mixture was purified via flash chromatography on silica gel (solvent gradient: 0-10% methanol in DCM) to yield 1.2 g (87%) of the title compound as a yellow solid. LCMS (ESI): [M+H]$^+$=604.

Step 3: tert-Butyl (5-(4-(1-(1-amino-1-oxobutan-2-yl)-1H-pyrazol-4-yl)-7,8,9,10-tetrahydro-6-oxa-2,10a-diazacycloocta[cd]inden-1-yl)thiazolo[5,4-b]pyridin-2-yl)carbamate

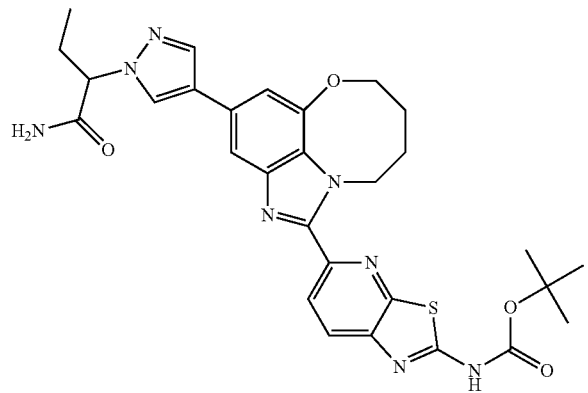 [SMILES: CCC(C(N)=O)n1cc(-c2cc3c4c(c2)nc(-c2ccc5nc(NC(=O)OC(C)(C)C)sc5n2)n4CCCCO3)cn1]

A mixture of methyl 2-(4-(1-(2-((tert-butoxycarbonyl)amino)thiazolo[5,4-b]pyridin-5-yl)-7,8,9,10-tetrahydro-6-oxa-2,10a-diazacycloocta[cd]inden-4-yl)-1H-pyrazol-1-yl)butanoate (1.2 g, 1.69 mmol) and ammonia (7 M solution in methanol, 15 mL) was stirred at 25° C. for 20 h. The reaction mixture was evaporated in vacuo to yield 1 g (85%) of the title compound as a brown solid LCMS (ESI): [M+H]$^+$=589.

Step 4

A mixture of tert-butyl (5-(4-(1-(1-amino-1-oxobutan-2-yl)-1H-pyrazol-4-yl)-7,8,9,10-tetrahydro-6-oxa-2,10a-diazacycloocta[cd]inden-1-yl)thiazolo[5,4-b]pyridin-2-yl)carbamate (1 g, 2.04 mmol) and TFA (10 mL) in DCM (30 mL) was stirred at 20° C. for 3 h. The reaction mixture was diluted with water and treated with saturated aqueous sodium hydrogen carbonate to reach pH 8, extracted with DCM, and evaporated in vacuo. The resultant mixture was purified via flash chromatography on silica gel (solvent gradient: 0-10% methanol in DCM) and the two stereoisomers were separated by chiral SFC to afford 298 and 299 each as a single unknown stereoisomer.

298 (143.2 mg, 14% yield): LCMS (ESI): R$_T$ (min)=1.23, [M+H]$^+$=489, method=D; $^1$H NMR (300 MHz, DMSO-d$_6$): 8.26 (s, 1H), 8.15-8.08 (m, 3H), 7.94 (s, 1H), 7.79-7.76 (m, 1H), 7.69 (s, 1H), 7.53 (s, 1H), 7.28 (s, 1H), 7.20 (s, 1H), 5.11-4.92 (m, 2H), 4.84-4.70 (m, 1H), 4.36-4.19 (m, 2H), 2.18-2.06 (m, 4H), 1.70-1.55 (m, 2H), 0.88-0.83 (m, 3H).

299 (68.6 mg, 7% yield): LCMS (ESI): R$_T$ (min)=1.23, [M+H]$^+$=489, method=D; $^1$H NMR (300 MHz, DMSO-d$_6$): 8.26 (s, 1H), 8.15-8.08 (m, 3H), 7.94 (s, 1H), 7.79-7.76 (m, 1H), 7.69 (s, 1H), 7.53 (s, 1H), 7.28 (s, 1H), 7.20 (s, 1H), 5.11-4.92 (m, 2H), 4.84-4.70 (m, 1H), 4.36-4.19 (m, 2H), 2.18-2.06 (m, 4H), 1.70-1.55 (m, 2H), 0.88-0.83 (m, 3H).

Example 300 (2S,3R)-1-(1-(2-Aminobenzo[d]thiazol-6-yl)-7,8,9,10-tetrahydro-6-oxa-2,10a-diazacycloocta[cd]inden-4-yl)-3-methoxypyrrolidine-2-carboxamide 300

Step 1: (2S,3R)-1-tert-Butyl 2-methyl 3-hydroxypyrrolidine-1,2-dicarboxylate

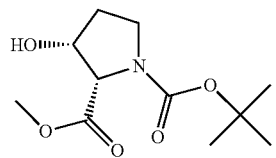 [SMILES: COC(=O)[C@@H]1[C@H](O)CCN1C(=O)OC(C)(C)C]

To a solution of (2S,3R)-1-(tert-butoxycarbonyl)-3-hydroxypyrrolidine-2-carboxylic acid (5.00 g, 21.6 mmol) in methanol (50.0 mL) was added (diazomethyl)trimethylsilane (50.0 mL, 2 mol/L in hexane) dropwise with stirring at room temperature. The reaction mixture was stirred for 1 h at room temperature, and then evaporated in vacuo to yield 5.30 g of the crude title compound as light yellow oil. LCMS (ESI): [M+H]$^+$=246. $^1$H NMR (300 MHz, DMSO-d$_6$) δ 5.44 (d, J=4.9 Hz, 1H), 4.48-4.42 (m, 1H), 4.20 (d, J=7.0 Hz, 1H), 3.63 and 3.60 (rotamers, two apparent s, total 3H), 3.47-3.39 (m, 1H), 3.31-3.21 (m, 1H), 1.98-1.91 (m, 1H), 1.83-1.74 (m, 1H), 1.39 and 1.32 (rotamers, two apparent s, total 9H).

Step 2: (2S,3R)-1-tert-Butyl 2-methyl 3-methoxypyrrolidine-1,2-dicarboxylate

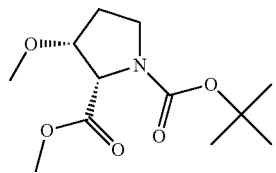 [SMILES: COC(=O)[C@@H]1[C@H](OC)CCN1C(=O)OC(C)(C)C]

A mixture of (2S,3R)-1-tert-butyl 2-methyl 3-hydroxypyrrolidine-1,2-dicarboxylate (5.30 g, 21.6 mmol), silver(I) oxide (17.0 g, 73.4 mmol) and iodomethane (11.0 mL, 176 mmol) in acetone (100 mL) was stirred for 84 h at room temperature. The mixture was filtered and evaporated in vacuo. The resultant residue was purified via flash chromatography on silica gel (solvent gradient: 0-50% ethyl acetate in petroleum ether) to yield 4.78 g (85%) of the title compound as a light yellow oil. LCMS (ESI): [M+H]$^+$=260. $^1$H NMR (300 MHz, DMSO-d$_6$) δ 4.42-4.38 (m, 1H), 4.19-4.13 (m, 1H), 3.63 and 3.61 (rotamers, two apparent s, total 3H), 3.44-3.36 (m, 1H), 3.32-3.19 (m, 4H), 2.12-1.95 (m, 1H), 1.91-1.82 (m, 1H), 1.38 and 1.32 (rotamers, two apparent s, total 9H).

Step 3: (2S,3R)-1-(tert-Butoxycarbonyl)-3-methoxypyrrolidine-2-carboxylic acid

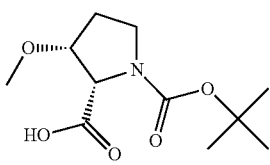 [SMILES: CO[C@@H]1CCN(C(=O)OC(C)(C)C)[C@@H]1C(=O)O]

A mixture of (2S,3R)-1-tert-butyl 2-methyl 3-methoxypyrrolidine-1,2-dicarboxylate (4.78 g, 18.4 mmol), lithium hydroxide hydrate (4.20 g, 100 mmol) in THF (40.0 mL) and water (20.0 mL) was heated at 50° C. for 24 h. The solvent was evaporated in vacuo. The resultant residue was diluted with water. The pH value was adjusted to 3 with a 1 M aqueous solution of hydrogen chloride solution. The mixture was extracted with ethyl acetate, washed with brine, dried over anhydrous sodium sulfate and evaporated in vacuo to afford 3.76 g (83%) of the title compound as an off-white solid. LCMS (ESI): $[M+H]^+=246$. $^1$H NMR (300 MHz, DMSO-$d_6$) δ 12.45 (s, 1H), 4.29-4.27 (m, 1H), 4.15-4.03 (m, 1H), 3.47-3.33 (m, 1H), 3.33-3.17 (m, 4H), 2.13-1.94 (m, 1H), 1.94-1.80 (m, 1H), 1.36 and 1.34 (rotamers, two apparent s, 9H).

Step 4: (2S,3R)-3-Methoxypyrrolidine-2-carboxylic acid trifluoroacetate salt

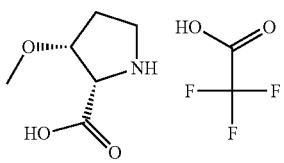

A mixture of (2S,3R)-1-(tert-butoxycarbonyl)-3-methoxypyrrolidine-2-carboxylic acid (3.50 g, 14.3 mmol) and trifluoroacetic acid (5.00 mL) in DCM (20.0 mL) was stirred for 3 h at room temperature. The reaction mixture was evaporated in vacuo to afford 3.30 g (crude) of the title compound as a light yellow solid. LCMS (ESI): $[M+H]^+=146$.

Step 5: tert-Butyl (6-(4-((2S,3R)-2-carbamoyl-3-methoxypyrrolidin-1-yl)-7,8,9,10-tetrahydro-6-oxa-2,10a-diazacycloocta[cd]inden-1-yl)benzo[d]thiazol-2-yl)carbamate

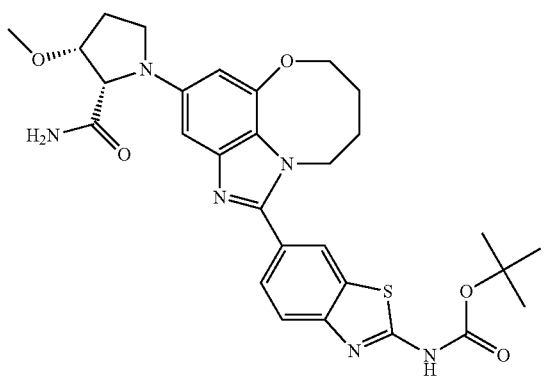 [SMILES: CO[C@@H]1CCN(c2cc3c4c(c2)nc(-c2ccc5nc(NC(=O)OC(C)(C)C)sc5c2)n4CCCCO3)[C@@H]1C(N)=O]

The title compound (176 mg, 47% yield over two steps) was generated from tert-butyl (6-(4-bromo-7,8,9,10-tetrahydro-6-oxa-2,10a-diazacycloocta[cd]inden-1-yl)benzo[d]thiazol-2-yl)carbamate (Example 214, step 3) (332 mg, 0.645 mmol) following procedures analogous to those of Example 104, steps 1-2. LCMS (ESI): $[M+H]^+=579$.

Step 6

A mixture of tert-butyl (6-(4-((2S,3R)-2-carbamoyl-3-methoxypyrrolidin-1-yl)-7,8,9,10-tetrahydro-6-oxa-2,10a-diazacycloocta[cd]inden-1-yl)benzo[d]thiazol-2-yl)carbamate (530 mg, 0.916 mmol), trifluoroacetic acid (3.00 mL) in DCM (10.0 mL) was stirred for 2 h at room temperature. The reaction mixture was diluted with water. The pH value of the mixture was adjusted to 8 with sodium bicarbonate solution and extracted with DCM, washed with brine, dried over anhydrous sodium sulfate and evaporated in vacuo. The resultant residue was purified via flash chromatography on silica gel (solvent gradient: 0-10% methanol in DCM) then purified by chiral HPLC to yield 123.4 mg (28%) of 300 as a light yellow solid. LCMS (ESI): $R_T$(min)=1.83, $[M+H]^+=479$, method=C; $^1$H NMR (400 MHz, DMSO-$d_6$) δ 7.99 (s, 1H), 7.72 (s, 2H), 7.53-7.43 (m, 3H), 7.05 (s, 1H), 6.47 (s, 1H), 6.24 (s, 1H), 4.37-4.30 (m, 2H), 4.26-4.09 (m, 4H), 3.60-3.56 (m, 1H), 3.39 (s, 3H), 3.24-3.17 (m, 1H), 2.33-2.08 (m, 4H), 1.75-1.65 (m, 2H).

Example 301 and 302 (S)-2-(4-(1-(2-Aminooxazolo[4,5-b]pyridin-5-yl)-7,8,9,10-tetrahydro-6-oxa-2,10a-diazacycloocta[cd]inden-4-yl)-1H-pyrazol-1-yl)butanamide 301 and (R)-2-(4-(1-(2-Aminooxazolo[4,5-b]pyridin-5-yl)-7,8,9,10-tetrahydro-6-oxa-2,10a-diazacycloocta[cd]inden-4-yl)-1H-pyrazol-1-yl)butanamide 302

Step 1: 5-Bromooxazolo[4,5-b]pyridin-2-amine

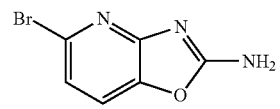 [SMILES: Nc1nc2nc(Br)ccc2o1]

A mixture of 2-amino-6-bromopyridin-3-ol (20.0 g, 105 mmol) and cyanic bromide (89.6 g, 846 mmol) in water (400 mL) was stirred at 100° C. for 20 min. The resultant mixture was quenched with sodium carbonate. The pH value of the solution was adjusted to 9 and diluted with DCM. The organic extracts were combined, dried over sodium sulfate and evaporated in vacuo. The residue was purified via flash chromatography on silica gel (solvent gradient: 0-5% methanol in DCM) to yield 10 g (44%) of the title compound as a yellow solid. LCMS (ESI): $[M+H]^+=214/216$.

Step 2: tert-Butyl 5-bromooxazolo[4,5-b]pyridin-2-ylcarbamate

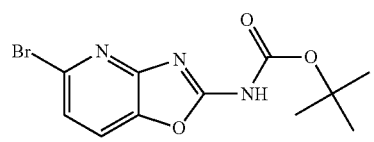 [SMILES: CC(C)(C)OC(=O)Nc1nc2nc(Br)ccc2o1]

A mixture of 5-bromooxazolo[4,5-b]pyridin-2-amine (10.0 g, 46.7 mmol), di-tert-butyl dicarbonate (22.4 g, 102 mmol), N,N-dimethylpyridin-4-amine (1.14 g, 9.33 mmol) and triethylamine (14.1 g, 140 mmol) in DCM (300 mL) was stirred at 25° C. for 16 hours. The resultant mixture was evaporated in vacuo. The residue was purified via flash chromatography on silica gel (solvent gradient: 0-1% methanol in DCM) to yield 7.80 g (53%) of the title compound as a light yellow solid. LCMS (ESI): [M+H]⁺=314/316.

Step 3: Methyl 2-(tert-butoxycarbonylamino)oxazolo[4,5-b]pyridine-5-carboxylate

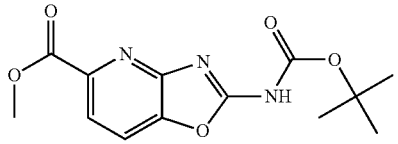 [SMILES: COC(=O)c1ccc2oc(NC(=O)OC(C)(C)C)nc2n1]

A mixture of tert-butyl 5-bromooxazolo[4,5-b]pyridin-2-ylcarbamate (7.80 g, 24.8 mmol), 1,1'-bis(diphenylphosphino)ferrocenyl palladium (II) dichloride (2.73 g, 3.73 mmol) and sodium carbonate (7.90 g, 74.5 mmol) in methanol (260 mL) was stirred at 60° C. for 16 h. The resultant mixture was concentrated in vacuo. The residue was purified via flash chromatography on silica gel (solvent gradient: 0-60% ethyl acetate in petroleum ether) to yield 7 g (96%) of the title compound as a light yellow solid. LCMS (ESI): [M+H]⁺=294.

Step 4: 2-(tert-Butoxycarbonylamino)oxazolo[4,5-b]pyridine-5-carboxylic acid

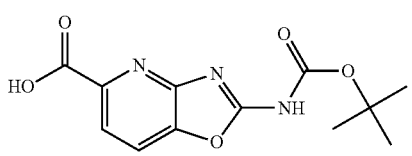 [SMILES: CC(C)(C)OC(=O)Nc1nc2nc(C(=O)O)ccc2o1]

A mixture of methyl 2-(tert-butoxycarbonylamino)oxazolo[4,5-b]pyridine-5-carboxylate (7.00 g, 23.8 mmol) and lithium hydroxide (2.00 g, 47.6 mmol) in THF (70.0 mL) and water (20 mL) was stirred at 25° C. for 1 h. The reaction mixture was extracted with ethyl acetate. The pH value of aqueous phase was adjusted to 3 with a 1M aqueous solution of hydrogen chloride. The solid was collected by filtration to yield 5 g (75%) of the title compound as a yellow solid. LCMS (ESI): [M+H]⁺=280.

Step 5: tert-Butyl (5-(4-bromo-7,8,9,10-tetrahydro-6-oxa-2,10a-diazacycloocta[cd]inden-1-yl)oxazolo[4,5-b]pyridin-2-yl)carbamate

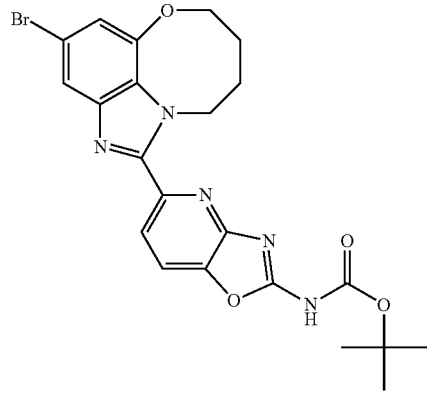 [SMILES: CC(C)(C)OC(=O)Nc1nc2nc(-c3nc4cc(Br)cc5c4n3CCCCO5)ccc2o1]

The title compound (2 g, 51% yield over 2 steps) was generated from 9-bromo-3,4,5,6-tetrahydro-2H-benzo[b][1,4]oxazocin-7-amine (2.00 g, 7.78 mmol) and 2-(tert-butoxycarbonylamino)oxazolo[4,5-b]pyridine-5-carboxylic acid (2.61 g, 9.34 mmol) following procedures analogous to those of Example 125, steps 1-2. LCMS (ESI): [M+H]⁺=500/502.

Step 6

301 and 302 were generated each as a single unknown stereoisomer from tert-butyl (5-(4-bromo-7,8,9,10-tetrahydro-6-oxa-2,10a-diazacycloocta[cd]inden-1-yl)oxazolo[4,5-b]pyridin-2-yl)carbamate (1.00 g, 1.99 mmol) following procedures analogous to those of Examples 298 and 299.

301 (74.5 mg, 23% yield): LCMS (ESI): R$_T$ (min)=3.00, [M+H]⁺=473, method=D; ¹H NMR (300 MHz, DMSO-d₆) δ 8.26 (s, 1H), 8.08 (s, 2H), 7.94 (s, 1H), 7.87-7.85 (m, 2H), 7.69-7.63 (m, 1H), 7.52 (s, 1H), 7.27-7.20 (m, 2H), 5.03-5.01 (m, 2H), 4.78-4.73 (m, 1H), 4.35-4.25 (m, 2H), 2.18-2.08 (m, 4H), 1.64-1.61 (m, 2H), 0.88-0.85 (m, 3H).

302 (128.9 mg, 39% yield): LCMS (ESI): R$_T$ (min)=3.00, [M+H]⁺=473, method=D; ¹H NMR (300 MHz, DMSO-d₆) δ 8.26 (s, 1H), 8.07 (s, 2H), 7.93-7.82 (m, 3H), 7.68 (d, J=1.4 Hz, 1H), 7.50 (s, 1H), 7.25-7.19 (m, 2H), 5.04-5.01 (m, 2H), 4.78-4.73 (m, 1H), 4.30-4.27 (m, 2H), 2.18-2.08 (m, 4H), 1.63-1.61 (m, 2H), 0.88-0.85 (m, 3H).

Examples 303 and 304 (S)-2-((1-(2-Aminobenzo[d]thiazol-6-yl)-7,8,9,10-tetrahydro-6-oxa-2,10a-diazacycloocta[cd]inden-4-yl)oxy)-3-methoxypropanamide 303 and (R)-2-((1-(2-Aminobenzo[d]thiazol-6-yl)-7,8,9,10-tetrahydro-6-oxa-2,10a-diazacycloocta[cd]inden-4-yl)oxy)-3-methoxypropanamide 304

303 and 304 were prepared each as a single unknown stereoisomer following procedures analogous to those of Examples 275 and 276.

303: LCMS (ESI): R$_T$ (min)=1.09, [M+H]⁺=454; method=D; ¹H NMR (400 MHz, DMSO-d₆): δ 8.00 (d, J=1.6 Hz, 1H), 7.73 (s, 2H), 7.61-7.60 (m, 1H), 7.54-7.51 (m, 1H), 7.48-7.46 (m, 1H), 7.40-7.39 (m, 1H), 6.96 (d, J=2.4 Hz, 1H), 6.62 (d, J=2.0 Hz, 1H), 4.72-4.70 (m, 1H), 4.41-4.39 (m, 2H), 4.27-4.24 (m, 2H), 3.77-3.67 (m, 2H), 3.33 (s, 3H), 2.18-2.12 (m, 2H), 1.72-1.67 (m, 2H).

304: LCMS (ESI): $R_T$ (min)=1.09 min, [M+H]$^+$=454, method=D; $^1$H NMR (400 MHz, DMSO-d$_6$): δ 8.01 (d, J=1.6 Hz, 1H), 7.75 (s, 2H), 7.61-7.60 (m, 1H), 7.54-7.52 (m, 1H), 7.48-7.46 (m, 1H), 7.40-7.39 (m, 1H), 6.96 (d, J=2.0 Hz, 1H), 6.63 (d, J=2.4 Hz, 1H), 4.73-4.70 (m, 1H), 4.42-4.39 (m, 2H), 4.27-4.25 (m, 2H), 3.77-3.68 (m, 2H), 3.33 (s, 3H), 2.18-2.12 (m, 2H), 1.72-1.67 (m, 2H).

Examples 305 and 306 (S)-2-Cyclopropyl-2-((1-(3-fluoro-4-(1H-1,2,4-triazol-5-yl)phenyl)-7,8,9,10-tetrahydro-6-oxa-2,10a-diazacycloocta[cd]inden-4-yl)oxy)acetamide 305 and (R)-2-cyclopropyl-2-((1-(3-fluoro-4-(1H-1,2,4-triazol-5-yl)phenyl)-7,8,9,10-tetrahydro-6-oxa-2,10a-diazacycloocta[cd]inden-4-yl)oxy)acetamide 306

Step 1: 4-Bromo-2-fluorobenzamide

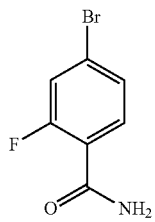

A mixture of 4-bromo-2-fluorobenzonitrile (50.0 g, 249 mmol) and aluminum oxide (76.5 g, 750 mmol) in methanesulfonic acid (650 mL) was stirred at 120° C. for 1 h. The resultant mixture was quenched with water and extracted with DCM. The organic extracts were dried over sodium sulfate and evaporated in vacuo. The residue was purified via flash chromatography on silica gel (solvent gradient: 0-50% ethyl acetate in petroleum ether) to yield 40 g (73%) of the title compound as a gray solid. LCMS (ESI): [M+H]$^+$= 218/220.

Step 2: (Z)-4-Bromo-N-((dimethylamino)methylene)-2-fluorobenzamide

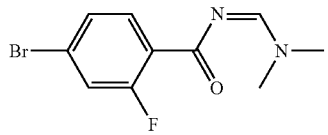

A mixture of 4-bromo-2-fluorobenzamide (20.0 g, 91.7 mmol) in dimethoxy-N,N-dimethylmethanamine (150 mL) was stirred at 100° C. for 3 h. The resulting mixture was cooled to room temperature and diluted with hexane. The solid was collected by filtration to yield 23 g (92%) of the title compound as an off-white solid. LCMS (ESI): [M+H]$^+$= 273/275.

Step 3: 3-(4-Bromo-2-fluorophenyl)-1H-1,2,4-triazole

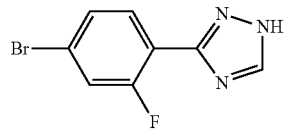 [SMILES: Fc1cc(Br)ccc1-c1nc[nH]n1]

A mixture of (Z)-4-bromo-N-((dimethylamino)methylene)-2-fluorobenzamide (20.0 g, 73.2 mmol) and hydrazine hydrate (100 mL, 80% in water, 2.06 mol) in acetic acid (500 mL) was stirred at 20° C. for 1 h. The residue was quenched with water and the solid was collected by filtration to yield 16.0 g (90%) of the title compound as a white solid. LCMS (ESI): [M+H]$^+$=242/244.

Step 4: 3-(4-Bromo-2-fluorophenyl)-1-(4-methoxybenzyl)-1H-1,2,4-triazole

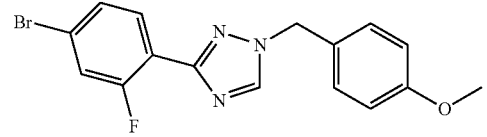 [SMILES: COc1ccc(Cn2cnc(-c3ccc(Br)cc3F)n2)cc1]

The title compound (12.0 g, 47% yield) was generated from 3-(4-bromo-2-fluorophenyl)-1H-1,2,4-triazole (17.0 g, 70.2 mmol) following a procedure analogous to Example 267, step 1. LCMS (ESI): [M+H]$^+$=362/364.

Step 5: 3-(2-Fluoro-4-(4,4,5,5-tetramethyl-1,3,2-dioxaborolan-2-yl)phenyl)-1-(4-methoxybenzyl)-1H-1,2,4-triazole

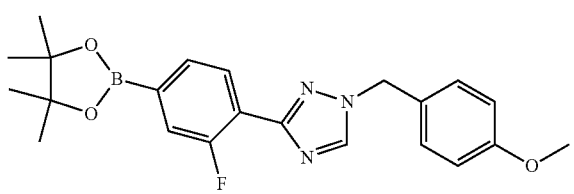

A mixture of 3-(4-bromo-2-fluorophenyl)-1-(4-methoxybenzyl)-1H-1,2,4-triazole (11.0 g, 30.3 mmol), 1,1'-bis(diphenylphosphino)ferrocenyl palladium (II) dichloride (2.22 g, 3.03 mmol), 4,4,4',4',5,5,5',5'-octamethyl-2,2'-bi(1,3,2-dioxaborolane) (9.25 g, 36.4 mmol) and potassium acetate (5.96 g, 60.7 mmol) in DMSO (300 mL) was stirred at 90° C. for 2 h. The resultant mixture was quenched with water and extracted with ethyl acetate. The organic extracts were combined, washed with brine, dried over sodium sulfate and the solvent was evaporated in vacuo. The residue was purified via flash chromatography on silica gel (solvent gradient: 0-50% ethyl acetate in petroleum ether) to yield 8.50 g (68%) of the title compound as a white solid. LCMS (ESI): [M+H]$^+$=410.

Step 6: 4-Bromo-1-(3-fluoro-4-(1-(4-methoxyben-zyl)-1H-1,2,4-triazol-3-yl)phenyl)-7,8,9,10-tetra-hydro-6-oxa-2,10a-diazacycloocta[cd]indene

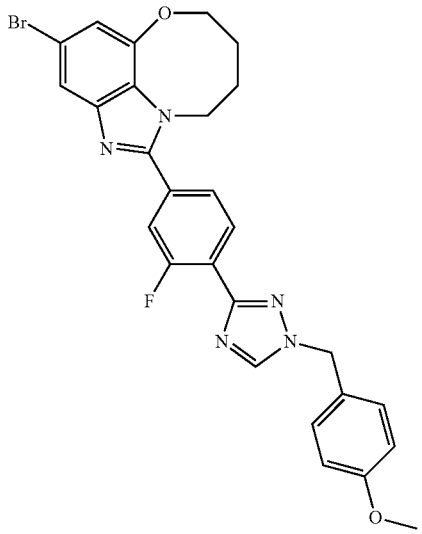 [SMILES: COc1ccc(Cn2cnc(-c3ccc(-c4nc5cc(Br)cc6c5n4CCCCO6)cc3F)n2)cc1]

A mixture of 4-bromo-1-iodo-7,8,9,10-tetrahydro-6-oxa-2,10a-diazacycloocta[cd]indene (Example 204, step 6) (5.00 g, 12.7 mmol), 3-(2-fluoro-4-(4,4,5,5-tetramethyl-1,3,2-di-oxaborolan-2-yl)phenyl)-1-(4-methoxybenzyl)-1H-1,2,4-triazole (6.25 g, 15.2 mmol), 1,1'-bis(diphenylphosphino)ferrocenyl palladium (II) dichloride (1.40 g, 1.91 mmol) and sodium carbonate (2 M in water, 2 mL, 4.00 mmol) in DMF (100 mL) was stirred at 90° C. for 2 h. The resultant mixture was quenched with water and extracted with ethyl acetate. The organic extracts were combined, washed with brine, dried over sodium sulfate and the solvent was evaporated in vacuo. The residue was purified via flash chromatography on silica gel (solvent gradient: 0-70% ethyl acetate in petroleum ether) to yield 3.10 g (44%) of the title compound as an off-white solid. LCMS (ESI): [M+H]$^+$=548/550.

Step 7: 1-(3-Fluoro-4-(1-(4-methoxybenzyl)-1H-1,2,4-triazol-3-yl)phenyl)-7,8,9,10-tetrahydro-6-oxa-2,10a-diazacycloocta[cd]inden-4-ol

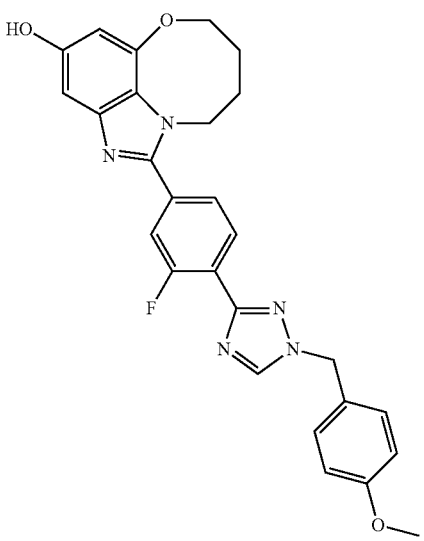 [SMILES: COc1ccc(Cn2cnc(-c3ccc(-c4nc5cc(O)cc6c5n4CCCCO6)cc3F)n2)cc1]

A mixture of 4-bromo-1-(3-fluoro-4-(1-(4-methoxyben-zyl)-1H-1,2,4-triazol-3-yl)phenyl)-7,8,9,10-tetrahydro-6-oxa-2,10a-diazacycloocta[cd]indene (3.00 g, 5.47 mmol), di-tert-butyl(2',4',6'-triisopropyl-[1,1'-biphenyl]-2-yl)phos-phine (1.16 g, 2.73 mmol), tris(dibenzylideneacetone)dipal-ladium(0) (2.50 g, 2.73 mmol) and potassium hydroxide (770 mg, 13.7 mmol) in dioxane (90 mL) and water (18 mL) was stirred at 100° C. for 4 h. The resulting mixture was evaporated in vacuo. The residue was purified via flash chromatography on silica gel (solvent gradient: 0-10% methanol in DCM) to yield 1.20 g (45%) of the title compound as a gray solid. LCMS: [M+H]$^+$=486.

Step 8

305 and 306 were prepared each as a single unknown stereoisomer from 1-(3-fluoro-4-(1-(4-methoxybenzyl)-1H-1,2,4-triazol-3-yl)phenyl)-7,8,9,10-tetrahydro-6-oxa-2,10a-diazacycloocta[cd]inden-4-ol (3.00 g, 5.47 mmol) following procedures analogous to those of Example 279, steps 1-3.

305 (124 mg, 4.3% yield over 3 steps): LCMS (ESI): $R_T$ (min)=2.46, [M+H]$^+$=463, method=E; $^1$H NMR (300 MHz, DMSO-$d_6$) δ 14.36 (s, 1H), 8.74 (s, 1H), 8.33-8.19 (m, 1H), 7.66-7.56 (m, 3H), 7.24 (s, 1H), 6.91 (d, J=2.1 Hz, 1H), 6.22 (d, J=1.8 Hz, 1H), 4.49-4.57 (m, 2H), 4.15-4.32 (m, 2H), 3.98-3.92 (m, 1H), 2.27-2.08 (m, 2H), 1.69-1.58 (m, 2H), 1.38-1.23 (m, 1H), 0.60-0.54 (m, 3H), 0.48-0.43 (m, 1H).

306 (110 mg, 3.9% yield over 3 steps): LCMS (ESI): $R_T$ (min)=2.45, [M+H]$^+$=463, method=E; $^1$H NMR (300 MHz, DMSO-$d_6$) δ 14.36 (s, 1H), 8.74 (s, 1H), 8.33-8.19 (m, 1H), 7.66-7.56 (m, 3H), 7.24 (s, 1H), 6.91 (d, J=2.1 Hz, 1H), 6.22 (d, J=1.8 Hz, 1H), 4.57-4.49 (m, 2H), 4.32-4.15 (m, 2H), 3.98-3.92 (m, 1H), 2.27-2.08 (m, 2H), 1.69-1.58 (m, 2H), 1.38-1.23 (m, 1H), 0.60-0.54 (m, 3H), 0.48-0.43 (m, 1H).

Example 307 (S)-2-((1-(5-Fluoro-6-(1H-1,2,4-tri-azol-5-yl)pyridin-3-yl)-7,8,9,10-tetrahydro-6-oxa-2,10a-diazacycloocta[cd]inden-4-yl)oxy)propanamide 307

Step 1: 4-Bromo-1-(5-fluoro-6-(1-(4-methoxyben-zyl)-1H-1,2,4-triazol-3-yl)pyridin-3-yl)-7,8,9,10-tetrahydro-6-oxa-2,10a-diazacycloocta[cd]indene

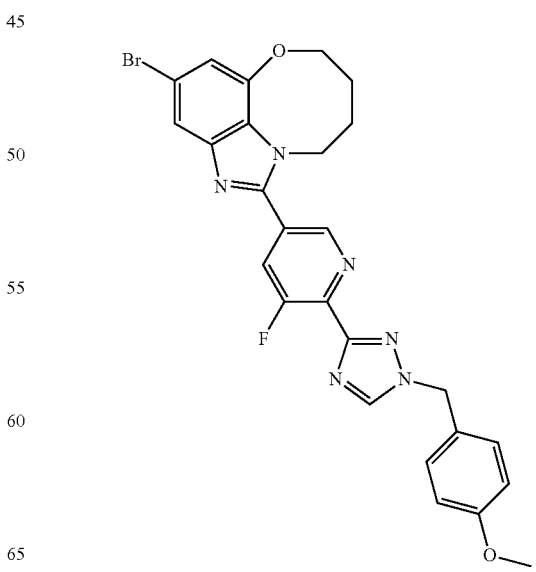

The title compound (1.60 g, 9% yield over six steps) was generated from 3-fluoro-2-(1-(4-methoxybenzyl)-1H-1,2,4-triazol-3-yl)-5-(4,4,5,5-tetramethyl-1,3,2-dioxaborolan-2-yl)pyridine (6.26 g, 15.2 mmol) following procedures analogous to those of Example 305, steps 1-6. LCMS (ESI): [M+H]$^+$=549/551.

Step 2: (S)-2-((1-(5-Fluoro-6-(1-(4-methoxybenzyl)-1H-1,2,4-triazol-3-yl)pyridin-3-yl)-7,8,9,10-tetrahydro-6-oxa-2,10a-diazacycloocta[cd]inden-4-yl)oxy)propanamide

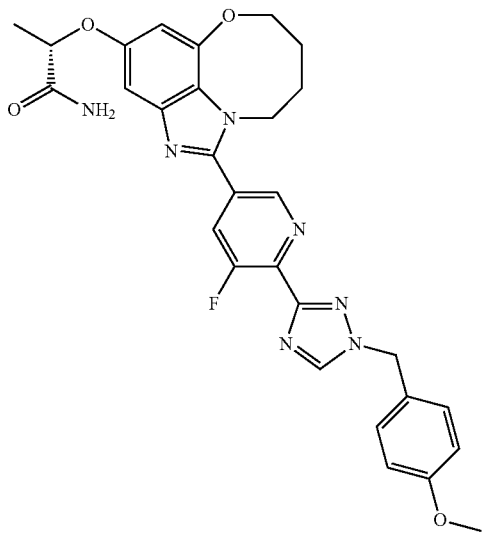 [SMILES: COc1ccc(Cn2cnc(-c3ncc(-c4nc5cc(O[C@@H](C)C(N)=O)cc6c5n4CCCCO6)cc3F)n2)cc1]

The title compound (0.80 g, 39.4% yield over four steps) was generated from 4-bromo-1-(5-fluoro-6-(1-(4-methoxybenzyl)-1H-1,2,4-triazol-3-yl)pyridin-3-yl)-7,8,9,10-tetrahydro-6-oxa-2,10a-diazacycloocta[cd]indene (2.00 g, 3.64 mmol) following procedures analogous to those of Example 204, steps 9-12. LCMS (ESI): [M+H]$^+$=558.

Step 3

307 (181 mg, 29% yield) was generated from (S)-2-((1-(5-fluoro-6-(1-(4-methoxybenzyl)-1H-1,2,4-triazol-3-yl)pyridin-3-yl)-7,8,9,10-tetrahydro-6-oxa-2,10a-diazacycloocta[cd]inden-4-yl)oxy)propanamide (800 mg, 1.44 mmol) following a procedure analogous to that of Example 267, step 6. LCMS (ESI): R$_T$=5.00, [M+H]$^+$=438, method=D; $^1$H NMR (300 MHz, DMSO-d$_6$) δ 14.67 (s, 1H), 8.87 (s, 1H), 8.52 (s, 1H), 8.18 (d, J=10.9 Hz, 1H), 7.56 (s, 1H), 7.26 (s, 1H), 6.99 (d, J=2.1 Hz, 1H), 6.66 (d, J=2.0 Hz, 1H), 4.68-4.64 (m, 1H), 4.52-4.46 (m, 2H), 4.28-4.25 (m, 2H), 2.17-2.14 (m, 2H), 1.79-1.61 (m, 2H), 1.47-1.45 (m, 3H).

Example 308 (2S,3S)-1-(1-(2-Aminobenzo[d]oxazol-5-yl)-8,9-dihydro-7H-6-oxa-2,9a-diazabenzo[cd]azulen-4-yl)-3-methylpyrrolidine-2-carboxamide 308

308 was prepared following procedures analogous to those of Example 104. LCMS (ESI): R$_T$ (min)=3.60, [M+H]$^+$=433, method=E; $^1$H NMR (300 MHz, DMSO-d$_6$) δ 7.57-7.53 (m, 3H), 7.47 (d, J=8.2 Hz, 1H), 7.36-7.32 (m, 2H), 6.99 (d, J=2.6 Hz, 1H), 6.32 (d, J=2.1 Hz, 1H), 6.05 (d, J=2.1 Hz, 1H), 4.37-4.32 (m, 2H), 4.26-4.18 (m, 2H), 3.58-3.55 (m, 1H), 3.44 (d, J=4.1 Hz, 1H), 2.37-2.12 (m, 5H), 1.59-1.52 (m, 1H), 1.09 (d, J=6.8 Hz, 3H).

Example 309 (2S,3S)-1-(1-(2-Aminobenzo[d]oxazol-5-yl)-7,8,9,10-tetrahydro-6-oxa-2,10a-diazacycloocta[cd]inden-4-yl)-3-methylpyrrolidine-2-carboxamide 309

309 was prepared following procedures analogous to those of Example 250. LCMS (ESI): R$_T$ (min)=0.83, [M+H]$^+$=447, Method=C; $^1$H NMR (300 MHz, DMSO-d$_6$) δ 7.58 (s, 2H), 7.48 (d, J=8.1 Hz, 1H), 7.43 (s, 1H), 7.39 (s, 1H), 7.26 (d, J=8.1 Hz, 1H), 7.03 (s, 1H), 6.44 (s, 1H), 6.22 (s, 1H), 4.45-4.29 (m, 2H), 4.28-4.15 (m, 2H), 3.58 (s, 1H), 3.47 (s, 1H), 3.41-3.38 (m, 1H), 2.33 (s, 1H), 2.19-2.11 (m, 3H), 1.70-1.59 (m, 3H), 1.12-1.09 (m, 3H).

Example 310 (2S,3R)-1-(1-(2-Aminobenzo[d]oxazol-5-yl)-7,8,9,10-tetrahydro-6-oxa-2,10a-diazacycloocta[cd]inden-4-yl)-3-methoxypyrrolidine-2-carboxamide 310

310 was prepared following procedures analogous to those of Example 300. LCMS (ESI): R$_T$ (min)=1.24, [M+H]$^+$=463, method=C; $^1$H NMR (300 MHz, DMSO-d$_6$): δ 7.57 (apparent s, 3H), 7.48 (d, J=8.1 Hz, 1H), 7.42 (d, J=1.5 Hz, 1H), 7.28-7.00 (m, 2H), 6.47-6.45 (m, 1H), 6.24-6.22 (m, 1H), 4.42-4.27 (m, 2H), 4.27-4.17 (m, 2H), 4.13-3.85 (m, 2H), 3.65-3.55 (m, 1H), 3.38 and 3.29 (rotamers, two apparent s, total 3H), 3.28-3.25 (m, 1H), 2.17-2.03 (m, 4H), 1.77-1.60 (m, 2H).

Examples 311 and 312 (S)-2-(4-(1-(2-Aminooxazolo[4,5-b]pyridin-5-yl)-8,9-dihydro-7H-6-oxa-2,9a-diazabenzo[cd]azulen-4-yl)-1H-pyrazol-1-yl)butanamide 311 and (R)-2-(4-(1-(2-Aminooxazolo[4,5-b]pyridin-5-yl)-8,9-dihydro-7H-6-oxa-2,9a-diazabenzo[cd]azulen-4-yl)-1H-pyrazol-1-yl)butanamide 312

311 and 312 were prepared each as a single unknown stereoisomer following procedures analogous to those of Examples 301 and 302.

311 (38.8 mg, 12% yield): LCMS (ESI): R$_T$ (min)=3.60, [M+H]$^+$=459, method=E; $^1$H NMR (300 MHz, DMSO-d$_6$) δ 8.24 (d, J=2.1 Hz, 1H), 8.10 (s, 2H), 7.92 (d, J=2.1 Hz, 1H), 7.84 (d, J=2.1 Hz, 2H), 7.55-7.41 (m, 2H), 7.27 (s, 1H), 7.08-7.05 (m, 1H), 4.78-4.72 (m, 3H), 4.45-4.41 (m, 2H), 2.37 (d, J=7.5 Hz, 2H), 2.10-2.05 (m, 2H), 0.87-0.82 (m, 3H).

312 (108.8 mg, 33% yield): LCMS (ESI): R$_T$ (min)=3.00, [M+H]$^+$=459, method=D; $^1$H NMR (300 MHz, DMSO-d$_6$) δ 8.26 (s, 1H), 8.11 (s, 2H), 7.93 (d, J=1.8 Hz, 1H), 7.84 (d, J=1.8 Hz, 2H), 7.54 (d, J=2.7 Hz, 2H), 7.28 (s, 1H), 7.08-7.06 (m, 1H), 4.78-4.72 (m, 3H), 4.45-4.41 (m, 2H), 2.37 (s, 2H), 2.11-2.03 (m, 2H), 0.87-0.83 (m, 3H).

Example 313 (S)-2-((1-(2-Aminobenzo[d]oxazol-5-yl)-7,8,9,10-tetrahydro-6-oxa-2,10a-diazacycloocta[cd]inden-4-yl)oxy)butanoic acid 313

313 was prepared following procedures analogous to those of Example 297. LCMS (ESI): R$_T$ (min)=0.90, [M+H]$^+$=423, method=D; $^1$H NMR (400 MHz, DMSO-d$_6$): δ 7.56 (s, 2H), 7.51-7.49 (m, 1H), 7.44 (d, J=1.6 Hz, 1H), 7.28-7.26 (m, 1H), 6.83 (d, J=2.4 Hz, 1H), 6.53 (d, J=2.0 Hz, 1H), 4.60-4.56 (m, 1H), 4.38-4.35 (m, 2H), 4.26-4.23 (m, 2H), 2.14-2.08 (m, 2H), 1.92-1.82 (m, 2H), 1.72-1.66 (m, 2H), 1.03-1.00 (m, 3H).

Examples 314 and 315 (R)-2-((1-(2-Aminothiazolo [5,4-b]pyridin-5-yl)-7,8,9,10-tetrahydro-6-oxa-2, 10a-diazacycloocta[cd]inden-4-yl)oxy)-3-methoxypropanamide 314 and (S)-2-((1-(2-Aminothiazolo[5, 4-b]pyridin-5-yl)-7,8,9,10-tetrahydro-6-oxa-2,10a-diazacycloocta[cd]inden-4-yl)oxy)-3-methoxypropanamide 315

314 and 315 were prepared each as a single unknown stereoisomer following procedures analogous to those of Examples 303 and 304.

314: LCMS (ESI): $R_T$ (min)=1.13, $[M+H]^+$=455, method=D; $^1$H NMR (300 MHz, DMSO-$d_6$): δ 8.12-8.07 (m, 3H), 7.77-7.75 (m, 1H), 7.63 (s, 1H), 7.41 (s, 1H), 6.97 (s, 1H), 6.63 (s, 1H), 5.11-4.88 (m, 2H), 4.74-4.66 (m, 1H), 4.35-4.18 (m, 2H), 3.81-3.63 (m, 2H), 3.32 (s, 3H), 2.21-2.05 (m, 2H), 1.71-1.56 (m, 2H).

315: LCMS (ESI): $R_T$ (min)=1.13, $[M+H]^+$=455, method=D; $^1$H NMR (300 MHz, DMSO-$d_6$): δ 8.12-8.07 (m, 3H), 7.77-7.75 (m, 1H), 7.63 (s, 1H), 7.41 (s, 1H), 6.97 (s, 1H), 6.63 (s, 1H), 5.11-4.88 (m, 2H), 4.74-4.66 (m, 1H), 4.35-4.18 (m, 2H), 3.81-3.63 (m, 2H), 3.32 (s, 3H), 2.21-2.05 (m, 2H), 1.71-1.56 (m, 2H).

Example 901 p110α (Alpha) PI3K Binding Assay

PI3K Binding assays are intended for determining the biochemical potency of small molecule PI3K inhibitors. The PI3K lipid kinase reaction is performed in the presence of PIP2:3PS lipid substrate (Promega #V1792) and ATP. Following the termination if the kinase reaction, turnover of ATP to ADP by the phosphorylation of the lipid substrate is detected using the Promega ADP-Glo™ (Promega #V1792) assay. Reactions are carried out using the following conditions:

| Kinase | Source | Final Kinase concentration | ATP (μM) | PIP2:3P5 (μM) | Reaction Time (min.) |
|---|---|---|---|---|---|
| PI3K alpha | Millipore #14-602-K | 0.2 nM | 40 | 50 | 120 |

After 120 minutes of reaction time, the kinase reaction is terminated. Any ATP remaining after the reaction is depleted, leaving only ADP. Then the Kinase Detection Reagent is added to convert ADP to ATP, which is used in a coupled luciferin/luciferase reaction. The luminescent output is measured and is correlated with kinase activity.

All reactions are carried out at room temperature. A 3 μl mixture (1:1) of enzyme/lipid substrate solution is added to a 384 well white assay plate (Perkin Elmer #6007299) containing 50 nl of test compound or DMSO only for untreated controls. The reaction is started by the addition of 2 μl ATP/MgCl$_2$. The kinase reaction buffer contains 50 mM HEPES, 50 mM NaCl, 3 mM MgCl$_2$, 0.01% BSA, 1% DMSO, and enzyme and substrate concentrations as indicated in the above table. The reaction is stopped by the addition of 10 μL ADP-Glo reagent. Plates are read in a Perkin Elmer Envision system using luminescence mode. 10 point dose response curves are generated for each test compound. Ki values for each compound are determined using the Morrison Equation.

Binding Assays: Initial polarization experiments were performed on an Analyst HT 96-384 (Molecular Devices Corp, Sunnyvale, Calif.). Samples for fluorescence polarization affinity measurements were prepared by addition of 1:3 serial dilutions of p110alpha PI3K (Upstate Cell Signaling Solutions, Charlottesville, Va.) starting at a final concentration of 20 ug/mL in polarization buffer (10 mM Tris pH 7.5, 50 mM NaCl, 4 mM MgCl$_2$, 0.05% Chaps, and 1 mM DTT) to 10 mM PIP$_2$ (Echelon-Inc., Salt Lake City, Utah) final concentration. After an incubation time of 30 minutes at room temperature, the reactions were stopped by the addition of GRP-1 and PIP3-TAMRA probe (Echelon-Inc., Salt Lake City, Utah) 100 nM and 5 nM final concentrations respectively. Read with standard cut-off filters for the rhodamine fluorophore (λex=530 nm; λem=590 nm) in 384-well black low volume Proxiplates® (PerkinElmer, Wellesley, Mass.) Fluorescence polarization values were plotted as a function of the protein concentration. EC$_{50}$ values were obtained by fitting the data to a four-parameter equation using KaleidaGraph® software (Synergy software, Reading, Pa.). This experiment also establishes the appropriate protein concentration to use in subsequent competition experiments with inhibitors.

Inhibitor IC$_{50}$ values were determined by addition of the 0.04 mg/mL p110alpha PI3K (final concentration) combined with PIP$_2$ (10 mM final concentration) to wells containing 1:3 serial dilutions of the antagonists in a final concentration of 25 mM ATP (Cell Signaling Technology, Inc., Danvers, Mass.) in the polarization buffer. After an incubation time of 30 minutes at room temperature, the reactions were stopped by the addition of GRP-1 and PIP3-TAMRA probe (Echelon-Inc., Salt Lake City, Utah) 100 nM and 5 nM final concentrations respectively. Read with standard cut-off filters for the rhodamine fluorophore (λex=530 nm; λem=590 nm) in 384-well black low volume Proxiplates® (PerkinElmer, Wellesley, Mass.) Fluorescence polarization values were plotted as a function of the antagonist concentration, and the IC$_{50}$ values were obtained by fitting the data to a 4-parameter equation in Assay Explorer software (MDL, San Ramon, Calif.).

Alternatively, inhibition of PI3K was determined in a radiometric assay using purified, recombinant enzyme and ATP at a concentration of 1 μM (micromolar). The compound was serially diluted in 100% DMSO. The kinase reaction was incubated for 1 h at room temperature, and the reaction was terminated by the addition of PBS. IC$_{50}$ values were subsequently determined using sigmoidal dose-response curve fit (variable slope).

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

We claim:

1. A method of treating cancer in a patient having a cancer selected from the group consisting of breast cancer, lung cancer, ovarian cancer, endometrial cancer, prostate cancer, and uterine cancer, comprising administering to said patient a therapeutically effective amount of a compound selected from Formula I:

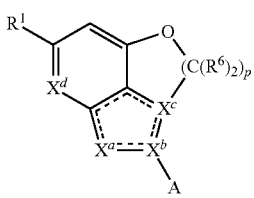

or stereoisomers, tautomers, and pharmaceutically acceptable salts thereof, wherein:

the dotted/solid lines represent a single or double bond;

$X^a$ is N;

$X^b$ is C and $X^c$ is N;

or $X^c$ is C and $X^b$ is N;

$X^d$ is $CR^2$;

$R^1$ is selected from Br, Cl, I, $C_2$-$C_{20}$ heterocyclyl, $C_1$-$C_{20}$ heteroaryl, —$NR^3R^4$, and –$OR^5$;

$R^2$ is selected from H, F, Cl, $C_1$-$C_6$ alkyl, and —O($C_1$-$C_6$ alkyl);

$R^3$ is selected from H, and $C_1$-$C_6$ alkyl;

$R^4$ is selected from H, $C_1$-$C_6$ alkyl, $C_2$-$C_{20}$ heterocyclyl, and $C_1$-$C_{20}$ heteroaryl;

or $R^3$ and $R^4$ form a 4-membered, 5-membered or 6-membered heterocyclyl ring;

$R^5$ is selected from $C_1$-$C_6$ alkyl, $C_2$-$C_{20}$ heterocyclyl, and $C_1$-$C_{20}$ heteroaryl;

$R^6$ is independently selected from H, $C_1$-$C_4$ alkyl, and F;

or two geminal or vicinal $R^6$ groups can form a 3, 4, or 5 membered-carbocyclic ring;

p is 2, 3, or 4;

A is selected from $C_6$-$C_{20}$ aryl, —($C_6$-$C_{20}$ aryl)-($C_6$-$C_{20}$ aryl), —($C_6$-$C_{20}$ aryl)-($C_1$-$C_{20}$ heteroaryl), —($C_6$-$C_{20}$ aryl)-($C_2$-$C_{20}$ heterocyclyl), —($C_1$-$C_{20}$ heteroaryl)-($C_2$-$C_{20}$ heterocyclyl), —($C_1$-$C_{20}$ heteroaryl)-($C_1$-$C_{20}$ heteroaryl), $C_2$-$C_{20}$ heterocyclyl, and $C_1$-$C_{20}$ heteroaryl; and where alkyl, aryl, heterocyclyl and heteroaryl are optionally substituted with one or more groups independently selected from F, Cl, I, —CN, —$CH_3$, —$CH_2CH_3$, —$CH(CH_3)_2$, $C(CH_3)_3$, —$CH_2CH(CH_3)_2$, —$CH_2OH$, —$CH_2OCH_3$, —$CH_2CH_2OH$, —$C(CH_3)_2OH$, —CH(OH)CH($CH_3$)$_2$, —$C(CH_3)_2CH_2OH$, —$CH_2CH_2SO_2CH_3$, —$CH_2OP(O)(OH)_2$, —$CHF_2$, —$CH_2NH_2$, —$CH_2NHSO_2CH_3$, —$CH_2NHCH_3$, —$CH_2N(CH_3)_2$, —$CF_3$, —$CH_2CF_3$, —$CH_2CHF_2$, $CH(CH_3)CN$, —$C(CH_3)_2CN$, —$CH_2CN$, —$CO_2H$, —$COCH_3$, —$CO_2CH_3$, —$CO_2C(CH_3)_3$, —COCH(OH)CH$_3$, —$CONH_2$, —$CONHCH_3$, —$CONHCH_2CH_3$, —$CONHCH(CH_3)_2$, —$CON(CH_3)_2$, —$C(CH_3)_2CONH_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —$S(O)_2N(CH_3)_2$, —$SCH_3$, —$S(O)_2CH_3$, —$S(O)_3H$, cyclopropyl, cyclobutyl, azetidinyl, oxetanyl, cyclopentyl, tetrahydrofuranyl, morpholinyl, piperidyl, piperazinyl, and tetrahydropyranyl.

2. The method of claim 1, wherein the compound is selected from Formulas Ia and Ic:

wherein p is 2, or 3.

3. The method of claim 1, wherein the compound is selected from Formula Ig:

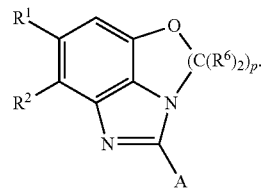

4. The method of claim 3, wherein the compound is selected from Formulas Ih, Ii and Ij:

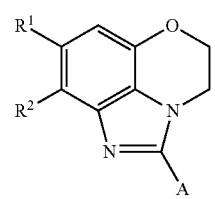

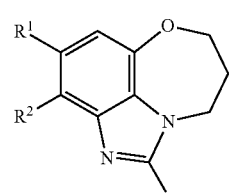

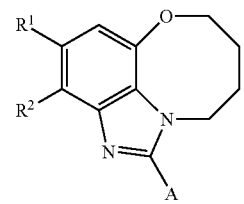

5. The method of claim 1, wherein the compound is selected from Formulas Ik, Il and Im:

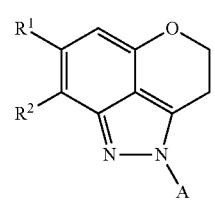

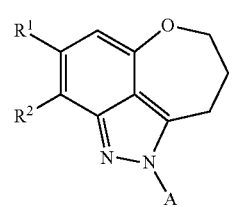

-continued

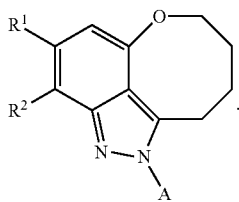

Im

6. The method of claim 4, wherein the compound is selected from Formula In, Io and Ip:

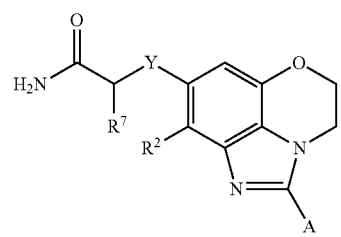

In

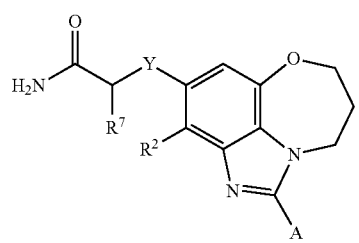

Io

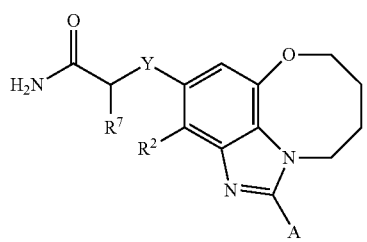

Ip wherein Y is O or NW; and

R⁷ is selected from H, cyclopropyl, cyclobutyl and $C_1$-$C_6$ alkyl optionally substituted with F, Cl, —OCH₃, or —OH; or R³ and R⁷ form a 4-membered, 5-membered or 6-membered heterocyclyl ring.

7. The method of claim 6 wherein Y is NH.

8. The method of claim 6 wherein Y is NR³, and R³ and R⁷ form a pyrrolidinyl ring.

9. The method of claim 6 wherein Y is O.

10. The method of claim 1 wherein R¹ is Br or substituted pyrazolyl.

11. The method of claim 1 wherein R¹ is selected from:

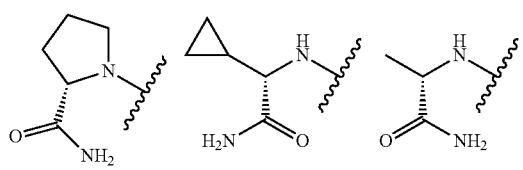

-continued

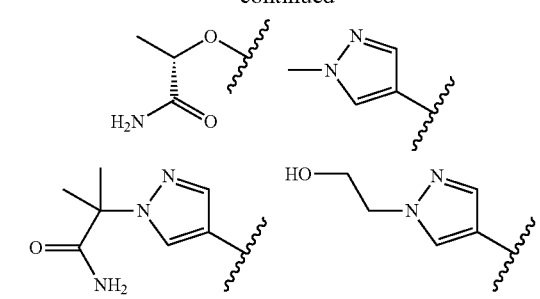

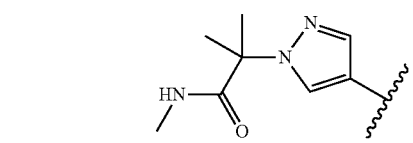

where the wavy line indicates the site of attachment.

12. The method of claim 1 wherein A is substituted benzo[d]oxazolyl or substituted benzothiazolyl.

13. The method of claim 1 wherein A is selected from the structures:

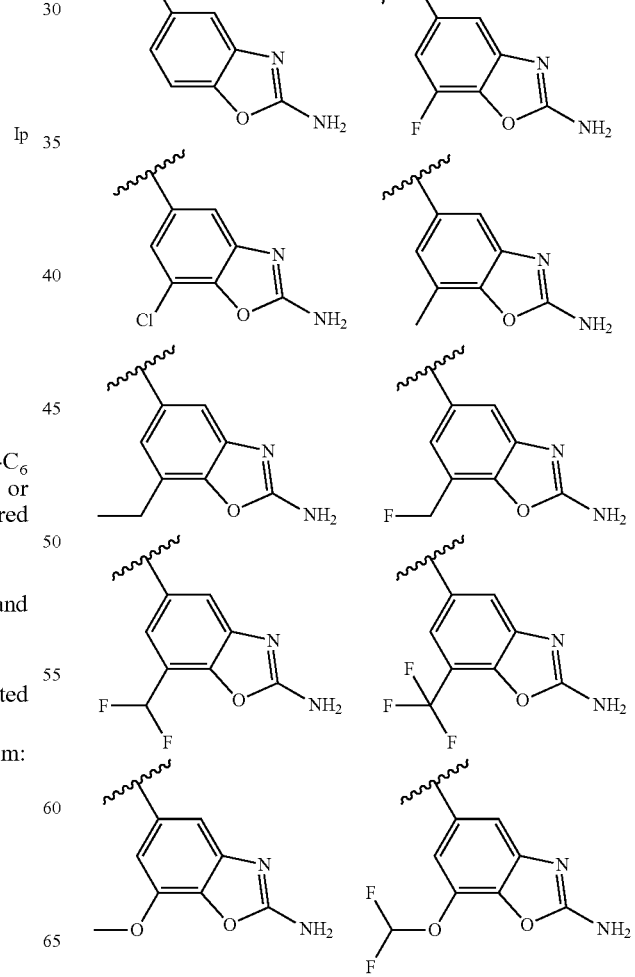

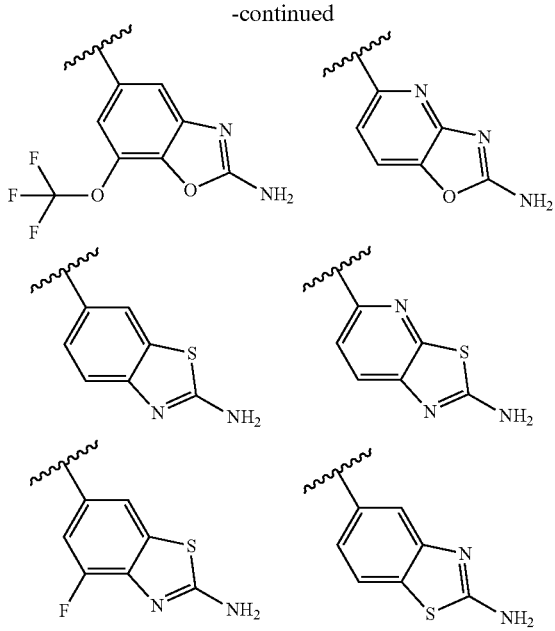

where the wavy line indicates the site of attachment.

14. The method of claim 1, wherein the compound is selected from the group consisting of:

5-(4-bromo-8,9-dihydro-7H-6-oxa-2,9a-diazabenzo[cd] azulen-1-yl)benzo[d]oxazol-2-amine;
4-bromo-1-(2-methyloxazolo[4,5-b]pyridin-5-yl)-8,9-dihydro-7H-6-oxa-2,9a-diazabenzo[cd]azulene;
1-(1-(2-methylbenzo[d]oxazol-5-yl)-8,9-dihydro-7H-6-oxa-2,9a-diazabenzo[cd]azulen-4-yl)pyrrolidine-2-carboxamide;
(S)-1-(1-(2-aminobenzo[d]oxazol-5-yl)-8,9-dihydro-7H-6-oxa-2,9a-diazabenzo[cd]azulen-4-yl)pyrrolidine-2-carboxamide;
(S)-2-((1-(2-aminobenzo[d]oxazol-5-yl)-8,9-dihydro-7H-6-oxa-2,9a-diazabenzo[cd]azulen-4-yl)amino)propanamide;
(S)-2-(41-phenyl-8,9-dihydro-7H-6-oxa-2,9a-diazabenzo[cd]azulen-4-yl)amino)propanamide;
(R)-2-((1-(2-aminobenzo[d]oxazol-5-yl)-8,9-dihydro-7H-6-oxa-2,9a-diazabenzo[cd]azulen-4-yl)amino)propanamide;
(S)-2-((1-(pyridin-3-yl)-8,9-dihydro-7H-6-oxa-2,9a-diazabenzo[cd]azulen-4-yl)amino)propanamide;
(S)-2-((1-(pyrimidin-4-yl)-8,9-dihydro-7H-6-oxa-2,9a-diazabenzo[cd]azulen-4-yl)amino)propanamide;
(S)-2-((1-(5-cyanopyridin-2-yl)-8,9-dihydro-7H-6-oxa-2,9a-diazabenzo[cd]azulen-4-yl)amino)propanamide;
(S)-2-((1-(6-methoxypyridin-3-yl)-8,9-dihydro-7H-6-oxa-2,9a-diazabenzo[cd]azulen-4-yl)amino)propanamide;
(S)-2-((1-(pyridin-2-yl)-8,9-dihydro-7H-6-oxa-2,9a-diazabenzo[cd]azulen-4-yl)amino)propanamide;
(S)-2-cyclopropyl-2-((1-(2,2-difluorobenzo[d][1,3]dioxol-5-yl)-8,9-dihydro-7H-6-oxa-2,9a-diazabenzo[cd]azulen-4-yl)amino)acetamide;
(S)-2-((1-(benzo[d][1,3]dioxol-5-yl)-8,9-dihydro-7H-6-oxa-2,9a-diazabenzo[cd]azulen-4-yl)amino)-2-cyclopropylacetamide,
(S)-2-cyclopropyl-2-((1-(3-oxoisoindolin-5-yl)-8,9-dihydro-7H-6-oxa-2,9a-diazabenzo[cd]azulen-4-yl)amino)acetamide;
(S)-2-cyclopropyl-2-((1-(quinazolin-7-yl)-8,9-dihydro-7H-6-oxa-2,9a-diazabenzo[cd]azulen-4-yl)amino)acetamide;
(S)-2-cyclopropyl-2-((1-(quinoxalin-6-yl)-8,9-dihydro-7H-6-oxa-2,9a-diazabenzo[cd]azulen-4-yl)amino)acetamide;
(S)-2-((1-(3-cyanophenyl)-8,9-dihydro-7H-6-oxa-2,9a-diazabenzo[cd]azulen-4-yl)amino)-2-cyclopropylacetamide;
(S)-2-cyclopropyl-2-((1-(quinazolin-6-yl)-8,9-dihydro-7H-6-oxa-2,9a-diazabenzo[cd]azulen-4-yl)amino)acetamide;
(S)-2-((1-(2-aminoquinazolin-6-yl)-8,9-dihydro-7H-6-oxa-2,9a-diazabenzo[cd]azulen-4-yl)amino)-2-cyclopropylacetamide;
(S)-2-cyclopropyl-2-((1-(2-methoxy-6-methylpyrimidin-4-yl)-8,9-dihydro-7H-6-oxa-2,9a-diazabenzo[cd]azulen-4-yl)amino)acetamide;
(S)-2-cyclopropyl-2-((1-(4-methylpyridin-3-yl)-8,9-dihydro-7H-6-oxa-2,9a-diazabenzo[cd]azulen-4-yl)amino)acetamide;
(S)-2-cyclopropyl-2-((1-(2-(hydroxymethyl)-6-methylpyrimidin-4-yl)-8,9-dihydro-7H-6-oxa-2,9a-diazabenzo[cd]azulen-4-yl)amino)acetamide;
2-(4-(1-(2-aminobenzo oxazol-5-yl)-8,9-dihydro-7H-6-oxa-2,9a-diazabenzo[cd]azulen-4-yl)-1H-pyrazol-1-yl)-2-methylpropanamide;
(S)-2-cyclopropyl-2-((1-(pyridazin-4-yl)-8,9-dihydro-7H-6-oxa-2,9a-diazabenzo[cd]azulen-4-yl)amino)acetamide;
(S)-2-cyclopropyl-2-((1-(4-(hydroxymethyl)piperidin-1-yl)-8,9-dihydro-7H-6-oxa-2,9a-diazabenzo[cd]azulen-4-yl)amino)acetamide;
(S)-2-cyclopropyl-2-((1-(piperidin-1-yl)-8,9-dihydro-7H-6-oxa-2,9a-diazabenzo[cd]azulen-4-yl)amino)acetamide;
(S)-2-cyclopropyl-2-((1-(2-methoxypyrimidin-5-yl)-8,9-dihydro-7H-6-oxa-2,9a-diazabenzo[cd]azulen-4-yl)amino)acetamide;
(S)-2-cyclopropyl-2-((1-(1-methyl-6-oxo-1,6-dihydropyridazin-3-yl)-8,9-dihydro-7H-6-oxa-2,9a-diazabenzo[cd]azulen-4-yl)amino)acetamide,
(S)-2-((1-(5-chloro-6-methoxypyridin-3-yl)-8,9-dihydro-7H-6-oxa-2,9a-diazabenzo[cd]azulen-4-yl)amino)-2-cyclopropylacetamide;
(S)-2-cyclopropyl-2-((1-(3-oxo-3,4-dihydro-2H-benzo[b][1,4]oxazin-6-yl)-8,9-dihydro-7H-6-oxa-2,9a-diazabenzo[cd]azulen-4-yl)amino)acetamide;
(S)-2-((1-([1,2,4]triazolo[1,5-a]pyridin-7-yl)-8,9-dihydro-7H-6-oxa-2,9a-diazabenzo[cd]azulen-4-yl)amino)-2-cyclopropylacetamide;
(S)-2-((1-(1H-indazol-5-yl)-8,9-dihydro-7H-6-oxa-2,9a-diazabenzo[cd]azulen-4-yl)amino)-2-cyclopropylacetamide;
(S)-2-cyclopropyl-2-((1-(pyrimidin-5-yl)-8,9-dihydro-7H-6-oxa-2,9a-diazabenzo[cd]azulen-4-yl)amino)acetamide;
(S)-2-((1-(2-aminobenzo[d]oxazol-5-yl)-8,9-dihydro-7H-6-oxa-2,9a-diazabenzo[cd]azulen-4-yl)amino)-2-cyclopropylacetamide;
(S)-2-cyclopropyl-2-((1-(thiazol-5-yl)-8,9-dihydro-7H-6-oxa-2,9a-diazabenzo[cd]azulen-4-yl)amino)acetamide;
(S)-2-cyclopropyl-2-((1-(4-(methylsulfonyl)phenyl)-8,9-dihydro-7H-6-oxa-2,9a-diazabenzo[cd]azulen-4-yl)amino)acetamide;

(S)-2-cyclopropyl-2-((1-(2,3-dihydrobenzo[b][1,4]di-oxin-6-yl)-8,9-dihydro-7H-6-oxa-2,9a-diazabenzo[cd]azulen-4-yl)amino)acetamide;
(S)-2-((1-((R)-3-(hydroxymethyl)piperidin-1-yl)-8,9-dihydro-7H-6-oxa-2,9a-diazabenzo[cd]azulen-4-yl)amino)propanamide;
(S)-2-((1-(4-(hydroxymethyl)piperidin-1-yl)-8,9-dihydro-7H-6-oxa-2,9a-diazabenzo[cd]azulen-4-yl)amino)propanamide;
(S)-2-cyclopropyl-2-(41-morpholino-8,9-dihydro-7H-6-oxa-2,9a-diazabenzo[cd]azulen-4-yl)amino)acetamide;
(S)-2-cyclopropyl-2-((1-(oxazol-2-yl)-8,9-dihydro-7H-6-oxa-2,9a-diazabenzo[cd]azulen-4-yl)amino)acetamide;
(S)-2-cyclopropyl-2-((1-(3-(difluoromethoxy)phenyl)-8,9-dihydro-7H-6-oxa-2,9a-diazabenzo[cd]azulen-4-yl)amino)acetamide;
(S)-2-cyclopropyl-2-((1-(2-fluoro-4-methoxyphenyl)-8,9-dihydro-7H-6-oxa-2,9a-diazabenzo[cd]azulen-4-yl)amino)acetamide;
(S)-2-cyclopropyl-2-((1-(2,4-difluorophenyl)-8,9-dihydro-7H-6-oxa-2,9a-diazabenzo[cd]azulen-4-yl)amino)acetamide;
(S)-3-(4-((2-amino-1-cyclopropyl-2-oxoethyl)amino)-8,9-dihydro-7H-6-oxa-2,9a-diazabenzo[cd]azulen-1-yl)benzamide;
(S)-2-cyclopropyl-2-((1-(1-methyl-6-oxo-1,6-dihydropyridin-3-yl)-8,9-dihydro-7H-6-oxa-2,9a-diazabenzo[cd]azulen-4-yl)amino)acetamide;
(S)-2-cyclopropyl-2-((1-(2,3-dihydro-[1,4]dioxino[2,3-b]pyridin-7-yl)-8,9-dihydro-7H-6-oxa-2,9a-diazabenzo[cd]azulen-4-yl)amino)acetamide;
(S)-2-((1-(2-amino-5,7-dihydro-6H-pyrrolo[3,4-d]pyrimidin-6-yl)-8,9-dihydro-7H-6-oxa-2,9a-diazabenzo[cd]azulen-4-yl)amino)-2-cyclopropylacetamide;
(S)-2-cyclopropyl-2-((1-(4-(difluoromethoxy)phenyl)-8,9-dihydro-7H-6-oxa-2,9a-diazabenzo[cd]azulen-4-yl)amino)acetamide;
(S)-4-(4-((2-amino-1-cyclopropyl-2-oxoethyl)amino)-8,9-dihydro-7H-6-oxa-2,9a-diazabenzo[cd]azulen-1-yl)picolinamide;
2-(4-(1-(2-aminobenzo[d]oxazol-5-yl)-8,9-dihydro-7H-6-oxa-2,9a-diazabenzo[cd]azulen-4-yl)-1H-pyrazol-1-yl)ethan-1-ol;
5-(4-(1-methyl-1H-pyrazol-4-yl)-8,9-dihydro-7H-6-oxa-2,9a-diazabenzo[cd]azulen-1-yl)benzo[d]oxazol-2-amine;
2-(4-(1-(2-aminobenzo[d]oxazol-5-yl)-8,9-dihydro-7H-6-oxa-2,9a-diazabenzo[cd]azulen-4-yl)-1H-pyrazol-1-yl)-N,2-dimethylpropanamide;
(S)-2-cyclopropyl-2-((1-(2-oxo-2,3-dihydrobenzo[d]oxazol-6-yl)-8,9-dihydro-7H-6-oxa-2,9a-diazabenzo[cd]azulen-4-yl)amino)acetamide;
(S)-2-((1-([1,2,4]triazolo[1,5-a]pyrimidin-5-yl)-8,9-dihydro-7H-6-oxa-2,9a-diazabenzo[cd]azulen-4-yl)amino)-2-cyclopropylacetamide;
(S)-5-(4-((2-amino-1-cyclopropyl-2-oxoethyl)amino)-8,9-dihydro-7H-6-oxa-2,9a-diazabenzo[cd]azulen-1-yl)-2-fluorobenzamide;
methyl (S)-5-(4-((2-amino-1-cyclopropyl-2-oxoethyl)amino)-8,9-dihydro-7H-6-oxa-2,9a-diazabenzo[cd]azulen-1-yl)-2-methoxybenzoate;
(S)-2-cyclopropyl-2-((1-(2-(methylsulfonyl)pyridin-4-yl)-8,9-dihydro-7H-6-oxa-2,9a-diazabenzo[cd]azulen-4-yl)amino)acetamide;
(S)-2-cyclopropyl-2-((1-(1,3-dimethyl-1H-pyrazol-4-yl)-8,9-dihydro-7H-6-oxa-2,9a-diazabenzo[cd]azulen-4-yl)amino)acetamide;
(S)-2-cyclopropyl-2-((1-(5,6-dihydro-[1,2,4]triazolo[1,5-a]pyrazin-7(8H)-yl)-8,9-dihydro-7H-6-oxa-2,9a-diazabenzo[cd]azulen-4-yl)amino)acetamide;
(S)-2-((1-(2-aminobenzo[d]oxazol-5-yl)-8,9-dihydro-7H-6-oxa-2,9a-diazabenzo[cd]azulen-4-yl)oxy)propanamide;
(S)-2-cyclopropyl-2-((1-(3-(difluoromethoxy)-4-methoxyphenyl)-8,9-dihydro-7H-6-oxa-2,9a-diazabenzo[cd]azulen-4-yl)amino)acetamide;
(S)-5-(4-((2-amino-1-cyclopropyl-2-oxoethyl)amino)-8,9-dihydro-7H-6-oxa-2,9a-diazabenzo[cd]azulen-1-yl)-2-methoxybenzamide;
(S)-2-cyclopropyl-2-((1-(pyridin-4-yl)-8,9-dihydro-7H-6-oxa-2,9a-diazabenzo[cd]azulen-4-yl)amino)acetamide;
(S)-2-cyclopropyl-2-((1-(1-methyl-1H-pyrazol-4-yl)-8,9-dihydro-7H-6-oxa-2,9a-diazabenzo[cd]azulen-4-yl)amino)acetamide;
(S)-2-cyclopropyl-2-((1-(2,3-dihydro-[1,4]dioxino[2,3-b]pyridin-6-yl)-8,9-dihydro-7H-6-oxa-2,9a-diazabenzo[cd]azulen-4-yl)amino)acetamide;
(S)-2-(4-bromo-8,9-dihydro-7H-6-oxa-2,9a-diazabenzo[cd]azulen-1-yl)benzo[d]oxazol-2-yl)methanol;
(S)-2-((1-(1H-pyrazolo[3,4-b]pyridin-4-yl)-8,9-dihydro-7H-6-oxa-2,9a-diazabenzo[cd]azulen-4-yl)amino)-2-cyclopropylacetamide;
(S)-2-((1-(2-aminobenzo[d]thiazol-6-yl)-8,9-dihydro-7H-6-oxa-2,9a-diazabenzo[cd]azulen-4-yl)amino)-2-cyclopropylacetamide;
(S)-2-((1-(2-aminobenzo[d]oxazol-5-yl)-7,8,9,10-tetrahydro-6-oxa-2,10a-diazacycloocta[cd]inden-4-yl)amino)-2-cyclopropylacetamide;
5-(4-bromo-7,8,9,10-tetrahydro-6-oxa-2,10a-diazacycloocta[cd]inden-1-yl)benzo[d]oxazol-2-amine;
(S)-2-cyclopropyl-2-((1-(2-methoxyquinoxalin-6-yl)-8,9-dihydro-7H-6-oxa-2,9a-diazabenzo[cd]azulen-4-yl)amino)acetamide;
2-((1-(3-cyanopiperidin-1-yl)-8,9-dihydro-7H-6-oxa-2,9a-diazabenzo[cd]azulen-4-yl)amino)-2-cyclopropylacetamide,
(S)-2-cyclopropyl-2-((1-(5-(methylsulfonyl)pyridin-3-yl)-8,9-dihydro-7H-6-oxa-2,9a-diazabenzo[cd]azulen-4-yl)amino)acetamide;
(S)-2-((1-(3H-imidazo[4,5-b]pyridin-7-yl)-8,9-dihydro-7H-6-oxa-2,9a-diazabenzo[cd]azulen-4-yl)amino)-2-cyclopropylacetamide;
(S)-2-cyclopropyl-2-((1-(thieno[2,3-b]pyridin-4-yl)-8,9-dihydro-7H-6-oxa-2,9a-diazabenzo[cd]azulen-4-yl)amino)acetamide;
(S)-2-((1-(benzo[d]thiazol-6-yl)-8,9-dihydro-7H-6-oxa-2,9a-diazabenzo[cd]azulen-4-yl)amino)-2-cyclopropylacetamide;
(S)-2-cyclopropyl-2-((1-(7,8-dihydropyrido[3,4-b]pyrazin-6(5H)-yl)-8,9-dihydro-7H-6-oxa-2,9a-diazabenzo[cd]azulen-4-yl)amino)acetamide;
(S)-2-((1-(1,4-oxazepan-4-yl)-8,9-dihydro-7H-6-oxa-2,9a-diazabenzo[cd]azulen-4-yl)amino)-2-cyclopropylacetamide;
(S)-2-(4-(4-(2-amino-1-cyclopropyl-2-oxoethyl)amino)-8,9-dihydro-7H-6-oxa-2,9a-diazabenzo[cd]azulen-1-yl)-1H-pyrazol-1-yl)-2-methylpropanamide;
(S)-2-cyclopropyl-2-((1-(3-hydroxypiperidin-1-yl)-8,9-dihydro-7H-6-oxa-2,9a-diazabenzo[cd]azulen-4-yl)amino)acetamide;
(S)-2-cyclopropyl-2-((1-(1-methyl-1H-1,2,4-triazol-5-yl)-8,9-dihydro-7H-6-oxa-2,9a-diazabenzo[cd]azulen-4-yl)amino)acetamide;

(S)-2-((1-(2-aminobenzo[d]thiazol-5-yl)-8,9-dihydro-7H-6-oxa-2,9a-diazabenzo[cd]azulen-4-yl)amino)-2-cyclopropylacetamide;

(S)-2-((1-(2-(methylamino)benzo[d]oxazol-5-yl)-8,9-dihydro-7H-6-oxa-2,9a-diazabenzo[cd]azulen-4-yl)amino)propanamide;

(S)-1-(1-(2-(methylamino)benzo[d]oxazol-5-yl)-8,9-dihydro-7H-6-oxa-2,9a-diazabenzo[cd]azulen-4-yl)pyrrolidine-2-carboxamide;

(S)-2-((1-(2-aminoquinoxalin-6-yl)-8,9-dihydro-7H-6-oxa-2,9a-diazabenzo[cd]azulen-4-yl)amino)-2-cyclopropylacetamide;

(S)-4-(4-((2-amino-1-cyclopropyl-2-oxoethyl)amino)-8,9-dihydro-7H-6-oxa-2,9a-diazabenzo[cd]azulen-1-yl)-2-fluorobenzamide;

(S)-2-cyclopropyl-2-((1-(3-hydroxyquinolin-6-yl)-8,9-dihydro-7H-6-oxa-2,9a-diazabenzo[cd]azulen-4-yl)amino)acetamide;

(S)-2-((1-(4-(1H-1,2,4-triazol-3-yl)phenyl)-8,9-dihydro-7H-6-oxa-2,9a-diazabenzo[cd]azulen-4-yl)amino)-2-cyclopropylacetamide;

(S)-5-(4-((2-amino-1-cyclopropyl-2-oxoethyl)amino)-8,9-dihydro-7H-6-oxa-2,9a-diazabenzo[cd]azulen-1-yl)picolinamide;

1-(2-aminobenzo[d]oxazol-5-yl)-N-(3,3-difluorocyclobutyl)-8,9-dihydro-7H-6-oxa-2,9a-diazabenzo[cd]azulen-4-amine;

5-(4-bromo-3-fluoro-8,9-dihydro-7H-6-oxa-2,9a-diazabenzo[cd]azulen-1-yl)benzo[d]oxazol-2-amine;

(S)-1-(2-aminobenzo[d]oxazol-5-yl)-3-fluoro-8,9-dihydro-7H-6-oxa-2,9a-diazabenzo[cd]azulen-4-yl)pyrrolidine-2-carboxamide;

(S)-2-((1-([1,3]dioxolo[4,5-b]pyridin-7-yl)-8,9-dihydro-7H-6-oxa-2,9a-diazabenzo[cd]azulen-4-yl)amino)-2-cyclopropylacetamide;

(S)-2-cyclopropyl-2-((1-(2-oxo-2,3-dihydrobenzo[d]oxazol-5-yl)-8,9-dihydro-7H-6-oxa-2,9a-diazabenzo[cd]azulen-4-yl)amino)acetamide;

(S)-2-((1-(2-chloro-[1,2,4]triazolo[1,5-a]pyridin-6-yl)-8,9-dihydro-7H-6-oxa-2,9a-diazabenzo[cd]azulen-4-yl)amino)-2-cyclopropylacetamide;

(6-(4-bromo-8,9-dihydro-7H-6-oxa-2,9a-diazabenzo[cd]azulen-1-yl)quinoxalin-2-yl)methanol;

(S)-1-(1-(1H-benzo[d]imidazol-5-yl)-8,9-dihydro-7H-6-oxa-2,9a-diazabenzo[cd]azulen-4-yl)pyrrolidine-2-carboxamide;

(S)-1-(1-(1H-benzo[d][1,2,3]triazol-5-yl)-8,9-dihydro-7H-6-oxa-2,9a-diazabenzo[cd]azulen-4-yl)pyrrolidine-2-carboxamide;

(S)-2-((1-(2-amino-[1,2,4]triazolo[1,5-a]pyridin-6-yl)-8,9-dihydro-7H-6-oxa-2,9a-diazabenzo[cd]azulen-4-yl)amino)-2-cyclopropylacetamide;

1-(2-aminobenzo[d]oxazol-5-yl)-N-((1r,3r)-3-fluorocyclobutyl)-8,9-dihydro-7H-6-oxa-2,9a-diazabenzo[cd]azulen-4-amine;

1-(2-aminobenzo[d]oxazol-5-yl)-N-((1s,3s)-3-fluorocyclobutyl)-8,9-dihydro-7H-6-oxa-2,9a-diazabenzo[cd]azulen-4-amine;

(S)-2-((1-(2-aminobenzo[d]oxazol-5-yl)-7,8,9,10-tetrahydro-6-oxa-2,10a-diazacycloocta[cd]inden-4-yl)oxy)propanamide, (S)-2-((1-(2-amino-7-methylbenzo[d]oxazol-5-yl)-8,9-dihydro-7H-6-oxa-2,9a-diazabenzo[cd]azulen-4-yl)amino)-2-cyclopropylacetamide;

(S)-1-(1-(3H-[1,2,3]triazolo[4,5-b]pyridin-7-yl)-8,9-dihydro-7H-6-oxa-2,9a-diazabenzo[cd]azulen-4-yl)pyrrolidine-2-carboxamide;

(S)-2-((1-(2-aminobenzo[d]oxazol-6-yl)-8,9-dihydro-7H-6-oxa-2,9a-diazabenzo[cd]azulen-4-yl)amino)-2-cyclopropylacetamide;

(S)-2-((2-(2-aminobenzo[d]oxazol-5-yl)-3,4-dihydro-5-oxa-1,2a-diazaacenaphthylen-7-yl)amino)-2-cyclopropylacetamide;

(S)-2-((1-(2-amino-7-chlorobenzo[d]oxazol-5-yl)-8,9-dihydro-7H-6-oxa-2,9a-diazabenzo[cd]azulen-4-yl)amino)-2-cyclopropylacetamide;

(S)-2-cyclopropyl-2-((1-(1-(oxetan-3-yl)-1H-pyrazol-4-yl)-8,9-dihydro-7H-6-oxa-2,9a-diazabenzo[cd]azulen-4-yl)amino)acetamide;

(S)-2-cyclopropyl-2-((1-(1-(2-hydroxyethyl)-1H-pyrazol-4-yl)-8,9-dihydro-7H-6-oxa-2,9a-diazabenzo[cd]azulen-4-yl)amino)acetamide;

(S)-2-((1-(1H-pyrazol-4-yl)-8,9-dihydro-7H-6-oxa-2,9a-diazabenzo[cd]azulen-4-yl)amino)-2-cyclopropylacetamide;

(S)-2-cyclopropyl-2-((1-(6-methoxypyridin-3-yl)-1,7,8,9-tetrahydrooxepino[4,3,2-cd]indazol-4-yl)amino)acetamide;

(S)-2-((1-(2-aminobenzo[d]thiazol-6-yl)-7,8,9,10-tetrahydro-6-oxa-2,10a-diazacycloocta[cd]inden-4-yl)amino)-2-cyclopropylacetamide;

(S)-2-cyclopropyl-2-((1-(8-fluoroquinoxalin-6-yl)-8,9-dihydro-7H-6-oxa-2,9a-diazabenzo[cd]azulen-4-yl)amino)acetamide;

(R)-2-(4-(1-(2-aminobenzo[d]oxazol-5-yl)-8,9-dihydro-7H-6-oxa-2,9a-diazabenzo[cd]azulen-4-yl)-1H-pyrazol-1-yl)butanamide;

(S)-2-(4-(1-(2-aminobenzo[d]oxazol-5-yl)-8,9-dihydro-7H-6-oxa-2,9a-diazabenzo[cd]azulen-4-yl)-1H-pyrazol-1-yl)butanamide;

(R)-2-(4-(1-(2-aminobenzo[d]oxazol-5-yl)-8,9-dihydro-7H-6-oxa-2,9a-diazabenzo[cd]azulen-4-yl)-1H-pyrazol-1-yl)propanamide;

(S)-2-(4-(1-(2-aminobenzo[d]oxazol-5-yl)-8,9-dihydro-7H-6-oxa-2,9a-diazabenzo[cd]azulen-4-yl)-1H-pyrazol-1-yl)propanamide, (S)-1-(1-(2-oxo-3,4-dihydro-2H-benzo[4,5] oxazolo[3,2-a]pyrimidin-7-yl)-8,9-dihydro-7H-6-oxa-2,9a-diazabenzo[cd]azulen-4-yl)pyrrolidine-2-carboxamide;

(S)-1-(1-(4-(1H-1,2,4-triazol-3-yl)phenyl)-8,9-dihydro-7H-6-oxa-2,9a-diazabenzo[cd]azulen-4-yl)pyrrolidine-2-carboxamide;

(S)-1-(1-(3-chloro-4-(1H-1,2,4-triazol-3-yl)phenyl)-8,9-dihydro-7H-6-oxa-2,9a-diazabenzo[cd]azulen-4-yl)pyrrolidine-2-carboxamide;

(S)-1-(1-(6-(1H-pyrazol-4-yl)pyridin-3-yl)-8,9-dihydro-7H-6-oxa-2,9a-diazabenzo[cd]azulen-4-yl)pyrrolidine-2-carboxamide;

(S)-1-(1-(2-amino-7-ethylbenzo[d]oxazol-5-yl)-8,9-dihydro-7H-6-oxa-2,9a-diazabenzo[cd]azulen-4-yl)pyrrolidine-2-carboxamide;

(S)-2-((1-(2-amino-7-ethylbenzo[d]oxazol-5-yl)-8,9-dihydro-7H-6-oxa-2,9a-diazabenzo[cd]azulen-4-yl)amino)-2-cyclopropylacetamide;

(5)-1-(1-(5-(1H-1,2,4-triazol-3-yl)pyridin-2-yl)-8,9-dihydro-7H-6-oxa-2,9a-diazabenzo[cd]azulen-4-yl)pyrrolidine-2-carboxamide;

(S)-1-(1-(4-(1,2,4-thiadiazol-3-yl)phenyl)-8,9-dihydro-7H-6-oxa-2,9a-diazabenzo[cd]azulen-4-yl)pyrrolidine-2-carboxamide;

(S)-2-cyclopropyl-2-((1-(pyrazolo[1,5-a]pyrimidin-5-yl)-8,9-dihydro-7H-6-oxa-2,9a-diazabenzo[cd]azulen-4-yl)amino)acetamide;

(S)-1-(1-(4-(1H-pyrazol-3-yl)phenyl)-8,9-dihydro-7H-6-oxa-2,9a-diazabenzo[cd]azulen-4-yl)pyrrolidine-2-carboxamide;

S)-2-(4-(1-(2-aminobenzo[d]oxazol-5-yl)-8,9-dihydro-7H-6-oxa-2,9a-diazabenzo[cd]azulen-4-yl)-1H-pyrazol-1-yl)-2-cyclopropylacetamide;

(R)-2-(4-(1-(2-aminobenzo[d]oxazol-5-yl)-8,9-dihydro-7H-6-oxa-2,9a-diazabenzo[cd]azulen-4-yl)-1H-pyrazol-1-yl)-2-cyclopropylacetamide;

(R)-2-(4-(1-(2-aminobenzo[d]oxazol-5-yl)-8,9-dihydro-7H-6-oxa-2,9a-diazabenzo[cd]azulen-4-yl)-1H-pyrazol-1-yl)-3-methoxy-2-methylpropanamide;

(S)-2-(4-(1-(2-aminobenzo[d]oxazol-5-yl)-8,9-dihydro-7H-6-oxa-2,9a-diazabenzo[cd]azulen-4-yl)-1H-pyrazol-1-yl)-3-methoxy-2-methylpropanamide;

(S)-1-(1-(4-(2-oxoimidazolidin-1-yl)phenyl)-8,9-dihydro-7H-6-oxa-2,9a-diazabenzo[cd]azulen-4-yl)pyrrolidine-2-carboxamide, (S)-2-((1-(2-amino-7-(trifluoromethyl)benzo[d]oxazol-5-yl)-8,9-dihydro-7H-6-oxa-2,9a-diazabenzo[cd]azulen-4-yl)amino)-2-cyclopropylacetamide;

(S)-1-(1-(2-aminobenzo[d]oxazol-5-yl)-8,9-dihydro-7H-6-oxa-2,9a-diazabenzo[cd]azulen-4-yl)-N-(4-methoxybenzyl)pyrrolidine-2-carboxamide;

(S)-1-(1-(3-oxo-2,3-dihydrobenzo[d]isoxazol-6-yl)-8,9-dihydro-7H-6-oxa-2,9a-diazabenzo[cd]azulen-4-yl)pyrrolidine-2-carboxamide;

(S)-2-4(R)-2-(2-aminobenzo[d]oxazol-5-yl)-4-methyl-3,4-dihydro-5-oxa-1,2a-diazaacenaphthylen-7-yl)amino)-2-cyclopropylacetamide;

(5)-1-(1-(2-aminobenzo[d]thiazol-6-yl)-7,8,9,10-tetrahydro-6-oxa-2,10a-diazacycloocta[cd]inden-4-yl)pyrrolidine-2-carboxamide;

(S)-2-((1-(2-aminobenzo[d]oxazol-5-yl)-3-fluoro-8,9-dihydro-7H-6-oxa-2,9a-diazabenzo[cd]azulen-4-yl)oxy)propanamide;

(S)-2-((1-(2-amino-4-fluorobenzo[d]oxazol-5-yl)-7,8,9,10-tetrahydro-6-oxa-2,10a-diazacycloocta[cd]inden-4-yl)oxy)propanamide;

(S)-2-((1-(2-amino-4-fluorobenzo[d]thiazol-6-yl)-7,8,9,10-tetrahydro-6-oxa-2,10a-diazacycloocta[cd]inden-4-yl)oxy)propanamide;

(S)-2-((1-(4-(1H-1,2,4-triazol-3-yl)phenyl)-7,8,9,10-tetrahydro-6-oxa-2,10a-diazacycloocta[cd]inden-4-yl)oxy)propanamide, and (S)-2-((1-(2-aminoquinoxalin-6-yl)-7,8,9,10-tetrahydro-6-oxa-2,10a-diazacycloocta[cd]inden-4-yl)oxy)propanamide;

or a pharmaceutically acceptable salt thereof.

15. The method of claim 1, wherein the compound is selected from the group consisting of:

(R)-2-((1-(2-aminobenzo[d]oxazol-5-yl)-7,8,9,10-tetrahydro-6-oxa-2,10a-diazacycloocta[cd]inden-4-yl)oxy)propanamide;

(S)-2-((1-(2-Aminobenzo[d]thiazol-5-yl)-7,8,9,10-tetrahydro-6-oxa-2,10a-diazacycloocta[cd]inden-4-yl)amino)-2-cyclopropylacetamide;

(S)-1-(1-(2-aminobenzo[d]oxazol-5-yl)-3-fluoro-7,8,9,10-tetrahydro-6-oxa-2,10a-diazacycloocta[cd]inden-4-yl)pyrrolidine-2-carboxamide, (S)-2-((1-(2-aminobenzo[d]thiazol-6-yl)-7,8,9,10-tetrahydro-6-oxa-2,10a-diazacycloocta[cd]inden-4-yl)oxy)propanamide;

(S)-2-((1-(2-amino-7-fluorobenzo[d]oxazol-5-yl)-'7,8,9,10-tetrahydro-6-oxa-2,10a-diazacycloocta[cd]inden-4-yl)oxy)propanamide;

(S)-1-(1-(2-aminobenzo[d]oxazol-5-yl)-7,8,9,10-tetrahydro-6-oxa-2,10a-diazacycloocta[cd]inden-4-yl)pyrrolidine-2-carboxamide;

(R)-2-(((R)-2-(2-aminobenzo[d]oxazol-5-yl)-4-methyl-3,4-dihydro-5-oxa-1,2a-diazaacenaphthylen-7-yl)oxy)propanamide;

(S)-2-4(R)-2-(2-aminobenzo[d]oxazol-5-yl)-4-methyl-3,4-dihydro-5-oxa-1,2a-diazaacenaphthylen-7-yl)oxy)propanamide;

5-(4-bromo-8,9-dihydrooxepino[4,3,2-cd]indazol-1(7H)-yl)benzo[d]oxazol-2-amine;

(S)-2-((1-(2-aminobenzo[d]oxazol-5-yl)-7,8,9,10-tetrahydro-6-oxa-2,10a-diazacycloocta[cd]inden-4-yl)(methyl)amino)propanamide;

(S)-2-((1-(2-aminobenzo[d]thiazol-6-yl)-7,8,9,10-tetrahydro-6-oxa-2,10a-diazacycloocta[cd]inden-4-yl)(methyl)amino)propanamide;

(S)-2-((1-(2-aminobenzo[d]oxazol-5-yl)-8,9-dihydro-7H-6-oxa-2,9a-diazabenzo[cd]azulen-4-yl)oxy)butanamide;

(R)-2-((1-(2-aminobenzo[d]oxazol-5-yl)-8,9-dihydro-7H-6-oxa-2,9a-diazabenzo[cd]azulen-4-yl)oxy)butanamide;

(S)-2-((1-(2-amino-7-fluorobenzo[d]oxazol-5-yl)-8,9-dihydro-7H-6-oxa-2,9a-diazabenzo[cd]azulen-4-yl)oxy)propanamide;

(R)-2-((1-(2-aminobenzo[d]oxazol-5-yl)-8,9-dihydro-7H-6-oxa-2,9a-diazabenzo[cd]azulen-4-yl)oxy)-2-cyclopropylacetamide;

(S)-2-((1-(2-aminobenzo[d]oxazol-5-yl)-8,9-dihydro-7H-6-oxa-2,9a-diazabenzo[cd]azulen-4-yl)oxy)-2-cyclopropylacetamide;

(S)-2-((1-(2-amino-4,7-difluorobenzo[d]oxazol-5-yl)-7,8,9,10-tetrahydro-6-oxa-2,10a-diazacycloocta[cd]inden-4-yl)oxy)propanamide;

(S)-4-(1-(2-aminobenzo[d]thiazol-6-yl)-7,8,9,10-tetrahydro-6-oxa-2,10a-diazacycloocta[cd]inden-4-yl)morpholine-3-carboxamide, (R)-2-((1-(2-Amino-7-fluorobenzo[d]oxazol-5-yl)-8,9-dihydro-7H-6-oxa-2,9a-diazabenzo[cd]azulen-4-yl)oxy)propanamide, (S)-2-((1-(2-amino-7-fluorobenzo[d]oxazol-5-yl)-'7,8,9,10-tetrahydro-6-oxa-2,10a-diazacycloocta[cd]inden-4-yl)(methyl)amino)propanamide;

(S)-2-((1-(2-aminothiazolo[5,4-b]pyridin-5-yl)-7,8,9,10-tetrahydro-6-oxa-2,10a-diazacycloocta[cd]inden-4-yl)oxy)propanamide, (S)-2-((1-(2-aminooxazolo[4,5-b]pyridin-5-yl)-8,9-dihydro-7H-6-oxa-2,9a-diazabenzo[cd]azulen-4-yl)oxy)propanamide, (R)-2-((1-(4-(1H-1,2,4-triazol-3-yl)phenyl)-7,8,9,10-tetrahydro-6-oxa-2,10a-diazacycloocta[cd]inden-4-yl)oxy)butanamide, (S)-2-((1-(4-(1H-1,2,4-triazol-3-yl)phenyl)-7,8,9,10-tetrahydro-6-oxa-2,10a-diazacycloocta[cd]inden-4-yl)oxy)butanamide, (S)-2-((1-(3-fluoro-4-(1H-1,2,4-triazol-3-yl)phenyl)-7,8,9,10-tetrahydro-6-oxa-2,10a-diazacycloocta[cd]inden-4-yl)oxy)propanamide, (S)-2-((1-(2-amino-4-fluorobenzo[d]oxazol-5-yl)-'7,8,9,10-tetrahydro-6-oxa-2,10a-diazacycloocta[cd]inden-4-yl)(methyl)amino)propanamide, (S)-2-((1-(2-aminobenzo[d]oxazol-5-yl)-7,8,9,10-tetrahydro-6-oxa-2,10a-diazacycloocta[cd]inden-4-yl)oxy)butanamide, (S)-2-((1-(2-amino-7-fluorobenzo[d]oxazol-5-yl)-'7,8,9,10-tetrahydro-6-oxa-2,10a-diazacycloocta[cd]inden-4-yl)oxy)butanamide, (S)-2-((1-(2-amino-4-fluorobenzo[d]thiazol-6-yl)-7,8,9,10-tetrahydro-6-oxa-2,10a-diazacycloocta[cd]inden-4-yl)oxy)butanamide;

(S)-2-((1-(2-aminobenzo[d]thiazol-6-yl)-8,9-dihydro-7H-6-oxa-2,9a-diazabenzo[cd]azulen-4-yl)oxy)propanamide, (R)-2-((1-(2-aminobenzo[d]thiazol-5-yl)-7,8,9,10-tetrahydro-6-oxa-2,10a-diazacycloocta[cd]inden-4-yl)oxy)propanamide, (S)-2-((1-(2-aminobenzo[d]thiazol-5-yl)-7,8,9,10-tetrahydro-6-oxa-2,10a-diazacycloocta[cd]inden-4-yl)oxy)propanamide, (S)-2-((1-(2-amino-5-fluorobenzo[d]thiazol-6-yl)-7,8,9,10-tetrahydro-6-oxa-2,10a-diazacycloocta[cd]inden-4-yl)oxy)propanamide, (R)-2-((1-(2-amino-5-fluorobenzo[d]thiazol-6-yl)-7,8,9,10-tetrahydro-6-oxa-2,10a-diazacycloocta[cd]inden-4-yl)oxy)propanamide, (R)-2-((1-(2-amino-4-fluorobenzo[d]thiazol-6-yl)-7,8,9,10-tetrahydro-6-oxa-2,10a-diazacycloocta[cd]inden-4-yl)oxy)-2-cyclopropylacetamide, (S)-2-((1-(2-amino-4-fluorobenzo[d]thiazol-6-yl)-7,8,9,10-tetrahydro-6-oxa-2,10a-diazacycloocta[cd]inden-4-yl)oxy)-2-cyclopropylacetamide, (S)-2-((1-(2-aminobenzo[d]thiazol-6-yl)-7,8,9,10-tetrahydro-6-oxa-2,10a-diazacycloocta[cd]inden-4-yl)oxy)-2-cyclopropylacetamide, (R)-2-((1-(2-aminobenzo[d]thiazol-6-yl)-7,8,9,10-tetrahydro-6-oxa-2,10a-diazacycloocta[cd]inden-4-yl)oxy)-2-cyclopropylacetamide, (R)-2-((1-(2-aminobenzo[d]oxazol-5-yl)-7,8,9,10-tetrahydro-6-oxa-2,10a-diazacycloocta[cd]inden-4-yl)oxy)-2-cyclopropylacetamide, (S)-2-((1-(2-aminobenzo[d]oxazol-5-yl)-7,8,9,10-tetrahydro-6-oxa-2,10a-diazacycloocta[cd]inden-4-yl)oxy)-2-cyclopropylacetamide, (S)-2-((1-(2-amino-7-fluorobenzo[d]thiazol-5-yl)-7,8,9,10-tetrahydro-6-oxa-2,10a-diazacycloocta[cd]inden-4-yl)oxy)propanamide, (S)-2-((1-(2-amino-7-fluorobenzo[d]thiazol-6-yl)-7,8,9,10-tetrahydro-6-oxa-2,10a-diazacycloocta[cd]inden-4-yl)oxy)propanamide, (R)-2-((1-(2-amino-7-fluorobenzo[d]thiazol-6-yl)-7,8,9,10-tetrahydro-6-oxa-2,10a-diazacycloocta[cd]inden-4-yl)oxy)propanamide, (R)-2-((1-(2-amino-7-fluorobenzo[d]oxazol-5-yl)-'7,8,9,10-tetrahydro-6-oxa-2,10a-diazacycloocta[cd]inden-4-yl)oxy)-2-cyclopropylacetamide, (S)-2-((1-(2-amino-7-fluorobenzo[d]oxazol-5-yl)-'7,8,9,10-tetrahydro-6-oxa-2,10a-diazacycloocta[cd]inden-4-yl)oxy)-2-cyclopropylacetamide, (S)-2-((2-(2-amino-4-fluorobenzo[d]thiazol-6-yl)-3,4-dihydro-5-oxa-1,2a-diazaacenaphthylen-7-yl)oxy)-2-cyclopropylacetamide, (R)-2-((2-(2-amino-4-fluorobenzo[d]thiazol-6-yl)-3,4-dihydro-5-oxa-1,2a-diazaacenaphthylen-7-yl)oxy)-2-cyclopropylacetamide, (S)-2-((1-(3-aminobenzo[e][1,2,4]triazin-7-yl)-7,8,9,10-tetrahydro-6-oxa-2,10a-diazacycloocta[cd]inden-4-yl)oxy)propanamide, (S)-2-((1-(2-fluoro-4-(1H-1,2,4-triazol-5-yl)phenyl)-7,8,9,10-tetrahydro-6-oxa-2,10a-diazacycloocta[cd]inden-4-yl)oxy)propanamide;

(2R,3S)-1-(1-(2-aminobenzo[d]oxazol-5-yl)-7,8,9,10-tetrahydro-6-oxa-2,10a-diazacycloocta[cd]inden-4-yl)-3-fluoropyrrolidine-2-carboxamide;

(S)-2-((1-(2,5-difluoro-4-(1H-1,2,4-triazol-5-yl)phenyl)-7,8,9,10-tetrahydro-6-oxa-2,10a-diazacycloocta[cd]inden-4-yl)oxy)butanamide;

(S)-2-((1-(5-(1H-1,2,4-triazol-5-yl)pyridin-2-yl)-7,8,9,10-tetrahydro-6-oxa-2,10a-diazacycloocta[cd]inden-4-yl)oxy)propanamide;

(S)-2-((1-(2-aminobenzo[d]oxazol-5-yl)-7,8,9,10-tetrahydro-6-oxa-2,10a-diazacycloocta[cd]inden-4-yl)oxy)propanoic acid;

(S)-2-(4-(1-(2-aminothiazolo[5,4-b]pyridin-5-yl)-7,8,9,10-tetrahydro-6-oxa-2,10a-diazacycloocta[cd]inden-4-yl)-1H-pyrazol-1-yl)butanamide;

(R)-2-(4-(1-(2-aminothiazol o[5,4-b]pyridin-5-yl)-7,8,9,10-tetrahydro-6-oxa-2,10a-diazacycloocta[cd]inden-4-yl)-1H-pyrazol-1-yl)butanamide;

(2S,3R)-1-(1-(2-aminobenzo[d]thiazol-6-yl)-7,8,9,10-tetrahydro-6-oxa-2,10a-diazacycloocta[cd]inden-4-yl)-3-methoxypyrrolidine-2-carboxamide;

(S)-2-(4-(1-(2-aminooxazolo[4,5-b]pyridin-5-yl)-7,8,9,10-tetrahydro-6-oxa-2,10a-diazacycloocta[cd]inden-4-yl)-1H-pyrazol-1-yl)butanamide;

(R)-2-(4-(1-(2-aminooxazolo[4,5-b]pyridin-5-yl)-7,8,9,10-tetrahydro-6-oxa-2,10a-diazacycloocta[cd]inden-4-yl)-1H-pyrazol-1-yl)butanamide;

(S)-2-((1-(2-aminobenzo[d]thiazol-6-yl)-7,8,9,10-tetrahydro-6-oxa-2,10a-diazacycloocta[cd]inden-4-yl)oxy)-3-methoxypropanamide;

(R)-2-((1-(2-aminobenzo[d]thiazol-6-yl)-7,8,9,10-tetrahydro-6-oxa-2,10a-diazacycloocta[cd]inden-4-yl)oxy)-3-methoxypropanamide;

(S)-2-cyclopropyl-2-((1-(3-fluoro-4-(1H-1,2,4-triazol-5-yl)phenyl)-7,8,9,10-tetrahydro-6-oxa-2,10a-diazacycloocta[cd]inden-4-yl)oxy)acetamide;

(R)-2-cyclopropyl-2-((1-(3-fluoro-4-(1H-1,2,4-triazol-5-yl)phenyl)-7,8,9,10-tetrahydro-6-oxa-2,10a-diazacycloocta[cd]inden-4-yl)oxy)acetamide;

(S)-2-((1-(5-fluoro-6-(1H-1,2,4-triazol-5-yl)pyridin-3-yl)-7,8,9,10-tetrahydro-6-oxa-2,10a-diazacycloocta[cd]inden-4-yl)oxy)propanamide;

(2S,3S)-1-(1-(2-aminobenzo[d]oxazol-5-yl)-8,9-dihydro-7H-6-oxa-2,9a-diazabenzo[cd]azulen-4-yl)-3-methylpyrrolidine-2-carboxamide;

(2S,3S)-1-(1-(2-aminobenzo[d]oxazol-5-yl)-7,8,9,10-tetrahydro-6-oxa-2,10a-diazacycloocta[cd]inden-4-yl)-3-methylpyrrolidine-2-carboxamide;

(2S,3R)-1-(1-(2-aminobenzo[d]oxazol-5-yl)-7,8,9,10-tetrahydro-6-oxa-2,10a-diazacycloocta[cd]inden-4-yl)-3-methoxypyrrolidine-2-carboxamide;

(S)-2-(4-(1-(2-aminooxazolo[4,5-b]pyridin-5-yl)-8,9-dihydro-7H-6-oxa-2,9a-diazabenzo[cd]azulen-4-yl)-1H-pyrazol-1-yl)butanamide;

(R)-2-(4-(1-(2-aminooxazolo[4,5-b]pyridin-5-yl)-8,9-dihydro-7H-6-oxa-2,9a-diazabenzo[cd]azulen-4-yl)-1H-pyrazol-1-yl)butanamide;

(S)-2-((1-(2-aminobenzo[d]oxazol-5-yl)-7,8,9,10-tetrahydro-6-oxa-2,10a-diazacycloocta[cd]inden-4-yl)oxy)butanoic acid;

(R)-2-((1-(2-aminothiazolo[5,4-b]pyridin-5-yl)-7,8,9,10-tetrahydro-6-oxa-2,10a-diazacycloocta[cd]inden-4-yl)oxy)-3-methoxypropanamide; and (S)-2-((1-(2-aminothiazolo[5,4-b]pyridin-5-yl)-7,8,9,10-tetrahydro-6-oxa-2,10a-diazacycloocta[cd]inden-4-yl)oxy)-3-methoxypropanamide;

or a pharmaceutically acceptable salt thereof.

16. The method of claim 1 further comprising administering to the patient a therapeutic agent selected from 5-FU, docetaxel, eribulin, gemcitabine, cobimetinib, ipatasertib, paclitaxel, tamoxifen, fulvestrant, GDC-0810, dexamethasone, palbociclib, bevacizumab, pertuzumab, trastuzumab emtansine, trastuzumab and letrozole.

17. The method of claim 1 wherein the cancer is breast cancer.

18. The method of claim 17 wherein the breast cancer is estrogen receptor positive (ER+) breast cancer.

19. The method of claim 1 wherein the breast cancer subtype is Basal or Luminal.

20. The method of claim 1 wherein the cancer expresses a PIK3CA mutant selected from E542K, E545K, Q546R, H1047L and H1047R.

21. The method of claim 1 wherein the cancer expresses a PTEN mutant.

22. The method of claim 1 wherein the cancer is hormone receptor positive (HR+).

23. The method of claim 1 wherein the patient is HER2 negative, ER (estrogen receptor) negative, and PR (progesterone receptor) negative.

\* \* \* \* \*